(12) United States Patent
Wegert et al.

(10) Patent No.: US 10,202,345 B2
(45) Date of Patent: *Feb. 12, 2019

(54) SUBSTITUTED AZASPIRO(4.5)DECANE DERIVATIVES

(71) Applicant: Gruenenthal GmbH, Aachen (DE)

(72) Inventors: Anita Wegert, Aldenhoven (DE); Bert Nolte, Bad Muenstereifel (DE); Klaus Linz, Rheinbach (DE); Stephanie Harlfinger, Basel (CH); Babette-Yvonne Koegel, Langerwehe-Hamich (DE); Paul Ratcliffe, Aachen (DE); Fritz Theil, Berlin (DE); Olga Groeger, Berlin (DE); Birgit Braun, Berlin (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,872

(22) Filed: Jul. 15, 2015

(65) Prior Publication Data

US 2016/0016903 A1    Jan. 21, 2016

(30) Foreign Application Priority Data

Jul. 15, 2014  (EP) .................... 14002438

(51) Int. Cl.
| | | |
|---|---|---|
| *C07D 209/54* | (2006.01) | |
| *C07D 405/06* | (2006.01) | |
| *C07D 409/04* | (2006.01) | |
| *C07D 409/14* | (2006.01) | |
| *C07D 209/96* | (2006.01) | |

(52) U.S. Cl.
CPC ......... *C07D 209/54* (2013.01); *C07D 209/96* (2013.01); *C07D 405/06* (2013.01); *C07D 409/04* (2013.01); *C07D 409/14* (2013.01)

(58) Field of Classification Search
CPC ............................ C07D 209/54; C07D 405/06
See application file for complete search history.

(56) References Cited

U.S. PATENT DOCUMENTS

| | | |
|---|---|---|
| 5,091,567 A | 2/1992 | Geibel et al. |
| 5,977,102 A | 11/1999 | Himmelsbach et al. |
| 6,573,386 B1 | 6/2003 | Goenczi et al. |
| 7,157,456 B2 | 1/2007 | Straub et al. |
| 8,093,272 B2 | 1/2012 | Sundermann et al. |
| 8,232,289 B2 | 7/2012 | Benito Collado et al. |
| 8,288,406 B2 | 10/2012 | Frormann et al. |
| 8,357,705 B2 | 1/2013 | Zemolka et al. |
| 8,530,494 B2 | 9/2013 | Kyle et al. |
| 8,778,956 B2 | 7/2014 | Battista et al. |
| 8,877,779 B2 | 11/2014 | Nakano et al. |
| 10,030,031 B2 | 7/2018 | Lewis et al. |
| 2002/0058687 A1 | 5/2002 | Marfat |
| 2005/0187281 A1 | 8/2005 | Hinze et al. |
| 2005/0192333 A1 | 9/2005 | Hinze et al. |
| 2006/0004034 A1 | 1/2006 | Hinze et al. |
| 2007/0117824 A1 | 5/2007 | Berk et al. |
| 2007/0213351 A1 | 9/2007 | Sundermann et al. |
| 2008/0221141 A1 | 9/2008 | Friderichs et al. |
| 2009/0111842 A1 | 4/2009 | Merla et al. |
| 2009/0156593 A1 | 6/2009 | Zemolka et al. |
| 2009/0247505 A1 | 10/2009 | Zemolka et al. |
| 2009/0247561 A1 | 10/2009 | Zemolka et al. |
| 2009/0286833 A1 | 11/2009 | Oberboersch et al. |
| 2010/0009986 A1 | 1/2010 | Zemolka et al. |
| 2010/0048553 A1 | 2/2010 | Schunk et al. |
| 2010/0048554 A1 | 2/2010 | Schunk et al. |

FOREIGN PATENT DOCUMENTS

| | | |
|---|---|---|
| WO | WO 97/32882 A1 | 9/1997 |
| WO | WO 02/085838 A1 | 10/2002 |
| WO | WO 2004/043967 A1 | 5/2004 |
| WO | WO 2005/063769 A1 | 7/2005 |
| WO | WO 2005/066183 A1 | 7/2005 |
| WO | WO 2006/018184 A2 | 2/2006 |
| WO | WO 2006/031610 A2 | 3/2006 |
| WO | WO 2006/034015 A1 | 3/2006 |
| WO | WO 2006/108565 A1 | 10/2006 |
| WO | WO 2007/019987 A1 | 2/2007 |
| WO | WO 2007/030061 A1 | 3/2007 |
| WO | WO 2007/070826 A1 | 6/2007 |
| WO | WO 2007/079930 A1 | 7/2007 |
| WO | WO 2007/124903 A1 | 11/2007 |
| WO | WO 2007/127763 A2 | 11/2007 |
| WO | WO 2008/009415 A2 | 1/2008 |
| WO | WO 2008/009416 A1 | 1/2008 |
| WO | WO 2008/034731 A1 | 3/2008 |

(Continued)

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/Health/conditions/09/24/alzheimers.drug.ap/indexhtml>.*
Eberhard Reimann et al., Pethidine Analogs with Restricted Conformation, III[1]: Stereoselective Synthesis and Pharmacological Examination of trans-3-Methyl-10b-carb-ethoxy-1,2,3,4,4a,5,6, 10b-octahydrobenzo(f)isoquinoline, Arch. Pharm. (Weinheim), vol. 321, May 31, 1988, with partial English translation, pp. 935-941.
Istvám E. Markó et al., Cer(IV)-katalysierte Hydrolyse von Acetalen and Ketalen unter schwach basischen Bedingungen, Angew. Chem., vol. 111, 1999, pp. 3411-3413.
Ali Ates et al., Mild and chemoselective catalytic deprotection of ketals and acetals using cerium (IV) ammonium nitrate, Tetrahedron, 2003, vol. pp. 8989-8999.

(Continued)

*Primary Examiner* — Shawquia Jackson
(74) *Attorney, Agent, or Firm* — Norris McLaughlin, PA

(57) ABSTRACT

The invention relates to substituted spirocyclic cyclohexane derivatives which have an affinity for the μ opioid receptor and the ORL1 receptor, processes for the preparation thereof, medicaments containing these compounds and the use of these compounds for the preparation of medicaments.

15 Claims, No Drawings

(56) References Cited

FOREIGN PATENT DOCUMENTS

| WO | WO 2008/036755 A1 | 3/2008 |
|---|---|---|
| WO | WO 2 008/1 01 66 | 8/2008 |
| WO | WO 2008/101659 A1 | 8/2008 |
| WO | WO 2008/129007 A1 | 10/2008 |
| WO | WO 2009/111056 A1 | 9/2009 |
| WO | WO 2009/118169 A1 | 10/2009 |
| WO | WO 2009/118173 A1 | 10/2009 |
| WO | WO 2013/057320 A1 | 4/2013 |

OTHER PUBLICATIONS

Bruce H. Lipshutz et al., Pd(II) Catalyzed Acetal/Ketal Hydrolysis/Exchange Reactions, Tetrahedron Letters, 1985, vol. 26, No. 6, pp. 705-708.

Enrico Macantoni et al., Cerium(III) Chloride, a Novel Reagent for Nonaqueous Selective Conversion of Dioxolanes to Carbonyl Compounds, J. Org. Chem., 1997, vol. 62, pp. 4183-4184.

Swapan Majumdar et al., Thiourea: A Novel Cleaving Agent for 1,3-Dioxolanes, J. Org. Chem. 1999, vol. 64, pp. 5682-5685.

Daniela Alberati et al., 4-Substituted-8-(1-phenyl-cyclohexyl)-2,8-diaza-spiro[4.5]decan-1-one as a novel class of highly selective GlyT1 inhibitors with superior pharmacological and pharmacokinetic parameters, Bioorganic & Medicinal Chemistry Letters 16, 2000, pp. 4321-4325.

Jun Wang et al., Discovery of Spiro-Piperidine Inhibitors and Their Modulation of the Dynamics of the M2 Proton Channel from Influenza A Virus, J. Am. Chem. Soc., vol. 131, No. 23, 2009, pp. 8066-8076.

Kalpana Bhandari et al., A convenient method for the reduction of amides to their corresponding amines, Chemistry & Industry, Sep. 3, 1990, pp. 547-548.

Robert O. Hutchins et al., Tetraalkylammonium Trihydridocyanoborates. Versatile, Selective Reagents for Reductive Aminations in Nonpolar Media, J. Org. Chem. 1981, vol. 46, pp. 3571-3574.

Despina Setaki et al., Synthesis, Conformational characteristics and anti-influenza virus a activity of some 2-adamantylsubstituted azacycles, Bioorganic Chemistry, vol. 34, 2006, pp. 248-273.

George Stamatiou et al., Novel 3-(2-Adamantyl)pyrrolidines with Potent Activity Against Influenza A Virus-Identification of Aminoadamantane Derivatives Bearing Two Pharmacophoric Amine Groups, Bioorganic & Medicinal Chemistry Letters, vol. 11, 2001, pp. 2137-2142.

Gary H. Posner et al., Nitroolefins in One-Flask, Tandem, A+B+C Coupling Reactions Producing Heterocycles, Tetrahedron, vol. 46, No. 21, 1990, pp. 7509-7530.

Rebecca J. Flintoft et al., Alkylation of Ketone and Ester Lithium Enolates with Nitroethylene, Tetrahedron Letters, vol. 40, 1999, pp. 4485-4488.

Eva A. Krafft et al., A Straightforward and Efficiently Scaleable Synthesis of Novel Racemic 4-Substituted-2,8-diazaspiro[4.5]decan-1-one Derivatives, Synthesis, 2005, No. 19, pp. 3245-3252.

Daan van Leusen et al., Synthetic Uses of Tosylmethyl Isocyanide (TosMIC), Organic Reactions, vol. 57, 2001, pp. 417-489 and 659-679.

Gavin A. Whitlock, Novel 2-imidazoles as potent and selective $\alpha_{1A}$ adrenoceptor partial agonists, Bioorganic & Medicinal Chemistry Letters, vol. 18, 2008, pp. 2930-2934.

Detlef Geffken et al., Synthesis and Properties of 2-Hydroxy Carbohydroximic Esters, Arch. Pharm. (Weinheim) vol. 321, 1988, with partial English translation, pp. 45-49.

Olof Lagerlund et al., Aminocarbonylations of alkenyl phosphates, chlorides, bromides, and triflates with $Mo(CO)_6$ as a solid CO source, Tetrahedron, vol. 65, 2009, pp. 7646, 7652.

A. I. Meyers et al., the Synthesis of Chiral $\alpha,\beta$-Unsaturated and Aryl Oxazolines From Ketones and Arols Via Their Triflates and Pd-Catalyzed CO and Amino Alcohol Coupling., Tetrahedron Letters, vol. 33, No. 9, 1992, pp. 1181-1184.

Margaretha Van der Mey et al., Novel Selective PDE4 Inhibitors. 3. In Vivo Antiinflammatory Activity of a New Series of N-Substituted cis-Tetra- and cis-Hexahydrophthalazinones, J. Med. Chem., vol. 45, 2002, pp. 2520-2525.

Thomas J. Murray et al., Synthesis of Heterocyclic Compounds Containing Three Contiguous Hydrogen Bonding Sites in All Possible Arrangements, Tetrahedron, vol. 51, No. 2, 1995, pp. 635-648.

W. S. Wadsworth, Jr. et al., Ethyl Cyclohexylideneacetate, Organic Syntheses, Coll. Vo. 5, p. 547, 1973; vol. 45, p. 44, 1965 (four (4) pages).

Justin S. Bryans et al., Identification of Novel Ligands for the Gabapentin Binding Site on the $\alpha_2\delta$ Subunit of a Calcium Channel and Their Evaluation as Anticonvulsant Agents, J. Med. Chem., vol. 41, 1998, pp. 1838-1845.

Ali Ardati et al., Interaction of[$^3$H]Orphanin FQ and $^{125}$I-Tyr14-Orphanin FQ with the Orphanin FQ Receptor: Kinetics and Modulation by Cations and Guanine Nucleotides, Molecular Pharmacology, vol. 51, 1997, pp. 816-824.

Fred E. D'Amour et al., A Method for Determining Loss of Pain Sensation, The Biologic Research Laboratory, university of Denver, Jan. 27, 1941, pp. 74-79.

Sun Ho Kim et al., An experimental model for peripheral neuropathy produced by segmental spinal nerve ligation in the rat, Pain, vol. 50, 1992, pp. 355-363.

Paul R. Halfpenny et al., Highly Selective $_\kappa$-Opioid Analgesics. 3. Synthesis and Structure-Activity Relationships of Novel N-[2-(1-Pyrrolidinyl)-4- or -5-substituted-cyclohexyl]arylacetamide Derivatives, Journal of Medicinal Chemistry, vol. 33, No. 1, 1990, XP2952674A, pp. 286-291.

Girolamo Calo et al., "Pharmacology of Nociceptin and Its Receptor : A Novel Theraputic Target", British Journal of Pharmacology, 2000, pp. 1261-1283, vol. 129, Macmillan Publishers Ltd.

Miyuki Nishi et al., "Unrestrained Nociceptive Response and Disregulation of Hearing Ability in Mice Lacking the Nonciceptin/OrphaninFQ Recptor", The EMBO Journal, 1997, pp. 1858-1864, vol. 16, No. 8, Oxford University Press.

Toshiya Manabe et al., "Facilitation of Long-term Potentiation and Memory in Mice Lacking Nociceptin Receptors", Nature, Aug. 6. 1998, vol. 394, Macmillan Publishers Ltd.

International Search Report (PCT/ISA/210) issued in PCT Application No. PCT/EP2015/001445 dated Sep. 28, 2015 (Three (3) pages).

Written Opinion (PCT/ISA/237) issued in PCT Application No. PCT/EP2015/001445 dated Sep. 28, 2015 (Five (5) pages).

V. Craig Jordan, "Tamoxifen: A Most Unlikely Pioneering Medicine", Nature Reviews: Drug Discovery, 2003, vol. 2, No. 3, pp. 205-213.

* cited by examiner

SUBSTITUTED AZASPIRO(4.5)DECANE DERIVATIVES

The present invention relates to substituted spirocyclic cyclohexane derivatives which have an affinity for the μ opioid receptor and the ORL1 receptor, processes for the preparation thereof, medicaments containing these compounds and the use of these compounds for the preparation of medicaments.

Spirocyclic cyclohexane derivatives which have an affinity for the μ opioid receptor and the ORL1 receptor are known in the prior art. In this connection reference may be made to, for example, the full scope of WO2004/043967, WO2005/063769, WO2005/066183, WO2006/018184, WO2006/108565, WO2007/124903, WO2008/009416, WO2008/101659, WO2009/118169 and WO2009/118173.

However, the known compounds are not satisfactory in all respects and there is a need for further compounds with comparable or better properties.

Thus, in suitable binding assays the known compounds sometimes show a certain affinity for the hERG ion channel, for the L-type calcium ion channel (phenylalkylamine, benzothiazepine, dihydropyridine binding sites) or for the sodium channel in the BTX assay (batrachotoxin), which can in each case be interpreted as an indication of cardiovascular side effects. Numerous of the known compounds furthermore show only a low solubility in aqueous media, which can have an adverse effect, inter alia, on the bioavailability. The chemical stability of the known compounds moreover is often only inadequate. Thus, the compounds sometimes do not show an adequate pH, UV or oxidation stability, which can have an adverse effect, inter alia, on the storage stability and also on the oral bioavailability. The known compounds furthermore in some cases have an unfavourable PK/PD (pharmacokinetic/pharmacodynamic) profile, which can manifest itself e.g. in too long a duration of action.

The metabolic stability of the known compounds also appears to be in need of improvement. An improved metabolic stability can indicate an increased bioavailability. A weak or non-existent interaction with transporter molecules involved in the uptake and excretion of drugs is also to be evaluated as an indication of an improved bioavailability and at all events low drug interactions. Furthermore, the interactions with the enzymes involved in the breakdown and excretion of drugs should be as low as possible, since such test results likewise indicate that at all events low drug interactions or none at all are to be expected.

The known compounds furthermore sometimes show an only low selectivity for the kappa opioid receptor, which is responsible for side effects, in particular dysphoria, sedation, diuresis. The known compounds moreover sometimes show a very high affinity for the μ opioid receptor, which appears to be connected with other side effects, in particular respiratory depression, constipation and addiction.

The invention is based on the object of providing compounds which are suitable for pharmaceutical purposes and have advantages over the compounds of the prior art.

This object is achieved by the subject matter of the claims.

It has been found, surprisingly, that substituted spirocyclic cyclohexane derivatives which have an affinity for the μ opioid receptor and the ORL1 receptor can be prepared.

The invention relates to compounds of the general formula (1)

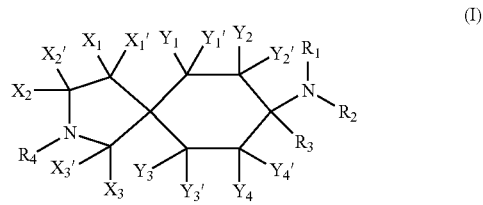

wherein
$Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)N(R$_0$)$_2$; preferably in each case independently of each other are chosen from the group consisting of —H, —F, —C$_{1-8}$-aliphatic, —C$_{1-8}$-aliphatic-NHC$_{1-8}$-aliphatic, —C$_{1-8}$-aliphatic-N(C$_{1-8}$-aliphatic)$_2$, —S—C$_{1-8}$-aliphatic, —S-aryl, -aryl, —C$_{1-8}$-aliphatic-aryl; or $Y_1$ and $Y_1'$, or $Y_2$ and $Y_2'$, or $Y_3$ and $Y_3'$, or $Y_4$ and $Y_4'$ together represent =O;
$X_1$, $X_1'$, $X_2$, $X_2'$, $X_3$ and $X_3'$ in each case independently of each other represent —H, —F, —Cl, —Br, —I, —NO$_2$, —CF$_3$, —OR$_5$, —SR$_5$, —SO$_2$R$_5$, —S(=O)$_2$OR$_5$, —CN, —COOR$_5$, —CONR$_5$, —NR$_6$R$_7$, or —R$_0$; or $X_1$ and $X_1'$, or $X_2$ and $X_2'$, or $X_3$ and $X_3'$ together represent =O; or $X_1$ and $X_2$ or $X_2$ and $X_3$ together represent —(CH$_2$)$_{2-6}$—, wherein individual hydrogen atoms can also be replaced by —F, —Cl, —Br, —I, —NO$_2$, —CF$_3$, —OR$_5$, —CN or —C$_{1-6}$-aliphatic; or $X_1$ and $X_1'$ or $X_2$ and $X_2'$ or $X_3$ and $X_3'$ together represent a C$_{3-6}$-cycloaliphatic, wherein individual hydrogen atoms can also be replaced by —F, —Cl, —Br, —NO$_2$, —CF$_3$, —OR$_5$, —CN or —C$_{1-6}$-aliphatic;
R$_0$ in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;
R$_1$ and R$_2$ independently of each other represent —H or —R$_0$; or R$_1$ and R$_2$ together represent —CH$_2$CH$_2$OCH$_2$CH$_2$—, —CH$_2$CH$_2$NR$_8$CH$_2$CH$_2$— or —(CH$_2$)$_{3-6}$—;
R$_3$ represents —R$_0$;
R$_4$ represents H or —Z—R$_{11}$,
wherein
Z can be absent or —C(=O)—, —S(=O)— or —S(=O)$_2$—, and
R$_{11}$ represents —C$_{1-6}$-alkyl, —C$_{3-6}$-cycloalkyl or —C$_{1-3}$-alkyl-C$_{3-6}$-cycloalkyl, wherein in the C$_{3-6}$-cycloalkyl group a ring carbon atom can be replaced by an oxygen atom and —C$_{1-6}$-alkyl, —C$_{3-6}$-cycloalkyl or —C$_{1-3}$-alkyl-C$_{3-6}$-cycloalkyl can be unsubstituted, mono- or polysubstituted with substituents independently of each other selected from the group consisting of —F, —Cl, —Br, —I, —ON, —OH, —SH, —O—$C_{1-3}$-alkyl and —S—$C_{1-3}$-alkyl, wherein —$C_{1-3}$-alkyl can be substituted by one or more substituents from the group consisting of —F, —Cl, —Br, —I, —CN, —OH, —$OCH_3$, —SH and —$SCH_3$;

$R_5$ in each case independently represents —H or —$R_0$;

$R_6$ and $R_7$ independently of each other represent —H or —$R_0$; or $R_6$ and $R_7$ together represent —$CH_2CH_2OCH_2CH_2$—, —$CH_2CH_2NR_{10}CH_2CH_2$— or —$(CH_2)_{3-6}$—;

$R_8$ represents —H, —$R_0$ or —$C(=O)R_0$;

$R_{10}$ represents —H or —$C_{1-6}$-aliphatic;

wherein

"aliphatic" in each case is a branched or unbranched, saturated or a mono- or polyunsaturated, unsubstituted or mono- or polysubstituted, aliphatic hydrocarbon radical;

"cycloaliphatic" in each case is a saturated or mono- or polyunsaturated, unsubstituted or mono- or polysubstituted, alicyclic, mono- or multicyclic hydrocarbon radical, the number of ring carbon atoms of which is preferably in the stated range (i.e. "$C_{3-8}$-" cycloaliphatic preferably has 3, 4, 5, 6, 7 or 8 ring carbon atoms);

wherein with respect to "aliphatic" and "cycloaliphatic", "mono- or polysubstituted" is understood as meaning substitution once or several times of one or more hydrogen atoms, e.g. substitution once, twice, three times or completely by substituents independently of each other chosen from the group consisting of —F, —Cl, —Br, —I, —CN, —$NO_2$, —CHO, =O, —$R_0$, —$C(=O)R_0$, —$C(=O)H$, —$C(=O)$—OH, —$C(=O)OR_0$, —$C(=O)NH_2$, —$C(=O)NHR_0$, —$C(=O)N(R_0)_2$, —OH, —$OR_0$, —$OC(=O)H$, —$OC(=O)R_0$, —$OC(=O)OR_0$, —$OC(=O)NHR_0$, —$OC(=O)N(R_0)_2$, —SH, —$SR_0$, —$SO_3H$, —$S(=O)_{1-2}$—$R_0$, —$S(=O)_{1-2}NH_2$, —$NH_2$, —$NHR_0$, —$N(R_0)_2$, —$N^+(R_0)_3$, —$N^+(R_0)_2O^-$, —$NHC(=O)R_0$, —$NHC(=O)OR_0$, —$NHC(=O)NH_2$, —$NHC(=O)NHR_0$, —NH—$C(=O)N(R_0)_2$, —$Si(R_0)_3$, —$PO(OR_0)_2$;

"aryl" in each case independently represents a carbocyclic ring system having at least one aromatic ring, but without hetero atoms in this ring, wherein the aryl radicals can optionally be fused with further saturated, (partially) unsaturated or aromatic ring systems and each aryl radical can be unsubstituted or mono- or polysubstituted, wherein the substituents on aryl can be identical or different and can be in any desired and possible position of the aryl;

"heteroaryl" represents a 5-, 6- or 7-membered cyclic aromatic radical which contains 1, 2, 3, 4 or 5 hetero atoms, wherein the hetero atoms are identical or different and are nitrogen, oxygen or sulfur and the heterocycle can be unsubstituted or mono- or polysubstituted; wherein in the case of substitution on the heterocycle the substituents can be identical or different and can be in any desired and possible position of the heteroaryl; and wherein the heterocycle can also be part of a bi- or polycyclic system;

wherein with respect to "aryl" and "heteroaryl", "mono- or polysubstituted" is understood as meaning substitution once or several times of one or more hydrogen atoms of the ring system by substituents chosen from the group consisting of —F, —Cl, —Br, —I, —CN, —$NO_2$, —CHO, =O, —$R_0$, —$C(=O)R_0$, —$C(=O)H$, —$C(=O)OH$, —$C(=O)OR_0$, —$C(=O)NH_2$, —$C(=O)NHR_0$, —$C(=O)$—$N(R_0)_2$, —OH, —$O(CH_2)_{1-2}O$—, —$OR_0$, —$OC(=O)H$, —$OC(=O)R_0$, —$OC(=O)OR_0$, —$OC(=O)NHR_0$, —$OC(=O)N(R_0)_2$, —SH, —$SR_0$, —$SO_3H$, —$S(=O)_{1-2}$—$R_0$, —$S(=O)_{1-2}NH_2$, —$NH_2$, —$NHR_0$, —$N(R_0)_2$, —$N^+(R_0)_3$, —$N^+(R_0)_2O^-$, —$NHC(=O)R_0$, —$NHC(=O)OR_0$, —$NHC(=O)NH_2$, —$NHC(=O)NHR_0$, —$NHC(=O)N(R_0)_2$, —$Si(R_0)_3$, —$PO(OR_0)_2$; wherein N ring atoms optionally present can in each case be oxidised (N-oxide);

in the form of an individual stereoisomer or mixture thereof, the free compounds and/or their physiologically acceptable salts and/or solvates.

Where various radicals are combined, for example $Y_1$, $Y_1'$, $Y_2$, $Y_2'$, $Y_3$, $Y_3'$, $Y_4$ and $Y_4'$, and where radicals on substituents thereof are combined, such as e.g. —$OR_0$, —$OC(=O)R_0$, —$OC(=O)NHR_0$, a substituent, e.g. $R_0$, can assume different meanings for two or more radicals, for example —$OR_0$, —$OC(=O)R_0$, —$OC(=O)NHR_0$, within a substance.

The compounds according to the invention show good binding to the ORL1 receptor and/or the μ opioid receptor, preferably to the ORL1 receptor and the μ opioid receptor.

The compounds according to the invention preferably have a $K_i$ value on the μ opioid receptor of at most 500 nM, more preferably at most 100 nM or at most 50 nM, still more preferably at most 10 nM, most preferably at most 1.0 nM and in particular at most 0.5 nM.

Methods for determination of the $K_i$ value on the μ opioid receptor are known to the person skilled in the art. The determination is preferably carried out as described in connection with the examples.

The compounds according to the invention preferably have a $K_i$ value on the ORL1 receptor of at most 500 nM, more preferably at most 100 nM or at most 50 nM, still more preferably at most 10 nM, most preferably at most 1.0 nM and in particular at most 0.75 nM.

Methods for determination of the $K_i$ value on the ORL1 receptor are known to the person skilled in the art. The determination is preferably carried out as described in connection with the examples.

It has been found, surprisingly, that the compounds according to the invention having affinity for the ORL1 and μ plaid receptor have a pharmacological profile which has significant advantages compared with the other opioid receptor ligands:

1. The compounds according to the invention show an activity in acute pain models which is sometimes comparable to that of the usual level 3 opioids. At the same time, however, they are distinguished by a clearly better tolerability compared with conventional μ opioids.
2. In contrast to the usual level 3 opioids, the compounds according to the invention show a clearly higher activity in mono- and polyneuropathy pain models, which is to be attributed to a synergism of the ORL1 and μ opioid component.
3. In contrast to the usual level 3 opioids, the compounds according to the invention show a substantial, preferably a complete separation of antiallodynic or antihyperalgesic action and antinociceptive effect in neuropathic animals.
4. In contrast to the usual level 3 opioids, the compounds according to the invention show a clear intensification of action against acute pain in animal models for chronic inflammation pain (inter alia carrageenan- or CFA-induced hyperalgesia, visceral inflammation pain).

5. In contrast to the usual level 3 opioids, side effects typical of μ opioids (inter alia respiratory depression, opioid-induced hyperalgesia, physical dependency/withdrawal, emotional dependency/addiction) are clearly reduced or preferably are not to be observed with the compounds according to the invention in the therapeutically active dose range.

On the basis of the reduced μ opioid side effects on the one hand and the increased activity on chronic, preferably neuropathic pain on the other hand, the mixed ORL1/μ agonists are thus distinguished by clearly increased safety margins compared with pure μ opioids. This results in a clearly increased "therapeutic window" in the treatment of states of pain, preferably chronic pain, still more preferably neuropathic pain.

A preferred embodiment of the invention relates to compounds of the general formula (2), i.e. $Y_1'$, $Y_2'$, $Y_3$ and $Y_4'$ are each —H:

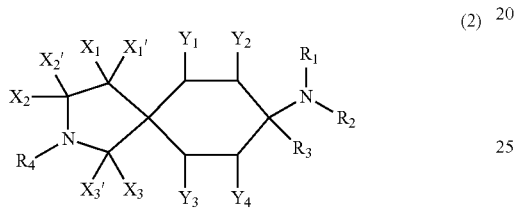

(2)

In a preferred embodiment of the compound (2) according to the invention $Y_1$, $Y_2$, $Y_3$ and $Y_4$ are not —H. In another preferred embodiment of the compound (2) according to the invention three of the radicals $Y_1$, $Y_2$, $Y_3$ and $Y_4$ are not —H and the remaining radical is —H. In another preferred embodiment two of the radicals $Y_1$, $Y_2$, $Y_3$ and $Y_4$ are not —H and the remaining two radicals are —H. In a further preferred embodiment of the compound (2) according to the invention one of the radicals $Y_1$, $Y_2$, $Y_3$ and $Y_4$ is not —H and the remaining radicals are —H.

In a particularly preferred embodiment of the compound (2) according to the invention $Y_1$, $Y_2$, $Y_3$ and $Y_4$ each represent —H.

Particularly preferred compounds of the general formula (1) or (2) are those wherein $R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, OH, —$OCH_3$, —$OC_2H_5$ and —$N(CH_3)_2$.

A preferred embodiment of the compound (2) according to the invention relates to compounds of the general formula (2.1):

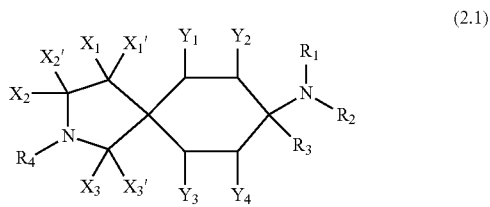

(2.1)

Particularly preferred compounds of the general formula (2) are those wherein $R_3$ represents —$C_{1-8}$-aliphatic, -aryl, -heteroaryl, —$C_{1-3}$-aliphatic-aryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, —OH, —$OCH_3$, —$OC_2H_5$ and —$N(CH_3)_2$; and $X_1$, $X_1'$, $X_2$, $X_2'$, $X_3$, $X_3'$ in each case independently of each other represent —H, —F, —Cl, —Br, —I, —$NO_2$, —$CF_3$, —$OR_5$, —$SR_5$, —$SO_2R_5$, —S(=O)$_2OR_5$, —CN, —$COOR_5$, —$CONR_5$, —$NR_6R_7$, or —$R_0$; or $X_1$ and $X_1'$, or $X_2$ and $X_2'$, or $X_3$ and $X_3'$ together represent =O.

Particularly preferred compounds are those of the general formula (3), i.e. $Y_1$, $Y_1'$, $Y_2$, $Y_2'$, $Y_3$, $Y_3'$, $Y_4$ and $Y_4'$ are each —H:

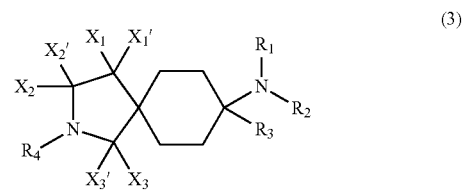

(3)

In further embodiments of the compounds of the general formula (3) one of the radicals $X_1$ and $X_1'$ represents H and the other represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, OH, —$OCH_3$, —$OC_2H_5$ and —$N(CH_3)_2$.

Preferred embodiments of the compounds of the general formula (3) have the general formula (3.1):

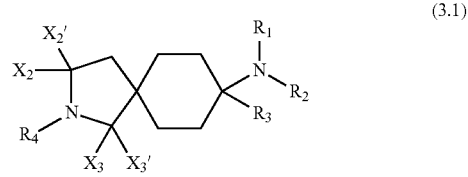

(3.1)

These embodiments relate to compounds of the general formula (3) in which $X_1$ and $X_1'$ are —H.

Particularly preferred compounds of the general formula (3.1) are those wherein $X_2$, $X_2'$, $X_3$ and $X_3'$ represent H; or $X_2$ and $X_2'$, or $X_3$ and $X_3'$ together represent =O;

$R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$;

R$_1$ represents CH$_3$;

R$_2$ represents —H or —CH$_3$; or

R$_1$ and R$_2$ together form a ring and represent —(CH$_2$)$_{3-4}$—; and

R$_3$ represents —C$_{1-8}$-aliphatic, -aryl, -heteroaryl, —C$_{1-3}$-aliphatic-aryl, —C$_{1-3}$-aliphatic-heteroaryl or —C$_{1-3}$-aliphatic-C$_{5-6}$-cycloaliphatic; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ and —N(CH$_3$)$_2$; and R$_4$ represents H or —Z—R$_{11}$, wherein Z can be absent or —C(=O)—, —S(=O)— or —S(=O)$_2$—, and R$_{11}$ represents —C$_{1-6}$-alkyl, —C$_{3-6}$-cycloalkyl or —C$_{1-3}$-alkyl-C$_{3-6}$-cycloalkyl, wherein in the C$_{3-6}$-cycloalkyl group a ring carbon atom can be replaced by an oxygen atom and —C$_{1-6}$-alkyl, —C$_{3-6}$-cycloalkyl or —C$_{1-3}$-alkyl-C$_{3-6}$-cycloalkyl can be unsubstituted, mono- or polysubstituted with substituents independently of each other selected from the group consisting of —F, —Cl, —Br, —I, —CN, —OH, —SH, —O—C$_{1-3}$-alkyl and —S—C$_{1-3}$-alkyl, wherein —C$_{1-3}$-alkyl can be substituted by one or more substituents from the group consisting of —F, —Cl, —Br, —I, —CN, —OH, —OCH$_3$, —SH and —SCH$_3$;

Preferred embodiments of the compounds of the general formula (3.1) have the general formula (3.1.1), (3.1.2), (3.1.3), (3.1.4), (3.1.5) or (3.1.6):

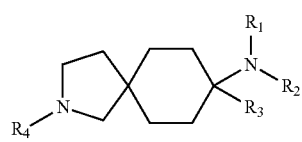

(3.1.1)

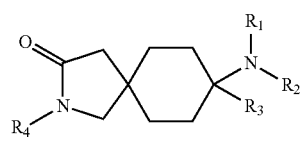

(3.1.2)

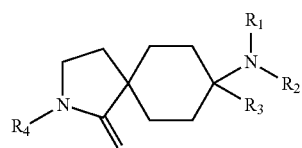

(3.1.3)

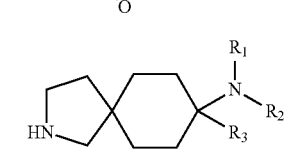

(3.1.4)

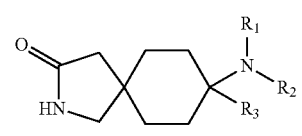

(3.1.5)

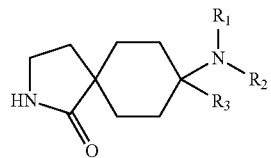

(3.1.6)

A further preferred embodiment relates to compounds of the general formula (4.1), i.e. R$_1$ and R$_2$ are in each case —CH$_3$.

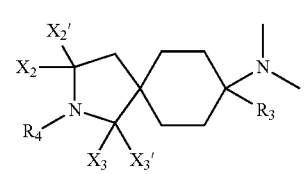

(4.1)

Preferred embodiments of the compounds of the general formula (4.1) have the general formula (4.1.1), (4.1.2), (4.1.3), (4.1.4), (4.1.5) or (4.1.6):

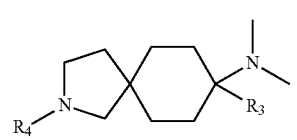

(4.1.1)

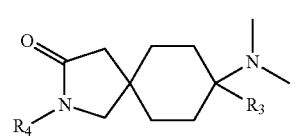

(4.1.2)

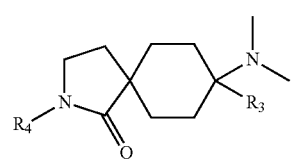

(4.1.3)

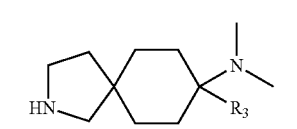

(4.1.4)

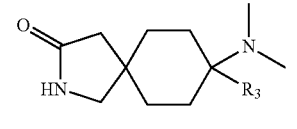

(4.1.5)

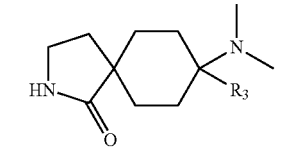

(4.1.6)

Preferably, Y$_1$, Y$_1'$, Y$_2$, Y$_2'$, Y$_3$, Y$_3'$, Y$_4$ and Y$_4'$ in each case independently of each other are chosen from the group consisting of —H, —F, —Cl, —Br, —I, —CN, —NH$_2$, —NH—C$_{1-6}$-aliphatic, —NH—C$_{3-6}$-cycloaliphatic, —NH—C$_{1-6}$-aliphatic-OH, —N(C$_{1-6}$-aliphatic)$_2$, —N(C$_{3-8}$- cycloaliphatic)$_2$, —N(C$_{1-6}$-aliphatic-OH)$_2$, —NO$_2$, —NH—C$_{1-6}$-aliphatic-C$_{3-6}$-cycloaliphatic, —NH—C$_{1-6}$-aliphatic-aryl, —NH—C$_{1-6}$-aliphatic-heteroaryl, —NH-aryl, —NH-heteroaryl, —SH, —S—C$_{1-6}$-aliphatic, —S—C$_{3-8}$-cycloaliphatic, —S—C$_{1-6}$-aliphatic-C$_{3-8}$-cycloaliphatic, —S—C$_{1-6}$-aliphatic-aryl, —S—C$_{1-6}$-aliphatic-heteroaryl, —S-aryl, —S-heteroaryl, —OH, —O—C$_{1-6}$-aliphatic, —O—C$_{3-8}$-cycloaliphatic, —O—C$_{1-6}$-aliphatic-OH, —O—C$_{1-6}$-aliphatic-C$_{3-8}$-cycloaliphatic, —O—C$_{1-6}$-aliphatic-aryl, —O—C$_{1-6}$-aliphatic-heteroaryl, —O-aryl, —O—heteroaryl, —O—C(=O)C$_{1-6}$-aliphatic, —O—C(=O)C$_{3-8}$-cycloaliphatic, —O—C(=O)C$_{1-6}$-aliphatic-OH, —O—C(=O)C$_{1-6}$-aliphatic-C$_{3-8}$-cycloaliphatic, —O—C(=O)C$_{1-6}$-aliphatic-aryl, —O—C(=O)C$_{1-6}$-aliphatic-heteroaryl, —O—C(=O)aryl, —O—C(=O)heteroaryl, —C$_{1-6}$-aliphatic, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, -aryl, -heteroaryl, —C(=O)C$_{1-6}$-aliphatic, —C(=O)C$_{3-8}$-cycloaliphatic, —C(=O)C$_{1-6}$-aliphatic-C$_{3-8}$-cycloaliphatic, —C(=O)C$_{1-6}$-aliphatic-aryl, —C(=O)C$_{1-6}$-aliphatic-heteroaryl, —C(=O)aryl, —C(=O)heteroaryl, —CO$_2$H, —CO$_2$—C$_{1-6}$-aliphatic, —CO$_2$—C$_{3-8}$-cycloaliphatic, —CO$_2$—C$_{1-6}$-aliphatic-C$_{3-8}$-cycloaliphatic, —CO$_2$—C$_{1-6}$-aliphatic-aryl, —CO$_2$—C$_{1-6}$-aliphatic-heteroaryl, —CO$_2$-aryl, —CO$_2$-heteroaryl; or Y$_1$ and Y$_1$', or Y$_2$ and Y$_2$', or Y$_3$ and Y$_3$', or Y$_4$ and Y$_4$' together represent =O.

More preferably, Y$_1$, Y$_1$', Y$_2$, Y$_2$', Y$_3$, Y$_3$', Y$_4$ and Y$_4$' in each case independently of each other are chosen from the group consisting of —H, —F, —Cl, —Br, —I, —CN, —C$_{1-6}$-aliphatic, —C$_{1-6}$-aliphatic-NHC$_{1-6}$-aliphatic, —C$_{1-6}$-aliphatic-N(C$_{1-8}$-aliphatic)$_2$, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, —S—C$_{1-8}$-aliphatic, —S-aryl, -aryl or -heteroaryl.

Particularly preferably, Y$_1$, Y$_1$', Y$_2$, Y$_2$', Y$_3$, Y$_3$', Y$_4$ and Y$_4$' in each case independently of each other are chosen from the group consisting of —H, —F, —Cl, —C$_{1-6}$-alkyl, —C$_{2-6}$-alkenyl, —C$_{1-6}$-alkyl-NH—C$_{1-6}$-alkyl, —C$_{1-6}$-alkyl-N(C$_{1-6}$-alkyl)$_2$, -aryl, —C$_{1-6}$-alkyl-aryl, —S—C$_{1-6}$-alkyl and —S-aryl.

In a preferred embodiment at least one of the radicals Y$_1$, Y$_1$', Y$_2$, Y$_2$', Y$_3$, Y$_3$', Y$_4$ and Y$_4$' is not —H and the remaining radicals represent —H.

Particularly preferably, Y$_1$, Y$_1$', Y$_2$, Y$_2$', Y$_3$, Y$_3$', Y$_4$ and Y$_4$' each represent —H.

Preferably, X$_1$, X$_1$', X$_2$, X$_2$', X$_3$ and X$_3$' in each case independently of each other represent —H, —F, —Cl, —Br, —I, —NO$_2$, —NR$_6$R$_7$, —C$_{1-6}$-aliphatic, —C$_{3-8}$-cycloaliphatic, -aryl, -heteroaryl, —C$_{1-6}$-aliphatic-aryl, —C$_{1-6}$-aliphatic-heteroaryl or —C$_{1-6}$-aliphatic-C$_{3-8}$-cycloaliphatic, or X$_1$ and X$_1$', or X$_2$ and X$_2$', or X$_3$ and X$_3$' together represent =O; or X$_1$ and X$_2$, or X$_2$ and X$_3$ together represent —(CH$_2$)$_{2-6}$; or X$_1$ and X$_1$' together represent a C$_3$-C$_6$-cycloaliphatic, preferably a C$_{3-6}$-cycloalkyl.

Preferred compounds are in particular also those in which X$_1$, X$_1$', X$_2$, X$_2$', X$_3$ and X$_3$' in each case independently of each other represent —H, —C$_{1-5}$-aliphatic, -aryl or -aryl linked via a —C$_{1-3}$-aliphatic group (bridge); or X$_1$ and X$_1$', or X$_2$ and X$_2$', or X$_3$ and X$_3$' together represent =O.

Particularly preferably, X$_1$, X$_1$', X$_2$, X$_2$', X$_3$ and X$_3$' in each case independently of each other represent —H, —CH$_3$, -phenyl or -benzyl, in particular —H, or X$_1$ and X$_1$', or X$_2$ and X$_2$', or X$_3$ and X$_3$' together represent =O.

Very particularly preferably, X$_1$, X$_1$', X$_2$, X$_2$', X$_3$ and X$_3$' represent H; or X$_2$ and X$_2$', or X$_3$ and X$_3$' together represent =O.

In a preferred embodiment X$_2$ and X$_2$' together represent =O, and X$_1$, X$_1$', X$_3$ and X$_3$' represent —H.

In another preferred embodiment X$_3$ and X$_3$' together represent =O, and X$_1$, X$_1$', X$_2$ and X$_2$' represent —H.

In a further preferred embodiment X$_1$, X$_1$', X$_2$, X$_2$', X$_3$ and X$_3$' represent H.

R$_0$ preferably in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl or —C$_{1-8}$-aliphatic-heteroaryl. In this context —C$_{1-8}$-aliphatic-C$_{3-12}$-cycloaliphatic, —C$_{1-8}$-aliphatic-aryl or —C$_{1-8}$-aliphatic-heteroaryl means that the radicals —C$_{3-12}$-cycloaliphatic, -aryl or -heteroaryl are in each case bonded via a divalent —C$_{1-8}$-aliphatic-bridge. Preferred examples for —C$_{1-8}$-aliphatic-aryl are —CH$_2$—C$_6$H$_5$, —CH=CH—C$_6$H$_5$ and —CH$_2$CH$_2$—C$_6$H$_5$. A preferred example for —C$_{1-8}$-aliphatic-heteroaryl is —CH$_2$-pyridyl. A preferred example for —C$_{1-8}$-aliphatic-C$_{3-12}$-cycloaliphatic is —CH$_2$-cyclopentyl.

Preferably, R$_1$ and R$_2$ independently of each other represent —H; —C$_{1-6}$-aliphatic; —C$_{3-8}$-cycloaliphatic, —C$_{1-6}$-aliphatic-aryl, —C$_{1-6}$-aliphatic-C$_{3-8}$-cycloaliphatic or —C$_{1-6}$-aliphatic-heteroaryl; or the radicals R$_1$ and R$_2$ together form a ring and denote —CH$_2$CH$_2$OCH$_2$CH$_2$—, —CH$_2$CH$_2$NR$_8$CH$_2$CH$_2$— or —(CH$_2$)$_{3-6}$—.

More preferably, R$_1$ and R$_2$ independently of each other represent —H; —C$_{1-5}$-aliphatic; or the radicals R$_1$ and R$_2$ together form a ring and denote —CH$_2$CH$_2$OCH$_2$CH$_2$—, —CH$_2$CH$_2$NR$_8$—CH$_2$CH$_2$— or —(CH$_2$)$_{3-6}$—, wherein R$_8$ preferably denotes —H or —C$_{1-5}$-aliphatic.

Particularly preferred compounds are those wherein R$_1$ and R$_2$ independently of each other represent —CH$_3$ or —H, wherein R$_1$ and R$_2$ do not simultaneously denote —H; or R$_1$ and R$_2$ form a ring and denote —(CH$_2$)$_{3-4}$—.

Very particularly preferred compounds are those wherein R$_1$ and R$_2$ represent —CH$_3$.

Preferably, R$_3$ represents —C$_{1-8}$-aliphatic, —C$_{3-8}$-cycloaliphatic, -aryl, -heteroaryl; or represents -aryl, -heteroaryl or —C$_{3-8}$-cycloaliphatic in each case bonded via a —C$_{1-3}$-aliphatic group.

Preferably, R$_3$ represents —C$_{1-5}$-aliphatic; in each case saturated or unsaturated, unsubstituted or mono- or polysubstituted by —OH, —OCH$_3$ or —OC$_2$H$_5$; -aryl, -heteroaryl; in each case unsubstituted or mono- or polysubstituted by —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; or represents —C$_{5-6}$-cycloaliphatic bonded via a —C$_{1-3}$-aliphatic group.

Most preferably, R$_3$ represents -aryl, -heteroaryl; in each case unsubstituted or mono- or polysubstituted by —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; or represents a —C$_{5-6}$-cycloaliphatic bonded via a —C$_{1-3}$-aliphatic group.

Particularly preferably, R$_3$ represents -vinyl, -ethyl, -allyl, -propyl, -butyl, -pentyl, -hexyl, -heptyl, -cyclopentyl, -cyclohexyl, -phenyl, -benzyl, -naphthyl, -anthracenyl, -thiophenyl (-thienyl), -benzothiophenyl, -furyl, -benzofuranyl, -benzodioxolanyl, -indolyl, -indanyl, -benzodioxanyl, -pyrrolyl, -pyridyl, -pyrimidyl or -pyrazinyl, in each case unsubstituted or mono- or polysubstituted; or —C$_{5-6}$-cycloaliphatic, -phenyl, -naphthyl, -anthracenyl, -thiophenyl, -benzothiophenyl, pyridyl, -furyl, -benzofuranyl, -benzodioxolanyl, -indolyl, -indanyl, -benzodioxanyl, -pyrrolyl, -pyrimidyl, -triazolyl or -pyrazinyl bonded via a saturated, unbranched —C$_{1-3}$-aliphatic group and in each case unsubstituted or mono- or polysubstituted.

Still more preferably, $R_3$ represents -propyl, -butyl, -pentyl, -hexyl, -phenyl, -phenethyl, -thiophenyl (-thienyl), -pyridyl, -triazolyl, -benzothiophenyl or -benzyl, in each case substituted or unsubstituted, particularly preferably -propyl, -3-methoxypropyl, -butyl, -pentyl, -hexyl, -phenyl, -3-methylphenyl, -3-fluorophenyl, -benzo[1,3]-dioxolyl, -thienyl, -5-methylthiophen-2-yl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

Most preferably, $R_3$ represents -phenyl, -benzyl, -phenethyl, in each case unsubstituted or mono- or polysubstituted on the ring; —$C_{1-5}$-aliphatic, —$C_{4-6}$-cycloaliphatic, -pyridyl, -thienyl, -thiazolyl, -imidazolyl, -1,2,4-triazolyl or -benzimidazolyl, unsubstituted or mono- or polysubstituted.

Particularly preferably, $R_3$ represents -phenyl, -benzyl, -phenethyl, -thienyl, -pyridyl, -thiazolyl, -imidazolyl, -1,2,4-triazolyl, -benzimidazolyl or -benzyl, unsubstituted or mono- or polysubstituted by —F, —Cl, —Br, —CN, —$CH_3$, —$C_2H_5$, —$NH_2$, —$NO_2$, —SH, —$CF_3$, —OH, —$OCH_3$, —$OC_2H_5$ or —$N(CH_3)_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, in each case unsubstituted or mono- or polysubstituted by —OH, —$OCH_3$ or —$OC_2H_5$.

Particularly preferably, $R_3$ represents -phenyl or -thienyl, in each case unsubstituted or monosubstituted by —F, —Cl, —$CH_3$; -ethyl, -n-propyl, -n-butyl, -vinyl, or -allyl, unsubstituted or mono- or polysubstituted by —$OCH_3$, —OH or —$OC_2H_5$, in particular by —$OCH_3$ or —$OC_2H_5$.

In further preferred embodiments, $R_3$ represents a radical selected from the group consisting of phenyl, benzyl and 2-thienyl, in each case unsubstituted or mono- or polysubstituted by substituents independently of each other selected from the group consisting of —F, —Cl, —Br, —CN, —$CH_3$, —$C_2H_5$, —$NH_2$, —$NO_2$, —SH, —$CF_3$, OH, —$OCH_3$, —$OC_2H_5$ and —$N(CH_3)_2$.

Preferably, $R_4$ represents H or —Z—$R_{11}$, wherein

Z can be absent or —C(=O)—, and $R_{11}$ represents —$C_{1-6}$-alkyl, —$C_{3-6}$-cycloalkyl, or $C_{1-3}$-alkyl-$C_{3-6}$-cycloalkyl, wherein in the $C_{3-6}$-cycloalkyl group a ring carbon atom can be replaced by an oxygen atom and —$C_{1-6}$-alkyl, —$C_{3-6}$-cycloalkyl or —$C_{1-3}$-alkyl-$C_{3-6}$-cycloalkyl can be unsubstituted, mono- or polysubstituted, by substituents independently of each other selected from the group consisting of —F, —Cl, —Br, —I, —CN, —OH, —SH, —O—$C_{1-3}$-alkyl, and —S—$C_{1-3}$-alkyl, wherein —$C_{1-3}$-alkyl can be substituted by one or more substituents independently of each other selected from the group consisting of —F, —Cl, —Br, —CN, —OH, —$OCH_3$, —SH and —$SCH_3$.

Preferably, in the radical $R_{11}$ the —$C_{3-6}$-cycloalkyl groups and oxygen-containing derivatives thereof are selected from the group consisting of cyclopropyl, cyclobutyl, cyclopentyl, cyclohexyl, oxetanyl, oxolanyl(tetrahydrofuranyl) and oxanyl(tetrahydropyranyl).

In further preferred embodiments $R_4$ represents H, $CH_3$, ethyl, n-propyl, i-propyl, n-butyl, s-butyl, iso-butyl, t-butyl, n-pentyl, s-pentyl, iso-pentyl,

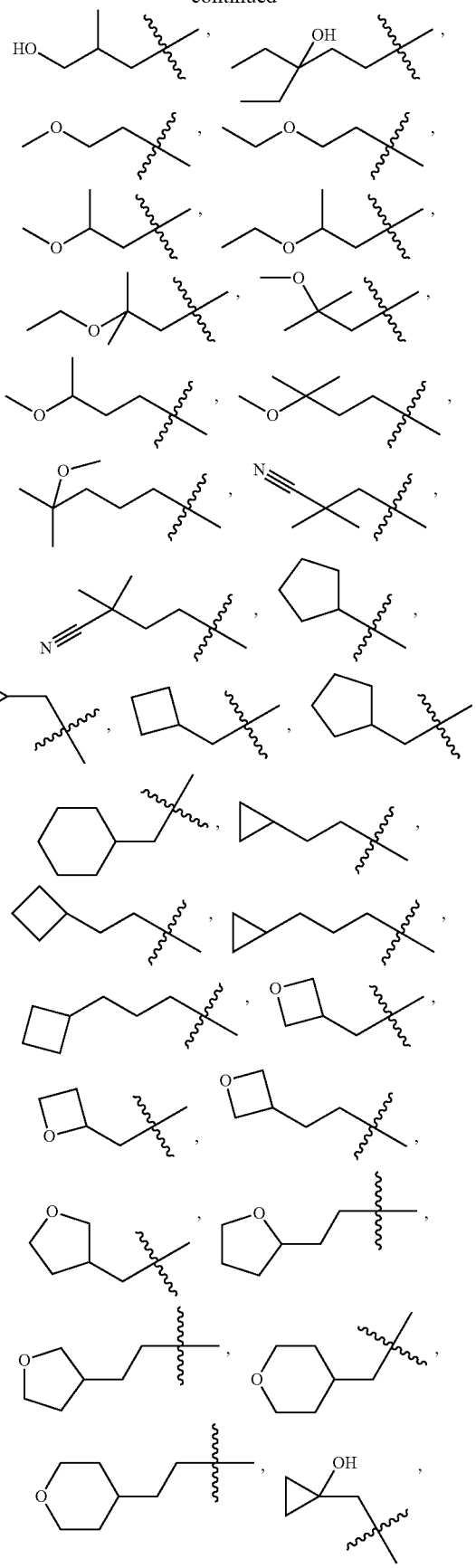

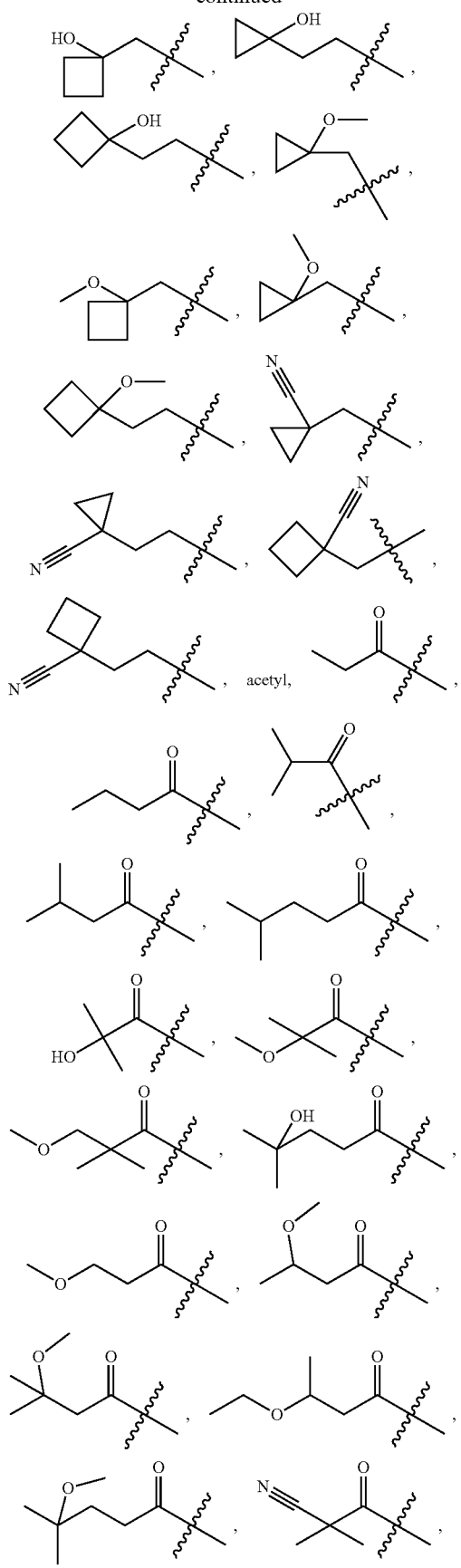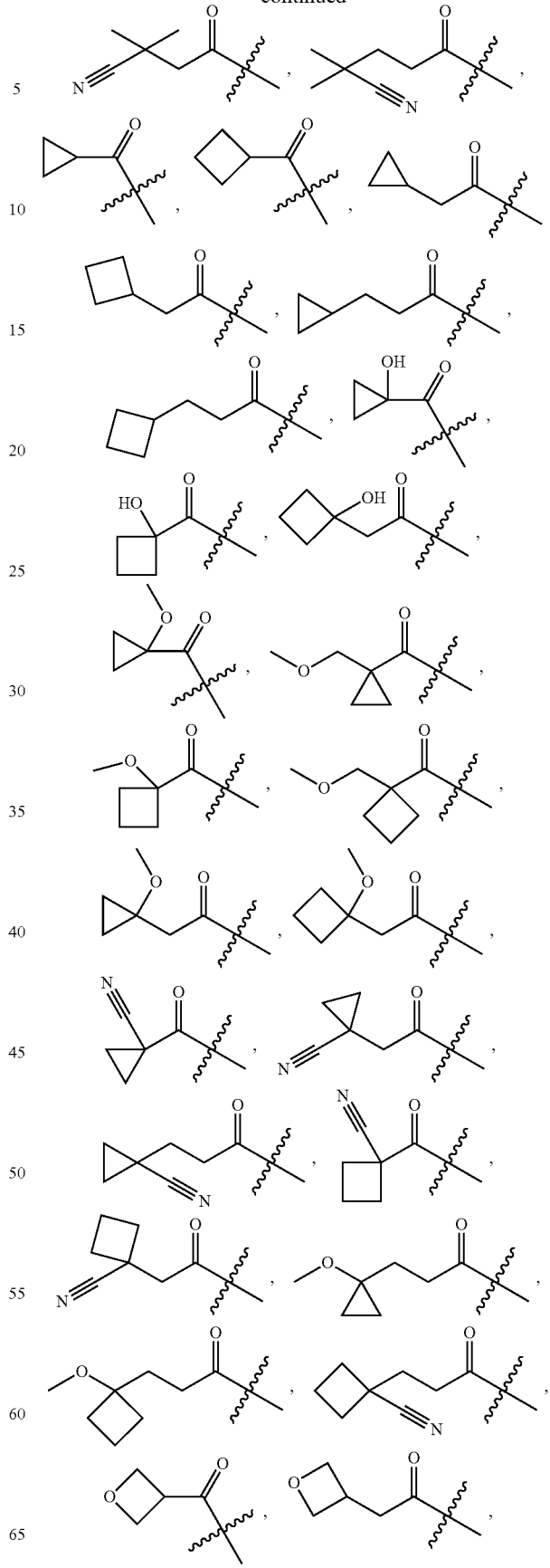

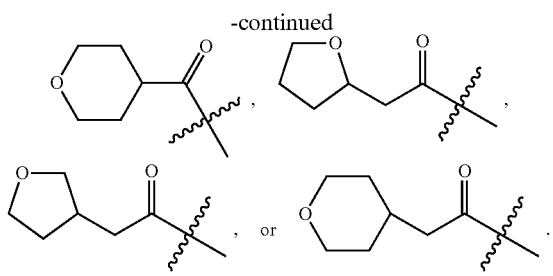
, or .

Preferably, $R_5$ represents —H, —$C_{1-5}$-aliphatic, —$C_{3-8}$-cycloaliphatic, -aryl, or -heteroaryl; or represents an -aryl, —$C_{3-8}$-cycloaliphatic or -heteroaryl in each case bonded via a —$C_{1-3}$-aliphatic group.

Preferably, $R_6$ and $R_7$ independently of each other represent —H, —$C_{1-5}$-aliphatic, —$C_{3-8}$-cycloaliphatic, -aryl, or -heteroaryl, or represent an -aryl, —$C_{3-8}$-cycloaliphatic or -heteroaryl in each case bonded via a —$C_{1-3}$-aliphatic group; or $R_6$ and $R_7$ together form —$CH_2CH_2OCH_2CH_2$—, —$CH_2CH_2N$—$R_{10}CH_2CH_2$— or —$(CH_2)_{3-6}$—. Particularly preferably, $R_6$ and $R_7$ independently of each other represent —H, —$C_{1-5}$-aliphatic; or $R_6$ and $R_7$ together form —$CH_2CH_2OCH_2CH_2$—, —$CH_2CH_2N$—$R_{10}CH_2CH_2$— or —$(CH_2)_{3-6}$—.

Preferably, $R_8$ represents —H, —$C_{1-5}$-aliphatic, —$C_{3-8}$-cycloaliphatic, -aryl, or -heteroaryl, —$C_{1-6}$-aliphatic-aryl, —$C_{1-6}$-aliphatic-$C_{3-8}$-cycloaliphatic, —$C_{1-6}$-aliphatic-heteroaryl, —C(=O)aryl, —C(=O)heteroaryl, or —C(=O)—$C_{1-6}$-aliphatic.

Particularly preferably, $R_{10}$ represents —H or —$C_{1-5}$-aliphatic.

For the purpose of the description, hydrocarbon radicals are divided into aliphatic hydrocarbon radicals on the one hand and aromatic hydrocarbon radicals on the other hand.

Aliphatic hydrocarbon radicals are in their turn divided into non-cyclic aliphatic hydrocarbon radicals on the one hand (="aliphatic") and cyclic aliphatic hydrocarbon radicals, i.e. alicylic hydrocarbon radicals, on the other hand (="cycloaliphatic"). Cycloaliphatics can be monocyclic or multicyclic. Alicyclic hydrocarbon radicals ("cycloaliphatic") include both pure aliphatic carbocycles and aliphatic heterocycles, i.e.—if not expressly specified—"cycloaliphatic" includes pure aliphatic carbocycles (e.g. cyclohexyl), pure aliphatic heterocycles (e.g. piperidyl or piperazyl) and non-aromatic, multicyclic, optionally mixed systems (e.g. decalinyl, decahydroquinolinyl). In other words the term "cycloaliphatic" is understood here as meaning that both cycloalkyls and heterocycloalkyls as well as unsaturated—but not aromatic—derivatives fall under this term. The term "$C_{3-8}$-cycloaliphatic" thus includes, inter alia, both 3- to 8-membered cycloalkyls, such as e.g. cyclopropyl, cyclobutyl, cyclopentyl and cyclohexyl, and 3- to 8-membered non-aromatic heterocycles in which one or more carbon atoms or —($CH_2$)— groups are replaced by a hetero atom (e.g. tetrahydrofuranyl, tetrahydropyranyl, piperidyl or piperazyl etc.).

Aromatic hydrocarbon radicals are in their turn divided into carbocyclic aromatic hydrocarbons on the one hand (="aryl") and heterocyclic aromatic hydrocarbons on the other hand (="heteroaryl").

The assignment of multicyclic, at least partially aromatic systems preferably depends on whether at least one aromatic ring of the multicyclic system contains at least one hetero atom (conventionally N, O or S) in the ring. If at least one such hetero atom is present in this ring, the system is preferably a "heteroaryl" (even if a further carbocyclic aromatic or non-aromatic ring with or without a hetero atom is present optionally as an additionally present ring of the multicyclic system); if such a hetero atom is present in none of the optionally several aromatic rings of the multicyclic system, the system is preferably "aryl" (even if a ring hetero atom is present in an optionally additionally present non-aromatic ring of the multicyclic system).

Within the cyclic substituents, the following priority of assignment accordingly preferably applies: heteroaryl>aryl>cycloaliphatic.

For the purpose of the description, monovalent and polyvalent, e.g. divalent hydrocarbon radicals are not differentiated with respect to terminology, i.e. "$C_{1-3}$-aliphatic" includes, depending on the sense, e.g. both —$C_{1-3}$-alkyl, —$C_{1-3}$-alkenyl and —$C_{1-3}$-alkynyl, and e.g. —$C_{1-3}$-alkylene-, —$C_{1-3}$-alkenylene- and —$C_{1-3}$-alkynylene-.

Preferably, "aliphatic" is in each case is a branched or unbranched, saturated or a mono- or polyunsaturated, unsubstituted or mono- or polysubstituted, aliphatic hydrocarbon radical. If aliphatic is mono- or polysubstituted, the substituents independently of each other are chosen from the group consisting of —F, —Cl, —Br, —I, —CN, —$NO_2$, —CHO, =O, —$R_0$, —C(=O)$R_0$, —C(=O)OH, —C(=O)$OR_0$, —C(=O)$NH_2$, —C(=O)$NHR_0$, —C(=O)$N(R_0)_2$, —OH, —$OR_0$, —OC(=O)H, —OC(=O)$R_0$, —OC(=O)$OR_0$, —OC(=O)—$NHR_0$, —OC(=O)$N(R_0)_2$, —SH, —$SR_0$, —$SO_3H$, —S(=O)$_{1-2}$—$R_0$, —S(=O)$_{1-2}NH_2$, —$NH_2$, —$NHR_0$, —$N(R_0)_2$, —$N^+(R_0)_3$, —$N^+(R_0)_2O^-$, —NHC(=O)$R_0$, —NHC(=O)$OR_0$, —NHC(=O)$NH_2$, —NHC(=O)$NHR_0$, —NHC(=O)$N(R_0)_2$, —NHS(=O)$_{1-2}R_0$, —Si($R_0)_3$, —PO($OR_0)_2$. "Aliphatic" thus includes acyclic saturated or unsaturated hydrocarbon radicals, which can be branched or straight-chain, i.e. alkanyls, alkenyls and alkynyls. In this context alkenyls have at least one C=C double bond and alkynyls have at least one C≡C triple bond. Preferred unsubstituted monovalent aliphatics include —$CH_3$, —$CH_2CH_3$, —$CH_2CH_2CH_3$, —CH($CH_3)_2$, —$CH_2CH_2CH_2CH_3$, —CH($CH_3)CH_2CH_3$, —$CH_2CH(CH_3)_2$, —C($CH_3)_3$, —$CH_2CH_2CH_2$—$CH_2CH_3$ and —$CH_2CH_2$—$CH_2CH_2CH_2CH_3$; but also —CH=$CH_2$, —C≡CH, —$CH_2CH=CH_2$, —CH=$CHCH_3$, —$CH_2C≡CH$, —C≡$CCH_3$ and —CH=CH—CH=$CH_2$. Preferred unsubstituted divalent aliphatics include —$CH_2$—, —$CH_2CH_2$—, —$CH_2CH(CH_3)$—, —CH($CH_3$)—$CH_2$—, —$CH_2CH_2CH_2$—, —CH($CH_3)CH_2CH_2$—, —$CH_2CH$($CH_3$)—$CH_2$—, —$CH_2CH_2CH(CH_3)$—, —CH—($CH_2CH_3)CH_2$— and —$CH_2CH_2$—$CH_2CH_2$—; but also —CH=CH—, —$CH_2CH$=CH—, —CH=$CHCH_2$—, —$CH_2C≡C$— and —C≡$CCH_2$—. Preferred substituted monovalent aliphatics include —$CH_2F$, —$CHF_2$, —$CF_3$, —$CH_2CF_3$, —$CF_2CF_3$, —$CH_2OH$, —$CH_2CH_2OH$, —$CH_2CHOHCH_3$, —$CH_2OCH_3$ and $CH_2CH_2OCH_3$. Preferred substituted divalent aliphatics include —$CF_2$—, —$CF_2CF_2$—, —$CH_2CHOH$—, —$CHOHCH_2$— and —$CH_2CHOHCH_2$—.

Methyl, ethyl, n-propyl and n-butyl are particularly preferred aliphatics.

Preferably, cycloaliphatic is in each case a saturated or a mono- or polyunsaturated, unsubstituted or mono- or polysubstituted, aliphatic (i.e. non-aromatic), mono- or multicyclic hydrocarbon radical. The number of ring carbon atoms is preferably in the stated range (i.e. a "$C_{3-8}$-" cycloaliphatic preferably has 3, 4, 5, 6, 7 or 8 ring carbon atoms). For the purpose of the description, "$C_{3-8}$-cycloaliphatic" is preferably a cyclic hydrocarbon having 3, 4, 5, 6, 7 or 8 ring carbon atoms, saturated or unsaturated, but not aromatic, one or two carbon atoms independently of each other optionally being replaced by a hetero atom S, N or O. If cycloalkyl is mono- or polysubstituted, the substituents independently of each other are chosen from the group consisting of —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, NHS(=O)$_{1-2}$R$_0$, —Si(R$_0$)$_3$, —PO(OR$_0$)$_2$. C$_{3-8}$-Cycloaliphatic is advantageously chosen from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

Cyclopentyl and cyclohexyl are particularly preferred C$_{3-8}$-cycloaliphatics.

Preferably, in connection with "aliphatic" or "cycloaliphatic", "mono- or polysubstituted" is understood as meaning substitution once or several times, e.g. once, twice, three times or four times, of one or more hydrogen atoms by —F, —Cl, —Br, —OH, —OC$_{1-6}$-alkyl, —OC(=O)C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds wherein "aliphatic substituted" or "cycloaliphatic substituted" means aliphatic or cycloaliphatic substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$ are preferred. Particularly preferred substituents are —F, —Cl, —OH, —SH, —NH$_2$ and —C(=O)OH.

Polysubstituted radicals are to be understood as meaning those radicals which are polysubstituted, e.g. di- or trisubstituted, either on different or on the same atoms, for example trisubstituted on the same C atom, as in the case of —CF$_3$ or —CH$_2$CF$_3$, or at different places, as in the case of —CH(OH)—CH=CH—CHCl$_2$. Polysubstitution can be with the same or with various substituents. A substituent can optionally also be substituted in its turn; thus -Oaliphatic, inter alia, also includes —OCH$_2$CH$_2$O—CH$_2$CH$_2$—OH. It is preferable for aliphatic or cycloaliphatic to be substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. It is very particularly preferable for aliphatic or cycloaliphatic to be substituted by —OH, —OCH$_3$ or —OC$_2$H$_5$.

Preferably, "aryl" in each case independently represents a carbocyclic ring system having at least one aromatic ring, but without hetero atoms in this ring, wherein the aryl radicals can optionally be fused with further saturated, (partially) unsaturated or aromatic ring systems and each aryl radical can be unsubstituted or mono- or polysubstituted, wherein the substituents on aryl can be identical or different and can be in any desired and possible position of the aryl. Preferred aryls are phenyl, naphthyl, anthracenyl, phenanthrenyl, fluoranthenyl, fluorenyl, indanyl and tetralinyl. Phenyl and naphthyl are particularly preferred. If aryl is mono- or polysubstituted, the substituents on aryl can be identical or different and can be in any desired and possible position of the aryl, and are independently of each other chosen from the group consisting of —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxyphenyl, 3-methoxyphenyl, 4-methoxyphenyl, 2,3-dimethoxyphenyl, 2,4-dimethoxyphenyl, 3,4-dimethoxyphenyl, 2-methylphenyl, 3-methylphenyl, 4-methylphenyl, 2,3-dimethylphenyl, 2,4-dimethylphenyl and 3,4-dimethylphenyl.

Preferably, heteroaryl represents a 5-, 6- or 7-membered cyclic aromatic radical which contains 1, 2, 3, 4 or 5 hetero atoms, wherein the hetero atoms are identical or different and are nitrogen, oxygen or sulfur and the heterocycle can be unsubstituted or mono- or polysubstituted; wherein in the case of substitution on the heterocycle the substituents can be identical or different and can be in any desired and possible position of the heteroaryl; and wherein the heterocycle can also be part of a bi- or polycyclic system. Preferably, "heteroaryl" is chosen from the group consisting of pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, where bonding can be via any desired and possible ring member of the heteroaryl radical. If heteroaryl is mono- or polysubstituted, the substituents on heteroaryl can be identical or different and can be in any desired and possible position of the heteroaryl, and are independently of each other chosen from the group consisting of —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NH—C(=O)R$_0$, —NHC(=O)OR$_0$, —NHC(=O)NH$_2$, —NHC(=O)NHR$_0$, —NH—C(=O)N(R$_0$)$_2$, —Si(R$_0$)$_3$, —PO(OR$_0$)$_2$; wherein N ring atoms optionally present can in each case be oxidised (N-oxide).

With respect to "aryl" or "heteroaryl", "mono- or polysubstituted" is understood as meaning substitution once or several times, e.g. twice, three times, four times or five times, of one or more hydrogen atoms of the ring system.

The substituents on aryl and heteroaryl are particularly preferably in each case independently of each other chosen from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds wherein "aryl substituted" or "heteroaryl substituted" means aryl or heteroaryl substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$ are preferred. Particularly preferred substituents are —F, —Cl, —CH$_3$, —OH, —SH, —NH$_2$ and —C(=O)OH.

The compounds according to the invention can be in the form of an individual stereoisomer or mixture thereof, the free compounds and/or their physiologically acceptable salts and/or solvates.

With respect to the Spiro ring, the compounds according to the invention are isomers in which the substitution pattern on the Spiro cyclohexane ring system can also be designated cis/trans, Z/E or syn/anti. "cis-trans isomers" are a subgroup of stereoisomers (configuration isomers).

The cis-trans isomers of the compound of the general formula (1) according to the invention have the general formula (1a) or (1b):

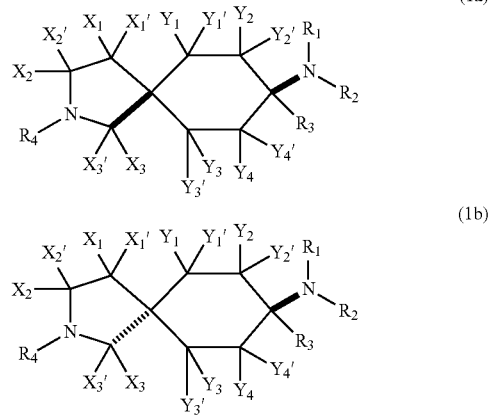

The assignment of the two stereoisomers (1a) and (1b) according to the substitution pattern as the cis or trans isomer is known to the person skilled in the art.

In a preferred embodiment the diastereomer excess of the cis isomer is at least 50% de, more preferably at least 75% de, still more preferably at least 90% de, most preferably at least 95% de and in particular at least 99% de. In another preferred embodiment, the diastereomer excess of the trans isomer is at least 50% de, more preferably at least 75% de, still more preferably at least 90% de, most preferably at least 95% de and in particular at least 99% de.

Suitable methods for separation of the isomers (diastereomers) are known to the person skilled in the art. Examples which may be mentioned are column chromatography, preparative HPLC and crystallization methods.

A person skilled in the art moreover recognises that the compounds according to the invention can be chiral or achiral, depending on the substitution pattern.

If the compounds according to the invention are chiral, they are preferably in the form of the racemate or in a concentrated form of one enantiomer. In a preferred embodiment the enantiomer excess (ee) of the S enantiomer is at least 50% ee, more preferably at least 75% ee, still more preferably at least 90% ee, most preferably at least 95% ee and in particular at least 99% ee. In another preferred embodiment the enantiomer excess (ee) of the R enantiomer is at least 50% ee, more preferably at least 75% ee, still more preferably at least 90% ee, most preferably at least 95% ee and in particular at least 99% de.

Suitable methods for separation of the enantiomers are known to the person skilled in the art. Examples which may be mentioned are preparative HPLC on chiral stationary phases and conversion into diastereomeric intermediates. The conversion into diastereomeric intermediates can be carried out, for example, as salt formation with the aid of chiral, enantiomerically pure acids. After the separation of the diastereomers formed in this way, the salt can then be converted back into the free base or another salt.

If not expressly specified, any reference to the compounds according to the invention includes all the isomers (e.g. stereoisomers, diastereomers, enantiomers) in any desired mixing ratio.

If not expressly specified, any reference to the compounds according to the invention includes the free compounds (i.e. the forms which are not in the form of a salt) and all physiologically acceptable salts.

For the purpose of the description, physiologically acceptable salts of the compounds according to the invention are in the form of salts with anions or acids of the particular compound with inorganic or organic acids which are physiologically acceptable—in particular when used in humans and/or mammals.

Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride, the citrate and the hemicitrate are particularly preferred.

Physiologically acceptable salts with cations or bases are salts of the particular compound—as the anion with at least one, preferably inorganic cation—which are physiologically acceptable—in particular when used in humans and/or mammals. The salts of alkali metals and alkaline earth metals but also ammonium salts are particularly preferred, but in particular (mono)- or (di)sodium, (mono)- or (di)potassium, magnesium or calcium salts.

The compounds according to the invention are defined by substituents, for example by $R_1$, $R_2$ and $R_3$ (substituents of the 1st generation), which in their turn are optionally substituted (substituents of the 2nd generation). Depending on the definition, these substituents of the substituents can in their turn be substituted again (substituents of the 3rd generation). For example, if $Y_1$=—$R_0$, wherein $R_0$=—$C_{1-8}$-aliphatic (substituent of the 1st generation), —$C_{1-8}$-aliphatic can in its turn be substituted, e.g. by —$OR_0$, wherein $R_0$=-aryl (substituent of the 2nd generation). The functional group —$C_{1-8}$-aliphatic-Oaryl results from this. -Aryl can then in its turn be substituted again, e.g. by —Cl (substituent of the 3rd generation). The functional group —$C_{1-8}$-aliphatic-Oaryl-Cl overall then results from this.

In a preferred embodiment, however, the substituents of the 3rd generation cannot be substituted again, i.e. there are then no substituents of the 4th generation.

In another preferred embodiment, however, the substituents of the 2nd generation cannot be substituted again, i.e. there are then already no substituents of the 3rd generation. In other words, in this embodiment the functional groups for $R_0$ to $R_{10}$ can in each case be optionally substituted, but the particular substituents cannot then in their turn be substituted again.

In another preferred embodiment the substituents of the 1st generation already cannot be substituted again, i.e. there are then neither substituents of the 2nd nor substituents of the 3rd generation. In other words, in this embodiment the functional groups for $R_0$ to $R_{10}$ in each case cannot be substituted.

Preferred compounds are those wherein "aliphatic substituted" or "cycloaliphatic substituted" means aliphatic or cycloaliphatic substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; and "aryl substituted" or "heteroaryl substituted" means aryl or heteroaryl substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$ in the form of the racemate; the enantiomers, diastereomers, mixtures of the enantiomers or diastereomers or of an individual enantiomer or diastereomer; the bases and/or salts of physiologically acceptable acids or cations.

Very particularly preferred compounds are those according to the general formula (3)

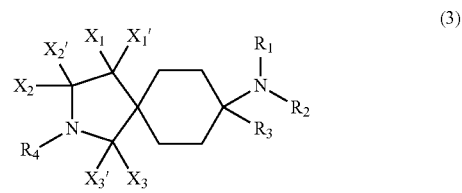

(3)

in which $X_1$ and $X_1'$ represent H and the radicals $R_1$, $R_2$, $R_3$, $R_4$, $X_2/X_2'$ and $X_3/X_3'$ have the following meaning:

| Example | $R_1$ | $R_2$ | $R_3$ | $X_2/X_2'$ | $X_3/X_3'$ | $R_4$ |
|---|---|---|---|---|---|---|
| 1; 2 | CH$_3$ | CH$_3$ | Benzyl | H/H | =O | H |
| 3; 4 | CH$_3$ | CH$_3$ | Benzyl | H/H | H/H | H |
| 5; 6 | CH$_3$ | CH$_3$ | Benzyl | H/H | H/H | CH$_3$ |
| 7; 8 | CH$_3$ | CH$_3$ | Benzyl | H/H | H/H | Acetyl |
| 9 | CH$_3$ | CH$_3$ | Benzyl | H/H | H/H | n-Butyl |
| 10; 11 | CH$_3$ | CH$_3$ | Benzyl | H/H | H/H | ![pentanone group] |
| 12 | CH$_3$ | CH$_3$ | Benzyl | H/H | H/H | ![cyclopentylmethyl group] |
| 13 | CH$_3$ | CH$_3$ | Phenyl | H/H | =O | H |
| 14; 15 | CH$_3$ | CH$_3$ | Phenyl | =O | H/H | H |
| 16 | CH$_3$ | CH$_3$ | n-Butyl | H/H | =O | H |
| 17 | CH$_3$ | CH$_3$ | 2-Thienyl | H/H | =O | H |
| 18; 25 | CH$_3$ | CH$_3$ | 2-Thienyl | H/H | H/H | H |
| 19 | CH$_3$ | CH$_3$ | 2-Thienyl | H/H | H/H | CH$_3$ |
| 20a/b | CH$_3$ | CH$_3$ | 2-Thienyl | H/H | H/H | ![pentanone group] |
| 21 | CH$_3$ | CH$_3$ | 2-Thienyl | H/H | H/H | n-Butyl |
| 22 | CH$_3$ | CH$_3$ | 2-Thienyl | H/H | H/H | ![cyclopentylmethyl group] |
| 24a/b | CH$_3$ | CH$_3$ | 2-Thienyl | =O | H/H | H |
| 27 | CH$_3$ | CH$_3$ | Benzyl | H/H | H/H | n-Butyl |
| 28; 29 | CH$_3$ | CH$_3$ | Phenyl | H/H | H/H | ![pentanone group] |
| 30 | CH$_3$ | CH$_3$ | ![thienyl group] | H/H | =O | H |
| 31 | CH$_3$ | CH$_3$ | ![thienyl group] | H/H | H/H | H |

-continued
| Example | R₁ | R₂ | R₃ | X₂/X₂' | X₃/X₃' | R₄ |
|---|---|---|---|---|---|---|
| 32 | CH₃ | CH₃ | 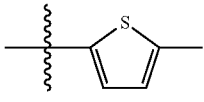 | H/H | H/H | 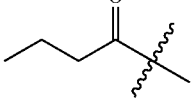 |
| 33 | CH₃ | CH₃ | 2-Thienyl | =O | H/H | n-Butyl |
| 34 | CH₃ | CH₃ | 2-Thienyl | =O | H/H | CH₃ |
| 35 | CH₃ | CH₃ | 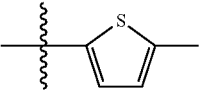 [SMILES: *c1ccc(C)s1] | H/H | H/H | n-Butyl |
| 36 | CH₃ | CH₃ | 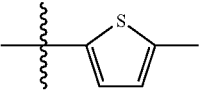 [SMILES: *c1ccc(C)s1] | H/H | H/H | 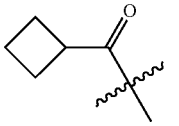 [SMILES: *C(=O)C1CCC1] |
| 37 | CH₃ | CH₃ | 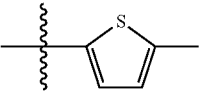 | H/H | H/H | 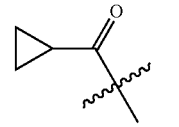 [SMILES: *C(=O)C1CC1] |
| 38 | CH₃ | CH₃ | 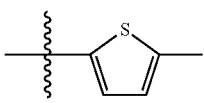 | H/H | H/H | 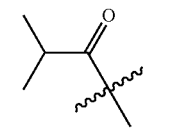 [SMILES: *C(=O)C(C)C] |
| 39 | CH₃ | CH₃ | 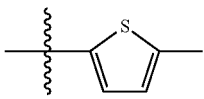 [SMILES: *c1ccc(C)s1] | H/H | H/H | 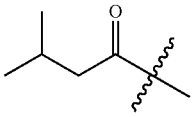 [SMILES: *C(=O)CC(C)C] |
| 40 | CH₃ | CH₃ | 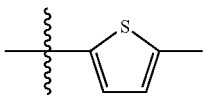 [SMILES: *c1ccc(C)s1] | H/H | H/H | 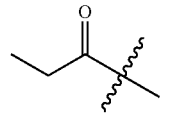 [SMILES: *C(=O)CC] |
| 41 | CH₃ | CH₃ | 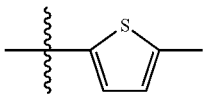 | H/H | H/H | 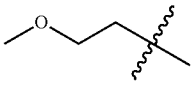 |
| 42 | CH₃ | CH₃ | 2-Thienyl | H/H | H/H | 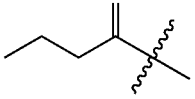 |
| 43 | CH₃ | CH₃ | 2-Thienyl | H/H | H/H | 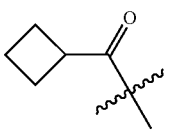 [SMILES: *C(=O)C1CCC1] |
| 44 | CH₃ | CH₃ | 2-Thienyl | H/H | H/H | 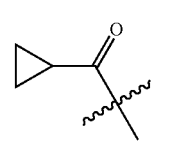 [SMILES: *C(=O)C1CC1] |

-continued
| Example | R₁ | R₂ | R₃ | X₂/X₂' | X₃/X₃' | R₄ |
|---|---|---|---|---|---|---|
| 45 | CH₃ | CH₃ | 2-Thienyl | H/H | H/H | 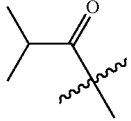 [SMILES: *C(=O)C(C)C] |
| 46 | CH₃ | CH₃ | 2-Thienyl | H/H | H/H | 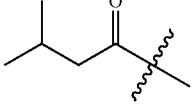 |
| 47 | CH₃ | CH₃ | 2-Thienyl | H/H | H/H | 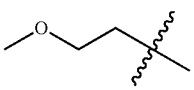 [SMILES: *CCOC] |
| 48 | CH₃ | CH₃ | 2-Thienyl | H/H | H/H | 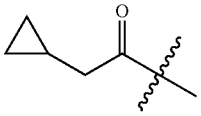 [SMILES: *C(=O)CC1CC1] |
| 49 | CH₃ | CH₃ | 2-Thienyl | H/H | H/H | 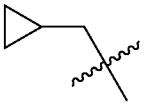 |
| 50 | CH₃ | CH₃ | 2-Thienyl | H/H | H/H | 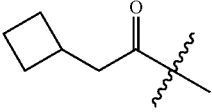 [SMILES: *C(=O)CC1CCC1] |
| 51 | CH₃ | CH₃ | 2-Thienyl | H/H | H/H | 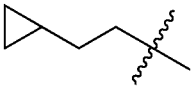 [SMILES: *CCC1CC1] |
| 52 | CH₃ | CH₃ | 2-Thienyl | H/H | H/H | 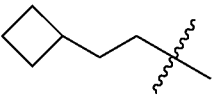 [SMILES: *CCC1CCC1] |
| 53 | CH₃ | CH₃ | 2-Thienyl | H/H | H/H | 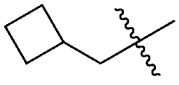 [SMILES: *CC1CCC1] |
| 54 | CH₃ | CH₃ | 2-Thienyl | H/H | H/H | 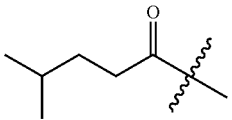 [SMILES: *C(=O)CCC(C)C] |
| 55 | CH₃ | CH₃ | 2-Thienyl | H/H | H/H | 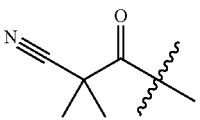 [SMILES: *C(=O)C(C)(C)C#N] |
| 56 | CH₃ | CH₃ | 2-Thienyl | H/H | H/H | 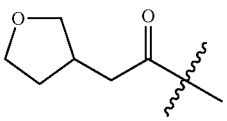 [SMILES: *C(=O)CC1CCOC1] |

-continued
| Example | R₁ | R₂ | R₃ | X₂/X₂' | X₃/X₃' | R₄ |
|---|---|---|---|---|---|---|
| 57 | CH₃ | CH₃ | 2-Thienyl | H/H | H/H | 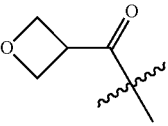 [SMILES: *C(=O)C1COC1] |
| 58 | CH₃ | CH₃ | 2-Thienyl | H/H | H/H | 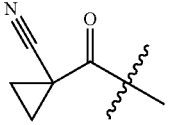 [SMILES: *C(=O)C1(C#N)CC1] |
| 59 | CH₃ | CH₃ | 2-Thienyl | H/H | H/H | 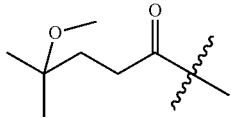 [SMILES: *C(=O)CCC(C)(C)OC] |
| 60 | CH₃ | CH₃ | 2-Thienyl | H/H | H/H | 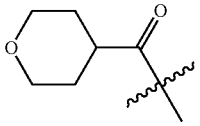 [SMILES: *C(=O)C1CCOCC1] |
| 61 | CH₃ | CH₃ | 2-Thienyl | H/H | H/H | 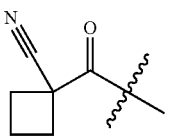 [SMILES: *C(=O)C1(C#N)CCC1] |
| 62 | CH₃ | CH₃ | 2-Thienyl | H/H | H/H | 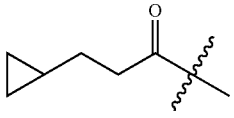 [SMILES: *C(=O)CCC1CC1] |
| 63 | CH₃ | CH₃ | 2-Thienyl | H/H | H/H | 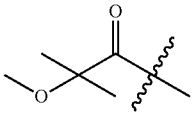 [SMILES: *C(=O)C(C)(C)OC] |
| 64 | CH₃ | CH₃ | 2-Thienyl | H/H | H/H | 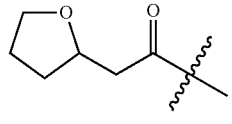 [SMILES: *C(=O)CC1CCCO1] |
| 65 | CH₃ | CH₃ | 2-Thienyl | H/H | H/H | 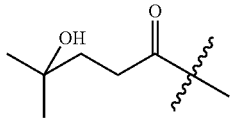 [SMILES: *C(=O)CCC(C)(C)O] |
| 66 | CH₃ | CH₃ | 2-Thienyl | H/H | H/H | 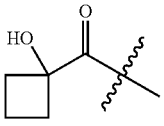 |
| 67 | CH₃ | CH₃ | 2-Thienyl | H/H | H/H | 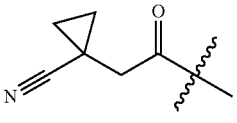 [SMILES: *C(=O)CC1(C#N)CC1] |

-continued

| Example | R₁ | R₂ | R₃ | X₂/X₂' | X₃/X₃' | R₄ |
|---|---|---|---|---|---|---|
| 68 | CH₃ | CH₃ | 2-Thienyl | H/H | H/H | 1-cyanocyclobutyl-CH₂-C(=O)- |
| 69 | CH₃ | CH₃ | 2-Thienyl | H/H | H/H | cyclobutyl-CH₂CH₂-C(=O)- |
| 70 | CH₃ | CH₃ | 2-Thienyl | H/H | H/H | oxetan-3-yl-CH₂- |
| 71 | CH₃ | CH₃ | Phenyl | H/H | H/H | H |
| 72 | CH₃ | CH₃ | Phenyl | H/H | H/H | CH₃CH₂CH₂-C(=O)- |
| 73 | CH₃ | CH₃ | Phenyl | H/H | H/H | Acetyl |
| 74 | CH₃ | CH₃ | Phenyl | H/H | H/H | n-Butyl |
| 75 | CH₃ | CH₃ | Phenyl | H/H | H/H | tetrahydrofuran-2-yl-CH₂-C(=O)- |
| 76 | CH₃ | CH₃ | Phenyl | H/H | H/H | 1-cyanocyclobutyl-CH₂-C(=O)- |
| 77 | CH₃ | CH₃ | Phenyl | H/H | H/H | 1-cyanocyclopropyl-CH₂-C(=O)- |
| 78 | CH₃ | CH₃ | Phenyl | H/H | H/H | oxetan-3-yl-CH₂-C(=O)- |
| 79 | CH₃ | CH₃ | Phenyl | H/H | H/H | (CH₃)₂CH-CH₂CH₂-C(=O)- |
| 80 | CH₃ | CH₃ | Phenyl | H/H | H/H | NC-C(CH₃)₂-C(=O)- |
| 81 | CH₃ | CH₃ | Phenyl | H/H | H/H | tetrahydropyran-4-yl-C(=O)- |

-continued
| Example | R₁ | R₂ | R₃ | X₂/X₂' | X₃/X₃' | R₄ |
|---|---|---|---|---|---|---|
| 82 | CH₃ | CH₃ | Phenyl | H/H | H/H | 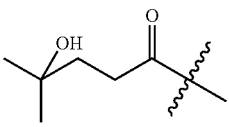 |
| 83 | CH₃ | CH₃ | Phenyl | H/H | H/H | 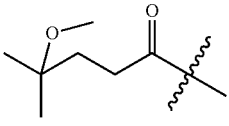 [SMILES: *C(=O)CCC(C)(C)OC] |
| 84 | CH₃ | CH₃ | Phenyl | H/H | H/H | 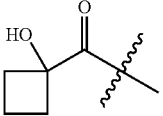 |
| 85 | CH₃ | CH₃ | Phenyl | H/H | H/H | 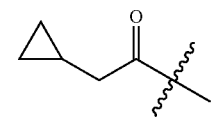 [SMILES: *C(=O)CC1CC1] |
| 86 | CH₃ | CH₃ | Phenyl | H/H | H/H | 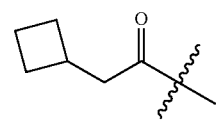 [SMILES: *C(=O)CC1CCC1] |
| 87 | CH₃ | CH₃ | Phenyl | H/H | H/H | 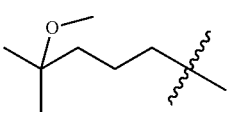 [SMILES: *CCCC(C)(C)OC] |
| 88 | CH₃ | CH₃ | 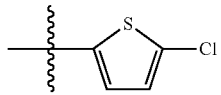 [SMILES: *c1ccc(Cl)s1] | H/H | H/H | 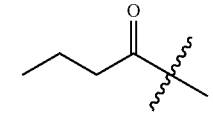 [SMILES: *C(=O)CCC] |
| 89 | CH₃ | CH₃ | 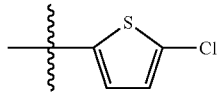 | H/H | H/H | n-Butyl |
| 90 | CH₃ | CH₃ | 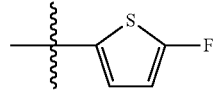 [SMILES: *c1ccc(F)s1] | H/H | H/H | 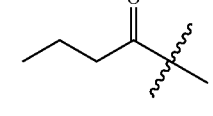 |
| 91 | CH₃ | CH₃ | 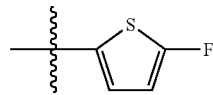 | H/H | H/H | n-Butyl |
| 92 | CH₃ | CH₃ | 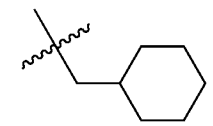 [SMILES: *CC1CCCCC1] | H/H | H/H | H |
| 93 | CH₃ | CH₃ | 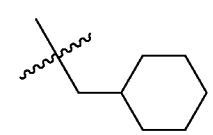 [SMILES: *CC1CCCCC1] | H/H | H/H | 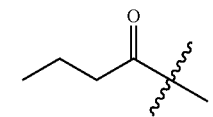 [SMILES: *C(=O)CCC] |

-continued
| Example | $R_1$ | $R_2$ | $R_3$ | $X_2/X_2'$ | $X_3/X_3'$ | $R_4$ |
|---|---|---|---|---|---|---|
| 94 | $CH_3$ | $CH_3$ | 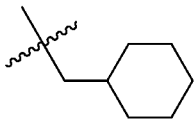 [SMILES: *CC1CCCCC1] | H/H | H/H | n-Butyl |
| 95 | $CH_3$ | $CH_3$ | 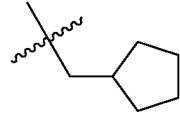 [SMILES: *CC1CCCC1] | H/H | H/H | 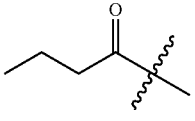 [SMILES: *C(=O)CCC] |
| 96 | $CH_3$ | $CH_3$ | 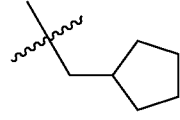 [SMILES: *CC1CCCC1] | H/H | H/H | n-Butyl |
| 97 | $CH_3$ | $CH_3$ | 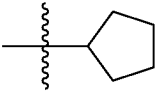 | H/H | H/H | 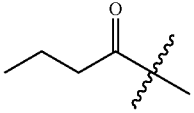 [SMILES: *C(=O)CCC] |
| 98 | $CH_3$ | $CH_3$ | 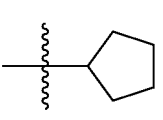 [SMILES: *C1CCCC1] | H/H | H/H | n-Butyl |
| 99 | $CH_3$ | $CH_3$ | 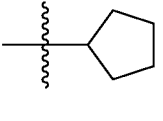 | H/H | H/H | 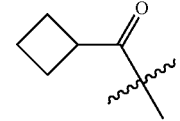 [SMILES: *C(=O)C1CCC1] |
| 100 | $CH_3$ | $CH_3$ | 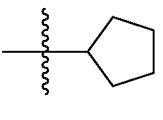 [SMILES: *C1CCCC1] | H/H | H/H | 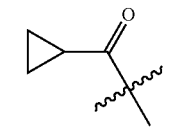 |
| 101 | $CH_3$ | $CH_3$ | 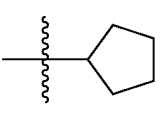 [SMILES: *C1CCCC1] | H/H | H/H | 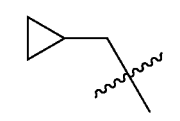 [SMILES: *CC1CC1] |
| 102 | $CH_3$ | $CH_3$ | 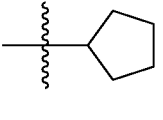 [SMILES: *C1CCCC1] | H/H | H/H | 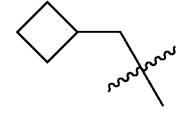 [SMILES: *CC1CCC1] |
| 103 | $CH_3$ | $CH_3$ | 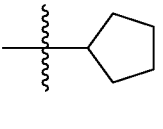 [SMILES: *C1CCCC1] | H/H | H/H | 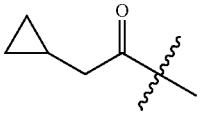 [SMILES: *C(=O)CC1CC1] |
| 104 | $CH_3$ | $CH_3$ | 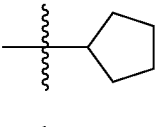 | H/H | H/H | 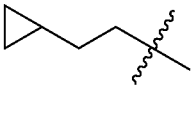 [SMILES: *CCC1CC1] |
| 105 | $CH_3$ | $CH_3$ | 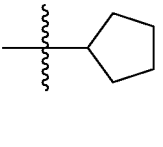 [SMILES: *C1CCCC1] | H/H | H/H | 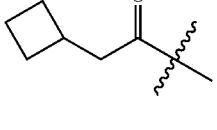 |

-continued

| Example | R₁ | R₂ | R₃ | X₂/X₂' | X₃/X₃' | R₄ |
|---|---|---|---|---|---|---|
| 106; 107 | CH₃ | CH₃ | benzoyl (C(=O)-Ph) | H/H | H/H | n-Butyl |
| 108; 109 | —CH₂CH₂CH₂— | | 2-Thienyl | H/H | H/H | 1-methyl-2-oxopentyl |
| 110; 111 | —CH₂CH₂CH₂— | | Phenyl | H/H | H/H | 1-methyl-2-oxopentyl |
| 112; 113 | —CH₂CH₂CH₂— | | Phenyl | H/H | H/H | n-Butyl |
| 114 | CH₃ | CH₃ | 2-Thienyl | H/H | =O | CH₃ |
| 115 | CH₃ | CH₃ | 2-Thienyl | H/H | =O | n-Butyl |
| 116 | CH₃ | CH₃ | 2-Thienyl | H/H | =O | cyclopentylmethyl |
| 117 | CH₃ | CH₃ | 5-chloro-2-thienyl | H/H | =O | H |
| 118; 119 | CH₃ | CH₃ | Benzyl | H/H | =O | CH₃ |
| 120; 121 | CH₃ | CH₃ | Benzyl | H/H | =O | n-Butyl |
| 122; 123 | CH₃ | CH₃ | Benzyl | H/H | =O | cyclopentylmethyl |
| 124 | CH₃ | CH₃ | 2-Thienyl | =O | H/H | CH₃ |
| 125 | CH₃ | CH₃ | 2-Thienyl | =O | H/H | n-Butyl |
| 126; 127 | CH₃ | CH₃ | 2-Thienyl | =O | H/H | cyclopentylmethyl |
| 128; 129 | CH₃ | CH₃ | 2-Thienyl | =O | H/H | 2-cyclobutylethyl |
| 130; 131 | CH₃ | CH₃ | 2-Thienyl | =O | H/H | 2-cyclopropylethyl |
| 132; 133 | CH₃ | CH₃ | 2-Thienyl | =O | H/H | cyclobutylmethyl |
| 134; 135 | CH₃ | CH₃ | 2-Thienyl | =O | H/H | cyclopropylmethyl |

-continued
| Example | R₁ | R₂ | R₃ | X₂/X₂' | X₃/X₃' | R₄ |
|---|---|---|---|---|---|---|
| 136; 137 | CH₃ | CH₃ | 2-Thienyl | =O | H/H | 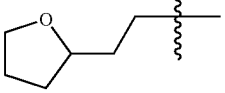 |
| 138; 139 | CH₃ | CH₃ | 2-Thienyl | =O | H/H | 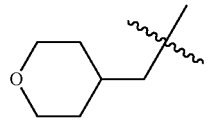 [SMILES: *CC1CCOCC1] |
| 140; 141 | CH₃ | CH₃ | 2-Thienyl | =O | H/H | 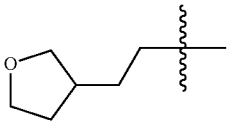 [SMILES: *CCC1CCOC1] |
| 142; 143 | CH₃ | CH₃ | 2-Thienyl | =O | H/H | 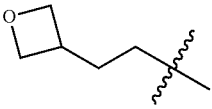 [SMILES: *CCC1COC1] |
| 144; 145 | CH₃ | CH₃ | 2-Thienyl | =O | H/H | 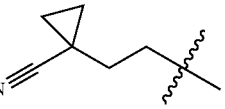 |
| 146; 147 | CH₃ | CH₃ | 2-Thienyl | =O | H/H | 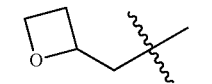 |
| 148; 149 | CH₃ | CH₃ | 2-Thienyl | =O | H/H |  |
| 150; 151 | CH₃ | CH₃ | 2-Thienyl | =O | H/H | 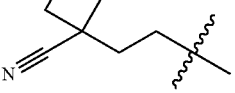 |
| 152; 153 | CH₃ | CH₃ | 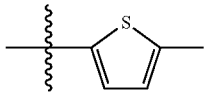 | =O | H/H | H |
| 154; 155 | CH₃ | CH₃ | 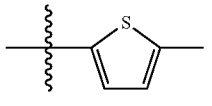 [SMILES: *c1ccc(C)s1] | =O | H/H | CH₃ |
| 156; 157 | CH₃ | CH₃ | 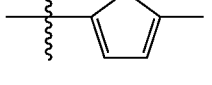 | =O | H/H | n-Butyl |
| 158; 159 | CH₃ | CH₃ | 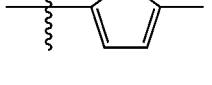 | =O | H/H | 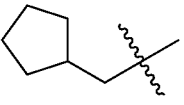 [SMILES: *CC1CCCC1] |
| 160 | CH₃ | CH₃ | 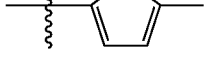 | =O | H/H |  |

-continued
| Example | R₁ | R₂ | R₃ | X₂/X₂' | X₃/X₃' | R₄ |
|---|---|---|---|---|---|---|
| 161 | CH₃ | CH₃ | 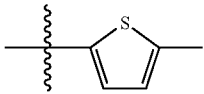 | =O | H/H | 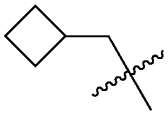 [SMILES: *CC1CCC1] |
| 162 | CH₃ | CH₃ | Phenyl | =O | H/H | CH₃ |
| 163; 164 | CH₃ | CH₃ | Phenyl | =O | H/H | n-Butyl |
| 165; 166 | CH₃ | CH₃ | Phenyl | =O | H/H | 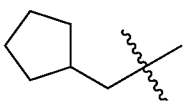 [SMILES: *CC1CCCC1] |
| 167; 168 | CH₃ | CH₃ | Phenyl | =O | H/H | 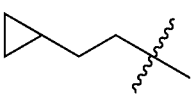 [SMILES: *CCC1CC1] |
| 169; 170 | CH₃ | CH₃ | Phenyl | =O | H/H | 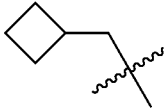 [SMILES: *CC1CCC1] |
| 171; 172 | CH₃ | CH₃ | Phenyl | =O | H/H |  |
| 173; 174 | CH₃ | CH₃ | Phenyl | =O | H/H | 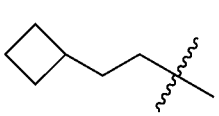 [SMILES: *CCC1CCC1] |
| 175; 176 | CH₃ | CH₃ | Phenyl | =O | H/H | 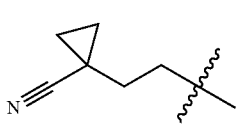 [SMILES: *CCC1(C#N)CC1] |
| 177; 178 | CH₃ | CH₃ | Phenyl | =O | H/H | 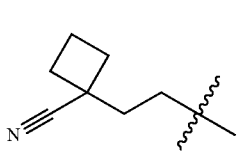 [SMILES: *CCC1(C#N)CCC1] |
| 179; 180 | CH₃ | CH₃ | Phenyl | =O | H/H | 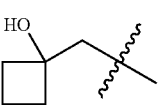 |
| 181 | CH₃ | CH₃ | Phenyl | =O | H/H | 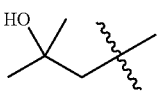 |
| 182; 183 | CH₃ | CH₃ | Phenyl | =O | H/H | 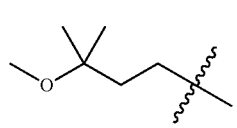 [SMILES: *CCC(C)(C)OC] |
| 184; 185 | CH₃ | CH₃ | Phenyl | =O | H/H | 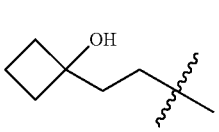 [SMILES: *CCC1(O)CCC1] |

-continued

| Example | R₁ | R₂ | R₃ | X₂/X₂' | X₃/X₃' | R₄ |
|---|---|---|---|---|---|---|
| 186; 187 | CH₃ | CH₃ | Phenyl | =O | H/H | (2-hydroxy-2-methylpropyl with gem-dimethyl attachment) |
| 188 | CH₃ | CH₃ | Phenyl | H/H | H/H | (tetrahydrofuran-3-yl methyl ketone) |
| 189 | CH₃ | CH₃ | Phenyl | H/H | H/H | (oxetan-3-yl ketone) |
| 190 | CH₃ | CH₃ | Phenyl | H/H | H/H | (methoxy-dimethyl ketone) |
| 191 | CH₃ | CH₃ | Phenyl | H/H | H/H | (cyclopropylethyl with gem-dimethyl) |
| 192 | CH₃ | CH₃ | Phenyl | H/H | H/H | (cyclobutylethyl with gem-dimethyl) |
| 193 | CH₃ | CH₃ | Phenyl | H/H | H/H | (1-hydroxycyclobutylmethyl with gem-dimethyl) |
| 194 | CH₃ | CH₃ | Phenyl | H/H | H/H | (1-cyanocyclobutylethyl) |
| 195 | CH₃ | CH₃ | Phenyl | H/H | H/H | (cyclobutylpropyl ketone) |
| 196 | CH₃ | CH₃ | Phenyl | H/H | H/H | (oxetan-3-ylmethyl) |
| 197 | CH₃ | CH₃ | Phenyl | H/H | H/H | (cyclopropylethyl ketone) |
| 198 | CH₃ | CH₃ | Phenyl | H/H | H/H | (1-cyanocyclopropyl ketone) |

-continued
| Example | R$_1$ | R$_2$ | R$_3$ | X$_2$/X$_2$' | X$_3$/X$_3$' | R$_4$ |
|---|---|---|---|---|---|---|
| 199 | CH$_3$ | CH$_3$ | Phenyl | H/H | H/H | 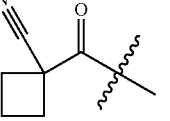 |
| 200 | CH$_3$ | CH$_3$ | Phenyl | H/H | H/H | 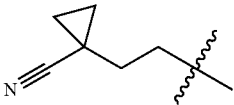 [SMILES: *CCC1(C#N)CC1] |
| 201 | CH$_3$ | CH$_3$ | Phenyl | H/H | H/H | 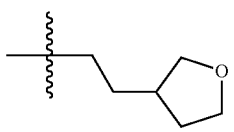 [SMILES: *CCC1CCOC1] |
| 202 | CH$_3$ | CH$_3$ | Phenyl | H/H | H/H | 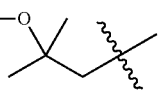 |
| 203 | CH$_3$ | CH$_3$ | Phenyl | H/H | H/H | 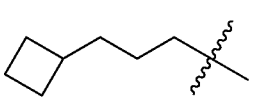 [SMILES: *CCCC1CCC1] |
| 204 | CH$_3$ | CH$_3$ | Phenyl | H/H | H/H | 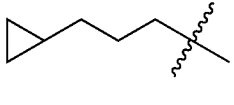 [SMILES: *CCCC1CC1] |
| 205 | CH$_3$ | CH$_3$ | Phenyl | H/H | H/H | 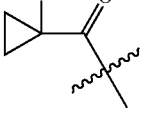 |
| 206 | CH$_3$ | CH$_3$ | Phenyl | H/H | H/H | 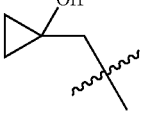 |
| 207 | CH$_3$ | CH$_3$ | 2-Thienyl | H/H | H/H |  |
| 208 | CH$_3$ | CH$_3$ | 2-Thienyl | H/H | H/H | 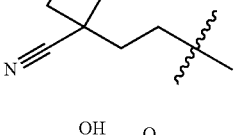 |
| 209 | CH$_3$ | CH$_3$ | 2-Thienyl | H/H | H/H | 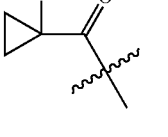 |
| 210 | CH$_3$ | CH$_3$ | 2-Thienyl | H/H | H/H |  |

-continued
| Example | R₁ | R₂ | R₃ | X₂/X₂' | X₃/X₃' | R₄ |
|---|---|---|---|---|---|---|
| 211 | CH₃ | CH₃ | 2-Thienyl | H/H | H/H | 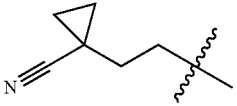 |
| 212 | CH₃ | CH₃ | 2-Thienyl | H/H | H/H | 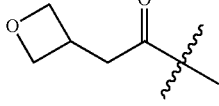 |
| 213 | CH₃ | CH₃ | 2-Thienyl | H/H | H/H | 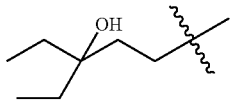 [SMILES: *CCC(O)(CC)CC] |
| 214 | CH₃ | CH₃ | 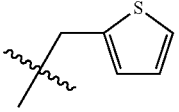 [SMILES: *Cc1cccs1] | H/H | H/H | 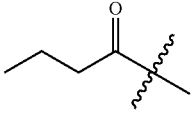 [SMILES: *C(=O)CCC] |
| 215; 216 | CH₃ | CH₃ | 2-Thienyl | =O | H/H | 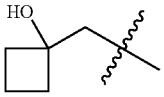 [SMILES: *CC1(O)CCC1] |
| 217; 218 | CH₃ | CH₃ | 2-Thienyl | =O | H/H | 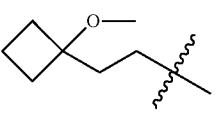 [SMILES: *CCC1(OC)CCC1] |
| 219; 220 | CH₃ | CH₃ | 2-Thienyl | =O | H/H | 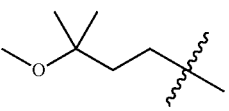 [SMILES: *CCC(C)(C)OC] |
| 221; 222 | CH₃ | CH₃ | 2-Thienyl | =O | H/H | 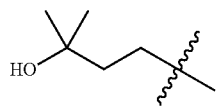 [SMILES: *CCC(C)(C)O] |
| 223 | CH₃ | CH₃ | 2-Thienyl | H/H | H/H | 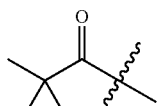 |
| 224; 225 | CH₃ | CH₃ | 2-Thienyl | =O | H/H | 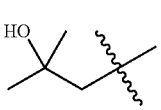 |
| 226 | CH₃ | CH₃ | 2-Thienyl | H/H | H/H | 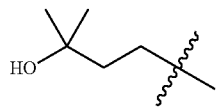 [SMILES: *CCC(C)(C)O] |
| 227 | CH₃ | CH₃ | 2-Thienyl | H/H | H/H | 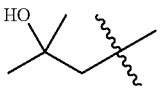 |
| 228 | CH₃ | CH₃ | Phenyl | H/H | H/H | 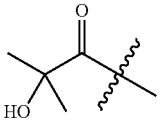 |

-continued
| Example | R₁ | R₂ | R₃ | X₂/X₂' | X₃/X₃' | R₄ |
|---|---|---|---|---|---|---|
| 229 | CH₃ | CH₃ | Phenyl | H/H | H/H |  |
| 230; 231 | CH₃ | CH₃ | Phenyl | =O | H/H | 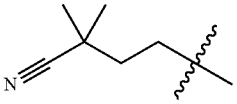 |
| 232 | CH₃ | CH₃ | Phenyl | H/H | H/H | 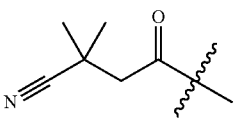 [SMILES: *C(=O)CC(C)(C)C#N] |
| 233 | CH₃ | CH₃ | 2-Thienyl | H/H | H/H | 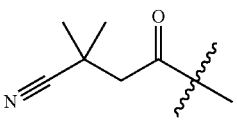 [SMILES: *C(=O)CC(C)(C)C#N] |
| 234 | CH₃ | CH₃ | 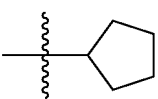 | =O | H/H | 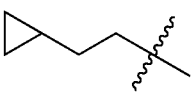 [SMILES: *CCC1CC1] |
| 235 | CH₃ | CH₃ | 2-Thienyl | H/H | H/H | 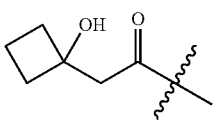 [SMILES: *C(=O)CC1(O)CCC1] |
| 236 | CH₃ | CH₃ | 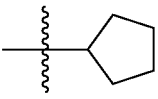 [SMILES: *C1CCCC1] | =O | H/H | 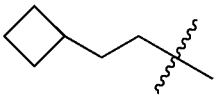 [SMILES: *CCC1CCC1] |
| 237 | CH₃ | CH₃ | Phenyl | H/H | H/H | 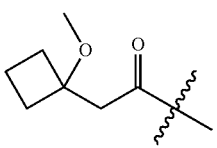 [SMILES: *C(=O)CC1(OC)CCC1] |
| 238 | CH₃ | CH₃ | 2-Thienyl | H/H | H/H | 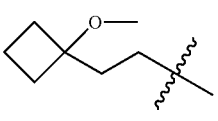 [SMILES: *CCC1(OC)CCC1] |
| 239 | CH₃ | CH₃ | 2-Thienyl | H/H | H/H | 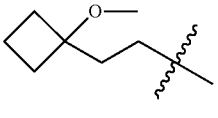 [SMILES: *CCC1(OC)CCC1] |
| 240 | CH₃ | CH₃ | 2-Thienyl | =O | H/H | 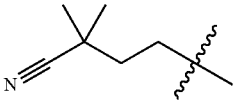 [SMILES: *CCC(C)(C)C#N] |
| 241; 242 | CH₃ | CH₃ | 2-Thienyl | =O | H/H | 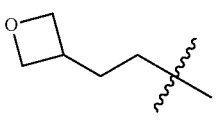 [SMILES: *CCC1COC1] |
| 243 | CH₃ | CH₃ | 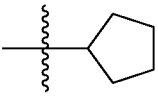 [SMILES: *C1CCCC1] | =O | H/H | 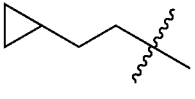 [SMILES: *CCC1CC1] |

-continued

| Example | R₁ | R₂ | R₃ | X₂/X₂' | X₃/X₃' | R₄ |
|---|---|---|---|---|---|---|
| 244 | CH₃ | CH₃ | cyclopentyl | =O | H/H | oxetan-3-ylmethyl |
| 245 | CH₃ | CH₃ | cyclopentyl | =O | H/H | 1-cyanocyclopropyl-ethyl |
| 246 | CH₃ | CH₃ | cyclopentyl | =O | H/H | 2-(oxetan-3-yl)ethyl |
| 247 | CH₃ | CH₃ | cyclopentyl | H/H | H/H | 1-methoxycyclobutyl-acetyl |
| 248 | CH₃ | CH₃ | 2-Thienyl | H/H | H/H | 2-cyano-2-methylpropyl |
| 249 | CH₃ | CH₃ | Phenyl | H/H | H/H | 2-cyano-2-methylpropyl |
| 250 | CH₃ | CH₃ | 2-Thienyl | =O | H/H | 2-cyano-2-methylpropyl |
| 251; 252 | CH₃ | CH₃ | Phenyl | =O | H/H | oxetan-3-ylmethyl |
| 253 | CH₃ | CH₃ | 2-Thienyl | H/H | H/H | (1-hydroxycyclopropyl)methyl |
| 254; 255 | CH₃ | CH₃ | Phenyl | =O | H/H | 2-(oxetan-3-yl)ethyl |
| 256 | CH₃ | CH₃ | cyclopentyl | =O | H/H | (1-cyanocyclobutyl)methyl |
| 257 | CH₃ | CH₃ | cyclopentyl | H/H | H/H | (1-methoxycyclobutyl)methyl |

-continued

| Example | R₁ | R₂ | R₃ | X₂/X₂' | X₃/X₃' | R₄ |
|---|---|---|---|---|---|---|
| 258 | CH₃ | CH₃ | cyclopentyl | H/H | H/H | 2-cyano-2-methylpropyl-like (NC-C(CH₃)₂-CH₂-) |
| 259 | CH₃ | CH₃ | cyclopentyl | H/H | H/H | NC-C(CH₃)₂-C(=O)-CH₂- |
| 260; 261 | CH₃ | CH₃ | Phenyl | =O | H/H | (tetrahydrofuran-3-yl)methyl with gem-dimethyl |
| 262; 263 | CH₃ | CH₃ | Phenyl | =O | H/H | 2-(tetrahydrofuran-2-yl)ethyl with gem-dimethyl |
| 264 | CH₃ | CH₃ | Phenyl | =O | H/H | 2-(tetrahydrofuran-3-yl)ethyl with gem-dimethyl |
| 265 | CH₃ | CH₃ | cyclopentyl | H/H | H/H | (tetrahydropyran-4-yl)methyl with gem-dimethyl |
| 266 | CH₃ | CH₃ | cyclopentyl | H/H | H/H | 4-methylpentyl with gem-dimethyl (isobutyl-C(CH₃)₂-) |
| 267 | CH₃ | CH₃ | cyclopentyl | H/H | H/H | 1-cyanocyclopropyl-CH₂-CH₂- |
| 268 | CH₃ | CH₃ | cyclopentyl | H/H | H/H | 1-cyanocyclobutyl-CH₂-CH₂- |
| 269; 270 | CH₃ | CH₃ | Phenyl | =O | H/H | (tetrahydropyran-4-yl)methyl with gem-dimethyl |
| 271 | CH₃ | CH₃ | Phenyl | =O | H/H | 2-(tetrahydrofuran-3-yl)ethyl with gem-dimethyl |
| 272 | CH₃ | CH₃ | Phenyl | H/H | H/H | HO-C(CH₃)₂-CH₂-CH₂-C(CH₃)₂- |

-continued

| Example | R₁ | R₂ | R₃ | X₂/X₂' | X₃/X₃' | R₄ |
|---|---|---|---|---|---|---|
| 273 | CH₃ | CH₃ | cyclopentyl | H/H | H/H | isobutyl |
| 274 | CH₃ | CH₃ | cyclopentyl | =O | H/H | cyclobutylmethyl |
| 275 | CH₃ | H | Phenyl | =O | H/H | cyclopropylethyl |
| 276 | CH₃ | CH₃ | cyclopentyl | =O | H/H | cyclopropylmethyl |
| 277 | CH₃ | CH₃ | cyclopentyl | =O | H/H | cyclohexylmethyl |
| 278 | CH₃ | CH₃ | cyclopentyl | =O | H/H | cyclopentylmethyl |
| 279; 280 | CH₃ | CH₃ | 2-Thienyl | =O | H/H | (tetrahydrofuran-3-yl)methyl |
| 281 | CH₃ | CH₃ | cyclopentyl | =O | H/H | n-Butyl |
| 282 | CH₃ | CH₃ | cyclopentyl | =O | H/H | CH₃ |
| 283 | CH₃ | CH₃ | Phenyl | H/H | H/H | (oxetan-3-yl)ethyl |
| 284 | CH₃ | CH₃ | Phenyl | H/H | H/H | (tetrahydrofuran-3-yl)ethyl |
| 285 | CH₃ | CH₃ | Phenyl | H/H | H/H | (1-hydroxycyclopropyl)ethyl |
| 286 | CH₃ | CH₃ | cyclopentyl | =O | H/H | cyclopentylmethyl |

-continued

| Example | R₁ | R₂ | R₃ | X₂/X₂' | X₃/X₃' | R₄ |
|---|---|---|---|---|---|---|
| 287 | CH₃ | CH₃ | cyclopentyl | =O | H/H | 1-methoxycyclobutyl-ethyl |
| 288; 289 | CH₃ | CH₃ | 2-Thienyl | =O | H/H | 2-cyano-2-methylpropyl |
| 290 | CH₃ | H | 2-Thienyl | =O | H/H | 2-cyclopropylethyl |
| 291 | CH₃ | CH₃ | cyclopentyl | H/H | H/H | oxetan-3-yl ketone |
| 292 | CH₃ | CH₃ | cyclopentyl | H/H | H/H | 2-methoxy-2-methylpropyl |
| 293; 294 | CH₃ | CH₃ | cyclopentyl | =O | H/H | tetrahydrofuran-3-yl-methyl |
| 295 | CH₃ | CH₃ | 2-Thienyl | H/H | H/H | oxetan-3-yl-ethyl |
| 296 | CH₃ | CH₃ | 2-Thienyl | H/H | H/H | tetrahydrofuran-2-yl-methyl |
| 297 | CH₃ | CH₃ | cyclopentyl | H/H | H/H | 2-methoxy-2-methylpropanoyl |
| 298 | CH₃ | CH₃ | cyclopentyl | H/H | H/H | 2-methoxy-2-methylpropyl |
| 299 | CH₃ | CH₃ | 2-Thienyl | H/H | H/H | 4-methoxy-4-methylpentyl |
| 300 | CH₃ | CH₃ | Phenyl | H/H | H/H | 4-methoxy-4-methylpentyl |
| 301 | CH₃ | CH₃ | cyclopentyl | H/H | H/H | 4-hydroxy-3-methylbutyl |

-continued

| Example | $R_1$ | $R_2$ | $R_3$ | $X_2/X_2'$ | $X_3/X_3'$ | $R_4$ |
|---|---|---|---|---|---|---|
| 302 | $CH_3$ | $CH_3$ | cyclopentyl | H/H | H/H | oxetan-3-ylmethyl |
| 303 | $CH_3$ | $CH_3$ | Phenyl | H/H | H/H | (tetrahydro-2H-pyran-4-yl)methyl |
| 304 | $CH_3$ | $CH_3$ | 2-Thienyl | H/H | H/H | (tetrahydro-2H-pyran-4-yl)methyl |
| 305 | $CH_3$ | $CH_3$ | Phenyl | H/H | H/H | 2-(tetrahydrofuran-2-yl)ethyl |
| 306 | $CH_3$ | $CH_3$ | 2-Thienyl | H/H | H/H | 2-(tetrahydrofuran-2-yl)ethyl |
| 307; 308 | $CH_3$ | H | 2-Thienyl | =O | H/H | 2-cyclobutylethyl |
| 309 | $CH_3$ | $CH_3$ | 2-Thienyl | H/H | H/H | 2-(tetrahydrofuran-3-yl)ethyl |
| 310 | $CH_3$ | $CH_3$ | Phenyl | =O | H/H | 2-cyano-2-methylpropyl |
| 311 | $CH_3$ | $CH_3$ | 2-Thienyl | =O | H/H | (1-methoxycyclobutyl)methyl |
| 312 | $CH_3$ | $CH_3$ | Phenyl | =O | H/H | (1-methoxycyclobutyl)methyl |
| 313 | $CH_3$ | $CH_3$ | 2-Thienyl | =O | H/H | 2-ethoxyethyl |
| 314 | $CH_3$ | $CH_3$ | 2-Thienyl | H/H | H/H | 4-methoxy-4-methyl-3-oxopentyl (methoxy-dimethyl ketone linker) |
| 315 | $CH_3$ | $CH_3$ | 2-Thienyl | H/H | H/H | 4-methoxy-2-oxobutyl |

-continued
| Example | R₁ | R₂ | R₃ | X₂/X₂' | X₃/X₃' | R₄ |
|---|---|---|---|---|---|---|
| 316 | CH₃ | H | 2-Thienyl | =O | H/H | 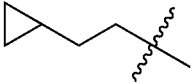 [SMILES: *CCC1CC1] |
| 317 | CH₃ | CH₃ | 2-Thienyl | =O | H/H | 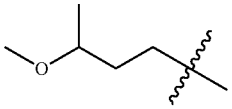 [SMILES: *CCC(C)OC] |
| 318 | CH₃ | CH₃ | 2-Thienyl | =O | H/H | 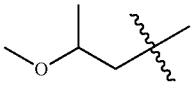 [SMILES: *CC(C)OC] |
| 319 | CH₃ | CH₃ | Phenyl | =O | H/H | 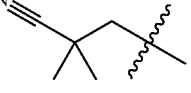 |
| 320 | CH₃ | CH₃ | Phenyl | H/H | H/H | 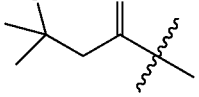 |
| 321 | CH₃ | CH₃ | 2-Thienyl | =O | H/H | 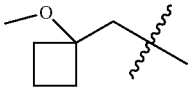 [SMILES: *CC1(OC)CCC1] |
| 322 | CH₃ | CH₃ | Phenyl | =O | H/H | 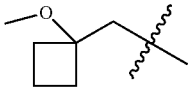 |
| 323 | CH₃ | CH₃ | Phenyl | =O | H/H | 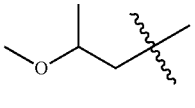 [SMILES: *CC(C)OC] |
| 324 | CH₃ | CH₃ | Phenyl | =O | H/H | 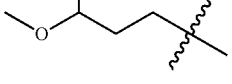 |
| 325 | CH₃ | CH₃ | Phenyl | =O | H/H | 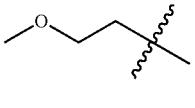 [SMILES: *CCOC] |
| 326 | CH₃ | CH₃ | Phenyl | =O | H/H | 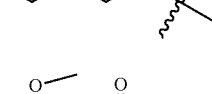 |
| 327 | CH₃ | CH₃ | 2-Thienyl | H/H | H/H | 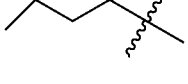 |
| 328 | CH₃ | CH₃ | Phenyl | H/H | H/H | 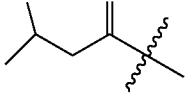 |

-continued
| Example | R₁ | R₂ | R₃ | X₂/X₂' | X₃/X₃' | R₄ |
|---|---|---|---|---|---|---|
| 329 | CH₃ | CH₃ | Phenyl | H/H | H/H | 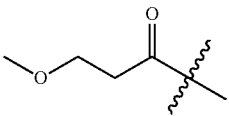 [SMILES: *C(=O)CCOC] |
| 330 | CH₃ | H | Phenyl | =O | H/H | 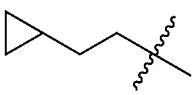 [SMILES: *CCC1CC1] |
| 331 | CH₃ | H | Phenyl | =O | H/H | 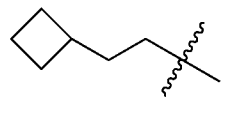 [SMILES: *CCC1CCC1] |
| 332 | CH₃ | CH₃ | 2-Thienyl | =O | H/H | 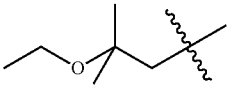 |
| 333 | CH₃ | CH₃ | 2-Thienyl | H/H | H/H | 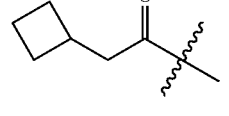 |
| 334 | CH₃ | CH₃ | 2-Thienyl | =O | H/H | 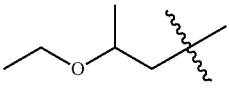 |
| 335 | CH₃ | CH₃ | Phenyl | =O | H/H | 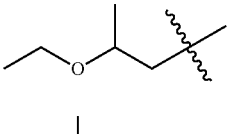 |
| 336 | CH₃ | CH₃ | 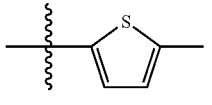 | =O | H/H | 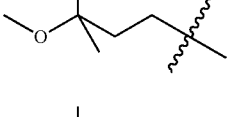 |
| 337 | CH₃ | CH₃ | 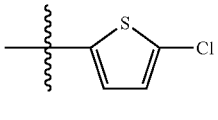 [SMILES: *c1ccc(Cl)s1] | =O | H/H | 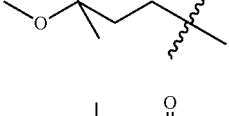 |
| 338 | CH₃ | CH₃ | Phenyl | H/H | H/H | 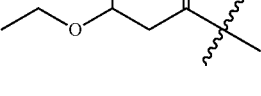 |
| 339 | CH₃ | CH₃ | 2-Thienyl | H/H | H/H | 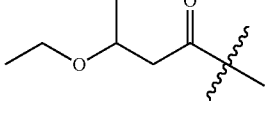 |
| 340 | CH₃ | CH₃ | Phenyl | =O | H/H |  |
| 341 | CH₃ | H | 2-Thienyl | =O | H/H | 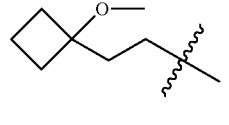 [SMILES: *CCC1(OC)CCC1] |

-continued
| Example | R₁ | R₂ | R₃ | X₂/X₂' | X₃/X₃' | R₄ |
|---|---|---|---|---|---|---|
| 342 | CH₃ | CH₃ | Phenyl | H/H | H/H | 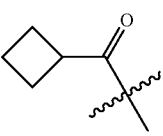 [SMILES: *C(=O)C1CCC1] |
| 343 | CH₃ | CH₃ | Phenyl | H/H | H/H | 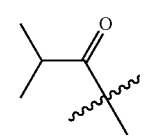 [SMILES: *C(=O)C(C)C] |
| 344 | CH₃ | CH₃ | 2-Thienyl | =O | H/H |  |
| 345 | CH₃ | CH₃ | Phenyl | H/H | H/H | 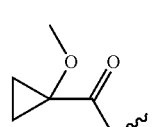 |
| 346 | CH₃ | H | 2-Thienyl | H/H | H/H | 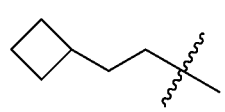 [SMILES: *CCC1CCC1] |
| 347 | CH₃ | CH₃ | 2-Thienyl | =O | H/H | 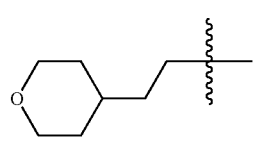 |
| 348 | CH₃ | CH₃ | Phenyl | =O | H/H | 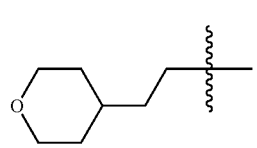 |
| 349 | CH₃ | CH₃ | Phenyl | =O | H/H |  |
| 350 | CH₃ | CH₃ | Phenyl | H/H | H/H | 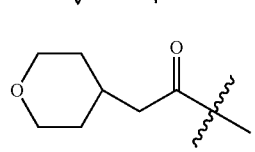 |
| 351 | CH₃ | CH₃ | 2-Thienyl | H/H | H/H | 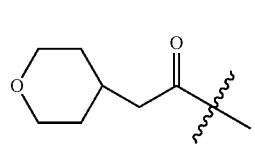 [SMILES: *C(=O)CC1CCOCC1] |
| 352 | CH₃ | CH₃ | Phenyl | H/H | H/H | 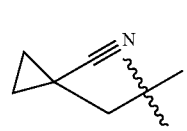 [SMILES: *CCC1(C#N)CC1] |

-continued
| Example | R₁ | R₂ | R₃ | X₂/X₂' | X₃/X₃' | R₄ |
|---|---|---|---|---|---|---|
| 353 | CH₃ | CH₃ | 2-Thienyl | =O | H/H | 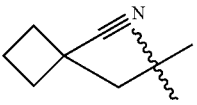 [SMILES: *CCC1(C#N)CCC1] |
| 354 | CH₃ | CH₃ | Phenyl | H/H | H/H | 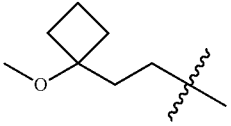 |
| 355 | CH₃ | CH₃ | 2-Thienyl | H/H | H/H | 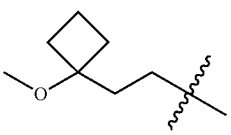 [SMILES: *CCC1(OC)CCC1] |
| 356 | CH₃ | CH₃ | 2-Thienyl | H/H | H/H | 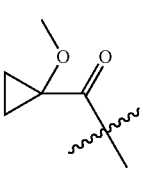 [SMILES: *C(=O)C1(OC)CC1] |
| 357 | CH₃ | CH₃ | Phenyl | =O | H/H | 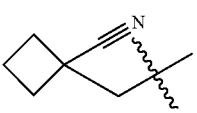 |
| 358 | CH₃ | CH₃ | 2-Thienyl | H/H | H/H | 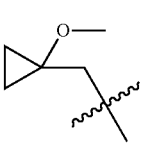 |
| 359 | CH₃ | CH₃ | Phenyl | H/H | H/H | 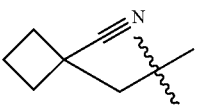 [SMILES: *CCC1(C#N)CCC1] |
| 360 | CH₃ | CH₃ | 2-Thienyl | H/H | H/H | 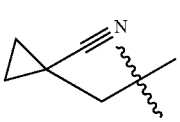 [SMILES: *CC1(C#N)CC1] |
| 361 | CH₃ | CH₃ | 2-Thienyl | H/H | H/H | 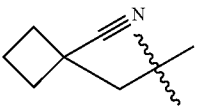 [SMILES: *CC1(C#N)CCC1] |
| 362 | CH₃ | CH₃ | Phenyl | H/H | H/H | 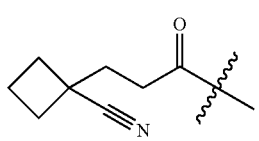 [SMILES: *C(=O)CCC1(C#N)CCC1] |
| 363 | CH₃ | CH₃ | 2-Thienyl | H/H | H/H | 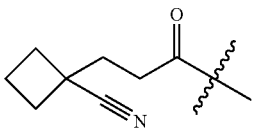 [SMILES: *C(=O)CCC1(C#N)CCC1] |

-continued
| Example | R₁ | R₂ | R₃ | X₂/X₂' | X₃/X₃' | R₄ |
|---|---|---|---|---|---|---|
| 364 | CH₃ | CH₃ | n-Butyl | H/H | H/H | 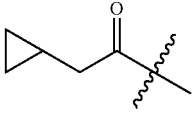 [SMILES: *C(=O)CC1CC1] |
| 365 | CH₃ | CH₃ | Phenyl | H/H | H/H | 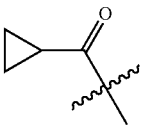 [SMILES: *C(=O)C1CC1] |
| 366 | CH₃ | CH₃ | Phenyl | H/H | H/H | 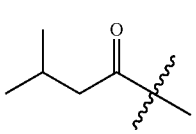 [SMILES: *C(=O)CC(C)C] |
| 367 | CH₃ | CH₃ | n-Butyl | H/H | H/H | 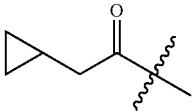 [SMILES: *C(=O)CC1CC1] |
| 368 | CH₃ | CH₃ | n-Butyl | H/H | H/H | 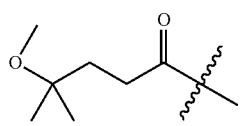 [SMILES: *C(=O)CCC(C)(C)OC] |
| 369 | CH₃ | CH₃ | Phenyl | H/H | H/H | 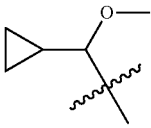 [SMILES: *C(OC)C1CC1] |
| 370 | CH₃ | CH₃ | 2-Thienyl | =O | H/H | 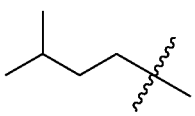 [SMILES: *CCC(C)C] |
| 371 | CH₃ | CH₃ | Phenyl | H/H | H/H | 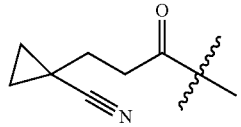 [SMILES: *C(=O)CCC1(C#N)CC1] |
| 372 | CH₃ | CH₃ | 2-Thienyl | H/H | H/H | 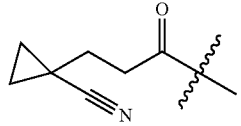 [SMILES: *C(=O)CCC1(C#N)CC1] |
| 373 | CH₃ | CH₃ | 2-Thienyl | H/H | H/H | 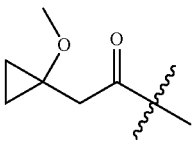 [SMILES: *C(=O)CC1(OC)CC1] |
| 374 | CH₃ | CH₃ | Phenyl | H/H | H/H | 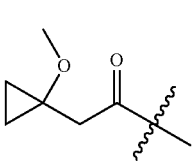 [SMILES: *C(=O)CC1(OC)CC1] |

-continued
| Example | R₁ | R₂ | R₃ | X₂/X₂' | X₃/X₃' | R₄ |
|---|---|---|---|---|---|---|
| 375 | CH₃ | CH₃ | n-Butyl | H/H | H/H | 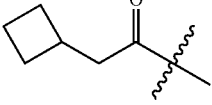 |
| 376 | CH₃ | CH₃ | Phenyl | =O | H/H | 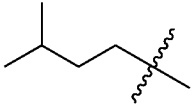 [SMILES: *CCC(C)C] |
| 377 | CH₃ | CH₃ | 2-Thienyl | =O | H/H | 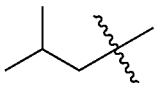 [SMILES: *CC(C)C] |
| 378 | CH₃ | CH₃ | Phenyl | =O | H/H | 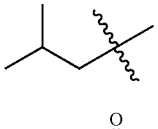 |
| 379 | CH₃ | CH₃ | Phenyl | H/H | H/H | 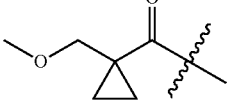 |
| 380 | CH₃ | CH₃ | Phenyl | H/H | H/H | 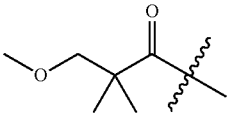 [SMILES: *C(=O)C(C)(C)COC] |
| 381 | CH₃ | CH₃ | Phenyl | H/H | H/H | 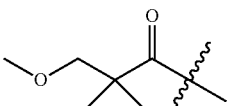 |
| 382 | CH₃ | CH₃ | 2-Thienyl | H/H | H/H | 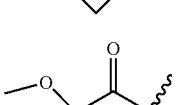 |
| 383 | CH₃ | CH₃ | 2-Thienyl | H/H | H/H | 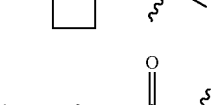 |
| 384 | CH₃ | CH₃ | 2-Thienyl | H/H | H/H | 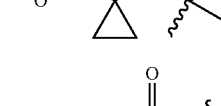 |
| 385 | CH₃ | CH₃ | 2-Thienyl | H/H | H/H | 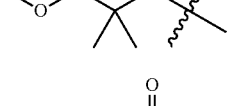 |
| 386 | CH₃ | CH₃ | 2-Thienyl | =O | H/H | 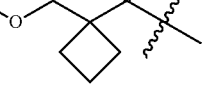 |

-continued
| Example | R₁ | R₂ | R₃ | X₂/X₂' | X₃/X₃' | R₄ |
|---|---|---|---|---|---|---|
| 387 | CH₃ | CH₃ | Phenyl | =O | H/H | 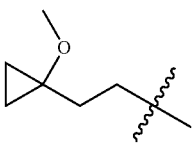 [SMILES: *CCC1(OC)CC1] |
| 388 | CH₃ | CH₃ | n-Butyl | H/H | H/H | 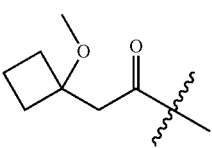 [SMILES: *C(=O)CC1(OC)CCC1] |
| 389 | CH₃ | CH₃ | n-Butyl | H/H | H/H | 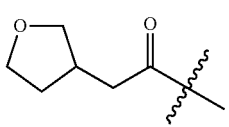 [SMILES: *C(=O)CC1CCOC1] |
| 390 | CH₃ | CH₃ | Phenyl | H/H | H/H | 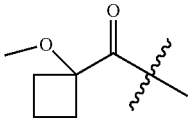 [SMILES: *C(=O)C1(OC)CCC1] |
| 391 | CH₃ | CH₃ | 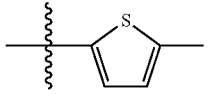 | H/H | H/H | 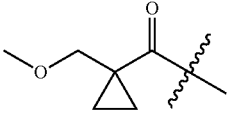 [SMILES: *C(=O)C1(COC)CC1] |
| 392 | CH₃ | CH₃ | 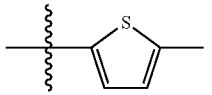 | H/H | H/H | 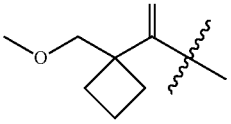 |
| 393 | CH₃ | CH₃ | 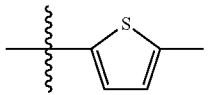 | H/H | H/H | 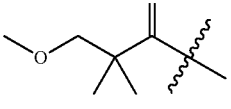 |
| 394 | CH₃ | CH₃ | Phenyl | H/H | H/H | 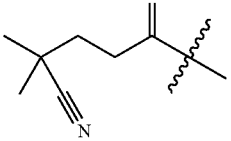 |
| 395 | CH₃ | CH₃ | 2-Thienyl | H/H | H/H | 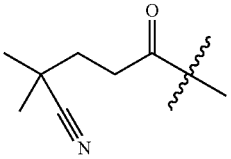 [SMILES: *C(=O)CCC(C)(C)C#N] |
| 396 | CH₃ | CH₃ | 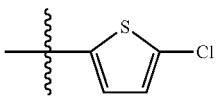 | H/H | H/H | 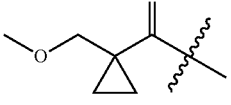 |

-continued

| Example | R₁ | R₂ | R₃ | X₂/X₂' | X₃/X₃' | R₄ |
|---|---|---|---|---|---|---|
| 397 | CH₃ | CH₃ | 2-chloro-5-thienyl | H/H | H/H | methoxymethyl-cyclobutyl ketone |
| 398 | CH₃ | CH₃ | 2-chloro-5-thienyl | H/H | H/H | methoxy-dimethyl ketone |
| 399; 400 | CH₃ | CH₃ | n-Butyl | =O | H/H | tetrahydrofuran-ethyl |
| 401; 402 | CH₃ | CH₃ | n-Butyl | =O | H/H | 1-cyanocyclopropyl-ethyl |
| 403; 404 | CH₃ | CH₃ | n-Butyl | =O | H/H | 1-cyanocyclobutyl-ethyl |
| 405 | CH₃ | CH₃ | Phenyl | H/H | H/H | 1-methoxycyclopropyl-propanone |
| 406 | CH₃ | CH₃ | n-Butyl | =O | H/H | 1-methoxycyclobutyl-propanone |
| 407 | CH₃ | CH₃ | 2-fluoro-5-thienyl | H/H | H/H | methoxymethyl-cyclobutyl ketone |
| 408 | CH₃ | CH₃ | Phenyl | H/H | H/H | cyclopropyl-methyl ketone |
| 409; 410 | CH₃ | CH₃ | n-Butyl | =O | H/H | oxetanyl-ethyl |
| 411 | CH₃ | CH₃ | 2-fluoro-5-thienyl | H/H | H/H | methoxymethyl-cyclopropyl ketone |

-continued
| Example | R₁ | R₂ | R₃ | X₂/X₂' | X₃/X₃' | R₄ |
|---|---|---|---|---|---|---|
| 412 | CH₃ | CH₃ | 2-Thienyl | H/H | H/H | 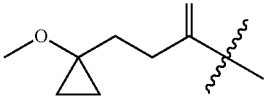 |
| 413 | CH₃ | CH₃ | n-Butyl | =O | H/H | 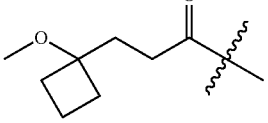 |
| 414 | CH₃ | CH₃ | Phenyl | H/H | H/H | 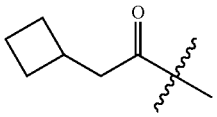 |
| 415 | CH₃ | CH₃ | 2-Thienyl | H/H | H/H | 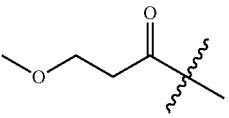 [SMILES: *C(=O)CCOC] |
| 416 | CH₃ | CH₃ | 2-Thienyl | H/H | H/H | 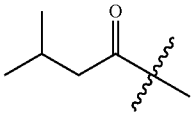 |
| 417 | CH₃ | CH₃ | 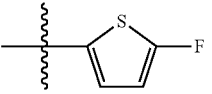 [SMILES: *c1ccc(F)s1] | =O | H/H | 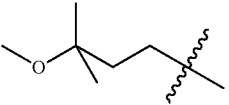 [SMILES: *CCC(C)(C)OC] |
| 418 | CH₃ | CH₃ | 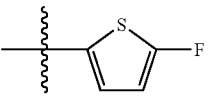 | H/H | H/H | 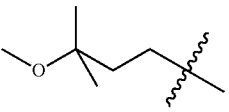 [SMILES: *CCC(C)(C)OC] |
| 419 | CH₃ | H | 2-Thienyl | H/H | H/H | 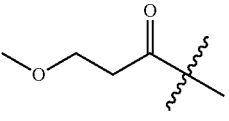 [SMILES: *C(=O)CCOC] |
| 420 | CH₃ | H | Phenyl | H/H | H/H | 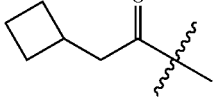 |
| 421 | CH₃ | CH₃ | 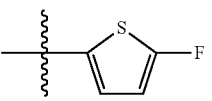 [SMILES: *c1ccc(F)s1] | =O | H/H | 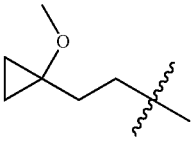 |
| 422 | CH₃ | H | Phenyl | H/H | H/H | 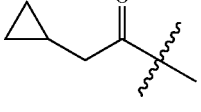 |
| 423 | CH₃ | H | 2-Thienyl | H/H | H/H | 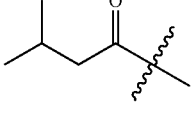 |

-continued

| Example | $R_1$ | $R_2$ | $R_3$ | $X_2/X_2'$ | $X_3/X_3'$ | $R_4$ |
|---|---|---|---|---|---|---|
| 424 | $CH_3$ | $CH_3$ | 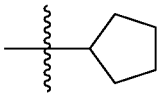 | H/H | H/H | H |
| 425 | $CH_3$ | $CH_3$ | 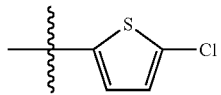 [SMILES: *c1ccc(Cl)s1] | H/H | H/H | H |
| 426 | $CH_3$ | $CH_3$ | 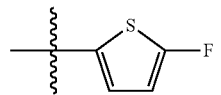 | H/H | H/H | H |
| 427; 428 | —$CH_2CH_2CH_2$— | | 2-Thienyl | H/H | H/H | H |
| 429; 430 | —$CH_2CH_2CH_2$— | | Phenyl | H/H | H/H | H |
| 431 | $CH_3$ | $CH_3$ | Phenyl | =O | H/H | H |
| 432; 433 | $CH_3$ | $CH_3$ | n-Butyl | =O | H/H | H | where these compounds can be in the form of an individual stereoisomer or mixture thereof, the free compounds and/or their physiologically acceptable salts and/or solvates.

The compounds according to the invention act, for example, on the ORL1 receptor relevant in connection with various diseases, so that they are suitable as a pharmaceutical active compound in a medicament.

The invention therefore also provides medicaments which contain at least one compound according to the invention and optionally suitable additives and/or auxiliary substances and/or optionally further active compounds.

The medicaments according to the invention optionally contain, in addition to at least one compound according to the invention, suitable additives and/or auxiliary substances, that is to say also carrier materials, fillers, solvents, diluents, dyestuffs and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example on the skin, the mucous membranes or into the eyes. Formulations in the form of tablets, coated tablets, capsules, granules, drops, juices and syrups are suitable for oral administration, solutions, suspensions, easily reconstitutable dry formulations and sprays are suitable for parenteral, topical and inhalatory administration. Compounds according to the invention in a depot, in dissolved form or in a plaster, optionally with the addition of agents which promote penetration through the skin, are suitable formulations for percutaneous administration. Formulation forms which can be used orally or percutaneously can release the compounds according to the invention in a delayed manner. The compounds according to the invention can also be used in parenteral long-term depot forms, such as e.g. implants or implanted pumps. In principle, other further active compounds known to the person skilled in the art can be added to the medicaments according to the invention.

The amount of active compound to be administered to patients varies as a function of the weight of the patient, of the mode of administration, the indication and the severity of the disease. 0.00005 to 50 mg/kg, preferably 0.001 to 0.5 mg/kg of at least one compound according to the invention are conventionally administered.

For all the above forms of the medicaments according to the invention, it is particularly preferable if the medicament also contains, in addition to at least one compound according to the invention, a further active compound, in particular an opioid, preferably a potent opioid, in particular morphine, or an anaesthetic, preferably hexobarbital or halothane.

In a preferred form of the medicament, a compound according to the invention contained therein is in the form of a pure diastereomer and/or enantiomer.

The ORL1 receptor has been identified in particular in the pain event. Compounds according to the invention can accordingly be used for the preparation of a medicament for treatment of pain, in particular acute, visceral, neuropathic or chronic pain.

The invention therefore also provides the use of a compound according to the invention for the preparation of a medicament for treatment of pain, in particular acute, visceral, neuropathic or chronic pain.

The invention also provides the use of a compound according to the invention for the preparation of a medicament for treatment of anxiety states, of stress and syndromes associated with stress, depression, epilepsy, Alzheimer's disease, senile dementia, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, urinary incontinence or as a muscle relaxant, anticonvulsive or anaesthetic or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids.

In this context, in one of the above uses it may be preferable for a compound which is used to be in the form of a pure diastereomer and/or enantiomer, a racemate or a non-equimolar or equimolar mixture of the diastereomers and/or enantiomers.

The invention also provides a method for the treatment, in particular in one of the abovementioned indications, of a non-human mammal or a human requiring treatment of pain, in particular chronic pain, by administration of a therapeutically active dose of a compound according to the invention, or of a medicament according to the invention.

The invention also provides a process for the preparation of the compounds according to the invention as described in the following description and examples.
General Synthesis Equations:

In a preferred embodiment the synthesis of the compounds according to the invention follows the following general synthesis equation:

to give the compound of the general formula G. The compounds of the general formula G are reduced by methods known from the literature, e.g. with lithium aluminium hydride (Wang, Jun et al., J. Am. Chem. Soc., 131(23), 8066-8076; 2009; Bhandari, Kalpana et al., Chemistry & Industry (London, United Kingdom), (17), 547-8; 1990). By methods known from the literature, the compounds of the general formula H are alkylated (Hutchins, Robert O., Markowitz, Morris J. Org. Chem. 46(17), 3571-4; 1981; Setaki, Despina et al., Bioorg. Chem., 34(5), 248-273; 2006; Stamatiou, G. et al.; Bioorg. & Med. Chem. Lett. 11(16), 2137-2142; 2001), arylated (WO2007070826, U.S. Pat. No. 7,157,456, WO2002085838) and acylated (WO2008034731, WO2008036755, US20070117824, WO2007030061) on the nitrogen. Alternatively, the compound G can also first be alkylated or arylated and thereafter

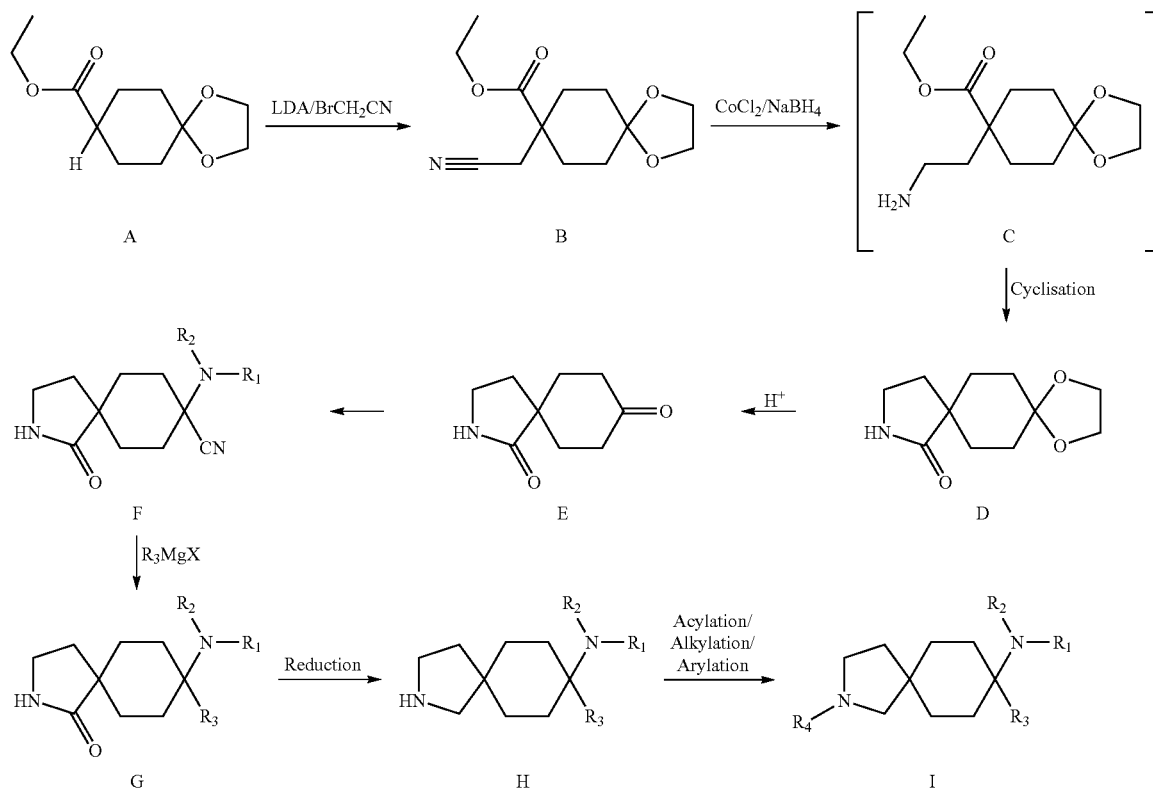

In step 1 compound A (WO2007079930) is converted into the nitrile B under basic conditions (WO2007127763; Reimann, Eberhard et al., Archiv der Pharmazie (Weinheim, Germany) (1988), 321(12), 935-41). The reduction of the nitrile B is carried out e.g. with cobalt boride (WO2007127763), the intermediate C cyclising spontaneously to the lactam D. The lactam D is deprotected under acid conditions (cerium ammonium nitrate/acetonitrile/water (I. Márko et al., Angew. Chem. 1999, 111, 3411-3413; Tetrahedron 2003, 59, 8989-8999), palladium chloride-bis-acetonitrile complex/acetone (B. H. Lipshutz et al., Tetrahedron Lett. 1985, 26, 705-708), sodium iodide/cerium(III) chloride/acetonitrile (E. Marcantoni et al., J. Org. Chem. 1997, 62, 4183-4184) and thiourea/ethanol/water (S. Majumdar, A. Bhattacharjya, J. Org. Chem. 1999, 64, 5682-5685) and then it is converted into the nitrile F in a Strecker reaction (WO2008101660, WO2008009415). The nitrile F reacts in a Bruylants reaction (D. Alberti et al., Bioorg. Med. Chem. Lett. 2006, 16, 4321-4325) with a Grignard reagent reduced. A polar and a non-polar diastereomer of the general formula G, but preferably the polar diastereomer G, are formed by this synthesis route.

In another preferred embodiment the synthesis of the compounds according to the invention follows the following general synthesis equation:

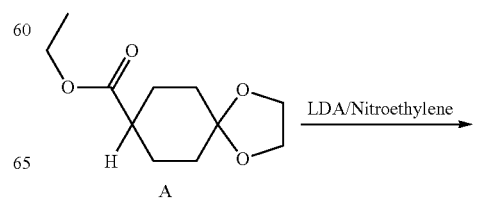

-continued

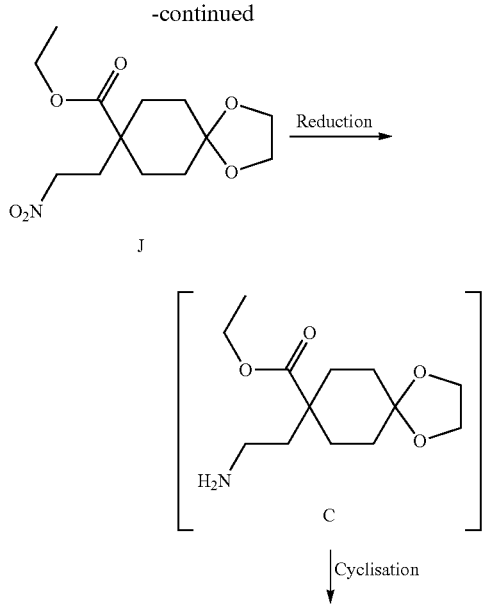

In step 1 compound A (WO2007079930) is converted into the nitro compound J under basic conditions and then reduced (G. H. Posner, D. R. Crouch, Tetrahedron 1990, 46, 7509-7530; R. J. Flintoft et al., Tetrahedron Lett. 1999, 44, 4485-4488; E. A. Krafft et al., Synthesis 2005, 3245-3252). Further reaction of the compound D is carried out as described in equation 1.

In another preferred embodiment the synthesis of the compounds according to the invention follows the following general synthesis equation:

In step 1 ketones of the general formula K (synthesised analogously to WO2006/031610 and U.S. Pat. No. 6,573,386) are converted into nitriles of the general formula L with TosMIC (Van Leusen, Daan et al., Organic Reactions (Hoboken, N.J., United States), 57, 2001). The nitrile L is converted into the imido-ester M in a Pinner reaction (Whitlock, Gavin A. et al., Bioorg. & Med. Chem. Lett. 18(9), 2930-2934, 2008; Geffken, Detlef et al., Archiv der Pharmazie (Weinheim, Germany), 321(1), 45-9; 1988) and then hydrolysed (US2002/58687). The ester N is converted into the nitrile O under basic conditions, like the ester A in equation 1. The nitrile O is reduced under conditions known from the literature and cyclised to the lactam G (WO2007127763). A polar and a non-polar diastereomer of the general formula G are formed by this synthesis route. Further reaction of compound G is carried out as described in equation 1.

In another preferred embodiment the synthesis of the compounds according to the invention follows the following general synthesis equation:

Equation 4

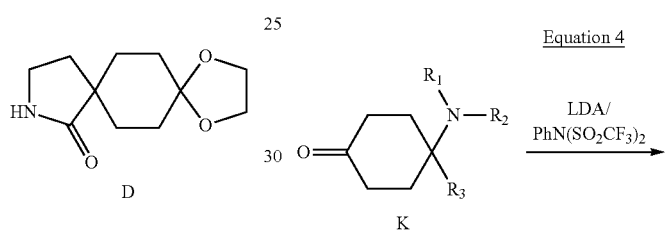

Equation 3

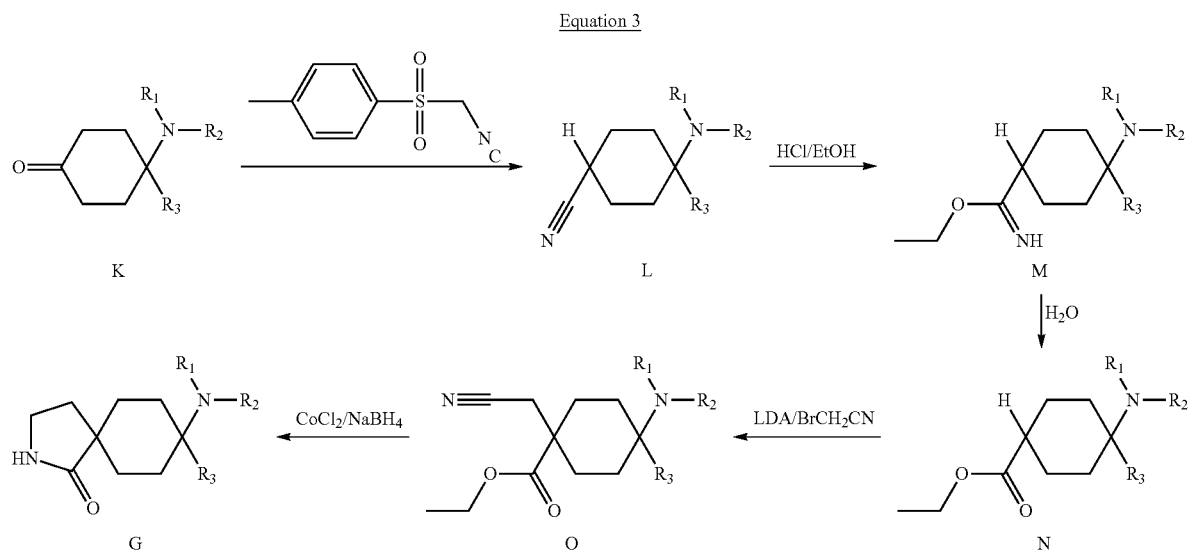

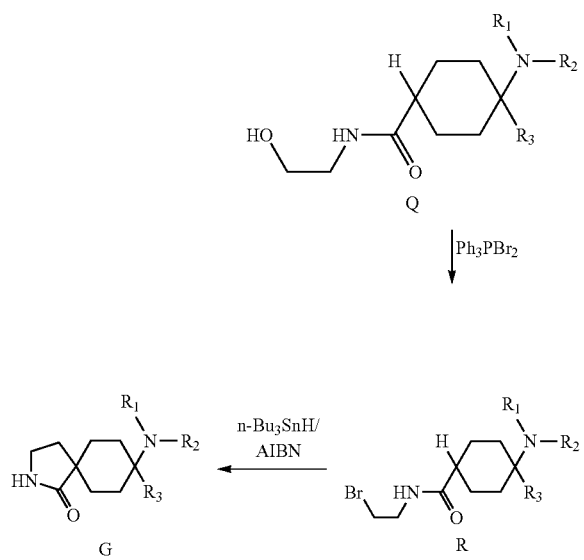

In step 1 ketones of the general formula K (synthesised analogously to WO2006/031610 and U.S. Pat. No. 6,573, 386) are converted into enol triflates (P) (WO2009111056). The aminocarbonylation with ethanolamine proceeds under extremely mild conditions (O. Lagerlund et al., Tetrahedron 2009, 65, 7646-7652; A. I. Meyers et al., Tetrahedron Lett. 1991, 33, 1181-1184). The alcohol Q is converted into a bromine derivative of the general formula R under conditions known from the literature (Van der Mey, Margaretha et al., J. Med. Chem. 45(12), 2520-2525; 2002). An exo-trig cyclisation between a primary radical and an α,β-unsaturated carboxylic acid derivative is then carried out to give the compound G (T. J. Murray et al. Tetrahedron 1995, 51, 635-640). A polar and a non-polar diastereomer of the general formula G are formed by this synthesis route. Further reaction of the compound G is carried out as described in equation 1.

In another preferred embodiment the synthesis of the compounds according to the invention follows the following general synthesis equation:

In step 1 ketones of the general formula K (synthesised analogously to WO2006/031610 and U.S. Pat. No. 6,573, 386) are converted into the compounds S in a Horner olefination known from the literature (Wadsworth, W. S., Jr. Et al., Organic Syntheses, 45, 1965). The compounds of the general formula S are reacted with nitromethane in a Michael addition to give the compound T (U.S. Pat. No. 5,091,567; WO2008/129007; J. S. Bryans et al., J. Med. Chem. 1998, 41, 1838-1845). The nitro compound T is reduced under conditions known from the literature and cyclised in situ to give the lactam U (G. H. Posner, D. R. Crouch, Tetrahedron 1990, 46, 7509-7530; R. J. Flintoft et al., Tetrahedron Lett. 1999, 44, 4485-4488; E. A. Krafft et al., Synthesis 2005, 3245-3252). By reduction of U the target compounds of the general formula H are obtained (Wang, Jun et al., J. Am, Chem. Soc., 131(23), 8066-8076; 2009; Bhandari, Kalpana et al., Chemistry & Industry (London, United Kingdom), (17), 547-8; 1990). A polar and a non-polar diastereomer of the general formula U are formed by this synthesis route. By methods known from the literature, the compounds of the general formula H are alkylated (Hutchins, Robert O., Markowitz, Morris J. Org. Chem. 46(17), 3571-4; 1981; Setaki, Despina et al., Bioorg. Chem., 34(5), 248-273; 2006; Stamatiou, G. et al.; Bioorg, & Med. Chem. Lett. 11(16), 2137-2142; 2001), arylated (WO2007070826, U.S. Pat. No. 7,157,456, WO2002085838) and acylated (WO2008034731, WO2008036755, US20070117824, WO2007030061) on the nitrogen. Alternatively, the compound U can also first be alkylated or arylated and thereafter reduced.

With respect to further details of the synthesis of the compounds according to the invention, in particular with respect to the synthesis of suitable educt units, reference is furthermore made to the full scope of WO2004/043967, WO2005/063769, WO2005/066183, WO2006/018184, WO2006/108565, WO2007/124903, WO2008/004915 and WO2008/009416. A person skilled in the art recognises that suitable educt units for the synthesis of the compounds according to the invention can be prepared analogously to the synthesis equations and embodiment examples disclosed in these publications.

EXAMPLES

The following examples serve to illustrate the invention in more detail, but are not to be interpreted as limiting.

The yields of the compounds prepared are not optimized. All the temperatures are uncorrected. The term "ether" means diethyl ether, "EA" ethyl acetate and "MC" methylene chloride. The term "equivalent" means equivalent substance amount, "m.p." melting point or melting range, "decomp." decomposition, "RT" room temperature, "abs." absolute (anhydrous), "rac." racemic, "conc." concentrated, "min" minutes, "h" hours, "d" days, "vol. %" percent by volume, "wt. %" percent by weight, and "M" is a concentration stated in mol/l.

Silica gel 60 (0.040-0.063 mm) from E. Merck, Darmstadt was employed as the stationary phase for the column chromatography. The thin layer chromatography investigations were carried out with HPTLC precoated plates, silica gel 60 F 254 from E. Merck, Darmstadt. The mixing ratios of mobile phases for chromatography investigations are always stated in volume/volume.

Synthesis Instructions

Example No. 1

Step 1: 8-Cyanomethyl-1,4-dioxaspiro[4.5]decane-8-carboxylic acid ethyl ester

A 2.5 M solution of n-buyllithium in n-hexane (22 ml, 55 mmol) was added dropwise to a solution of diisopropylamine (5.56 g, 55 mmol) in anhydrous tetrahydrofuran (80 ml) under argon at −78° C. and the mixture was than stirred for 15 min at 0° C. A solution of ethyl 1,4-dioxaspiro[4.5]decane-8-carboxylate (10.7 g, 50 mmol) in tetrahydrofuran (15 ml) was added dropwise to this lemon-yellow solution at −78° C. in the course of 20 min. The dark yellow mixture was stirred for 1.5 h at −78° C. and a solution of bromoacetonitrile (7.16 g, 3.98 ml, 60 mmol) and 1,3-dimethyl-3,4,5,6-tetrahydro-2-(1H)pyrimidone (DMPU, 3.20 g, 3.0 ml, 25 mmol) in tetrahydrofuran (15 ml) was then added dropwise. Thereafter, the orange-coloured solution was warmed slowly to room temperature and stirred overnight. 0.5 N hydrochloric acid (38 ml) was added to the now red-brown solution and the phases were separated. The aqueous phase was extracted with diethyl ether (3×50 ml). The combined organic phases were washed with saturated sodium bicarbonate solution (2×100 ml) and with saturated sodium chloride solution (4×100 ml), dried with sodium sulfate and concentrated i. vac. The crude product (12.1 g) was purified by flash chromatography (400 g, 20×7.5 cm) with ethyl acetate/cyclohexane (1:2).

Yield: 6.50 g (51%), yellowish oil.

$^1$H-NMR (CDCl$_3$): 1.29 (t, 3H, J=7.1 Hz); 1.62-1.76 (m, 6H); 2.17-2.29 (m, 2H); 2.57 (s, 2H): 3.93 (t, 4H, J=22 Hz); 4.23 (q, 2H, J=7.1 Hz).

Step 2: 1,4-Dioxa-10-azadispiro[4.2.4.2]tetradecan-9-one

Sodium borohydride (4.84 g, 128 mmol) was added in portions to a raspberry-coloured mixture of 8-cyanomethyl-1,4-dioxaspiro[4.5]decane-8-carboxylic acid ethyl ester (6.50 g, 25.6 mmol) and anhydrous cobalt(II) chloride (1.66 g, 12.8 mmol) in tetrahydrofuran (100 ml) and water (50 ml) under argon at 0° C. and the mixture was then stirred overnight at room temperature. During this operation the solution became black in colour. Since the reaction was not yet complete, cobalt(II) chloride (830 mg, 6.4 mmol) and sodium borohydride (2.42 g, 64 mmol) were again added and the mixture was stirred for a further 24 h. 25% strength aqueous ammonia solution (5 ml) was added to the reaction mixture and the mixture was filtered. The residue on the filter was washed with tetrahydrofuran/water (2:1). The filtrate was concentrated i. vac. and the aqueous solution was extracted with methylene chloride (3×50 ml). The combined organic extracts were dried with sodium sulfate and concentrated i. vac.

Yield: 4.64 g (86%), white solid which still contained approx. 30% of educt.

Step 3: 2-Azaspiro[4.5]decane-1,8-dione p-toluenesulfonic acid (5.00 g, 26.3 mmol) was added to a solution of 1,4-dioxa-10-azadispiro[4.2.4.2]tetradecan-9-one (4.64 g, 21.9 mmol) in methanol (75 ml) and water (25 ml) and the mixture was stirred for 24 h at room temperature and 24 h at 50° C. The reaction mixture was then rendered alkaline with 5 N sodium hydroxide solution and concentrated. The residue was diluted with water (50 ml) and the mixture was extracted with methylene chloride (6×30 ml). The organic phase was dried with sodium sulfate and concentrated i. vac. The crude product (2.09 g) was purified by flash chromatography (200 g, 20×5.7 cm) with ethyl acetate/methylene chloride (4:1) and ethyl acetate/methylene chloride/methanol (3:1:1). The mixed fractions (850 mg) were purified again by flash chromatography (100 g, 20×4.0 cm) with tert-butyl methyl ether/methanol (14:1).

Yield: 1.20 g (33%), white solid

Melting point: 128-130° C.

$^1$H-NMR (CDCl$_3$): 1.73-1.89 (m, 2H); 2.08-2.21 (m, 4H); 2.33 (ddd, 2H, J=5.8, 10.2 and 15.0 Hz); 2.70 (td, 2H, J=6.3 and 14.8 Hz); 3.41 (dt, 2H, J=0.8 and 7.1 Hz); 3.72 (s, 1H).

Step 4: Dimethylamino-1-oxo-2-azaspiro[4.5]decane-8-carbonitrile

4 N hydrochloric acid (2.15 ml, 8.56 mmol) and 2-azaspiro[4.5]decane-1,8-dione (1.20 g, 7.17 mmol) in methanol (16 ml) were added to a 40% strength aqueous dimethylamine solution (3.6 ml, 28.7 mmol), cooled to 0° C., and methanol (1.6 ml). Potassium cyanide (931 mg, 14.3 mmol) was added to this mixture and the mixture was stirred over the weekend at room temperature. After addition of water (30 ml) the solution was extracted with diethyl ether and methylene chloride (3×30 ml of each). The combined organic phases were dried with sodium sulfate and concentrated i. vac.

Yield: 1.40 g (88%), white solid $^1$H-NMR (CDCl$_3$): 1.35-1.67 (m, 3H); 1.76-2.09 (m, 5H); 2.18-2.31 (m, 2H); 2.33 and 2.35 (2s, 6H); 3.28-3.35 (m, 2H); 6.50 and 6.60 (2s, 1H). This is a diastereoisomer mixture in the ratio of approx. 2:1.

Step 5: 8-Benzyl-8-(dimethyl-amino)-3-azaspiro[4.5]decan-4-one (Example no. 1, polar diastereomer, Example no. 2, non-polar diastereomer)

A solution of dimethylamino-1-oxo-2-azaspiro[4.5]decane-8-carbonitrile (1.40 g, 6.3 mmol) in anhydrous tetrahydrofuran (60 ml) was added dropwise to a 2 M solution of benzylmagnesium chloride in tetrahydrofuran (9.5 ml, 19 mmol) at 0° C. under argon and thereafter the mixture was stirred at room temperature overnight. 20% strength ammonium chloride solution (25 ml) was then added to the reaction solution. The phases were separated and the aqueous phase was extracted with ethyl acetate (3×30 ml). The combined organic phases were dried with sodium sulfate and concentrated i. vac. The crude product (2.00 g) was purified by flash chromatography (100 g, 20×4.0 cm) with methylene chloride/methanol (48:1) and 0.25% ammonia (25% in water). The mixed fractions (560 mg) were purified again by flash chromatography (38 g, 20×2.5 cm) with methylene chloride/isopropanol (95:5) and 1% ammonia (25% in water).

Example No. 1 (Polar Diastereoisomer)

Yield: 511 mg (28%), colourless oil which also contains approx. 20% of the non-polar diastereoisomer.
$^1$H-NMR (CDCl$_3$): 1.53-1.63 (m, 4H); 1.67-1.75 (m, 2H); 1.85-1.92 (m, 2H); 1.95 (t, 2H, J 6.8 Hz); 2.28 (s, 6H); 2.77 (s, 2H); 3.21-3.26 (m, 2H); 5.71 (br s, 1H); 7.13-7.26 (m, 5H).
$^{13}$C-NMR (CDCl$_3$): 28.2; 29.0; 35.3; 36.7; 37.4; 38.6; 41.5; 57.6; 125.7; 127.7; 130.8; 139.2; 182.6.
LC-MS: m/z: [M+H]$^+$=287.3, R$_t$=1.0 min.

Example No. 2 (Non-polar Diastereoisomer)

Yield: 970 mg (54%), white solid
Melting point: 202-204° C.
$^1$H-NMR (CDCl$_3$): 1.05-1.19 (m, 4H); 1.67-1.80 (m, 4H); 2.00-2.14 (m, 2H); 2.30 (s, 6H); 2.62 (s, 2H); 3.15 (t, 2H, J=7.2 Hz); 5.90 (br s, 1H); 7.00-7.13 (m, 2H); 7.15-7.28 (m, 3H).
$^{13}$C-NMR (CDCl$_3$): 26.9; 28.6; 31.6; 37.0; 38.8; 43.6; 57.1; 125.6; 127.7; 130.6; 139.3; 183.3.
LC-MS: m/z: [M+H]$^+$=287.3, R$_t$=2.3 min.

Example No. 3

(8-Benzyl-3-azaspiro[4.5]decan-8-yl)-dimethylamine (Example no. 3, polar diastereomer)

A solution of 8-benzyl-8-(dimethylamino)-3-azaspiro[4.5]decan-4-one (polar diastereomer) (663 mg, 2.3 mmol) in anhydrous tetrahydrofuran (35 ml) was added to a suspension of lithium aluminium hydride (436 mg, 11.5 mmol) in anhydrous tetrahydrofuran (20 ml), while cooling with ice, and the mixture was then stirred overnight at 60° C. Water (300 µl), 1 N sodium hydroxide solution (1 ml) and again water (1 ml) were added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac.

Example No. 3 (Polar Diastereoisomer)

Yield: 588 mg (94%), colourless oil
A portion of the crude product (165 mg) was purified by flash chromatography (5 g, 15×0.9 cm) with methylene chloride/methanol (9:1) and 1% ammonia (25% in water), as a result of which the test substance (130 mg) was obtained.
$^1$H-NMR (CDCl$_3$): 1.07-1.22 (m, 4H); 1.48 (t, 2H, J=7.2 Hz); 1.62-1.75 (m, 4H); 2.30 (s, 6H); 2.41 (s, 2H); 2.60 (s, 2H); 2.80 (br s, 1H); 2.85 (t, 2H, J=7.2 Hz); 7.08-7.11 (m, 2H); 7.14-7.26 (m, 3H).
$^{13}$C-NMR (CDCl$_3$): 30.0; 31.3; 36.7; 37.1; 41.1; 42.2; 45.5; 55.9; 57.6; 125.6; 127.7; 130.6; 139.3.
LC-MS: m/z: [M+H]$^+$=273.4, R$_t$=0.2 min.

Example No. 4

(8-Benzyl-3-azaspiro[4.5]decan-8-yl)-dimethylamine (Example no. 4, non-polar diastereomer)

A solution of 8-benzyl-8-(dimethylamino)-3-azaspiro[4.5]decan-4-one (non-polar diastereomer) (700 mg, 2.44 mmol) in anhydrous tetrahydrofuran (30 ml) was added to a suspension of lithium aluminium hydride (463 mg, 12.2 mmol) in anhydrous tetrahydrofuran (20 ml), while cooling with ice, and the mixture was then stirred overnight at 60° C. Water (300 µl), 1 N sodium hydroxide solution (1 ml) and again water (1 ml) were added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac.

Example No. 4 (Non-polar Diastereoisomer)

Yield: 640 mg (96%), colourless oil
A portion of the crude product (154 mg) was purified by flash chromatography (5 g, 15×0.9 cm) with methylene chloride/methanol (9:1) and 1% ammonia (25% in water), as a result of which the test substance (117 mg) was obtained.
$^1$H-NMR (CDCl$_3$): 1.09-1.27 (m, 6H); 1.62-1.71 (m, 4H); 2.23 (br s, 1H); 2.29 (s, 6H); 2.58 (s, 2H); 2.61 (s, 2H); 2.82 (t, 2H, J=7.1 Hz); 7.09-7.26 (m, 5H).
$^{13}$C-NMR (CDCl$_3$): 29.8; 31.3; 36.0; 36.7; 37.1; 42.4; 46.6; 57.6; 61.3; 125.5; 127.6; 130.6; 139.4.
LC-MS: m/z: [M+H]$^+$=273.4, R$_t$=0.3 min.

Example No. 5

(8-Benzyl-3-methyl-3-azaspiro[4.5]decan-8-yl)-dimethylamine (Example no. 5, polar diastereomer)

37% strength formalin solution (1.30 ml), glacial acetic acid (650 µl) and sodium cyanoborohydride (205 mg, 3.2 mmol) were added to a solution of (8-benzyl-3-azaspiro[4.5]decan-8-yl)-dimethylamine (polar diastereomer) (207 mg, 0.76 mmol) in methanol (6.5 ml) and the mixture was stirred for 16 h at room temperature. After addition of saturated sodium bicarbonate solution (20 ml) the mixture was extracted with methylene chloride (3×20 ml). The combined organic phases were dried with sodium sulfate and concentrated i. vac. The crude product (220 mg) was purified by flash chromatography (10 g, 20×1.5 cm) with methylene chloride/methanol (9:1) and 1% ammonia (25% in water).

Example No. 5 (Polar Diastereoisomer)

Yield: 160 mg (73%), white solid
Melting point: 89-91° C.
$^1$H-NMR (CDCl$_3$): 1.07-1.17 (m, 2H); 1.26-1.33 (m, 2H); 1.56 (t, 2H, J=6.9 Hz); 1.62-1.72 (m, 4H); 2.07 (s, 2H); 2.21 (s, 3H); 2.29 (s, 6H); 2.43 (t, 2H, J=6.9 Hz); 2.61 (s, 2H); 7.09-7.13 (m, 2H); 7.15-7.27 (m, 3H).
$^{13}$C-NMR (CDCl$_3$): 30.1; 33.3; 36.8; 37.2; 40.8; 41.7; 42.7; 55.6; 57.5; 66.7; 125.6; 127.7; 130.7; 139.5.
LC-MS: m/z: [M+H]$^+$=287.3, R$_t$=0.2 min.

Example No. 6

(8-Benzyl-3-methyl-3-azaspiro[4.5]decan-8-yl)-dimethylamine (Example no. 6, non-polar diastereomer)

37% strength formalin solution (1 ml), glacial acetic acid (500 µl) and sodium cyanoborohydride (138 mg, 2.2 mmol) were added to a solution of (8-benzyl-3-azaspiro[4.5]decan-8-yl)-dimethylamine (non-polar diastereomer) (150 mg, 0.55 mmol) in methanol (5 ml) and the mixture was stirred for 16 h at room temperature. After addition of saturated sodium bicarbonate solution (20 ml) the mixture was extracted with methylene chloride (3×20 ml). The combined organic phases were dried with sodium sulfate and concentrated i. vac. The crude product (199 mg) was purified by flash chromatography (10 g, 20×1.5 cm) with methylene chloride/methanol (9:1) and 1% ammonia (25% in water).

Example No. 6 (Non-polar Diastereoisomer)

Yield: 110 mg (70%), white solid
Melting point: 57-58° C.
$^1$H-NMR (CDCl$_3$): 1.18-1.30 (m, 4H); 1.37 (t, 2H, J=6.9 Hz); 1.64-1.77 (m, 4H); 2.28 (s, 3H); 2.31 (s, 2H); 2.33 (s, 6H); 2.45 (t, 2H, J=6.9 Hz); 2.65 (s, 2H); 7.14-7.31 (m, 5H). The signal at 4.76 ppm (s) belongs to an unknown impurity.
$^{13}$C-NMR (CDCl$_3$): 29.4: 32.8; 36.0; 36.8; 37.1; 41.5; 42.7; 56.4; 57.5; 71.2; 74.8; 125.5; 127.7; 130.7; 139.4. One of the signals between 56.0 and 75.0 belongs to an unknown impurity.
LC-MS: m/z: [M+H]$^+$=287.4, R$_t$=0.2 min.

Example No. 7

1-[8-Benzyl-8-(dimethylamino)-3-azaspiro[4.5]decan-3-yl]-ethanone (Example no. 7, polar diastereomer)

Triethylamine (203 mg, 279 µl, 2.01 mmol) and acetic anhydride (137 mg, 126 µl, 1.34 mmol) were added to a solution of (8-benzyl-3-azaspiro[4.5]decan-8-yl)-dimethylamine (polar diastereomer) (183 mg, 0.67 mmol) in anhydrous methylene chloride (5 ml) and the mixture was stirred for 3 h at room temperature. After addition of methylene chloride (30 ml) the solution was washed with 25% strength saturated potassium carbonate solution (10 ml). The organic phase was dried with sodium sulfate and concentrated i. vac. The crude product (220 mg) was purified by flash chromatography (10 g, 20×1.5 cm) with methylene chloride/methanol (95:5) and 1% ammonia.

Example No. 7 (Polar Diastereoisomer)

Yield: 138 mg (65%), colourless oil
$^1$H-NMR (CDCl$_3$): 1.05-1.25 (m, 4H); 1.59-1.77 (m, 6H); 1.88 and 1.98 (2 s, 3H); 2.28 and 2.30 (2 s, 6H); 2.60 and 2.63 (2 s, 2H); 2.92 and 3.05 (2 s, 2H); 3.37-3.45 (m, 2H); 7.04-7.29 (m, 5H).
$^{13}$C-NMR (CDCl$_3$): 22.1; 22.4; 29.7; 29.74; 29.9; 36.8; 36.9; 37.0; 37.1; 38.2; 39.8; 40.2; 42.1; 43.7; 45.7; 54.0; 55.8; 57.6; 57.62; 125.8; 126.0; 127.8; 128.0; 130.5; 130.6; 138.8; 139.1; 169.2; 169.4.
The sometimes doubled signal sets are based on hindered rotation.
LC-MS: m/z: [M+H]$^+$=315.3, R$_t$=2.3 min.

Example No. 8

1-[8-Benzyl-8-(dimethylamino)-3-azaspiro[4.5]decan-3-yl]-ethanone (Example no. 8, non-polar diastereomer)

Triethylamine (188 mg, 258 µl, 1.86 mmol) and acetic anhydride (126 mg, 116 µl, 1.24 mmol) were added to a solution of (8-benzyl-3-azaspiro[4.5]decan-8-yl)-dimethylamine (non-polar diastereomer) (169 mg, 0.62 mmol) in anhydrous methylene chloride (5 ml) and the mixture was stirred for 3 h at room temperature. After addition of methylene chloride (40 ml) the solution was washed with 25% strength saturated potassium carbonate solution (10 ml). The organic phase was dried with sodium sulfate and concentrated i. vac. The crude product (203 mg) was purified by flash chromatography (10 g, 20×1.5 cm) with methylene chloride/methanol (95:5) and 1% ammonia.

Example No. 8 (Non-polar Diastereoisomer)

Yield: 146 mg (75%), colourless oil
$^1$H-NMR (CDCl$_3$): 1.11-1.26 (m, 4H); 1.54 and 1.52 (2 t, 2H, J=7.2 Hz); 1.63-1.77 (m, 4H); 1.97 and 1.98 (2 s, 3H); 2.28 and 2.95 (2 s, 6H); 2.63 (s, 2H); 3.14 and 3.19 (2 s, 2H); 3.34 and 3.38 (2 t, 2H, J=7.2 Hz); 7.09-7.29 (m, 5H).
$^{13}$C-NMR (CDCl$_3$): 22.0; 22.4; 29.0; 29.1; 29.54; 29.57; 32.2; 33.6; 36.5; 36.6; 37.0; 40.2; 41.9; 44.3; 46.1; 57.6; 57.62; 58.3; 60.8; 125.6; 125.8; 127.8; 127.9; 130.6; 130.7; 139.0; 139.3; 169.1; 169.2.
The sometimes doubled signal sets are based on hindered rotation.
LC-MS: m/z: [M+H]$^+$=315.3, R$_t$=2.5 min.

Example No. 9

(8-Benzyl-3-butyl-3-azaspiro[4.5]decan-8-yl)-dimethylamine (Example no. 9, non-polar diastereomer)

Sodium cyanoborohydride (177 mg, 2.82 mmol) and butyraldehyde (86 mg, 106 µl, 1.19 mmol) were added to a solution of (8-benzyl-3-azaspiro[4.5]decan-8-yl)-dimethylamine (non-polar diastereomer) (162 mg, 0.59 mmol) in methanol (5 ml) and the mixture was stirred for 30 min at room temperature. Glacial acetic acid (600 µl) was added to the mixture and the mixture was stirred for a further 16 h at room temperature. After addition of saturated sodium bicarbonate solution (20 ml) the mixture was extracted with methylene chloride (3×20 ml). The combined organic phases were dried with sodium sulfate and concentrated i. vac. The crude product (202 mg) was purified by flash chromatography (10 g, 20×1.5 cm) with methylene chloride/methanol (95:5) and 1% ammonia.

Example No. 9 (Non-polar Diastereoisomer)

Yield: 150 mg (87° A)), colourless oil
$^1$H-NMR (CDCl$_3$): 0.92 (t, 3H, J=7.3 Hz); 1.10-1.20 (m, 2H); 1.26-1.40 (m, 4H); 1.52-1.65 (m, 4H); 1.67-1.82 (m, 4H); 2.28 (s, 6H); 2.62 (s, 2H); 2.70-2.77 (m, 4H); 2.95 (br t, 2H, J=6.5 Hz); 7.07-7.11 (m, 2H); 7.16-7.28 (m, 3H).
$^{13}$C-NMR (CDCl$_3$): 13.6; 20.2; 28.5; 29.2; 31.4; 33.5; 36.5; 37.0; 41.3; 53.8; 56.3; 57.3; 66.7; 125.8; 127.9; 130.6; 138.8.
LC-MS: m/z: [M+H]$^+$=329.4, R$_t$=1.2 min.

Example No. 10

(8-Benzyl-3-butyl-3-azaspiro[4.5]decan-8-yl)-dimethylamine (Example no. 10, polar diastereomer)

Butyryl chloride (134 mg, 132 µl, 1.26 mmol) was added to a solution of (8-benzyl-3-azaspiro[4.5]decan-8-yl)-dimethylamine (polar diastereomer) (169 mg, 0.62 mmol) and triethylamine (193 mg, 264 µl, 1.9 mmol) in anhydrous methylene chloride (5 ml) and the mixture was stirred for 18 h at room temperature. The reaction mixture was diluted with methylene chloride (20 ml) and washed with 25% strength potassium carbonate solution (2×10 ml). The organic phase was dried with sodium sulfate and concentrated i. vac. The crude product (240 mg) was purified by flash chromatography (10 g, 20×1.5 cm) with methylene chloride/methanol (95:5) and 1% ammonia (25% in water).

Example No. 10 (Polar Diastereoisomer)

Yield: 159 mg (75%), colourless oil $^1$H-NMR (CDCl$_3$): 0.88 and 0.93 (2 t, 3H, J=7.4 Hz); 1.04-1.23 (m, 4H); 1.53-1.77 (m, 8H); 2.04 and 2.77 (2 t, 2H, J=7.5 Hz); 2.28 and 2.30 (2 s, 6H); 2.60 and 2.63 (2 s, 2H); 2.92 and 3.06 (2 s, 2H); 3.36-3.44 (m, 2H); 7.04-7.29 (m, 5H).

$^{13}$C-NMR (CDCl$_3$): 13.9; 14.0; 18.3; 18.5; 29.59; 29.6; 29.8; 29.9; 36.4; 36.7; 36.8; 36.84; 37.0; 37.1; 37.9; 39.7; 40.0; 42.0; 43.7; 44.9; 54.0; 54.9; 57.61; 57.64; 125.7; 125.9; 127.8; 128.0; 130.5; 130.6; 138.8; 139.1; 171.9.

The NMR spectra show sometimes doubled signal sets (rotamers).

LC-MS: m/z: [M+H]$^+$=343.4, R$_t$=2.7 min.

Example No. 11

(8-Benzyl-3-butyl-3-azaspiro[4.5]decan-8-yl)-dimethylamine (Example no. 11, non-polar diastereomer)

Butyryl chloride (134 mg, 132 µl, 1.26 mmol) was added to a solution of (8-benzyl-3-azaspiro[4.5]decan-8-yl)-dimethylamine (non-polar diastereomer) (173 mg, 0.63 mmol) and triethylamine (193 mg, 264 µl, 1.9 mmol) in anhydrous methylene chloride (5 ml) and the mixture was stirred for 18 h at room temperature. The reaction mixture was diluted with methylene chloride (20 ml) and washed with 25% strength potassium carbonate solution (2×10 ml). The organic phase was dried with sodium sulfate and concentrated i. vac. The crude product (220 mg) was purified by flash chromatography (10 g, 20×1.5 cm) with methylene chloride/methanol (300:5) and 1% ammonia (25% in water).

Example No. 11 (Non-polar Diastereoisomer)

Yield: 157 mg (73%), white solid
Melting point: 98-105° C.

$^1$H-NMR (CDCl$_3$): 0.93 and 0.94 (2 t, 3H, J=7.4 Hz); 1.12-1.26 (m, 4H); 1.41 and 1.50 (2 t, 2H, J=7.1 Hz); 1.59-1.77 (m, 6H); 2.13-2.19 (m, 2H); 2.28 and 2.30 (2 s, 6H); 2.62 (s, 2H); 3.16 and 3.19 (2 s, 2H); 3.33 and 3.38 (2 t, 2H, J=7.1 Hz); 7.09-7.28 (m, 5H).

$^{13}$C-NMR (CDCl$_3$): 14.0; 14.02; 18.3; 18.4; 29.0; 29.1; 29.5; 29.6; 32.0; 33.6; 36.2; 36.5; 36.6; 36.8; 37.0; 40.0; 41.9; 44.3; 45.3; 57.6; 57.7; 58.4; 60.0; 125.6; 125.7; 127.8; 127.9; 130.6; 130.7; 139.1; 139.3; 171.6; 171.7.

The NMR spectra show sometimes doubled signal sets (rotamers).

LC-MS: m/z: [M+H]$^+$=343.3, R$_t$=2.9 min.

Example No. 12

(8-Benzyl-3-(cyclopentylmethyl)-3-azaspiro[4.5]decan-8-yl)-dimethylamine (Example no. 12, non-polar diastereomer)

Cyclopentanecarbaldehyde (125 mg, 136 µl, 1.3 mmol) and glacial acetic acid (500 µl) were added to a solution of (8-benzyl-3-azaspiro[4.5]decan-8-yl)-dimethylamine (non-polar diastereomer) (202 mg, 0.74 mmol) in methanol (5 ml) and the mixture was stirred for 2 h at room temperature. After addition of sodium cyanoborohydride (200 mg, 3.1 mmol) the mixture was stirred for 24 h at room temperature. The reaction mixture was then diluted with methylene chloride (20 ml), saturated sodium bicarbonate solution (25 ml) was added and the phases were separated. The aqueous phase was extracted with methylene chloride (3×20 ml). The combined organic phases were dried with sodium sulfate and concentrated i. vac. The crude product (283 mg) was purified by flash chromatography (10 g, 20×1.5 cm) with methylene chloride/methanol (95:5) and 1% ammonia (25% in water).

Example No. 12 (Non-polar Diastereoisomer)

Yield: 192 mg (73%), colourless oil $^1$H-NMR (CDCl$_3$): 1.11-1.29 (m, 6H); 1.37 (t, 2H, J=6.9 Hz); 1.45-1.80 (m, 10H); 1.98 (td, 1H, J=15.4, 7.8 Hz); 2.29 (s, 6H); 2.39 (d, 2H, J=7.2 Hz); 2.41 (s, 2H); 2.58 (t, 2H, J=6.9 Hz); 2.62 (s, 2H); 7.09-7.25 (m, 5H).

$^{13}$C-NMR (CDCl$_3$): 25.1; 29.4; 31.5; 32.5; 34.6; 36.7; 37.1; 38.8; 41.0; 54.7; 57.5; 62.5; 68.5; 125.6; 127.7; 130.7; 139.3.

LC-MS: m/z: [M+H]$^+$=355.4, R$_t$=2.0 min.

Example No. 13

8-Dimethylamino-8-phenyl-3-azaspiro[4.5]decan-4-one (Example no. 13, a diastereomer)

A solution of dimethylamino-1-oxo-2-azaspiro[4.5]decane-8-carbonitrile (330 mg, 1.49 mmol) in tetrahydrofuran (15 ml) was added dropwise to a 2 M solution of phenylmagnesium chloride in tetrahydrofuran (2.4 ml, 4.8 mmol) at 0° C. and under argon and thereafter the mixture was stirred overnight at room temperature. 20% strength ammonium chloride solution (15 ml) was then added to the reaction solution. The phases were separated and the aqueous phase was extracted with ethyl acetate (2×15 ml). The combined organic phases were dried with sodium sulfate and concentrated i. vac. The crude product (520 mg) was purified by flash chromatography (45 g, 23×2.5 cm) with methylene chloride/methanol (95:5) and 0.5% ammonia (33% in H$_2$O).

Example No. 13 (A Diastereomer)

Yield: 155 mg (38%), white solid
Melting point: 183-185° C.

$^1$H-NMR (CDCl$_3$): 1.30-1.37 (m, 2H); 1.61 (t, 2H, J=13.5 Hz); 1.97 (t, 2H, J=6.9 Hz); 2.05 (s, 6H); 2.21 (dt, 2H, J=3.1 and 13.1 Hz); 2.62 (br d, 2H, J=14.4 Hz); 3.26-3.32 (m, 2H); 6.17 (br s, 1H); 7.21-7.30 (m, 1H); 7.30-7.39 (m, 4H).

$^{13}$C-NMR (CDCl$_3$): 28.2 (2C); 29.3; 32.8; 37.9 (2C); 38.8 (2C); 43.1; 58.7; 126.5; 126.8 (2C); 127.5 (2C); 139.4; 182.9.

LC-MS: m/z: [M+H]$^+$=273.3, R$_t$=1.4 min.

Example No. 14 and Example No. 15

Step 1:
(4-Dimethylamino-4-phenylcyclohexylidene)acetic acid ethyl ester

Potassium tert-butylate (1.93 g, 17.3 mmol) was added to a solution of phosphonoacetic acid triethyl ester (3.86 g, 314 ml, 17.3 mmol) in anhydrous N,N-dimethylformamide (20 ml) under argon. The mixture was stirred for 10 min at room temperature and a solution of 4-(dimethylamino)-4-phenyl-cyclohexanone (2.50 g, 11.5 mmol) in anhydrous N, N-dimethylformamide (40 ml) was then added and thereafter the mixture was stirred for 1 h at room temperature and then poured into ice-water (50 g). The aqueous suspension was extracted with diethyl ether (4×40 ml). The combined organic phases were dried with sodium sulfate and concentrated i. vac.

Yield: 3.39 g (100%)

$^1$H-NMR (CDCl$_3$): 1.26 (t, 3H, J=7.1 Hz); 2.06 (s, 6H); 2.10-2.25 (m, 5H); 2.45 (m, 1H); 2.67 (m, 1H); 3.20 (m, 1H); 4.13 (q, 2H, J=7.1 Hz); 5.60 (s, 1H); 7.26 (m, 1H); 7.31-7.40 (m, 4H).

LC-MS: [M+H]$^+$: m/z=288.3, R$_t$=2.7 min.

Step 2: (4-Dimethylamino-2-nitromethyl-4-phenyl-cyclohexyl)acetic acid ethyl ester Nitromethane (138 mg, 122 µl, 2.26 mmol) was added to a mixture of (4-dimethylamino-4-phenylcyclohexylidene) acetic acid ethyl ester (500 mg, 1.74 mmol) and tetra-n-butylammonium fluoride trihydrate (602 mg, 1.91 mmol) in tetrahydrofuran (30 ml) and the mixture was stirred for 6 h at 70° C. The reaction mixture was then concentrated in vacuo and the residue (1.10 g) was purified by flash chromatography (38 g, 20×2.5 cm) with ethyl acetate/methanol (95:5).

Yield: 453 mg (75%), yellowish oil.

$^1$H-NMR (DMSO-d$_6$): The spectrum shows all the required signals. This is a diastereoisomer mixture in the ratio of approx. 3:2.

Step 3: 8-(Dimethylamino)-8-phenyl-3-azaspiro[4.5] decan-2-one (Example no. 14, polar diastereomer, Example no. 15, non-polar diastereomer)

A solution of (4-dimethylamino-2-nitromethyl-4-phenyl-cyclohexyl)acetic acid ethyl ester (1.13 g, 3.24 mmol) in ethanol (32 ml) was added to a mixture of iron powder (904 mg, 16.2 mmol), ammonium chloride (4.33 g, 81 mmol) and water (3.3 ml) and the mixture was then stirred for 5 h at 80° C. The mixture was filtered and the residue was washed with ethanol. The filtrate was rendered alkaline with 5% strength sodium bicarbonate solution (1 ml) and then concentrated i. vac. The crude product was purified by flash chromatography (38 g, 20×2.5 cm) with methylene chloride/methanol (95:5) and 1% ammonia (25% in water). The diastereoisomer mixture isolated was separated by medium pressure chromatography on a PuriFlash cartridge (PF-15SIHP, 40 g) with the above eluent.

Example No. 14 (Polar Diastereoisomer)

Yield: 330 mg (37%), white solid
Melting point: 210-215° C.

$^1$H-NMR (CDCl$_3$): 1.35-1.45 (m, 2H); 1.73-1.82 (m, 2H); 1.86-2.01 (m, 2H); 2.02 (s, 6H); 2.05 (s, 2H); 2.10-2.30 (m, 2H); 3.26 (s, 2H); 6.28 (s, 1H); 7.25-7.30 (m, 3H); 7.35-7.40 (m, 2H).

$^{13}$C-NMR (CDCl$_3$): 30.2; 32.7; 37.98; 38.0; 39.0; 43.3; 52.8; 53.4; 60.1; 126.7; 127.4; 127.7; 136.0; 177.4.

LC-MS: m/z: [M+H]$^+$=273.3, R$_t$=1.3 min.

Example No. 15 (Non-Polar Diastereoisomer)

Yield: 215 mg (24%), white solid
Melting point: 218-223° C.

$^1$H-NMR (CDCl$_3$): 1.35-1.45 (m, 2H); 1.50-1.58 (m, 1H); 1.73-1.82 (m, 2H); 1.85-2.02 (m, 2H); 2.04 (s, 6H); 2.13-2.18 (m, 1H); 2.30 (s, 2H); 3.02 (s, 2H); 5.41 (br s, 1H); 7.27-7.32 (m, 3H); 7.36-7.41 (m, 2H).

$^{13}$C-NMR (CDCl$_3$): 30.2; 32.9; 38.0; 38.1; 39.2; 42.4; 53.9; 60.4; 126.6; 127.5; 127.7; 136.3; 177.6.

LC-MS: m/z: [M+H]$^+$=273.3, R$_t$=1.6 min.

Example No. 16

8-Butyl-8-dimethylamino-8-phenyl-3-azaspiro[4.5] decan-4-one (Example no 16, a diastereomer)

A solution of dimethylamino-1-oxo-2-azaspiro[4.5]decane-8-carbonitrile (390 mg, 1.76 mmol) in tetrahydrofuran (15 ml) was added dropwise to a 2 M solution of n-butyl-magnesium chloride in tetrahydrofuran (3.5 ml, 7 mmol) at 0° C. and under argon and thereafter the mixture was stirred overnight at room temperature. 20% strength ammonium chloride solution (15 ml) was then added to the reaction solution. The phases were separated and the aqueous phase was extracted with ethyl acetate (2×20 ml). The combined organic phases were dried with sodium sulfate and concentrated i. vac. The crude product (334 mg) was purified by flash chromatography (32 g, 20×2.5 cm) with methylene chloride/methanol [9:1→4:1→4:1+1% ammonia (33% in H$_2$O)]. Thereafter the mixed fractions were purified by renewed flash chromatography (12 g, 18×1.6 cm) with methylene chloride/methanol [9:1+0.5% ammonia (33% in H$_2$O)].

Example No. 16 (A Diastereomer)

Yield: 185 mg (42%), white solid
Melting point: 148-151° C.

$^1$H-NMR (CDCl$_3$): 0.89 (t, 3H, J=7.1 Hz); 1.08-1.35 (m, 10H); 1.71 (br d, 2H, J=13.0 Hz); 1.98 (t, 2H, J=6.9 Hz); 2.06 (dt, 2H, J=13.0 Hz); 2.20 (s, 6H); 3.23-3.31 (m, 2H); 6.85 (s, 1H).

$^{13}$C-NMR (CDCl$_3$): 14.1; 23.8 (2C); 26.7; 27.3; 28.4; 31.0 (2C); 32.3; 37.1 (2C); 39.0; 43.6; 55.9; 183.5.

LC-MS: m/z: [M+H]$^+$=253.3, R$_t$=1.5 min.

Example No. 17

8-Dimethylamino-8-thiophen-2-yl-3-azaspiro[4.5] decan-4-one (Example no. 17, a diastereomer)

A solution of dimethylamino-1-oxo-2-azaspiro[4.5]decane-8-carbonitrile (800 mg, 3.6 mmol) in tetrahydrofuran (15 ml) was added dropwise to a 1 M solution of 2-thienylmagnesium bromide in tetrahydrofuran (11.5 ml, 11.5 mmol) at 0° C. and under argon and thereafter the mixture was stirred overnight at room temperature. 20% strength ammonium chloride solution (35 ml) was then added to the reaction solution. The phases were separated and the aqueous phase was extracted with ethyl acetate (2×30 ml). The combined organic phases were dried with sodium sulfate and concentrated. The crude product (950 mg) was purified by flash chromatography (80 g, 17×3.7 cm) with methylene chloride/methanol [9:1+2% ammonia (33% in $H_2O$)].

Example No. 17 (A Diastereomer)

Yield: 840 mg (84%), yellowish solid
Melting point: 168-174° C.
$^1$H-NMR ($CDCl_3$): 1.26-1.36 (m, 2H); 1.69 (dt, 2H, J=3.2 and 13.8 Hz); 1.99 (t, 2H, J=6.9 Hz); 2.10 (s, 6H); 2.20 (dt, 2H, J=3.2 and 13.1 Hz); 2.45 (br d, 2H, J=13.6 Hz); 3.25-3.34 (m, 2H); 6.76 (br s, 1H); 6.85 (dd, 1H, J=1.1 and 3.6 Hz); 7.03 (dd, 1H, J=3.6 and 5.1 Hz); 7.21 (dd, 1H, J=1.1 and 5.1 Hz).
$^{13}$C-NMR ($CDCl_3$): 27.9 (2C); 31.9 (2C); 32.5; 38.0 (2C); 38.9; 43.4; 58.4; 122.8; 123.6; 126.0; 145.4; 183.0.
LC-MS: m/z: $[M+H]^+$=279.2, $R_t$=1.3 min.

Example No. 18

Dimethyl-(8-thiophen-2-yl-3-azaspiro[4.5]decan-8-yl)-amine (Example no. 18, polar diastereomer)

A solution of 8-(dimethylamino)-8-thiophen-2-yl-3-azaspiro[4.5]decan-4-one (polar diastereomer) (714 mg, 2.56 mmol) in tetrahydrofuran (20 ml) was added to a suspension of lithium aluminium hydride (490 mg, 12.9 mmol) in tetrahydrofuran (4 ml) at room temperature and the mixture was stirred for 18 h at 60° C. The reaction mixture was cooled to 0° C., water (0.5 ml), 1 N sodium hydroxide solution (1 ml) and again water (1 ml) were added and the mixture was then stirred for 1 h at room temperature. The precipitate was filtered off, ethyl acetate (20 ml) was added to the filtrate and the phases were separated. The organic phase was dried with sodium sulfate and the solvent was removed i. vac. The residue (570 mg) was purified by flash chromatography (30 g, 19×2.5 cm) with methylene chloride/methanol (4:1) and 1% ammonia (25% in $H_2O$).

Example No. 18 (Polar Diastereomer)

Yield: 280 mg (41%), white oily solid.
Melting point: 80-84° C.
$^1$H-NMR ($CDCl_3$): 1.38 (ddd, 2H, J=3.6, 13.3 Hz); 1.43-1.50 (m, 1H); 1.58-1.70 (m, 2H); 1.86-2.01 (m, 2H); 2.09 (m, 9H); 2.75 (s, 2H); 2.90 (t, 2H, J=7.1 Hz); 6.84 (dd, 1H, J=1.1 and 3.6 Hz); 7.03 (dd, 1H, J=3.6 and 5.1 Hz); 7.23 (dd, 1H, J=1.1 and 5.1 Hz). The NH proton could not be identified.
$^{13}$C-NMR ($CDCl_3$): 32.8 (2C); 33.7 (2C); 38.1; 39.0; 42.3; 57.8; 59.8; 123.2; 124.9; 126.1; 143.2.
LC-MS: m/z: $[M+H]^+$=265.2, $R_t$=0.5 min.

Example No. 19

Dimethyl-(3-methyl-8-thiophen-2-yl-3-azaspiro[4.5]decan-8-yl)-amine (Example no. 19, polar diastereomer)

37% strength aqueous formalin solution (1 ml) and sodium cyanoborohydride (151 mg, 2.4 mmol) were added to a solution of dimethyl-(8-thiophen-2-yl-3-azaspiro[4.5]decan-8-yl)-amine (polar diastereomer) (160 mg, 0.6 mmol) in methanol (6 ml) and the mixture was stirred for 30 min at room temperature. After addition of acetic acid (0.6 ml) the mixture was further stirred for 3 h at room temperature. The reaction solution was then diluted with saturated sodium bicarbonate solution (20 ml) and extracted with methylene chloride (3×20 ml). The combined organic phases were dried with sodium sulfate, the solvent was removed i. vac. and the residue (164 mg) was purified by flash chromatography (16 g, 16×2 cm) with methylene chloride/methanol (9:1) and 1% ammonia (25% in $H_2O$).

Example No. 19 (Polar Diastereomer)

Yield: 90 mg (54%), white solid
Melting point: 71-72° C.
$^1$H-NMR ($CDCl_3$): 1.34-1.43 (m, 2H); 1.52 (t, 2H, J=6.8 Hz); 1.64-1.75 (m, 2H); 1.84-1.99 (m, 2H); 2.08 (s, 8H); 2.30 (s, 3H); 2.40 (s, 2H); 2.48 (t, 2H, J=6.8 Hz); 6.83 (dd, 1H, J=1.0 and 3.5 Hz); 7.02 (dd, 1H, J=3.5 and 5.1 Hz); 7.21 (dd, 1H, J=1.0 and 5.1 Hz).
$^{13}$C-NMR ($CDCl_3$): 33.6 (2C); 34.4; 38.1 (2C); 38.6 (br.); 41.7; 42.6 (2C); 55.9; 59.6; 68.1 (br.); 74.8; 132.2; 124.9; 126.1; 143.3 (br).
LC-MS: $[MH-HNMe_2]^+$: m/z=234.2 (100%) and $[M+H]^+$: m/z=279.3 (8%), $R_t$=0.2 min.

Example No. 20a 1-(8-Dimethylamino-8-thiophen-2-yl-3-azaspiro[4.5]decan-3-yl)-butan-1-one (Example no. 20a, polar diastereomer)

Butyryl chloride (69 mg, 68 µl, 0.65 mmol) was added to a solution of dimethyl-(8-thiophen-2-yl-3-azaspiro[4.5]decan-8-yl)-amine (polar diastereomer) (142 mg, 0.54 mmol) and triethylamine (82 mg, 0.81 mmol) in methylene chloride (5 ml) and the mixture was stirred for 2.5 h at room temperature. 1 M potassium carbonate solution (6 ml) was then added to the reaction mixture and the mixture was stirred for 30 min at room temperature. The phases were separated and the aqueous phase was extracted with methylene chloride (2×10 ml). The combined organic phases were dried with sodium sulfate and concentrated i. vac. The residue (180 mg) was purified by flash chromatography (18 g, 19×2 cm) with methylene chloride/methanol (95:5).

Example No. 20a (Polar Diastereomer)

Yield: 140 mg (78%), colourless oil
$^1$H-NMR ($CDCl_3$): 0.96 (ddt, 3H, J=0.6; 4.5 and 7.4 Hz); 1.33-1.45 (m, 2H); 1.57-1.78 (m, 6H); 1.84-2.03 (m, 2H); 2.09 (d, 3H, J=0.7 Hz); 2.12 (s, 4H); 2.22 (dd, 3H, J=6.7 and 14.5 Hz); 3.31 (s, 1H); 3.37 (s, 1H); 3.41-3.50 (m, 2H); 6.83-6.88 (m, 1H); 7.01-7.07 (m, 1H); 7.22-7.26 (m, 1H).
$^{13}$C-NMR ($CDCl_3$): 14.0; 18.3; 18.4; 31.1; 31.2; 32.8; 33.4; 35.6; 36.3; 36.8; 37.1; 38.1; 40.1; 42.9; 45.0; 55.3; 56.4; 59.9; 123.3; 123.6; 124.9; 125.1; 126.1; 126.4; 171.9; 172.0. Some C signals are doubled due to the amide structure.
LC-MS: $[MH-HNMe_2]^+$: m/z=290.2 (100%) and $[M+H]^+$: m/z=335.3 (90%), $R_t$=2.7 min.

Example No. 20b

1-[8-(Dimethylamino)-8-thiophen-2-yl-3-azaspiro [4.5]decan-3-yl]-butan-1-one (Example no. 20b, non-polar diastereomer)

Butyryl chloride (63 mg, 62 µl, 0.59 mmol) was added to a solution of dimethyl-(8-thiophen-2-yl-3-azaspiro[4.5]decan-8-yl)-amine (non-polar diastereomer) (130 mg, 0.49 mmol) and triethylamine (75 mg, 103 µl, 0.74 mmol) in methylene chloride (5 ml) and the mixture was stirred for 1 h at room temperature. Potassium carbonate solution (5 ml) was then added to the mixture and the mixture was stirred for 15 min.

The phases were separated and the aqueous phase was subsequently extracted with methylene chloride (3×5 ml). The combined organic phases were dried with sodium sulfate and concentrated i. vac. The crude product (160 mg) was purified by means of flash chromatography (18 g, 20×2.0 cm) with methylene chloride/methanol (95:5).

Example No. 20b (Non-polar Diastereoisomer)

Yield: 116 mg (71%), yellow oil
$^1$H-NMR (CDCl$_3$): 0.91 (t, 1.5H, J=7.4 Hz); 0.96 (t, 1.5H, J=7.4 Hz); 1.37-1.45 (m, 2H); 1.57-1.73 (m, 4H); 1.76 (t, 1H, J=7.2 Hz); 1.86 (t, 1H, J=7.2 Hz); 2.00-2.09 (m, 4H); 2.12 (s, 6H); 2.13-2.23 (m, 2H); 3.14 (s, 1H); 3.23 (s, 1H); 3.47 (t, 1H, J=7.1 Hz); 3.52 (t, 1H, J=7.1 Hz); 6.84 (dd, 0.5H, J=0.8, 3.6 Hz); 6.86 (dd, 0.5H, J=1.1, 3.6 Hz); 7.02 (dd, 0.5H, J=3.6, 5.2 Hz); 7.04 (dd, 0.5H, J=3.6, 5.2 Hz); 7.22 (dd, 0.5H, J=0.8, 5.1 Hz); 7.24 (dd, 0.5H, J=1.1, 5.1 Hz).
$^{13}$C-NMR (CDCl$_3$): 13.97; 13.99; 18.4; 31.0; 33.1; 36.3; 36.7; 38.07; 38.09; 40.1; 42.1; 44.1; 45.2; 56.0; 57.6; 59.9; 123.5; 124.9; 126.21; 126.26; 171.8; 171.9.

The NMR spectra show sometimes doubled signal sets (rotamers).
LC-MS: m/z: [MH-HNMe$_2$]$^+$=290.2 (100%) and [M+H]$^+$=335.3 (50%), R$_t$=2.7 min.

Example No. 21

(3-Butyl-8-thiophen-2-yl-3-azaspiro[4.5]decan-8-yl)-dimethylamine (Example no. 21, polar diastereomer)

Butyraldehyde (49 mg, 61 µl, 0.68 mmol) and sodium cyanoborohydride (147 mg, 2.34 mmol) were added to a cloudy solution of dimethyl-(8-thiophen-2-yl-3-azaspiro [4.5]decan-8-yl)-amine (polar diastereomer) (137 mg, 0.52 mmol) in methanol (5 ml) and the mixture was stirred for 30 min at room temperature. After addition of acetic acid (0.52 ml) the mixture was stirred for a further 2 h at room temperature. The reaction mixture was then diluted with sodium bicarbonate solution (20 ml) and extracted with methylene chloride (3×20 ml). The combined organic phases were dried with sodium sulfate and concentrated i. vac. The crude product (157 mg) was purified by means of flash chromatography (16 g, 16×2.0 cm) with methanol and 0.5% ammonia (25% in H$_2$O).

Example No. 21 (Polar Diastereomer)

Yield: 105 mg (63%), colourless oil
$^1$H-NMR (CDCl$_3$): 0.91 (t, 3H, J=7.2 Hz); 1.27-1.53 (m, 8H); 1.64-1.74 (m, 2H); 1.85-1.99 (m, 2H); 2.10 (m, 8H); 2.33-2.40 (m, 2H); 2.42 (s, 2H); 2.50 (t, 2H, J=6.9 Hz); 6.85 (td, 1H, J=1.0 and 3.6 Hz); 7.02-7.05 (m, 1H); 7.21-7.24 (m, 1H).
$^{13}$C-NMR (CDCl$_3$): 14.1; 20.9; 31.0; 33.8; 34.5; 38.2; 40.8; 54.0; 56.8; 59.7; 65.6; 123.2; 124.9; 126.1. A thienyl-C signal (approx. 143 ppm) could not be identified.
LC-MS: [MH-HNMe$_2$]$^+$: m/z=276.3 (100%) and [M+H]$^+$: m/z=321.3 (16%), R$_t$=0.3 min.

Example No. 22

[3-(Cyclopentylmethyl)-8-thiophen-2-yl-3-azaspiro [4.5]decan-8-yl]-dimethylamine (Example no. 22, polar diastereomer)

A solution of cyclopentanecarbaldehyde (92 mg, 0.94 mmol) in methanol (1 ml) and sodium cyanoborohydride (204 mg, 3.24 mmol) was added to a cloudy solution of dimethyl-(8-thiophen-2-yl-3-azaspiro[4.5]decan-8-yl)-amine (polar diastereomer) (190 mg, 0.72 mmol) in methanol (6 ml) and the mixture was stirred for 30 min at room temperature. After addition of acetic acid (0.72 ml) the mixture was stirred for a further 3 h at room temperature. The reaction mixture was then diluted with sodium bicarbonate solution (30 ml) and extracted with methylene chloride/2-propanol (4:1, 2×30 ml) and methylene chloride (30 ml). The combined organic phases were dried with sodium sulfate and concentrated i. vac. The crude product (357 mg) was purified by means of flash chromatography (35 g, 22×2.5 cm) with methanol and 0.2% ammonia (25% in H$_2$O).

Example No. 22 (Polar Diastereomer)

Yield: 179 mg (72%), colourless oil
$^1$H-NMR (CDCl$_3$): 1.13-1.24 (m, 2H); 1.37 (ddd, 2H, J=3.5; 10.0 and 13.3 Hz); 1.44-1.63 (m, 6H); 1.64-1.81 (m, 4H); 1.84-2.03 (m, 3H); 2.10 (s, 8H); 2.31 (d, 2H, J=7.3 Hz); 2.41 (5, 2H); 2.49 (t, 2H, J=6.9 Hz); 6.85 (dd, 1H, J=1.1 and 3.6 Hz); 7.03 (dd, 1H, J=3.6 and 5.1 Hz); 7.22 (dd, 1H, J=1.1 and 5.1 Hz).
$^{13}$C-NMR (CDCl$_3$): 25.2 (2C); 31.5 (2C); 33.7 (2C); 34.3 (2C); 37.7; 38.2; 39.1; 41.0; 54.3; 59.7; 62.5; 65.6; 123.2; 124.9; 126.1; 143.2.
LC-MS: [MH-HNMe$_2$]$^+$: m/z=302.3 (100%) and [M+H]$^+$: m/z=347.3 (30%), R$_t$=1.9 min.

Example No. 24a and Example No. 24b

Step 1: (4-Dimethylamino-4-thiophen-2-ylcyclohexylidene)-acetic acid ethyl ester Potassium tert-butylate (3.01 g, 26.9 mmol) was added to a solution of triethyl phosphonoacetate (6.02 g, 5.33 ml, 26.9 mmol) in absolute N,N-dimethylformamide (30 ml) under argon. The mixture was stirred for 10 min at room temperature, before a solution of 4-(dimethylamino)-4-(thiophen-2-yl)cyclohexanone (4.0 g, 17.9 mmol) in absolute N,N-dimethylformamide (60 ml) was added, and the mixture was then stirred for 1 h at room temperature. The reaction mixture was then poured into ice-water (75 g) and the aqueous suspension was extracted with diethyl ether (4×50 ml). The combined organic phases were dried with sodium sulfate and concentrated i. vac.

Yield: 5.20 g (99%), yellow oil
$^1$H-NMR (CDCl$_3$): 1.26 (t, 3H, J=7.1 Hz); 2.03-2.12 (m, 2H); 2.13 (s, 6H); 2.15-2.27 (m, 2H); 2.90-3.09 (m, 4H);

4.13 (q, 2H, J=7.1 Hz); 5.61 (s, 1H); 6.87 (dd, 1H, J=1.1, 3.6 Hz); 7.03 (dd, 1H, J=3.6, 5.1 Hz); 7.23 (dd, 1H, J=1.1, 5.1 Hz).

LC-MS: m/z: [MH-HNMe$_2$]$^+$=249.2 (90%), R$_t$=2.8 min.

Step 2: (4-Dimethylamino-1-nitromethyl-4-thiophen-2-yl-cyclohexyl)-acetic acid ethyl ester Tetra-n-butylammonium fluoride trihydrate (5.10 g, 19.5 mmol) and nitromethane (5.40 g, 4.79 ml, 88.5 mmol) were added to a solution of the crude product of (4-dimethylamino-4-thiophen-2-ylcyclohexylidene)-acetic acid ethyl ester (5.20 g, 17.7 mmol) in tetrahydrofuran (120 ml) and the mixture was stirred for 3 h at 70° C. and then for 18 h at 45° C. The reaction mixture was then concentrated i. vac. The residue was purified by means of flash chromatography (200 g, 20×4.0 cm) with cyclohexane/ethyl acetate (1:9).

Yield: 4.9 g (78%), orange-coloured oil $^1$H-NMR (CDCl$_3$): 1.20-1.28 (m, 3H); 1.44-1.53 (m, 4H); 1.77-1.88 (m, 4H); 2.09 (s, 6H); 2.46 and 2.61 (2 s, 2H); 4.04-4.22 (m, 2H); 4.62 and 4.77 (s, 2H); 6.82-6.85 (m, 1H); 7.02 (m, 1H); 7.22-7.25 (m, 1H).

LC-MS: m/z: [M+H]$^+$=355.2, R$_t$=2.5 min.

This is a diastereoisomer mixture in the ratio of approx. 1:1 which is still contaminated with approx. 15% of educt.

Step 3: 8-(Dimethylamino)-8-thiophenyl-2-yl-3-azaspiro[4.5]decan-3-one (Example no. 30, polar diastereomer, Example no. 31, non-polar diastereomer)

A solution of the diastereoisomer mixture of (4-dimethylamino-1-nitromethyl-4-thiophen-2-ylcyclohexyl)-acetic acid ethyl ester (4.90 g, 13.8 mmol) in ethanol (138 ml) was added to a mixture of iron powder (3.85 g, 69 mmol) and ammonium chloride (18.5 g, 345 mmol) in water (14 ml) and the mixture was heated for 5 h under reflux. The reaction mixture was then filtered, saturated sodium bicarbonate solution (4 ml) was added to the filtrate and the mixture was concentrated i. vac. The residue was separated by flash chromatography (200 g, 20×5.7 cm) with methylene chloride/methanol (10:1) and 1% ammonia (32% in water).

Yield: 2.33 g (61%), diastereoisomer mixture in the ratio of approx. 1:1

The diastereoisomer mixture was separated by repeated medium pressure chromatography (230 g, 3.6×46 cm) or flash chromatography (100 g, 20×4.0 cm), the column material used being spherical silica gel (PharmPrep 60 CC (40-63 µm) and the eluent used being methylene chloride/methanol 95:5 and 1% ammonia (32% in H$_2$O). The ratio of sample to silica gel weight was in each case approx. 1:200.

Example No. 24a (Polar Diastereomer)

Melting point: 215° C., white solid $^1$H-NMR (CDCl$_3$): 1.47-1.55 (m, 2H); 1.78-1.86 (m, 2H); 1.97-2.09 (m, 4H); 2.10 (s, 6H); 2.12 (s, 2H); 3.23 (s, 2H); 5.69 (br s, 1H); 6.85 (dd, 1H, J=1.1, 3.6 Hz); 7.05 (dd, 1H, J=3.6, 5.1 Hz); 7.25 (dd, 1H, J=1.2, 5.1 Hz).

$^{13}$C-NMR (CDCl$_3$): 32.6; 32.7; 38.1; 38.8; 43.1; 53.0; 59.3; 123.4; 124.9; 126.3; 142.6; 177.5.

LC-MS: m/z: [MH-HNMe$_2$]$^+$=234.2 (100%) and [M+H]$^+$=279.2 (16%), R$_t$=1.3 min.

Example No. 24b (Non-Polar Diastereoisomer)

Melting point: 213-222° C., white solid $^1$H-NMR (CDCl$_3$): 1.46-1.54 (m, 2H); 1.76-1.84 (m, 2H); 1.93-2.12 (m, 4H); 2.09 (s, 6H); 2.26 (s, 2H); 3.08 (s, 2H); 5.78 (br s, 1H); 6.85 (dd, 1H, J=1.1, 3.6 Hz); 7.04 (dd, 1H, J=3.6, 5.1 Hz); 7.24 (dd, 1H, J=1.1, 5.1 Hz).

$^{13}$C-NMR (CDCl$_3$): 32.7; 32.8; 38.1; 38.9; 42.5; 53.6; 59.5; 123.4; 124.8; 124.9; 126.3; 142.7; 177.5.

LC-MS: m/z: [MH-HNMe$_2$]$^+$=234.2 (100%) and [M+H]$^+$=279.2 (22%), R$_t$=1.4 min.

Example No. 26

Dimethyl-(8-thiophen-2-yl-3-azaspiro[4.5]decan-8-yl)-amine (Example no. 25, non-polar diastereomer)

A solution of 8-dimethylamino-8-thiophen-2-yl-3-azaspiro[4.5]decan-4-one (non-polar diastereomer) (270 mg, 0.97 mmol) in absolute tetrahydrofuran (15 ml) was added to a suspension of lithium aluminium hydride (184 mg, 4.85 mmol) in absolute tetrahydrofuran (10 ml), while cooling with ice, and the mixture was stirred for 18 h at 60° C. Water (755 µl), 1 N sodium hydroxide solution (2.5 ml) and again water (2.5 ml) were then added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac. The crude product (300 mg) was purified by means of flash chromatography (18 g, 20×2.0 cm) with methylene chloride/methanol (4:1)+1% ammonia (25% in H$_2$O) →methanol+1% ammonia (25% in H$_2$O).

Example No. 25 (Non-polar Diastereoisomer)

Yield: 182 mg (71%), yellow oil $^1$H-NMR (CDCl$_3$): 1.37 (ddd, 2H, J=3.5, 10.1, 13.5 Hz); 1.57-1.65 (m, 4H); 1.89-1.99 (m, 2H); 2.06-2.15 (m, 3H); 2.10 (s, 6H); 2.57 (s, 2H); 2.93 (t, 2H, J=7.1 Hz); 6.84 (dd, 1H, J=1.1, 3.6 Hz); 7.02 (dd, 1H, J=3.6, 5.1 Hz); 7.22 (dd, 1H, J=1.1, 5.1 Hz).

$^{13}$C-NMR (CDCl$_3$): 32.9; 33.8; 38.2; 38.4; 42.4; 46.6; 59.4; 59.9; 123.2; 125.0; 126.1; 143.0.

LC-MS: m/z: [MH-HNMe$_2$]$^+$=220.2 (100%) and [M+H]$^+$=265.3 (48%), R$_t$=0.2 min.

Example No. 27

(8-Benzyl-3-butyl-3-azaspiro[4.5]decan-8-yl)-dimethylamine (Example no. 27, polar diastereomer)

Sodium cyanoborohydride (177 mg, 2.82 mmol) and butyraldehyde (86 mg, 106 µl, 1.19 mmol) were added to a solution of (8-benzyl-3-azaspiro[4.5]decan-8-yl)-dimethylamine (polar diastereomer) (162 mg, 0.59 mmol) in methanol (5 ml) and the mixture was stirred for 30 min at room temperature. After addition of glacial acetic acid (600 µl) the mixture was stirred for a further 2 h at room temperature. Thereafter saturated sodium bicarbonate solution (20 ml) was added and the solution was extracted with methylene chloride (3×20 ml). The combined organic phases were dried with sodium sulfate and concentrated i. vac. The crude product was purified by flash chromatography (10 g, 20×1.5 cm) with methylene chloride/methanol (95:5) and 1% ammonia (25% in water).

Example No. 27 (Polar Diastereoisomer)

Yield: 158 mg (93%), colourless oil
$^1$H-NMR (CDCl$_3$): 0.88 (t, 3H, J=7.3 Hz); 1.06-1.16 (m, 2H); 1.22-1.34 (m, 4H); 1.38-1.47 (m, 2H); 1.60 (t, 2H, J=6.9 Hz); 1.64-1.74 (m, 4H); 2.21 (s, 2H); 2.29 (s, 6H); 2.35-2.41 (m, 2H); 2.58 (t, 2H, J=6.9 Hz); 2.62 (s, 2H); 7.10-7.13 (m, 2H); 7.16-7.28 (m, 3H).
$^{13}$C-NMR (CDCl$_3$): 13.9; 20.7; 30.1; 30.3; 33.0; 36.8; 37.2; 39.7; 40.9; 53.2; 56.7; 57.5; 64.3; 125.6; 127.9; 130.7; 139.3.
LC-MS: m/z: [M+H]$^+$=329.4, R$_t$=0.9 min.

Example No. 28

1-[8-(Dimethylamino)-8-phenyl-3-azaspiro[4.5]decan-3-yl]-butan-1-one (Example no. 28, non-polar diastereomer)

Triethylamine (193 mg, 264 μl, 1.9 mmol) and butyryl chloride (134 mg, 132 μl, 1.26 mmol) were added to a solution of N,N-dimethyl-8-phenyl-3-azaspiro[4.5]decan-8-amine (non-polar diastereomer) (160 mg, 0.62 mmol) in anhydrous methylene chloride (5 ml) and the mixture was stirred for 20 h at room temperature. After addition of methylene chloride (20 ml) the solution was washed with 25% strength potassium carbonate solution (2×20 ml) and the organic phase was dried with sodium sulfate and concentrated i. vac. The crude product (205 mg) was purified by flash chromatography (10 g, 20×1.5 cm) with methylene chloride/methanol (95:5) and 1% ammonia (25% in water).

Example No. 28 (Non-polar Diastereoisomer)

Yield: 106 mg (50%), colourless oil
$^1$H-NMR (CDCl$_3$): 0.90 and 0.95 (2 t, 3H, J=7.4 Hz); 1.28-1.39 (m, 2H); 1.56-1.70 (m, 4H); 1.80 and 1.89 (2 t, 2H, J=7.1 Hz); 1.96-2.04 (m, 2H); 2.05 (s, 6H); 2.09-2.23 (m, 4H); 3.08 and 3.17 (2 s, 2H); 3.45-3.55 (m, 2H); 7.26-7.41 (m, 5H).
$^{13}$C-NMR (CDCl$_3$): 13.96; 14.0; 18.4; 30.4; 30.5; 31.10; 31.11; 34.3; 36.3; 36.7; 38.0; 40.3; 42.3; 44.1; 45.2; 56.4; 58.0; 60.7; 126.7; 127.4; 127.5; 127.6; 127.7; 136.5; 171.8.
The NMR spectra show sometimes doubled signal sets (rotamers).
LC-MS: m/z: [M+H]$^+$=329.4, R$_t$=2.7 min.

Example No. 29

1-[8-(Dimethylamino)-8-phenyl-3-azaspiro[4.5]decan-3-yl]-butan-1-one (Example no. 29, polar diastereomer)

Triethylamine (235 mg, 322 μl, 2.3 mmol) and butyryl chloride (164 mg, 161 μl, 1.5 mmol) were added to a solution of N,N-dimethyl-8-phenyl-3-azaspiro[4.5]decan-8-amine (polar diastereomer) (200 mg, 0.77 mmol) in anhydrous methylene chloride (5 ml) and the mixture was stirred for 4 h at room temperature. After addition of methylene chloride (20 ml) the solution was washed with 25% strength potassium carbonate solution (2×20 ml) and the organic phase was dried with sodium sulfate and concentrated i. vac. The crude product (260 mg) was purified by flash chromatography (10 g, 20×1.5 cm) with methylene chloride/methanol (95:5) and 1% ammonia (25% in water).

Example No. 29 (Polar Diastereoisomer)

Yield: 218 mg (86%), colourless oil
$^1$H-NMR (CDCl$_3$): 0.97 (t, 3H, J=7.4 Hz); 1.23-1.35 (m, 2H); 1.52-1.74 (m, 8H); 2.02 and 2.04 (2 s, 6H); 2.18-2.26 (m, 3H); 2.23-2.41 (br s, 1H); 3.34 and 3.41 (2 s, 2H); 3.39-3.48 (m, 2H); 7.23-7.42 (m, 5H).
$^{13}$C-NMR (CDCl$_3$): 13.7; 14.0; 18.4; 18.5; 18.9; 30.1; 30.9; 31.2; 31.5; 36.4; 36.9; 37.8; 38.0; 38.1; 40.3; 42.3; 43.9; 45.0; 55.1; 56.4; 60.8; 126.5; 126.7; 127.6; 127.63; 127.67; 127.7; 171.9; 172.0.
The NMR spectra show sometimes doubled signal sets (rotamers).
LC-MS: m/z: [M+H]$^+$=329.4, R$_t$=2.8 min.

Example No. 30

Step 1: 8-Cyanomethyl-1,4-dioxaspiro[4.5]decane-8-carboxylic acid ethyl ester A 2.5 M solution of n-buyllithium in n-hexane (11 ml, 27.5 mmol) was added dropwise to a solution of diisopropylamine (2.78 g, 3.92 ml, 27.5 mmol) in tetrahydrofuran (50 ml) in a thoroughly heated flask at −78° C. under argon. The reaction solution was stirred for 15 min at 0° C. and then cooled again to −78° C. and a solution of ethyl 1,4-dioxaspiro[4.5]decane-8-carboxylate (5.36 g, 25 mmol) in tetrahydrofuran (7.5 ml) was added dropwise in the course of 20 min. The resulting mixture was stirred for 1.5 h at −78° C. and a solution of bromoacetonitrile (3.58 g, 1.99 ml, 30 mmol) and 1,3-dimethyl-3,4,5,6-tetrahydro-2-(1H)pyrimidone (DMPU, 1.60 g, 1.5 ml, 12.5 mmol) in tetrahydrofuran (7.5 ml) was then slowly added dropwise. The reaction solution was then warmed to room temperature in the course of approx. 3 h and stirred for a further 20 h at room temperature. Thereafter 0.5 N hydrochloric acid (19 ml) was added to the reaction mixture and the phases were separated. The aqueous phase was extracted with diethyl ether (3×50 ml). The combined organic phases were washed with sodium bicarbonate solution (2×100 ml) and with sodium chloride solution (4×100 ml), dried with sodium sulfate and concentrated i. vac. The crude product (5.5 g) was purified by flash chromatography (250 g, 27×5.4 cm) with ethyl acetate/cyclohexane (1:2).
Yield: 3.60 g (57%), colourless oil
$^1$H-NMR (CDCl$_3$): 1.29 (t, 3H, J=7.1 Hz); 1.62-1.76 (m, 6H); 2.17-2.29 (m, 2H); 2.57 (s, 2H); 3.93 (t, 4H, J=2.2 Hz); 4.23 (q, 2H, J=7.1 Hz).

Step 2: 1,4-Dioxa-10-azadispiro[4.2.4.2]tetradecan-9-one

Sodium borohydride (2.68 g, 71 mmol) was added in portions to a mixture of 8-cyanomethyl-1,4-dioxaspiro[4.5]decane-8-carboxylic acid ethyl ester (3.6 g, 14.2 mmol) and cobalt(II) chloride (922 mg, 7.1 mmol) in tetrahydrofuran (50 ml) and water (25 ml) at 0° C. under argon. The reaction mixture was stirred for 2 d at room temperature. 25% strength ammonia solution (2.5 ml) was then added to the reaction mixture and the mixture formed was filtered. The residue on the filter was washed with tetrahydrofuran/water (2:1). The filtrate was concentrated i. vac. and the aqueous solution was extracted with methylene chloride (3×50 ml). The combined organic extracts were washed with sodium chloride solution, dried with sodium sulfate and concentrated i. vac.
Yield: 2.50 g (83%), white solid which still contained approx. 15% of educt.

¹H-NMR (CDCl₃): 1.49-1.64 (m, 5H); 1.82-1.91 (m, 2H); 1.96-2.04 (m, 2H); 2.03-2.08 (m, 2H); 3.29-3.34 (m, 2H); 3.95 (s, 4H); 5.51 (br s, 1H).

Step 3: 3-Azaspiro[4.5]decane-4.8-dione

5% strength aqueous sulfuric acid (60 ml) was added to a solution of 1,4-dioxa-10-azadispiro[4.2.4.2]tetradecan-9-one (3.48 g, 16.5 mmol) in acetone (50 ml) and the mixture was stirred for 1 d at room temperature. 1 M potassium carbonate solution (60 ml) was added to the reaction mixture and the mixture was concentrated i. vac. The aqueous solution obtained was extracted with methylene chloride (4×50 ml) and the combined organic phases were washed with saturated sodium chloride solution (50 ml), dried with sodium sulfate and concentrated i. vac.

Yield: 2.72 g (98%), white solid
¹H-NMR (CDCl₃): 1.73-1.89 (m, 2H); 2.08-2.21 (m, 4H); 2.33 (ddd, 2H, J=5.8, 10.2 and 15.0 Hz); 2.70 (td, 2H, J=6.3 and 14.8 Hz); 3.41 (dt, 2H, J=0.8 and 7.1 Hz); 3.72 (s, 1H).

Step 4: Dimethylamino-1-oxo-2-azaspiro[4.5]decane-8-carbonitrile

4 N hydrochloric acid (1.97 ml, 7.86 mmol) and then a solution of 3-azaspiro[4.5]decane-4.8-dione (1.09 mg, 6.55 mmol) in methanol (12 ml) were added to a 40° A) strength aqueous dimethylamine solution (3.3 ml, 26.2 mmol), cooled to 0° C., and methanol (1.5 ml). Potassium cyanide (853 mg, 13.1 mmol) was added to this mixture and the mixture was stirred for 20 h at room temperature. After addition of water (30 ml) the solution was extracted with diethyl ether (3×30 ml). The combined organic extracts were dried with sodium sulfate and concentrated, as a result of which the product (390 mg) was isolated. The aqueous solution was then subsequently extracted with methylene chloride (3×20 ml). The combined methylene chloride extracts were dried with sodium sulfate and concentrated, as a result of which 820 mg of the product were obtained.

Yield: 1.21 g (83%), white solid
¹H-NMR (CDCl₃): 1.35-1.67 (m, 3H); 1.76-2.09 (m, 5H); 2.18-2.31 (m, 2H); 2.33 and 2.35 (2s, 6H); 3.28-3.35 (m, 2H); 6.50 and 6.60 (2s, 1H). This is a diastereoisomer mixture in the ratio of approx. 2:1.

Step 5: 8-(Dimethylamino)-8-(5-methylthiophen-2-yl)-3-azaspiro[4.5]decan-4-one (Example no. 42, polar diastereomer)

Magnesium (292 mg, 12 mmol) and an iodine crystal were heated in a secure apparatus under argon until iodine gas evolved. After 10 min absolute diethyl ether (20 ml) and a further iodine crystal were added. The mixture was heated to the boiling point and a solution of 2-bromo-5-methylthiophene (2.12 g, 1.35 ml, 12 mmol) in absolute diethyl ether (20 ml) was then slowly added dropwise such that the solution continued to boil. After the end of the addition the mixture was heated for a further 30 min under reflux and the solution was then cooled to 0° C.

A solution of dimethylamino-1-oxo-2-azaspiro[4.5]decane-8-carbonitrile (1.06 g, 4.8 mmol) in absolute tetrahydrofuran (50 ml) was slowly added dropwise to this ice-cooled solution under argon and the mixture was then stirred overnight at room temperature. After addition of saturated ammonium chloride solution (50 ml) the tetrahydrofuran was removed i. vac. The aqueous solution obtained was extracted with methylene chloride (3×50 ml) and the combined organic phases were washed with saturated sodium chloride solution (50 ml), dried with sodium sulfate and concentrated i. vac. 160 mg of the crude product (1.56 g) were purified, for the purpose of release, by means of flash chromatography (10 g, 20×1.5 cm) with ethyl acetate/methanol (4:1), as a result of which 139 mg of pure target compound were obtained. This is the polar diastereoisomer. The remainder was reacted further as crude product.

Example No. 30 (Polar Diastereoisomer)

Yield: 1.56 g (crude product)
Melting point: 173-176° C.
¹H-NMR (CDCl₃): 1.27-1.33 (m, 2H); 1.66 (dt, J=12.9, 3.2 Hz, 2H); 2.00 (t, J=6.9 Hz, 2H); 2.11 (s, 6H); 2.18 (dt, J=13.2, 3.1 Hz, 2H); 2.36-2.43 (m, 2H); 2.46 (s, 3H); 3.27-3.31 (m, 2H); 6.21 (br s, 1H); 6.62 (d, J=3.5 Hz, 1H); 6.65-6.67 (m, 1H).
¹³C-NMR (CDCl₃): 15.2; 28.0; 31.8; 32.6; 37.9; 38.7; 43.3; 58.5; 123.6; 124.7; 137.2; 143.1; 182.8.
LC-MS: m/z: [MH-HNMe₂]⁺=248.2, R_f=2.5 min.

Example No. 31

Dimethyl-[8-(5-methylthiophen-2-yl)-3-azaspiro[4.5]decan-8-yl]-amine (Example no. 31, polar diastereomer)

A solution of 8-(dimethylamino)-8-(5-methylthiophen-2-yl)-3-azaspiro[4.5]decan-4-one (polar diastereomer) (1.40 g, 4.8 mmol) in anhydrous tetrahydrofuran (100 ml) was added to a suspension of lithium aluminium hydride (456 mg, 12 mmol) in anhydrous tetrahydrofuran (20 ml) in a thoroughly heated apparatus, while cooling with ice, and the mixture was then stirred at 60° C. overnight. Water (857 µl), 1 N sodium hydroxide solution (2.1 ml) and again water (2.1 ml) were added to the reaction solution, while cooling with ice, and the mixture was stirred for 1 h at room temperature. The mixture was filtered through sea sand and the residue was washed with tetrahydrofuran. The filtrate was dried with sodium sulfate and concentrated i. vac. 160 mg of the crude product (1.18 g) were purified, for the purpose of release, by means of flash chromatography (10 g, 20×1.5 cm) with ethyl acetate methanol (4:1)→methanol+1% ammonia (25% in water), as a result of which 80 mg of the target compound were obtained, which still contained minimal impurities.

Example No. 31 (Polar Diastereoisomer)

Yield: 1.18 g (crude product), yellow viscous oil
¹H-NMR (CDCl₃): 1.37-1.41 (m, 2H); 1.47 (t, J=7.1 Hz, 2H); 1.57-1.65 (m, 2H); 1.85-1.91 (m, 2H); 2.00-2.16 (m, 2H, overlapped); 2.11 (s, 6H); 2.47 (s, 3H); 2.75 (s, 2H); 2.91 (t, J=7.1 Hz, 2H); 6.62 (d, J=3.5 Hz, 1H); 6.67-6.68 (m, 1H). The NH proton could not be identified.
¹³C-NMR (CDCl₃): 15.3; 32.9; 33.6; 38.2; 42.4; 46.1; 57.9; 59.9; 64.2; 124.3; 124.9; 137.6; 140.8.
LC-MS: m/z: [MH-HNMe₂]⁺=234.2, R_f=0.7 min.

Example No. 32

1-[8-(Dimethylamino)-8-(5-methylthiophen-2-yl)-3-azaspiro[4.5]decan-3-yl]-butan-1-one (Example no. 32, polar diastereomer)

Butyryl chloride (91 mg, 90 µl, 0.86 mmol) was added to a solution of 8-(dimethylamino)-8-(5-methylthiophen-2-yl)-

3-azaspiro[4.5]decan-4-one (polar diastereomer) (200 mg, 0.72 mmol) and triethylamine (110 mg, 152 µl, 1.1 mmol) in absolute methylene chloride (10 ml) and the mixture was stirred for 2 h at room temperature. The reaction mixture was then adjusted to pH 9-10 with 1 M potassium carbonate solution and stirred for 15 min. The phases were separated and the aqueous phase was extracted with methylene chloride (3×50 ml). The combined organic phases were dried with sodium sulfate and concentrated i. vac. The residue (230 mg) was purified by flash chromatography on spherical silica gel (PharmPrep 60 CC, 40-63 mm, 10 g, 20×1.5 cm) with ethyl acetate/methanol (4:1).

Example No. 32 (Polar Diastereoisomer)

Yield: 153 mg (63%), colourless viscous oil
$^1$H-NMR (CDCl$_3$): 0.94-0.98 (m, 3H); 1.35-1.46 (m, 2H); 1.58-1.71 (m, 6H); 1.81-1.95 (m, 2H); 2.10 (s, 2H); 2.13 (s, 4H); 2.19 (m, 4H); 2.46 (d, J=1.0 Hz, 1H); 2.47 (d, J=1.0 Hz, 2H); 3.30 (s, 1.3H); 3.36 (s, 0.7H); 3.42-3.49 (m, 2H); 6.61 (d, J=3.5 Hz, 0.3H); 6.62 (d, J=3.5 Hz, 0.7H); 6.66 (dd, J=3.4; 1.1 Hz, 0.3H); 6.69 (dd, J=3.4; 1.1 Hz, 0.7H).
$^{13}$C-NMR (CDCl$_3$): 14.0; 15.3; 18.3; 18.5; 31.2; 31.3; 32.6; 33.3; 36.3; 36.3; 36.9; 37.3; 38.1; 40.1; 42.0; 43.9; 45.0; 55.2; 56.2; 60.1; 60.4; 124.3; 124.6; 124.9; 125.2; 137.7; 138.0; 171.8; 171.9.

The NMR spectra show sometimes doubled signal sets (rotamers).
LC-MS: m/z: [MH-HNMe$_2$]$^+$=304.3, R$_t$ 3.0 min.

Example No. 33

3-Butyl-8-(dimethylamino)-8-thiophen-2-yl-3-azaspiro[4.5]decan-2-one (Example no. 33, non-polar diastereomer)

A mixture of 8-(dimethylamino)-8-thiophen-2-yl-2-azaspiro[4.5]decan-3-one (non-polar diastereoisomer) (200 mg, 0.72 mmol) and potassium tert-butylate (92 mg, 0.82 mmol) in N,N-dimethylformamide (5 ml) was stirred for 40 min at room temperature, before iodobutane (151 mg, 94 µl, 0.82 mmol) was added and stirring was carried out for a further 18 h at room temperature. The reaction mixture was then diluted with ethyl acetate (50 ml) and washed with water (3×10 ml). The organic phase was dried with sodium sulfate and concentrated i. vac. The crude product (190 mg) was purified by means of flash chromatography (10 g, 20×1.5 cm) with methylene chloride methanol (95:5)+1% ammonia (25% in H$_2$O).

Example No. 33 (Non-Polar Diastereoisomer)

Yield: 130 mg (54%), yellow oil
$^1$H-NMR (CDCl$_3$): 0.89 (t, 3H, J=7.3 Hz); 1.22-1.33 (m, 2H); 1.39-1.50 (m, 4H); 1.70-1.79 (m, 2H); 1.92-2.08 (m, 4H); 2.10 (s, 6H); 2.32 (s, 2H); 3.04 (s, 2H); 3.22 (t, 2H, J=7.3 Hz); 6.84 (dd, 1H, J=1.1, 3.6 Hz); 7.04 (dd, 1H, J=3, 6, 5.1 Hz); 7.24 (dd, 1H, J=1.1, 5.1 Hz).
$^{13}$C-NMR (CDCl$_3$): 13.7; 20.0; 29.3; 32.7; 32.9; 35.6; 38.1; 42.0; 43.8; 58.6; 59.5; 123.4; 124.9; 126.2; 142.8; 173.5.
LC-MS: m/z: [MH-HNMe$_2$]$^+$=290.3 (100%) and [M+H]$^+$=335.3 (33%), R$_t$=2.9 min.

Example No. 34

8-(Dimethylamino)-3-methyl-8-thiophen-2-yl-3-azaspiro[4.5]decan-2-one (Example no. 34, non-polar diastereomer)

A mixture of 8-(dimethylamino)-8-thiophen-2-yl-2-azaspiro[4.5]decan-3-one (non-polar diastereoisomer) (200 mg, 0.72 mmol) and potassium tert-butylate (92 mg, 0.82 mmol) in N,N-dimethylformamide (5 ml) was stirred for 40 min at room temperature, before methyl iodide (116 mg, 51 µl, 0.82 mmol) was added and stirring was carried out for a further 5 h at room temperature. Since the reaction was not complete, potassium tert-butylate (40 mg, 0.36 mmol) and methyl iodide (58 mg, 25 µl, 0.41 mmol) were again added and the mixture was stirred for a further 18 h at room temperature. The reaction mixture was then diluted with ethyl acetate (50 ml) and washed with water (3×10 ml). The organic phase was dried with sodium sulfate and concentrated i. vac. The crude product was purified by means of flash chromatography (10 g, 20×1.5 cm) with methylene chloride/methanol (95:5)+1% ammonia (25% in H$_2$O).

Example No. 34 (Non-polar Diastereoisomer)

Yield: 124 mg (59%), white solid
Melting point: 88-94° C.
$^1$H-NMR (CDCl$_3$): 1.40-1.49 (m, 2H); 1.68-1.78 (m, 2H); 1.90-2.07 (m, 4H); 2.08 (s, 6H); 2.29 (s, 2H); 2.77 (s, 3H); 3.04 (s, 2H); 6.82 (dd, 1H, J=0.9, 3.4 Hz); 7.02 (dd, 1H, J=3.6, 5.0 Hz); 7.21 (dd, 1H, J=0.8, 5.1 Hz).
$^{13}$C-NMR (CDCl$_3$): 29.5; 32.6; 32.9; 35.3; 38.1; 43.4; 59.4; 61.0; 123.4; 124.9; 126.2; 142.7; 173.7.
LC-MS: m/z: [MH-HNMe$_2$]$^+$=248.2 (100%) and [M+H]$^+$=293.3 (50%), R$_t$=2.2 min.

Example No. 35

[3-Butyl-8-(5-methylthiophen-2-yl)-3-azaspiro[4.5]decan-8-yl]-dimethylamine (Example no. 35, polar diastereomer)

Butyraldehyde (61 mg, 75 µl, 0.84 mmol), acetic acid (650 µl) and sodium cyanoborohydride (184 mg, 2.9 mmol) were added successively to a solution of dimethyl-[8-(5-methylthiophen-2-yl)-3-azaspiro[4.5]decan-8-yl)-amine (polar diastereomer) (180 mg, 0.65 mmol) in absolute methanol (5 ml) and the mixture was stirred for 4 h at room temperature. Saturated potassium bicarbonate solution (30 ml) was then added to the reaction mixture and the mixture was extracted with methylene chloride/2-propanol (4:1) (3×30 ml). The combined organic phases were washed with saturated sodium chloride solution (50 ml), dried with sodium sulfate and concentrated i. vac. The residue (186 mg) was purified by flash chromatography on spherical silica gel (PharmPrep 60 CC, 40-63 mm, 10 g, 20×1.5 cm) with methanol which contained 1% ammonia (25% in H$_2$O).

Example No. 35 (Polar Diastereoisomer)

Yield: 106 mg (49%), colourless viscous oil
$^1$H-NMR (CDCl$_3$): 0.91 (t, J=7.3 Hz, 3H); 1.27-1.52 (m, 8H); 1.62-1.69 (m, 2H); 1.78-1.93 (m, 2H); 2.02-2.05 (m, 2H); 2.11 (s, 6H); 2.34-2.38 (m, 2H); 2.41 (s, 2H); 2.46 (d, J=1.1 Hz, 3H); 2.49 (d, J=6.9 Hz, 2H); 6.61 (d, J=3.5 Hz, 1H); 6.67 (qd, J=3.3, 1.0 Hz, 1H).
$^{13}$C-NMR (CDCl$_3$): 14.1; 15.3; 20.9; 31.1; 33.6; 34.6; 38.2; 40.8; 54.0; 56.8; 59.8; 65.6; 124.3; 124.9; 137.5.
LC-MS: m/z: [M+H]$^+$=335.2, R$_t$=1.6 min.

Example No. 41

1-[8-Dimethylamino-8-(5-methylthiophen-2-yl)-2-azaspiro[4.5]dec-2-yl]-2-methoxyethanone Dimethyl-[8-(5-methylthiophen-2-yl)-3-azaspiro[4.5]decan-8-yl]-amine (Example no. 31) (0.28 g, 1.00 mmol) and triethylamine (0.33 ml, 2.40 mmol) were dissolved in abs. THF (5 ml) under argon, methoxyacetyl chloride (0.11 ml, 0.13 g, 1.20 mmol) was added and the mixture was stirred at room temperature for 1 d. For working up the reaction mixture was concentrated to dryness i. vac., the residue was taken up in methylene chloride and the mixture was washed with saturated NaHCO$_3$ solution (2×25 ml) and water (2×25 ml). The organic phase was dried over Na$_2$SO$_4$, filtered and concentrated i. vac. The residue obtained was purified by means of a PuriFlash 430 and Interchim cartridge 15 μm×25 g with chloroform/methanol (100:0→0:100).

Yield: 120 mg (34%)

$^1$H-NMR (CDCl$_3$): 1.34-1.41 (2 H, m); 1.53-1.68 (4 H, m); 1.94 (2 H, m); 2.10 (2 H, s); 2.17 (6 H, s); 2.44 (3 H, m); 3.27 (1 H, s); 3.36-3.41 (4 H, m); 3.47 (2 H, t); 3.97 (2 H, d); 6.64 (2 H, m).

Step 2: [3-(2-Methoxyethyl)-8-(5-methylthiophen-2-yl)-3-azaspiro[4.5]decan-8-yl]-dimethylamine (Example no. 58, polar diastereomer)

LiAlH$_4$ (26 mg, 0.68 mmol) was added to a solution of 1-[8-dimethylamino-8-(5-methylthiophen-2-yl)-2-azaspiro[4.5]dec-2-yl]-2-methoxyethanone (0.12 g, 0.34 mmol) in abs. THF (5 ml) under argon and the mixture was stirred under reflux for 1 h. For working up the reaction mixture was hydrolysed with a few drops of water at 0° C. The suspension was then subsequently stirred for 1 h. The solution was filtered over a sea sand frit, the sand was rinsed with THF and methylene chloride and the combined solution was concentrated i. vac.

Example No. 41 (Polar Diastereoisomer)

Yield: 62 mg (54%)

$^1$H-NMR (CDCl$_3$): 1.34-1.42 (2 H, m); 1.50 (2 H, t); 1.66 (2 H, m); 1.81 (2 H, bs); 2.05 (1 H, m); 2.09 (6 H, s); 2.45 (5 H, s); 2.54 (2 H, t); 2.60 (2 H, t); 3.33 (3 H, s); 3.46 (2 H, t); 6.60 (1 H, m); 6.65 (1 H, m).

LC-MS: m/z: [M+H]$^+$=337.2, R$_t$=1.1 min.

Example No. 48

2-Cyclopropyl-1-[8-(dimethylamino)-8-thiophen-2-yl-3-azaspiro[4.5]decan-3-yl]-ethanone (Example no. 48, polar diastereomer)

Carbonyldiimidazole (365 mg, 2.25 mmol) was added to a solution of cyclopropylacetic acid (180 mg, 174 μl, 1.8 mmol) in absolute tetrahydrofuran (20 ml) and the mixture was stirred for 2 h under reflux (evolution of CO$_2$). A solution of dimethyl-(8-thiophen-2-yl-3-azaspiro[4.5]decan-8-yl)-amine (Example no. 18) (397 mg, 1.5 mmol) in tetrahydrofuran (10 ml) was added to the solution and the mixture was stirred for 2 h under reflux. The reaction mixture was then concentrated i. vac., the residue was dissolved in ethyl acetate (30 ml) and the solution was extracted with water (3×20 ml). The organic phase was dried with sodium sulfate and concentrated i. vac. The crude product was purified by means of flash chromatography (18 g, 20×2.0 cm) with methylene chloride/methanol (95:5).

Example No. 48 (Polar Diastereoisomer)

Yield: 280 mg (54%), brown oil $^1$H-NMR (CDCl$_3$): 0.12-0.19 (2 H, m); 0.55 (2 H, ddd, J=8.1, 5.8 and 4.6 Hz); 1.03-1.14 (1 H, m); 1.34-1.45 (2 H, m); 1.58-1.63 (1.4 H, m); 1.64-1.72 (3 H, m); 1.85-2.03 (2.6 H, m); 2.09 (3 H, s); 2.13 (3 H, br s); 2.17-2.20 (3 H, m); 3.29 (1.2 H, s), 3.38 (0.8 H, s); 3.41 (0.8 H, t, J=7.2 Hz); 3.49 (1.2 H, t, J=7.3 Hz); 6.85 (0.4 H, dd, J=3.6 and 1.1 Hz); 6.86-6.88 (0.6 H, m); 7.03 (0.4 H, dd, J=5.1 and 3.5 Hz); 7.06 (0.6 H, dd, J=5.1 and 3.6 Hz); 7.23 (0.4 H, dd, J=5.1 and 1.1 Hz); 7.24-7.28 (0.6 H, m).

$^{13}$C-NMR (CDCl$_3$): 4.4; 4.4; 6.8; 6.9; 31.1; 31.2; 32.8; 33.0; 33.3; 35.6; 37.2; 38.0; 38.1; 39.5; 39.9; 40.0; 42.0; 43.9; 45.0; 55.3; 56.4; 60.0; 123.4; 123.8; 124.9; 125.4; 126.1; 126.4; 143.5; 171.4; 171.5.

The NMR spectra show sometimes a doubled signal set (rotamers).

LC-MS: m/z: [MH-HNMe$_2$]$^+$=302.3 (100%) and [M+H]$^+$=347.3 (50% R$_t$=2.8 min.

Example No. 92

8-(Cyclohexylmethyl)-8-dimethylamino-3-azaspiro[4.5]decan-4-one (Example no. 92, a diastereoisomer)

A 0.5 M solution of cyclohexylmethylmagnesium bromide in tetrahydrofuran (63.2 ml, 31.6 mmol) was added dropwise to a solution of 8-(dimethylamino)-1-oxo-2-azaspiro[4.5]decane-8-carbonitrile (2 g, 9.03 mmol) in anhydrous tetrahydrofuran (75 ml) at 0° C. and the mixture was stirred for 18 h at room temperature. Saturated ammonium chloride solution (90 ml) was then added to the mixture, while cooling with ice. The phases were separated and the aqueous phase was extracted with ethyl acetate (2×25 ml). The combined organic phases were dried with sodium sulfate and concentrated i. vac. The residue (2.4 g) was purified by flash chromatography (200 g, 20×5.7 cm) with methylene chloride/methanol (98:2) and 1% ammonia (25% in water).

Example No. 92 (A Diastereoisomer)

Yield: 1.20 g (46%), white solid

Melting point: 190-193° C.

$^1$H-NMR (CDCl$_3$): 0.88-1.00 (2 H, m); 1.06-1.27 (8 H, m); 1.32 (2 H, dt, J=14.1 and 3.4 Hz); 1.54-1.74 (7 H, m); 2.03 (2 H, t, J=7.0 Hz); 2.08 (2 H, dt, J=13.2 and 3.2 Hz); 2.16 (6 H, s); 3.26-3.31 (2 H, m); 6.04 (1 H, br s).

$^{13}$C-NMR (CDCl$_3$): 26.2; 26.7; 27.0; 28.9; 32.0; 32.9; 33.5; 36.0; 36.9; 37.7; 38.1; 38.8; 43.8; 56.4; 183.5.

Only one diastereoisomer was isolated.

LC-MS: m/z: [M+H]$^+$=293.2, low UV activity.

Example No. 93

Step 1: (8-Cyclohexylmethyl-2-azaspiro[4.5]dec-8-yl)dimethylamine

A solution of 8-(cyclohexylmethyl)-8-dimethylamino-3-azaspiro[4.5]decan-4-one (Example no. 158, a diastereoisomer) (1.05 g, 3.59 mmol) in anhydrous tetrahydrofuran (40 ml) was added dropwise to a suspension of lithium aluminium hydride (683 mg, 18 mmol) in anhydrous tetrahydrofuran (20 ml), while cooling with ice. The mixture was stirred for 18 h at 50° C. and water (700 µl), 1 N sodium hydroxide solution (1.4 ml) and again water (1.4 ml) were then added dropwise, while cooling with ice. The suspension was stirred for 1 h at room temperature and thereafter filtered through sodium sulfate. The residue on the filter was washed with tetrahydrofuran and the filtrate was concentrated i. vac.

Yield: 884 mg (99%), colourless oil $^1$H-NMR (CDCl$_3$): 0.89-1.01 (2 H, m); 1.06-1.45 (9 H, m); 1.50-1.74 (10 H, m); 1.80-1.90 (2 H, m); 2.17 (6 H, s); 2.64 (2 H, s); 2.94 (2 H, t, J=7.1 Hz). The NH proton could not be identified.

Step 2: 1-[8-(Cyclohexylmethyl)-8-dimethylamino-3-azaspiro[4.5]decan-3-yl]-butan-1-one (Example no. 159, a diastereomer)

Butyryl chloride (193 mg, 190 µl, 1.80 mmol) was added to a solution of (8-cyclohexylmethyl-2-azaspiro[4.5]dec-8-yl)dimethylamine (420 mg, 1.5 mmol) and triethylamine (230 mg, 315 µl, 2.26 mmol) in anhydrous methylene chloride (15 ml) and the mixture was stirred overnight at room temperature. 25% strength potassium carbonate solution (15 ml) was then added to the mixture and the mixture was stirred for 15 min at room temperature. The phases were separated and the aqueous phase was extracted with methylene chloride (3×5 ml). The combined organic phases were dried with sodium sulfate and concentrated i. vac. The residue (515 mg) was purified by flash chromatography (38 g, 20×2.8 cm) with methylene chloride/methanol (95:5) and 1% ammonia (25% in water).

Example No. 93 (A Diastereoisomer)

Yield: 448 mg (85%), colourless oil $^1$H-NMR (CDCl$_3$): 0.88-1.01 (5 H, m); 1.05-1.46 (10 H, m); 1.52-1.91 (13 H, m); 2.157 and 2.164 (6 H, 2 s); 2.12-2.25 (2 H, m); 3.17 (1.2 H, s); 3.25 (0.8 H, s); 3.46 (0.8 H, t, J=7.1 Hz); (1.2 H, t, J=7.2 Hz).

$^{13}$C-NMR (CDCl$_3$): 14.0; 18.4; 18.5; 26.2; 26.5; 28.7; 29.2; 29.8; 30.3; 33.1; 33.2; 35.9; 36.1; 36.2; 36.8; 37.1; 37.7; 37.9; 40.3; 42.0; 44.3; 45.2; 57.1; 57.2; 59.5; 171.77; 171.84.

The NMR spectra show sometimes doubled signal sets (rotamers).

LC-MS: m/z: [M+H]$^+$=349.3, low UV activity.

Example No. 9

Step 1: 8-Cyclopentylmethyl-8-dimethylamino-2-azaspiro[4.5]decan-1-one

A solution of 8-(dimethylamino)-1-oxo-2-azaspiro[4.5]decane-8-carbonitrile (1.96 g, 8.8 mmol) in anhydrous tetrahydrofuran (40 ml) was added dropwise to a solution of cyclopentylmethylmagnesium iodide (approx. 32 mmol) under an argon atmosphere at 0° C. The reaction mixture was stirred for 18 h at room temperature and saturated ammonium chloride solution (80 ml) was then added, while cooling with ice. The phases were separated and the aqueous phase was extracted with ethyl acetate (2×30 ml). The combined organic phases were dried with sodium sulfate and concentrated i. vac. The residue (1.88 g) was purified by flash chromatography (100 g, 20×4.0 cm) with methylene chloride/methanol (95:5) and 1% ammonia (25% in water).

Yield: 519 mg (21%), white solid $^1$H-NMR (CDCl$_3$): 0.98-1.10 (2 H, m); 1.10-1.17 (2 H, m); 1.30-1.40 (4 H, m); 1.42-1.84 (9 H, m); 2.01 (2 H, t, J=6.9 Hz); 2.17 (6 H, s); 3.28 (2 H, dd, J=13.9 and 0.8 Hz); 6.51 (1 H, s).

$^{13}$C-NMR (CDCl$_3$): 25.2; 27.2; 29.1; 32.2; 35.3; 36.1; 36.9; 38.9; 43.8; 56.2; 183.3.

Step 2: (8-Cyclopentylmethyl-2-azaspiro[4.5]dec-8-yl)dimethylamine

A solution of 8-cyclopentylmethyl-8-dimethylamino-2-azaspiro[4.5]decan-1-one (539 mg, 1.93 mmol) in anhydrous tetrahydrofuran (20 ml) was added dropwise to a suspension of lithium aluminium hydride (368 mg, 9.7 mmol) in anhydrous tetrahydrofuran (10 ml), while cooling with ice. The mixture was stirred for 18 h at 50° C. and thereafter water (377 µl), 1 N sodium hydroxide solution (754 µl) and again water (754 µl) were added dropwise, while cooling with ice. The suspension was stirred for 1 h at room temperature and then filtered through sodium sulfate, the residue on the filter was washed with tetrahydrofuran and the filtrate was concentrated i. vac.

Yield: 463 mg (90%), colourless oil $^1$H-NMR (CDCl$_3$): 1.00-1.12 (2 H, m); 1.17-1.27 (2 H, m); 1.31-1.95 (17 H, m); 2.18 (6 H, s); 2.64 (2 H, s); 2.93 (2 H, t, J=7.0 Hz). The NH signal could not be identified.

$^{13}$C-NMR (CDCl$_3$): 25.0; 29.8; 31.8; 35.1; 36.0; 36.7; 37.2; 37.4; 42.6; 46.6; 56.9; 60.7.

Step 3

[3-Butyl-8-(cyclopentylmethyl)-3-azaspiro[4.5]decan-8-yl]-dimethylamine (Example no. 164, a diastereomer)

Butyryl chloride (114 mg, 112 µl, 1.07 mmol) was added to a solution of (8-cyclopentylmethyl-2-azaspiro[4.5]dec-8-yl)dimethylamine (237 mg, 0.89 mmol) and triethylamine (136 mg, 187 µl, 1.34 mmol) in anhydrous methylene chloride (10 ml) and the mixture was stirred for 18 h at room temperature. 25% strength potassium carbonate solution (9 ml) was added to the mixture and the mixture was stirred for 15 min at room temperature. The phases were separated and the aqueous phase was extracted with methylene chloride (2×15 ml). The combined organic phases were dried with sodium sulfate and concentrated vac. The residue (307 mg) was purified by flash chromatography (18 g, 20×2.0 cm) with methylene chloride/methanol (95:5) and 1% ammonia (25% in water).

Example No. 95 (A Diastereoisomer)

Yield: 206 mg (68%), colourless oil $^1$H-NMR (CDCl$_3$): 0.94 (1.5 H, t, J=7.4 Hz); 0.95 (1.5 H, t, J=7.4 Hz); 1.00-1.14 (2 H, m); 1.20-1.30 (2 H, m); 1.32-1.84 (20 H, m); 2.10-2.24 (7 H, m); 3.17 (1 H, s); 3.25 (1 H, s); 3.45 (1 H, t, J=7.2 Hz); 3.50 (1 H, t, J=7.2 Hz).

$^{13}$C-NMR (CDCl$_3$): 14.0; 18.4; 25.1; 28.8; 29.5; 29.8; 30.2; 33.0; 35.0; 35.1; 35.2; 35.5; 35.7; 36.1; 36.2; 36.5; 36.8; 36.9; 37.0; 37.2; 40.3; 42.2; 44.3; 45.3; 56.7; 56.8; 57.1; 59.5; 171.76; 171.84.

The NMR spectra show sometimes doubled signal sets (rotamers).

LC-MS: m/z: [M+H]⁺=335.3, low UV activity.

Example No. 106 and Example No. 107

Step 1: 10-Butyl-1,4-dioxa-10-azadispiro[4.2.4.2]tetradecan-9-one

Potassium tert-butylate (3.19 g, 28.4 mmol) was added to a solution of substance D (equation 1) (5.0 g, 23.7 mmol) in N,N-dimethylformamide (40 ml), whereupon a precipitate precipitated out, and the mixture was then stirred for 30 min at room temperature. n-Butyl iodide (5.23 g, 3.23 ml, 28.4 mmol) was then added to the suspension and the mixture was stirred for 18 h at room temperature. The reaction mixture was then concentrated i. vac., the residue was taken up in ethyl acetate (100 ml) and the solution was washed with water (3×40 ml). The organic phase was dried with sodium sulfate and concentrated i. vac.

Yield: 5.30 g (84%), yellow oil

¹H-NMR (CDCl₃): 0.91 (3 H, t, J=7.3 Hz); 1.22-1.34 (2 H, m); 1.42-1.50 (4 H, m); 1.53-1.62 (2 H, m); 1.81-1.88 (2 H, m); 1.91 (2 H, t, J=6.9 Hz); 1.93-2.02 (2 H, m); 3.26 (4 H, t, J=7.0 Hz); 3.92-3.95 (4 H, m).

LC-MS: m/z: [M+H]⁺=268.3, R$_t$=3.3 min.

Step 2: 10-Butyl-1,4-dioxa-10-azadispiro[4.2.4.2]tetradecane

A solution of 10-butyl-1,4-dioxa-10-azadispiro[4.2.4.2]tetradecan-9-one (5.22 g, 19.5 mmol) in absolute tetrahydrofuran (40 ml) was added to a suspension of lithium aluminium hydride (2.95 g, 77.8 mmol) in absolute tetrahydrofuran (20 ml), while cooling with ice, and the mixture was stirred for 66 h at 50° C. Water (2.95 ml), 15% strength sodium hydroxide solution (2.95 ml) and again water (8.85 ml) were then cautiously added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac.

Yield: 4.83 g (98%), colourless oil

¹H-NMR (CDCl₃): 0.90 (3 H, t, J=7.3 Hz); 1.26-1.36 (2 H, m); 1.40-1.49 (2 H, m); 1.55-1.66 (10 H, m); 2.33-2.38 (4 H, m); 2.53 (2 H, t, J=6.9 Hz); 3.92 (4 H, s).

LC-MS: m/z: [M+H]⁺=254.4, R$_t$=2.0 min.

Step 3: 2-Butyl-2-azaspiro[4.5]decan-8-one

A solution of 10-butyl-1,4-dioxa-10-azadispiro[4.2.4.2]tetradecane (4.83 g, 19.1 mmol) in 5% strength sulfuric acid (50 ml) was stirred for 18 h at room temperature. The reaction solution was then washed with diethyl ether (3×20 ml) in order to remove neutral substances present. The aqueous phase was then rendered alkaline (pH ~9) with 4 N sodium hydroxide solution and extracted with methylene chloride (4×30 ml). The combined organic phases of the alkaline extraction were dried with sodium sulfate and concentrated i. vac.

Yield: 3.54 g (89%), yellow oil

¹H-NMR (CDCl₃): 0.92 (3 H, t, J=6.9 Hz); 1.34 (2 H, qd, J=14.3 and 7.2 Hz); 1.43-1.52 (2 H, m); 1.76 (2 H, t, J=6.9 Hz); 1.87 (2 H, t, J=6.8 Hz); 2.31-2.38 (4 H, m); 2.39-2.44 (2 H, m); 2.49 (2 H, s); 2.62 (2 H, t, J=6.9 Hz).

Step 4: 2-Butyl-8-dimethylamino-2-azaspiro[4.5]decane-8-carbonitrile

4 N hydrochloric acid (4.23 ml) and then a solution of the crude product of 2-butyl-2-azaspiro[4.5]decan-8-one (3.54 g, 16.9 mmol) in methanol (20 ml) were added to a 40% strength aqueous dimethylamine solution (10.4 ml, 75.3 mmol), cooled to 0° C., and methanol (4.7 ml). Potassium cyanide (2.67 g, 40 mmol) was added to the mixture and the mixture was stirred for 18 h at room temperature. Water (75 ml) was then added to the reaction solution and the mixture was extracted with methylene chloride (6×15 ml). The combined organic phases were dried with sodium sulfate and concentrated i. vac.

Yield: 4.27 g (96%), yellow oil

This is a diastereoisomer mixture.

¹H-NMR (CDCl₃): All the characteristic signals are present.

Step 5: [2-Butyl-8-(iminophenylmethyl)-2-azaspiro[4.5]dec-8-yl]-dimethylamine

A 1.8 M phenyllithium solution in di-n-butyl ether (4.2 ml, 7.6 mmol) was added dropwise to a solution of 2-butyl-8-dimethylamino-2-azaspiro[4.5]decane-8-carbonitrile (1.0 g, 3.8 mmol) in absolute tetrahydrofuran (40 ml) at 0° C. under argon and the mixture was then stirred for 3 h at room temperature. Water (10 ml) and sodium chloride solution (10 ml) were then added, the phases were separated and the aqueous phase was extracted with methylene chloride (3×20 ml). The combined organic phases were dried with sodium sulfate and concentrated i. vac.

Yield: 1.59 g (>100%, crude product)

The crude product was reacted further without prior purification.

¹H-NMR (DMSO-d₆): All the characteristic signals are present (two diastereoisomers).

LC-MS: m/z: [M+H]⁺=342.3, R$_t$=0.6 min.

Step 6: [3-Butyl-8-(dimethylamino)-3-azaspiro[4.5]dec-8-yl]-phenylmethanone (Example no. 180, polar diastereomer and Example no. 181, non-polar diastereomer)

A solution of the crude product of [2-butyl-8-(iminophenylmethyl)-2-azaspiro[4.5]dec-8-yl]-dimethylamine (1.57 g, max. 3.8 mmol) in tetrahydrofuran/water (1:1, ~20 ml) was acidified with formic acid (5 ml) and stirred for 18 h at room temperature. The tetrahydrofuran was then concentrated i. vac. and the aqueous residue was extracted with ethyl acetate (3×10 ml). The combined acid, aqueous extracts were rendered alkaline with 1 N sodium hydroxide solution and extracted with methylene chloride (3×20 ml). The combined organic extracts of the alkaline extraction were dried with sodium sulfate and concentrated i. vac. The crude product was purified by means of flash chromatography (100 g, 20×4.0 cm) with chloroform/methanol (95:5) and 1% acetic acid. In order to obtain the free bases of the particular product batches, the fractions were in each case concentrated i. vac., the residues were taken up in 1 M potassium carbonate solution and the suspensions were extracted with methylene chloride (3×10 ml). The combined organic phases were dried with sodium sulfate and concentrated i. vac.

Example No. 106 (Polar Diastereoisomer)

Yield: 250 mg (19%), yellow oil
$^1$H-NMR (CDCl$_3$): 0.88 (3 H, t, J=7.3 Hz); 1.24-1.37 (4 H, m); 1.39-1.54 (4 H, m); 1.62-1.71 (4 H, m); 2.03-2.09 (2 H, m); 2.26 (2 H, s); 2.31 (6 H, s); 2.32-2.37 (2 H, m); 2.57 (2 H, t, J=6.8 Hz); 7.33-7.39 (2 H, m); 7.43-7.49 (1 H, m); 8.21-8.25 (2 H, m).
LC-MS: m/z: [M+H]$^+$=343.4, R$_t$=2.2 min.

Example No. 107 (Non-Polar Diastereoisomer)

Yield: 170 mg (13%), yellow oil
$^1$H-NMR (CDCl$_3$): 0.92 (3 H, t, J=7.3 Hz); 1.27-1.38 (4 H, m); 1.46-1.65 (8 H, m); 2.06-2.12 (2 H, m); 2.32 (6 H, s); 2.47-2.52 (2 H, m); 2.55 (s, 2 H); 2.63 (2 H, t, J=6.8 Hz); 7.34-7.39 (2 H, m); 7.44-7.49 (1 H, m); 8.20-8.24 (2 H, m).
LC-MS: m/z: [M+H]$^+$=343.4, R$_t$=2.2 min.

Example No. 117

8-(5-Chlorothiophen-2-yl)-8-dimethylamino-3-azaspiro[4.5]decan-4-one (Example no. 117, a diastereomer)

A suspension of 8-(dimethylamino)-1-oxo-2-azaspiro[4.5]decane-8-carbonitrile (1.76 g, 7.9 mmol) in absolute tetrahydrofuran (75 ml) was slowly added dropwise to a 0.5 M suspension of 5-chloro-2-thienylmagnesium bromide (5.29 g, 48 ml, 23.9 mmol) in tetrahydrofuran under argon, a clear solution being formed. The solution was then stirred overnight at 50° C. After addition of saturated ammonium chloride solution (100 ml) the tetrahydrofuran was removed i. vac. The aqueous solution obtained was extracted with methylene chloride (3×50 ml) and the combined organic phases were washed with saturated sodium chloride solution (50 ml), dried with sodium sulfate and concentrated i. vac. The crude product (2.45 g) was purified by means of flash chromatography (100 g, 20×4.0 cm) with ethyl acetate/methanol (97:3).

Example No. 117 (A Diastereoisomer)

Yield: 1.47 g (59%), yellow solid.
Melting point: 198-201° C.
$^1$H-NMR (CDCl$_3$): 1.28-1.34 (2 H, m); 1.61-1.68 (2 H, m); 2.01 (2 H, t, J=6.9 Hz); 2.12 (6 H, s); 2.17 (2 H, dt, J=13.1 and 3.1 Hz), 2.32-2.40 (2 H, m); 3.28-3.32 (2 H, m); 5.90 (1 H, br s); 6.60 (1 H, d, J=3.8 Hz); 6.83 (1 H, d, J=3.8 Hz).
$^{13}$C-NMR (CDCl$_3$): 27.9; 31.5; 32.7; 37.9; 38.7; 43.1; 58.9; 123.1; 125.2; 127.4; 144.4; 182.4.
LC-MS: m/z: [MH-HNMe$_2$]$^+$=268.2, R$_t$=2.6 min.

Example No. 152

8-(Dimethylamino)-8-(5-methylthiophen-2-yl)-3-azaspiro[4.5]decan-2-one (Example no 152, polar diastereomer)

Trifluoroacetic acid (5 ml) was added to a solution of 8-(dimethylamino)-8-(5-methylthiophen-2-yl)-2-oxo-3-azaspiro[4.5]decane-3-carboxylic acid tert-butyl ester (polar diastereoisomer) (900 mg, 2.3 mmol) in anhydrous methylene chloride (50 ml) and the mixture was stirred for 3 h at room temperature. The reaction mixture was concentrated i. vac., methylene chloride (30 ml) was added to the residue and the mixture was washed with saturated sodium bicarbonate solution (3×20 ml). The organic phase was dried with sodium sulfate and concentrated i. vac. The crude product (622 mg) was purified by flash chromatography (18 g, 20×2.0 cm) with methylene chloride/methanol (14:1) and 0.5% ammonia (25% in water).

Example No. 152 (Polar Diastereoisomer)

Yield: 502 mg (75%), white solid
Melting point: 198-201° C.
$^1$H-NMR (CDCl$_3$): 1.46-1.54 (2 H, m); 1.72-1.80 (2 H, m); 1.85-2.10 (4 H, m); 2.11 (6 H, s); 2.25 (2 H, s); 2.45 (3 H, d, J=1.0 Hz); 3.07 (2 H, s); 5.72 (1 H, br s); 6.61 (1 H, d, J=3.5 Hz); 6.66-6.69 (1 H, m).
$^{13}$C-NMR (CDCl$_3$): 15.2; 32.6; 32.8; 38.2; 38.9; 42.3; 53.7; 59.7; 124.5; 125.0; 137.9; 177.4.
LC-MS: m/z: [MH-HNMe$_2$]$^+$=248.3 (100%) and [M+H]$^+$=293.3 (10%), R$_t$=2.2 min.

Example No. 153

8-(Dimethylamino)-8-(5-methylthiophen-2-yl)-3-azaspiro[4.5]decan-2-one (Example no. 153, non-polar diastereomer)

Trifluoroacetic acid (5 ml) was added to a solution of 8-(dimethylamino)-8-(5-methylthiophen-2-yl)-2-oxo-3-azaspiro[4.5]decane-3-carboxylic acid tert-butyl ester (Example no. 251, non-polar diastereoisomer) (820 mg, 2.09 mmol) in anhydrous methylene chloride (50 ml) and the mixture was stirred for 3 h at room temperature. The reaction mixture was concentrated i. vac., methylene chloride (30 ml) was added to the residue and the mixture was washed with saturated sodium bicarbonate solution (3×20 ml). The organic phase was dried with sodium sulfate and concentrated I. vac. The crude product (530 mg) was purified by flash chromatography (18 g, 20×2.0 cm) with methylene chloride/methanol (95:5) and 1% ammonia (25% in water).

Example No. 153 (Non-polar Diastereoisomer)

Yield: 425 mg (70%), white solid
$^1$H-NMR (CDCl$_3$): 1.46-1.56 (2 H, m); 1.74-1.84 (2 H, m); 1.86-2.09 (4 H, m); 2.11 (6 H, s); 2.115 (2 H, s); 2.47 (3H, d, J=1.1 Hz); 3.22 (2 H, s); 5.78 (1 H, br s); 6.61 (1 H, d, J=3.5 Hz); 6.67-6.69 (1 H, m).
$^{13}$C-NMR (CDCl$_3$): 15.2; 32.6; 38.1; 38.8; 43.2; 52.7; 59.4; 124.5; 124.9; 137.9; 140.0; 177.4.
LC-MS: m/z: [M+H]$^+$=293.3, R$_t$=2.2 min.

Example No. 162

Step 1: 8-Dimethylamino-8-phenyl-2-azaspiro[4.5]decan-3-one

A suspension of 8-dimethylamino-3-oxo-2-azaspiro[4.5]decane-8-carbonitrile (536 mg, 2.4 mmol) in anhydrous tetrahydrofuran (30 ml) was added dropwise to a 2 M solution of phenylmagnesium chloride in tetrahydrofuran (3 ml, 6 mmol), cooled to 0° C., under argon and the mixture was then stirred for 18 h at room temperature. After addition of saturated ammonium chloride solution (15 ml) the phases were separated and the aqueous phase was extracted with ethyl acetate (3×30 ml). The combined organic phases were dried with sodium sulfate and concentrated i. vac.

Yield: 601 mg (92 white solid (crude product)
Diastereoisomer mixture: Polar:non-polar ratio=1:2.

The diastereoisomer ratio was determined with the aid of the singlets of the HN—CH$_2$ group at 3.27 (polar diastereoisomer) and 3.02 ppm (non-polar diastereoisomer) in the $^1$H-NMR spectrum.

Step 2: 8-Dimethylamino-3-oxo-8-phenyl-2-azaspiro[4.5]decan-2-carboxylic acid tert-butyl ester A solution of di-tert-butyl dicarbonate (4.05 g, 18.6 mmol) in anhydrous tetrahydrofuran (30 ml) and 4-dimethylaminopyridine (206 mg, 1.69 mmol) was added to a solution of 8-dimethylamino-8-phenyl-2-azaspiro[4.5]decan-3-one (4.60 g, 16.9 mmol) in anhydrous acetonitrile (300 ml) and anhydrous tetrahydrofuran (100 ml) and the mixture was stirred for 3 d at room temperature. Since the reaction was not complete, a solution of di-tert-butyl dicarbonate (2.00 g, 9 mmol) in anhydrous acetonitrile (10 ml) was again added and the mixture was stirred for 3 h at 50° C. and for 18 h at room temperature. The solvent was then removed i. vac., the residue was dissolved in methylene chloride (100 ml) and the solution was washed with water (3×50 ml) and saturated sodium chloride solution (50 ml). The organic phase was dried with sodium sulfate and concentrated i. vac. The crude product (7.00 g) was purified by flash chromatography (400 g, 20×7.5 cm) with ethyl acetate/methanol (9:1).

Non-Polar Diastereoisomer
Yield: 1.40 g (22%), white solid
Melting point: 174-176° C.
$^1$H-NMR (CDCl$_3$): 1.34-1.42 (2 H, m); 1.53 (9 H, s); 1.72-1.82 (2 H, m); 1.96-2.03 (2 H, m); 2.04 (6 H, s); 2.10-2.24 (2 H, m); 2.25 (2 H, s); 3.61 (2 H, s); 7.26-7.31 (3 H, m); 7.36-7.41 (2 H, m).
$^{13}$C-NMR (CDCl$_3$): 28.1; 30.0; 32.2; 34.3; 38.0; 45.8; 56.6; 60.1; 82.8; 126.8; 127.4; 127.8; 150.1; 173.4.
LC-MS: m/z: [M+H]$^+$=373.4, R$_t$=2.6 min.

Polar Diastereoisomer
Yield: 1.26 g (20%), white solid
Melting point: 176-181° C.
$^1$H-NMR (CDCl$_3$): 1.34-1.44 (2 H, m); 1.48 (9 H, s); 1.68-1.77 (2 H, m); 1.90-2.03 (2 H, m); 2.04 (6 H, s); 2.15-2.30 (2 H, m); 2.48 (2 H, s); 3.36 (2 H, s); 7.28-7.32 (3 H, m); 7.36-7.42 (2 H, m).
$^{13}$C-NMR (CDCl$_3$): 28.0; 29.8; 32.3; 34.5; 38.0; 44.9; 57.6; 60.3; 60.5; 82.7; 126.8; 127.5; 127.8; 136.2; 150.1; 173.4.
LC-MS: m/z: [M+H]$^+$=373.4, R$_t$=3.0 min.

Step 3: 8-Dimethylamino-8-phenyl-2-azaspiro[4.5]decan-3-one (non-polar diastereomer)

Trifluoroacetic acid (5 ml) was added to a solution of 8-dimethylamino-3-oxo-8-phenyl-2-azaspiro[4.5]decane-2-carboxylic acid tert-butyl ester (non-polar diastereoisomer) (1.46 g, 3.9 mmol) in anhydrous methylene chloride (50 ml) and the mixture was stirred for 3 h at room temperature. The reaction mixture was concentrated i. vac., the residue was dissolved in methylene chloride (50 ml) and the solution was washed with saturated sodium bicarbonate solution (3×20 ml). The organic phase was dried with sodium sulfate and concentrated i. vac.
Yield: 1.03 g (96%), white solid
Melting point: >260° C.
$^1$H-NMR (CDCl$_3$): 1.37-1.46 (2 H, m); 1.76-1.84 (2 H, m); 1.90-2.02 (2 H, br s); 2.04 (6 H, s); 2.06 (2 H, s); 2.15-2.27 (2 H, br s); 3.27 (2 H, s); 5.60 (1 H, s); 7.26-7.32 (3 H, m); 7.36-7.42 (2 H, m).

Step 4: 8-(Dimethylamino)-3-methyl-8-phenyl-3-azaspiro[4.5]decan-2-on (Example no. 162, non-polar diastereomer)

Potassium tert-butylate (74 mg, 0.66 mmol) was added to a suspension of 8-dimethylamino-8-phenyl-2-azaspiro[4.5]decan-3-one (non-polar diastereomer) (150 mg, 0.55 mmol) in anhydrous tetrahydrofuran (20 ml) and anhydrous N,N-dimethylformamide (3 ml) and the mixture was stirred for 30 min at room temperature. Methyl iodide (94 mg, 41 µl, 0.66 mmol) was then added and the mixture was stirred for 5 h at room temperature. The solution was then concentrated i. vac. After addition of ethyl acetate (50 ml) the mixture was washed with water (3×20 ml). The organic phase was then extracted with 5% strength formic acid (3×20 ml). The combined aqueous, acid phases were adjusted to pH 10 with 5 N sodium hydroxide solution and extracted with ethyl acetate (3×20 ml). The combined organic phases were dried with sodium sulfate and concentrated vac.

Example No. 162 (Non-polar Diastereoisomer)

Yield: 120 mg (76%), white solid
Melting point: 145-148° C.
$^1$H-NMR (CDCl$_3$): 1.33-1.42 (2 M, m); 1.70-1.78 (2 H, m); 1.85-2.02 (2 H, m); 2.03 (6 H, s); 2.12 (2 H, s); 2.13-2.25 (2 H, m); 2.83 (3 H, s); 3.34 (2 H, s); 7.24-7.31 (3 H, m); 7.35-7.41 (2 H, m).
$^{13}$C-NMR (CDCl$_3$): 29.7; 30.2; 33.1; 35.5; 38.0; 44.2; 60.1; 60.5; 126.7; 127.4; 127.7; 173.8. LC-MS: m/z: [M+H]$^+$=287.4, R$_t$=1.3 min.

Example No. 186

Step 1: 2-[3-(tert-Butyldimethylsilanyloxy)-3-methylbutyl]-8-dimethylamino-8-phenyl-2-azaspiro[4.5]decan-3-one A suspension of powdered sodium hydroxide dried i vac. (106 mg, 2.64 mmol) in absolute dimethylsulfoxide (5 ml) was stirred for 40 min at room temperature. 8-Dimethylamino-8-phenyl-2-azaspiro[4.5]decan-3-one (Example no. 152, step 3, non-polar diastereomer) (180 mg, 0.66 mmol) was then added to this, before a solution of 3-(tert-butyldimethylsilyloxy)-3-methylbutyl 4-methylbenzenesulfonate (272 mg, 0.73 mmol) in dimethylsulfoxide (2 ml) was added, and the mixture was stirred for 2 h at room temperature. A solution of 3-(tert-butyldimethylsilyloxy)-3-methylbutyl 4-methylbenzenesulfonate (136 mg, 0.37 mmol) in dimethylsulfoxide (2 ml) was then again added and the mixture was stirred for 18 h at room temperature. Water (100 ml) was then added to the mixture and the mixture was extracted with ethyl acetate (4×20 ml). The combined organic phases were dried with sodium sulfate and concentrated i. vac. The residue was repeatedly taken up in toluene (3×10 ml) and the mixture was each time concentrated again i. vac.

The crude product (420 mg, >100%) was reacted further without prior purification.

Step 2: 8-Dimethylamino-2-(3-hydroxy-3-methylbutyl)-8-phenyl-2-azaspiro[4.5]decan-3-one (Example no. 186, non-polar diastereomer)

2 N hydrochloric acid (7.5 ml) was added to a solution of the crude product of 2-[3-(tert-butyldimethylsilanyloxy)-3- methylbutyl]-8-dimethylamino-8-phenyl-2-azaspiro[4.5]decan-3-one (non-polar diastereomer) (420 mg, max. 0.66 mmol) in methanol (20 ml) and the mixture was stirred for 2 h at room temperature. The reaction mixture was rendered alkaline with 1 M potassium carbonate solution and the methanol was removed i. vac. The aqueous residue was extracted with methylene chloride (3×20 ml). The combined organic phases were dried with sodium sulfate and concentrated i. vac. The crude product was purified by means of flash chromatography (18 g, 20×2.0 cm) with methylene chloride/methanol (4:1).

Example No. 186 (Non-polar Diastereoisomer)

Yield: 105 mg (44%), white solid
Melting point: 114-119° C.
$^1$H-NMR (CDCl$_3$): 1.25 (6 H, s); 1.30-1.41 (2 H, m); 1.63-1.68 (2 H, m); 1.69-1.79 (2 H, m); 1.91-2.03 (2 H, m); 2.02 (6 H, s); 2.12 (2 H, s); 2.13-2.24 (4 H, m); 2.28-2.45 (1 H, br s); 3.27 (2 H, s); 3.37-3.42 (2 H, m); 7.25-7.30 (3 H, m); 7.35-7.40 (2 H, m).
$^{13}$C-NMR (CDCl$_3$): 29.6; 30.2; 32.8; 35.8; 38.0; 38.8; 40.1; 44.5; 58.3; 60.1; 69.5; 126.7; 127.4; 127.7; 136.4; 174.0.
LC-MS: m/z: [MH-HNMe$_2$]$^+$=314.3 (82%) and [M+H]$^+$=359.3 (100%), R$_t$=2.3 min.

Example No. 187

Step 1: 2-[3-(tert-Butyldimethylsilanyloxy)-3-methylbutyl]-8-dimethylamino-8-phenyl-2-azaspiro[4.5]decan-3-one A suspension of powdered sodium hydroxide dried i. vac. (106 mg, 2.64 mmol) in absolute dimethylsulfoxide (5 ml) was stirred for 40 min at room temperature. 8-Dimethylamino-8-phenyl-2-azaspiro[4.5]decan-3-one (180 mg, 0.66 mmol) was then added to this and a solution of 3-(tert-butyldimethylsilyloxy)-3-methylbutyl 4-methylbenzenesulfonate (272 mg, 0.73 mmol) in dimethylsulfoxide (2 ml) was added. After 2 h at room temperature a solution of 3-(tert-butyldimethylsilyloxy)-3-methylbutyl 4-methylbenzenesulfonate (136 mg, 0.37 mmol) in dimethylsulfoxide (2 ml) was again added and the mixture was stirred for 18 h at room temperature. Water (100 ml) was then added to the mixture and the mixture was extracted with ethyl acetate (4×20 ml). The combined organic phases were dried with sodium sulfate and concentrated i. vac. The residue was repeatedly taken up in toluene (3×10 ml) and the mixture was each time concentrated again i. vac.
The crude product (450 mg, >100%) was reacted further without prior purification.

Step 2: 8-Dimethylamino-2-(3-hydroxy-3-methylbutyl)-8-phenyl-2-azaspiro[4.5]decan-3-one (Example no. 187, polar diastereomer)

2 N hydrochloric acid (7.5 ml) was added to a solution of the crude product of 2-[3-(tert-butyldimethylsilanyloxy)-3-methylbutyl]-8-dimethylamino-8-phenyl-2-azaspiro[4.5]decan-3-one (polar diastereomer) (450 mg, max. 0.66 mmol) in methanol (20 ml) and the mixture was stirred for 2 h at room temperature. The reaction mixture was then rendered alkaline with 1 M potassium carbonate solution and the methanol was removed i. vac. The aqueous residue was extracted with methylene chloride (3×20 ml). The combined organic phases were dried with sodium sulfate and concentrated i. vac. The crude product was purified by means of flash chromatography (18 g, 20×2.0 cm) with methylene chloride/methanol (4:1). The product batch (150 mg) obtained by this procedure contained 3-methyl-1,3-butanediol as an impurity and was purified again by means of flash chromatography (10 g, 20×1.5 cm) with methylene chloride/methanol (9:1).

Example No. 187 (Polar Diastereoisomer)

Yield: 120 mg (51%), colourless oil
$^1$H-NMR (CDCl$_3$): 1.21 (6 H, s); 1.32-1.40 (2 H, m); 1.56-1.61 (2 H, m); 1.67-1.74 (2 H, m); 1.88-2.00 (2 H, m); 2.02 (6 H, s); 2.15-2.29 (2 H, m); 2.34 (2 H, s); 3.02 (2 H, s); 3.31-3.36 (2 H, m); 7.24-7.30 (3 H, m); 7.35-7.40 (2 H, m).
$^{13}$C-NMR (CDCl$_3$): 29.5; 30.0; 33.0; 35.9; 38.0; 38.6; 40.0; 43.6; 59.2; 60.7; 69.5; 126.7; 127.6; 127.8; 136.2; 174.0.
LC-MS: m/z: [MH-HNMe$_2$]$^+$=314.3 (100%) and [M+H]$^+$=359.4 (55%), R$_t$=2.6 min.

Example No. 213

Step 1: 3-(8-Dimethylamino-8-thiophen-2-yl-2-azaspiro[4.5]dec-2-yl)propionic acid methyl ester Methyl acetate (2.00 g, 2.16 ml, 24 mmol) was added to a solution of Example no. 21 (320 mg, 1.2 mmol) in anhydrous tetrahydrofuran (10 ml) and the mixture was stirred for 3 d at 150° C. The reaction mixture was then concentrated i. vac. and the residue (365 mg) was purified by flash chromatography (18 g, 20×2.0 cm) with methylene chloride/methanol (95:5) and 0.5% ammonia (25% in water).

Yield: 274 mg (65%), colourless oil
$^1$H-NMR (CDCl$_3$): 1.33-1.41 (2 H, m); 1.51 (2 H, t, J=6.8 Hz); 1.65-1.74 (2 H, m); 1.87-2.00 (2 H, m); 2.10 (8 H, s); 2.44 (2 H, s); 2.47-2.56 (4 H, m); 2.70-2.75 (2 H, m); 3.68 (3 H, s); 6.85 (1 H, d, J=3.0 Hz); 7.03 (1 H, dd, J=5.1 and 3.5 Hz); 7.23 (1 H, br d, J=4.8 Hz).

Step 2: 1-[8-(Dimethylamino)-8-thiophen-2-yl-3-azaspiro[4.5]decan-3-yl]-3-ethylpentan-3-ol (Example no. 213, polar diastereomer)

Titanium tetra-isopropylate (45 mg, 48 µl, 0.16 mmol) was added to a solution of 3-(8-dimethylamino-8-thiophen-2-yl-2-azaspiro[4.5]dec-2-yl)propionic acid methyl ester (274 mg, 0.78 mmol) in anhydrous tetrahydrofuran (5 ml) under argon. A 0.3 M solution of ethylmagnesium bromide (7.8 ml, 2.34 mmol) in diethyl ether was then slowly added dropwise in the course of 1 h and the mixture was stirred overnight at room temperature. 5% strength aqueous sulfuric acid (5 ml) was added to the honey-yellow solution and the mixture was stirred vigorously. pH 10 was established by addition of 2 M potassium carbonate solution and the mixture was extracted with methylene chloride (3×30 ml). The combined organic phases were dried with sodium sulfate and concentrated i. vac. The crude product (250 mg) was purified by flash chromatography (10 g, 20×1.5 cm) with methylene chloride/methanol (95:5) and 1% ammonia (25% in water).

Example No. 213 (Polar Diastereoisomer)

Yield: 85 mg (29%), oil
$^1$H-NMR (CDCl$_3$): 0.84 (6 H, t, J=7.5 Hz); 1.31-1.58 (10 H, m); 1.64-1.74 (2 H, m); 1.88-1.98 (2 H, m); 2.00-2.09 (2 H, m); 2.10 (6H, s); 2.48 (2 H, s); 2.58 (2 H, t, J=7.0 Hz); 2.64-2.69 (2 H, m); 6.25 (1 H, br s); 6.83 (1 H, dd, J=3.5 and 1.1 Hz); 7.02 (1 H, dd, J=5.1 and 3.5 Hz); 7.21 (1 H, dd, J=5.1 and 1.1 Hz).
$^{13}$C-NMR (CDCl$_3$): 8.1; 26.9; 30.9; 33.5; 33.9; 37.2; 38.1; 40.9; 52.2; 53.5; 59.6; 65.5; 74.9; 123.2; 124.8; 126.1; 143.1.
LC-MS: m/z: [M+H]$^+$=379.4, R$_t$=1.9 min.

Example No. 214

Step 1: 8-Dimethylamino-8-thiophen-2-ylmethyl-2-azaspiro[4.5]decan-1-one

Lithium chloride (269 mg, 6.33 mmol) was heated by means of a hot air gun in a Schlenk flask under a high vacuum for 10 min. Magnesium (220 mg, 9.05 mmol) was then added and the mixture was heated once more for 10 min by means of a hot air gun under a high vacuum. Absolute tetrahydrofuran (1.5 ml) freshly distilled over calcium hydride and one drop of a 25% strength diisobutylaluminum hydride solution in toluene were then added and the mixture was stirred for 5 min at room temperature. Substance F (equation 1, R$_1$=R$_2$=methyl) (400 mg, 1.18 mmol) was then added and a solution, dried for 40 min over a molecular sieve of 4 Å, of 2-(bromomethyl)thiophene (1.18 g, 6.66 mmol) in absolute tetrahydrofuran (2 ml) freshly distilled over calcium hydride was slowly added dropwise to this suspension, warming of the solution and dissolving of the starting substance being observed. The reaction mixture was stirred for 30 min at room temperature and then for 3 h at 55° C. Thereafter saturated ammonium chloride solution (6 ml) was slowly added and the mixture was stirred for 16 h at room temperature. After addition of 2 M sodium hydroxide solution (8 ml) and water (30 ml) the mixture was extracted with ethyl acetate (2×100 ml) and chloroform/methanol (7:1, 50 ml), the combined organic phases were washed with saturated sodium chloride solution (30 ml) and dried with magnesium sulfate and the solvent was removed i. vac. The residue (706 mg) was taken up in diethyl ether (20 ml), the suspension was filtered, the residue on the filter was washed with diethyl ether and the filtrate was concentrated i. vac. This residue was purified by flash chromatography (18 g, 20×2 cm) with ethyl acetate/methanol (2:0.1→2:0.4) and 1% ammonia (25% in water).
Non-Polar Diastereoisomer
Yield: 240 mg (45%), colourless oil.
$^1$H-NMR (CDCl$_3$): 1.15 (2 H, d, J=13.1 Hz); 1.32 (2 H, t, J=14.1 Hz); 1.74-1.87 (4 H, m); 2.02-2.12 (2 H, m); 2.29 (6 H, s); 2.85 (2 H, s); 3.21 (2 H, t, J=7.1 Hz); 6.16 (1 H, s); 6.75 (1 H, d, J=2.8 Hz); 6.92 (1 H, dd, J=5.2 and 3.4 Hz); 7.12 (1 H, dd, J=5.2 and 1.2 Hz).
LC-MS: [M+H]$^+$: m/z=293.3, R$_t$=2.2 min.
Polar Diastereoisomer
Yield: 20 mg (3.8%), colourless oil.
$^1$H-NMR (CDCl$_3$): 1.46-1.63 (4 H, m); 1.70-1.85 (4 H, m), 2.00 (2 H, t, J=6.9 Hz); 2.31 (6 H, s); 3.10 (2 H, s); 3.28 (2 H, t, J=6.9 Hz); 6.25 (1 H, s); 6.86 (1 H, dd, J=3.4 Hz); 6.90 (1 H, dd, J=5.1 Hz); 7.13 (1 H, dd, J=5.1 Hz).
LC-MS: [M+H]$^+$: m/z=293.3, R$_t$=0.6 min.

Step 2: N,N-Dimethyl-8-(thiophen-2-ylmethyl)-2-azaspiro[4.5]decan-8-amine (non-polar diastereomer)

8-Dimethylamino-8-thiophen-2-ylmethyl-2-azaspiro[4.5]decan-1-one (non-polar diastereomer) (230 mg, 0.79 mmol), dissolved in absolute tetrahydrofuran (6 ml) was slowly added to a suspension of lithium aluminium hydride (150 mg, 3.95 mmol) in absolute tetrahydrofuran (5 ml) in a Schlenk flask under argon at 0° C. The ice bath was then removed and the mixture was stirred for 16 h at 50° C. Water (150 µl), 15% strength sodium hydroxide solution (150 µl), tetrahydrofuran (10 ml) and water (450 µl) were then added successively at 0° C. and the suspension was stirred for 1 h at room temperature. The suspension was filtered through sodium sulfate, the residue was washed with methylene chloride (2×30 ml) and the filtrate was concentrated to dryness i. vac.
Yield: 207 mg (95%), yellow oil.
$^1$H-NMR (CDCl$_3$): 1.20-1.28 (2 H, m); 1.33-1.45 (4 H, m); 1.60-1.71 (4 H, m); 2.28 (6 H, s); 2.65 (2 H, s); 2.87-2.93 (4 H, m); 6.76 (1 H, dd, J=3.4 and 1.1 Hz); 6.92 (1 H, dd, J=5.2 and 3.4 Hz); 7.12 (1 H, dd, J=5.2 and 1.2 Hz).
LC-MS: [M+H]$^+$: m/z=279.3, R$_t$=0.2 min.

Step 3: 1-(8-Dimethylamino-8-thiophen-2-ylmethyl-2-azaspiro[4.5]dec-2-yl)-butan-1-one (Example no, 214, non-polar diastereomer)

First triethylamine (116 mg, 160 µl, 1.14 mmol) and then slowly butyryl chloride (99 mg, 96 µl, 0.93 mmol) were added to a solution of N,N-dimethyl-8-(thiophen-2-ylmethyl)-2-azaspiro[4.5]decan-8-amine (non-polar diastereomer) (199 mg, 0.72 mmol) in absolute methylene chloride (5 ml) in a 10 ml Schlenk flask under argon at room temperature. The reaction mixture was stirred for 16 h at room temperature and saturated sodium carbonate solution (20 ml) was then added. After addition of methylene chloride (10 ml) the phases were separated and the aqueous phase was extracted with methylene chloride (2×25 ml). The combined organic phases were washed successively with saturated sodium carbonate solution (20 ml), 0.2 M sodium hydroxide solution (10 ml) and saturated sodium chloride solution (10 ml) and dried with magnesium sulfate and the solvent was removed i. vac. The crude product (264 mg) was purified first by flash chromatography (PuriFlash PF-15SIHP, 8 g) with methylene chloride/methanol 95:5→80:20) and 1% ammonia (25% in water) and then again by flash chromatography (7 g, 20×1.5 cm) with methylene chloride/methanol (95:5→80:20) and 1% ammonia (25% in water).

Example No. 217 (Non-polar Diastereoisomer)

Yield: 161 mg (65%), yellow solid.
Melting point: 86° C.
1H-NMR (CDCl3): 0.94 (3 H, t, J=7.4 Hz); 1.21-1.47 (4 H, m); 1.56 (1 H, t, J=7.3 Hz); 1.60-1.77 (7 H, m); 2.18 (2 H, t, J=7.5 Hz); 2.27 and 2.28 (6 H, s); 2.88 and 2.90 (2 H, 2 s); 3.16 (1 H, s); 3.24 (1 H, s); 3.38-3.46 (2 H, m); 6.80-6.73 (1 H, m); 6.91-6.94 (1 H, m); 7.13 (1 H, d, J=5.1 Hz). Some signals are to be seen as a doubled signal set (rotamers).
$^{13}$C-NMR (CDCl$_3$): 13.99; 14.01; 18.3; 18.4; 28.5; 29.0; 29.8; 30.1; 31.1; 31.3; 32.7; 34.9; 36.3; 36.7; 37.1; 37.1;

40.1; 42.0; 44.2; 45.3; 57.36; 57.38; 59.4; 123.9; 124.0; 126.3; 126.5; 126.45; 126.60; 126.7; 141.0; 141.2; 171.7; 171.8.

LC-MS: [M+H]$^+$: m/z=349.3, $R_t$=2.8 min.

Example No. 234

Step 1: Cyclopent-1-enemagnesium bromide

Magnesium (1.70 g, 70 mmol) and an iodine crystal were heated in a secure apparatus such that iodine gas was formed. The mixture was cooled to room temperature and anhydrous tetrahydrofuran (17 ml) and a further iodine crystal were then added. A solution of 1-bromocyclopentene (10.3 g, 70 mmol) in anhydrous tetrahydrofuran (23 ml) was then added dropwise such that the reaction mixture started to boil. The mixture was stirred for a further 1 h under reflux and then cooled to room temperature. The solution obtained in this way was employed in the next step.

Step 2: (8-Cyclopent-1-enyl-1,4-dioxaspiro[4.5]dec-8-yl)-dimethylamine

A solution of 8-(dimethylamino)-1,4-dioxaspiro[4.5]decane-8-carbonitrile (6.05 g, 28.7 mmol) in anhydrous tetrahydrofuran (40 ml) was added dropwise to the solution from step 1 (max. 70 mmol). The mixture was stirred overnight at room temperature and then for 2 h at 60° C. and thereafter saturated ammonium chloride solution (50 ml) and water (50 ml) were added, while cooling with ice. The pH of the mixture was adjusted to 9 with 4 N sodium hydroxide solution. The phases were separated and the aqueous phase was extracted with ethyl acetate (3×50 ml). The combined organic phases were dried with sodium sulfate and concentrated i. vac. The crude product was purified by flash chromatography (400 g, 20×7.5 cm) with methylene chloride/methanol (95:5) and 1% ammonia (25% in water).

Yield: 2.54 g (35%), yellow oil
$^1$H-NMR (CDCl$_3$): 1.50-1.60 (2 H, m); 1.70-1.94 (8 H, m); 2.20 (6 H, s); 2.24-2.30 (2 H, m); 2.31-2.39 (2 H, m); 3.88-3.96 (4 H, m); 5.53 (1 H, m).
$^{13}$C-NMR (CDCl$_3$): 23.6; 29.0; 31.4; 32.2; 33.1; 38.5; 58.4; 64.1; 109.0; 128.2; 143.8.

LC-MS: [M+H]$^+$: m/z=252.3, $R_t$=1.9 min.

Step 3: (8-Cyclopentyl-1,4-dioxaspiro[4.5]dec-8-yl)-dimethylamine

5% rhodium on activated aluminium oxide (2.05 g, 1 mmol) was added to a solution of (8-cyclopent-1-enyl-1,4-dioxaspiro[4.5]dec-8-yl)-dimethylamine (2.53 g, 10 mmol) in anhydrous methanol (220 ml). The suspension was stirred for 18 h at 50° C. and under a hydrogen pressure of 4 bar and then filtered through Celite which had been washed with methanol beforehand. The filtrate was concentrated i. vac.

Yield: 2.51 g (100%), yellow oil
$^1$H-NMR (CDCl$_3$): 1.20-1.34 (2 H, m); 1.38-1.64 (10 H, m); 1.68-1.78 (2 H, m); 1.82-1.94 (2 H, m); 2.07 (1 H, m); 2.27 (6 H, s); 3.91-3.94 (4 H, m).
$^{13}$C-NMR (CDCl$_3$): 25.0; 28.0; 28.5; 30.0; 37.8; 43.8; 57.5; 64.1; 109.6.

Step 4: 4-Cyclopentyl-4-dimethylaminocyclohexanone

A solution of (8-cyclopentyl-1,4-dioxaspiro[4.5]dec-8-yl)-dimethylamine (5.21 g, 20.5 mmol) in 1 M aqueous sulfuric acid (150 ml) was stirred for 48 h at room temperature. The mixture was washed with methylene chloride (2×70 ml). The aqueous phase was rendered alkaline with 4 N sodium hydroxide solution and extracted with methylene chloride (4×50 ml). The combined organic phases were dried with sodium sulfate and concentrated i. vac.

Yield: 3.52 g (82%), yellow oil
$^1$H-NMR (CDCl$_3$): 1.18-1.34 (2 H, m); 1.40-1.80 (8 H, m); 1.96-2.08 (2 H, m); 2.10-2.22 (3 H, m); 2.34 (6 H, s); 2.51-2.63 (2 H, m).
$^{13}$C-NMR (CDCl$_3$): 24.9; 28.6; 30.1; 36.6; 37.2; 38.0; 43.4; 57.5.

The carbonyl carbon was detected by a gHMBC spectrum at 212 ppm.

LC-MS: [M+H]$^+$: m/z=210.3, $R_t$=0.8 min.

Step 5: (4-Cyclopentyl-4-dimethylaminocyclohexylidene)-acetic acid ethyl ester

Potassium tert-butanolate (2.99 g, 26.7 mmol) was added to a solution of phosphonoacetic acid triethyl ester (6.74 g, 5.98 ml, 30.1 mmol) in anhydrous N,N-dimethylformamide (30 ml) and the mixture was stirred for 1 h at 50° C. The solution was cooled to room temperature and a solution of 4-cyclopentyl-4-dimethylaminocyclohexanone (3.96 g, 18.9 mmol) in anhydrous N,N-dimethylformamide (50 ml) was then added. The reaction mixture was stirred for 20 h at room temperature and then poured into ice-water (75 g). The suspension was extracted with diethyl ether (4×40 ml). These combined organic phases were dried with sodium sulfate and concentrated i. vac. Toluene was first repeatedly added to the residue and the mixture concentrated i. vac. again each time and thereafter the procedure was repeated with cyclohexane. This residue (5.49 g) was taken up in ethyl acetate (30 ml) and the solution was extracted with 10% strength formic acid (5×30 ml). The combined acid, aqueous phases were rendered alkaline with 4 N sodium hydroxide solution and extracted with methylene chloride (5×30 ml). The combined organic phases were dried with sodium sulfate and concentrated i. vac.

Yield: 4.36 g (77%), colourless oil
$^1$H-NMR (CDCl$_3$): 1.14-1.70 (13 H, m); 1.78-2.40 (5 H, m); 2.32 (6 H, s); 2.57 (1 H, br t, J=13.9 Hz); 3.55 (1 H, br d, J=12.6 Hz); 4.13 (2 H, q, J=7.0 Hz); 5.58 (1 H, s).

Step 6: (4-Cyclopentyl-4-dimethylamino-1-nitromethylcyclohexyl)-acetic acid ethyl ester Nitromethane (1.22 ml, 1.07 ml, 20 mmol) was added to a mixture of (4-cyclopentyl-4-dimethylaminocyclohexylidene)acetic acid ethyl ester (4.35 g, 15.6 mmol) and tetra-n-butylammonium fluoride trihydrate (5.36 g, 17 mmol) in anhydrous tetrahydrofuran (37 ml). The solution was stirred for 7.5 h at 70° C. and then for 18 h at 45° C. The mixture was concentrated i. vac. The residue (9.9 g) was purified by flash chromatography (400 g, 20×7.5 cm) with cyclohexane/ethyl acetate (1:4).

Yield: 3.04 g (57%), yellowish oil.
$^1$H-NMR (CDCl$_3$): 1.26 (0.3 H, t, J=7.0 Hz); 1.27 (2.7 H, t, J=7.1 Hz); 1.30-1.75 (16 H, m); 2.06 (1 H, m); 2.24 (6 H, s); 2.46 (0.2 H, s); 2.59 (1.8 H, s); 4.15 (2 H, q, J=7.1 Hz); 4.58 (1.8 H, s); 4.81 (0.2 H, s)
$^{13}$C-NMR (CDCl$_3$): 14.2; 25.05; 24.14; 25.4; 28.1; 28.45; 28.50; 35.0; 36.8; 37.7; 43.6; 44.0; 44.1; 57.4; 60.1; 60.2; 84.3; 171.3.

This is a diastereoisomer mixture.

Step 7: 8-Cyclopentyl-8-dimethylamino-2-azaspiro[4.5]decan-3-one

A 50% strength aqueous Raney nickel suspension (1.15 ml) was added to a solution of (4-cyclopentyl-4-dimethylamino-1-nitromethylcyclohexyl)-acetic acid ethyl ester (3.04 g) in methanol (50 ml). The suspension was stirred for 5 h at 60° C. and under a hydrogen pressure of 5 bar. The suspension was filtered through Celite, the residue on the filter was washed with methanol (2×10 ml) and the filtrate was concentrated i. vac.

Yield: 2.36 g (100%), white solid $^1$H-NMR (CDCl$_3$): 1.16-1.80 (16 H, m); 2.05 (1 H, m); 2.12 (0.3 H, s); 2.20 (1.7 H, s); 2.26 (6 H, s); 3.09 (1.7 H, s); 3.18 (0.3 H, s); 6.04 (1 H, br s).

This is a diastereoisomer mixture in the ratio of approx. 7:1.

Step 8: 8-Cyclopentyl-8-dimethylamino-3-oxo-2-azaspiro[4.5]decan-2-carboxylic acid tert-butyl ester A solution of di-tert-butyl dicarbonate (2.14 g, 9.83 mmol) in anhydrous acetonitrile (20 ml) and 4-dimethylaminopyridine (69 mg, 0.87 mmol) was added to a solution of 8-cyclopentyl-8-dimethylamino-2-azaspiro[4.5]decan-3-one (2.36 g, 8.92 mmol) in anhydrous acetonitrile (60 ml) and the mixture was then stirred overnight at 50° C. Since the conversion ($^1$H-NMR) was not complete, further di-tert-butyl carbonate (2.14 g, 9.83 mmol) was added and the mixture was stirred for a further 18 h at 50° C. The mixture was concentrated I. vac. and the residue was taken up in methylene chloride (100 ml). The solution was washed with water (3×80 ml) and saturated sodium chloride solution (2×50 ml). The organic phase was dried with sodium sulfate and concentrated i. vac. The crude product (3.54 g) was purified by flash chromatography (200 g, 20×5.7 cm) with methylene chloride/methanol (98:2-95:5). Yield:

Nonpolar Diastereoisomer

Yield: 1.74 g (53%), yellowish solid $^1$H-NMR (CDCl$_3$): 1.16-1.36 (6 H, m); 1.38-1.63 (6 H, m); 1.51 (9 H, s); 1.64-1.80 (4 H, m); 2.05 (1 H, m); 2.26 (6 H, s); 2.40 (2 H, s); 3.44 (2 H, s).

Polar Diastereoisomer

Yield: 408 mg (12%), yellow oil $^1$H-NMR (CDCl$_3$): 1.10-1.85 (25 H, m); 2.06 (1 H, m); 2.25 (6 H, s); 2.32 (2 H, s); 3.54 (2 H, s).

Step 9: 8-Cyclopentyl-8-dimethylamino-2-azaspiro[4.5]decan-3-one (non-polar diastereoisomer)

Trifluoroacetic acid (10 ml) was added to a solution of 8-cyclopentyl-8-dimethylamino-3-oxo-2-azaspiro[4.5]decane-2-carboxylic acid tert-butyl ester—non-polar diastereoisomer (1.74 g, 4.77 mmol) in anhydrous methylene chloride (75 ml) and the mixture was stirred overnight at room temperature. The mixture was concentrated i. vac., the residue was taken up in methylene chloride (150 ml) and the solution was washed with saturated sodium bicarbonate solution (3×50 ml). The aqueous phase was extracted with a methylene chloride/isopropanol mixture (4:1, 3×50 ml). The combined organic phases were dried with sodium sulfate and concentrated i. vac.

Yield: 1.08 g (86%), white solid $^1$H-NMR (CDCl$_3$): 1.16-1.82 (16 H, m); 2.06 (1 H, m); 2.21 (2 H, s); 2.26 (6 H, s); 3.10 (2 H, s); 5.86 (1 H, br s).

Step 10: 8-Cyclopentyl-8-dimethylamino-2-azaspiro[4.5]decan-3-one (polar diastereoisomer)

Trifluoroacetic acid (3.38 ml) was added to a solution of 8-cyclopentyl-8-dimethylamino-3-oxo-2-azaspiro[4.5]decane-2-carboxylic acid tart-butyl ester—polar diastereoisomer (446 mg, max. 1.22 mmol, contaminated) in anhydrous methylene chloride (35 ml) and the mixture was stirred for 4 h at room temperature. The mixture was concentrated i. vac., the residue was taken up in methylene chloride (40 ml) and the solution was washed with saturated sodium bicarbonate solution (3×30 ml). The aqueous phase was extracted with a methylene chloride/isopropanol mixture (4:1, 3×50 ml). The combined organic phases were dried with sodium sulfate and concentrated i. vac. The residue (326 mg) was purified by flash chromatography (38 g, 20×2.5 cm) with methylene chloride/methanol (95:5) and 1% ammonia (25% in water).

Yield: 176 mg (54%), white solid $^1$H-NMR (CDCl$_3$): 1.16-1.32 (4 H, m); 1.36-1.62 (8 H, m); 1.63-1.82 (4 H, m); 2.06 (1 H, m); 2.14 (2 H, s); 2.26 (6H, s); 3.20 (2 H, s); 5.81 (1 H, br s).

Step 11: 8-Cyclopentyl-3-(2-cyclopropyl-ethyl)-8-(dimethylamino)-3-azaspiro[4.5]decan-2-one (Example no. 234, non-polar diastereoisomer)

A suspension of sodium hydroxide (96 mg, 2.39 mmol) in anhydrous dimethylsulfoxide (5 ml) was stirred for 40 min at room temperature, 8-cyclopentyl-8-dimethylamino-2-azaspiro[4.5]decan-3-one (non-polar diastereoisomer) (158 mg, 0.6 mmol) and subsequently a solution of 2-cyclopropylethyl 4-methylbenzenesulfonate (144 mg, 0.6 mmol) in anhydrous dimethylsulfoxide (2 ml) were then added and the mixture was stirred for 4 h at room temperature. A solution of 2-cyclopropylethyl 4-methylbenzenesulfonate (72 mg, 0.3 mmol) in anhydrous dimethylsulfoxide (2 ml) was again added to the reaction mixture and the mixture was stirred for a further 18 h at room temperature. Water (150 ml) was added to the mixture and the mixture was extracted with ethyl acetate (3×50 ml). The combined organic phases were dried with sodium sulfate and concentrated i. vac. The residue (300 mg) was purified by flash chromatography (18 g, 20×2.0 cm) with methylene chloride/methanol (98:2). 60 mg of the target compound were obtained in a pure form by this procedure. The contaminated product (90 mg) obtained by flash chromatography was taken up in ethyl acetate (10 ml) and the solution was extracted with 10% strength aqueous formic acid (4×20 ml). The combined acid, aqueous phases were rendered alkaline with 4 N sodium hydroxide solution and extracted with methylene chloride (4×20 ml). The combined organic phases were dried with sodium sulfate and concentrated i. vac.

Example No. 234 (Non-polar Diastereoisomer)

Yield: 131 mg (66%), yellowish oil $^1$H-NMR (CDCl$_3$): 0.00-0.05 (2 H, m); 0.38-0.45 (2 H, m); 0.61 (1 H, m); 1.10-1.80 (18 H, m); 2.03 (1 H, m); 2.24 (6 H, s), 2.25 (2 H, s); 3.08 (2 H, s); 3.29 (2 H, t, J=7.2 Hz).

$^{13}$C-NMR (CDCl$_3$): 4.2; 8.5; 25.1; 25.4; 25.8; 26.0; 26.9; 28.5; 31.6; 32.3; 32.4; 36.3; 37.8; 42.4; 42.5; 44.2; 57.7; 61.1; 173.7.

LC-MS: [M+H]$^+$: m/z=333.4, R$_t$=2.6 min.

Example No. 272

Step 1: 3-(8-Dimethylamino-8-phenyl-2-azaspiro
[4.5]dec-2-yl)propionic acid methyl ester Methyl acrylate (4.18 g, 4.20 ml, 46 mmol) was added to a solution of N,N-dimethyl-8-phenyl-2-azaspiro[4.5]decan-8-amine (600 mg, 2.32 mmol) in anhydrous tetrahydrofuran (20 ml) and the mixture was stirred for 18 h at 50° C. The reaction mixture was concentrated in vacuo and the residue (767 mg) was purified by flash chromatography (38 g, 20×2.5 cm) with methylene chloride/methanol (95:5) and 0.5% ammonia (25% in water).

Step 2: 4-(8-Dimethylamino-8-phenyl-2-azaspiro
[4.5]dec-2-yl)-2-methylbutan-2-ol (Example no. 272)

A 1.4 M solution of methylmagnesium bromide (1.26 ml, 1.76 mmol) in toluene/tetrahydrofuran (3:1) was added to a solution of 3-(8-dimethylamino-8-phenyl-2-azaspiro[4.5]dec-2-yl)propionic acid methyl-ester (150 mg, 0.44 mmol) in anhydrous tetrahydrofuran (5 ml) under argon and the mixture was stirred overnight at room temperature. 5% strength aqueous sulfuric acid (5 ml) was added to the solution and the mixture was stirred vigorously. pH 10 was established by addition of 2 M potassium carbonate solution and the mixture was extracted with methylene chloride (3×30 ml). The combined organic phases were dried with sodium sulfate and concentrated i. vac. The residue (130 mg) was taken up in ethyl acetate (30 ml) and the solution was then extracted with 5% strength aqueous formic acid (3×20 ml). The combined aqueous, acid phases were adjusted to pH 10 with 5 M sodium hydroxide solution and extracted with ethyl acetate (3×30 ml). The combined organic phases were dried with sodium sulfate and concentrated i. vac.

Analytical data of Example 272:
$^1$H-NMR (CDCl$_3$): 1.22 (6 H, s); 1.23-1.30 (2 H, m); 1.44 (2 H, t, J=7.1 Hz); 1.56-1.60 (2 H, m); 1.60-1.70 (2 H, m); 1.80-1.97 (2 H, m); 2.01 (6 H, s); 2.10-2.26 (2 H, m); 2.52 (2 H, s); 2.57 (2 H, t, J=7.1 Hz); 2.70-2.75 (2 H, m); 6.10-6.80 (1 H, br s); 7.22-7.30 (3 H, m); 7.32-7.39 (2 H, m).
$^{13}$C-NMR (CDCl$_3$): 29.6; 31.0; 34.2; 37.7; 38.0; 38.3; 41.2; 52.8; 53.4; 60.5; 65.4; 71.0; 126.4; 127.6; 127.61.
LC-MS (method 1): m/z: [M+H]$^+$=345.4, R$_t$=0.4 min.

Example No. 275

3-(2-Cyclopropyiethyl)-8-methylamino-8-phenyl-3-
azaspiro[4.5]decan-2-one (Example no. 275, non-
polar diastereoisomer)

N-Iodosuccinimide (348 mg, 1.55 mmol) was added to a solution of 3-(2-cyclopropylethyl)-8-(dimethylamino)-8-phenyl-3-azaspiro[4.5]decan-2-one (Ex. no. 184, non-polar series, 350 mg, 1.03 mmol) in anhydrous acetonitrile (10 ml) and the mixture was stirred for 5 h at room temperature. 4 M sodium hydroxide solution (3 ml) was then added to the reaction solution and the mixture was stirred for 20 min at room temperature. The phases were separated and the aqueous phase was extracted with methylene chloride (2×10 ml). The combined organic phases were concentrated i. vac. The residue (550 mg) was taken up in methanol (5 ml), 2 M hydrochloric acid (2 ml) was added to the solution and the mixture was stirred for 1 h at room temperature. The solution was then diluted with water (10 ml) and washed with diethyl ether (3×10 ml). The aqueous solution was rendered alkaline (pH ~10) with 2 M sodium hydroxide solution and extracted with methylene chloride (3×20 ml). The combined organic phases were dried with sodium sulfate and concentrated i. vac. The crude product (240 mg) was purified by means of flash chromatography on PharmPrep 60 CC (12 g, 18×1.5 cm) with methylene chloride/methanol (50:1)+0.5% ammonia (25% in water) and subsequent renewed flash chromatography on PharmPrep 60 CC (4 g, 14×1.0 cm) with methanol.

Example No. 275 (Non-polar Diastereoisomer)

Yield: 155 mg (46%), colourless resin
$^1$H-NMR (CDCl$_3$): 0.04-0.08 (2 H, m); 0.42-0.49 (2 H, m); 0.59-0.70 (1 H, m); 1.42 (2 H, dd, J=14.4 and 7.01 Hz); 1.45-1.53 (2 H, m); 1.73-1.99 (7 H, m); 2.00 (3 H, s); 2.24 (2 H, s); 3.22 (2 H, s); 3.32-3.37 (2 H, m); 7.18-7.28 (1 H, m); 7.32-7.39 (4 H, m).
$^{13}$C-NMR (CDCl$_3$): 4.3; 8.6; 28.6; 31.9; 32.4; 32.5; 35.8; 38.0; 42.6; 56.9; 59.7; 125.9; 126.5; 128.4; 173.5.
LC-MS: m/z: [M+H]$^+$=327.3, R$_t$=2.6 min.

Example No. 337

Step 1: 8-Dimethylamino-8-[1.2.3]triazol-1-yl-2-
azaspiro[4.5]decan-3-one

A 2 M dimethylamine solution in tetrahydrofuran (1.8 ml, 3.6 mmol), 1,2,3-triazole (228 mg, 191 µl, 3.3 mmol) and a molecular sieve 4 Å (1.00 g) were added to a solution of 2-azaspiro[4.5]decane-3,8-dione (500 mg, 3 mmol) in anhydrous tetrahydrofuran (30 ml) and the mixture was stirred for 18 h at room temperature. The reaction mixture was filtered and the filtrate was concentrated i. vac.

Yield: 704 mg (89%), white solid

Step 2: 8-(5-Chlorothiophen-2-yl)-8-dimethylamino-
2-azaspiro[4.5]decan-3-one

A suspension of 8-dimethylamino-8-[1.2.3]triazol-1-yl-2-azaspiro[4.5]decan-3-one (2.10 g, maximum 8 mmol) in anhydrous tetrahydrofuran (60 ml) was added dropwise to a 0.5 M suspension of 5-chloro-2-thienylmagnesium bromide (45 ml, 22.5 mmol) in tetrahydrofuran at room temperature and the mixture was then stirred for 6 h at 50° C. and for 18 h at room temperature. After addition of saturated ammonium chloride solution (100 ml) the phases were separated and the aqueous phase was extracted with ethyl acetate (3×30 ml). The combined organic phases were washed with saturated sodium chloride solution (50 ml), dried with sodium sulfate and filtered and the filtrate was concentrated i. vac.

Yield: 1.95 g (>100%), brown solid
The $^1$H-NMR spectrum (CDCl$_3$) shows all the required signals of the diastereoisomer mixture.
LC-MS: m/z: [M+H]$^+$=313.2, R$_t$=2.3 min.

Step 3:8-(5-acid tert-butyl ester (polar and
non-polar diastereoisomer)

Di-tert-butyl dicarbonate (1.92 g, 8.8 mmol) and 4-dimethylaminopyridine (100 mg, 0.8 mmol) were added to a solution of 8-(5-chlorothiophen-2-yl)-8-dimethylamino-2-azaspiro[4.5]decan-3-one (1.70 g, maximum 8 mmol) in anhydrous tetrahydrofuran (30 ml) and anhydrous acetonitrile (50 ml) and the mixture was stirred for 18 h at room temperature. After 4 h and 1 d in each case di-tert-butyl dicarbonate (1.92 g, 8.8 mmol) and dimethylaminopyridine (100 mg, 0.8 mmol) were added and the mixture was then stirred for 4 d at room temperature. The reaction mixture was concentrated i. vac., the residue was taken up in methylene chloride (100 ml) and the solution was washed with water (3×50 ml) and saturated sodium chloride solution (50 ml). The organic phase was dried with sodium sulfate and concentrated i. vac. The crude product (1.70 g) was purified by flash chromatography (100 g, 20×4.0 cm) with ethyl acetate/methanol (30:1).

Nonpolar Diastereoisomer

Yield: 224 mg (7%), brown oil $^1$H-NMR (CDCl$_3$): 1.42-1.50 (3 H, m); 1.52 (9 H, s); 1.75-1.83 (2 H, m); 1.90-2.03 (3 H, m); 2.12 (6 H, s); 2.32 (2 H, s); 3.56 (2 H, s); 6.60 (1 H, d, J=3.8 Hz); 6.85 (1 H, d, J=3.8 Hz).

Polar Diastereoisomer

Yield: 260 mg (8%), brown oil $^1$H-NMR (CDCl$_3$): 1.44-1.50 (3 H, m); 1.50 (9 H, s); 1.70-1.78 (2 H, m); 1.88-2.03 (3 H, m); 2.11 (6 H, s); 2.43 (2 H, s); 3.44 (2 H, s); 6.61 (1 H, d, J=3.8 Hz); 6.85 (1 H, d, J=3.8 Hz).

Step 4: 8-(5-Chlorothiophen-2-yl)-8-dimethylamino-2-azaspiro[4.5]decan-3-one

Trifluoroacetic acid (2 ml) was added to a solution of 8-(5-chlorothiophen-2-yl)-8-dimethylamino-3-oxo-2-azaspiro[4.5]decane-2-carboxylic acid tert-butyl ester (non-polar diastereoisomer) (224 mg, 0.54 mmol) in anhydrous methylene chloride (20 ml) and the mixture was stirred for 3 h at room temperature. The reaction mixture was concentrated i. vac., methylene chloride (20 ml) was added to the residue and the solution was washed with saturated sodium bicarbonate solution (3×20 ml). The organic phase was dried with sodium sulfate and concentrated i. vac.

Non-Polar Diastereoisomer

Yield: 126 mg (74%), brown solid

Melting point: 170-175° C.

$^1$H-NMR (CDCl$_3$): 1.46-1.55 (2 H, m); 1.76-1.85 (2 H, m); 1.90-2.01 (4 H, m); 2.11 (6 H, s); 2.14 (2 H, s); 3.22 (2 H, s); 5.55 (1 H, br s); 6.61 (1 H, d, J=3.8 Hz); 6.85 (1 H, d, J=3.8 Hz).

Trifluoroacetic acid (2 ml) was added to a solution of 8-(5-chlorothiophen-2-yl)-8-dimethylamino-3-oxo-2-azaspiro[4.5]decane-2-carboxylic acid tert-butyl ester (polar diastereoisomer) (155 mg, 0.37 mmol) in anhydrous methylene chloride (20 ml) and the mixture was stirred for 2 h at room temperature. The reaction mixture was concentrated i. vac., methylene chloride (20 ml) was added to the residue and the mixture was washed with saturated sodium bicarbonate solution (3×20 ml). The organic phase was dried with sodium sulfate and concentrated i. vac.

Polar Diastereoisomer

Yield: 66 mg (56%), brown solid $^1$H-NMR (CDCl$_3$): 1.46-1.54 (2 H, m); 1.75-1.83 (2 H, m); 1.89-2.03 (4 H, m); 2.12 (6 H, s); 2.25 (2 H, s); 3.10 (2 H, s); 5.48 (1 H, br s); 6.61 (1 H, d, J=3.8 Hz); 6.85 (1 H, d, J=3.8 Hz).

Step 5: 8-(5-Chlorothiophen-2-yl)-8-(dimethyl-amino)-3-(3-methoxy-3-methylbutyl)-3-azaspiro[4.5]decan-2-one (Example no. 460, non-polar diastereoisomer)

A suspension of powdered sodium hydroxide dried in vacuo (96 mg, 2.4 mmol) in anhydrous dimethylsulfoxide (10 ml) was stirred for 40 min at room temperature and 8-(5-chlorothiophen-2-yl)-8-dimethylamino-2-azaspiro[4.5]decan-3-one (non-polar series, 126 mg, 0.41 mmol) and 3-methoxy-3-methylbut-1-yl tosylate (136 mg, 0.5 mmol) were then added. Thereafter the reaction mixture was stirred for 1 d at room temperature. After addition of water (50 ml) the reaction mixture was extracted with ethyl acetate (3×30 ml). The combined organic phases were dried with sodium sulfate and filtered and the filtrate was concentrated i. vac. Toluene was repeatedly added to the residue and each time the mixture was concentrated i. vac. The crude product (152 mg) was purified by flash chromatography (10 g, 20×1.5 cm) with methylene chloride/methanol (95:5) and 0.5% ammonia (25% in water).

Example No. 337 (Non-polar Diastereoisomer)

Yield: 98 mg (58%), yellow solid.

Melting point: 86-90° C.

$^1$H-NMR (CDCl$_3$): 1.18 (6 H, s); 1.41-1.49 (2 H, m); 1.62-1.69 (2 H, m); 1.70-1.79 (2 H, m); 1.91-2.00 (4 H, m); 2.10 (6 H, s); 2.18 (2 H, s); 3.19 (3 H, s); 3.20 (2 H, s); 3.28-3.34 (2 H, m); 6.60 (1 H, d, J=3.8 Hz); 6.84 (1 H, d, J=3.8 Hz).

$^{13}$C-NMR (CDCl$_3$): 24.9; 32.4; 32.6; 35.5; 36.8; 38.0; 38.2; 44.3; 49.2; 58.0; 59.6; 73.5; 124.2; 124.5; 127.8; 173.2.

LC-MS: m/z: [M+H]$^+$=414.3, R$_t$=2.8 min.

Example No. 364

Step 1: (8-Butyl-2-azaspiro[4.5]dec-8-yl)-dimethyl-amine

A solution of Example no. 19 (5.00 g, 19.8 mmol) in anhydrous tetrahydrofuran (50 ml) was added to a suspension of lithium aluminium hydride (3.01 g, 79.2 mmol) in anhydrous tetrahydrofuran (50 ml) in a thoroughly heated apparatus, while cooling with ice, and the mixture was stirred for 18 h at 50° C. and then for 72 h at room temperature. Water (3 ml), 15% strength sodium hydroxide solution (3 ml) and again water (9 ml) were added dropwise to the reaction mixture, while cooling with ice, and the mixture was stirred for 2 h at room temperature. The suspension was then filtered through sea sand, the residue was washed with tetrahydrofuran and the filtrate was dried with sodium sulfate and concentrated i. vac. The residue was taken up several times in methylene chloride (3×25 ml) and the solution was in each case concentrated again i. vac. again.

Yield: 4.71 g (100%), yellow oil $^1$H-NMR (CDCl$_3$): 0.87 (3 H, t, J=7.1 Hz); 1.14-1.33 (10 H, m); 1.44-1.57 (8H, m); 2.13 (6 H, s); 2.80 (2 H, t, J=7.1 Hz); 3.65 (1 H, br s).

Step 2: 1-(8-Butyl-8-dimethylamino-3-azaspiro[4.5]decan-3-yl)-2-cyclopropylethanone (Example no. 364, polar diastereoisomer)

N,N'-Carbonyldiimidazole (122 mg, 0.8 mmol) was added to a solution of cyclopropylacetic acid (137 mg, 1.4 mmol) in absolute tetrahydrofuran (10 ml) and the mixture was stirred for 2 h under reflux. Thereafter a solution of (8-butyl-2-azaspiro[4.5]dec-8-yl)-dimethylamine (238 mg, 1.0 mmol) in absolute tetrahydrofuran (10 ml) was added and the mixture was stirred for a further 2 h under reflux. The reaction solution was then concentrated I. vac. and the residue was taken up in ethyl acetate (40 ml). The solution obtained was washed with 1 M potassium carbonate solution (2×20 ml), water (3×20 ml) and saturated sodium chloride solution (20 ml), dried with sodium sulfate and concentrated i. vac. The crude product (210 mg) was purified by flash chromatography (10 g, 20×1.5 cm) with ethyl acetate/methanol (9:1).

Example No. 364 (Polar Diastereoisomer)

Yield: 93 mg (33%), yellow oil
$^1$H-NMR (CDCl$_3$): 0.13-0.17 (2 H, m); 0.52-0.57 (2 H, m); 0.91 (3 H, t, J=7.1 Hz); 1.04-1.13 (1 H, m); 1.16-1.46 (10 H, m); 1.50-1.67 (4 H, m, overlapped by the water signal), 1.72 (0.8 H, t, J=7.2 Hz); 1.78 (1.2H, t, J=7.1 Hz); 2.19 (2 H, m); 2.21 (3 H, s); 2.22 (3 H, s); 3.18 (1 H, s); 3.30 (1 H, s); 3.43 (0.8H, t, J=7.1 Hz); 3.52 (1.2 H, t, J=7.2 Hz).
$^{13}$C-NMR (CDCl$_3$): 4.42; 4.44; 6.9; 7.0; 14.17; 14.20; 23.76; 23.81; 26.2, 26.6, 28.1; 28.9; 30.2; 30.5, 30.6; 30.8; 33.8; 36.3; 37.3; 37.4; 39.5; 39.9; 40.3; 42.2; 44.2; 45.3; 56.4; 56.5; 58.8; 171.40; 171.44.
LC-MS: m/z: [M+H]$^+$=321.4 (100%), R$_f$=2.8 min.

Example No. 408

Step 1: Dimethyl-(8-phenyl-2-azaspiro[4.5]dec-8-yl)amine

A solution of Example 431 (8-dimethylamino-8-phenyl-2-azaspiro[4.5]decan-3-one) (non-polar, diastereoisomer, 327 mg, 1.2 mmol) in anhydrous tetrahydrofuran (25 nil) was added dropwise to a suspension of lithium aluminium hydride (114 mg, 3 mmol) in anhydrous tetrahydrofuran (10 ml) under argon and the mixture was then stirred for 18 h at room temperature. Since the reaction was not complete, the mixture was heated to 50° C. and stirred for a further 3 h. After addition of water (200 µl), 1 M sodium hydroxide solution (500 µl) and water (500 µl) the mixture was stirred for 1 h and the suspension was filtered through sea sand. The filtrate was dried with sodium sulfate and concentrated i. vac.
Yield: 310 mg (100%), colourless oil
$^1$H-NMR (CDCl$_3$): 1.23-1.32 (2 H, m); 1.54-1.62 (2 H, m); 1.85 (2 H, t, J=7.1 Hz); 1.85-1.96 (2 H, m), 2.04 (6 H, s); 2.05-2.11 (1 H, m); 2.23-2.35 (2 H, m); 2.53 (2 H, s); 2.95 (2 H, t, J=7.1 Hz); 7.26-7.32 (3 H, m); 7.34-7.40 (2 H, m).

Step 2: 2-Cyclopropyl-1-[8-(dimethylamino)-8-phenyl-3-azaspiro[4.5]decan-3-yl]-ethanone (Example no. 408, non-polar diastereoisomer)

N,N'-Carbonyldiimidazole (130 mg, 0.8 mmol) was added to a solution of cyclopropylacetic acid (100 mg, 96 µl, 1 mmol) in anhydrous tetrahydrofuran (20 ml) and the mixture was stirred for 2 h under reflux. After addition of dimethyl-(8-phenyl-2-azaspiro[4.5]dec-8-yl)amine (155 mg, 0.6 mmol) in anhydrous tetrahydrofuran (5 ml) the solution was stirred for a further 2 h under reflux. The reaction mixture was then concentrated i. vac., the residue was taken up in ethyl acetate (30 ml) and the solution was washed with 2 M potassium carbonate solution (3×30 ml), water (3×30 ml) and saturated sodium chloride solution (30 ml). The organic phase was separated off, dried with sodium sulfate and filtered and the filtrate was concentrated i. vac. The crude product (210 mg) was purified by flash chromatography (10 g, 20×1.5 cm) with methylene chloride/methanol (95:5) and 0.5° A ammonia (25% in water).

Example No. 408 (Non-polar Diastereoisomer)

Yield: 65 mg (32%), colourless oil
$^1$H-NMR (CDCl$_3$): 0.06-0.16 (2 H, m); 0.47-0.57 (2 H, m); 0.97-1.12 (1 H, m); 1.24-1.40 (3 H, m); 1.60-1.70 (3 H, m); 1.80 (1 H, t, J=7.2 Hz); 1.88 (1 H, t, J=7.1 Hz); 2.04 (6 H, s); 2.07-2.22 (4 H, m); 3.06 and 3.18 (2 H, 2 s); 3.46 (1 H, t, J=7.1 Hz); 3.54 (1 H, t, J=7.2 Hz); 7.26-7.32 (3 H, m); 7.33-7.41 (2 H, m).
$^{13}$C-NMR (CDCl$_3$): 4.36; 4.42; 30.4; 30.5; 31.1; 34.2; 38.1; 39.4; 39.8; 40.3; 42.3; 44.2; 45.3; 58.0; 60.6; 126.7; 127.4; 127.5; 127.7; 171.4.
LC-MS: m/z: [M+H]$^+$=341.3, R$_f$=2.8 min.

Example No. 417

Step 1: [4-Dimethylamino-4-(5-fluorothiophen-2-yl)-cyclohexylidene]-acetic acid ethyl ester Potassium tert-butanolate (1.21 g, 10.8 mmol) was added to a solution of phosphonoacetic acid triethyl ester (2.73 g, 2.42 ml, 12.2 mmol) in anhydrous N,N-dimethylformamide (15 ml) and the mixture was stirred for 1 h at 50° C. The solution was cooled to room temperature and a solution of 4-(dimethylamino)-4-(5-fluorothiophen-2-yl)cyclohexanone (1.85 g, 7.66 mmol) in anhydrous N,N-dimethylformamide (20 ml) was then added. The reaction mixture was stirred for 20 h at room temperature and then poured into ice-water (30 g). The suspension was extracted with diethyl ether (4×20 ml). The combined organic phases were dried with sodium sulfate and concentrated i. vac. Toluene was repeatedly added to the residue and cyclohexane was then repeatedly added and in each case the mixture was concentrated again i. vac. The residue (2.42 g) was taken up in ethyl acetate (30 ml) and the solution was extracted with 10% strength aqueous formic acid (5×30 ml). The combined acid, aqueous phases were rendered alkaline with 4 N sodium hydroxide solution and extracted with methylene chloride (5×30 ml). The combined organic phases were dried with sodium sulfate and concentrated i. vac.
Yield: 2.0 g (84%), yellowish oil.
$^1$H-NMR (CDCl$_3$): 1.27 (3 H, t, J=7.1 Hz); 1.90-2.08 (2 H, m); 2.09-2.28 (4 H, m); 2.17 (6 H, s); 2.82-2.96 (1 H, m); 3.00-3.15 (1 H, m); 4.14 (2 H, q, J=7.1 Hz); 5.62 (1 H, s); 6.38 (1 H, dd, J=3.9 and 1.6 Hz); 6.47 (1 H, t, J=3.5 Hz).

Step 2: [4-Dimethylamino-4-(5-fluorothiophen-2-yl)-1-nitromethylcyclohexyl]-acetic acid ethyl ester Tetra-n-butylammonium fluoride trihydrate (555 mg, 1.8 mmol) and nitromethane (5.40 g, 4.79 ml, 88 mmol) were added to a solution of [4-dimethylamino-4-(5-fluorothiophen-2-yl)-cyclohexylidene]-acetic acid ethyl ester (500 mg, 1.6 mmol) in tetrahydrofuran (30 ml) and the mixture was stirred for 3 h at 70° C. and then for 18 h at 45° C. The reaction solution was then concentrated i. vac. and the residue (1.31 g) was purified by flash chromatography on spherical silica gel (PuriFlash PF-50SIHP, 50 µm, 100 g, 20×4.0 cm) with cyclohexane/ethyl acetate (2:1→1:1). The target compound is obtained as a diastereoisomer mixture (approx. 1:1).
Yield: 415 mg (70%), pale yellow viscous oil
$^1$H-NMR (CDCl$_3$): 1.24 and 1.26 (3 H, 2 t, J=7.1 Hz); 1.46-1.53 (2 H, m), 1.77-1.86 (2 H, m); 1.93-2.01 (4 H, m);

2.10 (6 H, s); 2.48 (1 H, s); 2.60 (1 H, s); 4.12 and 4.16 (2 H, 2 q, J=7.2 Hz); 4.64 (1 H, s); 4.76 (1 H, s); 6.38-6.43 (2 H, m).

LC-MS: m/z: [M+H]⁺=373.32 (55%) and [MH-NH-Me₂]⁺=328.2 (100%), $R_t$=2.7 and 2.9 min.

Step 3: 8-Dimethylamino-8-(5-fluorothiophen-2-yl)-2-azaspiro[4.5]decan-3-one A solution of [4-dimethylamino-4-(5-fluorothiophen-2-yl)-1-nitromethylcyclohexyl]-acetic acid ethyl ester (415 mg, 1.1 mmol) in ethanol (10 ml) was added to a mixture of iron powder (307 mg, 5.5 mmol), ammonium chloride (1.42 g, 28 mmol) and water (1.1 ml) and the mixture was then stirred for 4 h at 80° C. The reaction mixture was filtered and the residue was washed with ethanol. The ethanolic solution was rendered alkaline with 5% strength sodium bicarbonate solution and the ethanol was removed i. vac. The aqueous suspension was extracted with methylene chloride (3×20 ml), the combined organic phases were washed with saturated sodium chloride solution (20 ml) and filtered through phase separation paper and the filtrate was concentrated i. vac. The crude product (306 mg) was cyclised completely.

Step 4: 8-Dimethylamino-8-(5-fluorothiophen-2-yl)-2-azaspiro[4.5]decan-3-one Potassium tert-butylate (419 mg, 3.7 mmol) was added to a solution of step 3 (900 mg, 3.0 mmol) in anhydrous tetrahydrofuran (40 ml) and the mixture was stirred for 18 h overnight at room temperature. Saturated ammonium chloride solution (5 ml) was then added to the reaction solution, the mixture was concentrated i. vac. and water (50 ml) was added to the residue. The aqueous solution was extracted with methylene chloride (4×30 ml), the combined organic phases were washed with saturated sodium chloride solution (30 ml) and filtered through phase separation paper and the filtrate was concentrated i. vac.

Yield: 662 mg (66%), pale yellow, viscous foam

¹H-NMR (CDCl₃): 1.47-1.54 (2 H, m); 175-1.83 (2 H, m); 1.90-2.00 (4 H, m); 2.116 (3 H, s); 2.119 (3 H, s); 2.14 (1 H, s); 2.25 (1 H, s); 3.10 (1 H, s); 3.22 (1 H, s); 5.55 (1 H, br s); 6.38-6.40 (1 H, m); 8.42-6.44 (1 H, m).

LC-MS: m/z: [M+H]⁺=297.3 (60%) and [MH-NH-Me₂]⁺=252.2 (100%), $R_t$=1.8 min.

This is a diastereoisomer mixture in the ratio of approx. 1:1.

Step 5: 8-Dimethylamino-8-(5-fluorothiophen-2-yl)-3-oxo-2-azaspiro[4.5]decane-2-carboxylic acid tert-butyl ester (polar and non-polar diastereoisomer)

Di-tert-butyl dicarbonate (528 mg, 2.4 mmol) and 4-dimethylaminopyridine (25 mg, 0.2 mmol) were added to a solution of 8-dimethylamino-8-(5-fluorothiophen-2-yl)-2-azaspiro[4.5]decan-3-one (660 mg, crude product, maximum 2.2 mmol) in a mixture of anhydrous tetrahydrofuran (25 ml) and anhydrous acetonitrile (25 ml) and the mixture was stirred for 18 h at 50° C. The reaction solution was then concentrated i. vac. and the diastereoisomer mixture (890 mg) was separated by flash chromatography on spherical silica gel (PuriFlash PF-50SIHP, 50 μm, 38 g, 20×2.5 cm) with ethyl acetate which contained 1% methanol.

Non-Polar Diastereoisomer
  Yield: 447 mg (51%), pale yellow solid
  Melting point: 130-132° C.
  ¹H-NMR (CDCl₃): 1.43-1.51 (2 H, m); 1.53 (9 H, s); 175-1.81 (2 H, m); 1.89-2.02 (4H, m); 2.12 (6 H, s); 2.33 (2 H, s); 3.58 (3 H, s); 6.39 (1 H, dd, J=1.6 and 4.1 Hz); 8.42-0.43 (1 H, m).
Polar Diastereoisomer
  Yield: 337 mg (41%), pale yellow solid
  Melting point: 152-155° C.
  ¹H-NMR (CDCl₃): 1.46-1.51 (2 H, m, overlapped); 1.51 (9 H, s); 1.71-1.77 (2 M, m); 1.88-2.03(4 H, m); 2.11 (6 H, s); 2.43 (2 H, s); 3.45 (2 H, s); 6.39 (1 H, dd, J=1.5 and 4.1 Hz); 6.42-6.44 (1 H, m).

Step 6: 8-Dimethylamino-8-(5-fluorothiophen-2-yl)-2-azaspiro[4.5]decan-3-one (non-polar diastereoisomer)

Trifluoroacetic acid (2.5 ml, 25% v/v) was added to a solution of 8-dimethylamino-8-(5-fluorothiophen-2-yl)-3-oxo-2-azaspiro[4.5]decane-2-carboxylic acid tert-butyl ester (non-polar series, 430 mg, 1.1 mmol) in absolute methylene chloride (10 m) and the mixture was stirred for 1 h at room temperature. The reaction solution was then concentrated I. vac. and the residue was taken up in methylene chloride (50 ml). The solution was washed with 1 M potassium carbonate solution (3×30 ml) and saturated sodium chloride solution (30 ml) and filtered through phase separation paper and the filtrate was concentrated i. vac.
Non-Polar Diastereoisomer:
  Yield: 248 mg (77%), pale pink-coloured solid
  Melting point: 198-204° C.
  ¹H-NMR (CDCl₃): 1.48-1.54 (2 H, m); 1.76-1.83 (2 H, m); 1.91-1.97 (4 H, m); 2.11 (6 H, s); 2.14 (2 H, s); 3.22 (2 H, s); 5.70 (1 H, br s); 6.39 (1 H, dd, J=1.7 and 4.0 Hz); 6.42-6.44 (1 H, m).
  ¹³C-NMR (CDCl₃): 32.0; 32.1; 32.4; 38.0; 38.9; 43.0; 52.5; 59.5; 106.3; 106.4; 121.1; 162.5; 165.4; 177.2.
  LC-MS: m/z: [M+H]⁺=297.2 (72%) and [MH-NH-Me₂]⁺=252.2 (100%), $R_t$=1.7 min.

Step 7: 1-[8-Dimethylamino-8-(5-fluorothiophen-2-yl)-3-azaspiro[4.5]decan-3-yl]-3-methoxy-3-methylbutan-1-one (Example no. 549, non-polar diastereoisomer)

A suspension of powdered sodium hydroxide dried i. vac. (70 mg, 1.8 mmol) in absolute dimethylsulfoxide (5 ml) was stirred for 20 min at room temperature. A solution of 8-dimethylamino-8-(5-fluorothiophen-2-yl)-2-azaspiro[4.5]decan-3-one (non-polar diastereoisomer, 130 mg, 0.44 mmol) in absolute dimethylsulfoxide (5 ml) and a solution of 3-methoxy-3-methylbut-1-yl tosylate (144 mg, 0.53 mmol) in dimethylsulfoxide (5 ml) were then added to this and the mixture was stirred for 4 h at 80° C. Thereafter water (50 ml) was added to the reaction solution and the mixture was extracted with ethyl acetate (4×20 ml). The combined organic phases were washed with saturated sodium chloride solution (20 ml) and filtered through phase separation paper and the filtrate was concentrated i. vac. Toluene and methylene chloride (3×10 ml of each) were added several times in succession to the residue and the mixture was in each case concentrated again i. vac. at 60° C. in order to remove dimethylsulfoxide without trace. The crude product (154 mg) was purified by means of flash chromatography on spherical silica gel (PuriFlash PF-50SIHP, 50 µm, 5 g, 15×0.9 cm) with ethyl acetate/methanol (9:1).

Example No. 417 (Non-polar Diastereoisomer)

Yield: 116 mg (67%), white solid
Melting point: 93° C.
$^1$H-NMR (CDCl$_3$): 1.18 (6 H, m); 1.43-1.49 (2 H, m); 1.64-1.68 (2 H, m); 1.71-1.77 (2 H, m); 1.91-1.97 (4 H, m); 2.11 (6 H, s); 2.19 (2 H, s); 3.19 (3 H, s); 3.21 (2 H, s); 3.30-3.34 (2 H, m); 6.39 (1 H, dd, J=1.7 and 3.9 Hz); 6.41-6.43 (1 H, m).
$^{13}$C-NMR (CDCl$_3$): 24.9; 32.2; 32.6; 35.5; 36.8; 38.0; 38.3; 44.4; 49.2; 59.5; 73.6; 106.3; 106.4; 121.1; 162.5; 165.4; 173.3.
LC-MS: m/z: [M+H]$^+$=397.3 (100%) and [MH-NH-Me$_2$]$^+$=352.3 (35%), R$_t$=2.6 min.

Example No. 424

Step 1: 8-Cyclopent-1-enyl-8-dimethylamino-2-azaspiro[4.5]decan-1-one

A solution of cyclopentenylmethylmagnesium bromide (maximum 17 mmol) was added dropwise to a solution of 8-(dimethylamino)-1-oxo-2-azaspiro[4.5]decane-8-carbonitrile (958 mg, 4.32 mmol) in anhydrous tetrahydrofuran (20 ml) and the mixture was stirred for 1 h at room temperature. The mixture was heated to 60° C. and stirred for 1 h at this temperature. Saturated ammonium chloride solution (25 ml) and water (20 ml) were added to the suspension, while cooling with ice. The phases were separated and the aqueous phase was extracted with ethyl acetate (2×30 ml). The combined organic phases were dried with sodium sulfate and concentrated i. vac. The residue (900 mg) was purified by flash chromatography (85 g, 4.0×20 cm) with methylene chloride/methanol (9:1) and 1% ammonia (25% in water).
Yield: 527 mg (46%), white solid
$^1$H-NMR (CDCl$_3$): 1.18-1.26 (2 H, m); 1.31-1.41 (2 H, m); 1.75-1.85 (2 H, m); 1.97 (2 H, t, J=6.9 Hz); 2.01-2.10 (2 H, m); 2.11-2.20 (2 H, m); 2.18 (6 H, s); 2.22-2.36 (4 H, m); 3.25 (2 H, m); 5.44 (1 H, m); 6.38 (1 H, br s).
$^{13}$C-NMR (CDCl$_3$): 23.6; 28.2; 29.1; 31.9; 32.9; 34.0; 38.3; 38.6; 38.8; 43.2; 56.9; 125.8; 146.0; 183.2.
LC-MS: [M+H]$^+$: m/z=263.4, R$_1$=2.3 min.

Step 2: 8-Cyclopentyl-8-dimethylamino-2-azaspiro[4.5]decan-1-one

5% rhodium on aluminium oxide (960 mg, 0./47 mmol) was added to a solution of 8-cyclopent-1-enyl-8-dimethylamino-2-azaspiro[4.5]decan-1-one (2.5 g, 9.5 mmol) in anhydrous methanol (20 ml) and the mixture was stirred for 3 h under a hydrogen pressure of 2 bar. Methanol (20 ml) was added to the mixture again and the mixture was stirred for a further 2 h under a hydrogen pressure of 2 bar. Since the educt had not yet reacted, the reaction mixture was diluted with methanol (110 ml), 5% rhodium on aluminium oxide (1.92 g, 0.95 mmol) was again added and hydrogen was carried out for 20 h under a hydrogen pressure of 4 bar. The suspension was filtered through Celite, the residue was washed with methanol and the filtrate was concentrated i. vac. The residue was partitioned between ethyl acetate and 10% strength citric acid solution (40 ml of each). The organic phase was washed with 10% strength citric acid solution (3×80 ml). The combined acid, aqueous phases were rendered alkaline with 4 M sodium hydroxide solution and extracted with methylene chloride (4×50 ml). The combined organic phases were dried with sodium sulfate and concentrated i. vac. The crude product (202 mg) was purified by flash chromatography (85 g, 20×4.0 cm) with methylene chloride/methanol (95:5) and 1% ammonia (25% in water).
Yield: 757 mg (30%), white solid
$^1$H-NMR (CDCl$_3$): 1.14 (2 H, dd, J=11.8 and 1.2 Hz); 1.20-1.34 (4 H, m); 1.40-1.63 (6 H, m); 1.73 (2 H, dd, J=14.9 and 2.8 Hz); 1.98-2.14 (5 H, m); 2.28 (6 H, s); 3.29-3.30 (2 H, m); 6.20 (1 H, s).
$^{13}$C-NMR (CDCl$_3$): 25.0; 26.5; 27.3; 28.3; 31.9; 37.9; 38.9; 44.2; 44.4; 57.4; 183.4.
LC-MS: [M+H]$^+$: m/z=265.4.4; Rt=2.2 min.

Step 3: 8-Cyclopentyl-8-dimethylamino-2-azaspiro[4.5]decane

A solution of 8-cyclopentyl-8-dimethylamino-2-azaspiro[4.5]decan-1-one (758 mg, 2.8 mmol) in anhydrous tetrahydrofuran (30 ml) was added dropwise to a suspension of lithium aluminium hydride (542 mg, 14.3 mmol) in anhydrous tetrahydrofuran (10 ml), while cooling with ice. The suspension was stirred for 4 h at 50° C. Water (560 µl), 1 M sodium hydroxide solution (1.1 ml) and again water (1.1 ml) were added to the mixture, while cooling with ice. The suspension was stirred for 1 h at room temperature and then filtered through sodium sulfate. The residue was washed with tetrahydrofuran and the filtrate was concentrated vac.
Yield: 689 mg (96%), colourless oil
$^1$H-NMR (CDCl$_3$): 1.11-1.20 (2 H, m); 1.22-1.38 (4 H, m); 1.40-1.70 (12 H, m); 1.98 (1 H, br s); 2.05 (1 H, m); 2.26 (6 H, s); 2.61 (2 H, s); 2.93 (2 H, t, J=7.0 Hz).

Example No. 425

Step 1: 8-(5-Chlorothiophen-2-yl)-8-dimethylamino-2-azaspiro[4.5]decan-4-one

A suspension of 8-(dimethylamino)-1-oxo-2-azaspiro[4.5]decane-8-carbonitrile (1.76 g, 7.9 mmol) in absolute tetrahydrofuran (75 ml) was slowly added dropwise to a 0.5 M suspension of 5-chloro-2-thienylmagnesium bromide (5.29 g, 48 ml, 23.9 mmol) in tetrahydrofuran under argon, a clear solution being formed. The solution was then stirred overnight at 50° C. After addition of saturated ammonium chloride solution (100 ml) the tetrahydrofuran was removed i. vac. The aqueous solution obtained was extracted with methylene chloride (3×50 ml) and the combined organic phases were washed with saturated sodium chloride solution (50 ml), dried with sodium sulfate and concentrated i. vac. The crude product (2.45 g) was purified by means of flash chromatography (100 g, 20×4.0 cm) with ethyl acetate/methanol (97:3).
Yield: 1.47 g (59%), yellow solid.
Melting point: 198-201° C.
$^1$H-NMR (CDCl$_3$): 1.28-1.34 (2 H, m); 1.61-1.68 (2 H, m); 2.01 (2 H, t, J=6.9 Hz); 2.12 (6 H, s); 2.17 (2 H, dt, J=13.1 and 3.1 Hz), 2.32-2.40 (2 H, m); 3.28-3.32 (2 H, m); 5.90 (1 H, br s); 6.60 (1 H, d, J=3.8 Hz); 6.83 (1 H, d, J=3.8 Hz).
$^{13}$C-NMR (CDCl$_3$): 27.9; 31.5; 32.7; 37.9; 38.7; 43.1; 58.9; 123.1; 125.2; 127.4; 144.4; 182.4.
LC-MS: m/z: [MH-HNMe$_2$]$^+$=268.2, R$_t$=2.6 min.

Step 2: [8-(5-Chloro-2-thiophen-2-yl)-2-azaspiro[4.5]dec-8-yl]-dimethylamine (Example no. 425)

A 2 M solution of boron-dimethyl sulfide complex in tetrahydrofuran (6.42 ml, 12.8 mmol) was added to a solution of 8-(5-chlorothiophen-2-yl)-8-dimethylamino-2-azaspiro[4.5]decan-4-one (1.34 g, 4.3 mmol) in absolute tetrahydrofuran (150 ml) and the mixture was stirred for 4 h under reflux and overnight at 50° C. Since the reaction was not yet complete, this same amount of 2 M borane-dimethyl sulfide complex was again added and the mixture was stirred for a further 6 h under reflux and over the weekend at room temperature. Water (100 ml) was added to the reaction solution and the mixture was concentrated i. vac. Toluene, methanol and methylene chloride (3×30 ml of each) were added in succession to the residue and the mixture was again concentrated i. vac. The crude product was reacted further without purification.

Yield: 1.95 g (151%), viscous yellow oil

The $^1$H-NMR spectrum shows all the expected signals.

LC-MS: m/z: [MH-HNMe$_2$]$^+$=254.3, R$_t$=2.7 min.

The product content is a maximum of 66%.

Example No. 426

Step 1: 8-Dimethylamino-8-(5-fluorothiophen-2-yl)-2-azaspiro[4.5]decane-2-carboxylic acid tert-butyl ester A 2.5 M solution of n-butyllithium in hexane (2.2 ml, 5.5 mmol) was added dropwise to a solution of 8-dimethylamino-8-thiophen-2-yl-3-azaspiro[4.5]decane-3-carboxylic acid tert-butyl ester (Example no. 79) (1.55 g, 4.3 mmol) in absolute tetrahydrofuran (100 ml) in a thoroughly heated apparatus at −78° C. under argon and the mixture was stirred for 30 min at this temperature. The solution became yellow in colour. A solution of N-benzenesulfonyl-N-fluorobenzenesulfonamide (1.74 g, 5.5 mmol) in absolute tetrahydrofuran (50 ml) was added dropwise to this and the mixture was then warmed slowly to room temperature and further stirred for 18 h at this temperature. The solution became red in colour. After addition of saturated ammonium chloride solution (50 ml) the tetrahydrofuran was removed i. vac. The aqueous solution obtained was extracted with methylene chloride (3×30 ml) and the combined organic phases were washed with saturated sodium chloride solution (50 ml), dried with sodium sulfate and concentrated i. vac. The crude product (2.50 g) was purified by flash chromatography on spherical silica gel (PharmPrep 60 CC, 40-63 μm, 100 g, 20×4.0 cm) with ethyl acetate/isopropanol (99:1).

Yield: cannot be determined since various mixed fractions of differing purity were obtained, orange-coloured viscous oil $^1$H-NMR (CDCl$_3$): 1.34-1.42 (2 H, m); 1.46 (9 H, s); 1.57-1.66 (4 H, m); 1.78-1.97 (4 H, m); 2.11 (2 H, s); 2.13 (4 H, s); 3.18 (0.7 H, s); 3.22 (1.3 H, s); 3.32 (0.7 H, t, J=7.1 Hz); 3.37 (1.3 H, t, J=7.1 Hz); 6.35-6.40 (1 H, m); 6.42 (1 H, t, J=3.5 Hz).

$^{13}$C-NMR (DMSO-d$_6$): 28.6; 31.3; 32.1; 32.9; 36.6; 37.0; 38.1; 40.7; 41.5; 44.0; 44.4; 55.6; 60.2; 79.1; 106.3; 121.3; 154.8; 162.5; 165.4.

Some C signals are doubled due to the amide structure (rotamers). For this reason, also no C-F coupling constants were determined.

LC-MS: m/z: [MH-NHMe$_2$]$^+$=383.4, R$_t$=3.3 min.

Step 2: [8-(5-Fluorothiophen-2-yl)-2-azaspiro[4.6]dec-8-yl]-dimethylamine (Example 426)

Trifluoroacetic acid (15 ml) was added to a solution of 8-dimethylamino-8-(5-fluorothiophen-2-yl)-2-azaspiro[4.5]decane-2-carboxylic acid tert-butyl ester (1.35 g, max. 3.5 mmol, slightly contaminated) in absolute methylene chloride (60 ml) and the mixture was stirred for 1 h at room temperature. The reaction solution was concentrated i. vac. and methylene chloride (50 ml) was added to the residue. The solution obtained was washed with saturated potassium bicarbonate solution (3×30 ml) and saturated sodium chloride solution (50 ml), dried with sodium sulfate and concentrated i. vac. The crude product was reacted further without purification.

Yield: 738 mg (crude product), orange-coloured viscous oil $^1$H-NMR (CDCl$_3$): 1.43 (2 H, ddd, J=13.1, 8.1 and 4.9 Hz); 1.61 (2 H, t, J=7.3 Hz); 1.68-1.74 (2 H, m); 1.86-1.99 (4 H, m); 2.10 (6 H, s); 2.88 (2 H, s); 3.09 (2 H, t, J=7.3 Hz); 5.02 (1 H, br. s); 6.38 (1 H, dd, J=4.0 and 1.7 Hz); 6.42 (1 H, dd, J=4.0 and 3.1 Hz).

Example No. 427

Step 1: 2-[4-(Azetidin-1-yl)-4-(2-thienyl)cyclohexylidene]-acetic acid ethyl ester Potassium tert-butylate (2.82 g, 25.1 mmol) was added to a solution of phosphonoacetic acid triethyl ester (5.60 g, 4.8 ml, 25.1 mmol) in anhydrous N,N-dimethylformamide (30 ml) under argon and the mixture was stirred for 10 min at room temperature. A solution of 4-(azetidin-1-yl)-4-(thiophen-2-yl)cyclohexanone (3.96 g, 16.8 mmol) in anhydrous N,N-dimethylformamide (60 ml) was then added to the mixture and the mixture was stirred for 1 h at room temperature and then poured into ice-water (80 g). The aqueous suspension was extracted with diethyl ether (4×40 ml). The combined organic extracts were dried with sodium sulfate and concentrated i. vac.

Yield: 4.79 g (93%), brownish oil $^1$H-NMR (CDCl$_3$): 1.26 (t, 3H, J=7.1 Hz); 1.76-1.85 (m, 2H); 1.87-2.02 (m, 4H); 2.12-2.20 (m, 1H); 2.44-2.57 (m, 1H); 2.89-3.05 (m, 2H); 3.11 (t, 4H, J=6.9 Hz); 4.13 (q, 2H, J=7.1 Hz); 5.61 (br s, 1H); 6.89 (d, 1H, J=3.5 Hz); 7.08 (dd, 1H, J=5.1, 1.5 Hz); 7.25-7.28 (m, 1H, overlapped by the CDCl$_3$ signal).

Step 2: 2-[4-(Azetidin-1-yl)-1-(nitromethyl)-4-(2-thienyl)cyclohexyl]-acetic acid ethyl ester Nitromethane (1.24 g, 1.09 ml, 20.3 mmol) was added to a mixture of 2-[4-(azetidin-1-yl)-4-(2-thienyl)cyclohexylidene]-acetic acid ethyl ester (4.79 g, 15.7 mmol) and tetra-n-butylammonium fluoride trihydrate (5.43 g, 17.2 mmol) in tetrahydrofuran (150 ml) and the mixture was stirred for 6 h at 70° C. and for 18 h at 45° C. The reaction mixture was then concentrated in vacuo and the crude product (12.0 g) was purified by flash chromatography (200 g, 20×5.7 cm) with ethyl acetate/cyclohexane (9:1).

Yield: 4.18 g (74%), yellowish oil.

$^1$H-NMR (DMSO-d$_6$): 1.10-1.24 (m, 3H); 1.37-1.47 (m, 2H); 1.63-1.86 (m, 8H); 2.42 and 2.46 (2 s, 2H); 2.92-2.99 (m, 4H); 3.98-4.05 (m, 2H); 4.68 and 4.69 (2 s, 2H); 6.96 (dt, 1H, J=3.5, 1.1 Hz); 7.09-7.12 (m, 1H); 7.47 (dd, 1H, J=5.1, 1.0 Hz).

This is a diastereoisomer mixture in the ratio of approx. 2:3.

Step 3: 8-(Azetidin-1-yl)-8-(2-thienyl)-3-azaspiro[4.5]decan-2-one

A solution of 2-[4-(azetidin-1-yl)-1-(nitromethyl)-4-(2-thienyl)cyclohexyl]-acetic acid ethyl ester (3.90 g, 10.7 mmol) in ethanol (100 ml) was added to a mixture of iron powder (2.84 g, 53 mmol), ammonium chloride (14.2 g, 265 mmol) and water (10 ml) and the mixture was then stirred for 4 h at 80° C. The mixture was filtered and the residue was washed with ethanol. The filtrate was rendered alkaline by addition of 5% strength sodium bicarbonate solution (8 ml) and then concentrated i. vac. The crude product (6.30 g) was purified by flash chromatography (200 g, 20×5.7 cm) with methylene chloride/methanol (95:5) and 1% ammonia (25% in water). The mixture of non-polar and polar diastereoisomer isolated (1.60 g) was purified by medium pressure chromatography under 8-10 bar on a PuriFlash cartridge (PF-15SIHP, 40 g, 15 µm) and 2 PuriFlash cartridges (PF-15SIHP, 120 g, 15 µm) with methylene chloride/isopropanol (9:1) and 1% ammonia (25% in water).

Non-Polar Diastereoisomer

Yield: 504 mg (16%), white solid

Melting point: 180-183° C.

$^1$H-NMR (DMSO-$d_6$): 1.31-1.40 (m, 2H); 1.63-1.77 (m, 8H); 2.02 (s, 2H); 2.93 (s, 2H); 2.96 (t, 4H, J=6.9 Hz); 6.95 (d, 1H, J=3.5 Hz); 7.10 (dd, 1H, J=8.6, 3.5 Hz); 7.41 (br s, 1H); 7.46 (d, 1H, J=5.1 Hz).

Polar Diastereoisomer

Yield: 772 mg (25%), white solid

Melting point: 170-172° C.

$^1$H-NMR (DMSO-$d_6$): 1.30-1.40 (m, 2H); 1.62-1.82 (m, 8H); 1.93 (s, 2H); 2.96 (t, 4H, J=6.9 Hz); 3.03 (s, 2H); 6.95 (dd, 1H, J=3.5 Hz, 1.1 Hz); 7.10 (dd, 1H, J=5.1, 3.5 Hz); 7.45 (br s, 1H); 7.46 (dd, 2H, J=5.1 Hz, 1.0 Hz).

Step 4: 8-(Azetidin-1-yl)-8-(2-thienyl)-3-azaspiro[4.5]decane (polar diastereomer) (Example 427)

A solution of 8-(azetidin-1-yl)-8-(2-thienyl)-3-azaspiro[4.5]decan-2-one (polar diastereoisomer) (765 mg, 2.63 mmol) in anhydrous tetrahydrofuran (50 ml) was added dropwise to a suspension of lithium aluminium hydride (500 mg, 13.1 mmol) in anhydrous tetrahydrofuran (20 ml) at 0° C. under argon and the mixture was then stirred overnight at 60° C. After addition of water (500 µl), 1 N sodium hydroxide solution (1.3 ml) and water again (1.3 ml) the mixture was stirred for one hour at room temperature and thereafter filtered through sea sand and the filtrate was dried with sodium sulfate and concentrated i. vac.

Yield: 696 mg (96%), colourless oil $^1$H-NMR (CDCl$_3$): 1.35 (ddd, 2H, J=13.1, 9.4, 3.7 Hz); 1.40-1.46 (m, 3H); 1.60-1.90 (m, 8H); 2.75 (s, 2H); 2.89 (t, 2H, J=7.1 Hz); 3.07 (t, 4H, J=7.0 Hz); 6.88 (dd, 1H, J=3.5, 1.1 Hz); 7.09 (dd, 1H, J=5.1, 3.5 Hz); 7.27 (dd, 1H, J=5.1, 1.1 Hz).

Example No. 414

8-(Azetidin-1-yl)-8-(2-thienyl)-3-azaspiro[4.5]decane (non-polar diastereomer) (Example no 428)

A solution of 8-(azetidin-1-yl)-8-(2-thienyl)-3-azaspiro[4.5]decan-2-one (non-polar diastereoisomer) (504 mg, 1.73 mmol) in anhydrous tetrahydrofuran (50 ml) was added dropwise to a suspension of lithium aluminium hydride (330 mg, 8.65 mmol) in anhydrous tetrahydrofuran (20 ml) at 0° C. under argon and the mixture was then stirred overnight at 60° C. After addition of water (300 µl), 1 N sodium hydroxide solution (800 µl) and water again (800 µl) the mixture was stirred for 1 h at room temperature and thereafter was filtered through sea sand. The filtrate was dried with sodium sulfate and concentrated i. vac.

Yield: 414 mg (87%), oil $^1$H-NMR (CDCl$_3$): 1.35 (ddd, 2H, J=13.4, 9.9, 3.7 Hz); 1.56-1.64 (m, 3H); 1.70-1.93 (m, 8H); 2.55 (s, 2H); 2.94 M. 2H, J=7.1 Hz); 3.08 (t, 4H, J=7.1 Hz); 6.87 (dd, 1H, J=3.5, 1.1 Hz); 7.08 (dd, 1H, J=5.1, 3.5 Hz); 7.27 (dd, 1H, J=5.1, 1.1 Hz).

Example No. 429

Step 1: (4-Azetidin-1-yl-4-phenylcyclohexylidene)acetic acid ethyl ester

Potassium tert-butylate (3.52 g, 31.4 mmol) was added to a solution of phosphonoacetic acid triethyl ester (7.03 g, 6.2 ml, 31.4 mmol) in anhydrous N,N-dimethylformamide (30 ml) under argon and the mixture was stirred for 10 min at room temperature. A solution of 4-(azetidin-1-yl)-4-phenylcyclohexanone (4.81 g, 21 mmol) in anhydrous N,N-dimethylformamide (60 ml) was then added to the mixture and the mixture was stirred for 1 h at room temperature and then poured into ice-water 80 g). The aqueous suspension was extracted with diethyl ether (4×40 ml). The combined organic extracts were dried with sodium sulfate and concentrated i. vac.

Yield: 6.30 g (100%), yellowish oil.

$^1$H-NMR (DMSO-$d_6$): 1.18 (t, 3H, J=7.1 Hz); 1.65 (quin, 2H, J=7.0 Hz); 1.75-1.90 (m, 2H); 1.96-2.10 (m, 3H); 2.73-2.82 (m, 2H); 2.88-2.96 (m, 1H); 2.90 (t, 4H, J=6.9 Hz); 4.05 (q, 2H, J=7.1 Hz); 5.62 (s, 1H); 7.23-7.45 (m, 5H).

Step 2: (4-Azetidin-1-yl-1-nitromethyl-4-phenylcyclohexyl)acetic acid ethyl ester Nitromethane (1.65 g, 1.45 ml, 27.1 mmol) was added to a mixture of (4-azetidin-1-yl-4-phenylcyclohexylidene)acetic acid ethyl ester (6.30 g, 21 mmol) and tetra-n-butylammonium fluoride trihydrate (7.26 g, 23 mmol) in tetrahydrofuran (150 ml) and the mixture was stirred for 6 h at 70° C. and for 18 h at 45° C. Since the reaction was not complete, tetra-n-butylammonium fluoride trihydrate (2.42 g, 7.6 mmol) and nitromethane (550 mg, 483 µl, 9 mmol) were again added and the mixture was stirred for a further 5 h at 70° C. and for 18 h at 45° C. The reaction mixture was concentrated in vacuo and the residue (17.0 g) was purified by flash chromatography (200 g, 20×5.7 cm) with ethyl acetate/methanol (95:5).

Yield: 4.92 g (65%), brownish oil $^1$H-NMR (DMSO-$d_6$): 1.10 and 1.18 (2 t, 3H, J=7.1 Hz); 1.30-1.42 (m, 2H); 1.62 (t, 2H, J=6.8 Hz); 1.70-1.80 (m, 4H); 1.85-1.95 (m, 2H); 2.36 (s, 1H); 2.84 (t, 4H, J=6.8 Hz); 3.95-4.08 (m, 2H); 4.63 and 4.73 (m, 2H); 7.26-7.45 (m, 5H).

LC-MS: m/z: [M+H]$^+$=361.4, R$_t$=2.6 and 2.7 min.

A diastereoisomer mixture in the ratio of 4:3 is present.

Step 3: 8-Azetidin-1-yl-8-phenyl-2-azaspiro[4.5]decan-3-one

A solution of (4-azetidin-1-yl-1-nitromethyl-4-phenylcyclohexyl)acetic acid ethyl ester (4.92 g, 13.5 mmol) in ethanol (130 ml) was added to a mixture of iron powder (3.58 g, 67 mmol), ammonium chloride (17.9 g, 334 mmol) and water (13 ml) and the mixture was then stirred for 4 h at 80° C. and overnight at 65° C. The mixture was filtered and the residue on the filter was washed with ethanol. The filtrate was rendered alkaline by addition of 5% strength sodium bicarbonate solution (8 ml) and then concentrated i. vac. The residue (10.0 g) was purified by flash chromatography (400 g, 20×7.5 cm) with methylene chloride/methanol (95:5) and 1% ammonia (25% in water). The mixture of non-polar and polar diastereoisomer isolated (1.80 g) was purified by flash chromatography on two columns with PharmPrep (40-63 µm, 200 g, 20×5.7 cm) and the mixed fractions (670 mg) thereby obtained were purified on a PuriFlash cartridge (PF-15SIHP, 200 g, 15 µm) in each case with methylene chloride/ethanol (95:5) and 1% ammonia (25% in water).

Non-Polar Diastereoisomer

Yield: 719 mg (19%), white solid
Melting point: 180-187° C.
$^1$H-NMR (DMSO-$d_6$): 1.21-1.31 (m, 2H); 1.56-1.84 (m, 8H); 2.06 (s, 2H); 2.85 (t, 4H, J=6.8 Hz); 2.88 (s, 2H); 7.22-7.46 (m, 6H).
LC-MS: m/z: [M+H]$^+$=285.4, $R_t$=1.9 min.

Polar Diastereoisomer

Yield: 907 mg (24%), white solid
Melting point: 150-155° C.
$^1$H-NMR (DMSO-$d_6$): 1.20-1.33 (m, 2H); 1.58-1.87 (m, 8H); 1.88 (s, 2H); 2.84 (t, 4H, J=6.8 Hz); 3.07 (s, 2H); 7.25-7.49 (m, 6H).
LC-MS: m/z: [M+H]$^+$=285.4, $R_t$=1.8 min.

Step 4: 8-Azetidin-1-yl-8-phenyl-2-azaspiro[4.5]decane (polar diastereoisomer) (Example 429)

A solution of 8-azetidin-1-yl-8-phenyl)-2-azaspiro[4.5]decan-3-one (polar diastereoisomer) (892 mg, 3.14 mmol) in anhydrous tetrahydrofuran (80 ml) was added dropwise to a suspension of lithium aluminium hydride (599 mg, 15.7 mmol) in anhydrous tetrahydrofuran (20 ml) at 0° C. under argon and the mixture was then stirred at 60° C. overnight. After addition of water (500 µl), 1 N sodium hydroxide solution (1.3 ml) and water again (1.3 ml) the mixture was stirred for one hour at room temperature and thereafter filtered through sea sand and the filtrate was dried with sodium sulfate and concentrated i. vac.

Yield: 830 mg (98%), colourless oil
$^1$H-NMR (DMSO-$d_6$): 1.12-1.22 (m, 2H); 1.23-1.30 (m, 2H); 1.52-1.66 (m, 4H); 1.70-1.81 (m, 3H); 2.53 (s, 2H); 2.70 (t, 2H, J=7.1 Hz); 2.82 (t, 4H, J=6.8 Hz); 3.34-3.42 (m, 2H); 7.24 (m, 3H); 7.37-7.43 (m, 2H).
LC-MS: m/z: [M+H]$^+$=271.4, $R_t$=0.4 min.

Example No. 430

8-Azetidin-1-yl-8-phenyl-2-azaspiro[4.5]decane (non-polar diastereomer)

A solution of 8-azetidin-1-yl-8-phenyl)-3-azaspiro[4.5]decan-2-one (non-polar diastereoisomer) (701 mg, 2.46 mmol) in anhydrous tetrahydrofuran (100 ml) was added dropwise to a suspension of lithium aluminium hydride (470 mg, 12.3 mmol) in anhydrous tetrahydrofuran (20 ml) at 0° C. under argon and the mixture was then stirred at 60° C. overnight. After addition of water (500 µl), 1 N sodium hydroxide solution (1.3 ml) and water again (1.3 ml) the mixture was stirred for one hour at room temperature and thereafter filtered through sea sand and the filtrate was dried with sodium sulfate and concentrated i. vac.

Yield: 663 mg (95%), colourless oil
$^1$H-NMR (DMSO-$d_6$): 1.10-1.20 (m, 2H); 1.48 (t, 2H, J=7.0 Hz); 1.50-1.66 (m, 4H); 1.70 (m, 3H); 2.34 (s, 2H); 2.74 (t, 2H, J=7.0 Hz); 2.84 (t, 4H, J=6.8 Hz); 3.20-3.40 (m, 2H); 7.23-7.34 (m, 3H); 7.36-7.42 (m, 2H).
LC-MS: m/z: [M+H]$^+$=271.4, $R_t$=0.2 min.

Example No. 431

8-Dimethylamino-8-phenyl-2-azaspiro[4.5]decan-3-one (polar diastereomer)

Trifluoroacetic acid (5 ml) was added to a solution of 8-dimethylamino-3-oxo-8-phenyl-2-azaspiro[4.5]decane-2-carboxylic acid tert-butyl ester (polar diastereoisomer) (1.28 g, 3.43 mmol) in anhydrous methylene chloride (50 ml) and the mixture was stirred for 3 h at room temperature. The reaction mixture was concentrated i. vac., the residue was dissolved in methylene chloride (50 ml) and the solution was washed with saturated sodium bicarbonate solution (3×20 ml). The organic phase was dried with sodium sulfate and concentrated i. vac.

Yield: 875 mg (94%), white solid
Melting point: 220-222° C.
$^1$H-NMR (CDCl$_3$): 1.34-1.44 (2 H, m); 1.72-1.81 (2 H, m); 1.86-2.02 (2 H, br s); 2.04 (6 H, s); 2.16-2.29 (2 H, m); 2.30 (2 H, s); 3.01 (2 H, s); 5.60 (1 H, s); 7.26-7.32 (3 H, m); 7.36-7.41 (2 H, m).

Example No. 432 and 433

Step 1: 8-Butyl-8-dimethylamino-2-azaspiro[4.5]decan-3-one

A suspension of 8-(dimethylamino)-3-oxo-2-azaspiro[4.5]decane-8-carbonitrile (2.21 g, 10 mmol) in anhydrous tetrahydrofuran (140 ml) was added dropwise to a 2 M solution of n-butylmagnesium chloride in anhydrous tetrahydrofuran (20 ml, 40 mmol) at 0° C. under argon and the mixture was stirred for 20 h at room temperature. Saturated ammonium chloride solution (50 ml) was then added to the solution. The phases were separated and the aqueous phase was extracted with methylene chloride (3×20 ml). The combined organic phases were dried with sodium sulfate and concentrated i. vac. The crude product (3.97 g) was taken up in methylene chloride and the suspension was washed with potassium carbonate solution. The organic phase was then dried with sodium sulfate and concentrated i. vac.

Yield: 1.88 g (75%), colourless oil which crystallized over time
$^1$H-NMR (CDCl$_3$): 0.90 and 0.91 (3 H, 2 t, J=7.2 Hz); 1.14-1.47 (10 H, m); 1.51-1.61 (2 H, m); 1.87-1.82 (2 H, m); 2.18 and 2.19 (2 H, 2 s); 2.21 (s, 6 H); 3.15 and 3.18 (2 H, 2 s); 5.90 and 5.93 (1 H, br s).
This is a diastereoisomer mixture in the ratio of approx. 1:1.
LC/MS: m/z: [M+H]$^+$=253.3, $R_t$=1.3 min.

Step 2: 8-Butyl-8-dimethylamino-3-oxo-2-azaspiro[4.5]decane-2-carboxylic acid tert-butyl ester (polar and non-polar diastereoisomer)

Di-tert-butyl dicarbonate (2.71 g. 12.4 mmol) and 4-dimethylaminopyridine (90 mg, 0.75 mmol) were added to a solution of 8-butyl-8-dimethylamino-2-azaspiro[4.5]decan-3-one (1.84 g, 7.3 mmol) in anhydrous acetonitrile (60 ml) and anhydrous tetrahydrofuran (20 ml). The reaction mixture was stirred for 72 h at 50° C. It was then concentrated i. vac. The residue was taken up in methylene chloride (100 ml) and the solution was washed with water (3×80 ml) and saturated sodium chloride solution (50 ml). The organic phase was dried with sodium sulfate and concentrated i. vac. The crude product (2.37 g) was purified by flash chromatography (220 g, 20×5.7 cm) with methylene chloride/methanol (95:5-9:1-4:1).
Non-Polar Diastereoisomer:
  Yield: 819 mg (32%), orange-coloured solid
  $^1$H-NMR (CDCl$_3$): 0.90 (3 H, t, J=7.1 Hz); 1.17-1.40 (10 H, m); 1.51 (9 H, s); 1.54-1.76 (4 H, m); 2.21 (6 H, s); 2.39 (2 H, s); 3.49 (2 H, s).
Polar Diastereoisomer:
  Yield: 647 mg (25%), yellow oil
  $^1$H-NMR (CDCl$_3$): 0.90 (3 H, t, J=7.1 Hz); 1.22-1.48 (10 H, m); 1.53 (9 H, s); 1.58-1.76 (4 H, m); 2.25 (6 H, s); 2.39 (2 H, s); 3.52 (2 H, s).
Mixed Fraction:
  Yield: 310 mg (12%), yellow oil Step 3: 8-Butyl-8-dimethylamino-2-azaspiro[4.5]decan-3-one (polar diastereoisomer) (Example No. 432)

Trifluoroacetic acid (12.5 ml) was added to a solution of 8-butyl-8-dimethylamino-3-oxo-2-azaspiro[4.5]decane-2-carboxylic acid tert-butyl ester—polar diastereoisomer (603 mg, 1.71 mmol) in anhydrous methylene chloride (50 ml) and the mixture was stirred for 4 h at room temperature. The reaction mixture was then concentrated i. vac., the residue was taken up in methylene chloride (50 ml) and the solution was washed with 25% strength potassium carbonate solution (3×20 ml). The organic phase was dried with sodium sulfate and concentrated i. vac.
Polar Diastereoisomer:
  Yield: 365 mg (85%), yellowish solid
  $^1$H-NMR (CDCl$_3$): 0.90 (3 H, t, J=7.2 Hz); 1.11-1.48 (10 H, m); 1.53-1.64 (2 H, m); 1.69-1.79 (2 H, m); 2.17 (2 H, s); 2.21 (6 H, s); 3.17 (2 H, s); 6.10 (br s, 1 H).
  $^{13}$C-NMR (CDCl$_3$): 14.1; 23.7; 26.5; 28.3; 30.7 (2 C); 31.9 (2 C); 37.3 (2 C); 39.0; 44.0; 52.6; 56.2; 177.9.

Step 4: 8-Butyl-8-dimethylamino-2-azaspiro[4.5]decan-3-one (non-polar diastereoisomer) (Example No. 433)

Trifluoroacetic acid (12.5 ml) was added to a solution of 8-butyl-8-dimethylamino-3-oxo-2-azaspiro[4.5]decane-2-carboxylic acid tert-butyl ester—non-polar diastereoisomer (740 mg, 2.09 mmol) in anhydrous methylene chloride (50 ml) and the mixture was stirred for 2 h at room temperature. The reaction mixture was then concentrated i. vac., the residue was taken up in methylene chloride (50 ml) and the solution was washed with 25% strength potassium carbonate solution (3×20 ml). The organic phase was dried with sodium sulfate and concentrated i. vac.
Non-Polar Diastereoisomer:
  Yield: 416 mg (79%), yellow solid
  $^1$H-NMR (CDCl$_3$): 0.90 (3 H, t, J=7.2 Hz); 1.16-1.43 (10 H, m); 1.58-1.78 (4 H, m); 2.19 (2 M, s); 2.22 (6 H, s); 3.14 (2 H, s); 5.97 (br s, 1 H).
  $^{13}$C-NMR (CDCl$_3$): 14.1; 23.8; 26.6; 28.6; 30.6 (2 C); 31.8 (2 C); 37.3 (2 C); 39.1; 42.1; 54.6; 177.7.

In accordance with the general synthesis instructions described and analogously to the concrete synthesis examples given by way of example, the following examples were prepared from the polar and non-polar precursors (8-benzyl-8-(dimethylamino)-3-azaspiro[4.5]decan-4-one, (8-benzyl-3-azaspiro[4.5]decan-8-yl)-dimethylamine, 8-dimethylamino-8-phenyl-3-azaspiro[4.5]decan-4-one, 8-(dimethylamino)-8-phenyl-3-azaspiro[4.5]decan-2-one, 8-butyl-8-dimethylamino-3-azaspiro[4.5]decan-4-one, 8-dimethylamino-8-thiophen-2-yl-3-azaspiro[4.5]decan-4-one, dimethyl-(8-thiophen-2-yl-3-azaspiro[4.5]decan-8-yl)-amine, 8-(dimethylamino)-8-thiophen-2-yl-2-azaspiro[4.5]decan-3-one, 8-(dimethylamino)-8-(5-methylthiophen-2-yl)-3-azaspiro[4.5]decan-4-one, dimethyl-[8-(5-methylthiophen-2-yl)-3-azaspiro[4.5]decan-8-yl]-amine, dimethyl-(8-phenyl-3-azaspiro[4.5]decan-8-yl)-amine, 8-(cyclohexylmethyl)-8-dimethylamino-3-azaspiro[4.5]decan-4-one, 8-(cyclopentylmethyl)-N,N-dimethyl-2-azaspiro[4.5]decan-8-amine, 8-cyclopentyl-N,N-dimethyl-2-azaspiro[4.5]decan-8-amine, 8-(azetidin-1-yl)-8-(thiophen-2-yl)-2-azaspiro[4.5]decane, 8-(azetidin-1-yl)-8-phenyl-2-azaspiro[4.5]decane, 8-(5-chlorothiophen-2-yl)-8-dimethylamino-3-azaspiro[4.5]decan-4-one, 8-(dimethylamino)-8-(5-methylthiophen-2-yl)-3-azaspiro[4.5]decan-2-one) by acylation, arylation, alkylation, reductive amination or reduction of amides.

| Ex. no. | Diastereomer* | Building Block/Method/Yield | LC-MS [M + H]$^+$/R$_t$ | NMR spectrum |
|---|---|---|---|---|
| 36 | 1 | Ex. no. 31/ Acylation/ 19% | [M + H]$^+$ = 361.2, R$_t$ = 3.3 min. | $^1$H-NMR (CDCl$_3$): 1.37 (2 H, m); 1.53-1.65 (4 H, m); 1.81-1.93 (4 H, m); 2.10 (9 H, m); 2.29 (2 H, m); 2.44 (3 H, s); 3.14 (2 H, m); 3.32 (2 H, m); 3.43 (2 H, t); 6.60 (2 H, m). |
| 37 | 1 | Ex. no. 31/ Acylation/ 18% | [M + H]$^+$ = 347.1, R$_t$ = 2.7 min. | $^1$H-NMR (CDCl$_3$): 0.73 (2 H, m); 0.98 (2 H, m); 1.40-1.46 (2 H, m); 1.56-1.73 (5 H, m); 1.89 (2 H, m); 2.09 (4 H, s); 2.12 (4 H, s); 2.45 (3 H, s); 3.35 (1 H, s); 3.49 (3 H, t); 3.62 (1 H, t); 6.65 (2 H, m). |
| 38 | 1 | Ex. no. 31/ Acylation/ 18% | [M + H]$^+$ = 349.2, R$_t$ = 2.9 min. | $^1$H-NMR (CDCl$_3$): 1.10 (6 H, d); 1.37-1.44 (2 H, m); 1.57-1.71 (4 H, m); 1.80-1.94 (2 H, m); 2.01 (1 H, m); 2.11 (7 H, m); 2.45 (3 H, s); 2.59 (1 H, m); 3.33 (2 H, m); 3.45 (2 H, m); 6.64 (2 H, m). |
| 39 | 1 | Ex. no. 31/ Acylation/ 28% | [M + H]$^+$ = 363.2, R$_t$ = 3.3 min. | $^1$H-NMR (DMSO-d$_6$): 0.94 (6 H, m); 1.40 (2 H, m); 1.56-1.69 (4 H, m); 1.95 (2 H, m); 2.05 (3 H, m); 2.12 (8 H, m); 2.45 (3 H, s); 3.30 (1 H, s); 3.35 (1 H, s); 3.45 (2 H, m); 6.62 (1 H, m); 6.67 (1 H, m). |
| 40 | 1 | Ex. no. 31/ Acylation/ 27% | [M + H]$^+$ = 335.2, R$_t$ = 2.7 min | $^1$H-NMR (CDCl$_3$): 1.12 (3 H, t); 1.39 (2 H, m); 1.58 (4 H, m); 1.84 (2 H, m); 2.06 (4 H, s); 2.09 (4 H, s); 2.22 (2 H, m); 2.43 (3 H, s); 3.25 (1 H, s); 3.33 (1 H, s); 3.40 (2 H, m); 6.62 (2 H, m). |
| 42 | 1 | Ex. no. 18/ Acylation/ 90% | [M + H]$^+$ = 337.2, R$_t$ = 2.0 min | $^1$H-NMR (CDCl$_3$): 1.39 (2 H, m); 1.60-1.70 (4 H, m); 1.94 (2 H, m); 2.09 (7 H, m); 2.15 (1 H, b s); 3.28 (1 H, s); 3.42 (5 H, m); 3.51 (1 H, s); 3.99 (2 H, s); 6.84 (1 H, s); 7.03 (1 H, s); 7.22 (1 H, s). |
| 43 | 1 | Ex. no. 18/ Acylation/ 88% | [M + H]$^+$ = 347.2, R$_t$ = 1.8 mm | $^1$H-NMR (CDCl$_3$): 1.32 (2 H, m); 1.52 (1 H, t); 1.58 (3 H, t); 1.62-1.93 (4 H, m); 2.00-2.12 (10 H, m); 2.29 (2 H, m); 3.09 (2 H, m); 3.28 (1 H, m); 3.38 (1 H, t); 6.77 (1 H, m); 6.97 (1 H, m); 7.16 (1 H, m). |

| Ex. no. | Diastereomer* | Building Block/Method/Yield | LC-MS [M + H]+/R$_t$ | NMR spectrum |
|---|---|---|---|---|
| 44 | 1 | Ex. no. 18/ Acylation/ 37% | [M + H]+ = 333.2, R$_t$ = 2.4 mm | $^1$H-NMR (CDCl$_3$): 0.73 (2 H, m); 0.98 (2 H, m); 1.40-1.75 (6 H, b m); 1.94 (2 H, b s); 2.09 (2 H, s); 2.12 (4 H, s); 2.20 (2 H, b s); 3.38 (1 H, s); 3.49 (2 H, m); 3.64 (1 H, t); 6.86 (1 H, m); 7.04 (1 H, m); 7.27 (1 H, m). |
| 45 | 1 | Ex. no. 18/ Acylation/ 57% | [M + H]+ = 335.2, R$_t$ = 2.0 min | $^1$H-NMR (CDCl$_3$): 1.04 (6 H, m); 1.35 (2 H, m); 1.53 (1 H, t); 1.63 (3 H, m); 1.88 (2 H, m); 2.03 (6 H, m); 2.11 (2 H, m); 2.55 (1 H, m); 3.28 (2 H, m); 3.41 (2 H, m); 6.78 (1 H, m); 6.97 (1 H, m); 7.16 (1 H, m). |
| 46 | 1 | Ex. no. 18/ Acylation/ 51% | [M + H]+ = 349.2, R$_t$ = 2.2 min | $^1$H-NMR (DMSO-d$_6$): 0.93 (6 H, m); 1.37 (2 H, m); 1.56 (1 H, t); 1.63 (3 H, m); 1.89 (2 H, m); 2.01-2.17 (11 H, b m); 3.27 (1 H, s); 3.33 (1 H, s); 3.41 (2 H, m); 6.08 (1 H, m); 6.97 (1 H, m); 7.18 (1 H, m). |
| 47 | 1 | Ex. no. 70/ Reduction/ 90% | [M + H]+ = 323.2, R$_t$ = 0.5 min | $^1$H-NMR (CDCl$_3$): 1.36 (2 H, m); 1.50 (2 H, t); 1.68 (2 H, m); 1.89 (2 H, m); 2.08 (8 H, s); 2.46 (2 H, s); 2.54 (2 H, t); 2.60 (2 H, t); 3.33 (3 H, s); 3.46 (2 H, t); 6.82 (1 H, m); 7.01 (1 H, m); 7.20 (1 H, m). |
| 49 | 1 | Ex. no. 18/ Reductive amination/ 69% | [MH − HNMe$_2$]+ = 274.3 (100%) [M + H]+ = 319.3 (40%), R$_t$ = 0.4 min. | $^1$H-NMR (DMSO-d$_6$): 0.10-0.15 (2 H, m); 0.43-0.50 (2 H, m); 0.82-0.92 (1 H, m); 1.27-1.35 (2 H, m); 1.52 (2 H, t, J = 6.8 Hz); 1.62-1.71 (2 H, m); 1.82-2.01 (4 H, m); 1.99 (6 H, s); 2.30-2.45 (2 H, m); 2.51-2.56 (2 H m); 2.63-2.72 (2 H, m); 6.92 (1 H, dd, J = 3.5 and 1.1 Hz); 7.05 (1 H dd, J = 5.1 and 3.5 Hz); 7.41 (1 H, dd, J = 5.1 and 1.0 Hz). $^{13}$C-NMR (DMSO-d$_6$): 3.6; 8.7; 32.7; 33.0; 36.0; 37.7; 40.5; 41.3; 41.6; 52.9; 58.6; 59.9; 65.0; 123.5; 124.7; 126.3; 143.2. |
| 50 | 1 | Ex. no. 18/ Acylation/ 48% | [MH − HNMe$_2$]+ = 316.3 (100%) [M + H]+ = 361.4 (65%), R$_t$ = 3.0 min. | $^1$H-NMR (CDCl$_3$): 1.32-1.44 (2 H, m); 1.59 (1 H, t, J = 7.1 Hz); 1.62-1.75 (5 H, m); 1.77-2.01 (4 H, m); 2.02-2.24 (4 H, m); 2.11 (6 H, s); 2.33-2.38 (2 H, m); 2.66-2.78 (1 H, m); 3.29 (1.2 H, s); 3.34 (0.8 H, s); 3.42 (0.8 H, t, J = 7.6 Hz); 3.45 (1.2 H, t, J = 7.8 Hz); 6.82-6.86 (1 H, m); 7.00-7.06 (1 H, m); 7.20-7.26 (1 H, m). $^{13}$C-NMR (CDCl$_3$): 18.71; 18.74; 28.5; 28.6; 31.1; 31.2; 32.3; 32.8; 33.5; 35.6; 37.0; 38.08; 38.09; 40.1; 41.2; 41.7; 42.0; 43.7; 45.1; 53.4; 55.3; 56.5; 59.8; 123.3; 123.5; 124.8; 125.1; 126.1; 126.3; 142.1; 143.7; 171.0; 171.1. |
| 51 | 1 | Ex. no. 48/ Reduction/ 55% | [MH − HNMe$_2$]+ = 288.3 (100%) [M+H]+ = 333.4 (25%), R$_t$ = 0.7 min.h | $^1$H-NMR (CDCl$_3$): 0.01-0.06 (2 H, m); 0.38-0.44 (2 H, m); 0.59-0.72 (1 H, m); 1.34-1.43 (4 H, m); 1.52 (2 H, t, J = 6.8 Hz); 1.66-1.74 (2 H, m); 1.84-1.99 (2 H, m); 2.05-2.18 (2 H, m); 2.10 (6 H, s); 2.45 (2 H, s); 2.47-2.57 (4 H, m); 6.84 (1 H, dd, J = 3.6 and 1.1 Hz); 7.03 (1 H, dd, J = 5.1 and 3.6 Hz); 7.22 (1 H, dd, J = 5.1 and 1.0 Hz). $^{13}$C-NMR (CDCl$_3$): 4.3; 9.1; 33.7; 34.3; 38.2; 40.9; 54.0; 56.9; 59.6; 65.5; 123.2; 125.1; 126.2. |
| 52 | 1 | Ex. no. 50/ Reduction/ 65% | MH − HNMe$_2$]+ = 302.3 (100%) [M + H]+ = 347.4 (25%), R$_t$ = 1.9 mm | $^1$H-NMR (CDCl$_3$): 1.38 (2 H, ddd, J = 13.3, 10.0 and 3.5 Hz); 1.50 (2 H, t, J = 6.8 Hz); 1.54-1.64 (4 H, m); 1.65-1.73 (2 H, m); 1.78-1.96 (4 H, m); 1.98-2.16 (4 H, m); 2.10 (6 H, s); 2.20-2.30 (3 H, m); 2.41 (2 H, s); 2.49 (2 H, t, J = 6.8 Hz); 6.85 (1 H, dd, J = 3.6 and 1.1 Hz); 7.03 (1 H, dd, J = 5.1 and 3.6 Hz); 7.22 (1 H, dd, J = 5.1 and 1.1 Hz). $^{13}$C-NMR (CDCl$_3$): 18.7; 28.4; 33.7; 34.5; 36.1; 38.2; 40.8; 54.0; 54.8; 59.6; 65.8; 123.2; 124.9; 126.1. |
| 53 | 1 | Ex. no. 43/ Reduction/ 60% | [MH − HNMe$_2$]+ = 288.3 (100%) [M + H]+ = 333.4 (20%), R$_t$ = 1.1 mm | $^1$H-NMR (CDCl$_3$): 1.38-1.48 (2 H, m); 1.60-1.82 (8 H, m); 1.85-1.94 (1 H, m); 1.94-2.04 (1 H, m); 2.06-2.18 (4 H, m); 2.12 (6 H, s); 2.55-2.95 (6 H, m); 6.85 (1 H, br d, J = 3.0 Hz); 7.03 (1 H, dd, J = 5.1 and 3.6 Hz); 7.22-7.24 (1 H, dd, J = 5.0 and 0.8 Hz). $^{13}$C-NMR (CDCl$_3$): 18.7; 27.8; 30.3; 33.3; 33.6; 36.9; 38.1; 41.1; 53.5; 59.9; 62.2; 64.4; 123.6; 125.3; 126.3. |
| 54 | 1 | Ex. no. 18/ Acylation/ 55% | [M + H]+ = 363.3, R$_t$ = 3.1 min | $^1$H-NMR (CDCl$_3$): 0.91 (6 H, t, J = 6.1 Hz); 1.34-1.45 (2 H, m); 1.50-1.73 (8 H, m); 1.80-2.08 (2 H, m); 2.09 and 2.11 (6 H, 2 s); 2.15-2.26 (3 H, m); 3.30 (1.2 H, s); 3.36 (0.8 H, s); 3.41-3.50 (2 H, m); 6.83-6.87 (1 H, m); 7.01-7.07 (1 H, m); 7.23-7.26 (1 H, m). $^{13}$C-NMR (CDCl$_3$): 22.3; 22.38; 22.41; 27.9; 28.0; 31.1; 31.2; 32.4; 32.8; 33.4; 33.7; 33.8; 35.6; 37.2; 38.1; 40.1; 42.0; 44.0; 45.0; 55.5; 56.5; 59.9; 123.3; 123.5; 124.8; 125.0; 126.1; 126.3; 172.17; 172.2. |
| 55 | 1 | Ex. no. 18/ Acylation/ 36% | [MH − HNMe$_2$]+ = 315.2 (100%) [M + H]+ = 360.2 (10%), R$_t$ = 2.6 min | $^1$H-NMR (CDCl$_3$): 1.38-1.46 (2 H, m); 1.60 and 1.61 (6 H, 2 s); 1.65 (2 H, t, J = 7.4 Hz); 1.68-1.81 (3 H, m); 1.93-2.09 (3 H, m); 2.10 and 2.11 (6 H, 2 s); 3.43 (0.7 H, s); 3.63 (1.3 H, 3 s); 3.55 (1.3 H, t, J = 7.5 Hz); 3.83 (0.7 H, t, J = 7.0 Hz); 6.85 (1 H, dd, J = 3.5 and 0.9 Hz); 7.05 (1 H, dd, J = 5.1 and 3.5 Hz); 7.24 (1 H, d, J = 5.0 Hz). $^{13}$C-NMR (CDCl$_3$): 25.07; 25.1; 30.4; 31.2; 33.0; 33.1; 34.0; 36.7; 38.0; 38.1; 39.2; 43.0; 46.2; 46.4; 57.9; 59.8; 121.7; 121.8; 123.4; 124.8; 124.9; 126.2; 126.3; 165.9. |
| 56 | 1 | Ex. no. 18/ Acylation/ 50% | [MH − HNMe$_2$]+ = 332.2 (100%) [M + H]+ = 377.3 (50%), R$_t$ = 2.5 min. | $^1$H-NMR (CDCl$_3$): 1.33-1.45 (2 H, m); 1.50-1.74 (5 H, m); 1.76-2.06 (3 H, m); 2.09 and 2.10 (6 H, 2 s); 2.12-2.40 (2 H, m); 2.30-2.40 (2 H, m); 2.66-2.76 (1 H, m); 3.28 (1.2 H, s); 3.36 (0.8 H, s); 3.40-3.50 (3 H, m); 3.70-3.78 (1 H, m); 3.82-3.89 (1 H, m); 3.93-4.00 (1 H, m); 6.84 (1 H, dt, J = 3.7 and 1.1 Hz); 7.01-7.06 (1 H, m); 7.22 (0.4 H, dd, J = 5.1 and 1.1 Hz); 7.24 (0.6 H, dd, J = 5.1 and 1.1 Hz). $^{13}$C-NMR (CDCl$_3$): 31.1; 31.2; 32.3; 32.83; 32.85; 33.4; 35.3; 35.5; |

| Ex. no. | Diastereomer* | Building Block/Method/Yield | LC-MS [M + H]⁺/R$_t$ | NMR spectrum |
|---|---|---|---|---|
| | | | | 37.0; 38.1; 38.5; 40.1; 42.1; 43.9; 45.1; 55.4; 56.4; 59.8; 67.6; 73.31; 73.33; 123.3; 123.5; 124.8; 125.1; 126.1; 126.3; 143.6; 170.40; 170.44. |
| 57 | 1 | Ex. no. 18/ Acylation/ 41% | [M + H]⁺ = 349.3, R$_t$ = 2.3 min. | ¹H-NMR (CDCl₃): 1.33-1.44 (2 H, m); 1.60-1.72 (5 H, m); 1.85-2.08 (2 H, m); 2.09 and 2.11 (6 H, 2 s); 2.11-2.18 (1 H, m); 3.06 (1.2 H, s); 3.23 (0.8 H, t, J = 7.2 Hz); 3.40 (0.8 H, s); 3.52 (1.2 H, t, J = 7.2 Hz); 3.87-3.98 (1 H, m); 4.74-4.81 (2 H, m); 4.90-4.96 (2 H, m); 6.83-6.86 (1 H, m); 7.01-7.06 (1 H, m); 7.22-7.26 (1 H, m). ¹³C-NMR (CDCl₃): 30.9; 31.2; 32.9; 32.3; 35.0; 36.9; 38.04; 38.09; 38.3; 38.5; 40.1; 42.1; 44.2; 44.3; 55.6; 55.9; 59.8; 73.01; 73.03; 123.4; 123.5; 124.9; 125.0; 126.2; 126.3; 169.6; 169.7. |
| 58 | 1 | Ex. no. 18/ Acylation/ 23% | [MH – HNMe₂]⁺ = 313.2 (100%) [M + H]⁺ = 358.2 (6%), R$_t$ = 2.6 min. | ¹H-NMR (CDCl₃): 1.38-1.54 (4 H, m); 1.55-1.81 (8 H, m); 1.95-2.08 (2 H, m); 2.10 and 2.12 (6 H, 2 s); 3.38 (0.8 H, s); 3.50 (1.2 H, t, J = 7.3 Hz); 3.71 (1.2 H, s); 3.90 (0.8 H, t, J = 1.1 Hz); 6.86 (1 H, br d, J = 3.5 Hz); 7.03-7.07 (1 H, m); 7.23-7.26 (1 H, m). ¹³C-NMR (CDCl₃): 16.3; 16.7; 30.7; 31.1; 33.2; 38.07; 38.1; 39.9; 42.5; 45.7; 46.1; 120.3; 123.4; 124.9; 126.2; 126.3; 163.0. |
| 59 | 1 | Ex. no. 18/ Acylation/ 84% | [M + H]⁺ = 393.3, R$_t$ = 2.8 min. | ¹H-NMR (CDCl₃): 1.15 (2.4 H, s); 1.16 (3.6 H, s); 1.30-1.46 (2 H, m); 1.60 (1.2 H, t, J = 7.2 Hz); 1.63-1.74 (2.8 H, m); 1.80-2.02 (4 H, m); 2.04-2.22 (8 H, m); 2.23-2.30 (2 H, m); 3.16 (1.2 H, s); 3.18 (1.8 H, s); 3.32 (1.2 H, s); 3.36 (0.8 H, s); 3.44-3.50 (2 H, m); 6.83-6.87 (1 H, m); 7.01-7.07 (1 H, m); 7.21-7.26 (1 H, m). ¹³C-NMR (CDCl₃): 24.7; 25.0; 28.7; 29.1; 31.0; 31.1; 32.7; 33.4; 34.0; 34.2; 35.6; 37.1; 38.1; 40.0; 42.0; 44.0; 45.0; 49.1; 53.4; 55.5; 56.4; 59.8; 73.90; 73.94; 123.2; 124.7; 126.0; 126.2; 171.91; 171.94. |
| 60 | 1 | Ex. no. 18/ Acylation/ 57% | [M + H]⁺ = 377.3, R$_t$ = 2.5 min. | ¹H-NMR (CDCl₃): 1.34-1.46 (2 H, m); 1.56-1.74 (7 H, m); 1.84-2.02 (4 H, m); 2.09 and 2.12 (6 H, 2 s); 2.16-2.26 (1 H, m); 2.52-2.61 (1 H, m); 3.34-3.54 (6 H, m); 3.99-4.05 (2 H, m); 6.83-6.87 (1 H, m); 7.01-7.07 (1 H, m); 7.21-7.27 (1 H, m). ¹³C-NMR (CDCl₃): 28.58; 28.6; 31.0; 31.2; 32.8; 33.4; 35.5; 37.1; 38.1; 39.6; 39.8; 39.9; 40.2; 42.0; 44.7; 55.6; 56.0; 59.8; 67.3; 123.3; 123.6; 124.8; 125.1; 126.1; 126.4; 173.0; 173.1. |
| 61 | 1 | Ex. no. 18/ Acylation/ 68% | [MH – HNMe₂]⁺ = 327.2 (100%) [M + H]⁺ = 372.3 (5%), R$_t$ = 2.7 min. | ¹H-NMR (CDCl₃): 1.37-1.46 (2 H, m); 1.63-1.78 (4 H, m); 1.93-2.09 (4 H, m); 2.10 (6 H, s); 2.12-2.15 (1 H, m); 2.20-2.33 (1 H, m); 2.53-2.68 (2 H, m); 2.72-2.82 (2 H, m); 3.35 (1.2 H, s); 3.42 (0.8 H, s); 3.51-3.57 (2 H, m); 6.85 (1 H, dd, J = 3.5 and 0.9 Hz); 7.04 (1 H, td, J = 5.1 and 3.6 Hz); 7.22-7.26 (1 H, m). ¹³C-NMR (CDCl₃): 16.5; 30.5; 30.6; 31.2; 33.0; 33.1; 34.4; 37.2; 38.0; 38.1; 38.8; 39.0; 39.8; 42.7; 44.9; 45.5; 56.7; 57.1; 59.8; 120.8; 120.9; 123.4; 124.9; 126.2; 126.3; 164.4; 164.7. |
| 62 | 1 | Ex. no. 18/ Acylation/ 61% | [M + H]⁺ = 361.3, R$_t$ = 3.0 min. | ¹H-NMR (CDCl₃): 0.03-0.08 (2 H, m); 0.38-0.45 (2 H, m); 0.66-0.76 (1 H, m); 1.34-1.45 (2 H, m); 1.50-1.64 (3 H, m); 1.64-1.72 (3 H, m); 1.85-2.02 (3 H, m); 2.03 and 2.12 (6 H, 2 s); 2.14-2.25 (1 H, m); 2.31-2.38 (2 H, m); 3.32 (1.2 H, s); 3.36 (0.8 H, s); 3.34-3.50 (2 H, m); 6.83-6.87 (1 H, m); 7.01-7.07 (1 H, m); 7.21-7.26 (1 H, m). ¹³C-NMR (CDCl₃): 4.5; 10.7; 28.5; 30.12; 30.15; 31.1; 31.2; 32.8; 33.4; 34.4; 34.8; 35.6; 37.1; 38.1; 40.1; 42.0; 43.9; 45.0; 55.3; 56.5; 59.9; 123.3; 123.5; 124.9; 125.1; 126.1; 126.3; 171.87; 171.9. |
| 63 | 1 | Ex. no. 18/ Acylation/ 67% | [M + H]⁺ = 365.3, R$_t$ = 2.5 min. | ¹H-NMR (CDCl₃): 1.35-1.44 (8 H, m); 1.53-1.58 (1 H, m); 1.64-1.75 (3 H, m); 1.95-2.09 (3 H, m); 2.10 and 2.11 (6 H, 2 s); 2.12-2.18 (1 H, m); 3.18 and 3.19 (3 H, 2 s); 3.42 (0.7 H, s); 3.57 (1.3 H, t, J = 7.4 Hz); 3.62 (1.3 H, s); 3.73 (0.7 H, t, J = 7.0 Hz); 6.85 (1 H, dd, J = 3.5 and 0.7 Hz); 7.04 (1 H, dd, J = 5.0 and 3.6 Hz); 7.22-7.26 (1 H, m). ¹³C-NMR (CDCl₃): 24.1; 30.3; 30.6; 31.4; 32.9; 33.1; 34.0; 38.07; 38.1; 38.8; 42.4; 45.4; 45.8; 51.57; 51.59; 56.8; 57.7; 59.9; 79.8; 123.3; 124.8; 126.1; 126.3; 172.6; 172.9. |
| 64 | 1 | Ex. no. 18/ Acylation/ 58% | [M + H]⁺ = 377.3, R$_t$ = 2.7 min. | ¹H-NMR (CDCl₃): 1.34-1.45 (2 H, m); 1.51-1.73 (6 H, m); 1.84-2.00 (4 H, m); 2.09 and 2.11 (6 H, 2 s); 2.13-2.23 (2 H, m); 2.34-2.43 (1 H, m); 2.57-2.65 (1 H, m); 3.28-3.40 (2 H, m); 3.40-3.55 (2 H, m); 3.70-3.77 (1 H, m); 3.82-3.90 (1 H, m); 4.25-4.32 (1 H, m); 6.84-6.86 (1 H, m); 7.01-7.07 (1 H, m); 7.22-7.26 (1 H, m). ¹³C-NMR (CDCl₃): 25.63; 25.66; 31.1; 31.15; 31.2; 31.5; 31.6; 32.8; 32.9; 33.3; 38.1; 40.1; 40.5; 40.9; 42.0; 43.9; 45.2; 55.4; 56.6; 59.9; 67.81; 67.84; 75.99; 76.0; 123.3; 124.8; 126.1; 126.3; 169.5; 169.6. |
| 65 | 1 | Ex. no. 18/ Acylation/ 28% | [MH – HNMe₂]⁺ = 334.3, R$_t$ = 2.5 min. | ¹H-NMR (CDCl₃): 1.22 (2.6 H, s); 1.23 (3.4 H, s); 1.32-4.47 (2 H, m); 1.57-1.74 (4 H, m); 1.83 (2 H, t, J = 6.8 Hz); 1.87-2.02 (2 H, m); 2.02-2.24 (2 H, m); 2.08 (2.6 H, s); 2.11 (3.4 H, s); 2.36-2.44 (2 H, m); 3.32 (1.2 H, s); 3.36 (0.8 H, s); 3.43-3.50 (2 H, m); 6.84 (0.4 H, dd; J = 3.6 and 1.1 Hz); 6.85 (0.6 H, dd, J = 3.6 and 1.1 Hz); 7.02 (0.4 H, dd, J = 5.1 and 3.6 Hz); 7.05 (0.6 H, dd, J = 5.1 and 3.6 Hz); 7.23 (0.4 H, dd, J = 5.1 and 1.1 Hz); 7.25 (0.6 H, dd, J = 5.1 and 1.1 Hz). The OH signal could not be identified. ¹³C-NMR (CDCl₃): 29.1; 29.4; 29.5; 31.1; 31.2; 32.7; 33.4; 35.5; 37.2; 38.1; 40.0; 42.1; 44.1; 45.2; 55.7; 56.7; 59.7; 69.51; 69.55; 123.2; 123.4; 124.7; 125.1; 126.0; 126.2; 172.6; 172.7. |

| Ex. no. | Diastereomer* | Building Block/Method/Yield | LC-MS [M + H]⁺/$R_t$ | NMR spectrum |
|---|---|---|---|---|
| 66 | 1 | Ex. no. 18/ Acylation/ 50% | [M + H]⁺ = 363.2 (4%) [MH − NHMe₂]⁺ = 318.3 (100%), $R_t$ = 2.6 min. | ¹H-NMR (DMSO-d₆): 1.22-1.32 (2 H, m); 1.41-1.48 (1 H, m); 1.52-1.66 (6 H, m); 1.68-1.77 (1 H, m); 1.99 (4 H, s); 2.00 (2 H, s); 1.94-2.06 (4 H, m, overlapped); 2.45-2.52 (2 H, m, overlapped by the DMSO signal); 3.17 (0.8 H, s); 3.32 (1.2 H, t, J = 7.1 Hz, overlapped by the water signal); 3.35 (1.2 H; s); 3.54 (0.8 H; t, J = 7.1 Hz); 5.747 (0.3 H, s); 5.754 (0.7 H, s); 6.92-6.94 (1 H, m); 7.04-7.07 (1 H, m); 7.40-7.42 (1 H, m). ¹³C-NMR (DMSO-d₆): 12.2; 29.9; 30.0; 30.7; 32.4; 32.5; 33.4; 33.6; 37.7; 38.7; 41.5; 44.4; 44.5; 54.8; 59.0; 59.1; 75.2; 75.5; 123.6; 124.8; 124.9; 126.3; 170.1; 171.1; 171.2. |
| 67 | 1 | Ex. no. 18/ Acylation/ 30% | [MH − HNMe₂]⁺ = 327.2 (100%) [M + H]⁺ = 372.3 (98%), $R_t$ = 2.5 min. | ¹H-NMR (CDCl₃): 0.95-1.02 (2 H, m); 1.32-1.37 (2 H, m); 1.37-1.46 (2 H, m); 1.61-1.75 (4 H, m); 1.87-2.06 (3 H, m); 2.10 (2.5 H, s); 2.11 (3.5 H, s); 2.13-2.22 (1 H, m); 2.45 (2 H, s); 3.29 (1.1 H, s); 3.39 (0.9 H, s); 3.46 (0.9 H, t, J = 7.1 Hz); 3.52 (1.1 H, t, J = 7.3 Hz); 6.83-6.86 (1 H, m); 7.02 (0.5 H, dd, J = 5.1 and 3.6 Hz); 7.04 (0.5 H, dd, J = 5.1 and 3.6 Hz); 7.22 (0.5 H, dd, J = 5.1 and 1.1 Hz); 7.24 (0.5 H, dd, J = 5.1 and 1.1 Hz). ¹³C-NMR (CDCl₃): 6.6; 6.7; 14.0; 31.0; 31.1; 32.8; 33.3; 35.4; 36.9; 38.1; 38.1; 39.3; 39.7; 40.1; 42.3; 44.2; 45.2; 55.6; 58.5; 59.8; 59.8; 123.1; 123.2; 123.3; 123.6; 124.8; 125.1; 126.1; 126.3; 143.5; 167.2; 167.2. |
| 68 | 1 | Ex. no. 18/ Acylation/ 44% | [MH − HNMe₂]⁺ = 341.2 (95%) [M + H]⁺ = 386.3 (100%), $R_t$ = 2.7 min. | ¹H-NMR (CDCl₃): 1.34-1.46 (2 H, m); 1.60-1.75 (4 H, m); 1.85-2.06 (4 H, m); 2.08 (2.5 H, s); 2.11 (3.5 H, s); 2.16-2.30 (4 H, m); 2.58-2.67 (2 H, m); 2.69 (0.8 H, s); 2.70 (1.2 H, s); 3.30 (1.2 H, s); 3.37 (0.8 H, s); 3.45 (0.8 H, t, J = 7.1 Hz); 3.50 (1.2 H, t, J = 7.3 Hz); 6.84 (0.4 H, dd, J = 3.6 and 1.1 Hz); 6.86 (0.6 H, dd, J = 3.5 and 1.0 Hz); 7.02 (0.4 H, dd, J = 5.1 and 3.6 Hz); 7.05 (0.6 H, dd, J = 5.1 and 3.6 Hz); 7.23 (0.4 H, dd, J = 5.1 and 1.1 Hz); 7.25 (0.6 H, dd, J = 5.1 and 1.1 Hz). |
| 69 | 1 | Ex. no. 18/ Acylation/ 32% | [M + H]⁺ = 375.3, $R_t$ = 3.2 min. | ¹H-NMR (CDCl₃): 1.35-1.45 (2 H, m); 1.46-1.76 (10 H, m); 1.78-1.96 (3 H, m); 1.96-2.09 (3 H, m); 2.09 and 2.11 (6 H, 2 s); 2.16-2.32 (3 H, m); 3.29 (1.2 H, s); 3.36 (0.8 H, s); 3.40-3.50 (2 H, m); 6.83-6.87 (1 H, m); 7.01-7.09 (1 H, m); 7.21-7.25 (1 H, m). ¹³C-NMR (CDCl₃): 18.2; 18.29; 18.30; 27.8; 27.9; 27.96; 28.0; 31.1; 31.2; 31.5; 31.7; 31.97; 31.99; 32.04; 32.5; 32.8; 33.4; 35.2; 35.5; 35.7; 35.73; 37.1; 38.1; 40.1; 42.0; 43.9; 45.0; 55.4; 56.4; 59.9; 77.2; 77.5; 123.3; 123.5; 124.9; 125.1; 126.1; 126.3; 171.9; 172.0. |
| 70 | 1 | Ex. no. 57/ Reduction/ 44% | [M + H]⁺ = 335.3, $R_t$ = 0.2 min. | ¹H-NMR (CDCl₃): 1.32-1.40 (2 H, m); 1.48 (2 H, t, J = 6.9 Hz); 1.63-1.71 (2 H, m); 1.75-2.00 (3 H, m); 2.00-2.08 (1 H, m); 2.09 (6 H, s); 2.35 (1 H, s); 2.46 (2 H, t, J = 6.9 Hz); 2.73 (2 H, d, J = 7.3 Hz); 3.13-3.22 (1 H, m); 4.42 (2 H, t, J = 6.2 Hz); 4.78 (2 H, dd, J = 7.8 and 6.0 Hz); 6.84 (1 H, d, J = 3.5 Hz); 7.03 (1 H, dd, J = 5.1 and 3.5 Hz); 7.22 (1 H, d, J = 5.1 Hz). ¹³C-NMR (CDCl₃): 19.8; 33.6; 34.3; 34.7; 38.1; 41.0; 53.8; 59.6; 59.8; 65.7; 76.5; 123.2; 124.9; 126.1. |
| 71 | 1 | Ex. no. 13/ Reduction/ 77% | [M + H]⁺ = 259.2, $R_t$ = 0.6 min | ¹H-NMR (CDCl₃): 1.31 (2 H, m); 1.43 (2 H, m); 1.63 (2 H, m); 1.91 (2 H, m); 2.03 (6 H, s); 2.24 (2 H, m); 2.84 (2 H, s); 2.95 (2 H, m); 7.25-7.39 (5 H, m). |
| 72 | 1 | Ex. no. 71/ Acylation/ 86% | [M + H]⁺ = 329.4, $R_t$ = 2.8 min. | ¹H-NMR (CDCl₃): 0.97 (t, 3H, J = 7.4 Hz); 1.23-1.35 (m, 2H); 1.52-1.74 (m, 8H); 2.02 and 2.04 (2 s, 6H); 2.18-2.28 (m, 3H); 2.23-2.41 (br s, 1 H); 3.34 and 3.41 (2 s, 2H); 3.39-3.48 (m, 2H); 7.23-7.42 (m, 5H). ¹³C-NMR (CDCl₃): 13.7; 14.0; 18.4; 18.5; 18.9; 30.1; 30.9; 31.2; 31.5; 36.4; 36.9; 37.8; 38.0; 38.1; 40.3; 42.3; 43.9; 45.0; 55.1; 56.4; 60.8; 126.5; 126.7; 127.6; 127.63; 127.67; 127.7; 171.9; 172.0. |
| 73 | 1 | Ex. no. 71/ Acylation/ 56% | [M + H]⁺ = 301.2, $R_t$ = 1.5 min | ¹H-NMR (CDCl₃): 1.30 (1 H, m); 1.54 (1 H, m); 1.62 (3 H, m); 1.83-1.96 (2 H, m); 2.00-2.03 (9 H, m); 2.19 (1 H, m); 2.32 (1 H, m); 3.32-3.45 (4 H, m); 7.23-7.39 (5 H, m). |
| 74 | 1 | Ex. no. 71/ Reductive amination/ 83% | [M + H]⁺ = 315.3, $R_t$ = 1.4 min | ¹H-NMR (CDCl₃): 0.90 (3 H, t); 1.30 (4 H, m); 1.44 (4 H, m); 1.66 (2 H, m); 1.85 (2 H, m); 2.02 (6 H, s); 2.26 (2 H, m); 2.37 (2 H, m); 2.46 (4 H, m); 7.29 (5 H, m). |
| 75 | 1 | Ex. no. 71/ Acylation/ 51% | [M + H]⁺ = 371.4, $R_t$ = 2.8 min. | ¹H-NMR (CDCl₃): 1.23-1.34 (2 H, m); 1.51-1.70 (5 H, m); 1.83-1.98 (4 H, m); 2.03 and 2.05 (6 H, 2 s); 2.09-2.25 (2 H, m); 2.25-2.45 (2 H, m); 2.59 (0.6 H, d, J = 6.9 Hz); 2.63 (0.4 H, d, J = 6.9 Hz); 3.33-3.53 (4 H, m); 3.69-3.77 (1 H, m); 3.81-3.91 (1 H, m); 4.24-4.33 (1 H, m); 7.26-7.33 (3 H, m); 7.34-7.41 (2 H, m). ¹³C-NMR (CDCl₃): 25.6; 30.0; 30.1; 30.7; 31.16; 31.2; 31.4; 31.5; 31.57; 31.6; 36.0; 37.6; 38.0; 38.1; 40.4; 40.5; 40.9; 42.3; 43.9; 45.2; 55.1; 56.5; 60.9; 67.81; 67.85; 76.0; 126.5; 126.7; 127.6; 127.7; 127.8; 137.4; 169.7; 169.7. |
| 76 | 1 | Ex. no. 71/ Acylation/ 29% | [MH − HNMe₂]⁺ = 335.3 (22%) [M + H]⁺ = 380.4 (100%), $R_t$ = 2.7 min. | ¹H-NMR (CDCl₃): 1.24-1.36 (2 H, m); 1.56 (1 H, t, J = 7.3 Hz); 1.62 (3 H, m); 1.83-2.11 (9 H, m); 2.15-2.31 (4 H, m); 2.33-2.44 (1 H, m); 2.59-2.68 (2 H, m); 2.69 (0.8 H, s); 2.71 (1.2 H, s); 3.34 (1.2 H, s); 3.41 (0.8 H, s); 3.43-3.51 (2 H, m); 7.24-7.33 (3 H, m); 7.34-7.42 (2 H, m). |

| Ex. no. | Diastereomer* | Building Block/Method/Yield | LC-MS [M + H]+/$R_t$ | NMR spectrum |
|---|---|---|---|---|
| | | | | $^{13}$C-NMR (CDCl$_3$): 17.1; 30.0; 30.8; 31.2; 31.4; 32.5; 33.2; 33.3; 35.9; 37.5; 38.0; 38.1; 40.4; 41.5; 42.0; 42.5; 43.9; 45.2; 55.3; 56.2; 60.8; 124.5; 124.5; 126.5; 126.9; 127.6; 127.6; 127.7; 127.8; 137.5; 167.0; 167.1. |
| 77 | 1 | Ex. no. 71/ Acylation/ 25% | [MH − HNMe$_2$]+ = 321.3 (16%) [M + H]+ = 366.3 (100%), $R_t$ = 2.6 min. | $^1$H-NMR (CDCl$_3$): 0.96-1.02 (2 H, m); 1.25-1.37 (4 H, m); 1.57 (1 H, t, J = 7.3 Hz); 1.62-1.70 (3 H, m); 1.83-1.99 (2 H, m); 2.03 (2.6 H, s); 2.04 (3.4 H, s); 2.16-2.25 (1 H, m); 2.29-2.38 (1 H, m); 2.45 (0.8 H, s); 2.46 (1.2 H, s); 3.32 (1.2 H, s); 3.43 (0.8 H, s); 3.41-3.53 (2 H, s); 7.23-7.32 (3 H, m); 7.33-7.41 (2 H, m). $^{13}$C-NMR (CDCl$_3$): 6.7; 6.7; 14.0; 30.1; 30.8; 31.1; 31.4; 35.8; 37.5; 38.0; 38.1; 39.3; 39.7; 40.4; 42.5; 44.2; 45.2; 55.4; 56.4; 60.8; 123.1; 123.2; 126.5; 126.8; 127.6; 127.6; 127.7; 127.8; 137.3; 167.2; 167.2. |
| 78 | 1 | Ex. no. 71/ Acylation/ 25% | [M + H]+ = 357.3, $R_t$ = 2.4 min. | $^1$H-NMR (CDCl$_3$): 1.26-1.36 (2 H, m); 1.55 (1 H, t, J = 7.3 Hz); 1.59-1.70 (3 H, m); 1.82-2.00 (2 H, m); 2.02 and 2.05 (6 H, 2 s); 2.13-2.40 (2 H, m); 2.67 (2 H, t, J = 7.3 Hz); 3.34 (1.1 H, s); 3.37 (0.9 H, s); 3.38-3.46 (3 H, m); 4.38-4.44 (2 H, m); 4.90 (2 H, dd, J = 7.8 and 6.3 Hz); 7.24-7.32 (3 H, m); 7.34-7.42 (2 H, m). $^{13}$C-NMR (CDCl$_3$): 20.1; 30.1; 30.8; 31.1; 31.4; 31.5; 31.6; 35.8; 37.4; 37.9; 38.0; 38.1; 38.5; 39.8; 40.4; 42.3; 43.8; 44.9; 55.1; 56.3; 60.7; 77.4; 77.5; 126.5; 126.7; 127.5; 127.54; 127.6; 127.7; 137.3; 169.5; 169.6. |
| 79 | 1 | Ex. no. 71/ Acylation/ 58% | [M + H]+ = 357.4, $R_t$ = 3.1 min. | $^1$H-NMR (CDCl$_3$): 0.90 and 0.92 (6 H, 2 d, J = 6.3 Hz); 1.24-1.36 (2 H, m); 1.50-1.70 (7 H, m); 1.77-1.99 (2 H, m); 2.02 and 2.04 (6 H, 2 s); 2.16-2.27 (3 H, m); 2.29-2.40 (1 H, m); 3.40 (1.2 H, s); 3.34 (0.8 H, s); 3.41-3.48 (2 H, m); 7.24-7.32 (3 H, m); 7.34-7.41 (2 H, m). $^{13}$C-NMR (CDCl$_3$): 22.37; 22.4; 27.9; 28.0; 31.0; 30.9; 31.2; 31.5; 32.4; 32.9; 33.8; 36.0; 37.6; 38.0; 38.1; 40.3; 42.3; 43.9; 45.0; 55.2; 56.3; 60.8; 126.5; 126.7; 127.6; 127.63; 127.7; 127.8; 172.19; 172.2. |
| 80 | 1 | Ex. no. 71/ Acylation/ 58% | [M + H]+ = 354.4, $R_t$ = 2.6 min. | $^1$H-NMR (CDCl$_3$): 1.25-1.38 (2 H, m); 1.54-1.58 (1 H, m); 1.58 and 1.60 (6 H, 2 s); 1.62-1.73 (3 H, m); 1.88-2.00 (2 H, m); 1.98 and 2.02 (6 H, 2 s); 2.17-2.30 (2 H, m); 3.45 (0.7 H, s); 3.65 (1.3 H, s); 3.51 (1.3 H, t, J = 7.0 Hz); 3.79 (0.7 H, t, J = 7.0 Hz); 7.23-7.31 (3 H, m); 7.34-7.40 (2 H, m). $^{13}$C-NMR (CDCl$_3$): 25.01; 25.07; 30.2; 30.5; 30.6; 31.4; 34.4; 36.6; 37.9; 38.0; 39.3; 43.2; 46.1; 46.3; 57.5; 57.9; 60.8; 121.6; 121.8; 126.5; 126.6; 127.4; 127.5; 127.7; 165.6; 165.9. |
| 81 | 1 | Ex. no. 71/ Acylation/ 40% | [M + H]+ = 371.4, $R_t$ = 2.6 min. | $^1$H-NMR (CDCl$_3$): 1.24-1.35 (2 H, m); 1.52-1.68 (6 H, m); 1.80-1.98 (4 H, m); 2.02 and 2.04 (6 H, 2 s); 2.15-2.43 (2 H, m); 2.51-2.61 (1 H, m); 3.36-3.51 (6 H, m); 3.98-4.05 (2 H, m); 7.25-7.32 (3 H, m); 7.33-7.41 (2 H, m). $^{13}$C-NMR (CDCl$_3$): 28.6; 30.1; 31.0; 31.1; 31.4; 35.7; 37.6; 38.0; 39.6; 39.8; 40.1; 42.3; 44.1; 44.6; 55.4; 55.9; 60.7; 67.3; 67.32; 126.5; 126.7; 127.5; 127.6; 127.8; 135.2; 137.4; 173.0; 173.1. |
| 82 | 1 | Ex. no. 71/ Acylation/ 14% | [M + H]+ = 373.3, $R_t$ = 2.5 min. | $^1$H-NMR (CDCl$_3$): 1.23 (2.4 H, s); 1.24 (3.6 H, s); 1.27-1.35 (2 H, m); 1.51-1.57 (1.2 H, m); 1.59-1.70 (2.8 H, m); 1.81-1.98 (4 H, m); 2.03 (2.4 H, s); 2.06 (3.6 H, s); 2.16-2.45 (4 H, m); 3.35 (1.2 H, s); 3.40 (0.8 H, s); 3.41-3.49 (2 H, m); 7.23-7.41 (5 H, m). The OH signal could not be identified. The $^1$H-NMR spectrum in DMSO-d$_6$ shows the OH signal at 4.22 and 4.25 ppm. $^{13}$C-NMR (CDCl$_3$): 27.6; 29.1; 29.4; 29.5; 30.0; 30.7; 31.2; 31.3; 35.9; 37.2; 37.4; 37.9; 38.0; 40.3; 42.2; 44.2; 45.0; 55.3; 56.2; 60.7; 69.4; 74.7; 74.8; 75.2; 126.4; 126.9; 127.5; 127.7; 129.9; 137.4; 172.5; 172.6. |
| 83 | 1 | Ex. no. 71/ Acylation/ 77% | [M + H]+ = 387.4, $R_t$ = 2.8 min. | $^1$H-NMR (CDCl$_3$): 1.15 (2.6 H, s); 1.17 (3.4 H, s); 1.27-1.36 (2 H, m); 1.51-1.57 (1.2 H, m); 1.59-1.70 (2.6 H, m); 1.80-1.99 (4 H, m); 2.02 (2.8 H, s); 2.03 (3.4 H, m); 2.16-2.40 (4 H, m); 3.16 (1.3 H, s); 3.18 (1.7 H, s); 3.35 (1.2 H, s); 3.40 (0.8 H, s); 3.41-3.48 (2 H, m); 7.23-7.42 (5 H, m). $^{13}$C-NMR (CDCl$_3$): 25.0; 25.0; 28.7; 29.1; 30.1; 30.7; 31.3; 31.5; 34.0; 34.0; 34.2; 35.9; 37.5; 38.0; 40.4; 42.3; 44.0; 44.9; 49.1; 55.3; 56.2; 60.7; 73.90; 73.94; 126.5; 126.7; 127.6; 127.7; 171.92; 171.94. |
| 84 | 1 | Ex. no. 71/ Acylation/ 54% | [M + H]+ = 357.3 (29%) [MH − NHMe$_2$]+ = 312.3 (100%), $R_t$ = 2.7 min. | $^1$H-NMR (DMSO-d$_6$): 1.13-1.24 (2 H, m); 1.42-1.49 (2 H, m); 1.53-1.63 (2 H, m); 1.68-1.78 (1 H, m); 1.90 (4 H, s); 1.92 (2 H, s); 1.82-1.91 (1 H, m, overlapped); 1.95-2.13 (6 H, m); 2.46-2.54 (2 H, m, overlapped by the DMSO signal); 3.21 (0.8 H, s); 3.24 (1.2 H; t, J = 7.1 Hz, overlapped by the water signal); 3.39 (1.2 H; s); 3.52 (0.8 H; t, J = 7.1 Hz); 5.70 (0.3 H, s); 5.77 (0.7 H, s); 7.23-7.26 (1 H, m); 7.31-7.39 (4 H, m). $^{13}$C-NMR (DMSO-d$_6$): 12.2; 29.9; 30.2; 30.9; 33.4; 33.6; 37.7; 41.7; 44.4; 59.8; 60.0; 75.2; 75.5; 126.2; 127.2; 127.4; 171.1; 171.3. |
| 85 | 1 | Ex. no. 71/ Acylation/ 70% | [M + H]+ = 341.4, $R_t$ = 2.8 min. | $^1$H-NMR (CDCl$_3$): 0.10-0.19 (2 H, m); 0.51-0.58 (2 H, m); 1.08 (1 H, m); 1.22-1.35 (2 H, m); 1.50-1.67 (4 H, m); 1.75-1.98 (2 H, m); 2.02 (2.4 H, s); 2.03 (3.6 H, s); 3.31 (1.2 H, s); 2.17 (0.8 H, d, J = 6.7 |

-continued

| Ex. no. | Diastereomer* | Building Block/Method/Yield | LC-MS [M + H]⁺/R_t | NMR spectrum |
|---|---|---|---|---|
| | | | | Hz); 2.20 (1.2 H, d, J = 6.7 Hz); 2.18-2.40 (2 H, m); 3.38 (0.8 H, t, J = 7.2 Hz); 3.41 (0.8 H, s); 3.46 (1.2 H, t, J = 7.2 Hz); 7.22-7.40 (5 H, m). $^{13}$C-NMR (CDCl$_3$): 4.3; 6.9; 30.1; 30.9; 31.2; 31.3; 35.9; 37.7; 37.9; 38.1; 39.5; 39.9; 40.2; 42.3; 43.9; 44.9; 55.0; 56.3; 60.8; 126.3; 126.7; 127.4; 127.5; 127.6; 135.6; 137.4; 171.38; 171.44. |
| 86 | 1 | Ex. no. 71/ Acylation/ 79% | [M + H]⁺ = 355.4, R_t = 3.1 min. | $^1$H-NMR (CDCl$_3$): 1.24-1.35 (2 H, m); 1.53 (1 H, m); 1.56-176 (5 H, m); 1.78-1.98 (4 H, m); 2.02 (2.5 H, s); 2.04 (3.5 H, s); 2.10-2.24 (3 H, m); 2.30-2.42 (3 H, m); 2.74 (1 H, m); 3.33 (1.8 H, s); 3.37 (0.8 H, s); 3.38-3.46 (2 H, m); 7.22-7.42 (5 H, m). $^{13}$C-NMR (CDCl$_3$): 18.6; 28.6; 30.0; 30.8; 31.2; 31.3; 32.2; 32.4; 35.8; 37.5; 38.0; 38.1; 40.2; 41.3; 41.6; 42.3; 43.6; 45.1; 53.4; 55.1; 56.3; 60.8; 126.3; 126.7; 127.6; 171.06; 171.09. |
| 87 | 1 | Ex. no. 83/ Reduction/ 55% | [M + H]⁺ = 373.4, R_t = 2.1 min. | $^1$H-NMR (CDCl$_3$): 1.13 (6 H, s); 1.20-1.32 (2 H, m); 1.40-1.55 (6 H, m); 1.60-1.70 (2 H, m); 1.75-1.92 (2 H, m); 2.02 (6 H, s); 2.27 (2 H, br s); 2.34-2.40 (2 H, m); 2.48-2.54 (4 H, m); 3.17 (3 H, s); 7.24-7.40 (5 H, m). $^{13}$C-NMR (CDCl$_3$): 23.2; 24.9; 31.0; 34.7; 37.6; 38.1; 38.2; 41.0; 49.1; 53.4; 53.9; 57.4; 60.4; 65.4; 74.3; 126.4; 127.4; 127.6. |
| 88 | 3 | Ex. no. 425/ Acylation/ 41% | [MH − HNMe$_2$]⁺ = 324.3, R_t = 3.0 min. | $^1$H-NMR (CDCl$_3$): 0.96 (3 H, dt, J = 7.4 and 2.8 Hz); 1.34-1.44 (2 H, m); 1.61-1.73 (6 H, m); 1.83-2.02 (4 H, m); 2.10 (3 H, s); 2.12 (3 H, s); 2.21 (2 H, dt, J = 7.8 and 1.9 Hz); 3.29 (1 H, s); 3.36 (1 H, s); 3.46 (2 H, td, J = 14.6 and 7.2 Hz); 6.61 (1 H, t, J = 4.0 Hz); 6.84 (1 H, dd, J = 10.5 and 3.8 Hz). $^{13}$C-NMR (CDCl$_3$): 18.3; 18.4; 31.0; 31.2; 32.4; 33.0; 35.5; 36.3; 36.8; 37.2; 37.9; 38.1; 40.1; 42.0; 43.9; 45.0; 55.2; 55.5; 124.3; 124.5; 125.4; 125.6; 127.9; 142.7. |
| 89 | 3 | Ex. no. 425/ Reductive amination/ 44% | [M − HNMe$_2$]⁺ = 310.3, R_t = 2.0 min. | $^1$H-NMR (CDCl$_3$): 0.91 (3 H, t, J = 7.3 Hz); 1.28-135 (2 H, m); 1.37-1.41 (2 H, m); 1.43-1.47 (2 H, m); 1.51 (2 H, t, J = 6.9 Hz); 1.65-1.71 (2H, m); 1.81-1.87 (2 H, m); 1.98-2.06 (2 H, m); 2.11 (6 H, s); 2.34-2.38 (2 H, m); 2.39 (2 H, s); 2.50 (2 H, t, J = 6.8 Hz); 6.60 (1 H, dd, J = 3.8 and 0.9 Hz); 6.83 (1 H, dd, J = 3.8 and 0.9 Hz). $^{13}$C-NMR (CDCl$_3$): 14.1; 20.9; 31.0; 33.3; 33.8; 34.4; 38.1; 38.2; 40.8; 53.9; 56.8; 60.1; 124.3; 125.4; 126.1; 127.5. |
| 90 | 1 | Ex. no. 426/ Acylation/ 42% | [MH − HNMe$_2$]⁺ = 308.3, R_t = 2.9 min. | $^1$H-NMR (CDCl$_3$): 0.96 (3 H, dt, J = 7.4 and 2.6 Hz); 1.35-1.44 (2 H, m); 1.61-1.73 (6 H, m); 1.81-1.99 (4 H, m); 2.10 (3 H, s); 2.12 (3 H, s); 2.19-2.23 (2 H, m); 3.28 (1 H, s); 3.36 (1 H, s); 3.46 (2 H, td, J = 14.6 and 7.2 Hz); 6.38 (1 H, ddd, J = 12.6, 4.0 and 1.7 Hz); 6.42 (1 H, ddd, J = 4.8, 4.0 and 3.2 Hz). $^{13}$C-NMR (CDCl$_3$): 14.0; 18.3; 18.4; 31.0; 31.2; 32.1; 32.8; 35.6; 36.3; 36.8; 37.2; 37.9; 38.05; 38.08; 40.1; 42.0; 43.9; 45.0; 55.2; 56.4; 60.0; 60.1; 106.0; 106.2; 160.3; 160.4; 121.0; 121.1; 121.3; 162.5; 165.4; 171.87; 171.91. |
| 91 | 1 | Ex. no. 426/ Reductive amination/ 49% | [MH − HNMe$_2$]⁺ = 294.3, R_t = 1.0 min | $^1$H-NMR (CDCl$_3$): 0.91 (3 H, t, J = 7.3 Hz); 1.28-1.48 (6 H, m); 1.52 (2 H, t, J = 6.9 Hz); 1.64-1.70 (2 H, m); 1.83 (2 H, t, J = 11.4 Hz); 1.93-2.04 (2 H, m); 2.11 (6 H, s); 2.34-2.38 (2 H, m); 2.40 (2 H, s); 2.50 (2 H, t, J = 6.9 Hz,); 6.37 (1 H, dd, J = 4.0 and 1.7 Hz.); 6.42 (1 H, dd, J = 4.0 and 3.2 Hz). $^{13}$C-NMR (CDCl$_3$): 14.1; 20.9; 31.0; 33.1; 34.4; 38.0; 38.1; 40.8; 53.9; 56.8; 59.9; 65.6; 106.1 (d, J = 11 Hz); 121.1; 127.3; 129.2; 132.7; 133.1; 163.8 (d, J = 289 Hz). |
| 94 | 3 | Ex. no. 93/ Reduction/ 72% | [M + H]⁺ = 335.3, low UV activity | $^1$H-NMR (CDCl$_3$): 0.90 (3 H, t, J = 7.3 Hz); 0.92-1.00 (2 H, m); 1.06-1.75 (25 H, m); 2.17 (6 H, s); 2.30-2.39 (4 H, m); 2.53 (2 H, t, J = 6.8 Hz). $^{13}$C-NMR (CDCl$_3$): 14.1; 20.9; 26.2; 26.7; 29.4; 31.0; 33.1; 33.5; 36.1; 36.3; 37.3; 37.8; 41.0; 54.4; 56.8; 56.9; 68.3. |
| 96 | 3 | Ex. no. 95/ Reduction/ 66% | [M + H]⁺ = 321.3, low UV activity | $^1$H-NMR (CDCl$_3$): 0.89 (3 H , t, J = 7.3 Hz); 1.00-1.10 (2 H, m); 1.22-1.84 (23 H, m); 2.18 (6 H, s); 2.30-2.40 (4 H, m); 2.55 (2 H, t, J = 6.7 Hz). $^{13}$C-NMR (CDCl$_3$): 14.1; 20.9; 25.0; 29.5; 30.8; 33.3; 35.1; 36.0; 36.3; 36.7; 37.1; 37.3; 41.0; 54.2; 56.6; 56.7; 68.1. |
| 97 | 3 | Ex. no. 424/ Acylation/ 89% | [M + H]⁺ = 321.4, R_t = 2.8 min. | $^1$H-NMR (CDCl$_3$): 0.948 and 0.953 (3 H, 2 t, J = 7.4); 1.16-1.39 (6 H, m); 1.40-1.84 (14 H, m); 2.00-2.12 (2 H, m); 2.16-2.23 (2 H, m); 2.25 (2.4 H, s); 2.28 (3.6 H, s); 3.15 (1.2 H, s); 3.22 (0.8 H, t, J = 7.1 Hz); 3.46 (0.8 H, t, J = 7.1 Hz); 3.50 (1.2 H, t, J = 7.2 Hz). |
| 98 | 3 | Ex. no. 97/ Reduction/ 84% | [M + H]⁺ = 307.4, R_t = 1.3 min. | $^1$H-NMR (CDCl$_3$): 0.90 (3 H, t, J = 7.3 Hz); 1.20-1.36 (8 H, m); 1.38-1.70 (14 H, m); 2.04 (1 H, tt, J = 10.9 and 7.6 Hz); 2.26 (6 H, s); 2.30-2.40 (4 H, m); 2.57 (2 H, t, J = 6.5 Hz). $^{13}$C-NMR (CDCl$_3$): 14.1; 20.7; 25.0; 27.2; 28.4; 30.7; 33.1; 34.9; 38.0; 41.5; 44.5; 54.6; 56.9; 57.6; 69.2. |
| 99 | 3 | Ex. no. 424/ Acylation/ 86% | [M + H]⁺ = 333.4, R_t = 2.9 min. | $^1$H-NMR (CDCl$_3$): 1.12-1.38 (6 H, m); 1.40-2.18 (17 H, m); 2.25 (2 H, s); 2.28 (4 H, s); 2.28-2.37 (2 H, m); 3.05 (1.3 H, s); 3.15 (1 H, m); 3.21 (0.7 H, s); 3.37 (0.7 H, t, J = 7.1 Hz); 3.49 (1.3 H, t, J = 7.1 Hz). |

-continued

| Ex. no. | Diastereomer* | Building Block/Method/Yield | LC-MS [M + H]$^+$/R$_t$ | NMR spectrum |
|---|---|---|---|---|
| 100 | 3 | Ex. no. 424/ Acylation/ 75% | [M + H]$^+$ = 319.4, R$_t$ = 2.7 min. | $^{13}$C-NMR (CDCl$_3$): 18.0; 18.1; 24.7; 25.0; 25.1; 26.9; 27.1; 28.48; 28.53; 29.8; 29.9; 31.7; 33.4; 37.7; 37.9; 38.0; 38.4; 40.5; 42.5; 44.0; 44.1; 44.5; 44.7; 57.8; 57.8; 58.8; 59.4; 173.1; 173.3. $^1$H-NMR (CDCl$_3$): 0.68-0.75 (2 H, m); 0.94-1.66 (2 H, m); 1.14-1.40 (6 H, m); 1.41-1.78 (12 H, m); 1.84 (1 H, t, J = 7.1 Hz); 2.07 (1 H, m); 2.26 (3.6 H, s); 2.28 (2.4 H, s); 3.23 (0.8 H, s); 3.35 (1.2 H, s); 3.51 (1.2 H, t, J = 7.1 Hz); 3.66 (0.8 H, t, J = 7.1 Hz). $^{13}$C-NMR (CDCl$_3$): 7.2; 12.0; 12.3; 25.0; 25.2; 27.05; 27.1; 27.6; 28.51; 28.54; 29.7; 29.8; 32.1; 33.4; 37.7; 37.9; 37.8; 40.8; 42.4; 44.2; 44.3; 44.8; 45.3; 57.7; 57.9; 59.2; 60.3; 172.1. |
| 101 | 3 | Ex. no. 100/ Reduction/ 84% | [M + H]$^+$ = 305.4, R$_t$ = 0.6 min. | $^1$H-NMR (CDCl$_3$): 0.07-0.13 (2 H, m); 0.44-0.50 (2 H, m); 0.90 (1 H, m); 1.20-1.35 (6 H, m); 1.38-1.74 (12 H, m); 2.04 (1 H, tt, J = 10.8 and 7.6 Hz); 2.26 (6 H, s); 2.28 (2 H, d, J = 6.6 Hz); 2.42 (2 H, s); 2.63 (2 H, t, J = 6.8 Hz). $^{13}$C-NMR (CDCl$_3$): 3.8; 9.7; 25.0; 27.2; 28.4; 33.0; 34.9; 37.9; 41.5; 44.3; 54.6; 57.7; 61.8; 69.4. |
| 102 | 3 | Ex. no. 99/ Reduction/ 89% | [M + H]$^+$ = 319.4, R$_t$ = 1.4 min. | $^1$H-NMR (CDCl$_3$): 1.18-1.34 (6 H, m); 1.40-1.92 (16 H, m); 1.98-2.10 (3 H, m); 2.26 (6 H, s); 2.31 (2 H, s); 2.44 (2 H, d, J = 6.9 Hz); 2.48-2.60 (3 H, m). $^{13}$C-NMR (CDCl$_3$): 18.6; 25.0; 27.2; 27.7; 28.4; 33.1; 34.9; 35.4; 37.9; 41.6; 44.3; 54.8; 57.6; 63.3; 69.3. |
| 103 | 3 | Ex. no. 424/ Acylation/ 68% | [M + H]$^+$ = 333.4, R$_t$ = 2.8 min. | $^1$H-NMR (CDCl$_3$): 0.11-0.16 (2 H, m); 0.46-0.60 (2 H, m); 1.08 (1 H, m); 1.12-1.84 (18 H, m); 2.05 (1 H, tt, J = 11.0 and 7.6 Hz); 2.17 (2 H, dd, J = 6.7 and 4.8 Hz); 2.24 (2.5 H, s); 2.25 (3.5 H, s); 3.13 (1.2 H, s); 3.23 (0.8 H, s); 3.42 (0.8 H, t, J = 7.1 Hz); 3.51 (1.2 H, t, J = 7.2 Hz). $^{13}$C-NMR (CDCl$_3$): 4.4; 6.9; 7.0; 25.10; 25.12; 26.9; 27.1; 28.46; 28.50; 29.8; 29.79; 29.83; 31.9; 33.6; 37.81; 37.83; 39.3; 39.7; 40.4; 42.6; 44.0; 44.1; 44.3; 45.4; 53.4; 57.76; 57.85; 58.8; 60.3; 171.1; 171.2. |
| 104 | 3 | Ex. no. 103/ Reduction/ 58% | [M + H]$^+$ = 319.4, R$_t$ = 1.8 min. | $^1$H-NMR (CDCl$_3$): 0.00-0.05 (2 H, m); 0.32-0.44 (2 H, m); 0.64 (1 H, m); 1.20-1.70 (20 H, m); 2.04 (1 H, tt, J = 10.7 and 7.6 Hz); 2.26 (6 H, s); 2.31 (2 H, s); 2.42-2.48 (2 H, m); 2.54 (2 H, t, J = 6.8 Hz). $^{13}$C-NMR (CDCl$_3$): 4.3; 9.2; 25.0; 27.2; 28.4; 33.2; 34.0; 35.1; 37.9; 41.3; 44.3; 54.6; 57.0; 57.7; 69.5. |
| 105 | 3 | Ex. no. 424/ Acylation/ 54% | [M + H]$^+$ = 347.4, R$_t$ = 3.1 min. | $^1$H-NMR (CDCl$_3$): 1.13-1.95 (20 H, m); 2.00-2.19 (3 H, m); 2.25 (2.7 H, s); 2.27 (3.3 H, s); 2.34 (1.2 H, d, J = 7.4 Hz); 2.35 (0.8 H, d, J = 7.4 Hz); 2.73 (1 H, m); 3.16 (1.2 H, s); 3.20 (0.8 H, s), 3.46 (0.8 H, t, J = 7.1 Hz); 3.48 (1.2 H, t, J = 7.2 Hz). $^{13}$C-NMR (CDCl$_3$): 18.6; 18.8; 25.11; 2515; 26.9; 27.1; 28.48; 28.54; 28.6; 29.7; 32.1; 32.37; 32.39; 33.6; 37.7; 37.9; 40.6; 41.1; 41.5; 42.4; 44.0; 44.1; 44.3; 45.6; 57.7; 57.8; 58.5; 60.3; 170.8; 171.0. |
| 108 | 1 | Ex. no. 427/ Acylation/ 68% | [M + H]$^+$ = 347.4, R$_t$ = 2.8 min. | $^1$H-NMR (CDCl$_3$): 0.97 and 0.975 (2 t, 3H, J = 7.4 Hz); 1.30-1.42 (m, 2H); 1.58 (t, 1H, J = 7.2 Hz); 1.61-2.00 (m, 11H); 2.18-2.25 (m, 2H); 3.05 and 3.06 (2 t, 4H, J = 7.0 Hz); 3.30 and 3.36 (2 s, 2H); 3.40-3.49 (m, 2H); 6.87 and 6.89 (2 t, 1H, J = 3.6 Hz); 7.07 and 7.11 (2 dd, 1H, J = 5.1, 1.5 Hz); 7.26 and 7.29 (2 dd, 1H, J = 5.1, 1.5 Hz). $^{13}$C-NMR (CDCl$_3$): 13.7; 14.0; 15.9; 16.1; 18.3; 18.4; 18.9; 30.8; 31.0; 31.04; 31.7; 36.4; 36.9; 37.8; 40.2; 42.2; 43.9; 45.0; 46.7; 46.8; 55.6; 56.7; 58.7; 59.0; 123.5; 123.7; 124.6; 125.0; 126.4; 126.6; 171.8; 171.9. |
| 109 | 2 | Ex. no. 428/ Acylation/ 70% | [M + H]$^+$ = 347.2, R$_t$ = 1.8 min. | $^1$H-NMR (CDCl$_3$): 0.87-0.99 (m, 3H); 1.33-1.42 (m, 2H); 1.57-1.87 (m, 12H); 2.14 (t, 1H, J = 7.6 Hz); 2.20 (t, 1H, J = 7.5 Hz); 3.07 (t, 4H, J = 6.8 Hz); 3.11 (s, 1H); 3.20 (s, 1H); 3.44-3.58 (m, 2H); 6.84 (d, 0.5H, J = 3.5 Hz); 6.87 (d, 0.5H, J = 3.5 Hz); 7.05-7.11 (m, 1H); 7.24-7.30 (m, 1H). $^{13}$C-NMR (CDCl$_3$): 13.96; 14.0; 15.9; 16.4; 30.76; 30.81; 36.3; 36.7; 40.1; 42.2; 44.0; 45.1; 46.71; 46.72; 123.6; 124.7; 126.4; 126.5; 171.8. |
| 110 | 1 | Ex. no. 429/ Acylation/ 73% | [M + H]$^+$ = 341.4, R$_t$ = 2.8 min. | $^1$H-NMR (CDCl$_3$): 0.92-1.00 (m, 3H); 1.21-1.32 (m, 2H); 1.50 (t, 1H, J = 7.2 Hz); 1.58-1.82 (m, 9H); 1.94-2.14 (m, 2H); 2.17-2.26 (m, 2H); 2.92-2.98 (m, 4H); 3.25 (s, 1H); 3.38-3.48 (m, 3H); 7.26-7.34 (m, 3H); 7.36-7.46 (m, 2H). $^{13}$C-NMR (CDCl$_3$): 13.7; 14.01; 14.04; 16.5; 16.8; 18.3; 18.5; 18.9; 28.5; 29.4; 30.9; 31.2; 36.3; 36.9; 37.7; 40.4; 42.4; 43.8; 45.0; 46.6; 46.7; 55.3; 56.6; 59.3; 59.6; 126.5; 126.7; 127.5; 127.7; 127.87; 127.94; 171.8; 171.9. |
| 194 | 2 | Ex. no. 430/ Acylation/ 60% | [M + H]$^+$ = 341.4, R$_t$ = 2.7 min. | $^1$H-NMR (CDCl$_3$): 0.89 and 0.94 (2 t, 3H, J = 7.4 Hz); 1.25-1.35 (m, 2H); 1.54-2.00 (m, 12H); 2.10 and 2.19 (2 t, 2H, J = 7.5 Hz); 2.96 (t, 4H, J = 6.9 Hz); 3.14 and 3.05 (2s, 2H); 3.49 (td, 2H, J = 14.0, 7.1 Hz); 7.25-7.34 (m, 3H); 7.38-7.45 (m, 2H). $^{13}$C-NMR (CDCl$_3$): 13.9; 14.0; 16.6; 18.4; 28.8; 28.9; 30.88; 30.9; 34.4; 36.3; 36.7; 40.4; 42.4; 44.1; 45.2; 46.6; 56.1; 57.7; 59.3; 126.6; 126.7; 127.5; 127.6; 127.8; 127.9; 137.6; 171.8. |

| Ex. no. | Diastereomer* | Building Block/Method/Yield | LC-MS [M + H]⁺/$R_t$ | NMR spectrum |
|---|---|---|---|---|
| 112 | 1 | Ex. no. 429/ Reductive amination/ 52% | [M + H]⁺ = 327.4, $R_t$ = 0.7 min. | ¹H-NMR (CDCl₃): 0.95 (t, 3H, J = 7.3 Hz); 1.28-1.43 (m, 4H); 1.55-1.68 (m, 4H); 1.72-1.88 (m, 6H); 2.05 (br s, 2H); 2.66-2.73 (m, 2H); 2.80 (s, 2H); 2.83-2.90 (m, 2H); 3.10 (t, 4H, J = 7.0 Hz); 7.31-7.38 (m, 3H); 7.42-7.49 (m, 2H). ¹³C-NMR (CDCl₃): 13.8; 16.4; 20.4; 29.0; 29.2; 33.2; 41.5; 46.9; 56.4; 64.5; 127.4; 127.7; 128.3. |
| 113 | 2 | Ex. no. 430/ Reductive amination/ 42% | [M + H]⁺ = 327.4, $R_t$ = 1.9 min. | ¹H-NMR (CDCl₃): 0.78-0.94 (m, 3H); 1.20-1.50 (m, 6H); 1.54-1.80 (m, 8H); 1.90-2.10 (m, 2H); 2.17 (s, 2H); 2.28-2.43 (m, 2H); 2.46-2.58 (m, 2H); 2.93-3.00 (m, 4H); 7.25-7.34 (m, 3H); 7.40 (t, 2H, J = 7.6 Hz). ¹³C-NMR (CDCl₃): 14.0; 16.7; 20.8; 26.9; 27.0; 29.1; 30.9; 34.2; 41.3; 46.7; 54.4; 56.7; 126.5; 127.8; 127.9. |
| 114 | 3 | Ex. no. 17/ Alkylation/ 56% | [M + H]⁺ = 293.3, $R_t$ = 2.2 min. | ¹H-NMR (CDCl₃): 1.20-1.28 (m, 2H); 1.68 (dt, 2H, J = 3.0 and 14.0 Hz); 1.89 (t, 2H, J = 7.0 Hz); 2.11 (s, 6H); 2.20 (dt, 2H, J = 3.1 and 13.0 Hz); 2.45 (br d, 2H, J = 13.8 Hz); 2.85 (s, 3H); 3.23-3.28 (m, 2H); 6.85 (br d, 1H, J = 3.4 Hz); 7.02 (dd, 1H, J = 3.6 and 5.1 Hz); 7.20 (dd, 1H, J = 1.0 and 5.1 Hz). ¹³C-NMR (CDCl₃): 28.3 (2C); 29.8 (2C); 30.3; 31.7; 38.0 (2C); 44.3; 46.1; 58.4; 122.7; 123.6; 125.9; 145.8; 178.9. |
| 115 | 3 | Ex. no. 17/ Alkylation/ 67% | [M + H]⁺ = 335.3, $R_t$ = 2.8 min. | ¹H-NMR (CDCl₃): 0.92 (dt, 3H, J = 7.4 Hz); 1.20-1.35 (m, 4H); 1.44-1.53 (m, 2H); 1.61-1.73 (m, 2H); 1.87 (t, 2H, J = 6.9 Hz); 2.10 (m, 6H); 2.20 (dt, 2H, J = 13.1 Hz); 2.44 (d, 2H, J = 2.6 and 13.6 Hz); 3.21-3.30 (m, 4H); 6.83-6.86 (m, 1H); 6.99-7.03 (m, 1H); 7.18-7.21 (m, 1H). ¹³C-NMR (CDCl₃): 13.7; 19.9; 28.2 (2C); 29.3; 30.4; 31.8 (2C); 37.9 (2C); 42.2; 43.7; 44.6; 58.4; 122.7; 123.6; 125.9; 145.9; 178.7. |
| 116 | 3 | Ex. no. 17/ Alkylation/ 18% | [M + H]⁺ = 361.3, $R_t$ = 3.0 min, | ¹H-NMR (CDCl₃): 1.16 (m, 4H); 1.47-1.58 (m, 6H); 1.60-1.74 (m, 6H); 1.87 (t, 2H, J = 6.9 Hz); 2.11 (s, 6H); 2.12-2.25 (m, 3H); 2.45 (d, 2H, J = 13.8 Hz); 3.21 (d, 2 H, J = 7.8 Hz); 3.25-3.30 (m, 2H); 6.86 (d, 1H, J = 3.5 Hz); 7.02 (dd, 1H, J = 3.6 and 5.1 Hz); 7.20 (dd, 1H, J = 1.1 and 5.1 Hz). ¹³C-NMR (CDCl₃): 25.1 (2C); 28.2; 30.3 (2C); 30.6; 31.8; 37.9 (2C); 38.0; 44.1; 44.6; 47.5; 58.5; 122.8; 123.6; 126.0; 178.8. |
| 118 | 2 | Ex. no. 2/ Alkylation/ 71% | [M + H]⁺ = 301.3, $R_t$ = 2.4 min. | ¹H-NMR (DMSO-d₆): 0.93 (d, 2H, J = 13.0 Hz); 1.04 (dt, 2H, J = 14.0, 3.3 Hz); 1.45 (t, 2H, J = 6.9 Hz); 1.63 (dd, 2H, J = 14.8, 2.6 Hz); 1.82 (dt, 2H, J = 13.6, 3.0 Hz); 2.25 (s, 6H); 2.58 (s, 2H); 2.65 (s, 3H); 3.06-3.11 (m, 2H); 7.12-7.20 (m, 3H); 7.23-7.29 (m, 2H). ¹³C-NMR (DMSO-d₆): 26.7; 27.9; 28.8; 29.1; 36.2; 36.8; 43.5; 45.1; 56.6; 125.5; 127.6; 130.5; 139.0; 177.7. |
| 119 | 1 | Ex. no. 1/ Alkylation/ 45% | [M + H]⁺ = 301.3, $R_t$ = 2.1 min. | ¹H-NMR (CDCl₃): 1.52-1.60 (m, 4H); 1.67-1.75 (m, 2H); 1.83-1.94 (m, 4H); 2.28 (s, 6H); 2.78 (s, 3H); 2.79 (s, 2H); 3.21-3.42 (m, 2H); 7.14-7.20 (m, 1H); 7.21-7.25 (m, 4H). ¹³C-NMR (CDCl₃): 28.4; 29.4; 29.6; 32.8; 36.8; 37.4; 42.6; 46.0; 57.6; 125.7; 127.7; 130.7; 139.2; 179.0. |
| 120 | 2 | Ex. no. 2/ Alkylation/ 34% | [M + H]⁺ = 343.3, $R_t$ = 3.0 min | ¹H-NMR (CDCl₃): 0.90 (t, 3H, J = 7.3 Hz); 1.02 (d, 2H, J = 13.3 Hz); 1.13 (dt, 2H, J = 14.0, 3.3 Hz); 1.26 (qd, 2H, J = 14.0, 7.3 Hz); 1.39-1.48 (m, 2H); 1.58 (t, 2H, J = 7.0 Hz); 1.71-1.78 (m, 2H); 2.10 (dt, 2H, J = 13.4, 2.9 Hz); 2.30 (s, 6H); 2.61 (s, 2H); 3.11 (t, 2H, J = 6.9 Hz); 3.22 (t, 2H, J = 7.2 Hz); 7.09-7.13 (m, 2H); 7.15-7.28 (m, 3H). ¹³C-NMR (CDCl₃): 13.7; 19.9; 27.2; 28.6; 29.3; 29.6; 36.9; 37.0; 42.1; 43.6; 44.8; 57.2; 125.6; 127.6; 127.7; 130.7; 139.5; 179.0. |
| 121 | 1 | Ex. no. 1/ Alkylation/ 35% | [M + H]⁺ = 343.3, $R_t$ = 2.8 min. | ¹H-NMR (CDCl₃): 0.91 (t, 3H, J = 7.3 Hz); 1.23-1.34 (m, 2H); 1.41-1.61 (m, 6H); 1.69-1.77 (m, 2H); 1.82-1.92 (m, 4H); 2.28 (s, 6H); 2.81 (s, 2H); 3.19-3.25 (m, 4H); 7.13-7.19 (m, 1H); 7.20-7.25 (m, 4H). ¹³C-NMR (CDCl₃): 13.8; 20.0; 28.5; 29.3; 29.4; 32.7; 36.9; 37.5; 42.1; 43.1; 43.6; 57.6; 125.7; 127.8; 130.8; 139.4; 178.8. |
| 222 | 2 | Ex. no. 2/ Alkylation/ 31% | [M + H]⁺ = 369.3, $R_t$ = 3.2 min. | ¹H-NMR (CDCl₃): 1.00-1.20 (m, 6H); 1.45-1.65 (m, 8H); 1.70-1.78 (m, 2H); 2.00-2.20 (m, 3H); 2.31 (s, 6H); 2.62 (s, 2H); 3.11-3.18 (m, 4H); 7.09-7.28 (m, 5H). ¹³C-NMR (CDCl₃): 25.1; 27.1; 28.6; 29.7; 30.2; 36.9; 37.0; 44.1; 44.7; 47.5; 57.3; 125.6; 127.7; 130.7; 139.4; 179.2. |
| 123 | 1 | Ex. no. 1/ Alkylation/ 16% | [M + H]⁺ = 369.4, $R_t$ = 3.0 min. | ¹H-NMR (CDCl₃): 1.16-1.26 (m, 2H); 1.48-1.80 (m, 13H); 1.84-1.94 (m, 3H); 2.09-2.18 (m, 1H); 2.29 (s, 6H); 2.83 (s, 2H); 3.17 (d, 2H, J = 7.8 Hz); 3.26 (t, 2H, J = 6.9 Hz); 7.15-7.29 (m, 5H). ¹³C-NMR (CDCl₃): 25.1; 28.6; 29.4; 30.3; 32.7; 37.0; 37.6; 38.0; 43.2; 44.0; 47.4; 57.7; 125.7; 127.8; 130.8; 139.4; 179.0. |
| 124 | 1 | Ex. no. 24a/ Alkylation/ 38% | [MH – HNMe₂]⁺ = 248.3 (100%) [M + H]⁺ = 293.3 (70%), $R_t$ = 1.4 min. | ¹H-NMR (CDCl₃): 1.43-1.51 (m, 2H); 1.73-1.82 (m, 2H); 1.96-2.09 (m, 4H); 2.10 (s, 6H); 2.18 (s, 2H); 2.83 (s, 3H); 3.21 (s, 2H); 6.85 (dd, 1H, J = 1.1, 3.6 Hz); 7.04 (dd, 1H, J = 3.6, 5.1 Hz); 7.24 (dd, 1H, J = 1.1, 5.1 Hz). ¹³C-NMR (CDCl₃): 29.7; 32.7; 32.9; 35.3; 38.0; 44.0; 59.3; 62.4; 123.4; 124.9; 126.3; 173.8. |
| 125 | 1 | Ex. no. 24a/ Alkylation/ 52% | [M + H]⁺ = 335.3, $R_t$ = 2.1 min. | ¹H-NMR (CDCl₃): 0.93 (t, 3H, J = 7.3 Hz); 1.26-1.36 (m, 2H); 1.42-1.52 (m, 4H); 1.72-1.81 (m, 2H); 1.95-2.09 (m, 4H); 2.10 (s, 6H); 2.18 (s, 2H); 3.20 (s, 2H); 3.25 (t, 2H, J = 7.3 Hz); 6.85 (dd, 1H, J = |

| Ex. no. | Diastereomer* | Building Block/Method/Yield | LC-MS [M + H]+/Rt | NMR spectrum |
|---|---|---|---|---|
| | | | | 1.1, 3.6 Hz); 7.04 (dd, 1H, J = 3.6, 5.1 Hz); 7.24 (dd, 1H, J = 1.1, 5.1 Hz).<br>13C-NMR (CDCl3): 13.8; 20.0; 29.3; 32.7; 32.8; 35.5; 38.1; 42.1; 44.3; 57.9; 59.3; 123.4; 124.9; 126.3; 142.5; 173.5. |
| 126 | 1 | Ex. no. 24a/ Alkylation/ 33% | [MH − HNMe2]+ = 316.3 (100%)<br>[M + H]+ = 361.4 (70%), Rt = 2.7 min. | 1H-NMR (CDCl3): 1.16-1.26 (m, 2H); 1.42-1.59 (m, 4H); 1.60-1.82 (m, 7H); 1.97-2.17 (m, 4H); 2.12 (s, 6H); 2.19 (s, 2H); 3.19 (d, 2H, J = 7.9 Hz); 3.24 (s, 2H); 6.87 (br s, 1H); 7.03-7.07 (m, 1H); 7.23-7.28 (m, 1H).<br>1H-NMR (DMSO-d6): 1.09-1.19 (m, 2H); 1.30-138 (m, 2H); 1.44-1.74 (m, 9H); 1.77-1.94 (m, 2H); 2.01 (s, 6H); 2.08 (s, 2H); 2.09-2.18 (m, 2H); 3.07 (d, 2H, J = 7.8 Hz); 3.16 (s, 2H); 6.94 (s, 1H); 7.04-7.08 (m, 1H); 7.40-7.45 (m, 1H).<br>13C-NMR (DMSO-d6): 24.6; 29.7; 32.0; 35.1; 37.3; 37.6; 38.9; 43.0; 46.3; 57.8; 58.7; 123.5; 124.7; 126.3; 143.3; 172.4. |
| 127 | 2 | Ex. no. 24b/ Alkylation/ 25% | [MH − HNMe2]+ = 316.3 (100%)<br>[M + H]+ = 361.4 (8%), Rt = 3.1 min. | 1H-NMR (CDCl3): 1.12-1.22 (m, 2H); 1.42-1.56 (m, 4H); 1.57-1.70 (m, 4H); 1.73-1.81 (m, 2H); 2.01-2.17 (m, 5H); 2.18 (s, 6H); 2.36 (s, 2H); 3.06 (s, 2H); 3.15 (d, 2H, J = 7.8 Hz); 6.91 (br d, 1H, J = 3.4 Hz); 7.07 (dd, 1H, J = 3.6, 5.1 Hz); 7.29 (br d, 1H, 5.0 Hz).<br>13C-NMR (CDCl3): 25.1; 30.4; 32.4; 32.8; 35.6; 38.0; 38.1; 43.4; 47.4; 59.0; 124.2; 125.8; 126.5; 173.6. |
| 128 | 1 | Ex. no. 24a/ Alkylation/ 61% | [M + H]+ = 361.4, Rt = 2.7 min. | 1H-NMR (CDCl3): 1.41-1.50 (2 H, m); 1.55-1.70 (5 H, m); 1.72-1.91 (4 H, m); 1.93-2.04 (5 H, m); 2.10 (6 H, s); 2.17 (2 H, s); 2.25 (1 H, td, J = 15.6 and 7.9 Hz); 3.14-3.20 (4 H, m); 6.85 (1 H, dd, J = 3.5 and 1.0 Hz); 7.04 (1 H, dd, J = 5.1 and 3.5 Hz); 7.24 (1 H, dd, J = 5.1 and 1.0 Hz).<br>13C-NMR (CDCl3): 18.6; 28.2; 32.7; 32.8; 33.7; 34.3; 35.5; 38.1; 40.5; 44.3; 58.2; 59.3; 123.4; 124.9; 126.3; 173.4. |
| 129 | 2 | Ex. no. 24b/ Alkylation/ 50% | [M + H]+ = 361.3, Rt = 3.1 min. | 1H-NMR (CDCl3): 1.42-1.65 (6 H, m); 1.70-1.91 (4 H, m); 1.93-2.09 (6 H, m); 2.10 (6 H, s); 2.22 (1 H, td, J = 15.6 and 7.9 Hz); 2.31 (2 H, s); 3.03 (2 H, s); 3.13 (2 H, t, J = 7.4 Hz); 6.85 (1 H, dd, J = 3.5 and 1.0 Hz); 7.04 (1 H, dd, J = 5.1 and 3.5 Hz); 7.24 (1 H, dd, J = 5.1 and 1.0 Hz).<br>13C-NMR (CDCl3): 18.5; 28.2; 32.7; 32.9; 33.6; 34.2; 35.5; 38.1; 40.5; 43.8; 58.7; 59.5; 123.4; 125.0; 126.2; 173.4. |
| 130 | 1 | Ex. no. 24a/ Alkylation/ 58% | [M + H]+ = 347.3, Rt = 2.5 min. | 1H-NMR (CDCl3): 0.03-0.09 (2 H, m); 0.44-0.49 (2 H, m); 0.60-0.70 (1 H, m); 1.38-1.50 (4 H, m); 1.72-1.80 (2 H, m); 1.90-2.09 (4 H, m); 2.10 (6 H, s); 2.18 (2 H, s); 3.23 (2 H, s); 3.34 (2 H, t, J = 7.3 Hz); 6.85 (1 H, d, J = 3.4 Hz); 7.04 (1 H, dd, J = 5.0 and 3.5 Hz); 7.24 (1 H, d, J = 5.0 Hz).<br>13C-NMR (CDCl3): 4.3; 8.6; 32.5; 32.7; 32.8; 35.5; 38.0; 42.6; 44.3; 58.5; 59.3; 123.4; 124.8; 126.3; 173.5. |
| 131 | 2 | Ex. no. 24b/ Alkylation/ 38% | [M + H]+ = 347.3, Rt = 2.9 min. | 1H-NMR (CDCl3): 0.02 (2 H, q, J = 5.4 Hz); 0.39-0.45 (2 H, m); 0.55-0.65 (1 H, m); 1.36 (2 H, dd, J = 14.4 and 7.0 Hz); 1.42-1.51 (2 H, m); 1.70-1.79 (2 H, m); 1.92-2.09 (4 H, m); 2.10 (6 H, s); 2.32 (2 H, s); 3.08 (2 H, s); 3.30 (2 H, t, J = 7.3 Hz); 6.85 (1 H, d, J = 3.5 Hz); 7.04 (1 H, dd, J = 5.1 and 3.8 Hz); 7.24 (1 H, d, J = 5.1 Hz).<br>13C-NMR (CDCl3): 4.3; 8.6; 32.4; 32.7; 32.9; 35.5; 38.1; 42.6; 43.9; 59.0; 59.5; 123.4; 124.9; 126.2; 173.5. |
| 132 | 1 | Ex. no. 24a/ Alkylation/ 69% | [M + H]+ = 347.3, Rt = 2.5 min. | 1H-NMR (CDCl3): 1.40-1.49 (2 H, m); 1.63-1.78 (4 H, m); 1.85-2.09 (8 H, m); 2.10 (6 H, s); 2.17 (2 H, s); 2.52 (1 H, td, J = 15.6 and 7.8 Hz); 3.17 (2 H, s); 3.29 (2 H, d, J = 7.6 Hz); 6.84 (1 H, d, J = 3.4 Hz); 7.04 (1 H, dd, J = 5.0 and 3.6 Hz); 7.24 (1 H, d, J = 5.0 Hz).<br>13C-NMR (CDCl3): 18.4; 26.4; 32.6; 32.8; 33.9; 35.7; 38.1; 44.1; 47.8; 58.2; 59.3; 123.4; 124.9; 126.3; 173.6. |
| 133 | 2 | Ex. no. 24b/ Alkylation/ 83% | [M + H]+ = 347.3 Rt = 2.9 min. | 1H-NMR (CDCl3): 1.40-1.48 (2 H, m); 1.63-1.77 (4 H, m); 1.80-2.09 (8 H, m); 2.10 (6 H, s); 2.31 (2 H, s); 2.47 (1 H, sept, J = 7.7 Hz); 3.01 (2 H, s); 3.25 (2 H, d, J = 7.6 Hz); 6.85 (1 H, d, J = 3.5 Hz); 7.04 (1 H, dd, J = 5.1 and 3.5 Hz); 7.24 (1 H, d, J = 5.1 Hz).<br>13C-NMR (CDCl3): 18.4; 26.4; 32.7; 32.8; 33.9; 35.7; 38.1; 43.6; 47.8; 58.9; 59.6; 123.4; 125.0; 126.2; 173.6. |
| 134 | 1 | Ex. no. 24a/ Alkylation/ 61% | [M + H]+ = 333.3, Rt = 2.2 min. | 1H-NMR (CDCl3): 0.18-0.23 (2 H, m); 0.49-0.55 (2 H, m); 0.83-0.94 (1 H, m); 1.44-1.52 (2 H, m); 1.74-1.83 (2 H, m); 1.90-2.08 (4 H, m); 2.11 (6 H, s); 2.19 (2 H, s); 3.13 (2 H, d, J = 7.1 Hz); 3.32 (2 H, s); 6.85 (1 H, d, J = 3.5 Hz); 7.05 (1 H, dd, J = 5.1 and 3.5 Hz); 7.24 (1 H, d, J = 4.4 Hz).<br>13C-NMR (CDCl3): 3.4; 9.1; 19.8; 32.7; 32.9; 35.6; 38.1; 44.2; 47.0; 58.2; 59.3; 123.4; 124.9; 126.3; 173.4. |
| 135 | 2 | Ex. no. 24b/ Alkylation/ 40% | [M + H]+ = 333.3, Rt = 2.7 min. | 1H-NMR (CDCl3): 0.14-0.19 (2 H, m); 0.44-0.50 (2 H, m); 0.78-0.88 (1 H, m); 1.44-1.53 (2 H, m); 1.72-1.81 (2 H, m); 1.93-2.09 (4 H, m); 2.10 (6 H, s); 2.33 (2 H, s); 3.10 (2 H, d, J = 7.1 Hz); 3.16 (2 H, s); 6.86 (1 H, dd, J = 3.5 and 1.0 Hz); 7.05 (1 H, dd, J = 5.1 and 3.5 Hz); 7.25 (1 H, dd, J = 5.1 and 1.0 Hz).<br>13C-NMR (CDCl3): 3.4; 9.1; 32.7; 32.9; 35.7; 38.1; 43.7; 47.0; 58.7; 59.6; 123.4; 125.0; 126.2; 173.4. |

-continued

| Ex. no. | Diastereomer* | Building Block/Method/Yield | LC-MS [M + H]$^+$/R$_t$ | NMR spectrum |
|---|---|---|---|---|
| 136 | 1 | Ex. no. 24a/ Alkylation/ 57% | [M + H]$^+$ = 377.3, R$_t$ = 2.3 min. | $^1$H-NMR (CDCl$_3$): 1.40-1.52 (3 H, m); 1.63-1.93 (6 H, m); 1.95-2.08 (5 H, m); 2.10 (6 H, s); 2.17 (2 H, s); 3.20-3.27 (2 H, m); 3.28-3.41 (2 H, m); 3.67-3.74 (1 H, m); 3.75-3.88 (2 H, m); 6.84 (1 H, dd, J = 3.5 and 1.1 Hz); 7.04 (1 H, dd, J = 5.1 and 3.1 Hz); 7.23 (1 H, dd, J = 5.1 and 1.1 Hz). $^{13}$C-NMR (CDCl$_3$): 25.6; 31.4; 32.67; 32.72; 32.74; 33.3; 35.6; 38.0; 40.0; 44.2; 58.4; 59.2; 67.7; 77.0, 123.4; 124.8; 126.2; 173.6. |
| 137 | 2 | Ex. no. 24b/ Alkylation/ 53% | [MH − HNMe$_2$]$^+$ = 332.3 (100%) [M + H]$^+$ = 377.4 (10%), R$_t$ = 2.6 min. | $^1$H-NMR (CDCl$_3$): 1.39-1.50 (3 H, m); 1.60-1.80 (4 H, m); 1.80-1.90 (2 H, m); 1.94-2.09 (5 H, m); 2.10 (6 H, s); 2.31 (2 H, s); 3.05-3.12 (2 H, m); 3.24-3.38 (2 H, m); 3.64-3.71 (1 H, m); 3.72-3.85 (2 H, m); 6.84 (1 H, dd, J = 3.5 and 1.1 Hz); 7.04 (1 H, dd, J = 5.1 and 3.1 Hz); 7.23 (1 H, dd, J = 5.1 and 1.0 Hz). $^{13}$C-NMR (CDCl$_3$): 25.6; 31.4; 32.7; 32.73; 32.8; 33.2; 35.6; 39.9; 43.6; 58.9; 59.5; 67.7; 76.9, 123.4; 124.9; 126.2; 173.6. |
| 138 | 1 | Ex. no. 24a/ Alkylation/ 51% | [M + H]$^+$ = 377.4, R$_t$ = 2.2 min. | $^1$H-NMR (CDCl$_3$): 1.28-1.40 (2 H, m); 1.43-1.53 (2 H, m); 1.62-1.90 (3 H, m); 1.95-2.09 (4 H, m); 2.10 (6 H, s); 2.20 (2 H, s); 3.14 (2 H, d, J = 7.3 Hz); 3.23 (2 H, s); 3.35 (2 H, dt, J = 11.8 and 1.9 Hz); 3.96 (2 H, br dd, J = 11.5 and 2.6 Hz); 6.85 (1 H, dd, J = 3.3 and 1.1 Hz); 7.04 (1 H, dd, J = 4.9 and 3.6 Hz); 7.24 (1 H, d, J = 4.9 Hz). $^{13}$C-NMR (CDCl$_3$): 30.7; 32.7; 32.8; 33.7; 35.8; 38.0; 44.1; 48.4; 59.2; 59.9; 67.5; 67.7; 123.5; 124.8; 126.3; 174.1. |
| 139 | 2 | Ex. no. 24b/ Alkylation/ 45% | [M + H]$^+$ = 377.4, R$_t$ = 2.5 min. | $^1$H-NMR (CDCl$_3$): 1.31 (2 H, ddd, J = 17.6, 11.8 and 4.4 Hz); 1.43-1.54 (4 H, m); 1.71-1.85 (3 H, m); 1.93-2.09 (4 H, m); 2.10 (6 H, s); 2.34 (2 H, s); 3.05-3.12 (4 H, m); 3.32 (2 H, dt, J = 11.7 and 2.2 Hz); 3.91-3.97 (2 H, m); 6.85 (1 H, dd, J = 3.6 and 1.1 Hz); 7.04 (1 H, dd, J = 5.1 and 3.6 Hz); 7.24 (1 H, dd, J = 5.1 and 1.1 Hz). $^{13}$C-NMR (CDCl$_3$): 30.7; 32.7; 32.9; 33.7; 35.8; 38.1; 43.3; 48.3; 59.6; 59.9; 67.5; 123.5; 125.0; 126.3, 174.1. |
| 140 | 2 | Ex. no. 24b/ Alkylation/ 42% | [M + H]$^+$ = 377.2, low UV activity | $^1$H-NMR (CDCl$_3$): 1.40-1.61 (5 H, m); 1.70-1.80 (2 H, m); 1.91-2.09 (5 H, m); 2.10 (6 H, s); 2.11-1.26 (1 H, m); 2.32 (2 H, s); 3.05 (2 H, s); 3.24 (2 H, t, J = 7.4 Hz); 3.32 (1 H, dd, J = 8.3 and 6.9 Hz); 3.72 (1 H, dd, J = 15.4 and 7.7 Hz); 3.79-3.90 (2 H, m); 6.84 (1 H, dd, J = 3.5 and 1.0 Hz); 7.04 (1 H, dd, J = 5.1 and 3.5 Hz); 7.24 (1 H, dd, J = 5.1 and 0.9 Hz). $^{13}$C-NMR (CDCl$_3$): 30.7; 32.2; 32.7; 32.72; 32.9; 35.6; 36.9; 38.1; 41.3; 43.7; 58.6; 59.5; 67.8; 73.1; 123.5; 125.0; 126.2; 173.6. |
| 141 | 1 | Ex. no. 24a/ Alkylation/ 49% | [M + H]$^+$ = 377.2, low UV activity | $^1$H-NMR (CDCl$_3$): 1.41-1.70 (5 H, m); 1.72-1.81 (2 H, m); 2.00-2.09 (4 H, m); 2.10 (6 H, s); 2.11-1.18 (2 H, m); 2.19 (2 H, s); 3.20 (2 H, s); 3.28 (2 H, t, J = 7.4 Hz); 3.36 (1 H, dd, J = 8.3 and 6.9 Hz); 3.71-3.78 (1 H, m); 3.82-3.93 (2 H, m); 6.85 (1 H, dd, J = 3.5 and 1.0 Hz); 7.04 (1 H, dd, J = 5.1 and 3.5 Hz); 7.24 (1 H, dd, J = 5.1 and 1.0 Hz). $^{13}$C-NMR (CDCl$_3$): ): 30.7; 32.2; 32.7; 32.79; 35.6; 36.1; 36.9; 38.1; 41.4; 44.2; 58.1; 59.2; 67.9; 73.1; 123.5; 124.8; 126.3; 173.6. |
| 142 | 1 | Ex. no. 24a/ Alkylation/ 25% | [M + H]$^+$ = 363.2, low UV activity | $^1$H-NMR (CDCl$_3$): 1.43-1.51 (2 H, m); 1.57-1.67 (2 H, m); 1.73-1.82 (2 H, m); 1.95-2.09 (4 H, m); 2.10 (6 H, s); 2.20 (2 H, s); 2.47-2.56 (1 H, m); 3.19-3.26 (3 H, m); 3.36 (1 H, dd, J = 13.6 and 7.6 Hz); 3.47 (1 H, dd, J = 8.6 and 6.3 Hz); 3.76 (1 H, td, J = 8.5 and 7.3 Hz); 3.82-3.91 (2 H, m); 6.85 (1 H, dd, J = 3.5 and 0.9 Hz); 7.05 (1 H, dd, J = 5.1 and 3.5 Hz); 7.25 (1 H, dd, J = 5.0 and 0.8 Hz). $^{13}$C-NMR (CDCl$_3$): 30.1; 32.6; 32.8; 35.8; 38.0; 38.1; 44.0; 45.3; 58.8; 59.2; 67.7; 71.4; 123.5; 124.8; 126.3; 174.0. |
| 143 | 2 | Ex. no. 24b/ Alkylation/ 22% | [M + H]$^+$ = 363.2, low UV activity | $^1$H-NMR (CDCl$_3$): 1.40-1.51 (2 H, m); 1.52-1.62 (1 H, m); 1.70-1.79 (2 H, m); 1.89-2.09 (5 H, m); 2.10 (6 H, s); 2.32 (2 H, s); 2.42-2.50 (1 H, m); 3.07 (2 H, s); 3.18 (1 H, dd, J = 13.7 and 7.5 Hz); 3.31 (1 H, dd, J = 13.7 and 7.6 Hz); 3.42 (1 H, dd, J = 8.6 and 6.2 Hz); 3.68-3.88 (3 H, m); 6.84 (1 H, dd, J = 3.5 and 1.1 Hz); 7.03 (1 H, dd, J = 5.1 and 3.5 Hz); 7.24 (1 H, dd, J = 5.1 and 1.1 Hz). $^{13}$C-NMR (CDCl$_3$): 30.1; 32.7; 32.8; 35.8; 37.9; 38.1; 43.5; 45.2; 59.2; 59.5; 67.6; 71.3; 123.5; 125.0; 126.3; 174.0. |
| 144 | 1 | Ex. no. 24a/ Alkylation/ 49% | [MH − HNMe$_2$]$^+$ = 327.2 (95%) [M + H]$^+$ = 372.2 (100%), R$_t$ = 2.3 min. | $^1$H-NMR (CDCl$_3$): 0.87 (2 H, m); 1.26 (2 H, m); 1.44-1.52 (2 H, m); 1.70 (2 H, t, J = 7.0 Hz); 1.76-1.84 (2 H, m); 1.96-2.09 (4 H, m); 2.10 (6 H, s); 2.21 (2 H, s); 3.31 (2 H, t, J = 7.1 Hz); 3.48 (2 H, t, J = 7.1 Hz); 6.85 (1 H, dd, J = 3.6 and 0.8 Hz); 7.04 (1 H, dd, J = 5.0 and 3.6 Hz); 7.24 (1 H, dd, J = 5.1 and 0.7 Hz). $^{13}$C-NMR (CDCl$_3$): 7.6; 14.1; 32.6; 32.7; 35.7; 38.0; 41.2; 44.0; 59.2; 123.0; 123.4; 124.8; 126.3; 174.1. |
| 145 | 2 | Ex. no. 24b/ Alkylation/ 50% | [MH − HNMe$_2$]$^+$ = 327.2 (100%) [M + H]$^+$ = 372.2 (90%), R$_t$ = 2.5 min. | $^1$H-NMR (CDCl$_3$): 0.85 (2 H, m); 1.23 (2 H, m); 1.49 (2 H, ddd, J = 13.2, 9.1 and 4.0 Hz); 1.66 (2 H, t, J = 7.1 Hz); 1.72-1.80 (2 H, m); 1.92-2.09 (4 H, m); 2.10 (6 H, s); 2.33 (2 H, s); 3.16 (2 H, s); 3.44 (2 H, t, J = 7.1 Hz); 6.84 (1 H, dd, J = 3.6 and 1.1 Hz); 7.04 (1 H, dd, J = 5.1 and 3.6 Hz); 7.24 (1 H, dd, J = 5.1 and 1.1 Hz). $^{13}$C-NMR (CDCl$_3$): 7.5; 14.0; 32.5; 32.7; 32.9; 35.7; 38.1; 41.1; 43.4; 59.5; 122.9; 123.5; 125.0; 126.3; 174.1. |

| Ex. no. | Diastereomer* | Building Block/Method/Yield | LC-MS [M + H]⁺/R$_t$ | NMR spectrum |
|---|---|---|---|---|
| 146 | 1 | Ex. no. 24a/ Alkylation/ 51% | [M + H]⁺ = 349.2, R$_t$ = 2.1 min. | ¹H-NMR (CDCl₃): 1.42-1.53 (2 H, m); 1.73-1.85 (3 H, m); 1.97-2.08 (3 H, m); 2.09 (6 H, s); 2.21 (2 H, d, J = 2.8 Hz); 2.41-2.52 (1 H, m); 2.62-2.70 (1 H, m); 3.34 (1 H, d, J = 10.1 Hz); 3.44-3.57 (3 H, m); 4.46-4.53 (1 H, m); 4.62-4.69 (1 H, m); 4.93-5.00 (1 H, m); 6.84 (1 H, dd, J = 3.5 and 1.1 Hz); 7.04 (1 H, dd, J = 5.1 and 3.5 Hz); 7.23 (1 H, dd, J = 5.1 and 1.1 Hz). ¹³C-NMR (CDCl₃): 24.8; 32.6; 32.84; 32.7; 35.8; 38.0; 43.8; 48.1; 59.3; 60.0; 68.5; 81.5; 123.4; 124.8; 126.2; 142.8; 174.3. |
| 147 | 2 | Ex. no. 24b/ Alkylation/ 32% | [MH − HNMe₂]⁺ = 304.2, R$_t$ = 2.3 min. | ¹H-NMR (CDCl₃): 1.41-1.56 (2 H, m); 1.64-1.83 (3 H, m); 1.90-2.09 (3 H, m); 2.10 (6 H, s); 2.35 (2 H, d, J = 5.0 Hz); 2.39-2.49 (1 H, m); 2.58-2.60 (1 H, m); 3.20 (1 H, d, J = 10.0 Hz); 3.32 (1 H, d, J = 10.0 Hz); 3.42-3.53 (2 H, m); 4.41-4.48 (1 H, m); 4.59-4.65 (1 H, m); 4.90-4.97 (1 H, m); 6.83 (1 H, dd, J = 3.5 and 1.1 Hz); 7.03 (1 H, dd, J = 5.1 and 3.5 Hz); 7.23 (1 H, dd, J = 5.1 and 1.1 Hz). ¹³C-NMR (CDCl₃): 24.8; 32.66; 32.7; 32.8; 35.9; 38.1; 43.4; 48.1; 59.5; 60.4; 68.5; 81.5; 123.4; 124.9; 126.2; 142.7; 174.3. |
| 148 | 1 | Ex. no. 24a/ Alkylation/ 44% | [MH − HNMe₂]⁺ = 304.2 (100%) [M + H]⁺ = 349.3 (100%), R$_t$ = 2.0 min. | ¹H-NMR (CDCl₃): 1.40-1.50 (2 H, m); 1.67 (1 H, br s); 1.70-1.80 (2 H, m); 1.93-2.09 (3 H, m); 2.10 (6 H, s); 2.18 (2 H, s); 3.16 (2 H, s); 3.17-3.25 (1 H, m); 3.59 (2 H, d, J = 7.2 Hz); 4.46 (2 H, t, J = 6.2 Hz); 4.78 (2 H, dd, J = 7.8 and 6.2 Hz); 6.84 (1 H, dd, J = 3.6 and 1.1 Hz); 7.04 (1 H, dd, J = 5.1 and 3.6 Hz); 7.25 (1 H, dd, J = 5.1 and 1.1 Hz). ¹³C-NMR (CDCl₃): 32.6; 32.7; 34.1; 35.9; 38.0; 43.9; 45.4; 59.2; 75.4; 123.5; 124.8; 126.3; 174.0. |
| 149 | 2 | Ex. no. 24b/ Alkylation/ 48% | [MH − HNMe₂]⁺ = 304.2 (100%) [M + H]⁺ = 349.2 (100%), R$_t$ = 2.2 min. | ¹H-NMR (CDCl₃): 1.40-1.49 (2 H, m); 1.62-1.77 (3 H, m); 1.90-2.09 (3 H, m); 2.10 (6 H, s); 2.32 (2 H, s); 3.01 (2 H, s); 3.13-3.21 (1 H, m); 3.55 (2 H, d, J = 7.2 Hz); 4.42 (2 H, t, J = 6.2 Hz); 4.74 (2 H, dd, J = 7.8 and 6.2 Hz); 6.84 (1 H, dd, J = 3.5 and 1.1 Hz); 7.04 (1 H, dd, J = 5.1 and 3.5 Hz); 7.25 (1 H, dd, J = 5.1 and 1.1 Hz). ¹³C-NMR (CDCl₃): 32.7; 32.8; 34.0; 35.9; 38.1; 43.2; 45.4; 59.5; 75.4; 123.5; 125.0; 126.3; 174.0. |
| 150 | 1 | Ex. no. 24a/ Alkylation/ 58% | [MH − HNMe₂]⁺ = 346.3 (95%) [M + H]⁺ = 386.3 (100%), R$_t$ = 2.5 min. | ¹H-NMR (CDCl₃): 1.43-1.51 (2 H, m); 1.74-1.83 (2 H, m); 1.93-1.98 (2 H, m); 1.99-2.07 (4 H, m); 2.10 (6 H, s); 2.11-2.27 (6 H, m); 2.49-2.59 (2 H, m); 3.25 (2 H, s); 3.38-3.41 (2 H, m); 6.84 (1 H, dd, J = 3.5 and 0.9 Hz); 7.04 (1 H, dd, J = 5.1 and 3.6 Hz); 7.24 (1 H, dd, J = 5.1 and 0.9 Hz). ¹³C-NMR (CDCl₃): 16.8; 32.1; 32.7; 33.8; 34.8; 35.6; 38.0; 39.0; 44.0; 58.5; 59.2; 123.4; 124.1; 124.8; 126.3; 174.0. |
| 151 | 2 | Ex. no. 24b/ Alkylation/ 85% | [MH − HNMe₂]⁺ = 341.2 (100%) [M + H]⁺ = 386.3 (85%), R$_t$ = 2.7 min. | ¹H-NMR (CDCl₃): 1.43-1.52 (2 H, m); 1.72-1.80 (2 H, m); 1.89-1.94 (2 H, m); 1.95-2.07 (4 H, m); 2.11 (6 H, s); 2.12-2.23 (4 H, m); 2.33 (2 H, s); 2.47-2.56 (2 H, m); 3.11 (2 H, s); 3.33-3.38 (2 H, m); 6.85 (1 H, dd, J = 3.6 and 1.1 Hz); 7.04 (1 H, dd, J = 5.1 and 3.6 Hz); 7.24 (1 H, dd, J = 5.1 and 1.1 Hz). ¹³C-NMR (CDCl₃): 16.8; 32.1; 32.7; 32.9; 33.8; 34.8; 35.7; 38.1; 39.0; 59.0; 59.6; 123.5; 124.1; 125.0; 126.3; 174.0. |
| 154 | 2 | Ex. no. 153/ Alkylation/ 64% | [M + H]⁺ = 307.3, R$_t$ = 2.2 min. | ¹H-NMR (CDCl₃): 1.42-1.51 (2 H, m); 1.66-1.79 (2 H, m); 1.82-2.09 (4 H, m); 2.11 (6 H, s); 2.17 (2 H, s); 2.47 (3 H, d, J = 1.1 Hz); 2.82 (3 H, s); 3.20 (2 H, s); 6.51 (1 H, d, J = 3.5 Hz); 6.66-6.69 (1 H, m). ¹³C-NMR (CDCl₃): 15.2; 29.7; 32.6; 33.0; 35.3; 38.1; 44.1; 59.4; 60.5; 124.5; 124.9; 137.9; 173.8. |
| 155 | 1 | Ex. no. 152/ Alkylation/ 63% | [MH − HNMe₂]⁺ = 262.3 (100%) [M + H]⁺ = 307.3 (10%), R$_t$ = 2.4 min. | ¹H-NMR (CDCl₃): 1.43-1.52 (2 H, m); 1.68-1.76 (2 H, m); 1.85-2.09 (4 H, m); 2.10 (6 H, s); 2.30 (2 H, s); 2.46 (3 H, d, J = 1.1 Hz); 2.79 (3 H, s); 3.05 (2 H, s); 6.60 (1 H, d, J = 3.5 Hz); 6.66-6.68 (1 H, m). ¹H-NMR (CDCl₃): 15.2; 29.6; 32.6; 33.1; 35.4; 38.2; 43.3; 59.6; 61.2; 124.4; 124.9; 137.8; 173.8. |
| 156 | 2 | Ex. no. 153/ Alkylation/ 68% | [M + H]⁺ = 349.4, R$_t$ = 2.6 min. | ¹H-NMR (CDCl₃): 0.92 (3 H, t, J = 7.3 Hz); 1.25-1.36 (2 H, m); 1.43-1.52 (4 H, m); 1.68-1.77 (2 H, m); 1.85-2.09 (4 H, m); 2.11 (6 H, s); 2.18 (2 H, s); 2.46 (3 H, d, J = 1.1 Hz); 3.19 (2 H, s); 3.25 (2 H, t, J = 7.3 Hz); 6.61 (1 H, d, J = 3.5 Hz); 6.66-6.69 (1 H, m). ¹³C-NMR (CDCl₃): 13.8; 15.2; 20.0; 29.3; 32.7; 32.8; 35.5; 38.1; 42.0; 44.5; 57.8; 59.4; 124.5; 124.9; 137.8; 173.6. |
| 157 | 1 | Ex. no. 152/ Alkylation/ 68% | [MH − HNMe₂]⁺ = 304.3 (100%) [M + H]⁺ = 349.4 (10%), R$_t$ = 3.0 min. | ¹H-NMR (CDCl₃): 0.90 (3 H, t, J = 7.3 Hz); 1.22-1.33 (2 H, m); 1.39-1.51 (4 H, m); 1.66-1.76 (2 H, m); 1.86-2.09 (4 H, m); 2.10 (6 H, s); 2.31 (2 H, s); 2.46 (3 H, d, J = 1.0 Hz); 3.04 (2 H, s); 3.21 (2 H, t, J = 7.3 Hz); 6.60 (1 H, d, J = 3.5 Hz); 6.65-6.68 (1 H, m). ¹³C-NMR (CDCl₃): 13.7; 15.2; 20.0; 29.3; 32.6; 32.9; 35.8; 38.2; 42.0; 43.6; 58.7; 59.6; 124.4; 124.9; 137.8; 173.6. |
| 158 | 2 | Ex. no. 153/ Alkylation/ 13% | [M + H]⁺ = 375.4, R$_t$ = 2.9 min. | ¹H-NMR (CDCl₃): 1.16-1.27 (2 H, m); 1.42-1.80 (11 H, m); 1.84-2.20 (12 H, m); 2.48 (3 H, m); 3.19 (2 H, d, J = 7.8 Hz); 3.24 (2 H, br s); 6.63 (1 H, br s); 6.70 (1 H, br s). ¹³C-NMR (CDCl₃): 15.3; 25.1; 30.4; 32.3; 32.7; 35.5; 38.0; 47.4; 124.7; 173.6 . . All the other signals could not be identified due to a low sample concentration. |

| Ex. no. | Diastereomer* | Building Block/Method/Yield | LC-MS [M + H]+/Rt | NMR spectrum |
|---|---|---|---|---|
| 159 | 1 | Ex. no. 152/ Alkylation/ 32% | [MH − HNMe2]+ = 330.3 (100%) [M + H]+ = 375.4 (10%), Rt = 3.2 min. | 1H-NMR (CDCl3): 1.11-1.22 (2 H, m); 1.42-1.76 (10 H, m); 1.85-1.97 (2 H, m); 2.00-2.09 (3 H, m); 2.10 (6 H, s); 2.31 (2 H, s); 2.46 (3 H, d, J = 1.0 Hz); 3.06 (2 H, s); 3.15 (2 H, d, J = 7.8 Hz); 6.61 (1 H, d, J = 3.5 Hz); 6.65-6.88 (1 H, m). 13C-NMR (CDCl3): 15.2; 25.1; 30.4; 32.6; 32.9; 35.7; 38.0; 38.2; 43.5; 47.4; 59.1; 59.7; 126.4; 125.0; 137.8; 173.8. |
| 160 | 1 | Ex. no. 152/ Alkylation/ 66% | [M + H]+ = 347.3, Rt = 2.9 min. | 1H-NMR (CDCl3): 0.12-0.18 (2 H, m); 0.43-0.49 (2 H, m); 0.77-0.87 (1 H, m); 1.43-1.52 (2 H, m); 1.68-1.77 (2 H, m); 1.85-2.08 (4 H, m); 2.10 (6 H, s); 2.31 (2 H, s); 2.45 (3 H, s); 3.08 (2 H, d, J = 7.1 Hz); 3.14 (2 H, s); 6.60 (1 H, d, J = 3.4 Hz); 6.65-6.69 (1 H, m). 13C-NMR (CDCl3): 3.4; 9.0; 15.2; 32.5; 32.9; 35.6; 38.1; 43.5; 46.9; 58.8; 59.6; 124.4; 124.9; 137.8; 173.4. |
| 161 | 1 | Ex. no. 152/ Alkylation/ 69% | [MH − HNMe2]+ = 316.3 (100%) [M + H]+ = 361.3 (10%), Rt = 3.1 min. | 1H-NMR (CDCl3): 1.40-1.49 (2 H, m); 1.65-1.75 (4 H, m); 1.80-2.10 (8 H, m); 2.11 (6 H, s); 2.30 (2 H, s); 2.42-2.51 (1 H, m); 2.47 (3 H, d, J = 1.0 Hz); 3.01 (2 H, s); 3.25 (2 H, d, J = 7.6 Hz); 6.61 (1 H, d, J = 3.5 Hz); 6.66-6.69 (1 H, m). 13C-NMR (CDCl3): 15.2; 18.4; 18.5; 24.8; 26.4; 26.5; 32.6; 32.8; 33.9; 35.7; 38.2; 43.4; 47.8; 59.0; 59.7; 124.4; 124.9; 137.8; 173.7. |
| 163 | 2 | Ex. no. 162 Step 3/ Alkylation/ 87% | [M + H]+ = 329.4, Rt = 2.4 min. | 1H-NMR (CDCl3): 0.93 (3 H, t, J = 7.3 Hz); 1.27-1.42 (4 H, m); 1.45-1.53 (2 H, m); 1.70-1.78 (2 H, m); 1.85-2.20 (2 H, m); 2.03 (6 H, s); 2.13 (2 H, s); 2.14-2.25 (2 H, m); 3.23 (2 H, s); 3.26 (2 H, t, J = 7.3 Hz); 7.26-7.32 (3 H, m); 7.35-7.41 (2 H, m). 13C-NMR (CDCl3): 13.8; 20.0; 29.4; 30.2; 32.9; 35.7; 38.0; 42.1; 44.6; 57.9; 60.2; 126.7; 127.4; 127.8; 173.6. |
| 164 | 1 | Ex. no. 431/ Alkylation/ 61% | [M + H]+ = 329.4, Rt = 2.9 min. | 1H-NMR (CDCl3): 0.88 (3 H, t, J = 7.3 Hz); 1.22-1.46 (6 H, m); 1.66-1.75 (2 H, m); 1.85-2.00 (2 H, m); 2.03 (6 H, s); 2.15-2.31 (2 H, m); 2.35 (2 H, s); 2.97 (2 H, s); 3.20 (2 H, t, J = 7.3 Hz); 7.24-7.32 (3 H, m); 7.35-7.40 (2 H, m). 13C-NMR (CDCl3): 13.7; 20.0; 29.3; 30.1; 30.11; 30.2; 30.25; 32.9; 33.0; 35.8; 38.0; 41.9; 43.6; 58.9; 60.5; 126.6; 126.7; 127.6; 127.7; 136.4; 173.6. |
| 165 | 2 | Ex. no. 162 Step 3/ Alkylation/ 26% | [M + H]+ = 355.4, Rt = 2.7 min. | 1H-NMR (CDCl3): 1.14-1.27 (2 H, m); 1.33-1.43 (2 H, m); 1.50-1.80 (9 H, m); 1.90-2.20 (2 H, m); 2.03 (6 H, s); 2.08-2.20 (4 H, m); 3.19 (2 H, d, J = 7.8 Hz); 3.26 (2 H, s); 7.27-7.31 (3 H, m); 7.35-7.41 (2 H, m). 13C-NMR (CDCl3): 25.1; 30.2; 30.5; 32.8; 35.8; 38.0; 38.1; 44.5; 47.4; 58.3; 60.1; 126.7; 127.4; 173.8. |
| 166 | 1 | Ex. no. 431/ Alkylation/ 27% | [M + H]+ = 355.4, Rt = 3.1 min. | 1H-NMR (CDCl3): 1.10-1.20 (2 H, m); 1.30-1.40 (2 H, m); 1.42-1.75 (8 H, m); 1.84-2.20 (3 H, m); 2.02 (6 H, s); 2.10-2.30 (2 H, br s); 2.35 (2 H, s); 3.00 (2 H, s); 3.11 (2 H, d, J = 7.8 Hz); 7.24-7.31 (3 H, m); 7.34-7.40 (2 H, m). 13C-NMR (CDCl3): 25.1; 30.0; 30.2; 30.3; 33.0; 35.9; 37.9; 38.0; 43.6; 47.3; 59.2; 60.4; 126.6; 127.5; 127.7; 173.7. |
| 167 | 2 | Ex. no. 162 Step 3/ Alkylation/ 58% | [M + H]+ = 369.4, Rt = 2.5 min. | 1H-NMR (CDCl3): 1.30-1.39 (2 H, m); 1.65-1.73 (2 H, m); 1.80-195 (2 H, m); 2.00 (6 H, s); 2.13-2.25 (2 H, m); 2.16 (2 H, s); 3.20 (2 H, s); 4.62 (2 H, s); 6.95-6.98 (2 H, m); 7.23-7.30 (4 H, m); 7.35-7.40 (2 H, m). 13C-NMR (CDCl3): 30.2; 32.7; 35.7; 38.0; 41.0; 44.6; 56.9; 60.1; 125.5; 126.72; 126.74; 126.8; 127.4; 127.8; 139.0; 173.4. |
| 167 | 2 | Ex. no. 162 Step 3/ Alkylation/ 45% | [M + H]+ = 341.4, Rt = 2.5 min. | 1H-NMR (CDCl3): 0.03-0.09 (2 H, m); 0.43-0.49 (2 H, m); 0.59-0.70 (1 H, m); 1.33-1.45 (4 H, m); 1.69-1.78 (2 H, m); 1.85-2.01 (2 H, m); 2.03 (6 H, d, J = 1.3 Hz); 2.13 (2 H, s); 2.15-2.26 (2 H, m); 3.26 (2 H, s); 3.34 (2 H, t, J = 7.2 Hz); 7.27-7.31 (3 H, m); 7.35-7.41 (2 H, m). 13C-NMR (CDCl3): 4.7; 8.9; 30.6; 32.8; 33.4; 36.0; 38.3; 43.0; 44.9; 58.6; 60.4; 127.0; 127.7; 128.0; 173.9. |
| 168 | 1 | Ex. no. 431/ Alkylation/ 50% | [M + H]+ = 341.4, Rt = 2.9 min. | 1H-NMR (CDCl3): 0.01-0.04 (2 H, m); 0.38-0.44 (2 H, m); 0.54-0.64 (1 H, m); 1.30-1.40 (4 H, m); 1.66-1.76 (2 H, m); 1.85-2.00 (2 H, m); 2.03 (6 H, s); 2.16-2.32 (2 H, m; ); 2.36 (2 H, s); 3.01 (2 H, s); 3.38 (2 H, t, J = 7.2 Hz); 7.24-7.32 (3 H, m); 7.34-7.40 (2 H, m). 13C-NMR (CDCl3): 4.3; 8.6; 30.1; 32.4; 33.1; 35.8; 38.1; 42.6; 43.7; 59.2; 60.6; 126.6; 127.6; 127.7; 173.6. |
| 169 | 2 | Ex. no. 162 Step 3/ Alkylation/ 64% | [M + H]+ = 341.3, Rt = 2.5 min. | 1H-NMR (CDCl3): 1.32-1.41 (2 H, m); 1.65-1.79 (5 H, m); 1.85-1.95 (3 H, m); 2.03 (6 H, s); 2.03-2.09 (2 H, m); 2.12 (2 H, s); 2.12-2.27 (2 H, m); 2.53 (1 H, td, J = 15.6, 7.8 Hz); 3.20 (2 H, s); 3.29 (2 H, d, J = 7.6 Hz); 7.26-7.30 (3 H, m); 7.35-7.41 (2 H, m). 13C-NMR (CDCl3): 18.4; 26.4; 30.3; 32.8; 34.0; 35 8; 38.0; 44.3; 47.9; 58.1; 60.1; 126.7; 127.4; 173.7. |
| 170 | 1 | Ex. no. 431/ Alkylation/ 45% | [M + H]+ = 341.5, Rt = 3.0 min, | 1H-NMR (CDCl3): 1.30-1.40 (2 H, m); 1.60-1.73 (4 H, m); 1.80-2.02 (6 H, m); 2.03 (6 H, s); 2.15-2.33 (2 H, m); 2.35 (2 H, s); 2.45 (1 H, td, J = 15.6, 7.8 Hz); 2.95 (2 H, s); 3.24 (2 H, d, J = 7.6 Hz); 7.27-7.32 (3 H, m); 7.35-7.41 (2 H, m). 13C-NMR (CDCl3): 18.3; 26.4; 30.1; 33.0; 33.8; 36.0; 38.1; 43.5; 47.8; 59.3; 60.5; 126.7; 127.6; 127.7; 173.7. |

-continued

| Ex. no. | Diastereomer* | Building Block/Method/Yield | LC-MS [M + H]+/Rt | NMR spectrum |
|---|---|---|---|---|
| 171 | 2 | Ex. no. 162 Step 3/ Alkylation/ 56% | [M + H]+ = 327.4, Rt = 2.3 min. | 1H-NMR (CDCl3): 0.18-0.23 (2 H, m); 0.49-0.55 (2 H, m); 0.83-0.94 (1 H, m); 1.35-1.43 (2 H, m); 1.71-1.79 (2 H, m); 1.85-2.02 (2 H, m); 2.04 (6 H, s); 2.13 (2 H, s); 2.16-2.30 (2 H, m); 3.13 (2 H, d, J = 7.1 Hz); 3.35 (2 H, s); 7.26-7.31 (3 H, m); 7.36-7.41 (2 H, m). 13C-NMR (CDCl3): 3.4; 9.1; 30.3; 32.9; 35.8; 38.0; 44.6; 47.0; 57.9; 60.2; 126.7; 127.5; 127.7; 173.4. |
| 172 | 1 | Ex. no. 431/ Alkylation/ 58% | [M + H]+ = 327.4, Rt = 2.8 min. | 1H-NMR (CDCl3): 0.11-0.16 (2 H, m); 0.42-0.47 (2 H, m); 0.75-0.85 (1 H, m); 1.32-1.41 (2 H, m); 1.67-1.76 (2 H, m); 1.87-2.00 (2 H, m); 2.03 (6 H, s); 2.15-2.33 (2 H, m); 2.36 (2 H, s); 3.05-3.10 (4 H, m); 7.24-7.31 (3 H, m); 7.35-7.40 (2 H, m). 13C-NMR (CDCl3): 3.3; 9.0; 30.1; 33.0; 35.9; 38.0; 43.5; 46.9; 59.0; 60.4; 126.6; 127.5; 127.7; 173.4. |
| 173 | 2 | Ex. no. 162 Step 3/ Alkylation/ 60% | [M + H]+ = 355.4, Rt = 2.7 min. | 1H-NMR (CDCl3): 1.33-142 (2 H, m); 1.56-1.68 (5 H, m); 1.68-2.02 (6 H, m); 2.03 (6 H, s); 2.04-2.10 (2 H, m); 2.12 (2 H, s); 2.13-2.30 (2 H, m); 3.14-3.20 (2 H, m); 3.22 (2 H, s); 7.26-7.31 (3 H, m); 7.35-7.41 (2 H, m). 13C-NMR (CDCl3): 18.6; 28.2; 30.2; 32.9; 33.7; 34.3; 35.6 38.0; 40.5; 44.6; 58.0; 60.1; 126.7; 127.4; 127.7; 173.5. |
| 174 | 1 | Ex. no. 431/ Alkylation/ 51% | [M + H]+ = 355.4, Rt = 3.2 min. | 1H-NMR (CDCl3): 1.31-1.40 (2 H, m); 147-153 (4 H, m); 1.66-1.85 (5 H, m); 188-2.02 (3 H, m); 2.03 (6 H, s); 2.14-2.30 (3 H, m); 2.35 (2 H, s); 2.97 (2 H, s); 3.08-3.14 (2 H, m); 7.26-7.32 (3 H, m); 7.35-7.41 (2 H, m). 13C-NMR (CDCl3): 18.5; 28.2; 30.1; 33.1; 33.6; 34.2; 35.8; 38.1; 40.4; 43.7; 59.0; 60.5; 126.6; 127.6; 127.7; 173.5. |
| 175 | 2 | Ex. no. 162 Step 3/ Alkylation/ 47% | [MH − HNMe2]+ = 321.3 (20%) [M + H]+ = 366.3 (100%), Rt = 2.3 min. | 1H-NMR (CDCl3): 0.87 (2 H, dd, J = 5.1 Hz); 1.26 (2 H, dd, J = 5.0 Hz); 135-1.44 (2 H, m); 1.71 (2 H, t, J = 7.1 Hz); 1.74-1.82 (2 H, m); 2.03 (8 H, s); 2.10-2.21 (2 H, m); 3.35 (2 H, s); 3.48 (2 H, t, J = 7.1 Hz); 7.29 (3 H, d, J = 7.5 Hz); 7.35-7.41 (2 H, m). 13C-NMR (CDCl3): 7.6; 14.1; 30.1; 32.6; 32.9; 35.8; 38.0; 41.2; 44.2; 58.9; 60.1; 123.0; 126.7; 127.4; 127.7; 174.2. |
| 176 | 1 | Ex. no. 431/ Alkylation/ 54% | [MH-HNMe2]+ = 321.3 (25%) [M + H]+ = 366.3 (100%), Rt = 2.6 min. | 1H-NMR (CDCl3): 0.84 (2 H, dd, J = 5.2 Hz); 1.22 (2 H, dd, J = 4.9 Hz); 1.34-1.42 (2 H, m); 1.65 (2 H, t, J = 7.1 Hz); 169-1.77 (2 H, m); 187-2.00 (2 H, m); 2.03 (6 H, s); 2.18-2.33 (2 H, m); 2.37 (2 H, s); 3.10 (2 H, s); 3.42 (2 H, t, J = 7.1 Hz); 7.25-7.31 (3 H, m); 7.35-7.40 (2 H, m). 13C-NMR (CDCl3): 7.5; 14.0; 30.1; 32.5; 33.1; 36.0; 38.0; 41.1; 43.4; 59.9; 60.5; 122.9; 126.7; 127.6; 127.8; 174.2. |
| 177 | 2 | Ex. no. 162 Step 3/ Alkylation/ 58% | [MH − HNMe2]+ = 335.3 (12%) [M + H]+ = 380.3 (100%), Rt = 2.3 min. | 1H-NMR (CDCl3): 1.34-1.43 (2 H, m); 1.72-180 (2 H, m); 1.93-1.98 (2 H, m); 1.99-2.07 (3 H, m); 2.03 (6 H, s); 2.11-2.25 (7 H, m); 2.49-2.58 (2 H, m); 3.29 (2 H, s); 3.37-3.41 (2 H, m); 7.27-7.30 (3 H, m); 7.35-7.40 (2 H, m). 13C-NMR (CDCl3): 16.8; 30.1; 32.1; 32.9; 33.8; 34.9; 35.8; 38.0; 39.0; 44.3; 58.3; 60.2; 124.1; 126.8; 127.4; 127.8; 174.0. |
| 178 | 1 | Ex. no. 431/ Alkylation/ 65% | [MH − HNMe2]+ = 335.3 (20%) [M + H]+ = 380.3 (100%), Rt = 2.6 min. | 1H-NMR (CDCl3): 1.32-1.41 (2 H, m); 1.68-1.76 (2 H, m); 1.87-1.92 (2 H, m); 1.94-2.32 (8 H, m); 2.05 (6 H, s); 2.37 (2 H, s); 2.46-2.55 (2 H, m); 3.04 (2 H, s); 3.30-3.36 (2 H, m); 7.28-7.32 (3 H, m); 7.36-7.41 (2 H, m). 13C-NMR (CDCl3): 16.8; 30.1; 32.1; 33.1; 33.8; 34.8; 38.0; 38.1; 39.0; 43.4; 59.3; 60.5; 124.1; 126.7; 127.6; 127.8; 174.1. |
| 179 | 2 | Ex. no. 162 Step 3/ Alkylation/ 83% | [M + H]+ = 357.3 (100%) [MH − NHMe2]+ = 312.3 (92%), Rt = 2.3 min. | 1H-NMR (CDCl3): 1.37-1.43 (2 H, m); 1.49-1.59 (1 H, m); 1.72-1.81 (4 H, m); 2.04 (6 H, s); 2.03-2.09 (5 H, m); 2.18 (2 H, s); 2.12-2.22 (2 H, m, overlapped); 3.44 (2 H, s); 3.46 (2 H, s); 4.09 (1 H, m); 7.27-7.31 (3 H, m); 7.37-7.41 (2 H, m). 13C-NMR (CDCl3): 11.9; 30.1; 32.7; 34.5; 36.7; 38.0; 44.1; 51.7; 61.3; 75.6; 126.9; 127.4; 127.8; 176.3. |
| 180 | 1 | Ex. no. 431/ Alkylation/ 63% | [M + H]+ = 357.3 (43%) [MH − NHMe2]+ = 312.3 (100%), Rt = 2.5 min. | 1H-NMR (CDCl3): 1.35-1.43 (2 H, m); 1.45-1.50 (1 H, m); 1.67-1.77 (4 H, m); 2.04 (6 H, s); 2.00-2.08 (5 H, m, overlapped); 2.11-2.33 (2 H, m); 2.41 (2 H, s); 3.20 (2 H, s); 3.38 (2 H, s); 4.06 (1 H, br s); 7.28-7.30 (3 H, m); 7.36-7.40 (2 H, m). 13C-NMR (CDCl3): 11.9; 30.1; 32.9; 34.5; 36.8; 38.1; 43.2; 51.6; 62.3; 75.6; 126.7; 127.6; 127.8; 176.3. |
| 181 | 2 | Ex. no. 21/ Alkylation/ 78% | [M + H]+ = 345.4, Rt = 2.2 min. | 1H-NMR (CDCl3): 1.23 (6 H, s); 1.36-1.46 (2 H, m); 1.72-1.82 (2 H, m); 1.90-2.01 (2 H, m); 2.02 (6 H, s); 2.04-2.16 (2 H, m); 2.18 (2 H, s); 3.26 (2 H, s); 3.45 (2 H, s); 3.53 (1 H, br s); 7.26-7.31 (3 H, m); 7.35-7.41 (2 H, m). 13C-NMR (CDCl3): 27.6; 29.9; 30.0; 32.7; 35.8; 36.3; 37.9; 43.9; 55.0; 60.0; 61.4; 71.9; 126.6; 127.3; 127.6; 136.3; 174.6; 175.7. |
| 182 | 2 | Ex. no. 162 Step 3/ Alkylation/ 55% | [MH − HNMe2]+ = 328.3 (72%) [M + H]+ = 373.4 (100%), Rt = 2.5 min. | 1H-NMR (CDCl3): 1.18 (6 H, s); 1.32-1.41 (2 H, m); 1.64-1.69 (2 H, m); 1.70-1.77 (2 H, m); 1.91-2.01 (2 H, m); 2.02 (6 H, s); 2.11 (2 H, s); 2.13-2.27 (2 H, m); 3.20 (3 H, s); 3.25 (2 H, s); 3.29-3.34 (2 H, m); 7.25-7.31 (3 H, m); 7.35-7.41 (2 H, m). 13C-NMR (CDCl3): 24.9; 30.2; 32.9; 35.7; 36.7; 38.0; 38.2; 44.6; 49.2; 58.0; 60.2; 73.6; 126.7; 127.4; 127.7; 173.4. |
| 183 | 1 | Ex. no. 431/ Alkylation/ 82% | [MH − HNMe2]+ = 328.3 (100%) [M + H]+ = 373.4 | 1H-NMR (CDCl3): 1.14 (6 H, s); 1.31-140 (2 H, m); 1.57-162 (2 H, m); 1.67-1.74 (2 H, m); 1.90-2.02 (2 H, m); 2.03 (6 H, s); 2.14-2.29 (2 H, m); 2.34 (2 H, s); 3.00 (2 H, s); 3.15 (3 H, s); 3.23-3.29 (2 H, |

| Ex. no. | Diastereomer* | Building Block/Method/Yield | LC-MS [M + H]+/Rt | NMR spectrum |
|---|---|---|---|---|
| | | | (75%), Rt = 2.9 min. | m); 7.25-7.31 (3 H, m); 7.35-7.40 (2 H, m). <br> 13C-NMR (CDCl3): 24.8; 30.1; 33.0; 35.8; 36.8; 38.1; 43.7; 49.1; 59.1; 60.5; 73.5; 126.6; 127.6; 127.7; 173.5. |
| 184 | 2 | Ex. no. 162 Step 3/ Alkylation/ 47% | [M + H]+ = 385.4 [MH − HNMe2]+ = 340.3, Rt = 2.5 min. | 1H-NMR (CDCl3) 1.32-1.44 (2 H, m); 1.52-1.66 (1 H, m); 1.69-1.80 (3 H, m); 1.82-1.93 (4 H, m); 1.94-2.02 (2 H, m); 2.03 (6 H, s); 2.07-2.18 (5 H, m); 2.19-2.31 (1 H, m); 3.15 (3 H, s); 3.23-3.30 (4 H, m); 7.26-7.32 (3 H, m); 7.34-7.43 (2 H, m). <br> 13C-NMR (CDCl3): 12.4; 30.2; 31.3; 31.8; 32.9; 35.6; 37.8; 38.0; 44.7; 49.3; 58.3; 60.2; 78.2; 126.7; 127.4; 127.7; 173.4. |
| 185 | 1 | Ex. no. 431/ Alkylation/ 54% | [M + H]+ = 385.4 [MH − HNMe2]+ = 340.3, Rt = 2.9 min. | 1H-NMR (CDCl3) 1.32-1.41 (2 H, m); 1.54 (1 H, dq, J = 11.6 and 8.9 Hz); 1.66-1.75 (3 H, m); 1.76-1.89 (4 H, m); 1.91-2.01 (2 H, m); 2.03-2.13 (8 H, m); 2.16-2.30 (2 H, m); 2.35 (2 H, s); 3.02 (2 H, s); 3.11 (3 H, s); 3.21 (2 H, ddd, J = 15.9, 7.9 and 5.1 Hz); 7.25-7.32 (3 H, m); 7.35-7.40 (2 H, m). <br> 13C-NMR (CDCl3): 12.4; 30.1; 31.2; 31.9; 33.1; 35.8; 37.7; 38.1; 43.7; 49.3; 59.4; 60.5; 78.2; 126.6; 127.6; 127.7; 136.4; 173.5. |
| 188 | 1 | Ex. no. 71/ Acylation/ 57% | [M + H]+ = 371.4, Rt = 2.7 min. | 1H-NMR (CDCl3): 1.24-1.34 (2 H, m); 1.50-1.68 (5 H, m); 1.78-1.98 (2 H, m); 2.01 and 2.03 (6 H, 2 s); 2.10-2.23 (2 H, m); 2.29-2.40 (3 H, m); 2.64-2.76 (1 H, m); 3.31 (1 H, m); 3.36-3.47 (4 H, m); 3.70-3.78 (1 H, m); 3.81-3.89 (1 H, m); 3.93-4.00 (1 H, m); 7.24-7.31 (3 H, m); 7.33-7.40 (2 H, m). <br> 13C-NMR (CDCl3): 30.0; 30.8; 31.1; 31.2; 31.4; 32.3; 35.3; 35.33; 35.8; 37.5; 38.0; 38.04; 38.06; 38.5; 40.3; 42.3; 43.9; 45.0; 55.2; 56.4; 60.7; 67.6; 73.29; 73.31; 126.5; 126.7; 127.5; 127.6; 127.65; 127.7; 135.6; 137.4; 170.39; 170.4. |
| 189 | 1 | Ex. no. 71/ Acylation/ 35% | [M + H]+ = 343.3, Rt = 2.5 min. | 1H-NMR (CDCl3): 1.22-1.35 (2 H, m); 1.54-1.67 (4 H, m); 1.70-2.02 (2 H, m); 2.03 and 2.04 (6 H, 2 s); 2.05-2.36 (9 H, m); 3.09 (1.2 H, s); 3.20 (0.8 H, t, J = 7.2 Hz); 3.43 (0.8 H, s); 3.49 (1.2 H, t, J = 7.3 Hz); 3.87-3.98 (1 H, m); 4.73-4.83 (2 H, m); 4.91-4.96 (2 H, m); 7.26-7.34 (3 H, m); 7.34-7.42 (2 H, m). <br> 13C-NMR (CDCl3): 30.1; 30.8; 31.0; 31.4; 35.5; 38.0; 38.1; 38.3; 38.5; 40.4; 42.3; 44.16; 44.2; 55.4; 55.7; 60.7; 73.03; 73.04; 126.5; 126.8; 127.5; 127.6; 127.7; 127.8; 169.6; 169.7. |
| 190 | 1 | Ex. no. 71/ Acylation/ 66% | [M + H]+ = 359.4, Rt = 2.8 min. | 1H-NMR (CDC3): 1.25-1.35 (2 H, m); 1.41 and 1.42 (6 H, 2 s); 1.49 (1 H, t, J = 7.4 Hz); 1.55-1.70 (5 H, m); 1.85-2.03 (2 H, m); 2.04 (6 H, s); 2.16-2.34 (2 H, m); 3.18 (1 H, s); 3.20 (2 H, s); 3.46 (0.6 H, s); 3.50 (1.4 H, t, J = 7.2 Hz); 3.66 (1.4 H, s); 3.71 (0.6 H, t, J = 7.0 Hz); 7.26-7.33 (3 H, m); 7.34-7.41 (2 H, m). <br> 13C-NMR (CDCl3): 24.1; 30.2; 30.6; 30.8; 31.7; 34.6; 38.0; 38.1; 38.8; 42.6; 45.3; 45.7; 51.5; 51.6; 56.6; 57.4; 60.8; 79.5; 79.8; 126.5; 126.6; 127.5; 127.6; 127.68; 127.7; 172.6; 172.9. |
| 191 | 1 | Ex. no. 85/ Reduction/ 100% | [M + H]+ = 327.4, Rt = 1.3 min. | 1H-NMR (CDCl3): 0.01-0.06 (2 H, m); 0.38-0.44 (2 H, m); 0.66 (1 H, m); 1.22-1.32 (2 H, m); 1.34-1.48 (4 H, m); 1.60-1.70 (2 H, m); 1.76-1.94 (2 H, m); 2.02 (8 H, s); 2.26 (2 H, br s); 2.44-2.52 (6 H, m); 7.22-7.40 (5 H, m). <br> 13C-NMR (CDCl3): 4.3; 9.2; 31.0; 34.1; 34.6; 38.1; 38.3; 41.0; 53.9; 56.9; 60.4; 65.6; 70.6; 126.4; 127.4; 127.6; 136.9. |
| 192 | 1 | Ex. no. 86/ Reduction/ 88% | [M + H]+ = 341.4, Rt = 2.2 min. | 1H-NMR (CDCl3): 1.22-1.33 (2 H, m); 1.44 (2 H, t, J = 6.8 Hz); 1.54-1.72 (6 H, m); 1.74-1.92 (4 H, m); 1.95-2.08 (2 H, m); 2.02 (6 H, s); 2.20-2.32 (5 H, m); 2.41-2.50 (4 H, m); 7.22-7.40 (5 H, m). <br> 13C-NMR (CDCl3): 18.7; 28.2; 31.1; 34.5; 34.7; 36.0; 38.1; 41.0; 53.8; 54.7; 65.5; 70.6; 126.4; 127.4; 127.6; 136.8. |
| 193 | 1 | Ex. no. 84/ Reduction/ 69% | [M + H]+ = 343.4, Rt = 0.5 min. | 1H-NMR (DMSO-d6): 1.14-1.24 (2 H, m); 1.30 (1 H, t, J = 7.0 Hz); 1.36 (2 H, t, J = 6.9 Hz); 1.40-1.47 (1 H, m); 1.57-1.67 (4 H, m); 1.90 (6 H, s); 1.82-1.92 (2 H, m, overlapped); 1.94-2.03 (4 H, m); 2.448 (2 H, s); 2.453 (2 H, s); 2.53-2.57 (2 H, m); 4.58 (1 H, br s); 7.21-7.25 (1 H, m); 7.30-7.37 (4 H, m). <br> 13C-NMR (DMSO-d6): 12.0; 26.8; 30.3; 33.8; 33.8; 37.7; 40.7; 54.4; 63.2; 73.4; 126.1; 127.2; 127.3. |
| 194 | 1 | Ex. no. 71/ Reductive amination/ 56% | [MH − HNMe2]+ = 321.3 (100%) [M + H]+ = 366.4 (80%), Rt = 0.5 min. | 1H-NMR (CDCl3): 1.24-1.35 (2 H, m); 1.46 (2 H, t, J = 6.9 Hz); 1.63-1.70 (2 H, m); 1.79-1.95 (4 H, m); 2.03 (6 H, s); 2.05-2.22 (4 H, m); 2.23-2.34 (2 H, m); 2.48-2.55 (8 H, m); 7.24-7.32 (3 H, m); 7.34-7.39 (2 H, m); <br> 13C-NMR (CDCl3): 17.0; 31.1; 32.3; 34.5; 36.7; 38.1; 41.3; 50.8; 52.6; 53.4; 53.8; 60.6; 65.6; 124.5; 126.5; 127.6; 127.7. |
| 195 | 1 | Ex. no. 71/ Acylation/ 49% | [M + H]+ = 369.4, Rt = 3.2 min. | 1H-NMR (CDCl3): 1.24-1.35 (2 H, m); 1.51-1.68 (6 H, m); 1.69-1.76 (3 H, m); 1.78-1.99 (4 H, m); 2.03 and 2.05 (6 H, 2 s); 2.06-2.17 (3 H, m); 2.18-2.40 (3 H, m); 3.32 (1 H, s); 3.32-3.49 (3 H, m); 7.26-7.33 (3 H, m); 7.34-7.42 (2 H, m). <br> 13C-NMR (CDCl3): 18.28; 18.3; 27.97; 28.0; 30.0; 30.9; 31.2; 31.5; 32.0; 32.1; 32.5; 35.71; 35.74; 36.0; 37.6; 38.0; 38.1; 40.3; 42.3; 43.9; 45.0; 55.2; 56.4; 60.8; 126.5; 126.7; 127.6; 127.63; 127.67; 127.8; 171.98; 172.0. |
| 196 | 1 | Ex. no. 189/ Reduction/ 23% | [M + H]+ = 329.4, Rt = 0.6 min. | 1H-NMR (CDCl3): 1.20-1.30 (2 H, m); 1.41 (2 H, t, J = 6.8 Hz); 1.58-1.70 (2 H, m); 1.79-1.99 (2 H, m); 2.01 (6 H, s); 2.10-2.30 (2 H, m); 2.39 (2 H, s); 2.43 (2 H, t, J = 6.8 Hz); 2.72 (1 H, s); 2.74 (1 H, s); |

-continued

| Ex. no. | Diastereomer* | Building Block/Method/Yield | LC-MS [M + H]⁺/R_t | NMR spectrum |
|---|---|---|---|---|
| | | | | 3.12-3.22 (1 H, m); 4.41 (2 H, dd, J = 6.2 and 6.2 Hz); 4.77 (2 H, dd, J = 7.8 and 6.0 Hz); 7.22-7.39 (5 H, m).<br>$^{13}$C-NMR (CDCl$_3$): 31.0; 34.5; 34.7; 38.0; 41.2; 53.7; 59.9; 60.4; 65.7; 76.5; 126.4; 126.5; 127.5; 127.6; 127.7. |
| 197 | 1 | Ex. no. 71/ Acylation/ 76% | [M + H]⁺ = 355.4, R_t = 3.0 min. | $^1$H-NMR (CDCl$_3$): 0.02-0.09 (2 H, m); 0.38-0.46 (2 H, m); 0.65-0.78 (1 H, m); 1.24-1.35 (2 H, m); 1.50-1.70 (6 H, m); 1.80-2.00 (2 H, m); 2.02 and 2.04 (6 H, 2 s); 2.16-2.26 (1 H, m); 2.28-2.40 (3 H, m); 3.32 (1 H, s); 3.40 (1 H, s); 3.45 (2 H, dt, J = 7.3 and 1.9 Hz); 7.25-7.32 (3 H, m); 7.34-7.41 (2 H, m).<br>$^{13}$C-NMR (CDCl$_3$): 4.41; 4.45; 10.5; 10.71; 10.76; 28.5; 30.0; 30.1; 30.5; 30.9; 31.2; 31.4; 34.4; 34.8; 35.9; 37.6; 38.0; 38.1; 40.4; 42.3; 43.9; 45.0; 55.2; 56.4; 60.8; 126.5; 126.7; 127.6; 127.62; 127.66; 127.7; 137.4; 171.87; 171.92. |
| 198 | 1 | Ex. no. 71/ Acylation/ 92% | [M + H]⁺ = 352.3, R_t = 2.6 min. | $^1$H-NMR (CDCl$_3$): 1.32 (1 H, dd, J = 10.6 and 3.1 Hz); 1.35 (1 H, dd, J = 10.6 and 3.1 Hz); 1.45-1.54 (2 H, m); 1.56-1.74 (6 H, m); 1.85-2.01 (2 H, m); 2.02 and 2.04 (6 H, 2 s); 2.16-2.35 (2 H, m); 3.41 (0.8 H, s); 3.48 (1.2 H, t, J = 7.3 Hz); 3.73 (1.2 H, s); 3.87 (0.8 H, t, J = 7.1 Hz); 7.26-7.32 (3 H, m); 7.35-7.42 (2 H, m).<br>$^{13}$C-NMR (CDCl$_3$): 13.2; 13.7; 16.2; 16.6; 30.2; 30.7; 30.8; 31.2; 35.1; 37.6; 38.0; 38.04; 40.1; 42.7; 45.6; 46.0; 57.2; 57.4; 60.7; 120.0; 120.2; 126.6; 126.7; 127.4; 127.5; 127.71; 127.73; 136.0; 137.0; 162.8; 163.0. |
| 199 | 1 | Ex. no. 71/ Acylation/ 84% | [M + H]⁺ = 366.3, R_t = 2.7 min. | $^1$H-NMR (CDCl$_3$): 1.28-1.37 (2 H, m); 1.56-1.74 (5 H, m); 1.88-2.00 (2 H, m); 2.028 and 2.03 (6 H, 2 s); 2.17-2.33 (3 H, m); 2.53-2.69 (2 H, m); 2.73-2.82 (2 H, m); 3.38 (1.2 H, s); 3.45 (0.8 H, s); 3.49-3.55 (2 H, m); 7.26-7.32 (3 H, m); 7.35-7.41 (2 H, m).<br>$^{13}$C-NMR (CDCl$_3$): 16.47; 16.5; 30.3; 30.5; 30.56; 30.7; 31.4; 34.9; 37.7; 38.0; 38.05; 38.8; 38.98; 40.0; 42.9; 44.9; 45.5; 56.4; 56.9; 60.7; 120.8; 120.9; 126.6; 126.7; 127.5; 127.6; 127.71; 127.75; 137.0; 164.4; 164.7. |
| 200 | 1 | Ex. no. 71/ Reductive amination/ 51% | [MH − HNMe$_2$]⁺ = 307.3 (100%) [M + H]⁺ = 352.4 (82%), R_t = 0.8 min. | $^1$H-NMR (CDCl$_3$): 0.79-0.83 (2 H, m); 1.20-1.23 (2 H, m); 1.24-1.32 (2 H, m); 1.45 (2 H, t, J = 6.9 Hz); 1.60-1.70 (4 H, m); 1.77-1.92 (2 H, m); 2.02 (6 H, s); 2.16-2.34 (2 H, m); 2.47 (2 H, s); 2.52 (2 H, t, J = 6.9 Hz); 2.62-2.67 (2 H, m); 7.23-7.32 (3 H, m); 7.34-7.39 (2 H, m).<br>$^{13}$C-NMR (CDCl$_3$): 8.2; 13.9; 31.1; 34.3; 34.5; 38.1; 41.3; 53.8; 54.5; 60.5; 65.5; 123.3; 126.4; 126.5; 127.7. |
| 201 | 1 | Ex. no. 188/ Reduction/ 20% | [M + H]⁺ = 357.4, R_t = 1.3 min. | $^1$H-NMR (CDCl$_3$): 1.23-1.32 (2 H, m); 1.45 (2 H, t, J = 6.8 Hz); 1.49-1.62 (3 H, m); 1.62-1.70 (2 H, m); 1.80-1.93 (2 H, m); 2.03 (6 H, s); 2.03-2.09 (1 H, m); 2.15-2.31 (3 H, m); 2.34-2.45 (2 H, m); 2.45 (2 H, s); 2.48 (2 H, t, J = 6.8 Hz); 3.33 (1 H, t, J = 7.9 Hz); 3.74 (1 H, dd, J = 15.4 and 7.9 Hz); 3.84 (1 H, dt, J = 8.2 and 4.7 Hz); 3.89-3.95 (1 H, m); 7.23-7.40 (5 H, m).<br>$^{13}$C-NMR (CDCl$_3$): 31.1; 32.4; 32.5; 34.6; 37.8; 38.0; 38.5; 41.08; 53.8; 55.8; 60.5; 65.6; 67.8; 73.4; 126.4; 127.5; 127.7; 136.6. |
| 202 | 1 | Ex. no. 190/ Reduction/ 10% | [M + H]⁺ = 345.4, R_t = 2.0 min. | $^1$H-NMR (CDCl$_3$): 1.16 (6 H, s); 1.22-1.30 (2 H, m); 1.46 (2 H, t, J = 6.9 Hz); 1.63-1.70 (2 H, m); 1.80-1.95 (2 H, m); 2.03 (6 H, s); 2.15-2.30 (2 H, m); 2.43 (2 H, s); 2.57 (2 H, s); 2.60 (2 H, t, J = 6.9 Hz); 3.21 (3 H, s); 7.23-7.40 (5 H, m).<br>$^{13}$C-NMR (CDCl$_3$): 23.6; 30.9; 31.0; 34.2; 38.1; 41.5; 49.3; 55.4; 60.7; 64.5; 67.3; 75.9; 126.4; 127.5; 127.8. |
| 203 | 1 | Ex. no. 195/ Reduction/ 67% | [M + H]⁺ = 355.4, R_t = 2.7 min. | $^1$H-NMR (CDCl$_3$): 1.22-1.32 (2 H, m); 1.34-1.48 (6 H, m); 1.52-1.70 (4 H, m); 1.74-1.90 (4 H, m); 1.98-2.01 (1 H, m); 2.03 (6 H, s); 2.04-2.08 (1 H, m); 2.19-2.38 (5 H, m); 2.46 (2 H, s); 2.48 (2 H, t, J = 6.9 Hz); 7.23-7.40 (5 H, m).<br>$^{13}$C-NMR (CDCl$_3$): 18.4; 26.5; 28.3; 31.1; 34.7; 35.0; 36.1; 38.1; 38.4; 41.1; 53.9; 57.1; 60.5; 65.5; 126.4; 127.3; 127.7. |
| 204 | 1 | Ex. no. 197/ Reduction/ 72% | [M + H]⁺ = 341.4, R_t = 2.3 min. | $^1$H-NMR (CDCl$_3$): −0.02-0.03 (2 H, m); 0.37-0.43 (2 H, m); 0.60-0.70 (1 H, m); 1.18-1.52 (4 H, m); 1.44 (2 H, t, J = 6.8 Hz); 1.54-1.70 (4 H, m); 1.75-1.95 (2 H, m); 2.03 (6 H, s); 2.15-2.35 (2 H, m); 2.37-2.43 (2 H, m); 2.45-2.51 (4 H, m); 7.24-7.40 (5 H, m).<br>$^{13}$C-NMR (CDCl$_3$): 4.4; 10.8; 28.4; 28.9; 31.1; 32.8; 33.7; 34.7; 38.1; 38.3; 41.1; 53.9; 56.8; 56.9; 60.5; 65.6; 126.4; 127.5; 127.7. |
| 205 | 1 | Ex. no. 71/ Acylation/ 59% | [M + H]⁺ = 343.3 (99%) [MH − NHMe$_2$]⁺ = 298.3 (100%), R_t = 2.6 min. | $^1$H-NMR (DMSO-d$_6$): 0.73-0.81 (2 H, m); 0.91-0.97 (2 H, m); 1.14-1.24 (2 H, m); 1.49 (1 H, t, J = 6.9 Hz); 1.54-1.64 (3 H, m); 1.92 (6 H, s); 1.93-2.13 (4 H, m, overlapped); 3.20 (0.8 H, s); 3.26-3.30 (1.2 H, m, overlapped by the water signal); 3.63 (1.2 H; s); 3.74-3.78 (0.8 H, m); 6.02 (0.3 H, s); 6.08 (0.7 H, s); 7.23-7.28 (1 H, m); 7.32-7.39 (4 H, m).<br>$^{13}$C-NMR (DMSO-d$_6$): 13.9; 14.1; 29.1; 30.4; 30.7; 33.9; 36.6; 37.7; 41.6; 44.7; 45.2; 55.4; 56.9; 59.9; 126.2; 127.2; 127.4; 170.5. |
| 206 | 1 | Ex. no. 205/ Reduction/ 85% | [M + H]⁺ = 329.3 (100%) [MH − NHMe$_2$]⁺ = 284.3 (58%), | $^1$H-NMR (DMSO-d$_6$): 0.37 (2 H, dd, J = 6.7 and 4.6 Hz); 0.54 (2 H, dd, J = 6.9 and 4.6 Hz); 1.16-1.23 (2 H, m); 1.38 (2 H, t, J = 6.9 Hz); 1.60-1.66 (2 H, m); 1.86-2.08 (4 H, m, overlapped); 1.91 (6 H, s), 2.41 (2 H, s); 2.44 (2 H, s); 2.51-2.53 (2 H, m, overlapped by the |

| Ex. no. | Diastereomer* | Building Block/Method/Yield | LC-MS [M + H]⁺/$R_t$ | NMR spectrum |
|---|---|---|---|---|
| | | | $R_t$ = 0.3 min. | DMSO signal); 4.82 (1 H, s); 7.21-7.26 (1 H, m); 7.30-7.38 (4 H, m).<br>¹³C-NMR (DMSO-d₆): 12.1; 30.4; 34.0; 37.7; 40.6; 52.8; 53.6; 54.8; 59.5; 63.1; 126.1; 127.2; 127.4. |
| 207 | 1 | Ex. no. 66/ Reduction/ 73% | [M + 1]⁺ = 349.3 (43%)<br>[MH − NHMe₂]⁺ = 304.3 (100%),<br>$R_t$ = 0.3 min. | ¹H-NMR (DMSO-d₆): 1.25-1.31 (2 H, m); 1.40-1.47 (4 H, m); 1.57-1.67 (4 H, m); 1.86-2.02 (6 H, m, overlapped); 1.99 (6 H, s); 2.42 (2 H, s); 2.44 (2 H, s); 2.56 (2 H, t, J = 6.9 Hz); 4.57 (1 H, br s); 6.91 (1 H, dd, J = 3.6 and 1.2 Hz); 7.04 (1 H, dd, J = 5.1 and 3.5 Hz); 7.40 (1 H, dd, J = 5.1 and 1.1 Hz).<br>¹³C-NMR (DMSO-d₆): 12.0; 26.8; 32.9; 33.6; 34.8; 37.7; 40.4; 54.5; 58.7; 63.1; 73.4; 123.4; 124.6; 126.2. |
| 208 | 1 | Ex. no. 18/ Reductive amination/ 40% | [MH − HNMe₂]⁺ = 327.3 (100%)<br>[M + H]⁺ = 372.3 (15%), $R_t$ = 0.4 min. | ¹H-NMR (CDCl₃): 1.38 (2 H, ddd, J = 13.2, 9.8 and 3.5 Hz); 1.51 (2 H, t, J = 6.9 Hz); 1.65-1.73 (2 H, m); 1.86-1.97 (4 H, m); 1.98-2.21 (2 H, m); 2.10 (6 H, s); 2.45 (2 H, s); 2.47-2.56 (6 H, m); 6.85 (1 H, dd, J = 3.5 and 1.1 Hz); 7.02 (1 H, dd, J = 5.1 and 3.5 Hz); 7.22 (1 H, dd, J = 5.1 and 1.0 Hz).<br>¹³C-NMR (CDCl₃): 17.0; 32.3; 33.7; 34.3; 34.5; 36.7; 38.1; 41.0; 52.6; 53.9; 59.6; 65.7; 123.3; 124.4; 124.9; 126.1. |
| 209 | 1 | Ex. no. 18/ Acylation/ 49% | [M + H]⁺ = 349.3 (3%)<br>[MH − NHMe₂]⁺ = 304.2 (100%),<br>$R_t$ = 2.5 min. | ¹H-NMR (DMSO-d₆): 0.72-0.80 (2 H, m); 0.91-0.97 (2 H, m); 1.24-1.35 (2 H, m); 1.54-1.69 (4 H, m); 1.93-1.99 (4 H, m); 2.01 (6 H, s); 3.17 (0.8 H, s); 3.28-3.37 (1.2 H, m, overlapped by the water signal); 3.61 (1.2 H; s); 3.75-3.82 (0.8 H, m); 6.06 (1 H, br s); 6.94 (1 H, dd, J = 3.6 and 1.1 Hz); 7.06 (1 H, dd, J = 5.1 and 3.5 Hz); 7.42 (1 H, dd, J = 5.1 and 1.1 Hz).<br>¹³C-NMR (DMSO-d₆): 13.9; 14.1; 30.3; 30.4; 32.5; 33.5; 37.7; 41.4; 44.7; 45.3; 57.1; 59.1; 123.6; 124.8; 126.3; 170.5. |
| 210 | 1 | Ex. no. 209/ Reduction/ 69% | [M + H]⁺ = 335.3 (40%)<br>[MH − NHMe₂]⁺ = 290.3 (100%),<br>$R_t$ = 0.2 min. | ¹H-NMR (DMSO-d₆): 0.36 (2 H, dd, J = 6.9 and 4.6 Hz); 0.54 (2 H, dd, J = 6.9 and 4.6 Hz); 1.26-1.32 (2 H, m); 1.44 (2 H, t, J = 6.8 Hz); 1.62-1.68 (2 H, m); 1.83-1.97 (4 H, m); 1.99 (6 H, s), 2.41 (4 H, s); 2.51-2.55 (2 H, m, overlapped by the DMSO signal); 4.82 (1 H, s); 6.91 (1 H, dd, J = 3.5 and 1.1 Hz); 7.05 (1 H, dd, J = 5.1 and 3.5 Hz); 7.40 (1 H, dd, J = 5.1 and 1.0 Hz).<br>¹³C-NMR (DMSO-d₈): 12.6; 33.4; 34.2; 36.9; 38.2; 40.9; 53.2; 54.2; 59.2; 63.5; 123.9; 125.2; 128.7. |
| 211 | 1 | Ex. no. 18/ Reductive amination/ 45% | [MH − HNMe₂]⁺ = 313.3 (100%)<br>[M + H]⁺ = 358.3 (10%), $R_t$ = 0.7 min. | ¹H-NMR (CDCl₃): 0.79-0.83 (2 H, m); 1.19-1.23 (2 H, m); 1.38 (2 H, ddd, J = 13.3, 9.9 and 3.5 Hz); 1.51 (2 H, t, J = 6.9 Hz); 1.60-1.65 (2 H, m); 1.66-1.73 (2 H, m); 1.84-1.97 (2 H, m); 2.04-2.18 (8 H, m); 2.43 (2 H, s); 2.59 (2 H, t, J = 6.9 Hz); 2.61-2.67 (2 H, m); 6.84 (1 H, dd, J = 3.6 and 1.1 Hz); 7.03 (1 H, dd, J = 5.1 and 3.6 Hz); 7.22 (1 H, dd, J = 5.1 and 1.1 Hz).<br>¹³C-NMR (CDCl₃): 8.2; 13.9; 33.7; 34.3; 37.8; 38.1; 41.0; 53.9; 54.4; 59.6; 65.7; 123.2; 123.3; 124.9; 126.1; 143.2. |
| 212 | 1 | Ex. no. 18/ Acylation/ 33% | [M + H]⁺ = 363.3, $R_t$ = 2.3 min. | ¹H-NMR (CDCl₃): 1.33-1.46 (2 H, m); 1.59-1.80 (5 H, m); 1.83-2.07 (3 H, m); 2.08 and 2.12 (6 H, 2 s); 2.66 (2 H, dd, J = 7.8 and 2.5 Hz); 3.30 (1.2 H, s); 3.33 (0.8 H, s); 3.36-3.50 (3 H, m); 4.40 (0.8 H, dd, J = 6.3 and 2.5 Hz); 4.41 (1.2 H, dd, J = 6.3 and 2.5 Hz); 4.88 (1.2 H, dd, J = 6.3 and 1.4 Hz); 4.90 (0.8 H, dd, J = 6.3 and 1.4 Hz); 6.83-6.87 (1 H, m); 7.01-7.07 (1 H, m); 7.22-7.26 (1 H, m).<br>¹³C-NMR (CDCl₃): 19.8; 31.1; 31.2; 31.5; 31.6; 32.8; 33.0; 33.4; 35.4; 38.03; 38.07; 38.09; 38.2; 38.5; 40.1; 42.1; 43.9; 45.0; 55.4; 56.4; 59.8; 77.5; 77.54; 123.3; 123.6; 124.9; 125.1; 126.1; 126.4; 169.58; 169.64. |
| 215 | 2 | Ex. no. 24b/ Alkylation/ 79% | [MH − NHMe₂]⁺ = 318.2, $R_t$ = 2.5 min. | ¹H-NMR (CDCl₃): 1.44-1.54 (4 H, m); 1.68-1.81 (4 H, m); 1.98-2.68 (6 H, m); 2.10 (6 H, s); 2.37 (2 H, s); 3.27 (2 H, s); 3.39 (2 H, s); 4.03 (1 H, br. s); ); 6.85 (1 H, dd, J = 3.6 and 1.0 Hz); 7.04 (1 H, dd, J = 5.1 and 3.6 Hz); 7.24 (1 H, dd, J = 5.1 and 1.0 Hz).<br>¹³C-NMR (CDCl₃): 11.9; 30.3; 32.7; 34.5; 36.5; 38.1; 43.3; 51.5; 59.5; 60.4; 75.6; 123.5; 125.0; 126.3; 176.2. |
| 216 | 1 | Ex. no. 24a/ Alkylation/ 81% | [M + 1]⁺ = 363.3 (61%)<br>[MH − NHMe₂]⁺ = 318.3 (100%),<br>$R_t$ = 2.2 min. | ¹H-NMR (CDCl₃): 1.46-1.58 (4 H, m); 171-1.83 (4 H, m); 2.04-2.09 (6 H, m); 2.10 (6 H, s); 2.23 (2 H, s); 3.42 (2 H, s); 3.43 (2 H, s); 4.07 (1 H, brs); ); 6.85 (1 H, dd, J = 3.6 and 1.1 Hz); 7.05 (1 H, dd, J = 5.1 and 3.6 Hz); 7.25 (1 H, dd, J = 5.1 and 1.0 Hz).<br>¹³C-NMR (CDCl₃): 11.9; 32.5; 32.8; 34.5; 36.5; 38.1; 43.8; 51.6; 59.3; 75.6; 123.5; 124.9; 126.3; 176.2. |
| 217 | 1 | Ex. no. 24a/ Alkylation/ 52% | [M + H]⁺ = 391.3, $R_t$ = 2.5 min. | ¹H-NMR (CDCl₃): 1.47 (2 H, ddd, J = 13.1, 7.6 and 4.9 Hz); 1.54-1.64 (1 H, m); 1.72-1.80 (3 H, m); 1.83-1.93 (4 H, m); 1.99-2.13 (12 H, m); 2.17 (2 H, s); 3.15 (3 H, s); 3.22-3.30 (4 H, m); 6.85 (1 H, d, J = 2.9 Hz); 7.05 (1 H, dd, J = 5.1 and 3.6 Hz); 7.25 (1 H, d, J = 4.8 Hz).<br>¹³C-NMR (CDCl₃): 12.4; 31.2; 31.8; 32.7; 32.8; 35.4; 37.7; 38.0; 44.3; 49.3; 58.3; 59.3; 78.2; 123.4; 124.9; 126.3; 173.3. |
| 218 | 2 | Ex. no. 24b/ Alkylation/ 47% | [M + H]⁺ = 391.4, [M − HNMe₂]⁺ = 346.4, $R_t$ = 2.8 min. | ¹H-NMR (CDCl₃): 1.43-1.51 (2 H, m); 1.52-1.62 (1 H, m); 1.68-1.90 (7 H, m); 1.98-2.14 (12 H, m); 2.31 (2 H, s); 3.09 (2 H, s); 3.12 (3 H, s); 3.23 (2 H, ddd, J = 16.0, 7.9 and 5.1 Hz); 6.85 (1 H, dd, J = 3.6 and 1.1 Hz); 7.04 (1 H, dd, J = 5.1 and 3.6 Hz); 7.24 (1 H, dd, J = 5.1 and 1.1 Hz). |

-continued

| Ex. no. | Diastereomer* | Building Block/Method/Yield | LC-MS [M + H]+/Rt | NMR spectrum |
|---|---|---|---|---|
| 219 | 2 | Ex. no. 24b/ Alkylation/ 54% | [MH − HNMe$_2$]$^+$ = 334.2 (100%) [M + H]$^+$ = 379.3 (2%), R$_t$ = 2.8 min. | $^{13}$C-NMR (CDCl$_3$): 12.4; 31.2; 31.9; 32.7; 32.9; 35.5; 37.8; 38.1; 43.8; 49.3; 59.1; 59.5; 78.2; 123.5; 125.0; 126.2; 173.4. $^1$H-NMR (CDCl$_3$): 1.14 (6 H, s); 1.41-1.49 (2 H, m); 1.58-1.63 (2 H, m); 1.69-1.78 (2 H, m); 1.93-2.08 (4 H, m); 2.09 (6 H, s), 2.30 (2 H, s); 3.06 (2 H, s); 3.15 (3 H, s); 3.25-3.30 (2 H, m); 6.83-6.85 (1 H, m); 7.03 (1 H, dd, J = 5.1 and 3.5 Hz); 7.22-7.24 (1 H, m). $^{13}$C-NMR (CDCl$_3$): 24.8; 32.7; 32.8; 35.5; 36.8; 38.1; 38.2; 43.7; 49.1; 58.7; 59.5; 73.5; 123.4; 124.9; 126.2; 142.9; 173.4. |
| 220 | 1 | Ex. no. 24a/ Alkylation/ 70% | [MH − HNMe$_2$]$^+$ = 334.2 (100%) [M + H]$^+$ = 379.3 (55%), R$_t$ = 2.5 min. | $^1$H-NMR (CDCl$_3$): 1.17 (6 H, s); 1.41-1.49 (2 H, m); 1.63-1.68 (2 H, m); 1.71-1.79 (2 H, m); 1.93-2.08 (4 H, m); 2.09 (6 H, s), 2.16 (2 H); 3.19 (3 H, s); 3.21 (2 H, s); 3.28-3.33 (2 H, m); 6.84 (1 H, dd, J = 3.6 and 1.0 Hz); 7.04 (1 H, dd, J = 5.1 and 3.6 Hz); 7.23 (1 H, dd, J = 5.1 and 1.0 Hz). $^{13}$C-NMR (CDCl$_3$): 24.9; 32.7; 32.8; 35.5; 36.7; 38.1; 38.2; 44.3; 49.2; 58.1; 59.3; 73.5; 123.4; 124.9; 126.3; 142.5; 173.4. |
| 221 | 1 | Ex. no. 24a/ Alkylation/ 37% | [MH − HNMe$_2$]$^+$ = 320.3 (95%) [M + H]$^+$ = 365.3 (100%), R$_t$ = 2.3 min. | $^1$H-NMR (CDCl$_3$): 1.23 (6 H, s); 1.38-1.47 (2 H, m); 1.62-1.67 (2 H, m); 1.73-1.81 (2 H, m); 2.05-2.20 (4 H, m); 2.15 (2 H, s, overlapped); 2.17 (6 H, s, overlapped); 2.52 (1 H, br s); 3.27 (2 H, s); 3.36-3.41 (2 H, m); 6.89 (1 H, dd, J = 3.5 and 0.9 Hz); 7.05 (1 H, dd, J = 5.1 and 3.6 Hz); 7.28 (1 H, dd, J = 5.1 and 0.8 Hz). $^{13}$C-NMR (CDCl$_3$): 29.5; 32.3; 32.6; 35.5; 37.9; 38.7; 40.0; 44.4; 57.8; 60.5; 69.5; 124.3; 125.7; 126.6; 173.8. |
| 222 | 2 | Ex. no. 24b/ Alkylation/ 56% | [MH − HNMe$_2$]$^+$ = 320.2 (100%) [M + H]$^+$ = 365.3 (1%), R$_t$ = 2.5 min. | $^1$H-NMR (CDCl$_3$): 1.21 (6 H, s); 1.41-1.49 (2 H, m); 1.57-1.62 (2 H, m); 1.70-1.78 (2 H, m); 1.98-2.17 (4 H, m); 2.14 (6 H, s, overlapped); 2.32 (2 H, s); 2.44 (1 H, s); 3.07 (2 H, s); 3.32-3.37 (2 H, m); 6.86-6.89 (1 H, m); 7.04 (1 H, dd, J = 5.1 and 3.6 Hz); 7.24-7.27 (1 H, m). $^{13}$C-NMR (CDCl$_3$): 29.5; 32.4; 32.8; 35.6; 38.0; 38.6; 40.0; 43.4; 58.9; 69.5; 124.0; 125.4; 126.4; 173.9. |
| 223 | 1 | Ex. no. 18/ Acylation; 58% | m/z: [M + H]$^+$ = 351.3 (43%) [MH − NHMe$_2$]$^+$ = 306.3 (100%), R$_t$ = 2.4 min. | $^1$H-NMR (DMSO-d$_6$): 1.28 (2 H, s); 1.29 (6 H, s); 1.51 (1 H, t, J = 7.4 Hz); 1.57-1.67 (3 H, m); 1.93-1.98 (4 H, m); 2.09 (6 H, s); 3.18 (0.7 H, s); 3.33 (1.3 H; t, J = 7.0 Hz, overlapped by the water signal); 3.59 (1.3 H; s); 3.76 (0.7 H, t, J = 6.8 Hz); 5.07 (0.4 H, s); 5.14 (0.6 H, s); 6.94 (1 H, dd, J = 3.5 and 1.0 Hz); 7.06 (1 H, dd, J = 4.8 and 3.7 Hz); 7.42 (1 H, dd, J = 5.1 and 0.7 Hz). $^{13}$C-NMR (DMSO-d$_6$): 27.8; 30.0; 30.6; 32.5; 32.9; 37.7; 38.0; 41.8; 45.5; 45.8; 57.4; 59.0; 59.1; 72.6; 72.8; 123.6; 124.8; 126.3; 142.9; 173.7. |
| 224 | 2 | Ex. no. 24b/ Alkylation/ 55% | [M + H]$^+$ = 351.3, R$_t$ = 2.2 min. | $^1$H-NMR (CDCl$_3$): 1.22 (6 H, s); 1.45-1.54 (2 H, m); 1.77-1.85 (2 H, m); 2.00-2.10 (4 H, m); 2.11 (6 H, s); 2.23 (2 H, s); 3.25 (2 H, s); 3.33 (2 H, s); 3.41 (2 H, s); 6.85 (1 H, dd, J = 3.5 and 1.0 Hz); 7.05 (1 H, dd, J = 5.1 and 3.5 Hz); 7.25 (1 H, dd, J = 5.1 and 1.0 Hz). $^{13}$C-NMR (CDCl$_3$): 27.7; 32.6; 32.7; 36.3; 38.0; 43.8; 55.1; 59.4; 61.4; 72.1; 123.6; 124.9; 126.3; 175.8. |
| 225 | 1 | Ex. no. 24a/ Alkylation/ 71% | m/z: [MH − HNMe$_2$]$^+$ = 306.2, R$_t$ = 2.3 min. | $^1$H-NMR (CDCl$_3$): 1.19 (6 H, s); 1.45-1.54 (2 H, m); 1.74-1.83 (2 H, m); 1.96-2.09 (4 H, m); 2.10 (6 H, s); 2.37 (2 H, s); 3.21 (2 H, s); 3.25 (2 H, s); 3.26 (1 H, s); 6.85 (1 H, dd, J = 3.5 and 1.0 Hz); 7.02 (1 H, dd, J = 5.1 and 3.5 Hz); 7.24 (1 H, dd, J = 5.1 and 1.0 Hz). $^{13}$C-NMR (CDCl$_3$): 27.7; 32.6; 32.8; 36.3; 38.1; 43.2; 55.0; 59.6; 62.0; 72.1; 123.5; 125.0; 126.3; 175.8. |
| 226 | 1 | Ex. no. 18/ Alkylation/ Reduction/ 2 Steps 27% | m/z: [M + H]$^+$ = 351.3, R$_t$ = 0.3 min. | $^1$H-NMR (CDCl$_3$): 1.21 (6 H, s); 1.30-1.40 (2 H, m); 1.48-1.52 (2 H, m); 1.55-1.60 (2 H, m); 1.60-1.70 (2 H, m); 180-2.05 (3 H, m); 2.08 (6 H, s); 2.10 (2 H, s); 2.49 (2 H, s); 2.56-2.61 (2 H, m); 2.70-2.74 (2 H, m); 6.83 (1 H, dd, J = 3.6 and 1.2 Hz); 7.02 (1 H, dd, J = 5.2 and 3.6 Hz); 7.21 (1 H, dd, J = 5.2 and 1.2 Hz). $^{13}$C-NMR (CDCl$_3$): 29.6; 33.6; 33.9; 37.4; 38.1; 38.3; 40.9; 52.7; 53.5; 59.6; 65.5; 71.0; 123.2; 124.8; 126.1. |
| 227 | 1 | Ex. no. 223/ Reduction/ 79% | m/z: [M + H]$^+$ = 337.3 (42%) [MH − NHMe$_2$]$^+$ = 292.2 (100%), R$_t$ = 0.3 min. | $^1$H-NMR (DMSO-d$_6$): 1.04 (6 H, s) 1.20-1.28 (2 H, m); 1.38 (2 H, t, J = 6.9 Hz); 1.57-1.63 (2 H, m); 1.79-1.92 (4 H, m); 1.95 (6 H, s); 2.25 (2 H, s); 2.41 (2 H, s); 2.54 (2 H, t, J = 7.0 Hz); 3.93 (1 H, s); 6.87 (1 H, dd, J = 3.6 and 1.1 Hz); 7.01 (1 H, dd, J = 5.1 and 3.5 Hz); 6.87 (1 H, dd, J = 5.1 and 1.1 Hz). $^{13}$C-NMR (DMSO-d$_6$): 28.2; 32.9; 33.4; 37.7; 40.6; 55.1; 58.8; 67.2; 69.8; 123.4; 124.6; 126.2. |
| 228 | 1 | Ex. no. 71/ Acylation/ 74% | m/z [M + H]$^+$ = 345.4 (100%) [MH − NHMe$_2$]$^+$ = 303.3 (73%), R$_t$ = 2.5 min. | $^1$H-NMR (DMSO-d$_6$): 1.14-1.24 (2 H, m); 1.28 (2 H, s); 1.30 (4 H, s); 1.44 (1 H, t, J = 7.3 Hz); 1.54-1.64 (3 H, m); 1.91 (6 H, s); 1.95-2.15 (4 H, m); 3.21 (0.7 H, s); 3.30 (1.3 H, t, J = 7.3 Hz, overlapped by the water signal); 3.63 (1.3 H; s); 3.74 (0.7 H, t, J = 7.0 Hz); 5.07 (0.3 H, s); 5.15 (0.7 H, s); 7.23-7.27 (1 H, m); 7.32-7.39 (4 H, m). $^{13}$C-NMR (DMSO-d$_6$): 27.7; 27.8; 29.9; 30.2; 30.8; 33.4; 37.1; 37.7; 38.1; 42.0; 45.4; 45.8; 57.3; 59.8; 59.9; 72.6; 72.8; 126.2; 127.2; 127.4; 136.8; 173.7. |
| 229 | 1 | Ex. no. 228/ Reduction/ 82% | m/z: [M + H]$^+$ = 331.3 (100%) [MH − NHMe$_2$]$^+$ = 236.3 (36%), | $^1$H-NMR (DMSO-d$_6$): 1.09 (6 H, s); 1.16-1.24 (2 H, m); 1.35 (2 H, t, J = 6.9 Hz); 1.58-1.65 (2 H, m); 1.90 (6 H, s); 1.92-2.02 (4 H, m); 2.30 (2 H, s); 2.48 (2 H, s); 2.56 (2 H, t, J = 6.9 Hz); 3.97 (1 H, s); 7.22-7.25 (1 H, m); 7.30-7.37 (4 H, m). |

-continued

| Ex. no. | Diastereomer* | Building Block/Method/Yield | LC-MS [M + H]⁺/R_t | NMR spectrum |
|---|---|---|---|---|
| | | | R_t = 0.3 min. | ¹³C-NMR (DMSO-d₆): 28.2; 30.3; 33.7; 37.1; 37.7; 40.8; 55.1; 67.2; 67.7; 69.8; 126.1; 127.2; 127.3; 137.4. |
| 230 | 2 | Ex. no. 162 Step 3/ Alkylation/ 48% | m/z: [MH − HNMe₂]⁺ = 323.3 (14%) [M + H]⁺ = 368.4 (100%), R_t = 2.4 min. | ¹H-NMR (CDCl₃): 1.34-1.43 (8 H, m); 1.72-1.80 (4 H, m); 1.96-2.07 (8 H, m); 2.12-2.24 (4 H, m); 2.37 (2 H, s); 3.29 (2 H, s); 3.43-3.49 (2 H, m); 7.25-7.30 (3 H, m); 7.35-7.40 (2 H, m). |
| 231 | 1 | Ex. no. 431/ Alkylation/ 60% | m/z: [MH − HNMe₂]⁺ = 323.3 (20%) [M + H]⁺ = 368.4 (100%), R_t = 2.7 min. | ¹H-NMR (CDCl₃): 1.33-1.41 (8 H, m); 1.65-1.76 (4 H, m); 1.88-2.01 (2 H, m); 2.04 (6 H, s); 2.15-2.32 (2 H, m); 2.37 (2 H, s); 3.04 (2 H, s); 3.37-3.42 (2 H, m); 7.25-7.31 (3 H, m); 7.35-7.40 (2 H, m). ¹³C-NMR (CDCl₃): 26.6; 30.0; 30.5; 33.0; 35.9; 37.4; 38.0; 38.9; 43.3; 59.0; 60.6; 124.4; 126.7; 127.6; 127.8; 136.2; 173.9. |
| 232 | 1 | Ex. no. 71/ Acylation/ 54% | m/z: [MH − HNMe₂]⁺ = 323.3 (10%) [M + H]⁺ = 368.4 (100%), R_t = 2.7 min. | ¹H-NMR (CDCl₃): 1.27-1.36 (2 H, m); 1.52 (6 H, s); 1.54-1.59 (1.2 H, m); 1.62-1.70 (2.8 H, m); 1.82-2.00 (2 H, m); 2.03 (2.4 H, s); 2.05 (3.6 H, s); 2.14-2.24 (0.8 H, m); 2.31-2.43 (1.2 H, m); 2.48 (0.8 H, s); 2.49 (1.2 H, s); 3.36 (1.2 H, s); 3.43 (0.8 H, s); 3.46 (0.8 H, t, J = 7.2 Hz); 3.50 (1.2 H, t, J = 7.3 Hz); 7.27-7.32 (3 H, m); 7.34-7.42 (2 H, m). ¹³C-NMR (CDCl₃): 27.05; 27.11; 30.0; 30.3; 30.4; 30.8; 31.2; 31.3; 35.9; 37.5; 37.95; 38.03; 40.3; 42.5; 43.7; 44.1; 45.4; 55.4; 56.4; 60.8; 61.0; 124.6; 124.7; 126.5; 126.8; 127.58; 127.59; 127.7; 127.8; 135.1; 137.4; 166.9; 167.0. |
| 233 | 1 | Ex. no. 18/ Acylation/ 39% | m/z: [MH − HNMe₂]⁺ = 329.3 (63%) [M + H]⁺ = 374.3 (100%), R_t = 2.6 min. | ¹H-NMR (CDCl₃): 1.34-1.46 (2 H, m); 1.51 (6 H, s); 1.60-1.64 (1.3 H, m); 1.65-1.75 (2.7 H, m); 1.86-2.06 (2.7 H, m); 2.09 (2.4 H, s); 2.12 (3.6 H, s); 2.17-2.26 (1.3 H, m); 2.48 (1.2 H, s); 3.32 (1.2 H, s); 3.39 (0.8 H, s); 3.45-3.54 (2 H, m); 6.84 (0.4 H, dd, J = 3.8 and 1.1 Hz); 6.86 (0.6 H, dd, J = 3.6 and 1.0 Hz); 7.03 (0.4 H, dd, J = 5.1 and 3.6 Hz); 7.05 (0.6 H, dd, J = 5.1 and 3.6 Hz); 7.23 (0.4 H, dd, J = 5.1 and 1.1 Hz); 7.24-7.26 (0.6 H, m). ¹³C-NMR (CDCl₃): 27.05; 27.11; 30.65; 30.44; 31.09; 31.11; 32.8; 33.5; 35.5; 36.9; 38.1; 40.1; 42.3; 43.7; 44.0; 44.08; 44.11; 45.5; 55.7; 56.6; 59.8; 67.7; 123.3; 123.6; 124.6; 124.7; 124.8; 125.2; 126.1; 126.4; 166.8; 166.9. |
| 235 | 1 | Ex. no. 18/ Acylation/ 48% | m/z: [M + H]⁺ = 391.3 (42%) [MH − NHMe₂]⁺ = 346.3 (100%), R_t = 2.9 min. | ¹H-NMR (CDCl₃): 1.35-1.44 (2 H, m); 1.58-1.63 (2 H, m), 1.66-1.76 (4 H, m); 1.81-2.05 (4 H, m); 2.04 (2 H, s); 2.11 (4 H, s); 2.14-2.22 (2 H, m); 2.23-2.34 (2 H, m); 2.58 (0.7 H, s); 2.60 (1.3 H, s); 3.23 (1 H, s); 3.24 (2 H, s); 3.37 (0.7 H, s); 3.41 (1.3 H, s), 3.48 (1.3 H, t, J = 7.2 Hz); 3.54 (0.7 H, t, J = 7.2 Hz); 6.84-6.86 (1 H, m); 7.04 (1 H, ddd, J = 9.7, 5.1 and 3.6 Hz); 7.22-7.25 (1 H, m). ¹³C-NMR (CDCl₃): 12.5; 12.6; 30.5; 30.7; 31.1; 31.2; 32.8; 33.4; 35.8; 37.1; 38.1; 40.1; 40.4; 41.0; 42.0; 43.9; 45.7; 50.19; 50.22; 55.5; 56.9; 59.9; 76.9; 77.2; 77.5; 79.48; 79.50; 123.3; 123.5; 124.8; 125.1; 126.1; 126.3; 169.5; 169.6. |
| 236 | 2 | Ex. no. 234 Step Alkylation/ 77% | [M + H]⁺: m/z = 347.4, R_t = 2.9 min. | ¹H-NMR (CDCl₃): 1.12-1.36 (4 H, m); 1.38-1.92 (17 H, m); 1.98-2.12 (3 H, m); 2.18-2.30 (2 H, m); 2.25 (8 H, s); 3.06 (2 H, s); 3.15 (2 H, t, J = 7.3 Hz). ¹³C-NMR (CDCl₃): 18.6; 25.1; 26.9; 28.1; 28.5; 31.8; 33.7; 34.3; 36.3; 37.9; 40.3; 42.4; 44.2; 57.7; 60.8; 173.6. |
| 237 | 1 | Ex. no. 71/ Acylation/ 53% | m/z: [M + H]⁺ = 385.4 (83%) [MH − NHMe₂]⁺ = 340.3 (100%), R_t = 3.0 min; | ¹H-NMR (CDCl₃): 1.25-1.33 (2 H, m); 1.51-1.55 (1 H, m); 1.58-1.66 (3 H, m); 1.68-1.79 (1 H, m); 1.81-1.88 (2.6 H, m); 1.91-1.99 (1.4 H, m); 2.03 (2 H, s); 2.04 (4 H, s); 2.11-2.19 (2 H, m); 2.23-2.34 (2 H, m); 2.35-2.42 (1 H, m); 2.58 (0.7 H, s); 2.60 (1.3 H, s); 3.23 (1.2 H, s); 3.25 (1.8 H, s); 3.41 (0.7 H, s); 3.45 (1.3 H, s); 3.46 (1.3 H, t, J = 7.2 H); 3.51 (0.7 H, t, J = 7.2 Hz); 7.27-7.32 (3 H, m); 7.35-7.40 (2 H, m). ¹³C-NMR (CDCl₃): 12.5; 12.6; 30.0; 30.5; 30.7; 30.8; 31.2; 31.4; 36.1; 37.7; 38.0; 38.1; 40.3; 40.4; 41.0; 42.3; 43.9; 45.6; 50.19; 50.22; 55.2; 56.9; 60.8; 76.8; 77.2; 77.5; 79.48; 79.50; 126.5; 126.7; 127.6; 127.66; 127.75; 137.7; 169.5; 169.6. |
| 238 | 1 | Ex. no. 235/ Reduction/ 79% | m/z: [M + H]⁺ = 377.4 (100%) [MH − NHMe₂]⁺ = 332.3 (38%), R_t = 0.5 min. | ¹H-NMR (CDCl₃): 1.39 (2 H, ddd, J = 13.4, 10.2 and 3.4 Hz); 1.53 (2 H, t, J = 6.8 Hz); 1.58-1.83 (1 H, m); 1.65-1.89 (4 H, m); 1.83-1.94 (5 H, m); 2.03-2.09 (2 H, m); 2.10 (6 H, s); 2.11-2.19 (2 H, m); 2.39-2.43 (2 H, m); 2.46 (2 H, s); 2.54 (2 H, t, J = 6.8 Hz); 3.12 (3 H, s); 6.85 (1 H, dd, J = 3.6 and 1.1 Hz); 7.04 (1 H, dd, J = 5.1 and 3.6 Hz); 7.23 (1 H, dd, J = 5.1 and 1.1 Hz). ¹³C-NMR (CDCl₃): 12.5; 28.4; 31.7; 33.3; 33.8; 34.6; 38.2; 40.9; 49.2; 51.3; 54.3; 59.7; 77.5; 78.6; 123.2; 125.0; 126.2. |
| 239 | 1 | Ex. no. 237/ Reduction/ 78% | m/z: [M + H]⁺ = 371.4 (100%) [MH − NHMe₂]⁺ = 326.3 (22%), R_t = 2.0 min. | ¹H-NMR (CDCl₃): 1.26-1.32 (2 H, m); 1.47 (2 H, t, J = 6.8 Hz); 1.53-1.63 (1 H, m); 1.64-1.71 (2 H, m); 1.72-1.80 (2 H, m); 1.84-1.93 (5 H, m); 2.03 (6 H, s); 2.04-2.11 (2 H, m); 2.22-2.36 (2 H, m); 2.40-2.44 (2 H, m); 2.49-2.55 (4 H, m); 3.13 (3 H, s); 7.25-7.39 (5 H, m). ¹³C-NMR (CDCl₃): 12.5; 31.2; 31.7; 33.3; 34.7; 38.1; 38.4; 41.2; |

| Ex. no. | Diastereomer* | Building Block/Method/Yield | LC-MS [M + H]⁺/$R_t$ | NMR spectrum |
|---|---|---|---|---|
| | | | | 49.2; 51.3; 54.2; 60.6; 65.8; 76.8; 77.1; 77.2; 77.4; 78.6; 126.4; 127.6; 127.8. |
| 240 | 1 | Ex. no. 24a/ Alkylation/ 93% | m/z: [MH − HNMe₂]⁺ = 329.3 (100%) [M + H]⁺ = 374.3 (98%), $R_t$ = 2.6 min. | ¹H-NMR (CDCl₃): 1.37 (6 H, s); 1.43-1.51 (2 H, m); 1.67-1.72 (2 H, m); 1.73-1.80 (2 H, m); 1.98-2.18 (4 H, m); 2.14 (6 H, s); 2.34 (2 H, s); 3.10 (2 H, s); 3.39-3.44 (2 H, m); 6.86-6.89 (1 H, m); 7.05 (1 H, dd, J = 5.1 and 3.6 Hz); 7.25-7.28 (1 H, m). ¹³C-NMR (CDCl₃): 26.6; 30.5; 32.5; 32.9; 35.6; 37.4; 37.9; 38.1; 38.9; 43.3; 58.7; 123.9; 124.4; 125.4; 126.4; 173.8. |
| 241 | 2 | Ex. no. 24b/ Alkylation/ 55% | m/z: [M + H]⁺ = 363.3, $R_t$ = 2.2 min. | ¹H-NMR (CDCl₃): 1.42-1.50 (2 H, m); 1.72-1.82 (2 H, m); 1.90 (2 H, dd, J = 14.4 and 7.5 Hz); 1.97-2.09 (4 H, m); 2.10 (6 H, s); 2.18 (2 H, s); 2.90-3.01 (1 H, m); 3.17-3.23 (4 H, m); 4.38 (2 H, t, J = 6.1 Hz); 4.79 (2 H, dd, J = 7.8 and 6.0 Hz); 6.85 (1 H, d, J = 3.2 Hz); 7.04 (1 H, dd, J = 5.1 and 3.6 Hz); 7.24 (1 H, d, J = 5.0 Hz). ¹³C-NMR (CDCl₃): 31.2; 32.7; 33.0; 35.5; 38.0; 40.2; 44.1; 58.2; 59.2; 77.3; 123.5; 124.9; 126.3; 174.0. |
| 242 | 1 | Ex. no. 24a/ Alkylation/ 66% | m/z: [M + H]⁺ = 363.3, $R_t$ = 2.4 min. | ¹H-NMR (CDCl₃): 1.42-1.50 (2 H, m); 1.70-1.80 (2 H, m); 1.85 (2 H, dd, J = 14.4 and 7.5 Hz); 1.94-2.10 (4 H, m); 2.11 (6 H, s); 2.32 (2 H, s); 2.90-2.99 (1 H, m); 3.04 (2 H, s); 3.14-3.20 (2 H, m); 4.36 (2 H, t, J = 6.1 Hz); 4.77 (2 H, dd, J = 7.8 and 6.0 Hz); 6.86 (1 H, dd, J = 3.5 and 0.7 Hz); 7.05 (1 H, dd, J = 5.1 and 3.5 Hz); 7.25 (1 H, dd, J = 5.0 and 0.9 Hz). ¹³C-NMR (CDCl₃): 31.2; 32.7; 32.9; 33.0; 35.6; 38.1; 38.1; 40.1; 43.5; 58.8; 77.2; 123.6; 125.1; 126.3; 173.6. |
| 243 | 1 | Ex. no. 234 Step 10/ Alkylation/ 86% | [M + H]⁺: m/z = 333.4, $R_t$ = 2.9 min. | ¹H-NMR (CDCl₃): 0.03-0.09 (2 H, m); 0.40-0.48 (2 H, m); 0.64 (1 H, m); 1.10-1.85 (18 H, m); 2.07 (1 H, m); 2.21 (2 H, s); 2.26 (6 H, s); 3.19 (2 H, s); 3.33 (2 H, t, J = 7.3 Hz). ¹³C-NMR (CDCl₃): 4.2; 8.5; 25.1; 26.9; 28.4; 31.8; 32.3; 35.8; 37.8; 41.0; 42.6; 44.0; 46.9; 56.8; 57.2; 173.8. |
| 244 | 2 | Ex. no. 234 Step 9/ Alkylation/ 89% | [M + H]⁺: m/z = 335.4, $R_t$ = 2.1 min. | ¹H-NMR (CDCl₃): 1.14-1.34 (6 H, m); 1.36-1.62 (6 H, m); 1.62-1.76 (4 H, m); 2.04 (1 H, m); 2.25 (6 H, s); 2.26 (2 H, s); 3.03 (2 H, s); 3.20 (1 H, m); 3.57 (2 H, d, J = 7.3 Hz); 4.45 (2 H, t, J = 6.1 Hz); 4.76 (2 H, dd, J = 6.1 and 7.7 Hz). ¹³C-NMR (CDCl₃): 25.0; 26.7; 28.5; 31.6; 34.0; 36.7; 37.9; 41.9; 44.1; 45.3; 57.5; 61.4; 75.4; 174.2. |
| 245 | 2 | Ex. no. 234 Step 9/ Alkylation/ 59% | M + H]⁺: m/z = 358.4, $R_t$ = 2.4 min. | ¹H-NMR (CDCl₃): 0.85 (2 H, m); 1.14-1.36 (8 H, m); 1.38-1.62 (6 H, m); 1.62-1.80 (6 H, m); 2.04 (1 H, m); 2.26 (6 H, s); 2.28 (2 H, s); 3.18 (2 H, s); 3.45 (2 H, t, J = 7.0 Hz). ¹³C-NMR (CDCl₃): 7.5; 14.0; 25.0; 26.9; 28.3; 31.6; 32.5; 36.3; 37.7; 40.9; 42.0; 44.0; 57.6; 61.8; 122.8; 174.4. |
| 246 | 2 | Ex. no. 234 Step 9/ Alkylation/ 87% | [M + H]⁺: m/z = 349.4, $R_t$ = 2.2 min. | ¹H-NMR (CDCl₃): 1.16-1.36 (6 H, m); 1.38-1.62 (6 H, m); 1.62-1.82 (4 H, m); 1.87 (2 H, q, J = 7.3 Hz); 2.05 (1 H, m); 2-22-2.30 (2 H, m); 2.26 (6 H, s); 2.96 (1 H, m); 3.06 (2 H, s); 3.18 (2 H, t, J = 7.1 Hz); 4.37 (2 H, t, J = 6.1 Hz); 4.77 (2 H, dd, J = 6.2 and 7.6 Hz). ¹³C-NMR (CDCl₃): 25.0; 26.7; 28.5; 31.1; 31.8; 32.9; 36.2; 37.9; 40.0; 41.0; 42.2; 44.0; 57.5; 60.8; 77.3; 173.9. |
| 247 | 3 | Ex. no. 424/ Acylation/ 72% | m/z: [M + H]⁺ = 377.4 (100%) [MH − NHMe₂]⁺ = 332.4 (56%), $R_t$ = 2.9 min. | ¹H-NMR (CDCl₃): 1.17-1.37 (6 H, m); 1.41-1.60 (6 H, m); 1.63-2.21 (7 H, m); 2.02-2.21 (5 H, m); 2.24-2.30 (1 H, m, overlapped); 2.26 (6 H, s); 2.570 (1 H, s); 2.575 (1 H, s); 3.221 (1.8 H, s); 3.224 (1.2 H, s); 3.23 (0.8 H, s); 3.26 (1.2 H, s); 3.52 (0.8 H, t, J = 7.3 Hz); 3.56 (1.2 H, t, J = 7.3 Hz). ¹³C-NMR (CDCl₃): 12.6; 25;1; 25.2; 27.0; 27.1; 28.49; 28.52; 29.78; 29.82; 30.8; 32.1; 33.6; 37.9; 40.3; 40.57; 40.60; 40.61; 42.6; 44.2; 44.3; 44.5; 46.1; 50.21; 50.24; 57.9; 58.8; 61.0; 76.8; 77.16; 77.21; 79.46; 79.52; 169.3; 169.4. |
| 248 | 1 | Ex. no. 18/ Reductive Amination/ 33% | m/z: [MH − HNMe₂]⁺ = 315.2 (100%) [M + H]⁺ = 360.3 (17%), $R_t$ = 0.6 min. | ¹H-NMR: 1.34-1.42 (2 H, m); 1.37 (6 H, s); 1.51 (2 H, t, J = 6.9 Hz); 1.66-1.74 (4 H, m); 1.82-1.97 (4 H, m); 2.06-2.16 (2 H, m); 2.10 (6 H, s); 2.45 (2 H, s); 2.54 (2 H, t, J = 6.9 Hz); 2.56-2.61 (2 H, m); 6.84-6.86 (1 H, m); 7.03 (0.4 H, dd, J = 3.6 and 0.4 Hz); 7.04 (0.6 H, dd, J = 3.6 and 0.4 Hz); 7.21-7.24 (1 H, m). ¹³C-NMR (CDCl₃): 27.0; 31.2; 33.7; 34.3; 38.1; 39.4; 40.9; 52.7; 53.9; 59.6; 65.6; 123.2; 124.8; 124.9; 126.2. |
| 249 | 1 | Ex. no. 71/ Reductive amination/ 54% | m/z: [MH − HNMe₂]⁺ = 309.3 (70%) [M + H]⁺ = 354.4 (100%), $R_t$ = 0.5 min. | ¹H-NMR (CDCl₃): 1.24-1.32 (2 H, m); 1.37 (6 H, s); 1.46 (2 H, t, J = 6.8 Hz); 1.63-1.70 (2 H, m); 1.70-1.75 (2 H, m); 1.79-1.95 (2 H, m); 2.03 (6 H, s); 2.20-2.35 (2 H, m); 2.49 (2 H, s); 2.53 (2 H, t, J = 6.8 Hz); 2.57-2.62 (2 H, m); 7.24-7.34 (3 H, m); 7.35-7.40 (2 H, m). ¹³C-NMR (CDCl₃): 27.0; 31.1; 31.2; 34.5; 38.1; 39.5; 41.2; 52.8; 53.8; 60.5; 65.6; 124.8; 126.5; 127.6; 127.7. |
| 250 | 2 | Ex. no. 24b/ Alkylation/ 64% | m/z: [MH − HNMe₂]⁺ = 329.2 (67%) [M + H]⁺ = 374.3 (100%), $R_t$ = 2.3 min. | ¹H-NMR (CDCl₃): 1.40 (6 H, s); 1.42-1.50 (2 H, m); 1.72-1.83 (4 H, m); 2.00-2.11 (4 H, m); 2.12 (6 H, s); 2.19 (2 H, s); 3.27 (2 H, s); 3.43-3.48 (2 H, m); 6.85-6.87 (1 H, m); 7.05 (1 H, dd, J = 5.1 and 3.6 Hz); 7.24-7.26 (1 H, m). ¹³C-NMR (CDCl₃): 26.6; 30.5; 32.7; 35.6; 37.5; 38.0; 39.0; 44.0; 58.0; 59.6; 123.6; 124.4; 125.0; 126.4; 173.9. |
| 251 | 2 | Ex. no. 162 Step3/ Alkylation/ | m/z: [M + H]⁺ = 343.3, $R_t$ = 2.1 min. | ¹H-NMR (CDCl₃): 1.33-1.41 (2 H, m); 1.68-1.77 (2 H, m); 1.90-2.02 (2 H, m); 2.03 (6 H, s); 2.12 (2 H, s); 2.13-2.22 (2 H, m); 3.19 (2 H, s); 3.20-3.26 (1 H, m); 3.59 (2 H, d, J = 7.2 Hz); 4.46 (2 H, t, J = 6.2 |

| Ex. no. | Diastereomer* | Building Block/Method/Yield | LC-MS [M + H]⁺/R_t | NMR spectrum |
|---|---|---|---|---|
| | | 49% | | Hz); 4.78 (2 H, dd, J = 7.8 and 6.2 Hz); 7.25-7.31 (3 H, m); 7.35-7.41 (2 H, m).<br>¹³C-NMR (CDCl₃): 30.2; 32.7; 34.0; 36.0; 37.9; 44.0; 45.4; 58.7; 60.1; 75.4; 126.8; 127.4; 127.8; 174.0. |
| 252 | 1 | Ex. no. 431/ Alkylation/ 55% | m/z: [M + H]⁺ = 343.3, R_t = 2.3 min. | ¹H-NMR (CDCl₃): 1.29-1.38 (2 H, m); 1.65-1.73 (2 H, m); 1.85-2.00 (2 H, m); 2.03 (6 H, s); 2.15-2.31 (2 H, m); 2.35 (2 H, s); 2.94 (2 H, s); 3.10-3.19 (1 H, m); 3.53 (2 H, d, J = 7.2 Hz); 4.40 (2 H, t, J = 6.2 Hz); 4.72 (2 H, dd, J = 7.8 and 6.2 Hz); 7.25-7.31 (3 H, m); 7.35-7.41 (2 H, m).<br>¹³C-NMR (CDCl₃): 30.0; 32.9; 34.0; 36.2; 38.0; 43.1; 45.3; 59.6; 60.6; 75.3; 126.7; 127.5; 127.8; 136.1; 174.0. |
| 253 | 1 | Ex. no. 18/ Alkylation/ 2Steps 19% | [M + H]⁺ = 349.3, R_t = 0.5 min. | ¹H-NMR (CDCl₃): 0.35-0.46 (2 H, m); 0.70-0.74 (2 H, m); 1.32-1.41 (2 H, m); 1.53 (2 H, t, J = 7.0 Hz); 1.62-1.74 (4 H, m); 1.90-2.09 (5 H, m); 2.09 (6 H, s); 2.54 (2 H, s); 2.64 (2 H, t, J = 6.8 Hz); 2.79 (2 H, t, J = 5.5 Hz); 6.84 (1 H, dd, J = 3.5 and 0.8 Hz); 7.03 (1 H, dd, J = 5.1 and 3.5 Hz); 7.22 (1 H, dd, J = 5.0 and 0.8 Hz).<br>¹³C-NMR (CDCl₃): 12.8; 33.5; 34.0; 34.3; 37.5; 38.1; 41.0; 53.6; 55.5; 57.7; 59.6; 65.6; 123.2; 124.9; 126.2. |
| 254 | 2 | Ex. no. 162 Step3/ Alkylation/ 57% | m/z: [M + H]⁺ = 357.3, R_t = 2.2 min. | ¹H-NMR (CDCl₃): 1.34-1.43 (2 H, m); 1.70-1.79 (2 H, m); 1.91 (2 H, dd, J = 14.4 and 7.4 Hz); 2.05 (8 H, br s); 2.12 (2 H, s); 2.14-2.27 (2 H, m); 2.93-3.03 (1 H, m); 3.18-3.26 (4 H, m); 4.40 (2 H, t, J = 6.1 Hz); 4.80 (2 H, dd, J = 7.8 and 6.0 Hz); 7.26-7.33 (3 H, m); 7.36-7.42 (2 H, m).<br>¹³C-NMR (CDCl₃): 30.1; 31.2; 32.9; 33.0; 35.7; 38.0; 40.2; 44.4; 58.0; 77.3; 126.9; 127.4; 127.8; 147.2; 173.7. |
| 255 | 1 | Ex. no. 431/ Alkylation/ 58% | m/z: [M + H]⁺ = 357.4, R_t = 2.5 min. | ¹H-NMR (CDCl₃): 1.32-1.41 (2 H, m); 1.62-1.75 (2 H, m); 1.83 (2 H, dd, J = 14.4 and 7.4 Hz); 1.91-2.04 (3 H, m); 2.05 (6 H, s); 2.17-2.33 (2 H, m); 2.35 (2 H, s); 2.88-2.96 (1 H, m); 2.98 (2 H, s); 3.15 (2 H, t, J = 7.1 Hz); 4.34 (2 H, t, J = 6.1 Hz); 4.76 (2 H, dd, J = 7.8 and 6.0 Hz); 7.25-7.32 (3 H, m); 7.36-7.41 (2 H, m).<br>¹³C-NMR (CDCl₃): 30.0; 31.2; 33.0; 33.1; 35.9; 38.0; 40.1; 43.4; 59.0; 77.2; 126.8; 127.6; 127.8; 173.7. |
| 256 | 2 | Ex. no. 234 Step9/ Alkylation/ 42% | [M + H]⁺: m/z = 372.4, R_t = 2.6 min. | ¹H-NMR (CDCl₃): 1.14-1.36 (6 H, m); 1.38-1.62 (6 H, m); 1.62-1.78 (4 H, m); 1.91-1.97 (2 H, m); 1.98-2.22 (5 H, m); 2.26 (6 H, s); 2.28 (2 H, s); 2.47-2.58 (2 H, m); 3.12 (2 H, s); 3.33-3.40 (2 H, m).<br>¹³C-NMR (CDCl₃): 16.9; 25.1; 26.9; 28.5; 31.6; 32.1; 33.7; 34.9; 36.3; 37.9; 38.8; 42.0; 44.2; 57.5; 61.1; 124.0; 174.3. |
| 257 | 3 | Ex. no. 247/ Reduction/ 87% | m/z: [M + H]⁺ = 363.4 (100%) [MH − NHMe₂]⁺ = 318.4 (13%), R_t = 1.9 min | ¹H-NMR (CDCl₃): 1.21-1.34 (6 H, m); 1.43-1.76 (14 H, m); 1.85-1.92 (4 H, m); 2.00-2.10 (3 H, m); 2.27 (6 H, s); 2.37-2.44 (4 H, m); 2.57-2.64 (2 H, m); 3.12 (3 H, s).<br>¹³C-NMR (CDCl₃): 12.5; 25.1; 27.4; 28.5; 31.6; 33.1; 35.1; 38.0; 41.5, 44.3; 49.2; 51.4; 54.8; 57.6; 69.5; 76.9, 77.2; 77.5; 78.6. |
| 258 | 3 | Ex. no. 424/ Reductive amination/ 52% | m/z: [MH − HNMe₂]⁺ = 301.3 (15%) [M + H]⁺ = 346.4 (100%), R_t = 0.3 min. | ¹H-NMR (CDCl₃): 1.20-1.34 (6 H, m); 1.35 (6 H, s); 1.39-1.67 (12 H, m); 1.68-1.74 (4 H, m); 1.99-2.10 (1 H, m); 2.26 (6 H, s); 2.33 (2 H, s); 2.53-2.60 (4 H, m).<br>¹³C-NMR (CDCl₃): 25.1; 27.0; 27.3; 28.5; 31.2; 33.0; 35.0; 38.0; 39.4; 41.5; 44.3; 52.8; 54.5; 57.7; 69.4; 124.9. |
| 259 | 3 | Ex. no. 424/ Acylation/ 26% | m/z: [MH − HNMe₂]⁺ = 315.3 (2%) [M + H]⁺ = 360.4 (100%), R_t = 2.7 min. | ¹H-NMR (CDCl₃): 1.16-1.38 (6 H, m); 1.43-1.61 (4 H, m); 1.49 (3.6 H, s); 1.50 (2.4 H, s); 1.63-1.77 (5.2 H, m); 1.83 (0.8 H, t, J = 7.1 Hz); 2.01-2.12 (1 H, m); 2.26 (6 H, s); 2.47 (1.2 H, s); 2.48 (0.8 H, s); 3.17 (1.2 H, s); 3.24 (0.8 H, s); 3.49 (0.8 H, t, J = 7.1 Hz); 3.54 (1.2 H, t, J = 7.2 Hz).<br>¹³C-NMR (CDCl₃): 25.09; 25.12; 27.00; 27.03; 28.48; 28.51; 29.8; 30.36; 30.43; 32.0; 33.5; 37.8; 40.6; 42.8; 43.6; 43.9; 44.1; 44.2; 44.6; 45.9; 57.77; 57.84; 58.8; 60.5; 124.7; 124.8; 166.7; 166.8. |
| 260 | 2 | Ex. no. 162 Step3/ Alkylation/ 45% | m/z: [M + H]⁺ = 357.3, R_t = 2.2 min. | ¹H-NMR (CDCl₃): 1.34-1.43 (2 H, m); 1.58-1.67 (1 H, m); 1.70-1.79 (2 H, m); 1.95-2.02 (3 H, m); 2.04 (6 H, s); 2.14 (2 H, s); 2.15-2.30 (2 H, m); 2.47-2.57 (1 H, m); 3.23 (1 H, dd, J = 13.7 and 7.5 Hz); 3.28 (2 H, s); 3.36 (1 H, dd, J = 13.6 and 7.6 Hz); 3.47 (1 H, dd, J = 8.6 and 6.3 Hz); 3.73-3.80 (1 H, m); 3.82-3.91 (2 H, m); 7.26-7.32 (3 H, m); 7.36-7.42 (2 H, m).<br>¹³C-NMR (CDCl₃): 30.2; 32.7; 32.8; 35.9; 38.0; 44.2; 45.3; 58.6; 60.1; 71.4; 126.8; 127.4; 127.8; 174.0. |
| 261 | 1 | Ex. no. 431/ Alkylation/ 42% | m/z: [M + H]⁺ = 357.3, R_t = 2.5 min. | ¹H-NMR (CDCl₃): 1.32-1.41 (2 H, m); 1.58-1.62 (1 H, m); 1.67-1.76 (2 H, m); 1.85-2.03 (3 H, m); 2.05 (6 H, s); 2.15-2.35 (2 H, m); 2.37 (2 H, s); 2.40-2.49 (1 H, m); 3.01 (2 H, s); 3.17 (1 H, dd, J = 13.7 and 7.6 Hz); 3.30 (1 H, dd, J = 13.7 and 7.6 Hz); 3.41 (1 H, dd, J = 8.6 and 6.3 Hz); 3.68-3.88 (3 H, m); 7.26-7.32 (3 H, m); 7.36-7.42 (2 H, m).<br>¹³C-NMR (CDCl₃): 30.0; 31.1; 32.9; 33.0; 36.1; 37.9; 38.0; 43.3; 45.2; 59.6; 60.7; 67.7; 71.3; 126.8; 127.6; 127.8; 136.1; 174.0. |
| 262 | 2 | Ex. no. 162 Step3/ Alkylation/ 58% | m/z: [M + H]⁺ = 371.3, R_t = 2.5 min. | ¹H-NMR (CDCl₃): 1.32-1.41 (2 H, m); 1.44-1.58 (1 H, m); 1.64-1.93 (7 H, m); 1.95-2.03 (2 H, m); 2.04 (6 H, br s); 2.12 (2 H, s); 2.13-2.30 (2 H, m); 3.24-3.42 (4 H, m); 3.67-3.74 (1 H, m); 3.76-3.89 (2 H, m); 7.26-7.33 (3 H, m); 7.35-7.41 (2 H, m). |

| Ex. no. | Diastereomer* | Building Block/Method/Yield | LC-MS [M + H]+/R_t | NMR spectrum |
|---|---|---|---|---|
| 263 | 1 | Ex. no. 431/ Alkylation/ 57% | m/z: [M + H]+ = 371.4, R_t = 2.7 min. | $^{13}$C-NMR (CDCl$_3$): 25.6; 30.1; 31.4; 32.9; 33.3; 35.7; 38.0; 40.0; 44.6; 58.3; 67.7; 77.02; 126.8; 127.5; 128.0; 173.6. $^1$H-NMR (CDCl$_3$): 1.31-1.49 (3 H, m); 1.58-1.76 (4 H, m); 1.78-1.89 (2 H, m); 1.90-2.03 (3 H, m); 2.04 (6 H, s); 2.15-2.33 (2 H, m); 2.35 (2 H, s); 2.99-3.06 (2 H, m); 3.23-3.38 (2 H, m); 3.63-3.84 (3 H, m); 7.27-7.32 (3 H, m); 7.35-7.41 (2 H, m). |
| 264 | 2 | Ex. no. 162 Step3/ Alkylation/ 50% | m/z: [M + H]+ = 371.4, R_t = 2.4 min. | $^{13}$C-NMR (CDCl$_3$): 25.6; 30.0; 30.01; 31.3; 33.0; 33.2; 35.8; 38.0; 39.8; 43.6; 59.2; 60.6; 67.6; 76.9; 126.7; 127.5; 127.7; 173.6. $^1$H-NMR (CDCl$_3$): 1.33-1.42 (2 H, m); 1.47-1.67 (4 H, m); 1.69-1.77 (2 H, m); 1.90-2.01 (3 H, m); 2.03 (3 H, m); 2.05-2.21 (4 H, m); 3.23 (2 H, s); 3.28 (2 H, t, J = 7.4 Hz); 3.35 (1 H, dd; J = 8.2 and 6.9 Hz); 3.70-3.77 (1 H, m); 3.81-3.93 (2 H, m); 7.26-7.32 (3 H, m); 7.35-7.41 (2 H, m). |
| 265 | 3 | Ex. no. 424/ Reductive amination/ 68% | [M + H]+: m/z = 349.4, R_t = 0.6 min. | $^{13}$C-NMR (CDCl$_3$): 30.2; 30.7; 32.2; 32.8; 35.7; 36.9; 38.0; 41.4; 44.4; 57.9; 60.1; 67.8; 73.1; 126.8; 127.4; 127.7; 173.6. $^1$H-NMR (CDCl$_3$): 1.18-1.36 (10 H, m); 1.38-1.74 (15 H, m); 2.04 (1 H, m); 2.12-2.36 (2 H, m); 2.26 (6 H, s); 2.53 (2 H, br s); 3.35 (2 H, dt, J = 1.8 and 12.1 Hz); 3.94 (2 H, dd, J = 3.7 and 10.9 Hz). |
| 266 | 3 | Ex. no. 424/ Reductive amination/ 30% | [M + H]+: m/z = 321.4, R_t = 1.9 min. | $^{13}$C-NMR (CDCl$_3$): 25.0; 27.2; 28.4; 31.7; 33.0; 34.3; 34.8; 38.0; 41.6; 44.2; 55.0; 57.8; 63.2; 68.0; 69.2. $^1$H-NMR (CDCl$_3$): 0.91 (6 H, d, J = 6.5 Hz); 1.16-1.40 (6 H, m); 1.40-1.78 (13 H, m); 1.81 (2 H, t, J = 7.1 Hz); 2.05 (1 H, m); 2.28 (6 H, s); 2.60-2.76 (4 H, m); 2.96 (2 H, br s). |
| 267 | 3 | Ex. no. 424/ Reductive amination/ 74% | [M + H]+: m/z = 344.4, R_t = 0.6 min. | $^{13}$C-NMR (CDCl$_3$): 22.3; 25.1; 26.3; 27.2; 28.4; 31.9; 33.7; 35.6; 37.8; 41.7; 44.0; 54.0; 55.1; 67.3. $^1$H-NMR (CDCl$_3$): 0.81 (2 H, dd, J = 5.0 and 7.1 Hz); 1.20 (2 H, partially overlapped dd, J = 4.9 and 7.1 Hz); 1.16-1.36 (6 H, m); 1.38-1.74 (14 H, m); 2.04 (1 H, m); 2.26 (6 H, s); 2.33 (2 H, s); 2.54-2.67 (4 H, m). |
| 268 | 3 | Ex. no. 424/ Reductive amination/ 83% | [M + H]+: m/z = 358.4, R_t = 1.3 min. | $^{13}$C-NMR (CDCl$_3$): 8.1; 13.9; 25.0; 27.3; 28.4; 32.9; 34.1; 34.9; 38.0; 41.4; 44.3; 54.4; 57.7; 69.3; 123.4. $^1$H-NMR (CDCl$_3$): 1.57-1.36 (6 H, m); 1.38-1.75 (12 H, m); 1.87-1.95 (2 H, m); 1.97-2.21 (5 H, m); 2.26 (6 H, s); 2.34 (2 H, s); 2.45-2.54 (4 H, m); 2.58 (2 H, t, J = 6.8 Hz). |
| 269 | 2 | Ex. no. 162 Step3/ Alkylation/ 44% | m/z: [M + H]+ = 371.4, R_t = 2.4 min. | $^{13}$C-NMR (CDCl$_3$): 17.0; 25.0; 27.3; 28.4; 32.2; 33.0; 34.6; 35.0; 36.6; 37.9; 41.4; 44.3; 52.5; 54.6; 57.7; 69.4; 124.5. $^1$H-NMR (CDCl$_3$): 1.25-1.45 (4 H, m); 1.50-1.58 (2 H, m); 1.70-1.80 (2 H, m); 1.80-1.93 (1 H, m); 2.00 (8 H, s); 2.14 (2 H, s); 2.15-2.22 (2 H, m); 3.14 (2 H, d, J = 7.3 Hz); 3.26 (2 H, s); 3.35 (2 H, dt, J = 11.7 and 2.1 Hz); 3.94-3.99 (2 H, m); 7.26-7.32 (3 H, m); 7.35-7.41 (2 H, m). |
| 270 | 1 | Ex. no. 431 / Alkylation/ 35% | m/z: [M + H]+ = 371.3, R_t = 2.6 min. | $^{13}$C-NMR (CDCl$_3$): 30.1; 30.7; 32.8; 33.7; 35.9; 37.9; 44.3; 48.4; 59.2; 60.0; 67.5; 126.8; 127.4; 127.8; 174.1. $^1$H-NMR (CDCl$_3$): 1.23-1.40 (4 H, m); 1.45-1.52 (2 H, m); 1.68-1.84 (3 H, m); 1.90-2.02 (2 H, m); 2.05 (6 H, s); 2.18-2.35 (2 H, m); 2.38 (2 H, s); 3.01 (2 H, s); 3.09 (2 H, d, J = 7.3 Hz); 3.30 (2 H, dt, J = 11.7 and 2.2 Hz); 3.90-3.96 (2 H, m); 7.26-7.32 (3 H, m); 7.36-7.41 (2 H, m). |
| 271 | 1 | Ex. no. 431/ Alkylation/ 40% | m/z: [M + H]+ = 371.4, R_t = 2.6 min. | $^{13}$C-NMR (CDCl$_3$): 30.0; 30.7; 33.1; 33.7; 36.1; 38.0; 43.4; 48.3; 60.2; 67.5; 126.8; 127.6; 127.8; 174.1. $^1$H-NMR (CDCl$_3$): 1.30-1.40 (2 H, m); 1.41-1.59 (3 H, m); 1.67-1.76 (2 H, m); 1.90-2.01 (2 H, m); 2.04 (6 H, s); 2.05-2.15 (2 H, m); 2.16-2.33 (2 H, m); 2.36 (2 H, s); 2.98 (2 H, s); 3.23 (2 H, t, J = 7.4 Hz); 3.30 (1 H, dd; J = 8.2 and 6.9 Hz); 3.68-3.75 (1 H, m); 3.78-3.90 (2 H, m); 7.26-7.32 (3 H, m); 7.35-7.41 (2 H, m). |
| 272 | 1 | | | $^{13}$C-NMR (CDCl$_3$): 30.0; 30.6; 32.2; 33.1; 35.9; 36.9; 38.0; 41.3; 43.5; 58.9; 60.7; 67.8; 73.1; 126.7; 127.6; 127.8; 173.6. |
| 273 | 3 | Ex. no. 424/ Reductive amination/ 62% | [M + H]+: m/z = 307.4, R_t = 0.6 min. | $^1$H-NMR (CDCl$_3$): 0.89 (6 H, d, J = 6.5 Hz); 1.18-1.36 (6 H, m); 1.38-1.80 (13 H, m); 2.64 (1 H, m); 2.13 (2 H, d, J = 7.3 Hz); 2.25 (2 H, s); 2.27 (6 H, s); 2.51 (2 H, t, J = 6.5 Hz). $^{13}$C-NMR (CDCl$_3$): 21.0; 25.1; 27.2; 27.4; 28.4; 33.1; 34.7; 38.0; 41.5; 44.4; 54.8; 57.8; 65.3; 69.1. |
| 274 | 2 | Ex. no. 234 Step9/ Alkylation/ 90% | [M + H]+ m/z = 333.4, R_t = 2.6 min. | $^1$H-NMR (CDCl$_3$): 1.14-1.36 (6 H, m); 1.38-1.60 (6 H, m); 1.60-1.78 (6 H, m); 1.80-1.94 (2 H, m); 1.96-2.10 (3 H, m); 2.25 (8 H, s); 2.51 (1 H, m); 3.03 (2 H, s); 7.57 (2 H, d, J = 7.6 Hz). $^{13}$C-NMR (CDCl$_3$): 18.4; 25.1; 26.4; 26.9; 28.5; 31.5; 33.8; 36.5; 37.9; 42.0; 44.0; 47.6; 57.7; 61.2; 173.8. |
| 276 | 2 | Ex. no. 234 Step9/ Alkylation/ 50% | [M + H]+ m/z = 319.4, R_t = 2.4 min. | $^1$H-NMR (CDCl$_3$): 0.19 (2 H, td, J = 4.6 and 5.8 Hz); 0.49 (2 H, m); 8.58 (1 H, m); 1.16-1.37 (6 H, m); 1.38-1.62 (6 H, m); 1.64-1.79 (4 H, m); 2.06 (1 H, m); 2.27 (6 H, s); 2.28 (2 H, s); 3.11 (2 H, d, J = 7.1 Hz); 3.19 (2H, s). $^{13}$C-NMR (CDCl$_3$): 3.3; 9.0; 25.1; 26.8; 28.5; 31.8; 36.3; 37.9; 42.3; 44.2; 46.8; 57.7; 60.9; 173.6. |

| Ex. no. | Diastereomer* | Building Block/Method/Yield | LC-MS [M + H]⁺/$R_t$ | NMR spectrum |
|---|---|---|---|---|
| 277 | 2 | Ex. no. 234 Step9/ Alkylation/ 51% | [M + H]⁺: m/z = 361.4, $R_t$ = 3.0 min. | ¹H-NMR (CDCl₃): 0.84-1.02 (2 H, m); 1.06-1.36 (10 H, m); 1.38-1.84 (15 H, m); 2.04 (1 H, m); 2.26 (6 H, s); 2.28 (2 H, s); 3.06 (2 H, d, J = 7.9 Hz), 3.07 (2 H, s). ¹³C-NMR (CDCl₃): 25.1; 25.7; 26.3; 26.9; 28.5; 30.1; 30.8; 31.8; 35.9; 36.4; 37.9; 42.3; 44.2; 48.6; 57.7; 61.6; 174.3. |
| 278 | 2 | Ex. no. 234 Step9/ Alkylation/ 61% | [M + H]⁺: m/z = 347.4, $R_t$ = 2.8 min. | ¹H-NMR (CDCl₃): 1.10-1.36 (8 H, m); 1.38-180 (16 H, m); 1.98-2.18 (2 H, m); 2.26 (6 H, s); 2.28 (2 H, s); 3.09 (2 H, s); 3.17 (2 H, d, J = 7.9 Hz). ¹³C-NMR (CDCl₃): 25.07; 25.14; 26.9; 28.5; 30.3; 31.7; 36.3; 37.9; 38.0; 42.2; 44.2; 47.2; 57.7; 61.1; 174.0. |
| 279 | 2 | Ex. no. 24b/ Alkylation/ 58% | m/z: [M + H]⁺ = 363.3, $R_t$ = 2.2 min. According to HPLC on Chiracel OD [(cyclohexane/ 2 PrOH/Et2NH (70:30:0.1)] the enantiomer excess is > 98%. | Optical rotation□□□□□□□□ = +4.74°, (c = 1.0, MeOH) ¹H-NMR (CDCl₃): 1.41-1.50 (2 H, m); 1.57-1.67 (1 H, m); 1.72-1.82 (2 H, m); 1.94-2.07 (5 H, m); 2.10 (6 H, s); 2.19 (2 H, s); 2.45-2.57 (1 H, m); 3.18-3.26 (3 H, m); 3.35 (1 H, dd, J = 13.6 and 7.6 Hz); 3.46 (1 H, dd, J = 8.6 and 6.3 Hz); 3.72-3.79 (1 H, m); 3.81-3.91 (2 H, m); 6.82-6.86 (1 H, m); 7.04 (1 H, dd, J = 5.0 and 3.6 Hz); 7.22-7.26 (1 H, m). ¹³C-NMR (CDCl₃): 30.1; 32.6; 32.7; 35.8; 38.0; 38.02; 44.0; 45.3; 58.7; 59.2; 67.7; 71.4; 123.4; 124.8; 126.3; 173.9. |
| 280 | 2 | Ex. no. 24b/ Alkylation/ 60% | m/z: [M + H]⁺ = 363.3, $R_t$ = 2.2 min According to HPLC on Chiracel OD [(cyclohexane/ 2 PrOH/Et2NH (70:30:0.1)] the enantiomer excess is 91%. | Optical rotation□□□□□□□□□ –3.28°, (c = 1.0, MeOH) ¹H-NMR (CDCl₃): 1.42-1.50 (2 H, m); 1.57-1.67 (1 H, m); 1.73-1.83 (2 H, m); 1.94-2.08 (5 H, m); 2.10 (6 H, s); 2.19 (2 H, s); 2.46-2.56 (1 H, m); 3.19-3.27 (3 H, m); 3.35 (1 H, dd, J = 13.6 and 7.6 Hz); 3.46 (1 H, dd, J = 8.6 and 6.3 Hz); 3.72-3.79 (1 H, m); 3.82-3.92 (2 H, m); 6.83-6.88 (1 H, m); 7.03-7.07 (1 H, m); 7.22-7.27 (1 H, m). ¹³C-NMR (CDCl₃): 30.1; 32.6; 32.7; 35.8; 37.9; 38.0; 44.0; 45.3; 58.8; 59.2; 67.7; 71.4; 123.5; 124.8; 126.3; 173.9. |
| 281 | 2 | Ex. no. 347 Step9/ Alkylation/ 65% | [M + H]⁺: m/z = 321.4, $R_t$ = 2.6 min. | ¹H-NMR (CDCl₃): 0.91 (3 H, t, J = 7.3 Hz); 1.16-1.36 (8 H, m); 1.40-1.80 (12 H, m); 2.04 (1 H, m); 2.26 (6 H, s); 2.27 (2 H, s); 3.06 (2 H, s); 3.23 (2 H, t, J = 7.3 Hz). ¹³C-NMR (CDCl₃): 13.6; 19.9; 25.1; 26.9; 28.5; 29.2; 31.5; 31.6; 36.2; 41.8; 42.2; 44.2; 57.7; 60.7; 173.9. |
| 282 | 2 | Ex. no. 234 Step9/ Alkylation/ 78% | [M + H]⁺: m/z = 279.3, $R_t$ = 1.4 min. | ¹H-NMR (CDCl₃): 1.12-1.34 (6 H, m); 1.38-1.60 (6 H, m); 1.61-1.78 (4 H, m); 2.04 (1 H, s); 2.25 (8 H, s); 2.80 (3 H, s); 3.07 (2 H, s). ¹³C-NMR (CDCl₃): 25.0; 26.9; 28.3; 29.5; 31.9; 36.0; 37.9; 42.0; 44.0; 57.6; 63.3; 174.0. |
| 283 | 1 | Ex. no. 71/ Reductive amination/ 9% | m/z: [M + H]⁺ = 343.3, $R_t$ = 0.3 min. | ¹H-NMR (CDCl₃): 1.23-1.32 (2 H, m); 1.44 (2 H, t, J = 6.9 Hz); 1.61-1.69 (2 H, m); 1.81-1.89 (4 H, m); 1.98-2.02 (1 H, m); 2.03 (6 H, s); 2.18-2.33 (3 H, m); 2.43 (2 H, s); 2.47 (2 H, t, J = 6.9 Hz); 2.97-3.07 (1 H, m); 4.41 (2 H, t, J = 6.2 Hz); 4.78 (2 H, dd, J = 7.9 and 5.9 Hz); 7.27-7.33 (3 H, m); 7.34-7.39 (2 H, m). ¹³C-NMR (CDCl₃): 31.1; 32.8; 34.0; 37.9; 37.93; 38.1; 41.2; 53.9; 54.3; 60.5; 65.7; 77.8; 126.4; 127.6; 127.7. |
| 284 | 1 | Ex. no. 71/ Reductive amination/ 10% | m/z: [M + H]⁺ = 343.3, $R_t$ = 0.7 min. | ¹H-NMR (CDCl₃): 1.23-1.31 (2 H, m); 1.40-1.46 (2 H, m); 1.56-1.70 (3 H, m); 1.80-1.95 (2 H, m); 1.97-2.02 (1 H, m); 2.04 (6 H, s); 2.17-2.33 (2 H, m); 2.34-2.42 (3 H, m); 2.42-2.54 (4 H, m); 3.47-3.52 (1 H, m); 3.70-3.77 (1 H, m); 3.80-3.90 (2 H, m); 7.24-7.40 (5 H, m). ¹³C-NMR (CDCl₃): 31.0; 31.02; 34.5; 37.9; 38.0; 38.7; 41.2; 53.9; 59.8; 65.6; 67.7; 72.4; 126.5; 127.6; 127.7. |
| 285 | 1 | Ex. no. 71/ Alkylation/ 2Steps 6% | m/z: [M + H]⁺ = 343.4, $R_t$ = 0.5 min. | ¹H-NMR (CDCl₃): 0.38 (2 H, dd, J = 6.3 and 5.1 Hz); 0.73 (2 H, dd, J = 6.3 and 5.1 Hz); 1.24-1.33 (2 H, m); 1.44-1.51 (2 H, m); 1.63-1.72 (4 H, m); 1.87-2.00 (2 H, m); 2.05 (6 H, s); 2.15-2.28 (2 H, m); 2.55-2.67 (4 H, m); 2.78-2.84 (2 H, m); 6.40-6.80 (1 H, br s); 7.26-7.34 (3 H, m); 7.35-7.40 (2 H, m). ¹³C-NMR (CDCl₃): 12.7; 30.9; 34.3; 38.0; 41.2; 51.0; 53.4; 53.5; 55.6; 57.7; 65.4; 126.5; 127.6; 127.65. |
| 286 | 2 | Ex. no. 234 Step9/ Alkylation/ 33% | [M + H]⁺: m/z = 333.4, $R_t$ = 2.6 min. | ¹H-NMR (CDCl₃): 1.16-1.34 (6 H, m); 1.38-1.86 (18 H, m); 2.04 (1 H, m); 2.26 (6 H, s); 2.27 (2 H, s); 3.03 (2 H, s); 4.48 (1 H, m). ¹³C-NMR (CDCl₃): 24.3; 25.1; 26.9; 28.5; 28.8; 31.3; 36.4; 37.9; 42.5; 44.2; 51.9; 56.6; 57.6; 173.6. |
| 287 | 2 | Ex. no. 234 Step9/ Alkylation/ 79% | [M + H]⁺: m/z = 377.4, $R_t$ = 2.7 min. | ¹H-NMR (CDCl₃): 1.14-1.34 (6 H, m); 1.38-178 (12 H, m); 1.80-1.94 (4 H, m); 1.98-2.16 (3 H, m); 2.25 (6 H, s); 2.26 (2 H, s); 3.10 (2 H, s); 3.13 (3 H, s); 3.20-3.27 (2 H, m). ¹³C-NMR (CDCl₃): 12.3; 25.0; 26.9; 28.3; 31.3; 31.6; 31.9; 36.3; 37.5; 37.9; 42.4; 44.2; 49.2; 57.5; 61.2; 78.1; 173.6. |
| 288 | 2 | Ex. no. 24b/ Alkylation/ 14% | m/z: [MH − HNMe₂]⁺ = 315.3 (100%) [M + H]⁺ = 380.3 | ¹H-NMR (CDCl₃): 1.37 (6 H, s); 1.44-1.53 (2 H, m); 1.80-1.88 (2 H, m); 1.95-2.15 (4 H, m); 2.10 (6 H, s); 2.23 (2 H, s); 3.39 (2 H, s); 3.53 (2 H, s); 6.86 (1 H, dd, J = 3.6 and 1.0 Hz); 7.04 (1 H, dd, J = 5.1 and 3.6 Hz); 7.24 (1 H, dd, J = 5.1 and 1.1 Hz). |

| Ex. no. | Diastereomer* | Building Block/Method/Yield | LC-MS [M + H]⁺/R_t | NMR spectrum |
|---|---|---|---|---|
| 289 | 1 | Ex. no. 24a/ Alkylation/ 28% | (35%), R_t = 2.5 min. m/z: [MH − HNMe₂]⁺ = 315.2 (100%) [M + H]⁺ = 360.3 (50%), R_t = 2.6 min. | ¹³C-NMR (CDCl₃): 24.8; 32.4; 32.5; 33.0; 36.1; 38.0; 43.4; 51.2; 59.4; 59.7; 123.5; 124.6; 124.8; 128.3; 142.8; 175.2. ¹H-NMR (CDCl₃): 1.34 (6 H, s); 1.52 (2 H, ddd, J = 13.3, 9.4 and 4.0 Hz); 1.73-1.81 (2 H, m); 1.94-2.05 (2 H, m); 2.07-2.16 (2 H, m); 2.10 (6 H, s); 2.36 (2 H, s); 3.35 (2 H, s); 3.37 (2 H, s); 6.84 (1 H, dd, J = 3.6 and 1.0 Hz); 7.03 (1 H, dd, J = 5.1 and 3.5 Hz); 7.24 (1 H, dd, J = 5.1 and 0.9 Hz). ¹³C-NMR (CDCl₃): 24.7; 32.6; 32.9; 36.1; 38.1; 43.0; 51.2; 59.6; 60.0; 123.6; 124.6; 125.1; 126.3; 142.3; 175.2. |
| 290 | 2 | Ex. no. 130/ N-Demethyl-ation/23% | m/z: [M + H]⁺ = 333.3 and 302.2, R_t = 2.6 min. | ¹H-NMR (CDCl₃): 0.03-0.07 (2 H, m); 0.41-0.48 (2 H, m); 0.59-0.69 (1 H, m); 1.41 (1 H, dd, J = 14.4 and 7.0 Hz); 1.47-1.57 (2 H, m); 1.71-2.03 (6 H, m); 2.11 (3 H, s); 2.24 (2 H, s); 3.21 (2 H, s); 3.31-3.36 (2 H, m); 6.87 (1 H, dd, J = 3.5 and 1.0 Hz); 6.95 (1 H, dd, J = 5.1 and 3.5 Hz); 7.21 (1 H, dd, J = 5.1 and 1.0 Hz). The replaceable proton was not identified. ¹³C-NMR (CDCl₃): 4.3; 8.6; 28.7; 32.4; 32.5; 33.7; 35.8; 42.6; 43.3; 56.3; 59.3; 123.6; 126.4; 173.4. |
| 291 | 3 | Ex. no. 424/ Acylation/ 37% | m/z: [M + H]⁺ = 335.4, R_t = 2.4 min. | ¹H-NMR (CDCl₃): 1.10-1.38 (6 H, m); 1.40-1.88 (10 H, m); 2.04 (1 H, m); 2.25 (6 H, s); 2.91 (2 H, s); 3.22-3.27 (2 H, m); 3.53 (2 H, t, J = 7.3 Hz); 3.90 (1 H, m); 4.75 (2 H, dd, J = 5.6 and 8.6 Hz); 4.89-4.93 (2 H, m). ¹³C-NMR (CDCl₃): 25.08; 25.10; 26.8; 27.0; 28.5; 29.7; 31.6; 33.4; 37.7; 38.3; 38.4; 40.6; 42.6; 44.0; 44.2; 44.5; 44.6; 57.6; 57.7; 58.8; 59.6; 73.03; 73.07; 169.3; 169.4. |
| 292 | 3 | Ex. no. 424/ Alkylation/ 60% | m/z: [M + H]⁺ = 351.4, R_t = 2.0 min. | ¹H-NMR (CDCl₃): 1.15 (6 H,s); 1.19-1.35 (6 H, m); 1.39-1.75 (14 H, m); 2.04 (1 H, m); 2.26 (6 H, s); 2.31 (2 H, s); 2.36-2.43 (2 H, m); 2.54 (2 H, t, J = 6.8 Hz); 3.17 (3 H, s). ¹³C-NMR (CDCl₃): 25.0; 25.2; 27.2; 28.5; 33.1; 35.0; 37.9; 38.0; 41.4; 44.2; 49.1; 52.0; 54.8; 57.7; 69.5; 73.9. |
| 293 | 2 | Ex. no. 234 Step9/ Alkylation/ 60% | m/z: [M + H]⁺ = 349.4, R_t = 2.3 min. According to HPLC on Chiracel OD [(cyclohexane/ 2 PrOH/Et2NH (90:10:0.1)] the enantiomer excess is ≥ 97%. | ¹H-NMR (CDCl₃): 1.17-1.35 (5 H, m); 1.40-1.78 (12 H, m); 1.93-2.10 (2 H, m); 2.26 (6 H, s); 2.29 (2 H, s); 2.51 (1 H, td, J = 14.2 and 6.9 Hz); 3.10 (2 H, s); 3.20 (1 H, dd, J = 13.6 and 7.6 Hz); 3.35 (1 H, dd, J = 13.6 and 7.6 Hz); 3.46 (1 H, dd, J = 8.6 and 6.2 Hz); 3.70-3.79 (1 H, m), 3.80-3.90 (2 H, m). ¹³C-NMR (CDCl₃): 25.0; 26.9; 28.5; 30.1; 31.62; 31.65; 36.6; 37.9; 37.94; 42.1; 44.1; 45.2; 57.7; 61.5; 67.7; 71.4; 174.3. Optical rotation: □□□□D□□□□□4.57°, (c = 1.13, MeOH). |
| 294 | 2 | Ex. no. 234 Step9/ Alkylation/ 44% | m/z: [M + H]⁺ = 349.4, R_t = 2.3 min. According to HPLC on Chiracel OD [(cyclohexane/ 2 PrOH/Et2NH (90:10:0.1)] the enantiomer excess = 93%. | ¹H-NMR (CDCl₃): 1.16-1.33 (6 H, m); 1.39-1.76 (11 H, m); 1.91-2.09 (2 H, m); 2.25 (6 H, s); 2.27 (2 H, s); 2.49 (1 H, td, J = 14.1 and 7.0 Hz); 3.09 (2 H, s); 3.18 (1 H, dd, J = 13.6 and 7.6 Hz); 3.33 (1 H, dd, J = 13.6 and 7.6 Hz); 3.44 (1 H, dd, J = 8.6 and 6.3 Hz); 3.73 (1 H, dd, J = 15.4 and 7.6 Hz); 3.78-3.88 (2 H, m). ¹³C-NMR (CDCl₃): 25.0; 26.8; 28.4; 30.1; 31.57; 31.59; 36.5; 37.8; 37.9; 42.0; 44.1; 45.1; 57.8; 61.4; 67.6; 71.3; 174.2. LC-MS (Method 1): m/z: [M + H]⁺ = 349.4, R_t = 2.3 min. Optical rotation: □□□□D□□□□□6.24°, (c = 1.0, MeOH). |
| 295 | 1 | Ex. no. 18/ Reductive amination/ 10% | m/z: [M + H]⁺ = 349.3, R_t = 0.3 min. | ¹H-NMR (CDCl₃): 1.33-1.42 (2 H, m); 1.50 (2 H, t, J = 6.9 Hz); 1.64-1.73 (2 H, m); 1.86 (2 H, dd, J = 15.0 and 7.6 Hz); 1.89-1.97 (2 H, m); 2.04-2.10 (2 H, m); 2.10 (6 H, s); 2.26-2.34 (2 H, m); 2.41 (2 H, s); 2.50 (2 H, t, J = 6.8 Hz); 2.96 (1 H, m); 4.41 (2 H, t, J = 6.2 Hz); 4.78 (2 H, dd, J = 7.9 and 6.0 Hz); 6.85 (1 H, dd, J = 3.5 and 1.0 Hz); 7.04 (1 H, dd, J = 5.1 and 3.6 Hz); 7.23 (1 H, dd, J = 5.1 and 1.0 Hz). ¹³C-NMR (CDCl₃): 32.9; 33.7; 34.0; 34.4; 38.1; 40.9; 53.9; 54.3; 59.7; 65.7; 77.8; 123.2; 124.9; 126.2. |
| 296 | 1 | Ex. no. 18/ Reductive amination/ 12% | m/z: [M + H]⁺ = 349.3, R_t = 0.4 min. | ¹H-NMR (CDCl₃): 1.32-1.76 (8 H, m); 1.85-2.06 (4 H, m); 2.13 (6 H, s); 2.34-2.57 (7 H, m); 3.47-3.52 (1 H, m); 3.69-3.77 (1 H, m); 3.80-3.90 (2 H, m); 6.87(1 H, dd, J = 3.1 Hz); 7.04 (1 H, dd, J = 5.1 and 3.5 Hz); 7.24 (1 H, br d, J = 5.2 Hz). ¹³C-NMR (CDCl₃): 31.0; 33.6; 34.2; 38.1; 38.6; 41.0; 53.9; 59.8; 67.8; 72.4; 123.4; 125.2; 126.2. |
| 297 | 3 | Ex. no. 424/ Acylation/ 70% | m/z: [M + H]⁺ = 351.4, R_t = 2.8 min. | ¹H-NMR (CDCl₃): 1.08-1.38 (6 H, m); 1.40 and 1.41 (6 H, 2 s); 1.42-1.82 (12 H, m); 2.08 (1 H, m); 2.26 (6 H, s); 3.17 (2 H, s); 3.18 (1 H, s); 3.28 (0.5 H, s); 3.48 (1.5 H, s); 3.54 (1.6 H, t, J = 7.4 Hz); 3.74 (0.4 H, t, J = 7.0 Hz). ¹³C-NMR (CDCl₃): 24.1; 25.0; 26.9; 27.0; 28.4; 29.4; 30.0; 30.6; 30.9; 34.4; 37.7; 39.1; 42.8; 44.1; 45.8; 46.3; 51.5; 51.7; 57.8; 57.9; 60.3; 60.9; 79.6; 79.8; 172.5. |
| 298 | 3 | Ex. no. 297/ Reduction/ 84% | m/z: [M + H]⁺ = 337.4, R_t = 1.3 min. | ¹H-NMR (CDCl₃): 1.15 (6 H, s); 1.20-1.35 (6 H, m); 1.39-1.72 (12 H, m); 2.04 (1 H, m); 2.26 (6 H, s); 2.39 (2 H, s) 2.41 (2 H, s); 2.65 (2 H, t, J = 6.9 Hz); 3.20 (3 H, s). |

-continued

| Ex. no. | Diastereomer* | Building Block/Method/Yield | LC-MS [M + H]⁺/R_t | NMR spectrum |
|---|---|---|---|---|
| 299 | 1 | Ex. no. 18/ Alkylation/ 2Steps 82% | m/z: [M + H]⁺ = 385.3, $R_t$ = 1.9 min. | $^{13}$C-NMR (CDCl$_3$): 23.7; 25.2; 27.3; 28.4; 32.6; 34.9; 37.9; 41.7; 44.4; 49.3; 56.0; 57.9; 64.5; 71.1; 75.9.<br>$^1$H-NMR (CDCl$_3$): 1.16 (6 H, s); 1.39 (2 H, ddd, J = 13.3 and 10.2 and 3.4 Hz); 1.52 (2 H, t, J = 6.7 Hz); 1.65-1.74 (4 H, m); 1.85-1.96 (2 H, m); 2.10 (6 H, s); 2.11-2.18 (2 H, m); 2.41-2.49 (4 H, m); 2.50-2.57 (2 H, m); 3.18 (3 H, s); 6.84 (1 H, dd, J = 3.5 and 1.1 Hz); 7.03 (1 H, dd, J = 5.1 and 3.5 Hz); 7.22 (1 H, dd, J = 5.1 and 1.1 Hz). |
| 300 | 1 | Ex. no. 71/ Alkylation/ 2Steps 60% | m/z: [M + H]⁺ = 359.4, $R_t$ = 2.0 min. | $^{13}$C-NMR (CDCl$_3$): 25.3; 33.7; 34.4; 38.0; 38.1; 40.9; 49.1; 52.0; 54.1; 59.6; 65.8; 73.9; 123.2; 124.9; 126.1.<br>$^1$H-NMR (CDCl$_3$): 1.16 (6 H, s); 1.24-1.33 (2 H, m); 1.47 (2 H, t, J = 6.6 Hz); 1.63-1.74 (4 H, m); 1.80-1.93 (2 H, m); 2.03 (6 H, s); 2.19-2.33 (2 H, m); 2.43-2.58 (6 H, m); 3.19 (3 H, s); 7.23-7.40 (5 H, m). |
| 301 | 3 | Ex. no. 291/ Reduction/ 25% | m/z: [M + H]⁺ = 323.4, $R_t$ = 0.4 min. | $^{13}$C-NMR (CDCl$_3$): 25.3; 31.1; 34.6; 37.9; 38.0; 38.1; 41.2; 49.1; 52.1; 54.0; 60.5; 65.7; 73.9; 126.6; 127.6; 127.7.<br>$^1$H-NMR (CDCl$_3$): 0.71 (3 H, d, J = 6.8 Hz); 1.12-1.32 (6 H, m); 1.36-1.74 (12 H, m); 1.96-2.12 (2 H, m); 2.22 (1 H, d, J = 9.3 Hz); 2.24 (6 H, s); 2.32 (1 H, td, J = 2.8 and 11.9 Hz); 2.46-2.54 (2 H, m); 2.64 (1 H, t, J = 11.8 Hz); 2.69-2.77 (1 H, m); 3.47 (1 H, t, J = 10.3 Hz); 3.66 (1 H, ddd, J = 2.6, 3.7 and 10.4 Hz); 6.53 (1 H, br s). |
| 302 | 3 | Ex. no. 291/ Reduction/ 20% | m/z: [M + H]⁺ = 321.4, $R_t$ = 0.3 min. | $^{13}$C-NMR (CDCl$_3$): 15.0; 25.0; 27.15; 27.20; 28.5; 32.3; 32.5; 32.6; 34.7; 37.8; 41.5; 44.3; 54.4; 57.6; 64.8; 69.5; 71.7.<br>$^1$H-NMR (CDCl$_3$): 1.15-1.34 (6 H, m); 1.38-1.74 (12 H, m); 2.04 (1 H, m); 2.23 (2 H, s); 2.26 (6 H, s); 2.49 (2 H, t, J = 6.8 Hz); 2.69 (2 H, d, J = 7.2 Hz); 3.18 (1 H, m); 4.41 (2 H, t, J = 6.2 Hz); 4.76 (2 H, dd, J = 6.0 and 7.9 Hz). |
| 303 | 1 | Ex. no. 71/ Reductive amination/ 51% | m/z: [M + H]⁺ = 357.3, $R_t$ = 1.3 min. | $^{13}$C-NMR (CDCl$_3$): 25.0; 27.3; 28.4; 33.1; 34.9; 35.0; 37.9; 41.6; 44.3; 54.6; 57.6; 59.9; 69.4; 76.6.<br>$^1$H-NMR (CDCl$_3$): 1.21-1.34 (4 H, m); 1.43 (2 H, t, J = 6.7 Hz); 1.62-1.73 (5 H, m); 1.80-2.00 (2 H, m); 2.05 (6 H, s); 2.23-2.37 (4 H, m); 2.41-2.56 (4 H, m); 3.37 (2 H, dt, J = 12.0 and 1.9 Hz); 3.96 (2 H, dd, J = 10.8 and 3.5 Hz); 7.25-7.33 (3 H, m); 7.35-7.41 (2 H, m). |
| 304 | 1 | Ex. no. 18/ Reductive amination/ 70% | m/z: [M + H]⁺ = 363.4, $R_t$ = 0.6 min. | $^{13}$C-NMR (CDCl$_3$): 31.1; 31.8; 34.4; 34.5; 38.0; 41.3; 54.2; 63.1; 65.2; 68.0; 126.6; 127.6; 127.8.<br>$^1$H-NMR (CDCl$_3$): 1.20-1.42 (4 H, m); 1.50 (2 H, t, J = 6.5 Hz); 1.63-1.73 (5 H, m); 1.85-1.97 (2 H, m); 2.11 (6 H, m); 2.12-2.18 (2 H, m); 2.27 (2 H, d, J = 6.3 Hz); 2.40 (2 H, s); 2.45-2.54 (2 H, m); 3.37 (2 H, dt, J = 12.1 and 1.9 Hz); 3.95 (2 H, dd, J = 10.7 and 3.4 Hz); 6.85 (1 H, d, J = 3.4 Hz); 7.04 (1 H, dd, J = 5.1 and 3.5 Hz); 7.23 (1 H, dd, J = 5.1 and 0.7 Hz). |
| 305 | 1 | Ex. no. 71/ Reductive amination/ 36% | m/z: [M + H]⁺ = 357.4, $R_t$ = 1.9 min. | $^{13}$C-NMR (CDCl$_3$): 31.8; 33.8; 34.3; 34.4; 37.8; 38.1; 41.0; 54.3; 60.0; 63.1; 65.4; 68.0; 123.3; 125.0; 126.2.<br>$^1$H-NMR (CDCl$_3$): 1.25-1.53 (2H, m); 1.43-1.53 (3 H, m); 1.65-1.80 (4 H, m); 1.82-1.93 (4 H, m); 1.95-2.02 (1 H, m); 2.04 (6 H, s); 2.13-2.32 (2 H, m); 2.50-2.65 (6 H, m); 3.67-3.74 (1 H, m); 3.80-3.89 (2 H, m); 7.23-7.33 (3 H, m); 7.34-7.40 (2 H, m). |
| 306 | 1 | Ex. no. 18/ Reductive amination/ 34% | m/z: [M + H]⁺ = 363.3, $R_t$ = 1.3 min. | $^{13}$C-NMR (CDCl$_3$): 25.6; 30.9; 31.5; 34.3; 34.5; 38.0; 41.2; 53.7; 54.0; 60.7; 65.4; 67.6; 77.6; 126.6; 127.6; 127.7.<br>$^1$H-NMR (CDCl$_3$): 1.35-1.59 (5 H, m); 1.65-2.05 (9 H, m); 2.10 (6 H, s); 2.05-2.15 (2 H, m); 2.48-2.65 (6 H, m); 3.67-3.74 (1 H, m); 3.79-3.89 (2 H, m); 6.84 (1 H, dd, J = 3.5 and 1.0 Hz); 7.03 (1 H, dd, J = 5.1 and 3.5 Hz); 7.22 (1 H, dd, J = 5.1 and 1.0 Hz). |
| 307 | 1 | Ex. no. 129/ N-Demethyl-ation/18% | m/z: [MH − HNMe]+ = 316.3, $R_t$ = 3.1 min. | $^{13}$C-NMR (CDCl$_3$): 25.6; 31.5; 33.6; 34.2; 34.5; 37.6; 38.1; 41.0; 53.8; 54.0; 59.6; 65.6; 67.6; 77.6; 123.3; 124.9; 126.2.<br>$^1$H-NMR (CDCl$_3$): 1.33 (1 H, br s); 1.47-1.68 (6 H, m); 1.70-1.92 (6 H, m); 1.93-2.09 (4 H, m); 2.11 (3 H, m); 2.21 (1 H, td, J = 15.4, 7.8 Hz); 2.29 (2 H, s); 3.10 (2 H, s); 3.11-3.18 (2 H, m); 6.88 (1 H, dd, J = 3.5 and 1.1 Hz); 6.96 (1 H, dd, J = 5.1 and 3.5 Hz); 7.22 (1 H, dd, J = 5.1 and 1.1 Hz). |
| 308 | 2 | Ex. no. 128/ N-Demethyl-ation/35% | | $^{13}$C-NMR (CDCl$_3$): 18.5; 28.2; 28.7; 32.7; 33.6; 33.8; 34.2; 35.7; 38.1; 40.5; 44.6; 56.3; 57.7; 123.7; 126.3; 173.3.<br>$^1$H-NMR (CDCl$_3$): 1.37 (1 H, s); 1.47-1.69 (6 H, m); 1.69-2.11 (10 H, m); 2.12 (3 H, m); 2.22-2.25 (2 H, m); 2.21-2.30 (1 H, m); 3.15-3.20 (4 H, m); 6.86-6.90 (1 H, m); 6.96 (1 H, dd, J = 5.0 and 3.6 Hz); 7.22 (1 H, dd, J = 5.0 and 0.6 Hz). |
| 309 | 1 | Ex. no. 18/ Reductive amination/ 63% | m/z: [M + H]⁺ = 363.3, $R_t$ = 0.6 min. | $^{13}$C-NMR (CDCl$_3$): 18.5; 28.2; 28.7; 32.5; 336.; 33.7; 34.3; 35.7; 40.5; 43.3; 56.3; 58.9; 132.6; 126.4; 173.3.<br>$^1$H-NMR (CDCl$_3$): 1.38 (2 H, ddd, J = 13.2 and 10.0 and 3.4 Hz); 1.46-1.62 (5 H, m); 1.65-1.74 (2 H, m); 1.84-1.98 (2 H, m); 1.99-2.08 (2 H, m); 2.10 (6 H, s); 2.11-2.27 (2 H, m); 2.33-2.47 (4 H, m); 2.52 (2 H, t, J = 6.6 Hz); 3.30-3.36 (1 H, m); 3.74 (1 H, dd, J = 15.8 and 7.5 Hz); 3.83 (1 H, dt, J = 8.2 and 4.7 Hz); 3.91 (1 H, dd, J = 8.1 and 7.4 Hz); 6.85 (1 H, dd, J = 3.5 and 0.9 Hz); 7.03 (1 H, dd, J = 5.1 and 3.5 Hz); 7.22 (1 H, dd, J = 5.1 and 0.6 Hz).<br>$^{13}$C-NMR (CDCl$_3$): 32.3; 32.5; 33.7; 34.3; 37.8; 38.1; 40.9; 53.9; 55.8; 59.6; 65.6; 67.8; 73.4; 77.2; 123.2; 125.0; 126.2; 143.1. |

-continued

| Ex. no. | Diastereomer* | Building Block/Method/Yield | LC-MS [M + H]+/R$_t$ | NMR spectrum |
|---|---|---|---|---|
| 310 | 1 | Ex. no. 431/ Alkylation/ 58% | m/z: [M + H]+ = 354.3, R$_t$ = 2.6 min. | $^1$H-NMR (CDCl$_3$): 1.33 (6 H, s); 1.37-1.47 (2 H, m); 1.69-1.79 (2 H, m); 1.85-2.02 (2 H, m); 2.03 (6 H, s); 2.18-2.30 (2 H, m); 2.39 (2 H, s); 3.31 (2 H, s); 3.34 (2 H, s); 7.24-7.31 (3 H, m); 7.34-7.41 (2 H, m). $^{13}$C-NMR (CDCl$_3$): 24.7; 30.1; 32.78; 32.84; 36.2; 38.0; 42.9; 51.0; 60.3; 124.5; 126.6; 127.5; 127.8; 175.3. |
| 311 | 2 | Ex. no. 24b/ Alkylation/ 43% | m/z: [M + H]+ = 377.3 (100%) [MH − NHMe$_2$]+ = 332.3 (99%), R$_t$ = 2.5 min. | $^1$H-NMR (CDCl$_3$): 1.42-1.49 (2 H, m); 1.64-1.81 (4 H, m); 1.86-1.92 (2 H, m); 1.94-2.05 (4 H, m); 2.06-2.14 (2 H, m, overlapped); 2.10 (6 H, s); 2.18 (2 H, s); 3.19 (3 H, s); 3.34 (2 H, s); 3.50 (2 H, s); 6.84 (1 H, dd, J = 3.5 and 0.8 Hz); 7.05 (1 H, dd, J = 5.1 and 3.5 Hz); 7.24 (1 H, dd, J = 5.1 and 0.7 Hz). $^{13}$C-NMR (CDCl$_3$): 12.2; 29.6; 32.6; 32.8; 35.8; 38.1; 43.9; 45.0; 49.6; 59.4; 79.8; 123.4; 124.9; 126.3; 174.6. |
| 312 | 1 | Ex. no. 431/ Alkylation/ 55% | m/z: [M + H]+ = 371.3 (47%) [MH − NHMe$_2$]+ = 326.3 (100%), R$_t$ = 2.9 min. | $^1$H-NMR (CDCl$_3$): 1.32-1.39 (2 H, m); 1.66-1.78 (4 H, m); 1.82-1.88 (2 H, m); 1.90-1.99 (2 H, m); 2.01-2.09 (2 H, m, overlapped); 2.03 (6 H, s); 2.11-2.23 (2 H, m); 2.36 (2 H, s); 3.11 (3 H, s); 3.44 (2 H, s); 7.28-7.31 (3 H, m); 7.36-7.40 (2 H, m). $^{13}$C-NMR (CDCl$_3$): 12.2; 29.5; 30.1; 32.9; 36.2; 38.1; 44.9; 49.5; 60.2; 79.7; 126.6; 127.6; 127.7; 174.6. |
| 313 | 2 | Ex. no. 24b/ Alkylation/ 79% | m/z: [M + H]+ = 351.3, R$_t$ = 2.3 min. | $^1$H-NMR (CDCl$_3$): 1.19 (3 H, t, J = 7.0 Hz); 1.42-1.51 (2 H, m); 1.73-1.82 (2 H, m); 1.93-2.07 (4 H, m); 2.11 (6 H, s); 2.18 (2 H, s); 3.35 (2 H, s); 3.44 (2 H, t, J = 5.3 H); 3.48 (2 H, q, J = 7.0 Hz); 3.52-3.57 (2 H, m); 6.85 (1 H, dd, J = 3.5 and 1.1 Hz); 7.05 (1 H, dd, J = 5.1 and 3.5 Hz); 7.24 (1 H, dd, J = 5.1 and 1.1 Hz). $^{13}$C-NMR (CDCl$_3$): 15.2; 32.6; 32.7; 35.8; 38.1; 42.4; 44.2; 59.3; 66.2; 68.5; 123.4; 124.9; 126.2; 173.8. |
| 314 | 1 | Ex. no. 18/ Acylation/ 47% | m/z: [M + H]+ = 379.3, R$_t$ = 2.8 min. | $^1$H-NMR (CDCl$_3$): 1.25 (1.4 H, m); 1.32 (6 H, s); 1.36-1.46 (2 H, m); 1.58-1.74 (4 H, m); 1.84-2.06 (1.5 H, m); 2.09 (2.5 H, s); 2.11 (3.5 H, s); 2.14-2.24 (0.5 H, m); 2.45 (0.7 H, s); 2.46 (1.3 H, s); 3.21 (1.4 H, s); 3.22 (1.6 H, s); 3.36 (0.8 H, s); 3.40 (1.2 H, s); 3.47 (1.2 H, t, J = 7.3 Hz); 3.53 (0.8 H, t, J = 7.2 Hz); 6.83 (1 H, m); 7.04 (1 H, m); 7.24 (1 H, m). $^{13}$C-NMR (CDCl$_3$): 19.1; 24.6; 24.8; 29.7; 31.0; 32.8; 33.2; 35.7; 37.0; 38.08; 38.10; 40.0; 42.0; 43.9; 45.0; 45.5; 45.8; 49.2; 49.3; 53.4; 55.6; 57.0; 59.7; 59.8; 74.9; 75.0; 123.3; 123.4; 124.8; 125.0; 126.1; 126.3; 143.7; 169.3; 169.4. |
| 315 | 1 | Ex. no. 18/ Acylation/ 48% | m/z: [M + H]+ = 351.3, R$_t$ = 2.6 min. | $^1$H-NMR (CDCl$_3$): 1.32-1.46 (2 H, m); 1.56-1.74 (4 H, m); 1.84-2.22 (4 H, m); 2.09 (3.5 H, s); 2.11 (2.5 H, s); 2.51 (2 H, t, J = 6.4 Hz); 3.34 (1.2 H, s); 3.35 (3 H, s); 3.37 (0.8 H, s); 3.47 (2 H, dd, J = 6.8 and 13.8 Hz); 3.60-3.73 (2 H, m); 6.83-6.86 (1 H, m); 7.01-7.06 (1 H, m); 7.21-7.25 (1 H, m). $^{13}$C-NMR (CDCl$_3$): 31.0; 31.2; 32.9; 33.3; 34.6; 35.0; 35.4; 36.9; 38.1; 40.0; 42.0; 43.9; 45.1; 56.6; 58.8; 58.9; 59.9; 68.5; 123.2; 123.5; 124.9; 125.0; 126.0; 126.3; 169.6; 169.7. |
| 316 | 1 | Ex. no. 131/ N-Demethyl- ation/12% | m/z: [MH − HNMe]+ = 302.3, R$_t$ = 2.8 min. | $^1$H-NMR (CDCl$_3$): 0.00-0.05 (2 H, m); 0.40-0.45 (2 H, m); 0.55-0.66 (1 H, m); 1.38 (2 H, dd, J = 14.4 and 7.0 Hz); 1.43-1.57 (3 H, m); 1.69-1.81 (2 H, m); 1.82-2.04 (4 H, m); 2.11 (3 H, m); 2.30 (2 H, s); 3.13 (2 H, s); 3.28-3.34 (2 H, m); 6.88 (1 H, dd, J = 3.5 and 1.1 Hz); 6.95 (1 H, dd, J = 5.1 and 3.5 Hz); 7.21 (1 H, dd, J = 5.1 and 1.1 Hz). $^{13}$C-NMR (CDCl$_3$): 4.3; 8.5; 28.7; 32.4; 32.7; 33.7; 35.7; 38.1; 42.6; 44.5; 56.3; 58.1; 123.7; 126.3; 173.4. |
| 317 | 2 | Ex. no. 24b/ Alkylation/ 72% | m/z: [M + H]+ = 365.3, R$_t$ = 2.4 min. | $^1$H-NMR (CDCl$_3$): 1.16 (3 H, d, J = 6.1 Hz); 1.42-1.51 (2 H, m); 1.56-1.81 (4 H, m); 1.95-2.09 (4 H, m); 2.10 (6 H, s); 2.18 (2 H, s); 3.21 (2 H, s); 3.30-3.38 (3 H, m); 3.31 (3 H, s); 6.85 (1 H, d, J = 3.5 Hz); 7.04 (1 H, dd, J = 5.0 and 3.6 Hz); 7.24 (1 H, d, J = 5.0 Hz). $^{13}$C-NMR (CDCl$_3$): 19.0; 32.8; 34.1; 35.6; 38.1; 39.4; 44.3; 56;1; 58.4; 59.3; 74.7; 123.4; 124.8; 126.3; 173.6. |
| 318 | 2 | Ex. no. 24b/ Alkylation/ 54% | m/z: [M + H]+ = 351.3, R$_t$ = 2.2 min. | $^1$H-NMR (CDCl$_3$): 1.12 (3 H, d, J = 6.2 Hz); 1.40-1.51 (2 H, m); 1.72-1.82 (2 H, m); 1.95-2.09 (4 H, m); 2.10 (6 H, s); 2.18 (2 H, s); 3.23 (1 H, dd, J = 14.1 and 6.8 Hz); 3.31-3.37 (3 H, m); 3.32 (3 H, s); 3.48-3.55 (1 H, m); 6.85 (1 H, d, J = 3.3 Hz); 7.05 (1 H, dd, J = 5.1 and 3.5 Hz); 7.24 (1 H, br d, J = 5.1 Hz). $^{13}$C-NMR (CDCl$_3$): 16.8; 32.6; 32.7; 32.8; 35.8; 39.1; 44.0; 47.4; 56.1; 59.4; 75.9; 123.4; 124.9; 126.3; 174.1. |
| 319 | 2 | Ex. no. 162 Step3/ Alkylation/ 12% | m/z: [M + H]+ = 354.3, R$_t$ = 2.5 min. | $^1$H-NMR (CDCl$_3$): 1.35-1.48 (4 H, m); 1.37 (6 H, s); 1.64-1.88 (2 H, m); 2.00-2.16 (2 H, m); 2.02 (6 H, s); 2.17 (2 H, s); 3.39 (2 H, s); 3.55 (2 H, s); 7.23-7.32 (3 H, m); 7.34-7.41 (2 H, m). $^{13}$C-NMR (CDCl$_3$): 24.8; 29.9; 32.4; 33.0; 36.3; 37.9; 43.5; 49.0; 50.2; 51.1; 59.5; 59.7; 124.6; 126.7; 127.3; 127.8; 175.3. |
| 320 | 1 | Ex. no. 71/ Acylation/ 40% | m/z: [M + H]+ = 373.4, R$_t$ = 2.9 min. | $^1$H-NMR (CDCl$_3$): 1.24-1.31 (2 H, m); 1.33 (6 H, s); 1.48-1.70 (4 H, m); 1.74-2.00 (4 H, m); 2.02 (2.6 H, s); 2.04 (3.4 H, s); 2.13-2.25 (0.8 H, m); 2.28-2.44 (1.2 H, m); 2.45 (0.8 H, s); 2.47 (1.2 H, s); 3.20 (1.2 H, s); 3.22 (1.8 H, s); 3.38-3.54 (4 H, m); 7.22-7.42 (5 H, m). |

| Ex. no. | Diastereomer* | Building Block/Method/Yield | LC-MS [M + H]+/Rt | NMR spectrum |
|---|---|---|---|---|
| | | | | $^{13}$C-NMR (CDCl$_3$): 24.6; 24.8; 29.9; 30.6; 31.0; 31.4; 36.1; 37.6; 38.0; 40.3; 42.3; 43.8; 44.9; 45.5; 45.6; 46.19; 49.23; 55.2; 57.0; 60.6; 60.7; 74.7; 74.8; 126.3; 126.5; 127.57; 127.59; 127.63; 127.70; 137.5; 169.3; 169.4. |
| 321 | 1 | Ex. no. 24a/ Alkylation/ 64% | m/z: [M + H]+ = 377.3 (1%) [MH − NHMe$_2$]+ = 332.3 (100%), R$_t$ = 2.8 min. | $^1$H-NMR (CDCl$_3$): 1.42-1.49 (2 H, m); 1.64-1.78 (4 H, m); 1.82-1.89 (2 H, m); 1.92-2.01 (2 H, m); 2.02-2.09 (4 H, m); 2.10 (6 H, s); 2.32 (2 H, s); 3.13 (3 H, s); 3.18 (2 H, s); 3.46 (2 H, s); 6.85 (1 H, dd, J = 3.6 and 1.1 Hz); 7.04 (1 H, dd, J = 5.1 and 3.6 Hz); 7.24 (1 H, dd, J = 5.1 and 1.1 Hz). <br> $^{13}$C-NMR (CDCl$_3$): 12.2; 29.5; 32.7; 35.9; 38.1; 45.0; 49.5; 59.9; 79.7; 123.5; 125.0; 126.3; 174.6. |
| 322 | 2 | Ex. no. 162 Step3/ Alkylation/ 40% | m/z: [M + H]+ = 371.3 (100%) [MH − NHMe$_2$]+ = 326.3 (73%), R$_t$ = 2.5 min. | $^1$H-NMR (CDCl$_3$): 1.31-1.38 (2 H, m); 1.66-1.81 (4 H, m); 1.87-1.93 (2 H, m); 1.95-2.03 (2 H, m); 2.06 (6 H, s); 2.09-2.15 (4 H, m); 2.35-2.46 (2 H, m); 3.20 (3 H, s); 3.40 (2 H, s); 3.50 (2 H, s); 7.28-7.32 (3 H, m); 7.38-7.41 (2 H, m). <br> $^{13}$C-NMR (CDCl$_3$): 12.2; 29.6; 30.0; 32.8; 35.9; 37.9; 44.2; 45.0; 49.6; 58.7; 79.8; 126.9; 127.7; 127.9; 174.6. |
| 323 | 2 | Ex. no. 162 Step3/ Alkylation/ 51% | m/z: [M + H]+ = 345.4, R$_t$ = 2.3 min. | $^1$H-NMR (CDCl$_3$): 1.13 (3 H, d, J = 6.2 Hz); 1.32-1.42 (2 H, m); 1.70-1.79 (2 H, m); 1.86-2.03 (2 H, m); 2.04 (6 H, s); 2.12 (2 H, d, J = 1.3 Hz); 2.15-2.26 (2 H, m); 3.24 (1 H, dd, J = 14.0 and 6.8 Hz); 3.30-3.43 (3 H, m); 3.33 (3 H, s); 3.48-3.56 (1 H, m); 7.26-7.32 (3 H, m); 7.36-7.42 (2 H, m). <br> $^{13}$C-NMR (CDCl$_3$): 16.8; 30.1; 32.8; 36.0; 38.0; 44.4; 47.3; 56.1; 59.7; 75.9; 126.8; 127.5; 127.8; 174.1. |
| 324 | 2 | Ex. no. 162 Step3/ Alkylation/ 69% | m/z: [M + H]+ = 359.4, R$_t$ = 2.5 min. | $^1$H-NMR (CDCl$_3$): 1.16 (3 H, d, J = 6.1 Hz); 1.32-1 42 (2 H, m); 1.55-1.80 (5 H, m); 1.90-2.00 (2 H, m); 2.04 (6 H, s); 2.12 (2 H, s); 2.14-2.28 (1 H, m); 3.26 (1 H, m); 3.30-3.37 (3 H, m); 3.32 (3 H, s); 7.26-7.32 (3 H, m); 7.35-7.42 (2 H, m). <br> $^{13}$C-NMR (CDCl$_3$): 19.0; 30.1; 32.9; 34.1; 35.7; 38.0; 39.4; 44.6; 56.1; 58.1; 74.7; 126.6; 127.4; 127.8; 173.6. |
| 325 | 2 | Ex. no. 162 Step3/ Alkylation/ 53% | m/z: [M + H]+ = 331.3, R$_t$ = 2.2 min. | $^1$H-NMR (CDCl$_3$): 1.32-1.41 (2 H, m); 1.470-1.79 (2 H, m); 1.70-2.02 (2 H, m); 2.04 (6 H, s); 2.12 (2 H, s); 2.13-2.30 (2 H, m); 3.34 (3 H, s); 3.37 (2 H, s); 3.42-3.47 (2 H, m); 3.48-3.53 (2 H, m); 7.27-7.32 (3 H, m); 7.35-7.41 (2 H, m). <br> $^{13}$C-NMR (CDCl$_3$): 30.1; 32.8; 36.0; 38.0; 42.2; 44.4; 58.6; 59.0; 70.7; 126.7; 127.5; 127.8; 173.9. |
| 326 | 2 | Ex. no. 162 Step3/ Alkylation/ 65% | m/z: [M + H]+ = 345.4, R$_t$ = 2.3 min. | $^1$H-NMR (CDCl$_3$): 1.20 (3 H, t, J = 7.0 Hz); 1.30-1.41 (2 H, m); 1.54-1.56 (2 H, m); 1.99-2.00 (2 H, m); 2.00 (6 H, s); 2.10 (2 H, s); 2.20 (2 H, br s); 3.38 (2 H, s); 3.44 (2 H, t, J = 5.3 Hz); 3.48 (2 H, q, J = 7.0 Hz); 3.52-3.57 (2 H, m); 7.26-7.32 (3 H, m); 7.35-7.41 (2 H, m). <br> $^{13}$C-NMR (CDCl$_3$): 15.2; 30.1; 32.8; 36.0; 38.0; 42.4; 44.5; 59.2; 60.2; 66.2.; 68.6; 126.7; 127.5; 127.8; 173.8. |
| 327 | 1 | Ex. no. 18/ Acylation/ 42% | m/z: [M + H]+ = 385.3, R$_t$ = 2.7 min. | $^1$H-NMR (CDCl$_3$): 1.20 (3 H, d, J = 6.1 Hz); 1.33-1.46 (2 H, m); 1.57-1.74 (4 H, m); 1.82-2.20 (4 H, m); 2.08 (2.5 H, s); 2.11 (3.5 H, s); 2.20-2.27 (1 H, m); 2.58 (1 H, dd, J = 7.2 and 14.8 Hz); 3.24-3.58 (7 H, m); 3.82-3.94 (1 H, m); 6.83-6.86 (1 H, m); 7.01-7.06 (1 H, m); 7.21-7.25 (1 H, m). <br> $^{13}$C-NMR (CDCl$_3$): 19.46; 19.52; 30.9; 31.0; 31.2; 32.7; 33.1; 33.4; 38.1; 40.0; 41.5; 41.9; 42.0; 43.9; 45.3; 56.4; 56.5; 59.7; 74.26; 74.29; 123.3; 123.4; 124.7; 124.9; 126.0; 126.3; 169.9. |
| 328 | 1 | Ex. no. 71/ Acylation/ 40% | m/z: [M + H]+: = 359.4, R$_t$ = 2.8 min. | $^1$H-NMR (CDCl$_3$): 1.21 (1.3 H, d, J = 6.1 Hz); 1.22 (1.7 H, J = 6.1 Hz); 1.24-1.36 (2 H, m); 1.54 (1.2 H, t, J = 7.3 Hz); 1.58-1.70 (2 H, m); 1.72-2.00 (8 H, m); 2.02 (2.6 H, s); 2.03 (3.4 H, s); 2.12-2.40 (3 H, m); 2.52-2.64 (1 H, m); 3.24-3.56 (7 H, m); 3.80-3.94 (1 H, m); 7.20-7.44 (5 H, m). <br> $^{13}$C-NMR (CDCl$_3$): 19.46; 19.53; 30.0; 30.1; 30.5; 30.8; 31.0; 31.3; 31.36; 31.40; 35.9; 37.5; 38.0; 38.1; 40.4; 41.5; 42.0; 42.3; 43.8; 45.1; 55.2; 56.3; 56.5; 60.8; 74.3; 77.5; 126.5; 126.7; 127.58; 127.60; 127.67; 127.73; 169.8; 169.9. |
| 329 | 1 | Ex. no. 71/ Acylation/ 50% | m/z: [M + H]+ = 345.3, R$_t$ = 2.7 min. | $^1$H-NMR (CDCl$_3$): 1.22-1.36 (2 H, m); 1.50-1.70 (4 H, m); 1.78-2.00 (2 H, m); 2.02 (2.8 H, s); 2.03 (3.2 H, s); 2.14-2.40 (2 H, m); 2.51 (2 H, dd, J = 12.5 and 6.3 Hz); 3.348 (1.4 H, m); 3.353 (1.6 H, s); 3.37 (1.2 H, s); 3.41 (0.8 H, s); 3.35 (2 H, dd, J = 14.5 and 7.3 Hz); 3.68-3.73 (2 H, m); 7.22-7.40 (5 H, m). <br> $^{13}$C-NMR (CDCl$_3$): 30.1; 30.6; 31.2; 31.4; 34.6; 35.0; 38.0; 38.1; 40.4; 42.3; 43.8; 45.1; 58.7; 58.8; 68.58; 68.60; 126.5; 126.6; 127.55; 127.60; 127.65; 127.71; 169.7. |
| 330 | 1 | Ex. no./168 N-Demethyl- ation/31% | [M + H]+ = 327.3 (22%) [MH − HNMe]+ = 296.3 (100%), R$_t$ = 2.9 min. | $^1$H-NMR (CDCl$_3$): 0.04 (2 H, m); 0.39-0.45 (2 H, m); 0.56-0.66 (1 H, m); 1.37 (3 H, dd, J = 14.4 and 7.0 Hz); 1.43-1.53 (2 H, m); 1.73-1.88 (4 H, m); 1.94 (1 H, s); 1.99 (3 H, s); 2.32 (2 H, s); 3.13 (2 H, s); 3.27-3.33 (2 H, m); 7.20-7.26 (1 H, m); 7.31-7.37 (4 H, m). <br> $^{13}$C-NMR (CDCl$_3$): 4.3; 8.5; 28.6; 31.9; 32.4; 32.6; 35.3; 35.7; 42.6; 45.0; 56.7; 57.8; 126.0; 126.5; 128.3; 145.1; 173.5. |

| Ex. no. | Diastereomer* | Building Block/Method/Yield | LC-MS [M + H]⁺/$R_t$ | NMR spectrum |
|---|---|---|---|---|
| 331 | 2 | Ex. no. 173/ N-Demethyl- ation/60% | m/z: [M + H]⁺ = 341.4 (22%) [MH − HNMe]+ = 310.3 (100%), $R_t$ = 2.5 min. | ¹H-NMR (CDCl₃): 1.40 (1 H , br s); 1.44-1.53 (2 H, m); 1.56-1.69 (4 H, m); 1.72-1.98 (8 H, m); 2.00 (3 H, s); 2.02-2.12 (1 H, m); 2.23 (2 H, s); 2.24-2.31 (1 H, m); 3.15-3.20 (4 H, m); 7.19-7.27 (1 H, m); 7.34-7.38 (4 H, m). ¹³C-NMR (CDCl₃): 18.6; 28.2; 28.7; 31.9; 32.5; 33.7; 34.3; 35.8; 40.5; 43.1; 56.8; 59.5; 125.9; 126.5; 128.3; 173.4. |
| 332 | 2 | Ex. no. 24b/ Alkylation/ 36% | m/z: [M + H]⁺ = 365.3 (98%) [MH − NHMe₂]⁺ = 320.3 (100%), $R_t$ = 2.4 min. | ¹H-NMR (CDCl₃): 1.15 (6 H, s); 1.43-1.49 (2 H, m); 1.74-1.80 (2 H, m); 1.97-2.08 (4 H, m); 2.10 (6 H, s); 2.18 (2 H, s); 3.20 (3 H; s); 3.26 (2 H; s); 3.41 (2 H, s); 6.85 (1 H, dd, J = 3.6 and 0.9 Hz); 7.04 (1 H, dd, J = 5.1 and 3.6 Hz); 7.24 (1 H, dd, J = 5.0 and 0.8 Hz). ¹³C-NMR (CDCl₃): 22.7; 32.65; 32.74; 35.6; 38.1; 43.9; 49.2; 50.5; 59.4; 76.2; 123.4; 124.9; 126.3; 174.4. |
| 333 | 1 | Ex. no. 50/ N-Demethyl- ation/ 29% | m/z: [M + H]⁺ = 347.3 (26%) [MH − HNMe]+ = 316.3 (100%), $R_t$ = 2.9 min. | ¹H-NMR (CDCl₃): 1.39-1.51 (3 H, m); 1.64-1.93 (10 H, m); 1.94-2.09 (2 H, m); 2.11 (1.4 H, s); 2.13 (1.6 H, s); 2.13-2.20 (2 H, m); 2.36 (1 H, d, J = 7.4 Hz); 2.37 (1 H, d, J = 7.4 Hz); 2.68-2.80 (1 H, m); 3.28 (1.2 H, s); 3.33 (0.8 H, s); 3.43-3.51 (2 H, m); 6.88-6.91 (1 H, m); 6.96 (1 H, dt, J = 5.1 and 3.5 Hz); 7.22 (1 H, ddd, J = 5.1, 3.3 and 1.15 Hz). ¹³C-NMR (CDCl₃): 18.74; 18.76; 28.58; 28.62; 28.65; 28.68; 30.79; 30.95; 32.23; 32.37; 34.17; 34.18; 35.82; 38.10; 40.25; 41.24; 41.68; 42.31; 43.90; 45.20; 56.19; 56.76; 56.83; 57.6; 123.70; 123.72; 126.29; 126.44; 171.08. |
| 334 | 2 | Ex. no. 24b/ Alkylation/ 69% | m/z: [M + H]⁺ = 365.3, $R_t$ = 2.4 min. | ¹H-NMR (CDCl₃): 1.12 (3 H, d, J = 6.2 Hz); 1.19 (3 H, t, J = 7.0 Hz); 1.41-1.51 (2 H, m); 1.73-1.82 (2 H, m); 1.95-2.09 (4 H, m); 2.10 (6 H, s); 2.18 (2 H, s); 3.17 (1 H, dd, J = 14.0 and 7.2 Hz); 3.31-3.44 (4 H, m); 3.52-3.67 (2 H, m); 6.85 (1 H, br d, J = 3.0 Hz); 7.04 (1 H, dd, J = 5.1 and 3.5 Hz); 7.24 (1 H, br d, J = 5.2 Hz). ¹³C-NMR (CDCl₃): 15.7; 17.6; 32.7; 35.8; 38.1; 44.0; 47.9; 59.3; 60.2; 63.9; 74.1; 123.4; 124.8; 126.3; 174.0. |
| 335 | 2 | Ex. no. 162 Step3/ Alkylation/ 47% | m/z: [M + H]⁺ = 359.4, $R_t$ = 2.5 min. | ¹H-NMR (CDCl₃): 1.13 (3 H, d, J = 6.2 Hz); 1.20 (3 H, t, J = 7.0 Hz); 1.30-1.44 (2 H, m); 1.71-1.79 (2 H, m); 1.90-2.02 (2 H, m); 2.03 (6 H, s); 2.12 (2 H, d, J = 1.7 Hz); 2.13-2.25 (2 H, m); 3.18 (1 H, dd, J = 14.0 and 7.2 Hz); 3.33-3.47 (4 H, m); 3.53-3.68 (2 H, m); 7.26-7.32 (3 H, m); 7.35-7.41 (2 H, m). ¹³C-NMR (CDCl₃): 15.7; 17.6; 30.1; 32.8; 35.9; 38.0; 44.4; 47.9; 60.1; 63.9; 74.1; 126.7; 127.5; 127.7; 174.0. |
| 336 | 2 | Ex. no. 153/ Alkylation/ 71% | m/z: [M + H]⁺ = 393.4, $R_t$ = 2.7 min. | ¹H-NMR (CDCl₃): 1.18 (6 H, s); 1.41-1.50 (2 H, m); 1.63-1.76 (4 H, m); 1.85-1.97 (2 H, m); 1.99-2.09 (2 H, m); 2.12 (6 H, s); 2.16 (2 H, s); 2.46 (3 H, d, J = 1.0 Hz); 3.19 (3 H, s); 3.21 (2 H, s); 3.28-3.34 (2 H, m); 6.61 (1 H, d, J = 3.5 Hz); 6.66-6.69 (1 H, m). ¹³C-NMR (CDCl₃): 15.2; 24.9; 32.7; 32.8; 35.5; 36.7; 38.1; 38.2; 44.5; 49.1; 49.2; 57.9; 59.4; 73.5; 124.5; 124.9; 137.9; 173.4. |
| 338 | 1 | Ex. no. 71/ Acylation/ 30% | m/z: [M + H]⁺ = 373.4, $R_t$ = 3.0 min. | ¹H-NMR (CDCl₃): 1.15 (1.4 H, t, J = 7.0 Hz); 1.17 (1.6 H, t, J = 7.0 Hz); 1.21 (1.4 H, d, J = 6.1 Hz); 1.22 (1.6 H, d, J = 6.1 Hz); 1.24-1.36 (2 H, m); 1.50-1.70 (4 H, m); 1.80--2.0 (2 H, m); 2.02 (3 H, s); 2.03 (3 H, s); 2.14-2.40 (2 H, m); 2.23 (0.5 H, dd, J = 5.7 and 2.2 Hz, overlapped); 2.26 (0.5 H, dd, J = 5.7 and 2.1 Hz, overlapped); 2.58 (0.6 H, dd, J = 13.8 and 6.4 Hz); 2.60 (0.4 H, dd, J = 13.9 and 7.0 Hz); 3.26-3.70 (6 H, m); 3.90-4.01 (1 H, m); 7.20-7.42 (5 H, m). ¹³C-NMR (CDCl₃): 15.61; 15.63; 20.28; 20.32; 29.5; 30.0; 30.7; 30.8; 31.0; 31.4; 36.0; 37.4; 38.0; 38.1; 40.4; 42.0; 42.1; 42.3; 43.8; 45.3; 53.4; 55.1; 56.7; 60.7; 64.09; 64.13; 72.7; 72.8; 126.5; 126.6; 127.58; 127.61; 127.67; 127.72; 137.5; 169.9; 170.1. |
| 339 | 1 | Ex. no. 18/ Acylation/ 40% | m/z: [M + H]⁺ = 379.3, $R_t$ = 2.9 min. | ¹H-NMR (CDCl₃): 1.151 (1.4 H, t, J = 7.0 Hz); 1.158 (1.6 H, t, J = 7.0 Hz); 1.21 (3 H, d, J = 6.1 Hz); 1.33-1.46 (2 H, m); 1.57-1.74 (4 H, m); 1.76-2.20 (4 H, m); 2.09 (2.5 H, s); 2.10 (3.5 H, s); 2.22 (0.4 H, dd, J = 5.7 and 2.1 Hz); 2.26 (0.6 H, dd, J = 5.7 and 2.1 Hz); 2.58 (1 H, dd, J = 7.4 and 14.5 Hz); 3.20-3.70 (6 H, m); 3.90-4.00 (1 H, m); 6.83-6.87 (1 H, m); 7.00-7.06 (1 H, m); 7.21-7.25 (1 H, m). ¹³C-NMR (CDCl₃): 15.61; 15.63; 20.27; 20.32; 30.9; 31.1; 31.2; 32.80; 32.83; 33.28; 33.35; 35.6; 36.8; 38.08; 38.09; 40.0; 41.9; 42.0; 42.3; 43.8; 45.2; 53.4; 55.4; 56.7; 59.9; 64.09; 64.13; 72.6; 72.8; 123.3; 123.4; 124.7; 124.9; 126.0; 126.3; 169.9; 170.1. |
| 340 | 2 | Ex. no. 162 Step3/ Alkylation/ 33% | m/z: [M + H]⁺ = 359.4 (100%) [MH − NHMe₂]⁺ = 314.3 (99%), $R_t$ = 2.4 min. | ¹H-NMR (CDCl₃): 1.15 (6 H, s); 1.34-1.41 (2 H, m); 1.72-1.78 (2 H, m); 1.92-2.06 (2 H, m, overlapped); 2.04 (6 H, s); 2.12 (2 H, s); 2.15-2.25 (2 H, m); 3.21 (3 H; s); 3.27 (2 H; s); 3.45 (2 H, s); 7.28-7.30 (3 H, m); 7.37-7.41 (2 H, m). ¹³C-NMR (CDCl₃): 22.7; 30.2; 32.8; 35.8; 38.0; 44.2; 49.2; 50.4; 60.3; 76.2; 126.7; 127.5; 127.7; 174.5. |
| 341 | 2 | Ex. no. 217/ N-Demethyl- ation/40% | m/z: [M + H]⁺ = 377.3 (100%) [MH − HNMe]+ = 346.3 (50%), $R_t$ = 2.5 min. | ¹H-NMR (CDCl₃): 1.43 (1 H, s); 1.49-1.66 (3 H, m); 1.68-2.05 (11 H, m); 2.05-2.19 (2 H, m); 2.12 (3 H, s); 2.24 (2 H, s); 3.16 (3 H, s); 3.23 (2 H, s); 3.24-3.30 (2 H, m); 6.88 (1 H, dd, J = 3.5 and 1.1 Hz); 6.97 (1 H, dd, J = 5.1 and 3.5 Hz); 7.22 (1 H, dd, J = 5.1 and 1.0 Hz). ¹³C-NMR (CDCl₃): 12.5; 28.8; 31.3; 32.0; 32.5; 33.7; 35.8; 37.8; 43.5; 49.4; 56.3; 78.3; 123.7; 126.5; 173.4. |

-continued

| Ex. no. | Diastereomer* | Building Block/Method/Yield | LC-MS [M + H]⁺/R_t | NMR spectrum |
|---|---|---|---|---|
| 342 | 1 | Ex. no. 71/ Acylation/ 71% | [M + H]⁺: m/z = 341.3, R_t = 2.9 min. | ¹H-NMR (CDCl₃): 1.22-1.36 (2 H, m); 1.48-1.68 (4 H, m); 1.72-2.00 (4 H, m); 2.02 (2.6 H, s); 2.03 (3.4 H, s); 2.06-2.42 (6 H, m); 3.01-3.21 (1 H, m); 3.23 (1.2 H, s); 3.32 (0.8 H, t, J = 7.1 Hz); 3.39 (0.8 H, s); 3.44 (1.2 H, t, J = 7.2 Hz); 7.20-7.42 (5 H, m). ¹³C-NMR (CDCl₃): 18.1; 24.7; 24.65; 24.71; 25.4; 25.4; 30.1; 30.9; 31.0; 31.5; 35.7; 38.0; 38.1; 38.2; 38.3; 39.1; 40.1; 42.2; 43.8; 44.2; 47.8; 55.3; 55.5; 60.7; 126.5; 126.7; 127.59; 127.63; 127.66; 127.73; 137.3; 173.4. |
| 343 | 1 | Ex. no. 71/ Acylation/ 86% | [M + H]⁺: m/z = 329.4, R_t = 2.8 min. | ¹H-NMR (CDCl₃): 1.11 and 1.13 (6 H, 2 d, J = in each case 4.5 Hz); 1.20-1.38 (2 H, m); 1.54 (1.2 H, t, J = 7.3 Hz); 1.58-1.70 (2.8 H, m); 1.74-2.00 (2 H, m); 2.02 (2.6 H, s); 2.04 3.4 H, s); 2.14-2.44 (2 H, m); 2.54-2.68 (1 H, m); 3.28 (1.2 H, s); 3.40 (0.8 H, s); 3.42-3.50 (2 H, m); 7.22-7.44 (5 H, m). ¹³C-NMR (CDCl₃): 19.07; 19.08; 30.1; 30.9; 31.0; 31.5; 32.0; 32.2; 35.8; 37.7; 38.0; 38.1; 40.2; 42.1; 44.0; 44.7; 53.4; 55.2; 56.0; 60.8; 126.5; 126.7; 127.58; 127.62; 127.66; 127.75; 137.5; 175.79; 175.83. |
| 344 | 2 | Ex. no. 24b/ Alkylation/ 68% | m/z: [M + H]⁺ = 358.3, R_t = 2.2 min. | ¹H-NMR (CDCl₃): 1.07 (2 H, dd, J = 7.3 and 5.1 Hz); 1.28 (2 H, dd, J = 7.3 and 5.1 Hz); 1.46-1.56 (2 H, m); 1.80-1.92 (2 H, m); 2.00-2.15 (4 H, m); 2.10 (6 H, s); 2.23 (2 H, s); 3.35 (2 H, s); 3.47 (2 H, s); 6.85 (1 H, dd, J = 3.5 and 1.0 Hz); 7.05 (1 H, dd, J = 5.1 and 3.5 Hz); 7.24 (1 H, dd, J = 5.1 and 1.0 Hz). ¹³C-NMR (CDCl₃): 9.3; 13.4; 32.5; 32.6; 36.1; 38.0; 41.0; 43.6; 46.9; 58.6; 59.1; 122.3; 123.3; 124.7; 126.3; 142.8; 174.4. |
| 345 | 1 | Ex. no. 71/ Acylation/ 19% | [M + H]⁺ = 357.3, R_t = 2.7 min. | ¹H-NMR (CDCl₃): 0.88-0.98 (2 H, m); 1.08-1.16 (2 H, m); 1.27-1.37 (2 H, m); 1.50-1.58 (1 H, m); 1.58-1.72 (3 H, m); 1.85-2.01 (2 H, m); 2.05 (6 H, s); 2.16-2.39 (2 H, m); 3.28 (3 H, s); 3.44 (0.8 H, s); 3.49 (1.2 H, t, J = 7.4 Hz); 3.67 (1.2 H, s); 3.74 (0.8 H, t, J = 7.2 Hz); 7.26-7.43 (5 H, m). ¹³C-NMR (CDCl₃): 12.3; 12.5; 29.7; 30.2; 30.6; 31.0; 31.5; 35.3; 38.0; 38.1; 39.7; 42.1; 44.8; 45.2; 56.1; 56.2; 56.5; 64.1; 1266.; 127.6; 127.7; 169.7. |
| 346 | 1 | Ex. no. 333/ Reduction/ 48% | m/z: [M + H]⁺ = 333.3, [MH − HNMe]+ = 302.3, R_t = 1.3 and 1.7 min. | ¹H-NMR (CDCl₃): 1.43-1.51 (2 H, m); 1.54-1.71 (8 H, m); 1.77-1.88 (4 H, m); 1.90-2.08 (5 H, m); 2.11 (3 H, s); 2.21-2.30 (3 H, m); 2.39 (2 H, s); 2.52 (2 H, t, J = 6.9 Hz); 6.88 (1 H, dd, J = 3.5 and 1.1 Hz); 6.94 (1 H, dd, J = 5.1 and 3.5 Hz); 7.20 (1 H, dd, J = 5.1 and 1.1 Hz). ¹³C-NMR (CDCl₃): 18.7; 28.4; 28.7; 34.1; 34.5; 36.1; 36.4; 41.0; 54.2; 54.8; 56.5; 66.9; 123.5; 126.2. |
| 347 | 2 | Ex. no. 24b/ Alkylation/ 67% | m/z: [M + H]⁺ = 391.3, R_t = 2.4 min. | ¹H-NMR (CDCl₃): 1.22-1.35 (2 H, m); 1.40-1.50 (5 H, m); 1.60-1.68 (2 H, m); 1.70-1.81 (2 H, m); 1.95-2.09 (4 H, m); 2.10 (6 H, s); 2.13 (2 H, s); 3.19 (2 H, s); 3.30 (2 H, t, J = 7.2 Hz); 3.36 (2 H, dt, J = 11.8 and 2.0 Hz); 3.94 (2 H, br dd, J = 10.5 and 3.2 Hz); 6.85 (1 H, d, J = 3.2 Hz); 7.05 (1 H, dd, J = 5.0 and 3.6 Hz); 7.24 (1 H, d, J = 4.9 Hz). ¹³C-NMR (CDCl₃): 32.7; 32.8; 32.9; 34.1; 35.6; 38.0; 39.6; 44.2; 57.8; 59.2; 67.9; 123.4; 124.9; 126.3; 173.5. |
| 348 | 2 | Ex. no. 162 Step3/ Alkylation/ 52% | m/z: [M + H]⁺ = 385.4, R_t = 2.4 min. | ¹H-NMR (CDCl₃): 1.23-1.52 (7 H, m); 1.60-1.68 (2 H, m); 1.69-1.79 (2 H, m); 1.80-2.03 (2 H, m); 2.05 (6 H, s); 2.13 (2 H, s); 2.14-2.30 (2 H, m); 3.24 (2 H, s); 3.30 (2 H, t, J = 7.2 Hz); 3.36 (2 H, dt, J = 11.8 and 2.2 Hz); 3.95 (2 H, br dd, J = 10.6 and 4.5 Hz); 7.27-7.33 (3 H, m); 7.36-7.42 (2 H, m). ¹³C-NMR (CDCl₃): 30.2; 32.7; 32.8; 32.9; 34.1; 35.7; 38.0; 39.6; 44.5; 57.7; 60.1; 67.9; 126.8; 127.5; 127.8; 173.6. |
| 349 | 2 | Ex. no. 162 Step3/ Alkylation/ 70% | m/z: [M + H]⁺ = 352.3, R_t = 2.3 min. | ¹H-NMR (CDCl₃): 1.07 (2 H, dd, J = 7.5 and 5.1 Hz); 1.29 (2 H, dd, J = 7.4 and 5.1 Hz); 1.37-1.49 (2 H, m); 1.76-1.89 (2 H, m); 1.96-2.12 (2 H, m); 2.03 (6 H, s); 2.12-2.25 (4 H, m); 3.36 (2 H, s); 3.51 (2 H, s); 7.24-7.32 (3 H, m); 7.35-7.42 (2 H, m). ¹³C-NMR (CDCl₃): 9.3; 13.4; 30.2; 32.7; 36.3; 37.9; 43.7; 46.9; 58.5; 60.0; 122.3; 126.6; 127.4; 127.6; 174.3. |
| 350 | 1 | Ex. no. 71/ Acylation/ 62% | m/z: [M + H]⁺ = 385.4, R_t = 2.7 min. | ¹H-NMR (CDCl₃): 1.23-1.39 (4 H, m); 1.52-1.73 (6 H, m); 1.80-2.01 (2 H, m); 2.03 and 2.06 (6 H, 2 s); 2.10-2.26 (4 H, m); 2.32-2.43 (1 H, m); 3.35 (1 H, s); 3.38-3.49 (5 H, m); 3.90-3.97 (2 H, m); 7.27-7.42 (5 H, m). ¹³C-NMR (CDCl₃): 30.1; 30.8; 31.2; 31.4; 32.0; 33.10; 33.13; 35.9; 37.5; 38.0; 38.1; 40.3; 41.2; 41.7; 42.3; 43.9; 45.2; 55.2; 56.5; 60.9; 67.9; 126.5; 126.8; 127.6; 127.7; 127.9; 170.4; 170.5. |
| 351 | 1 | Ex. no. 18/ Acylation/ 78% | m/z: [M + H]⁺ = 391.3, R_t = 2.7 min. | ¹H-NMR (CDCl₃): 1.20-1.45 (4 H, m); 1.58-1.64 (1 H, m); 1.64-1.74 (5 H, m); 1.80-2.08 (3 H, m); 2.10 and 2.12 (6 H, 2 s); 2.14-2.28 (4 H, m); 3.31 (1 H, s); 3.36-3.50 (5 H, m); 3.90-3.97 (2 H, m); 6.83-6.88 (1 H, m); 7.01-7.08 (1 H, m); 7.22-7.26 (1 H, m). ¹³C-NMR (CDCl₃): 31.1; 31.2; 31.9; 32.0; 32.8; 33.10; 33.14; 33.4; 35.5; 37.0; 38.1; 40.1; 41.3; 41.7; 42.0; 43.9; 45.2; 55.4; 56.6; 59.9; 67.9; 123.3; 123.6; 124.9; 125.1; 126.2; 126.4; 170.40; 170.44. |

-continued

| Ex. no. | Diastereomer* | Building Block/Method/Yield | LC-MS [M + H]⁺/R_t | NMR spectrum |
|---|---|---|---|---|
| 352 | 1 | Ex. no. 71/ Reductive amination/ 37% | m/z [M + H]⁺ = 338.3, R_t = 0.4 min. | ¹H-NMR (CDCl₃): 0.84 (2 H, dd, J = 7.1 and 5.1 Hz); 1.24 (2 H, dd, J = 7.1 and 5.0 Hz); 1.26-1.35 (2 H, m); 1.47 (2 H, t; J = 6.9 Hz); 1.62-1.76 (2 H, m); 1.77-1.96 (2 H, m); 2.03 (6 H, s); 2.12-2.40 (2 H, m); 2.47 (2 H, s); 2.54 (2 H, s); 2.59 (2 H, t, J = 6.9 Hz); 7.23-7.41 (5 H, m). ¹³C-NMR (CDCl₃): 9.7; 13.1; 28.4; 31.2; 34.3; 38.1; 41.4; 53.4; 60.2; 60.6; 65.4; 123.2; 126.3; 127.6. |
| 353 | 2 | Ex. no. 24b/ Alkylation/ 73% | [M + H]⁺: m/z = 372.3, R_t = 2.4 min. | ¹H-NMR (CDCl₃): 1.43-1.53 (2 H, m); 1.77-1.87 (2 H, m); 1.90-2.32 (8 H, m); 2.10 (6 H, s); 2.22 (2 H, s); 2.43-2.53 (2 H, m); 3.42 (2 H, s); 3.62 (2 H, s); 6.84 (1 H, dd, J = 3.5 and 1.1 Hz); 7.04 (1 H, dd, J = 5.1 and 3.5 Hz); 7.24 (1 H, dd, J = 5.1 and 1.0 Hz). ¹³C-NMR (CDCl₃): 16.7; 30.4; 32.4; 32.6; 35.3; 36.0; 38.0; 42.7; 43.3; 48.2; 53.4; 59.3; 123.3; 123.9; 124.8; 126.3; 175.0. |
| 354 | 1 | Ex. no. 71/ Acylation/ 51% | m/z: [M + H]⁺ = 354.3 (100%) [MH − NHMe₂]⁺ = 399.4 (87%), R_t = 4.5 min. | ¹H-NMR (CDCl₃): 1.25-1.35 (2 H, m); 1.53-1.57 (1 H, m); 1.58-1.69 (3 H, m); 1.70-1.80 (2 H, m); 1.83-1.89 (3 H, m); 1.92-2.00 (1 H, m); 2.01-2.14 (4 H, m, overlapped); 2.03 (4 H, s); 2.04 (2 H, s); 2.20-2.26 (3 H, m); 2.28-2.37 (1 H, m); 3.11 (1 H, s); 3.13 (2 H, s); 3.35 (1 H, s); 3.41 (1 H, s); 3.46 (2 H, dd, J = 13.4 and 7.0 Hz); 7.27-7.32 (3 H, m); 7;35-7.40 (2 H, m). ¹³C-NMR (CDCl₃): 12.3; 12.4; 28.1; 28.5; 29.3; 29.4; 30.1; 30.7; 31.2; 31.29; 31.33; 31.5; 36.0; 37.7; 38.0; 38.1; 40.4; 42.3; 44.1; 45.0; 49.2; 49.3; 55.3; 55.4; 78.87; 78.89; 126.5; 126.7; 127.60; 127.65; 127.70; 127.8; 171.9; 172.0. |
| 355 | 1 | Ex. no. 18/ Acylation/ 36% | m/z: [M + H]⁺ = 405.3 (26%) [MH − NHMe₂]⁺ = 360.3 (100%), R_t = 4.5 min. | ¹H-NMR (CDCl₃): 1.35-1.45 (2 H, m); 1.56-1.80 (8 H, m); 1.83-1.89 (2 H, m); 1.92-1.99 (2 H, m); 2.01-2.06 (2 H, m); 2.07-2.13 (2 H, m, overlapped); 2.10 (3 H, s); 2.11 (3 H, s); 2.20-2.26 (2 H, m); 3.11 (1.3 H, s); 3.13 (1.7 H, s); 3.32 (1 H, s); 3.38 (1 H, s); 3.47 (2 H, td, J = 12.0 and 7.2 Hz); 6.85-6.87 (1 H, m); 7.02-7.06 (1 H, m); 7.22-7.26 (1 H, m). ¹³C-NMR (CDCl₃): 12.4; 28.1; 28.5; 29.3; 29.4; 31.15; 31.22; 31.3; 32.9; 33.3; 38.1; 40.1; 42.1; 44.1; 45.0; 49.2; 78.9; 123.4; 123.5; 124.9; 126.2; 126.3; 171.9. |
| 356 | 1 | Ex. no. 18/ Acylation/ 21% | [M + H]⁺: m/z = 363.3. R_t = 2.6 min. | ¹H-NMR (CDCl₃): 0.89-0.96 (2 H, m); 1.08-1.15 (2 H, m); 1.35-1.46 (2 H, m); 1.57-1.64 (1 H, m); 1.64-1.76 (3 H, m); 1.90-2.05 (2 H, m); 2.05-2.20 (2 H, m); 2.10 and 2.11 (6 H, 2s); 3.28 (3 H, s); 3.40 (0.8 H, s); 3.51 (1.2 H, t, J = 7.4 Hz); 3.62 (1.2 H, s); 3.76 (0.8 H, t, J = 7.1 Hz); 6.85 (1 H, dd, J = 3.6 and 1.1 Hz); 7.02-7.07 (1 H, m); 7.22-7.26 (1 H, m). ¹³C-NMR (CDCl₃): 12.3; 12.5; 30.8; 31.2; 32.9; 33.2; 34.8; 37.2; 38.1; 39.5; 41.9; 44.8; 45.2; 56.1; 56.2; 56.7; 59.9; 64.1; 64.2; 123.3; 123.4; 124.8; 126.1; 126.2; 169.6. |
| 357 | 2 | Ex. no. 162 Step3/ Alkylation/ 67% | [M + H]⁺: m/z = 366.3, R_t = 2.4 min. | ¹H-NMR (CDCl₃): 1.33-1.45 (2 H, m); 1.72-1.85 (2 H, m); 2.01 (6 H, s); 2.03-2.30 (8 H, m); 2.16 (2 H, s); 2.42-2.53 (2 H, m); 3.44 (2 H, s); 3.62 (2 H, s); 7.24-7.31 (3 H, m); 7.34-7.41 (2 H, m). ¹³C-NMR (CDCl₃): 16.5; 30.0; 30.4; 32.4; 35.3; 36.3; 37.9; 41.0; 43.7; 48.2; 59.0; 59.9; 123.9; 126.7; 127.2; 127.7; 175.1. |
| 358 | 1 | Ex. no. 356/ Reduction/ 80% | [M + H]⁺: m/z = 349.3, R_t = 0.3 min. | ¹H-NMR (CDCl₃): 0.44-0.48 (2 H, m); 0.74-0.80 (2 H, m); 1.34-1.44 (2 H, m); 1.52 (2 H, t, J = 6.8 Hz); 1.66-1.77 (2 H, m); 1.85-2.00 (2 H, m, 2H); 2.1 (6 H, s); 2.06-2.15 (2 H, m); 2.53 (2 H, s); 2.58 (2 H, s); 2.61 (2 H, t, J = 6.8 Hz); 3.34 (3 H, s); 6.85 (1 H, dd, J = 3.6 and 1.1 Hz); 7.03 (1 H, dd, J = 5.1 and 3.6 Hz); 7.22 (1 H, dd, J = 5.1 and 1.1 Hz,). ¹³C-NMR (CDCl₃): 11.7; 29.7; 33.7; 34.2; 38.1; 41.0; 54.2; 54.6; 59.4; 59.8; 60.3; 66.1; 123.3; 125.0; 126.1. |
| 359 | 1 | Ex. no. 71/ Reductive amination/ 19% | [M + H]⁺: m/z = 352.4, R_t = 0.6 min. | ¹H-NMR (CDCl₃): 1.23-1.33 (2 H, m); 1.44 (2 H, t, J = 6.9 Hz); 1.65-1.75 (2 H, m); 1.80-2.35 (8 H, m); 2.05 (6 H, br s); 2.43-2.52 (2 H, m); 2.57 (2 H, s); 2.62 (2 H, t, J = 6.9 Hz); 2.72 (2 H; s); 7.25-7.42 (5 H, m). ¹³C-NMR (CDCl₃): 17.00; 25.9; 30.9; 31.3; 34.1; 36.5; 38.0; 41.6; 54.1; 62.1; 66.1; 124.7; 126.5; 127.5; 127.6. |
| 360 | 1 | Ex. no. 18/ Reductive amination/ 28% | m/z: [M + H]⁺ = 344.3, R_t = 0.5 min. | ¹H-NMR (CDCl₃): 6.83 (2 H, dd, J = 7.1 and 5.0 Hz); 1.24 (2 H, dd, J = 7.1 and 5.0 Hz); 1.34-1.44 (2 H, m); 153 (2 H, t, J = 8.9 Hz); 1.68-1.80 (2 H, m); 1.84-2.20 (2 H, m); 2.30-2.22 (8 H, m); 2.47 (2 H, s); 2.51 (2 H, s); 2.61 (2 H, t, J = 8.9 Hz); 6.86 (1 H, d, J = 3.2 Hz); 7.04 (1 H, d, J = 5.1 and 3.6 Hz); 7.23 (1 H, d, J = 4.9 Hz). ¹³C-NMR (CDCl₃): 9.7; 13.0; 33.7; 34.1; 38.0; 41.1; 53.6; 60.0; 123.2; 124.9; 126.2. |
| 361 | 1 | Ex. no. 18/ Reductive amination/ 20% | [M + H]⁺: m/z = 358.3, R_t = 0.4 min. | ¹H-NMR (CDCl₃): 1.33-1.43 (2 H, m); 1.56 (2 H, t, J = 6.9 Hz); 1.65-1.78 (2 H, m); 1.80-2.26 (8 H, m); 2.10 (6 H, s); 2.42-2.55 (2 H, m); 2.52 (2 H, s); 2.64 (2 H, t, J = 8.9 Hz); 3.80 (2 H, s); 6.85 (1 H, br d, J = 3 Hz); 7.03 (1 H, dd, J = 5.0 and 3.6 Hz); 7.23 (1 H, br d, J = 5 Hz). ¹³C-NMR (CDCl₃): 16.6; 16.9; 28.4; 31.3; 33.4; 33.7; 36.6; 37.4; 38.1; 41.3; 54.0; 62.0; 65.9; 123.3; 124.8; 126.0. |

| Ex. no. | Diastereomer* | Building Block/Method/Yield | LC-MS [M + H]⁺/$R_t$ | NMR spectrum |
|---|---|---|---|---|
| 362 | 1 | Ex. no. 71/ Acylation/ 51% | [M + H]⁺: m/z = 394.4, $R_t$ = 2.9 min. | ¹H-NMR (CDCl₃): 1.23-1.37 (2 H, m); 1.56 (1 H, t, J = 7.2 Hz); 1.59-1.72 (3 H, m); 1.84-1.99 (2 H, m); 2.024 (2.7 H, s); 2.035 (3.3 H, s); 2.05-2.40 (10 H, m); 2.44-2.57 (2 H, m); 3.34 (1.1 H, s); 3.40 (0.9 H, s); 3.44 (2 H, m); 7.23-7.32 (3 H, m); 7.33-7.41 (2 H, m).<br>¹³C-NMR (CDCl₃): 16.7; 30.1; 30.3; 30.7; 31.0; 31.4; 31.8; 32.6; 32.7; 35.3; 35.95; 38.03; 37.5; 37.8; 40.4; 42.2; 44.0; 44.8; 55.2; 56.3; 60.7; 124.23; 124.33; 126.4; 126.7; 127.5; 127.6; 127.67; 127.73; 169.8. |
| 363 | 1 | Ex. no. 18/ Acylation/ 60% | [M + H]⁺: m/z = 400.3, $R_t$ = 2.9 min. | ¹H-NMR (CDCl₃): 1.32-1.46 (2 H, m); 1.58-1.76 (4 H, m); 1.85-2.22 (16 H, m); 2.30-2.38 (2 H, m); 2.42-2.58 (2 H, m); 3.30 (1.1 H, s); 3.36 (0.9 H, s); 3.47 (2 H, m); 6.81-6.87 (1 H, m); 7.00-7.06 (1 H, m), 7.20-7.25 (1 H, m).<br>¹³C-NMR (CDCl₃): 16.6; 30.1; 30.3; 30.9; 31.2; 31.80; 31.83; 32.71; 32.77; 33.1; 35.3; 35.2; 36.8; 38.0; 38.1; 40.0; 42.1; 44.2; 45.0; 55.4; 56.4; 59.9; 64.1; 123.4; 123.5; 124.28; 124.33; 124.9; 126.0; 126.3; 169.8. |
| 365 | 1 | Ex. no. 71/ Acylation/ 64% | m/z: [M + H]⁺ = 327.3, $R_t$ = 2.7 min. | ¹H-NMR (CDCl₃): 0.70-0.78 (2 H, m); 0.95-1.01 (2 H, m); 1.26-1.37 (2 H, m); 1.52-1.73 (5 H, m); 1.85-2.00 (2 H, m); 2.03 and 2.08 (5 H, 2 s); 2.15-2.30 (1 H, m); 2.33-2.45 (1 H, m); 3.41 (1 H, s); 3.44-3.49 (1 H, m); 3.56 (1 H, s); 3.62 (1 H, t, J = 7.2 Hz); 7.24-7.43 (5 H, m).<br>¹³C-NMR (CDCl₃): 7.3; 7.33; 12.2; 12.5; 30.0; 30.7; 31.3; 31.4; 36.1; 37.6; 38.0; 38.1; 40.3; 42.2; 44.2; 44.9; 54.5; 56.1; 126.5; 127.6; 127.7; 127.9; 172.1; 172.2. |
| 366 | 1 | Ex. no. 71/ Acylation/ 63% | m/z: [M + H]⁺ = 343.4, $R_t$ = 3.0 min. | ¹H-NMR (CDCl₃): 0.97 (6 H, t, J = 6.5 Hz); 1.24-1.35 (2 H, m); 1.51-1.56 (1 H, m); 1.59-1.68 (3 H, m); 1.75-2.03 (2 H, m); 2.04 and 2.07 (6 H, 2 s); 2.10-2.25 (4 H, m); 2.30-2.45 (1 H, m); 3.36 (1 H, s); 3.40-3.49 (3 H, m); 7.24-7.43 (5 H, m).<br>¹³C-NMR (CDCl₃): 22.7; 22.73; 25.57; 25.6; 30.0; 30.8; 31.2; 31.4; 36.1; 38.0; 38.1; 40.3; 42.2; 43.3; 43.75; 43.8; 45.2; 55.1; 56.4; 126.5; 127.6; 127.7; 127.8; 171.4; 171.5. |
| 367 | 1 | Ex. no. 364 Step1/ Acylation/ 45% | m/z: [M + H]⁺ = 335.4 (100%), $R_t$ = 3.0 min. | ¹H-NMR (CDCl₃): 0.03-0.07 (2 H, m); 0.39-0.43 (2 H, m); 0.67-0.77 (1 H, m); 0.91 (3 H, d, J = 7.1 Hz); 1.16-1.68 (16 H, m); 1.71 (1 H, t, J = 7.2 Hz); 1.78 (1 H, t, J = 7.1 Hz); 2.20 (3 H, s); 2.22 (3 H, s); 2.31-2.36 (2 H, m); 3.23 (1 H, s); 3.28 (1 H, s); 3.49 (2 H, dt, J = 7.2 and 2.7 Hz).<br>¹³C-NMR (CDCl₃): 4.5; 10.73; 10.74; 14.17; 14.19; 23.7; 23.8; 26.1; 26.6; 28.0; 28.9; 30.17; 30.20; 30.5; 30.6; 30.8; 33.8; 34.4; 34.8; 36.3; 37.3; 37.4; 40.3; 42.2; 44.2; 45.3; 56.5; 58.7; 171.85; 171.89. |
| 368 | 1 | Ex. no. 364Step1/ Acylation/ 17% | m/z: [M + H]⁺ = 367.4 (100%), $R_t$ = 2.9 min, | ¹H-NMR (CDCl₃): 0.88 (3 H, t, J = 7.1 Hz); 1.125 (3 H, s); 1.128 (3 H, s); 1.15-1.42 (10 H, m); 1.49-1.65 (4 H, m); 1.68 (1 H, t, J = 7.3 Hz); 1.76 (1 H, t, J = 7.1 Hz); 1.79-1.83 (2 H, m); 2.17 (3 H, s); 2.18 (3 H, s); 2.21-2.26 (2 H, m); 3.14 (3 H, s); 3.19 (1.2 H, s); 3.25 (0.8 H, s); 3.44-3.48 (2 H, m).<br>¹³C-NMR (CDCl₃): 14.1; 14.2; 23.7; 23.8; 25.0; 25.1; 26.1; 26.6; 28.0; 28.6; 28.8; 29.1; 30.2; 30.46; 30.52; 30.7; 33.8; 34.0; 34.1; 36.2; 37.29; 37.34; 40.3; 42.2; 44.3; 45.2; 49.15; 49.17; 56.4; 56.5; 58.6; 73.90; 73.93; 171.88; 171.91. |
| 389 | 1 | Ex. no. 345/ Reduction/ 68% | [M + H]⁺: m/z = 343.4, $R_t$ = 0.3 min. | ¹H-NMR (CDCl₃): 0.44-0.48 (2 H, m); 0.75-0.80 (2 H, m); 1.22-1.34 (2 H, m); 1.45 (2 H, t, J = 6.8 Hz); 1.64-1.73 (2 H, m); 1.78-1.96 (2 H, m); 2.03 (6 H, s); 2.20-2.34 (2 H, m); 2.55-2.62 (6 H, m); 3.34 (3 H, s); 7.23-7.40 (5 H, m).<br>¹³C-NMR (CDCl₃): 11.6 (2 C); 31.13 (2 C); 34.5 (2 C); 38.1 (2 C); 38.3; 41 2; 54.2; 54.7; 59.6; 60.3; 60.6; 66.2; 126.4; 127.6 (2 C); 127.8 (2 C); 136.6. |
| 370 | 2 | Ex. no. 24b/ Alkylation/ 65% | m/z: [M + H]⁺ = 349.3, $R_t$ = 2.6 min. | ¹H-NMR (CDCl₃): 0.92 (6 H, d, J = 6.6 Hz); 1.34-1.60 (5 H, m); 1.70-1.80 (3 H, m); 1.90-2.09 (3 H, m); 2.11 (6 H, s); 2.17 (2 H, s); 3.20 (2 H, s); 3.24-3.30 (2 H, m); 6.85 (1 H, d, J = 3.1 Hz); 7.05 (1 H, dd, J = 5.1 and 3.5 Hz); 7.24 (1 H, d, J = 5.0 Hz).<br>¹³C-NMR (CDCl₃): 22.5; 25.9; 32.7; 32.8; 35.5; 36.0; 38.1; 40.7; 44.4; 57.8; 59.3; 123.5; 124.9; 126.3; 173.4. |
| 371 | 1 | Ex. no. 71/ Acylation/ 62% | [M + H]⁺: m/z = 380.4, $R_t$ = 2.7 min | ¹H-NMR (CDCl₃): 0.84-0.89 (2 H, m); 1.14-1.22 (2 H, m); 1.23-1.36 (2 H, m); 1.51-1.71 (4 H, m); 1.79-1.85 (2 H, m); 1.86-1.98 (2 H, m); 2.00 (2.8 H, s); 2.03 (3.2 H, s); 2.12-2.40 (2 H, m); 2.46-2.55 (2 H, m); 3.37 (1.1 H, s); 3.38 (0.9 H, s); 3.40-3.50 (2 H, m); 7.20-7.40 (5 H, m).<br>¹³C-NMR (CDCl₃): 9.4; 13.97; 13.99; 30.1; 30.2; 30.5; 30.6; 31.0; 31.2; 32.0; 32.5; 35.7; 37.5; 37.9; 38.0; 40.4; 42.2; 44.0; 45.0; 55.2; 56.7; 60.7; 123.16; 123.25; 126.4; 126.6; 127.5; 127.6; 127.69 ; 127.74; 137.0; 169.8; 169.8. |
| 372 | 1 | Ex. no. 18/ Acylation/ 59% | [M + H]⁺: m/z = 386.3, $R_t$ = 2.7 min. | ¹H-NMR (CDCl₃): 0.85-0.90 (2 H, m); 1.17-1.26 (2 H, m); 1.32-1.46 (2 H, m); 1.56-1.77 (4 H, m); 1.80-1.87 (2 H, m); 1.89-2.05 (4 H, m); 2.06-2.25 (6 H, m); 2.49-2.57 (2 H, m); 3.31 (0.4 H, s); 3.36 (1.6 H, s); 3.41-3.55 (2 H, m); 6.83-6.88 (1 H, m); 7.01-7.07 (1 H, m); 7.21-7.26 (1 H, m). |

| Ex. no. | Diastereomer* | Building Block/Method/Yield | LC-MS [M + H]+/R_t | NMR spectrum |
|---|---|---|---|---|
| | | | | 13C-NMR (CDCl3): 9.4; 30.1; 30.2; 31.0; 32.1; 32.5; 32.9; 33.2; 37.1; 38.05; 38.12; 40.0; 40.2; 42.0; 42.1; 43.9; 44.2; 45.1; 45.8; 55.4; 56.8; 59.8; 114.6; 123.2; 123.3; 123.4; 123.5; 124.8; 126.13; 126.18; 126.3; 169.7. |
| 373 | 1 | Ex. no. 18/ Acylation/ 80% | m/z: [M + H]+ = 377.3 (77%) [MH − NHMe2]+ = 332.3 (100%), R_t = 2.7 min. | 1H-NMR (CDCl3): 0.64-0.68 (2 H, m); 0.83-0.87 (2 H, m); 1.35-1.45 (2 H, m); 1.63 (1.2 H, t, J = 7.2 Hz); 1.66-1.78 (4 H, m, overlapped); 1.72 (0.8 H, t, J = 7.2 Hz); 1.94-2.21 (4 H, m, overlapped); 2.09 (2.5 H, s); 2.11 (3.5 H, s); 2.67 (2 H, d, J = 3.3 Hz); 3.28 (1.2 H, s); 3.30 (1.8 H, s); 3.37 (0.8 H, s); 3.40 (1.2 H, s); 3.49 (0.8 H, t, J = 7.1 Hz); 3.56 (1.2 H, t, J = 7.1 Hz); 6.84-686 (1 H, m); 7.02-7.06 (1 H, m); 7.22-725 (1 H, m). 13C-NMR (CDCl3): 11.8; 11.87; 11.90; 31.0; 31.2; 32.8; 33.2; 35.4; 37.0; 38.1; 38.4; 38.7; 40.1; 42.1; 44.1; 45.5; 54.42; 54.44; 55.6; 57.2; 59.7; 59.76; 59.81; 123.3; 123.4; 124.8; 125.0; 126.1; 126.3; 169.2; 169.3. |
| 374 | 1 | Ex. no. 71/ Acylation/ 65% | m/z: [M + H]+ = 371.4 (100%) [MH − NHMe2]+ = 326.3 (87%), R_t = 2.8 min. | 1H-NMR (CDCl3): ): 0.64-0.68 (2 H, m); 0.83-0.88 (2 H, m); 1.32 (2 H, ddd, J = 13.6, 8.0 and 3.0 Hz); 1.56 (1.2 H, t, J = 7.2 Hz); 1.62-1.70 (2 H, m, overlapped); 1.65 (0.8 H, t, J = 7.2 Hz); 1.86-1.99 (2 H, m); 2.03 (2 H, s); 2.04 (4 H, s); 2.16-2.25 (0.8 H, m); 2.27-2.35 (1.2 H, m); 2.66 (0.8 H, s); 2.68 (1.2 H, s); 3.28 (1.2 H, s); 3.31 (1.8 H, s); 3.41 (0.8 H, s); 3.44 (1.2 H; s); 3.47 (1.2 H, t, J = 7.2 Hz); 3.54 (0.8 H, t, J = 7.2 Hz); 7.26-7.32 (3 H, m); 7.35-7.41 (2 H, m). 13C-NMR (CDCl3): 11.90; 30.0; 30.7; 31.2; 31.5; 35.8; 37.6; 38.0; 38.1; 38.4; 38.8; 40.3; 42.4; 44.1; 45.5; 54.45; 54.46; 55.4; 57.0; 59.80; 59.83; 60.8; 126.5; 126.7; 127.56; 127.62; 127.68; 127.75; 169.27; 169.31. |
| 375 | 1 | Ex. no. 364 Step1/ Acylation/ 37% | m/z: [M + H]+ = 335.4 (100%), R_t = 3.1 min. | 1H-NMR (CDCl3): 0.91 (3 H, t, J = 7.2 Hz); 1.16-1.46 (10 H, m); 1.51-1.94 (10 H, m); 2.10-2.17 (2 H, m); 2.20 (3 H, s); 2.22 (3 H, s); 2.35 (2 H, dd, J = 7.4-2.7 Hz); 2.66-2.78 (1 H, m); 3.19 (1.2 H, s); 3.26 (0.8 H, s); 3.43-3.49 (2 H, m). 13C-NMR (CDCl3): 14.16; 14.18; 18.74; 18.75; 23.7; 23.8; 26.1; 26.6; 28.0; 28.57; 28.62; 28.9; 30.2; 30.4; 30.6; 30.8; 32.3; 32.4; 33.8; 36.3; 37.3; 37.4; 40.3; 41.2; 41.6; 42.2; 44.1; 45.3; 56.4; 56.6; 58.7; 171.06; 171.08. |
| 376 | 2 | Ex. no. 162 Step3/ Alkylation/ 78% | m/z: [M + H]+ = 343.4, R_t = 2.7 min. | 1H-NMR (CDCl3): 0.93 (6 H, d, J = 6.6 Hz); 1.33-1.42 (4 H, m); 1.57 (1 H, td, J = 13.4 and 6.7 Hz); 1.61-1.78 (3 H, m); 1.85-2.03 (1 H, m); 2.05 (6 H, s); 2.12 (2 H, s); 2.14-2.32 (2 H, m); 3.23 (2 H, s); 3.25-3.30 (2 H, m); 7.27-7.32 (3 H, m); 7.36-7.42 (2 H, m). 13C-NMR (CDCl3): 22.5; 25.9; 30.2; 32.9; 35.7; 36.0; 38.0; 40.7; 44.6; 57.7; 126.8; 127.5; 127.8; 173.5. |
| 377 | 2 | Ex. no. 24b/ Alkylation/ 50% | m/z: [M + H]+ = 335.3, R_t = 2.4 min. | 1H-NMR (CDCl3): 0.90 (6 H, d, J = 6.7 Hz); 1.43-1.52 (2 H, m); 1.56-1.71 (1 H, m); 1.72-1.82 (2 H, m); 1.84-1.95 (1 H, m); 1.97-2.10 (3 H, m); 2.11 (6 H, s); 2.20 (2 H, s); 3.06 (2 H, d, J = 7.5 Hz); 3.21 (2 H, s); 6.86 (1 H, d, J = 3.0 Hz); 7.05 (1 H, dd, J = 5.1 and 3.5 Hz); 7.25 (1 H, d, J = 4.7 Hz). 13C-NMR (CDCl3): 20.1; 26.7; 32.7; 35.6; 38.0; 40.7; 44.2; 50.0; 59.3; 123.5; 124.9; 126.3; 173.9. |
| 378 | 2 | Ex. no. 162 Step3/ Alkylation/ 63% | m/z: [M + H]+ = 329.4, R_t = 2.4 min. | 1H-NMR (CDCl3): 0.90 (6 H, d, J = 6.6 Hz); 1.34-1.43 (2 H, m); 1.71-1.79 (3 H, m); 1.85-2.02 (3 H, m); 2.04 (6 H, s); 2.15 (2 H, s); 2.16-2.25 (1 H, m); 3.07 (2 H, d, J = 7.5 Hz); 3.24 (2 H, s); 7.26-7.31 (3 H, m); 7.36-7.41 (2 H, m). 13C-NMR (CDCl3): 20.1; 26.7; 32.9; 35.7; 38.0; 44.5; 50.0; 58.6; 126.8; 127.4; 127.8; 174.0. |
| 379 | 1 | Ex. no. 71/ Acylation/ 71% | [M + H]+: m/z = 371.4, R_t = 2.7 min. | 1H-NMR (CDCl3): 0.75 (2 H, br s); 0.94-1.00 (2 H, m); 1.20-1.35 (2 H, m); 1.44-1.70 (4 H, m); 1.76-1.98 (2 H, m); 2.04 (6 H, s); 2.21 (0.6 H, br s); 2.37 (1.4 H, br s); 3.32 (3 H, s); 3.36-3.48 (2 H, m); 3.45 (2 H, s); 3.61 (1.7 H, s); 3.69 (0.3 H, br s); 7.20-7.44 (5 H, m). 13C-NMR (CDCl3): 10.5; 26.5; 29.5; 30.0; 30.6; 30.7; 31.7; 35.9; 38.0; 42.0; 44.3; 44.8; 56.1; 58.7; 77.4; 126.7; 127.7; 170.9. |
| 380 | 1 | Ex. no. 71/ Acylation/ 76% | [M + H]+: m/z = 373.4, R_t = 2.8 min. | 1H-NMR (CDCl3): 1.20-1.35 (2 H, m); 1.27 (2 H, m); 1.49 (2 H, br s); 1.58-1.68 (2 H, m); 1.91 (6 H, br s); 2.04 (6 H, s); 2.30 (2 H, br s); 3.35 (3 H, s); 3.45 (2 H, s); 3.47-3.60 (4 H, m); 7.24-7.44 (5 H, m). 13C-NMR (CDCl3): 22.9; 30.9; 38.0; 43.4; 46.1; 59.3; 80.2; 126.5; 127.7; 127.6; 174.8. |
| 381 | 1 | Ex. no. 71/ Acylation/ 65% | [M + H]+: m/z = 385.4, R_t = 2.9 min. | 1H-NMR (CDCl3): 1.17-1.33 (2 H, m); 1.42-1.48 (2 H, m); 1.49-2.00 (8 H, m); 2.03 (6 H, s); 2.14-2.38 (2 H, m); 2.39-2.50; (2 H, m); 3.30-3.50 (7 H, m); 3.61 (0.6 H, s); 3.62 (1.4 H, s); 7.22-7.44 (5 H, m). 13C-NMR (CDCl3): 15.3; 28.3; 28.5; 30.1; 30.6; 30.8; 31.6; 35.7; 38.0; 38.1; 38.2; 39.5; 42.4; 44.3; 44.9; 48.7; 48.8; 55.3; 56.3; 59.1; 59.3; 61.1; 77.6; 77.7; 126.5; 127.7; 136.1; 137.3; 174.8; 175.2. |
| 382 | 1 | Ex. no. 18/ Acylation/ 58% | m/z: [M + H]+ = 377.3, R_t = 2.9 min. | 1H-NMR (CDCl3): 1.34-1.44 (2 H, m); 1.55-1.76 (6 H, m); 1.77-1.90 (1 H, m); 1.90-2.10 (3 H, m); 2.11 (6 H, 2 s); 2.14-2.22 (2 H, m); 2.50-2.60 (2 H, m); 3.091 and 3.094 (3 H, 2 s); 3.41 and 3.42 (2 H, 2 s); 3.50-3.55 (2 H, m); 6.85-6.89 (1 H, m); 7.02-7.07 (1 H, m); 7.23-7.26 (1 H, m). |

-continued

| Ex. no. | Diastereomer* | Building Block/Method/Yield | LC-MS [M + H]⁺/Rₜ | NMR spectrum |
|---|---|---|---|---|
| 383 | 1 | Ex. no. 18/ Acylation/ 78% | [M + H]⁺: m/z = 377.3, Rₜ = 2.6 min. | $^{13}$C-NMR (CDCl$_3$): 12.7; 12.8; 29.8; 30.0, 30.1; 30.6; 31.3; 32.9; 33.0; 38.0; 38.1; 39.2; 42.1; 44.6; 44.7; 51.3; 51.4; 55.9; 56.7; 59.9; 81.8; 82.1; 123.3; 123.4; 124.9; 125.0; 126.1; 126.2; 170.5; 170.8. $^1$H-NMR (CDCl$_3$): 0.74 (2 H, br s); 0.96 (2 H, m); 1.37 (2 H, ddd, J = 13.7, 10.4 and 3.5 Hz); 1.50-1.74 (4 H, m); 1.80-2.02 (2 H, m); 2.11 (6 H, s); 2.13-2.28 (2 H, m); 3.31 (3 H, s); 3.33-3.39 (2 H, m); 4.49 (2 H, s); 3.57 (1.4 H, br s); 3.71 (0.6 H, br s); 6.84 (1 H, br d, J = 3.2 Hz); 6.99-7.08 (1 H, m); 7.23 (1 H, br d, J = 4.6 Hz). $^{13}$C-NMR (CDCl$_3$): 10.5; 26.6; 30.6; 31.4; 32.9; 33.1; 35.5; 37.1; 38.1; 39.6; 41.7; 44.5; 44.9; 56.1; 58.7; 60.2; 77.3; 123.6; 125.2; 126.3; 142.0; 143.7; 170.9. |
| 384 | 1 | Ex. no. 18/ Acylation/ 76% | [M + H]⁺: m/z = 379.3, Rₜ = 2.8 min. | $^1$H-NMR (CDCl$_3$): 1.25 (6 H, s); 1.32-1.43 (2 H, m); 1.47-1.61 (2 H, br s); 1.62-1.71 (2 H, m); 1.95 (2 H, br s); 2.02-2.20 (8 H, br s); 3.34 (3 H, s); 3.43 (2 H, s); 3.46 (2 H, br s); 3.54 (2 H, very br s); 6.84 (1 H, d, J = 3.0 Hz); 7.03 (1 H, dd, J = 5.1 and 3.5 Hz); 7.23 (1 H, d, J = 4.9 Hz). $^{13}$C-NMR (CDCl$_3$): 22.7; 30.7; 33.0; 38.1; 43.4; 46.0; 57.2; 59.1; 59.8; 80.2; 123.4; 124.8; 126.1; 174.6. |
| 385 | 1 | Ex. no. 18/ Acylation/ 65% | [M + H]⁺: m/z = 391.3, Rₜ = 2.9 min. | $^1$H-NMR (CDCl$_3$): 1.28-1.42 (2 H, m); 1.49-1.55 (2 H, m); 1.56-1.76 (4 H, m); 1.76-2.24 (12 H, m); 2.35-2.48 (2 H, m); 3.32 (1.4 H, s); 3.33 (3 H, s); 3.37 (0.6 H, s); 3.42-3.52 (2 H, m); 3.61 (2 H, s); 8.83 (1 H, dd, J = 3.5 and 0.9 Hz); 7.00-7.05 (1 H, m); 7.20-7.25 (1 H, m). $^{13}$C-NMR (CDCl$_3$): 15.24; 15.27; 28.4; 28.5; 30.5; 31.3; 32.9; 33.0; 35.0; 38.1; 39.1; 42.1; 44.3; 44.7; 48.7; 48.8; 55.3; 56.5; 59.0; 59.3; 59.9; 60.1; 77.57; 77.63; 123.1; 123.3; 124.7; 125.1; 126.1; 126.3; 174.8; 175.0. |
| 386 | 2 | Ex. no. 24b/ Alkylation/ 67% | m/z: [M + H]⁺ = 377.3 (100%) [MH − NHMe$_2$]⁺ = 332.3 (65%), Rₜ = 2.4 min. | $^1$H-NMR (CDCl$_3$): 0.40-0.44 (2 H, m); 0.75-0.78 (2 H, m); 1.43-1.49 (2 H, m); 1.74-1.80 (4 H, m); 1.93-2.13 (4 H, m, overlapped); 2.10 (6 H, s); 2.17 (2 H, s); 3.25 (3 H, s); 3.29 (2 H, s); 3.40-3.43 (2 H, m); 6.85 (1 H, dd, J = 3.8 and 1.1 Hz); 7.04 (1 H, dd, J = 5.1 and 3.6 Hz); 7.24 (1 H, dd, J = 5.1 and 1.1 Hz). $^{13}$C-NMR (CDCl$_3$): 12.0; 30.4; 32.8; 34.5; 38.1; 39.9; 44.4; 53.8; 59.3; 60.0; 123.5; 123.9; 126.3; 173.6. |
| 387 | 2 | Ex. no. 162 Step3/ Alkylation/ 66% | m/z: [M + H]⁺ = 371.4 (100%) [MH − NHMe$_2$]⁺ = 326.3 (51%), Rₜ = 2.5 min. | $^1$H-NMR (CDCl$_3$): 0.41-0.44 (2 H, m); 0.76-0.79 (2 H, m); 1.37 (2 H, ddd, J = 13.1, 10.4 and 3.0 Hz); 1.71-1.79 (4 H, m); 1.89-2.04 (2 H, m, overlapped); 2.03 (6 H, s); 2.12 (2 H, s); 2.15-2.30 (2 H, m); 3.26 (3 H, s); 3.33 (2 H, s); 3.40-3.44 (2 H, m); 7.28-7.30 (3 H, m); 7.36-7.40 (2 H, m). $^{13}$C-NMR (CDCl$_3$): 12.1; 30.3; 30.4; 33.0; 35.7; 38.0; 39.9; 44.7; 53.9; 58.8; 60.0; 126.7; 127.5; 127.8; 173.6. |
| 388 | 1 | Ex. no. 364Step1/ Acylation/ 29% | m/z [M + H]⁺ = 365.4 (100%), Rₜ = 3.0 min. | $^1$H-NMR (CDCl$_3$): 0.92 (3 H, dt, J = 7.2 and 2.0 Hz); 1.22-1.33 (8 H, m);); 1.37-1.44 (2 H, m); 1.55-1.74 (8 H, m, overlapped); 1.70 (1 H, t, J = 7.3 Hz, overlapped); 1.77 (1 H, t, J = 7.1 Hz); 2.12-2.19 (2 H, m); 2.22-2.30 (6 H, m); 2.58 (0.8 H, s); 2.60 (1.2 H, br. s); 3.23 (3 H, s); 3.30 (1 H, s); 3.35 (1 H, br s); 3.49-3.57 (2 H, m). $^{13}$C-NMR (CDCl$_3$): 12.57; 12.59; 14.1; 14.2; 23.71; 23.74; 26.0; 26.6; 27.9; 28.7; 30.1; 30.5; 30.6; 30.8; 34.2; 36.5; 37.4; 40.2; 40.4; 40.6; 42.1; 44.2; 45.8; 50.20; 50.23; 79.47; 79.52; 169.5; 169.6. |
| 389 | 1 | Ex. no. 364Step1/ Acylation/ 41% | m/z: [M + H]⁺ = 351.4 (100%), Rₜ = 2.7 min. | $^1$H-NMR (CDCl$_3$): 0.91 (3 H, J = 7.3 = Hz); 1.18-1.69 (14 H, m); 1.71 (1 H, t, J = 7.2 Hz); 1.79 (1 H, t, J = 7.1 Hz); 2.10-2.19 (2 H, m); 2.21 (3 H, s), 2.25 (3 H, br s); 2.28-2.39 (2 H, m); 2.64-2.76 (1 H, m); 3.21 (1 H, br s); 3.28 (1 H, s); 3.40-3.36 (2 H, m); 3.50 (1 H, t, J = 7.3 Hz); 3.71-3.77 (1 H, m); 3.82-3.88 (1 H, m); 3.94-3.98 (1 H, m). $^{13}$C-NMR (CDCl$_3$): 14.1; 14.2; 23.7; 23.8; 26.1; 26.7; 28.0; 28.91; 28.93; 30.1; 30.2; 30.4; 30.5; 30.7; 32.3; 33.9; 35.36; 35.41; 36.1; 37.4; 38.1; 38.4; 40.3; 42.2; 44.2; 45.3; 56.5; 58.5; 67.6; 73.32; 73.35; 170.4; 170.5. |
| 390 | 1 | Ex. no. 71/ Acylation/ 62% | m/z: [M + H]⁺ = 371.4, Rₜ = 3.0 min. | $^1$H-NMR (CDCl$_3$): 1.22-1.35 (2 H, m); 1.47-1.53 (1 H, m); 1.55-1.75 (4 H, m); 1.80-2.00 (4 H, m); 2.03 and 2.04 (6 H, 2 s); 2.06-2.20 (2 H, m); 2.23-2.34 (1 H, m); 2.51-2.60 (2 H, m); 3.09 (3 H, s); 3.43 and 3.45 (2 H, 2 s); 3.47-3.53 (2 H, m); 7.27-7.33 (3 H, m); 7.34-7.40 (2 H, m). $^{13}$C-NMR (CDCl$_3$): 12.7; 12.8; 30.0, 30.1; 30.2; 30.5; 30.8; 31.6; 35.1; 38.0; 38.1; 39.5; 42.4; 44.6; 44.7; 51.3; 51.4; 55.8; 56.5; 60.9; 81.8; 82.1; 126.5; 126.7; 127.6; 127.7; 127.74; 170.5; 170.8. |
| 391 | 1 | Ex. no. 31/ Acylation/ 65% | m/z: [M + H]⁺ = 391.3, Rₜ = 2.9 min. | $^1$H-NMR (CDCl$_3$): 0.70-0.78 (2 H, m); 0.94-0.99 (2 H, m); 1.35-1.44 (2 H, m); 1.53-1.70 (4 H, m); 1.73-1.97 (3 H, m); 2.00-2.10 (1 H, m); 2.13 (6 H, br s); 2.46 (3 H, s); 3.32 (3 H, s); 3.42-3.50 (2 H, m); 3.44 (2 H, s); 3.57 (2 H, br s); 6.59-6.64 (1 H, m); 6.65-6.70 (1 H, m). $^{13}$C-NMR (CDCl$_3$): 10.5; 15.2; 26.6; 30.8; 31.5; 32.7; 33.1; 35.7; 38.1; 41.8; 44.5; 45.0; 50.8; 56.1; 58.7; 60.3; 77.4; 124.5; 125.2; 137.9; 171.0. |

-continued

| Ex. no. | Diastereomer* | Building Block/Method/Yield | LC-MS [M + H]⁺/Rₜ | NMR spectrum |
|---|---|---|---|---|
| 392 | 1 | Ex. no. 31/ Acylation/ 62% | m/z: [M + H]⁺ = 405.3, Rₜ = 3.0 min. | ¹H-NMR (CDCl₃): 1.32-1.42 (2 H, m); 1.49-1.62 (3 H, m); 1.63-1.96 (6 H, m); 1.97-2.08 (3 H, m); 2.10 and 2.13 (6 H, 2 s); 2.37-2.45 (2 H, m); 2.46 (3 H, s); 3.33 (3 H, s); 3.32 and 3.37 (2 H, 2 s); 3.42-3.52 (2 H, m); 3.62 (2 H, s); 6.57-6.63 (1 H, m); 6.64-6.69 (1 H, m). ¹³C-NMR (CDCl₃): 15.2; 28.4; 28.5; 30.7; 31.6; 32.7; 33.0; 35.4; 38.1; 39.2; 42.3; 44.3; 44.9; 48.7; 48.8; 55.3; 58.5; 59.1; 59.3; 60.0; 77.6; 124.3; 124.5; 124.8; 125.1; 137.7; 175.0; 175.2. |
| 393 | 1 | Ex. no. 31/ Acylation/ 60% | m/z: [M + H]⁺ = 393.3, Rₜ = 3.0 min. | ¹H-NMR (CDCl₃): 1.26 (6 H, s); 1.39 (2 H, ddd, J = 13.6 and 10.3 and 3.5 Hz); 1.50-1.72 (5 H, m); 1.81-1.97 (2 H, m); 1.81-1.97 (2 H, m); 2.00-2.10 (1 H, m); 2.12 (6 H, s); 2.47 (3 H, s); 3.35 (3 H, s); 3.44 (2 H, br s); 3.54 (2 H, br s); 6.60-6.64 (1 H, m); 6.66-6.70 (1 H, m). ¹³C-NMR (CDCl₃): 15.2; 22.9; 30.9; 33.0; 38.1; 43.5; 46.2; 56.8; 59.2; 60.1; 80.2; 124.4; 125.0; 137.8; 174.8. |
| 394 | 1 | Ex. no. 71/ Acylation/ 51% | [M + H]⁺: m/z = 382.4, Rₜ = 2.8 min. | ¹H-NMR (CDCl₃): 1.24-1.34 (2 H, m); 1.36 (2.7 H, s); 1.38 (3.3 H, s); 1.53-1.59 (1.1 H, m); 1.60-1.72 (2.9 H, m); 1.84-1.98 (4 H, m); 2.03 (2.7 H, s); 2.05 (3.3 H, s); 2.14-2.37 (2 H, m); 2.38-2.48 (2 H, m); 3.36 (1.1 H, s); 3.40 (0.9 H s); 3.46 (2 H, t, J = 7.0 Hz); 7.22-7.42 (5 H, m). ¹³C-NMR (CDCl₃): 26.5; 30.1; 30.2; 30.6; 30.7; 31.2; 31.4; 31.8; 31.9; 32.00; 32.02; 35.5; 35.7; 37.5; 37.9; 38.0; 40.37; 40.41; 42.2; 44.2; 44.9; 55.2; 58.4; 60.9; 124.5; 124.7; 126.4; 126.8; 127.4; 127.6; 127.7; 127.8; 137.0; 169.8. |
| 395 | 1 | Ex. no. 18/ Acylation/ 64% | [M + H]⁺: m/z = 388.3, Rₜ = 2.8 min. | ¹H-NMR (CDCl₃): 1.34-1.46 (2 H, m); 1.36 (2.7 H, s); 1.37 (3.3 H, s); 1.58-1.76 (4 H, m); 1.85-2.04 (4 H, m); 2.05-2.21 (2 H, m); 2.09 (2.7 H, s); 2.12 (3.3 H, s); 2.38-2.47 (2 H, m); 3.32 (1.2 H, s); 3.36 (0.8 H, s); 3.48 (2 H, t, J = 7.2 Hz); 6.82-6.88 (1 H, m); 7.01-7.07 (1 H, m); 7.21-7.26 (1 H, m). ¹³C-NMR (CDCl₃): 26.4; 26.5; 30.0; 30.2; 30.6; 31.0; 31.2; 31.8; 31.9; 32.0; 32.9; 33.1; 35.1; 35.6; 35.7; 36.8; 37.9; 38.1; 40.0; 42.1; 44.2; 44.9; 55.4; 56.4; 59.9; 123.4; 123.6; 124.60; 124.64; 124.9; 126.2; 126.2; 169.8. |
| 396 | 1 | Ex. no. 425/ Acylation/ 24% | m/z: [MH − HNMe₂]⁺ = 366.2 (100%), Rₜ = 3.0 min. | ¹H-NMR (CDCl₃): 0.70-0.78 (2 H, m); 0.93-1.00 (2 H, m); 1.32-1.42 (2 H, m); 1.54-1.70 (4 H, m); 1.80-2.00 (4 H, m); 2.04-2.10 (1 H, m); 2.13 (6 H, br s); 3.32 (3 H, s); 3.42 (2 H, s); 3.44-3.50 (1 H, m); 3.54-3.76 (2 H, m); 6.61 (1 H, br d, J = 3.6 Hz); 8.84 (1 H, br d, J = 2.7 Hz). ¹³C-NMR (CDCl₃): 10.5; 28.6; 30.6; 31.3; 32.4; 32.8; 35.4; 38.0; 41.8; 44.4; 44.9; 56.1; 58.7; 60.4; 77.5; 124.6; 125.5; 171.0. |
| 397 | 1 | Ex. no. 425/ Acylation/ 24% | m/z: [MH − HNMe₂]⁺ = 380.2 (100%), Rₜ = 3.2 min. | ¹H-NMR (CDCl₃): 1.30-1.41 (2 H, m); 1.52-1.77 (6 H, m); 1.78-2.08 (6 H, m); 2.10 and 2.11 (6 H, 2 s); 2.37-2.48 (2 H, m); 3.33 and 3.37 (5 H, 2 s); 3.44-3.57 (2 H, m); 3.62 (2 H, s); 6.60 (1 H, d, J = 3.8 Hz); 6.82-6.86 (1 H, m). ¹³C-NMR (CDCl₃): 15.3; 28.4; 28.5; 30.5; 31.4; 32.5; 32.7; 35.2; 38.1; 39.2; 42.2; 44.3; 44.9; 48.7; 48.8; 55.4; 56.5; 59.1; 59.3; 60.5; 77.6; 77.7; 124.5; 125.4; 125.5; 127.8; 175.0; 175.2. |
| 398 | 1 | Ex. no. 425/ Acylation/ 28% | m/z: [MH − HNMe₂]⁺ = 368.2 (100%), Rₜ = 3.1 min. | ¹H-NMR (CDCl₃): 1.26 (6 H, s); 1-34-1.42 (2 m); 1.50-1.70 (5 H, m); 1.80-1.95 (2 H, m); 1.95-2.10 (2 H, m); 2.11 (6 H, s); 3.35 (3 H, s); 3.44 (2 H, s); 3.44-3.60 (3 H, m); 6.60 (1 H, br d, J = 3.5 Hz); 6.84 (1 H, br d, J = 3.6 Hz). ¹³C-NMR (CDCl₃): 22.9; 30.7; 31.5; 32.7; 37.9; 38.0; 43.6; 46.2; 57.5; 59.2; 60.4; 80.2; 124.4; 125.2; 125.5; 174.8. |
| 399 | 1 | Ex. no. 432/ Alkylation/ 76% | [M + H]⁺: m/z = 351.4, Rₜ = 2.6 min. | ¹H-NMR (CDCl₃): 0.90 (3 H, t, J = 7.2 Hz); 1.10-1.45 (10 H, m); 1.46-1.80 (7 H, m); 2.20-2.18 (2 H, m); 2.19 (6 H, s); 2.23 (2 H, s); 3.13 (2 H, s); 3.26-3.30 (2 H, m); 3.35 (1 H, dd; J = 8.3 and 6.9 Hz); 3.72 (1 H, dd, J = 15.4 and 7.7 Hz); 3.80-3.92 (2 H, m). ¹³C-NMR (CDCl₃): 14.2; 23.6; 26.5; 28.2; 30.7; 30.6; 32.1; 32.4; 35.5; 36.8; 37.3; 41.5; 45.3; 55.8; 57.6; 67.7; 73.0; 76.7; 77.0; 77.2; 173.9. |
| 400 | 2 | Ex. no. 433/ Alkylation/ 59% | [M + H]⁺ m/z = 351.4, Rₜ = 2.4 min. | ¹H-NMR (CDCl₃): 0.90 (3 H, t, J = 7.1 Hz); 1.10-1.42 (10 H, m); 1.46-1.80 (7 H, m); 2.02-2.19 (2 H, m); 2.20 (6 H, s); 2.26 (2 H, s); 3.10 (2 H, s); 3.26 (2 H, t, J = 7.4 Hz); 3.35 (1 H, dd, J = 8.3 and 6.9 Hz); 3.70-3.77 (1 H, m); 3.80-3.93 (2 H, m). ¹³C-NMR (CDCl₃): 14.0; 23.8; 26.5; 28.5; 30.4; 30.6; 31.8; 32.3; 35.9; 36.8; 37.3; 41.2; 43.2; 56.0; 59.8; 67.9; 73.2; 173.7. |
| 401 | 1 | Ex. no. 432/ Alkylation/ 67% | [M + H]⁺: m/z = 346.4, Rₜ = 2.6 min. | ¹H-NMR (CDCl₃): 0.87 (2 H, m); 0.91 (3 H, t, J = 7.2 Hz); 1.10-1.44 (12 H, m); 1.52-1.64 (2 H, m); 1.66-1.80 (4 H, m); 2.20 (6 H, s); 2.25 (2 H, s); 3.26 (2 H, s); 3.46 (2 H, m). ¹³C-NMR (CDCl₃): 7.8; 13.9; 14.2; 23.8; 26.4; 28.4; 30.7; 30.8; 31.8; 32.1; 32.6; 35.7; 37.2; 41.1; 45.2; 55.8; 58.7; 123.0; 174.4. |
| 402 | 2 | Ex. no. 433/ Alkylation/ 37% | [M + H]⁺: m/z = 346.4, Rₜ = 2.3 min. | ¹H-NMR (CDCl₃): 0.83-0.88 (2 H, m); 0.90 (3 H, t, J = 7.1 Hz); 1.12-1.45 (12 H, m); 1.50-1.84 (6 H, m); 2.20 (6 H, s); 2.27 (2 H, s); 3.22 (2 H, s); 3.47 (2 H, t, J = 7.2 Hz). ¹³C-NMR (CDCl₃): 7.5; 14.1; 14.0; 23.8; 26.5; 28.6; 30.6; 31.8; 32.5; 36.0; 37.3; 41.3; 43.0; 56.0; 60.7; 122.8; 174.2. |

| Ex. no. | Diastereomer* | Building Block/Method/Yield | LC-MS [M + H]⁺/$R_t$ | NMR spectrum |
|---|---|---|---|---|
| 403 | 1 | Ex. no. 432/ Alkylation/ 57% | [M + H]⁺: m/z = 360.4, $R_t$ = 2.8 min. | ¹H-NMR (CDCl₃): 0.90 (3 H, t, J = 7.2 Hz); 1.12-1.44 (8 H, m); 1.52-1.64 (2 H, m); 1.67-1.77 (2 H, m); 1.92-1.98 (2 H, m); 1.92-1.98 (2 H, m); 1.99-2.18 (4 H, m); 2.19 (6 H, s); 2.24 (2 H, s); 2.43-2.58 (2 H, m); 3.19 (2 H, s); 3.34-3.40 (2 H, m).<br>¹³C-NMR (CDCl₃): 14.2; 16.9; 23.8; 26.4; 28.4; 30.5; 32.0; 33.7; 34.7; 35.6; 37.3; 39.1; 45.2; 53.4; 55.9; 58.0; 124.2; 174.1. |
| 404 | 2 | Ex. no. 433/ Alkylation/ 57% | [M + H]⁺: m/z = 360.4, $R_t$ = 2.6 min. | ¹H-NMR (CDCl₃): 0.90 (3 H, t, J = 7.1 Hz); 1.10-1.45 (10 H, m); 1.46-1.82 (4 H, m); 1.88-2.24 (6 H, m); 2.21 (6 H, s); 2.27 (2 H, s); 2.48-2.58 (2 H, m); 3.16 (2 H, s); 3.33-3.41 (2 H, m).<br>¹³C-NMR (CDCl₃): 14.5; 17.2; 24.1; 26.8; 28.9; 30.9; 32.1; 32.3; 34.0; 35.2; 36.2; 37.6; 39.3; 43.4; 56.2; 60.5; 124.5; 174.4. |
| 405 | 1 | Ex. no. 71/ Acylation/ 60% | m/z: [M + H]⁺ = 385.4, $R_t$ = 2.9 min. | ¹H-NMR (CDCl₃): 0.40-0.46 (2 H, m); 0.70-0.77 (2 H, m); 1.20-1.36 (2 H, m); 1.52-1.57 (2 H, m); 1.60-1.70 (2 H, m); 1.85-2.00 (4 H, m); 2.03 and 2.05 (6 H, 2 s); 2.17-2.36 (2 H, m); 2.41-2.48 (2 H, m); 3.23 and 3.25 (3 H, 2 s); 3.39 and 3.40 (2 H, 2 s); 3.43-3.50 (2 H, m); 7.26-7.33 (3 H, m); 7.34-7.41 (2 H, m).<br>¹³C-NMR (CDCl₃): 12.27; 12.3; 28.0; 28.1; 30.1; 30.6; 30.64; 31.0; 31.3; 31.4; 36.0; 37.6; 38.0; 38.1; 40.4; 42.3; 44.0; 45.0; 53.75; 55.2; 56.4; 60.9; 61.56; 61.59; 126.5; 126.7; 127.6; 127.63; 127.7; 127.74; 171.7. |
| 406 | 1 | Ex. no. 432/ Alkylation/ 66% | [M + H]⁺: m/z = 365.4, $R_t$ = 2.9 min. | ¹H-NMR (CDCl₃): 0.91 (3 H, t, J = 7.1 Hz); 1.10-1.40 (10 H, m); 1.52-1.80 (6 H, m); 1.82-1.94 (4 H, m); 2.06-2.18 (2 H, m); 2.21 (6 H, s); 2.24 (2 H, s); 3.16 (3 H, s); 3.18 (2 H, s); 3.23-3.29 (2 H, m).<br>¹³C-NMR (CDCl₃): 12.5; 14.2; 23.8; 26.5; 28.4; 30.8; 31.2; 32.0; 32.2; 35.5; 37.4; 37.9; 45.4; 49.3; 56.8; 58.4; 78.3; 173.8. |
| 407 | 1 | Ex. no. 426/ Acylation/ 91% | m/z: [M + H]⁺ = 409.3 (58%) [MH − NHMe₂]⁺ = 364.3 (100%), $R_t$ = 3.0 min, | ¹H-NMR (CDCl₃): 1.31-1.42 (2 H, m); 1.54-2.04 (14 H, m); 2.11 (2 H, s); 2.12 (4 H, m); 2.39-2.46 (2 H, m); 3.33 (3 H, s); 3.44-3.53 (2 H, m); 3.62 (2 H, s); 6.36-6.39 (1 H, m); 6.41-6.43 (1 H, m).<br>¹³C-NMR (CDCl₃): 15.3; 28.45; 28.52; 30.6; 31.4; 32.2; 32.5; 35.2; 38.1; 39.3; 42.3; 44.3; 44.9; 45.3; 47.3; 48.7; 48.8; 54.5; 56.5; 59.1; 59.3; 77.6; 77.7; 106.0; 106.2; 106.3; 121.4; 162.5; 165.4; 175.2. |
| 409 | 2 | Ex. no. 433/ Alkylation/ 43% | [M + H]⁺: m/z = 337.3, $R_t$ = 2.1 min. | ¹H-NMR (CDCl₃): 0.89 (3 H, t, J = 7.2 Hz); 1.10-1.42 (10 H, m); 1.52-1.62 (2 H, m); 1.66-1.78 (2 H, m); 1.87 (2 H, dd, J = 14.5 and 7.4 Hz); 2.19 (6 H, s); 2.24 (2 H, s); 2.90-3.02 (1 H, m); 3.09 (2 H, s); 3.18 (2 H, t, J = 7.1 Hz); 4.37 (2 H, t, J = 6.1 Hz); 4.77 (2 H, dd, J = 7.7 and 5.9 Hz).<br>¹³C-NMR (CDCl₃): 14.0; 23.6; 26.6; 28.6; 30.5; 31.2; 31.8; 32.9; 35.7; 37.1; 40.0; 43.1; 55.9; 59.9; 77.5; 173.9. |
| 410 | 1 | Ex. no. 432/ Alkylation/ 35% | [M + H]⁺: m/z = 337.4, $R_t$ = 2.5 min. | ¹H-NMR (CDCl₃): 0.91 (3 H, t, J = 7.2 Hz); 1.10-1.40 (10 H, m); 1.52-1.64 (2 H, m); 1.66-1.78 (2 H, m); 1.89 (2 H, dd, J = 14.5 and 7.5 Hz); 2.20 (6 H, s); 2.23 (2 H, s); 2.90-3.02 (1 H, m); 3.14 (2 H, s); 3.19 (2 H, t, J = 7.1 Hz); 4.38 (2 H, t, J = 6.1 Hz); 4.78 (2 H, dd, J = 7.7 and 6.0 Hz).<br>¹³C-NMR (CDCl₃): 14.2; 23.8; 26.4; 28.4; 30.7; 31.1; 32.0; 33.0; 35.5; 37.2; 40.2; 45.1; 55.8; 57.7; 77.6; 173.9. |
| 411 | 1 | Ex. no. 426/ Acylation/ 45% | m/z: [M + H]⁺ = 395.3 (55%) [MH − NHMe₂]⁺ = 350.2 (100%), $R_t$ = 2.7 min. | ¹H-NMR (CDCl₃): 0.72-0.76 (2 H, m); 0.94-0.98 (2 H, m); 1.35-1.42 (2 H, m); 1.58-1.68 (4 H, m); 1.82-1.95 (2 H, m); 1.95-2.15 (2 H, m, overlapped); 2.12 (6 H, s); 3.32 (3 H, s); 3.33-3.40 (0.7 H, m); 3.43-3.50 (1.1 H, m, overlapped); 3.44 (2 H, s); 3.56 (1.3 H, br. s); 3.72 (0.7 H, br. s); 6.36-6.40 (1 H, m); 6.41-6.43 (1 H, m).<br>¹³C-NMR (CDCl₃): 10.5; 26.6; 30.6; 31.4; 32.1; 32.6; 35.5; 38.1; 41.9; 44.5; 56.2; 58.7; 60.2; 77.5; 106.3; 121.3; 126.5; 165.4; 171.0. |
| 412 | 1 | Ex. no. 18/ Acylation/ 29% | m/z [M + H]⁺ = 391.3, $R_t$ = 2.8 min. | ¹H-NMR (CDCl₃): 0.41-0.46 (2 H, m); 0.71-0.77 (2 H, m); 1.23-1.45 (2 H, m); 1.58-1.74 (5 H, m); 1.87-2.08 (4 H, m); 2.09 and 2.11 (6 H, 2 s); 2.13-2.22 (1 H, m); 2.41-2.48 (2 H, m); 3.23 and 3.25 (3 H, 2 s); 3.36 and 3.37 (2 H, 2 s); 3.49 (2 H, q, J = 7.2 Hz); 6.84-6.87 (1 H, m); 7.02-7.06 (1 H, m); 7.22-7.26 (1 H, m).<br>¹³C-NMR (CDCl₃): 12.28; 12.3; 28.0; 28.1; 30.6; 31.0; 31.1; 31.2; 32.9; 33.2; 35.6; 37.1; 38.1; 38.11; 40.2; 42.0; 44.0; 45.1; 53.75; 53.77; 55.4; 56.5; 59.9; 61.57; 61.6; 123.4; 124.9; 126.2; 126.3; 171.7. |
| 413 | 2 | Ex. no. 433; Alkylation/ 36% | [M + H]⁺: m/z = 365.4, $R_t$ = 2.7 min. | ¹H-NMR (CDCl₃): 0.90 (3 H, t, J = 7.1 Hz); 1.10-1.46 (10 H, m); 1.50-1.92 (12 H, m); 2.05-2.16 (2 H, m); 2.20 (6 H, s); 2.26 (2 H, s); 3.15 (3 H, s); 3.22-3.28 (2 H, m).<br>¹³C-NMR (CDCl₃): 12.5; 14.0; 23.8; 26.5; 28.7; 29.7; 30.4; 31.3; 31.8; 35.7; 37.2; 37.6; 41.0; 43.4; 49.4; 56.1; 60.1; 78.3; 173.7. |
| 414 | 2 | Ex. no. 408 Step1/ Acylation/ 44% | m/z: [M + H]⁺ = 355.4, $R_t$ = 3.0 min. | ¹H-NMR (CDCl₃): 1.27-1.37 (2 H, m); 1.57-1.75 (4 H, m); 1.75-1.92 (4 H, m); 1.93-2.03 (1 H, m); 2.04 (6 H, s); 2.06-2.22 (5 H, m); 2.26 (2 H, d, J = 7.4 Hz); 2.34 (1 H, d, J = 7.4 Hz); 2.62-2.76 (1 H, m); 3.07 and 3.14 (2 H, 2 s); 3.48 (2 H, t, J = 7.2 Hz); 3.50 (2 H, t, J = 7.2 Hz); 7.28-7.32 (3 H, m); 7.33-7.41 (2 H, m).<br>¹³C-NMR (CDCl₃): 18.69; 18.74; 28.5; 28.6; 30.4; 30.5; 31.1; 31.11; 32.27; 32.34; 34.3; 36.0; 38.0; 40.2; 41.2; 41.6; 42.3; 44.0; 45.3; 56.2; 58.1; 60.7; 128.6; 127.4; 127.5; 127.86; 127.72; 171.0. |

-continued

| Ex. no. | Diastereomer* | Building Block/Method/Yield | LC-MS [M + H]⁺/$R_t$ | NMR spectrum |
|---|---|---|---|---|
| 415 | 2 | Ex. no. 25/ Acylation/ 46% | m/z: [M + H]⁺ = 351.3, $R_t$ = 2.4 min. | $^1$H-NMR (CDCl$_3$): 1.36-1.46 (2 H, m); 1.63-1.74 (2 H, m); 1.77 (1 H, t, J = 7.2 Hz); 1.85 (1 H, t, J = 7.2 Hz); 196-2.09 (4 H, m); 2.10 (6 H, s); 2.45 (1 H, t, J = 6.4 Hz); 2.51 (1 H, t, J = 6.6 Hz); 3.18 and 3.24 (2 H, 2 s); 3.31 and 3.34 (3 H, 2 s); 3.48-3.55 (2 H, m); 3.66 (1 H, t, J = 6.4 Hz); 3.69 (1 H, t, J = 6.6 Hz); 6.80-6.86 (1 H, m); 7.00-7.06 (1 H, m); 7.20-7.25 (1 H, m). $^{13}$C-NMR (CDCl$_3$): 30.9; 33.1; 34.7; 35.1; 36.3; 38.1; 40.1; 42.1; 44.1; 45.2; 55.9; 57.5; 58.8; 58.9; 59.7; 68.6; 123.4; 124.8; 126.17; 126.24; 143.0; 169.58; 169.61. |
| 416 | 2 | Ex. no. 25/ Acylation/ 65% | m/z: [M + H]⁺ = 349.3, $R_t$ = 2.9 min. | $^1$H-NMR (CDCl$_3$): 0.92 (3 H, d, J = 6.3 Hz); 0.95 (3 H, d, J = 6.3 Hz); 1.37-1.45 (2 H, m); 1.62-1.74 (2 H, m); 1.77 (1 H, t, J = 7.2 Hz); 1.85 (1 H, t, J = 7.1 Hz); 2.00-2.10 (5 H, m); 2.109 and 2.11 (6 H, 2 s); 2.12-2.20 (2 H, m); 3.15 and 3.24 (2 H, 2 s); 3.46-3.55 (2 H, m); 6.82-6.87 (1 H, m); 7.00-7.06 (1 H, m); 7.21-7.26 (1 H, m). $^{13}$C-NMR (CDCl$_3$): 22.6; 22.7; 25.5; 25.6; 30.9; 33.1; 34.4; 36.3; 38.1; 40.0; 42.1; 43.3; 43.7; 44.1; 45.4; 56.0; 57.7; 59.8; 123.4; 124.9; 126.2; 126;3; 143.0; 171.38; 17144. |
| 418 | 1 | Ex. no. 426/ Acylation/ 73% | m/z: [M + H]⁺ = 397.3 (41%) [MH − NHMe$_2$]⁺ = 352.3 (100%), $R_t$ = 2.9 min. | $^1$H-NMR (CDCl$_3$): 1.26 (6 H, s); 1.34-1.42 (2 H, m); 1.55-1.68 (4 H, m); 1.84-1.91 (2 H, m); 1.96-2.05 (2 H, m); 2.12 (6 H, s); 3.35 (3 H, s); 3.43 (2 H, s); 3.45 (2 H, s); 3.56 (2 H, br. s); 6.37-6.39 (1 H, m); 6.41-6.43 (1 H, m). $^{13}$C-NMR (CDCl$_3$): 22.9; 30.7; 32.5; 38.1; 43.6; 46.2; 53.4; 57.2; 59.3; 60.1; 80.2; 106.2; 106.3; 110.0; 121.1; 162.5; 165.4; 174.8. |
| 552 | 2 | Ex. no. 86/ N-Demethylation/ 34% | m/z: [M + H]⁺ = 341.3 (88%) [MH − H2NMe]+ = 310.3 (100%), $R_t$ = 3.0 min. | $^1$H-NMR (CDCl$_3$): 1.34-1.46 (2 H, m); 1.45-1.64 (1 H, m); 1.64-1.98 (11 H, m); 2.00 (1.3 H, s); 2.01 (1.7 H, s); 2.02-2.10 (1 H, m); 2.20-2.10 (2 H, m); 2.36 (1 H, d, J = 7.3 Hz); 2.38 (1 H, d, J = 7.3 Hz); 2.70-2.80 (1 H, m); 3.30 (1.2 H, s); 3.34 (0.8 H, s); 3.43-3.51 (2 H, m); 7.20-7.28 (1 H, m); 7.32-7.44 (4 H, m). $^{13}$C-NMR (CDCl$_3$): 4.4; 6.88; 6.99; 28.6; 30.7; 31.0; 32.2; 32.3; 34.0; 35.6; 39.5; 39.9; 40.3; 42.4; 44.1; 45.2; 56.8; 57.3; 58.1; 126.1; 126.3; 126.5; 128.3; 128.4; 128.5; 171.41; 171.45. |
| 521 | 2 | Ex. no. 417 Step6/ Alkylation/ 85% | m/z: [M + H]⁺ = 395.3 (100%) [MH − NHMe$_2$]⁺ = 350.3 (37%), $R_t$ = 2.6 min. | $^1$H-NMR (CDCl$_3$): 0.40-0.43 (2 H, m); 0.75-0.78 (2 H, m); 1.43-1.49 (2 H, m); 1.72-178 (4 H, m); 191-197 (4 H, m); 2.11 (6 H, s); 2.19 (2 H, s); 3.25 (3 H, s); 3.28 (2 H, s); 3.39-3.43 (2 H, m); 6.39 (1 H, dd, J = 4.0 and 1.7 Hz); 6.42 (1 H, m). $^{13}$C-NMR (CDCl$_3$): 12.1; 30.4; 32.2; 32.7; 35.5; 38.0; 39.9; 44.4; 53.9; 58.9; 59.5; 60.0; 106.3; 106.4; 121.1; 162.5; 165.4; 173.5. |
| 422 | 1 | Ex. no. 85/ N-Demethylation/ 30% | m/z: [M + H]⁺ = 327.3 (76%) [MH − H2NMe]+ = 296.3 (100%), $R_t$ = 2.9 min. | $^1$H-NMR (CDCl$_3$): 0.12-0.21 (2 H, m); 0.53-0.59 (2 H, m); 1.05-1.15 (1 H, m); 1.34-1.46 (2 H, m); 1.64-1.79 (4 H, m); 1.79-1.87 (2 H, m); 1.96-2.10 2 H, m); 2.01 (3 H, s); 2.20 (2 H, t, J = 6.5 Hz); 3.28 (1.1 H, s); 3.38 (0.9 H, s); 3.44 (1.1 H, t, J = 7.1 Hz); 3.52 (0.9 H, t, J = 7.3 Hz); 7.20-7.29 (1 H, m); 7.32-7.43 (4 H, m). $^{13}$C-NMR (CDCl$_3$): 18.75; 18.76; 28.58; 28.62; 30.7; 30.9; 32.3; 32.4; 34.0; 35.5; 40.3; 41.2; 41.7; 42.3; 44.0; 45.3; 56.7; 57.2; 57.3; 58.2; 126.1; 126.2; 126.4; 128.2; 128.3; 171.1. |
| 423 | 1 | Ex. no. 74/ N-Demethylation/ 33% | m/z: [M + H]⁺ = 335.3 (46%) [MH − H2NMe]+ = 304.2 (100%), $R_t$ = 2.9 min. | $^1$H-NMR (CDCl$_3$): 0.96 (3 H, d, J = 2.1 Hz); 0.97 (3 H, d, J = 2.1 Hz); 1.34-1.52 (3 H, m); 1.63-1.73 (3 H, m); 1.74-1.80 (1 H, m); 1.80-1.90 (2 H, m); 1.95-2.10 (2 H, m); 2.12 (3 H, d, J = 2.2 Hz); 2.13-2.15 (2 H, m); 2.15-2.23 (1 H, m); 3.30 (1.1 H, s); 3.36 (0.9 H, s); 3.49 (2 H, td, J = 13.9, 7.2 Hz); 6.88-6.91 (1 H, m); 6.94-6.98 (1 H, m); 7.20-7.24 (1 H, m). $^{13}$C-NMR (CDCl$_3$): 22.7; 22.8; 25.59; 25.62; 28.6; 28.7; 30.8; 30.9; 34.2; 40.2; 42.3; 43.3; 43.7; 44.0; 45.3; 563.; 56.7; 56.8; 57.8; 132.7; 123.8; 126.3; 126.4; 171.5. |

* 1 = polar, 2 = non-polar, 3 = a diastereomer

Investigations of the Activity of the Compounds According to the Invention

Measurement of the ORL1 Binding

The compounds were investigated in a receptor binding assay with $^3$H-nociceptin/orphanin FQ with membranes from recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 µg of membrane protein per 200 µl batch in 50 mM hepes, pH 7.4, 10 mM MgCl$_2$ and 1 mM EDTA. The binding to the ORL1 receptor was determined using in each case 1 mg of WGA-SPA beads (Amersham-Pharmacia, Freiburg) by incubation of the batch at RT for one hour and subsequent measurement in a Trilux scintillation counter (Wallac, Finland). The affinity is stated in Table 1 as the nanomolar $K_1$ value in or % inhibition at c=1 µM.

Measurement of the µ Binding

The receptor affinity for the human µ opiate receptor was determined in a homogeneous set-up in microtitre plates. For this, dilution series of the compound to be tested in each case were incubated with a receptor membrane preparation (15-40 µg of protein per 250 µl of incubation batch) of CHO-K1 cells which express the human µ opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and of 1 mg of WGA-SPA-Beads (wheat germ agglutinin SPA beads from Amersham/Pharmacia, Freiburg, Germany) in a total volume of 250 µl for 90 minutes at room temperature. 50 mmol/l of Tris-HCl supplemented with 0.05 wt. % of sodium azide and with 0.06 wt. % of bovine serum albumin was used as the incubation buffer. 25 μmol/l of naloxone were additionally added for determination of the non-specific binding. After the end of the ninety-minute incubation time, the microtitre plates were centrifuged for 20 minutes at 1,000 g and the radioactivity was measured in a β-counter (Microbeta-Trilux, PerkinElmer Wallac, Freiburg, Germany). The percentage displacement of the radioactive ligand from its binding to the human μ opiate receptor was determined at a concentration of the test substances of 1 μmol/l and stated as the percentage inhibition (% inhibition) of the specific binding. Starting from the percentage displacement by various concentrations of the substances of the general formula I to be tested, $IC_{50}$ inhibitory concentrations which cause a 50 percent displacement of the radioactive ligand were calculated in some cases. By conversion by means of the Cheng-Prusoff relationship, Ki values for the test substances were obtained. In some cases determination of the Ki value was dispensed with and only the inhibition at a test concentration of 1 μM was determined.

Testing of Analgesia in the Tail Flick Test in Rats

The analgesic activity of the test compounds was investigated in the focal ray (tail flick) test in rats in accordance with the method of D'Amour and Smith (J. Pharm. Exp. Ther. 72, 74 79 (1941)). Female Sprague Dawley rats weighing between 130 and 190 g were used for this. The animals were placed individually in special test cages and the base of the tail was exposed to a focused heat ray of a lamp (Tail-flick type 50/08/1.bc, Labtec, Dr Hess). The intensity of the lamp was adjusted such that in the case of untreated animals the time between switching on of the lamp to sudden pulling away of the tail (pain latency) was 2.5-5 seconds. Before administration of a test compound, the animals were pretested twice in the course of 30 minutes and the mean of these measurements was calculated as the pretest mean The pain was measured 20, 40 and 60 min after intravenous administration. The analgesic action was determined as the increase in pain latency (% MPE) according to the following formula: $[(T_1-T_0)/(T_2-T_0)] \times 100$. In this, $T_0$ is the latency period before and $T_1$ the latency period after administration of the substance, $T_2$ is the maximum exposure time (12 sec). To determine the dose dependency, the particular test compound was administered in 3-5 logarithmically increasing doses, which included the threshold and the maximum active dose in each case, and the $ED_{50}$ values were determined with the aid of regression analysis. The $ED_{50}$ calculation was performed at the action maximum, 20 minutes after intravenous administration of the substance.

Chung Model: Mononeuropathy Pain Following Spinal Nerve Ligation

Animals: Male Sprague Dawley rats (140-160 g), from a commercial breeder (Janvier, Genest St. Isle, France), were kept under a 12:12 h light-dark rhythm. The animals were kept with food and tap water ad libitum. A pause of one week was maintained between delivery of the animals and the operation. After the operation the animals were tested several times over a period of 4-5 weeks, a wash-out time of at least one week being adhered to.

Description of the Model: The left L5, L6 spinal nerves were exposed under pentobarbital narcosis (Narcoren®, 60 mg/kg i.p., Merial GmbH, Hallbergmoos, Germany) by removing a piece of the paravertebral muscle and a part of the left spinal process of the L5 lumbar vertebra. The spinal nerves L5 and L6 were carefully isolated and tied off with a firm ligature (NC-silk black, USP 5/0, metric 1, Braun Melsungen AG, Melsungen, Germany) (Kim and Chung 1992). After ligation the muscle and adjacent tissue were sewn up and the wound was closed by means of metal clamps.

After a recovery period of one week the animals were placed in cages with a wire floor for measurement of the mechanical allodynia. The withdrawal threshold was determined on the ipsi- and/or contralateral hind paw by means of an electronic von Frey filament (Somedic AB, Malmö, Sweden). The median of five stimulations gave one data point. The animals were tested 30 min before and at various times after administration of the test substance or vehicle solution. The data were determined as % maximum possible effect (% MPE) from the pretesting of the individual animals (=0% MPE) and the test values of an independent sham control group (=100% MPE). Alternatively, the withdrawal thresholds were shown in grams.

Statistical Evaluation: $ED_{50}$ values and 95% confidence intervals were determined via semilogarithmic regression analysis at the point in time of the maximum effect. The data were analysed via a variance analysis with repeated measurements and a post hoc Bonferroni analysis. The group size was usually n=10.

References : Kim, S. H. and Chung, J. M., An experimental model for peripheral neuropathy produced by segmental spinal nerve ligation in the rat, Pain, 50 (1992) 355-363.

Results

| No. | Diastereomer | % inhibition (ORL1) [1 μM] | Ki (ORL1) mean [μM] | % inhibition (μ) [1 μM] | Ki (μ) mean [μm] | Tail flick rat, i.v. $ED_{50rat}$ [μg/kg] or % MPE (@μg/kg) | SNL rat, i.v. $ED_{50rat}$ [μg/kg] or % MPE (@μg/kg) |
|---|---|---|---|---|---|---|---|
| 1 | 1 | 9 | | 26 | 1.06 | nd | nd |
| 2 | 2 | 11.5 | | 4 | 4.79 | nd | nd |
| 3 | 1 | 15 | | 31.5 | 1.83 | nd | nd |
| 4 | 2 | 9 | | 28.5 | 0.92 | nd | nd |
| 5 | 1 | 15 | | 33 | 1.45 | nd | nd |
| 6 | 2 | 23.5 | | 49 | 1.1 | nd | nd |
| 7 | 1 | 16 | 2.16 | 37.5 | 1.59 | nd | nd |
| 8 | 2 | 25 | | 45.5 | 1.05 | nd | nd |
| 9 | 2 | 92.5 | 0.17 | 7.4 | 0.0045 | nd | nd |
| 10 | 1 | 27.67 | 2.02 | 67 | 0.41 | nd | nd |
| 11 | 2 | 43.5 | 0.16 | 71.5 | 0.034 | nd | nd |
| 12 | 2 | 74.33 | 0.12 | 100.5 | 0.0079 | nd | nd |
| 13 | 3 | 13 | | 34 | 1.885 | nd | nd |
| 14 | 1 | 57.5 | 0.068 | 76.5 | 0.026 | 83%@1000 | nd |

-continued

| No. | Diastereomer | % inhibition (ORL1) [1 μM] | Ki (ORL1) mean [μM] | % inhibition (μ) [1 μM] | Ki (μ) mean [μm] | Tail flick rat, i.v. ED$_{50rat}$ [μg/kg] or % MPE (@μg/kg) | SNL rat, i.v. ED$_{50rat}$ [μg/kg] or % MPE (@μg/kg) |
|---|---|---|---|---|---|---|---|
| 15 | 2 | 37.5 | 0.49 | 50.5 | 0.22 | nd | nd |
| 16 | 1 | 10 | | 0 | | nd | nd |
| 17 | 3 | 19 | | 28 | 0.895 | nd | nd |
| 18 | 1 | 47 | 0.175 | 90 | 0.018 | nd | nd |
| 19 | 1 | 70 | 0.08 | 85 | 0.044 | nd | nd |
| 20 | 1 | 82.5 | 0.0096 | 98.5 | 0.00227 | 26 | 30 |
| 21 | 1 | 89.5 | 0.0029 | 98.5 | 0.0028 | 414 | 105 |
| 22 | 1 | 94 | 0.0008 | 98.5 | 0.00114 | 100%@1000 | nd |
| 23 | 1 | 58 | 0.068 | 84.5 | 0.05 | nd | nd |
| 24 | 2 | 49.5 | 0.74 | 70 | 0.13 | nd | nd |
| 25 | 2 | 43.5 | 0.21 | 65.5 | 0.17 | nd | nd |
| 26 | 2 | 63 | 0.38 | 77.5 | 0.12 | nd | nd |
| 27 | 1 | 21.67 | | 61.5 | 1105 | nd | nd |
| 28 | 2 | 49 | 0.15 | 70.5 | 0.2 | nd | nd |
| 29 | 1 | 81.5 | 0.00585 | 93 | 0.0305 | 157 | 100 |
| 30 | 1 | 16.5 | | 32 | 4.04 | nd | nd |
| 31 | 1 | 57.5 | 1135 | 79.5 | 0.13 | nd | nd |
| 32 | 1 | 77.5 | 0.0155 | 93.5 | 0.00765 | 6.54 | 44%@6.81 |
| 33 | 2 | 31 | 0.425 | 16 | 1.2 | nd | nd |
| 34 | 2 | 57.5 | 0.805 | 41 | 12420 | nd | nd |
| 35 | 1 | 91 | 0.039 | 98.5 | 0.00815 | 0%@100 | nd |
| 36 | 1 | 73.5 | 0.023 | 98.5 | 0.00805 | nd | nd |
| 37 | 1 | 34.5 | 0.26 | 86.5 | 0.077 | nd | nd |
| 38 | 1 | 26 | 0.15 | 86 | 0.045 | nd | nd |
| 39 | 1 | 84.5 | 0.027 | 100.5 | 0.0048 | 100%@100 | nd |
| 40 | 1 | 34.5 | 0.15 | 80.5 | 0.125 | nd | nd |
| 41 | 1 | 64.5 | 0.064 | 83.5 | 0.078 | nd | nd |
| 42 | 1 | 63 | | 60 | | nd | nd |
| 43 | 1 | 73 | 0.00845 | | 0.00805 | 100%@100 | nd |
| 44 | 1 | 48 | 0.085 | 80.5 | 0.0115 | nd | nd |
| 45 | 1 | 61 | 0.102 | 85 | 0.077 | nd | nd |
| 46 | 1 | 94 | 0.00235 | 98 | 0.0048 | 3.53 | 28%@3 |
| 47 | 1 | 71.5 | 0.018 | 80.5 | 0.0465 | 5260 | nd |
| 48 | 1 | 94 | | 99.5 | | 3.36 | nd |
| 49 | 1 | 92.33 | 0.0145 | 98.5 | 0.00895 | nd | nd |
| 50 | 1 | 97.5 | 0.00024 | 99.5 | 0.00037 | 94%@10 | nd |
| 51 | 1 | 98 | 0.00145 | 99 | 0.0015 | nd | nd |
| 52 | 1 | 98 | 0.00052 | 101.5 | 0.0006 | 52.8 | nd |
| 53 | 1 | 97 | 0.0017 | 100 | 0.00102 | 63%@1000 | nd |
| 54 | 1 | 93.5 | 0.00044 | 100 | 0.0004 | nd | nd |
| 55 | 1 | 43.5 | 0.105 | 87 | 0.047 | nd | nd |
| 56 | 1 | 89 | 0.0034 | 99 | 0.00175 | 7.16 | nd |
| 57 | 1 | 64 | 0.0715 | 92 | 0.037 | 25%@100 | nd |
| 58 | 1 | 52.67 | 0.155 | 93.5 | 0.0535 | nd | nd |
| 59 | 1 | 97 | 0.00116 | 99.5 | 0.00062 | nd | nd |
| 60 | 1 | 77 | 0.036 | 93.5 | 0.0215 | 90%@1000 | nd |
| 61 | 1 | 78 | 0.02 | 96.5 | 0.00715 | 87%@100 | nd |
| 62 | 1 | 98 | 0.00072 | 99 | 0.00052 | nd | nd |
| 63 | 1 | 76 | 0.0825 | 90.5 | 0.0365 | nd | nd |
| 64 | 1 | 96 | 0.00205 | 100.5 | 0.0013 | 1.86 | nd |
| 65 | 1 | 89.5 | 0.0165 | 99.5 | 0.00305 | nd | nd |
| 66 | 1 | 81.5 | 0.0185 | 99.5 | 0.00545 | nd | nd |
| 67 | 1 | 92 | 0.00295 | 99.5 | 0.00107 | 14.6 | nd |
| 68 | 1 | 97.5 | 0.00073 | 100.5 | 0.00039 | nd | nd |
| 69 | 1 | 97.5 | 0.00076 | 99.5 | 0.00035 | nd | nd |
| 70 | 1 | 84.5 | 0.0305 | 94.5 | 0.022 | nd | nd |
| 71 | 1 | 62.5 | 0.057 | 65.5 | 0.215 | nd | nd |
| 72 | 1 | 81.5 | 0.00585 | 93 | 0.0305 | nd | nd |
| 73 | 1 | 43 | 0.161 | 58.5 | 0.275 | nd | nd |
| 74 | 1 | 80 | 0.00975 | 93 | 0.0065 | 40%@1000 | nd |
| 75 | 1 | 97 | 0.00111 | 99.5 | 0.00115 | 16.2 | 69%@21.5 |
| 76 | 1 | 96.5 | 0.00075 | 100.5 | 0.00104 | 15.2 | 65%@21.5 |
| 77 | 1 | 94.5 | 0.00247 | 99 | 0.00165 | 78.6 | nd |
| 78 | 1 | 86.5 | | 97.5 | | nd | nd |
| 79 | 1 | 98.5 | 0.0003 | 100 | 0.00036 | nd | nd |
| 80 | 1 | 60.5 | 0.24 | 90 | 0.0795 | nd | nd |
| 81 | 1 | 78.5 | 0.054 | 92.5 | 0.064 | 55%@1000 | nd |
| 82 | 1 | 90 | 0.015 | 97.5 | 0.00935 | 0%@100 | nd |
| 83 | 1 | 97.5 | 0.00056 | 99.5 | 0.0004 | 8.03 | nd |
| 84 | 1 | 81 | 0.0215 | 95.5 | 0.0134 | nd | nd |
| 85 | 1 | 94.5 | 0.0018 | 99.5 | 0.00113 | 16.3 | nd |
| 86 | 1 | 95.5 | 0.00045 | 101.5 | 0.00063 | 4.17 | nd |

-continued

| No. | Diastereomer | % inhibition (ORL1) [1 µM] | Ki (ORL1) mean [µM] | % inhibition (µ) [1 µM] | Ki (µ) mean [µm] | Tail flick rat, i.v. ED$_{50rat}$ [µg/kg] or % MPE (@µg/kg) | SNL rat, i.v. ED$_{50rat}$ [µg/kg] or % MPE (@µg/kg) |
|---|---|---|---|---|---|---|---|
| 87 | 1 | 96 | 0.00106 | 100 | 0.00075 | 0%@100 | nd |
| 88 | 3 | 72 | 0.0735 | 97.5 | 0.0125 | nd | nd |
| 89 | 3 | 89 | | 100 | | nd | nd |
| 90 | 1 | 86.5 | 0.03 | 97.5 | 0.026 | nd | nd |
| 91 | 1 | 86.5 | 0.0068 | 95.5 | 0.00805 | nd | nd |
| 92 | 3 | 41395 | | 23 | 3585 | nd | nd |
| 93 | 3 | 12 | 24108 | 92 | 0.0265 | nd | nd |
| 94 | 3 | 35.5 | 0.8 | 102.5 | 0.0053 | nd | nd |
| 95 | 3 | 46 | 0.44 | 96.5 | 0.0265 | nd | nd |
| 96 | 3 | 57.5 | 0.275 | 103 | 0.0068 | nd | nd |
| 97 | 3 | 67.5 | | 94.5 | | nd | nd |
| 98 | 3 | 85 | 0.019 | 99.5 | 0.0096 | nd | nd |
| 99 | 3 | 67.5 | 0.028 | 97 | 0.0052 | 100%@100 | nd |
| 100 | 3 | 45 | 0.185 | 86.5 | 0.052 | nd | nd |
| 101 | 3 | 82.5 | 0.011 | 88.67 | 0.017 | 0%@1000 | nd |
| 102 | 3 | 94.5 | 0.00435 | 99.5 | 0.00465 | nd | nd |
| 103 | 3 | 79 | 0.0295 | 99.5 | 0.00405 | 5.43 | 2.44 |
| 104 | 3 | 88.5 | 0.0155 | 98.5 | 0.00245 | 162 | 107 |
| 105 | 3 | 90 | 0.00625 | 99.5 | 0.00069 | nd | nd |
| 106 | 1 | 78 | 0.62 | 65.5 | 1775 | nd | nd |
| 107 | 2 | 13.5 | | 54.5 | 0.95 | nd | nd |
| 108 | 1 | 21.5 | 0.91 | 54 | 0.64 | nd | nd |
| 109 | 2 | 8 | | 6 | | nd | nd |
| 110 | 1 | 24.5 | 1.52 | 43.5 | 1.21 | nd | nd |
| 111 | 2 | 0 | | 5 | | nd | nd |
| 112 | 1 | 59.5 | | 54 | | nd | nd |
| 113 | 2 | 38.5 | 1.34 | 44 | 2.54 | nd | nd |
| 114 | 3 | 30 | | 34 | 0.71 | nd | nd |
| 115 | 3 | 28 | 0.6 | 65 | 0.17 | nd | nd |
| 116 | 3 | 20 | 1.57 | 67.5 | 0.145 | nd | nd |
| 117 | 3 | 15 | | 31.5 | 2.55 | nd | nd |
| 118 | 2 | 6.5 | | 3.5 | 5.5 | nd | nd |
| 119 | 1 | 29 | | 23 | 3.57 | nd | nd |
| 120 | 2 | 13 | | 31 | 7.07 | nd | nd |
| 121 | 1 | 26 | 1.51 | 58 | 0.23 | nd | nd |
| 122 | 2 | 21 | | 45 | 0.67 | nd | nd |
| 123 | 1 | 22 | 1.88 | 71.5 | 0.15 | nd | nd |
| 124 | 1 | 55 | 0.089 | 79.5 | 0.17 | nd | nd |
| 125 | 1 | 87 | 0.0039 | 98 | 0.00615 | 7.09 | nd |
| 126 | 1 | 97 | 0.00088 | 99 | 0.00185 | nd | nd |
| 127 | 2 | 30 | 0.36 | 25.5 | 3.97 | nd | nd |
| 128 | 1 | 98 | 0.00042 | 100.5 | 0.00034 | nd | nd |
| 129 | 2 | 47 | 0.022 | 51.5 | 0.36667 | nd | nd |
| 130 | 1 | 90.5 | 0.00075 | 99 | 0.00064 | nd | nd |
| 131 | 2 | 47 | 0.22 | 37 | 1.18 | nd | nd |
| 132 | 1 | 91.5 | 0.00079 | 99 | 0.0014 | nd | nd |
| 133 | 2 | 47.5 | 0.175 | 32 | 1.4 | nd | nd |
| 134 | 1 | 87 | | 98 | | 100%@100 | nd |
| 135 | 2 | 47.5 | 0.195 | 35.5 | 1.51 | nd | nd |
| 136 | 1 | 87.5 | 0.00135 | 100 | 0.00102 | nd | nd |
| 137 | 2 | 43 | 0.475 | 44 | 0.595 | 100%@100 | nd |
| 138 | 1 | 74 | 0.0215 | 97 | 0.00705 | 30.1 | nd |
| 139 | 2 | 28.5 | 0.68 | 23 | 3.88 | nd | nd |
| 140 | 2 | 34 | 0.235 | 44 | 1.25 | nd | nd |
| 141 | 1 | 90.5 | 0.0027 | 97.5 | 0.0019 | 4.84 | nd |
| 142 | 1 | 85 | 0.00575 | 94 | 0.0074 | 126 | 96 |
| 143 | 2 | 33 | 0.35 | 24 | 1.38 | nd | nd |
| 144 | 1 | 91 | 0.0041 | 99.5 | 0.00205 | 11.5 | 64%@21.5 |
| 145 | 2 | 53 | 0.0675 | 77 | 0.161 | nd | nd |
| 146 | 1 | 80.5 | 0.016 | 94.5 | 0.03 | nd | nd |
| 147 | 2 | 46 | 0.225 | 50.5 | 0.59 | nd | nd |
| 148 | 1 | 78 | 0.032 | 91 | 0.0425 | 70%@1000 | nd |
| 149 | 2 | 22.5 | 0.785 | 54.5 | 3.41 | nd | nd |
| 150 | 1 | 95 | 0.00205 | 99 | 0.0004 | 90%@10 | nd |
| 151 | 2 | 63 | 0.022 | 95 | 0.029 | nd | nd |
| 152 | 1 | 14 | 1.2 | 42 | 0.885 | nd | nd |
| 153 | 2 | 36.5 | 0.41 | 72 | 0.28 | nd | nd |
| 154 | 2 | 45 | 0.19 | 63.5 | 0.145 | nd | nd |
| 155 | 1 | 19 | 0.79 | 21.5 | 2.82 | nd | nd |
| 156 | 2 | 86 | 0.006 | 98 | 0.0036 | nd | nd |
| 157 | 1 | 24 | 0.805 | 11.5 | 4.77 | nd | nd |
| 158 | 2 | 94 | 0.00056 | 100 | 0.00054 | nd | nd |

-continued

| No. | Diastereomer | % inhibition (ORL1) [1 µM] | Ki (ORL1) mean [µM] | % inhibition (µ) [1 µM] | Ki (µ) mean [µm] | Tail flick rat, i.v. ED$_{50rat}$ [µg/kg] or % MPE (@µg/kg) | SNL rat, i.v. ED$_{50rat}$ [µg/kg] or % MPE (@µg/kg) |
|---|---|---|---|---|---|---|---|
| 159 | 1 | 31.5 | 0.0915 | 32.5 | 0.185 | nd | nd |
| 160 | 1 | 33 | 0.455 | 44 | 1.13 | nd | nd |
| 161 | 1 | 63 | 0.345 | 97 | 0.0535 | nd | nd |
| 162 | 2 | 82 | 0.029 | 95 | 0.038 | 422 | nd |
| 163 | 2 | 93.5 | 0.0022 | 97 | 0.003 | nd | nd |
| 164 | 1 | 39 | 0.28 | 73 | 0.365 | nd | nd |
| 165 | 2 | 96 |  | 100 |  | nd | nd |
| 166 | 1 | 76 | 0.101 | 83 | 0.17 | nd | nd |
| 167 | 2 | 97 | 0.00071 | 100.67 | 0.00108 | nd | nd |
| 168 | 1 | 37.5 | 0.235 | 70 | 2.06 | nd | nd |
| 169 | 2 | 95.5 | 0.00103 | 102 | 0.0012 | nd | nd |
| 170 | 1 | 56.5 | 0.0825 | 37 | 0.63 | nd | nd |
| 171 | 2 | 91 | 0.0047 | 99 | 0.003 | 26.8 | nd |
| 172 | 1 | 39.5 | 0.083 | 35.5 | 0.63 | nd | nd |
| 173 | 2 | 96.5 | 0.00032 | 97.5 | 0.00061 | nd | nd |
| 174 | 1 | 49.5 | 0.135 | 28 | 1.67 | nd | nd |
| 175 | 2 | 96 | 0.00395 | 99.5 | 0.0024 | 55 | 72%@46.4 |
| 176 | 1 | 63 | 0.1045 | 72 | 0.175 | nd | nd |
| 177 | 2 | 97.33 | 0.00165 | 99.5 | 0.0012 | 100%@100 | nd |
| 178 | 1 | 82.5 | 0.0395 | 96.5 | 0.0185 | nd | nd |
| 179 | 2 | 93 | 0.0067 | 99 | 0.0075 | nd | nd |
| 180 | 1 | 49.5 | 0.18 | 66.5 | 0.3 | nd | nd |
| 181 | 2 | 77 | 0.01015 | 91.5 | 0.044 | nd | nd |
| 182 | 2 | 96.5 | 0.0013 | 97 | 0.00075 | 6.92 | nd |
| 183 | 1 | 39.5 | 0.3 | 23.5 | 0.795 | nd | nd |
| 184 | 2 | 97 | 0.00066 | 95.5 | 0.0003 | 3.25 | nd |
| 185 | 1 | 49 | 0.1045 | 60.5 | 0.255 | nd | nd |
| 186 | 2 | 98.5 | 0.00205 | 99.5 | 0.0032 | nd | nd |
| 187 | 1 | 59 | 0.34 | 58.5 | 41579 | nd | nd |
| 188 | 1 | 91.5 | 0.0026 | 98 | 0.0026 | nd | nd |
| 189 | 1 | 77.5 | 0.0425 | 93.5 | 0.036 | nd | nd |
| 190 | 1 | 57 | 0.18 | 85.5 | 0.049 | nd | nd |
| 191 | 1 | 93 | 0.0015 | 98 | 0.00195 | 0%@100 | nd |
| 192 | 1 | 96 | 0.0007 | 97.5 | 0.00044 | nd | nd |
| 193 | 1 | 89 | 0.0097 | 97 | 0.0061 | nd | nd |
| 194 | 1 | 92.5 | 0.0023 | 98 | 0.00135 | nd | nd |
| 195 | 1 | 93.5 | 0.0005 | 99.5 | 0.00053 | 100%@100 | nd |
| 196 | 1 | 71.5 |  | 95 |  | nd | nd |
| 197 | 1 | 95.5 | 0.00046 | 99.5 | 0.00048 | 100%@100 | nd |
| 198 | 1 | 48.5 | 0.1025 | 87 | 0.084 | nd | nd |
| 199 | 1 | 72 | 0.073 | 93 | 0.03 | nd | nd |
| 200 | 1 | 89 | 0.0119 | 98.5 | 0.00325 | nd | nd |
| 201 | 1 | 94 | 0.0067 | 97.5 | 0.0039 | 0%@100 | nd |
| 202 | 1 | 88.5 | 0.0125 | 98 | 0.0054 | nd | nd |
| 203 | 1 | 97.33 | 0.00127 | 98 | 0.00072 | nd | nd |
| 204 | 1 | 95 | 0.00063 | 98 | 0.00145 | nd | nd |
| 205 | 1 | 48.5 | 0.185 | 82.5 | 0.0745 | nd | nd |
| 206 | 1 | 79 | 0.035 | 92 | 0.0255 | nd | nd |
| 207 | 1 | 94.5 | 0.00417 | 99.5 | 0.00475 | nd | nd |
| 208 | 1 | 96 | 0.00205 | 100 | 0.00067 | nd | nd |
| 209 | 1 | 60 | 0.1125 | 94 | 0.0315 | nd | nd |
| 210 | 1 | 80 | 0.023 | 94.5 | 0.0108 | nd | nd |
| 211 | 1 | 95.5 | 0.0053 | 99.5 | 0.00073 | nd | nd |
| 212 | 1 | 82.5 | 0.01967 | 99.33 | 0.00305 | nd | nd |
| 213 | 1 | 98 | 0.00034 | 101.5 | 0.00072 | nd | nd |
| 214 | 2 | 41.5 | 0.23 | 79.5 | 0.0645 | nd | nd |
| 215 | 2 | 42 | 0.305 | 59 | 0.285 | nd | nd |
| 216 | 1 | 85 | 0.00955 | 98.5 | 0.00615 | 52%@100 | nd |
| 217 | 1 | 97 | 0.00115 | 100 | 0.0004 | 0.7 | nd |
| 218 | 2 | 50.5 | 0.185 | 76.5 | 0.165 | nd | nd |
| 219 | 2 | 36 | 0.315 | 46 | 0.945 | nd | nd |
| 220 | 1 | 99 | 0.0012 | 97 | 0.00041 | nd | nd |
| 221 | 1 | 96.5 | 0.002 | 101 | 0.0048 | nd | nd |
| 222 | 2 | 46.5 | 0.265 | 62 | 0.605 | nd | nd |
| 223 | 1 | 55 | 0.082 | 90.5 | 0.052 | nd | nd |
| 224 | 2 | 73.5 | 0.036 | 97 | 0.02 | nd | nd |
| 225 | 1 | 49 | 0.23 | 63 | 0.545 | nd | nd |
| 226 | 1 | 94 | 0.0035 | 98 | 0.00255 | nd | nd |
| 227 | 1 | 81.5 | 0.0165 | 94 | 0.0175 | nd | nd |
| 228 | 1 | 46 | 0.23 | 79 | 0.082 | nd | nd |
| 229 | 1 | 66 | 0.025 | 87 | 0.0445 | nd | nd |
| 230 | 2 | 96.5 | 0.00315 | 98.5 | 0.0013 | nd | nd |

-continued

| No. | Diastereomer | % inhibition (ORL1) [1 μM] | Ki (ORL1) mean [μM] | % inhibition (μ) [1 μM] | Ki (μ) mean [μm] | Tail flick rat, i.v. ED$_{50rat}$ [μg/kg] or % MPE (@μg/kg) | SNL rat, i.v. ED$_{50rat}$ [μg/kg] or % MPE (@μg/kg) |
|---|---|---|---|---|---|---|---|
| 231 | 1 | 43 | 0.18 | 91.5 | 0.0585 | nd | nd |
| 232 | 1 | 97.5 | 0.00285 | 97.5 | 0.0031 | nd | nd |
| 233 | 1 | 96 | 0.00225 | 98.5 | 0.0013 | nd | nd |
| 234 | 2 | 81.5 | 0.0225 | 99.5 | 0.00435 | nd | nd |
| 235 | 1 | 98.5 | 0.00047 | 100.5 | 0.00044 | 1.44 | nd |
| 236 | 2 | 91.5 | 0.016 | 100 | 0.00155 | nd | nd |
| 237 | 1 | 97.5 | 0.00058 | 99.5 | 0.00055 | 100%@10 | nd |
| 238 | 1 | 98 | 0.00095 | 103 | 0.00082 | nd | nd |
| 239 | 1 | 98 | 0.00083 | 103.5 | 0.00069 | nd | nd |
| 240 | 1 | 45 | 0.195 | 91 | 0.08 | nd | nd |
| 241 | 2 | 89.5 | 0.015 | 99 | 0.00875 | nd | nd |
| 242 | 1 | 38.5 | 0.45 | 51 | 0.87 | nd | nd |
| 243 | 1 | 36 | 41518 | 78 | 0.12 | nd | nd |
| 244 | 2 | 26 | 0.255 | 74.5 | 0.0985 | nd | nd |
| 245 | 2 | 59.5 | 0.115 | 95 | 0.066 | nd | nd |
| 246 | 2 | 40 | 0.205 | 87.5 | 0.034 | nd | nd |
| 247 | 3 | 91.5 | 0.01015 | 98.5 | 0.00265 | 100%@100 | nd |
| 248 | 1 | 90.5 | 0.00875 | 100 | 0.0012 | nd | nd |
| 249 | 1 | 88 | 0.0117 | 99 | 0.002 | nd | nd |
| 250 | 2 | 94.5 | 0.0019 | 99.5 | 0.00079 | nd | nd |
| 251 | 2 | 82 | 0.0215 | 87 | 0.054 | nd | nd |
| 252 | 1 | 46.5 | 0.3 | 37.5 | 14.305 | nd | nd |
| 253 | 1 | 97.5 | 0.00165 | 98.5 | 0.0025 | nd | nd |
| 254 | 2 | 94.5 | 0.00875 | 94 | 0.0185 | nd | nd |
| 255 | 1 | 37.5 | 0.26 | 58.5 | 4385 | nd | nd |
| 256 | 2 | 70.5 | 0.064 | 97.33 | 0.00565 | nd | nd |
| 257 | 3 | 89 | 0.01365 | 98 | 0.0028 | nd | nd |
| 258 | 3 | 63.5 | 0.084 | 97.5 | 0.00465 | nd | nd |
| 259 | 3 | 67 | 0.062 | 95.5 | 0.062 | nd | nd |
| 260 | 2 | 90 | 0.00865 | 93.5 | 0.0535 | nd | nd |
| 261 | 1 | 42.5 | 0.395 | 40 | 1.4 | nd | nd |
| 262 | 2 | 98.5 | 0.00155 | 98 | 0.00067 | 6.6 | nd |
| 262 | 1 | 50.5 | 0.245 | 37 | 1.51 | nd | nd |
| 264 | 2 | 96.5 | 0.00275 | 98.5 | 0.0034 | 36.7 | nd |
| 265 | 3 | 71 | 0.029 | 95.5 | 0.006 | nd | nd |
| 266 | 3 | 91 | 0.00633 | 100 | 0.00145 | nd | nd |
| 267 | 3 | 64 | 0.039 | 97.7 | 0.0016 | nd | nd |
| 268 | 3 | 76.5 | 0.093 | 99 | 0.01225 | nd | nd |
| 269 | 2 | 89.5 | 0.0125 | 93 | 0.01005 | nd | nd |
| 270 | 1 | 33.5 | 0.31 | 34 | 1.16 | nd | nd |
| 271 | 1 | 54 | 0.245 | 53.5 | 1.41 | nd | nd |
| 272 | 1 | 91 | 0.00705 | 95.5 | 0.00745 | nd | nd |
| 273 | 3 | 81 |  | 89 |  | nd | nd |
| 274 | 2 | 0 | 0.00745 | 0 | 0.002 | nd | nd |
| 275 | 2 | 92 | 0.0079 | 96.5 | 0.00435 | nd | nd |
| 276 | 2 | 73.5 | 0.021 | 95 | 0.0165 | nd | nd |
| 277 | 2 | 91 | 0.0064 | 99 | 0.0008 | nd | nd |
| 278 | 2 | 88.5 | 0.0079 | 99 | 0.0014 | nd | nd |
| 279 | 2 | 93 | 0.01225 | 98.5 | 0.0106 | nd | nd |
| 280 | 2 | 93.5 | 0.0088 | 97 | 0.0076 | nd | nd |
| 281 | 2 | 75.5 | 0.0635 | 99.5 | 0.0087 | nd | nd |
| 282 | 2 | 19.5 | 1.38 | 67.5 | 0.295 | nd | nd |
| 283 | 1 | 91.5 | 0.031 | 99.5 | 0.011 | nd | nd |
| 284 | 1 | 92.5 | 0.0195 | 95.5 | 0.00765 | nd | nd |
| 285 | 1 | 95 | 0.0034 | 99 | 0.00255 | nd | nd |
| 286 | 2 | 88 | 0.02 | 99.5 | 0.0013 | nd | nd |
| 287 | 2 | 83 | 0.027 | 99 | 0.00105 | nd | nd |
| 288 | 2 | 87.5 | 0.00595 | 98.5 | 0.0046 | nd | nd |
| 289 | 1 | 45.5 | 0.17 | 69 | 0.27 | nd | nd |
| 290 | 2 | 82 | 0.019 | 97 | 0.00565 | nd | nd |
| 291 | 3 | 0.5 | 1225 | 66 | 0.175 | nd | nd |
| 292 | 3 | 69 | 0.163 | 98 | 0.0084 | nd | nd |
| 293 | 2 | 43.5 | 0.265 | 92 | 0.029 | nd | nd |
| 294 | 2 | 52.5 | 0.07733 | 95 | 0.0275 | nd | nd |
| 295 | 1 | 89 | 0.018 | 98.5 | 0.00635 | nd | nd |
| 296 | 1 | 87 | 0.0111 | 98 | 0.0053 | nd | nd |
| 297 | 3 | 26 | 0.91 | 90 | 0.055 | nd | nd |
| 298 | 3 | 85 | 0.0205 | 98 | 0.00305 | nd | nd |
| 299 | 1 | 94.5 | 0.00395 | 101 | 0.06661 | nd | nd |
| 300 | 1 | 92 | 0.0073 | 100 | 0.00155 | nd | nd |
| 301 | 3 | 66 | 0.071 | 90.5 | 0.0495 | nd | nd |
| 302 | 3 | 48 | 0.1225 | 83 | 0.06 | nd | nd |

-continued

| No. | Diastereomer | % inhibition (ORL1) [1 μM] | Ki (ORL1) mean [μM] | % inhibition (μ) [1 μM] | Ki (μ) mean [μm] | Tail flick rat, i.v. ED$_{50rat}$ [μg/kg] or % MPE (@μg/kg) | SNL rat, i.v. ED$_{50rat}$ [μg/kg] or % MPE (@μg/kg) |
|---|---|---|---|---|---|---|---|
| 303 | 1 | 93 | 0.0051 | 97.5 | 0.007 | nd | nd |
| 304 | 1 | 95 | 0.00445 | 99 | 0.0049 | nd | nd |
| 305 | 1 | 93 | 0.00245 | 99.5 | 0.00093 | nd | nd |
| 306 | 1 | 97 | 0.00114 | 96.5 | 0.00057 | nd | nd |
| 307 | 1 | 14.5 | 0.535 | 19 | 0.54 | nd | nd |
| 308 | 2 | 92 | 0.01005 | 99 | 0.00155 | nd | nd |
| 309 | 1 | 94 | 0.00113 | 100 | 0.0015 | nd | nd |
| 310 | 1 | 52 | 0.195 | 29.5 | 1.03 | nd | nd |
| 311 | 2 | 95.5 | 0.0021 | 98 | 0.00125 | nd | nd |
| 312 | 1 | 54.5 | 0.12 | 74.5 | 0.295 | nd | nd |
| 313 | 2 | 92.5 | 0.00345 | 99.5 | 0.00415 | nd | nd |
| 314 | 1 | 94 | 0.0011 | 100 | 0.00073 | nd | nd |
| 315 | 1 | 90 | 0.01055 | 100 | 0.0045 | 19.4 | nd |
| 316 | 1 | 10.5 | 1.23 | 27 | 2.15 | nd | nd |
| 317 | 2 | 92.5 | 0.0027 | 99 | 0.0015 | nd | nd |
| 318 | 2 | 88.5 | 0.0092 | 97.5 | 0.00715 | nd | nd |
| 319 | 2 | 91 | 0.005 | 96.5 | 0.005 | nd | nd |
| 320 | 1 | 93 | 0.0019 | 99.5 | 0.0018 | nd | nd |
| 321 | 1 | 52 | 0.086 | 83 | 0.1495 | nd | nd |
| 322 | 2 | 97 | 0.00165 | 101 | 0.00138 | nd | nd |
| 323 | 2 | 93 | 0.00275 | 98 | 0.00905 | nd | nd |
| 324 | 2 | 95 | 0.00135 | 100 | 0.0024 | nd | nd |
| 325 | 2 | 88 | 0.0084 | 95 | 0.013 | nd | nd |
| 326 | 2 | 96 | 0.00375 | 97.5 | 0.0043 | nd | nd |
| 327 | 1 | 93 | 0.00555 | 101.5 | 0.00155 | nd | nd |
| 328 | 1 | 96 | 0.00325 | 99 | 0.0024 | nd | nd |
| 329 | 1 | 92 | 0.0088 | 97.5 | 0.0059 | nd | nd |
| 330 | 1 | 24 | 0.69 | 60 | 0.97 | nd | nd |
| 331 | 2 | 91 | 0.0076 | 100 | 0.00165 | nd | nd |
| 332 | 2 | 96 | 0.0018 | 104 | 0.0027 | nd | nd |
| 333 | 1 | 96 | 0.0055 | 102.5 | 0.0024 | nd | nd |
| 334 | 2 | 95.5 | 0.0021 | 101 | 0.0052 | nd | nd |
| 335 | 2 | 95.5 | 0.0015 | 99 | 0.0043 | nd | nd |
| 336 | 2 | 93.5 | 0.0035 | 101 | 0.0014 | nd | nd |
| 337 | 2 | 91 | 0.0021 | 101.5 | 0.00041 | nd | nd |
| 338 | 1 | 96.5 | 0.002 | 97.5 | 0.0026 | nd | nd |
| 339 | 1 | 93 | 0.0046 | 101 | 0.001 | nd | nd |
| 340 | 2 | 95.5 | 0.00175 | 99 | 0.00285 | nd | nd |
| 341 | 2 | 90.5 | 0.00935 | 99 | 0.0013 | nd | nd |
| 342 | 1 | 94 | 0.0021 | 99.5 | 0.0032 | nd | nd |
| 343 | 1 | 66 | 0.0595 | 92 | 0.024 | nd | nd |
| 344 | 2 | 95.5 | 0.00143 | 99.5 | 0.00135 | nd | nd |
| 345 | 1 | 48.5 | 0.15 | 90.5 | 0.0655 | nd | nd |
| 346 | 1 | 93.5 | 0.00435 | 101 | 0.00165 | nd | nd |
| 347 | 2 | 95.5 | 0.013 | 99 | 0.0037 | nd | nd |
| 348 | 2 | 94 | 0.013 | 98.5 | 0.0047 | nd | nd |
| 349 | 2 | 96.5 | 0.0018 | 98 | 0.0036 | nd | nd |
| 350 | 1 | 92 | 0.01 | 95 | 0.0019 | nd | nd |
| 351 | 1 | 93.5 | 0.0098 | 98.5 | 0.0016 | nd | nd |
| 352 | 1 | 82 | 0.047 | 93.5 | 0.031 | nd | nd |
| 353 | 2 | 98.5 | 0.00046 | 100 | 0.00098 | nd | nd |
| 354 | 1 | 99 | 0.00052 | 100.5 | 0.00044 | nd | nd |
| 355 | 1 | 98.5 | 0.00047 | 100 | 0.00025 | nd | nd |
| 356 | 1 | 65 | 0.0855 | 91.5 | 0.0235 | nd | nd |
| 357 | 2 | 98 | 0.00061 | 100.5 | 0.00155 | nd | nd |
| 358 | 1 | 94 | 0.0039 | 98.5 | 0.0039 | nd | nd |
| 359 | 1 | 92 | 0.0076 | 98 | 0.0025 | nd | nd |
| 360 | 1 | 85 | 0.019 | 96 | 0.013 | nd | nd |
| 361 | 1 | 91 | 0.0032 | 99 | 0.00145 | nd | nd |
| 362 | 1 | 94.5 | 0.00086 | 98.5 | 0.00083 | nd | nd |
| 363 | 1 | 95.5 | 0.00086 | 101 | 0.00037 | nd | nd |
| 364 | 1 | 61.5 | 0.044 | 90.5 | 0.017 | nd | nd |
| 365 | 1 | 71.5 | 0.02 | 89.5 | 0.0205 | nd | nd |
| 366 | 1 | 95 | 0.00064 | 99.5 | 0.00135 | nd | nd |
| 367 | 1 | 66.5 | 0.0405 | 98 | 0.016 | nd | nd |
| 368 | 1 | 60.5 | 0.058 | 96.5 | 0.01215 | nd | nd |
| 369 | 1 | 88 | 0.0115 | 97.5 | 0.011 | nd | nd |
| 370 | 2 | 93.5 | 0.00053 | 97.5 | 0.00043 | nd | nd |
| 371 | 1 | 96 | 0.00073 | 99 | 0.00106 | nd | nd |
| 372 | 1 | 95 | 0.00145 | 99 | 0.00125 | nd | nd |
| 373 | 1 | 93.5 | 0.00037 | 100.5 | 0.00066 | nd | nd |
| 374 | 1 | 96 | 0.00038 | 100.5 | 0.00057 | nd | nd |

-continued

| No. | Diastereomer | % inhibition (ORL1) [1 μM] | Ki (ORL1) mean [μM] | % inhibition (μ) [1 μM] | Ki (μ) mean [μm] | Tail flick rat, i.v. ED$_{50rat}$ [μg/kg] or % MPE (@μg/kg) | SNL rat, i.v. ED$_{50rat}$ [μg/kg] or % MPE (@μg/kg) |
|---|---|---|---|---|---|---|---|
| 375 | 1 | 77 | 0.043 | 99 | 0.0135 | nd | nd |
| 376 | 2 | 93 | 0.00199 | 99 | 0.0005 | nd | nd |
| 377 | 2 | 90 | 0.0065 | 99.5 | 0.00405 | nd | nd |
| 378 | 2 | 90.5 | 0.00525 | 98 | 0.00615 | nd | nd |
| 379 | 1 | 58 | 0.1045 | 93.5 | 0.045 | nd | nd |
| 380 | 1 | 79 | 0.01685 | 97.5 | 0.00635 | nd | nd |
| 381 | 1 | 74 | 0.0275 | 96 | 0.0195 | nd | nd |
| 382 | 1 | 87 | 0.07 | 99 | 0.00915 | nd | nd |
| 383 | 1 | 78.5 | 0.0865 | 96 | 0.0135 | nd | nd |
| 384 | 1 | 95.5 | 0.00945 | 99 | 0.00165 | nd | nd |
| 385 | 1 | 74 | 0.055 | 99.5 | 0.00735 | nd | nd |
| 386 | 2 | 96.5 | 0.00091 | 100.5 | 0.00098 | 1.45 | nd |
| 387 | 2 | 97 | 0.00077 | 100 | 0.00067 | nd | nd |
| 388 | 1 | 76 | 0.03 | 97.33 | 0.00825 | nd | nd |
| 389 | 1 | 20.5 | 0.405 | 90 | 0.051 | nd | nd |
| 390 | 1 | 66.5 | 0.0545 | 96 | 0.0195 | nd | nd |
| 391 | 1 | 23.5 | 0.355 | 92 | 0.037 | nd | nd |
| 392 | 1 | 42 | 0.114 | 96.5 | 0.00635 | nd | nd |
| 393 | 1 | 57.5 | 0.048 | 98.5 | 0.00225 | nd | nd |
| 394 | 1 | 98 | 0.0015 | 100 | 0.00094 | nd | nd |
| 395 | 1 | 96.5 | 0.0017 | 101 | 0.00056 | nd | nd |
| 396 | 1 | 37 | 0.355 | 97.5 | 0.0115 | nd | nd |
| 397 | 1 | 48.5 | 0.1485 | 98 | 0.00525 | nd | nd |
| 398 | 1 | 55 | 0.098 | 99 | 0.0016 | nd | nd |
| 399 | 1 | 0 | | 20 | 5.77 | nd | nd |
| 400 | 2 | 34 | 0.825 | 86 | 0.0515 | nd | nd |
| 401 | 1 | 0 | | 23 | 2.76 | nd | nd |
| 402 | 2 | 34.5 | 0.51 | 89 | 0.038 | nd | nd |
| 403 | 1 | 6.5 | | 23.5 | 4.125 | nd | nd |
| 404 | 2 | 52.5 | 0.1385 | 96.5 | 0.0063 | nd | nd |
| 405 | 1 | 99.5 | 0.00034 | 101.5 | 0.00044 | nd | nd |
| 406 | 1 | 5 | | 31 | 4.65 | nd | nd |
| 407 | 1 | | 0.135 | 94.5 | 0.0099 | nd | nd |
| 408 | 2 | | 0.139 | 82.5 | 0.08 | nd | nd |
| 409 | 2 | | 1.27 | 78.5 | 0.081 | nd | nd |
| 410 | 1 | 8 | | 20.5 | 5.77 | nd | nd |
| 411 | 1 | | 0.1695 | 93 | 0.0225 | nd | nd |
| 412 | 1 | | 0.00051 | 102.5 | 0.00044 | nd | nd |
| 413 | 2 | | 0.0605 | 98 | 0.00345 | nd | nd |
| 414 | 2 | 67.5 | 0.0665 | 83.5 | 0.0595 | nd | nd |
| 415 | 2 | 46.5 | 0.245 | 81 | 0.0685 | nd | nd |
| 416 | 2 | 53 | 0.165 | 87.5 | 0.069 | nd | nd |
| 417 | 2 | 93.5 | 0.0022 | 99.5 | 0.0004 | nd | nd |
| 418 | 1 | 72 | 0.049 | 99 | 0.00265 | nd | nd |
| 419 | 1 | 44.5 | 0.12 | 92 | 0.0385 | nd | nd |
| 420 | 1 | 92.5 | 0.00605 | 100.5 | 0.0013 | nd | nd |
| 421 | 2 | 95.5 | 0.00129 | 99.5 | 0.00031 | nd | nd |
| 422 | 1 | 73.5 | 0.01125 | 98.5 | 0.00265 | nd | nd |
| 423 | 1 | 72 | 0.018 | 98 | 0.00415 | nd | nd |
| 424 | | | | | | | |
| 425 | | | | | | | |
| 426 | | | | | | | |
| 427 | | | | | | | |
| 428 | | | | | | | |
| 429 | | | | | | | |
| 430 | | | | | | | |
| 431 | | | | | | | |
| 432 | | | | | | | |
| 433 | | | | | | | | nd = not determined
* 1 = polar, 2 = non-polar, 3 = a diastereomer

If the experimental data summarised in the above table give the appearance that individual compounds according to the invention have a comparatively only low receptor affinity, it cannot be concluded from this that these compounds are pharmacologically completely inactive. Rather, these measurement results are connected with the chiefly arbitrarily chosen test concentration of 1 μM. It can be assumed that at a correspondingly higher concentration, e.g. at 10 μM, significantly higher values would also be measured for the receptor affinity.

The invention claimed is:
1. A compound of formula (1)

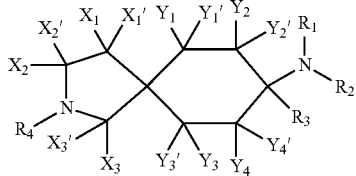

wherein
$Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —C(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)N(R$_0$)$_2$; or $Y_1$ and $Y_1'$, or $Y_2$ and $Y_2'$, or $Y_3$ and $Y_3'$, or $Y_4$ and $Y_4'$ together represent =O;
$X_1$, $X_1'$, $X_2$, $X_2'$, $X_3$ and $X_3'$ in each case independently of each other represent —H, —F, —Cl, —Br, —I, —NO$_2$, —CF$_3$, —OR$_5$, —SR$_5$, —SO$_2$R$_5$, —S(=O)$_2$OR$_5$, —CN, —COOR$_5$, —CONR$_5$, —NR$_6$R$_7$, or —R$_0$; or $X_1$ and $X_1'$, or $X_2$ and $X_2'$, or $X_3$ and $X_3'$ together represent =O; or $X_1$ and $X_2$, or $X_2$ and $X_3$ together represent —(CH$_2$)$_{2-6}$—, wherein individual hydrogen atoms can also be replaced by —F, —Cl, —Br, —I, —NO$_2$, —CF$_3$, —OR$_5$, —CN or —C$_{1-6}$-aliphatic; or $X_1$ and $X_1'$, or $X_2$ and $X_2'$ or $X_3$ and $X_3'$ together represent a C$_{3-6}$-cycloaliphatic, wherein individual hydrogen atoms can also be replaced by —F, —Cl, —Br, —I, —NO$_2$, —CF$_3$, —OR$_5$, —CN or —C$_{1-6}$-aliphatic;
R$_0$ in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;
R$_1$ and R$_2$ independently of each other represent —H or —R$_0$; or R$_1$ and R$_2$ together represent —CH$_2$CH$_2$OCH$_2$CH$_2$—, —CH$_2$CH$_2$NR$_8$CH$_2$CH$_2$— or —(CH$_2$)$_{3-6}$—;
R$_3$ represents —R$_0$;
R$_4$ represents H or —Z—R$_{11}$,
wherein
Z can be absent or —C(=O)—, —S(=O)— or —S(=O)$_2$—, and
R$_{11}$ represents —C$_{1-6}$-alkyl, —C$_{3-6}$-cycloalkyl or —C$_{1-3}$-alkyl-C$_{3-6}$-cycloalkyl, wherein in the C$_{3-6}$-cycloalkyl group a ring carbon atom can be replaced by an oxygen atom and —C$_{1-6}$-alkyl, —C$_{3-6}$-cycloalkyl or —C$_{1-3}$-alkyl-C$_{3-6}$-cycloalkyl can be unsubstituted, mono- or polysubstituted with substituents selected from the group consisting of —F, —Cl, —Br, —I, —CN, —OH, —SH, —O—C$_{1-3}$-alkyl and —S—C$_{1-3}$-alkyl, wherein —C$_{1-3}$-alkyl can be substituted by one or more substituents from the group including the substituents —F, —Cl, —Br, —I, —CN, —OH, —SH;
R$_5$ in each case independently represents —H or —R$_0$;
R$_6$ and R$_7$ independently of each other represent —H or —R$_0$; or R$_6$ and R$_7$ together represent —CH$_2$CH$_2$OCH$_2$CH$_2$—, —CH$_2$CH$_2$NR$_{10}$CH$_2$CH$_2$— or —(CH$_2$)$_{3-6}$—;
R$_8$ represents —H, —R$_0$ or —C(=O)R$_0$;
R$_{10}$ represents —H or —C$_{1-6}$-aliphatic;
wherein
"aliphatic" in each case is a branched or unbranched, saturated or a mono or polyunsaturated, unsubstituted or mono- or polysubstituted, aliphatic hydrocarbon radical;
"cycloaliphatic" in each case is a saturated or mono- or polyunsaturated, unsubstituted or mono or polysubstituted, alicyclic, mono- or multicyclic hydrocarbon radical;
wherein with respect to "aliphatic" and "cycloaliphatic", "mono- or polysubstituted" is understood as meaning substitution of one or more hydrogen atoms by —F, —Cl, —Br, —I, —CN, —NO$_2$, —CHO, =O, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NH—C(=O)N(R$_0$)$_2$, —Si(R$_0$)$_3$, —PO(OR$_0$)$_2$;
"aryl" in each case independently represents a carbocyclic ring system having at least one aromatic ring, but without hetero atoms in this ring, wherein the aryl radicals can optionally be fused with further saturated, (partially) unsaturated or aromatic ring systems and each aryl radical can be unsubstituted or mono- or polysubstituted, wherein the substituents on aryl can be identical or different and can be in any desired and possible position of the aryl;
"heteroaryl" represents a 5-, 6- or 7-membered cyclic aromatic radical which contains 1, 2, 3, 4 or 5 hetero atoms, wherein the hetero atoms are identical or different and are nitrogen, oxygen or sulfur and the heterocycle can be unsubstituted or mono- or polysubstituted; wherein in the case of substitution on the heterocycle the substituents can be identical or different and can be in any desired and possible position of the heteroaryl; and wherein the heterocycle can also be part of a bi- or polycyclic system;
wherein with respect to "aryl" and "heteroaryl", "mono- or polysubstituted" is understood as meaning substitution once or several times of one or more hydrogen atoms of the ring system by substituents chosen from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N($R_0$)$_2$, —Si($R_0$)$_3$, —PO(O$R_0$)$_2$; wherein N ring atoms optionally present can in each case be oxidised (N-oxide);

in the form of an individual stereoisomer or mixture thereof, the free compound and/or its physiologically acceptable salt and/or solvate.

2. A compound as claimed in claim 1, wherein $Y_1'$, $Y_2'$, $Y_3'$ and $Y_4'$ each represent —H.

3. A compound as claimed in claim 1, wherein
$R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$.

4. A compound as claimed in claim 1, wherein
$R_3$ represents —$C_{1-8}$-aliphatic, -aryl, -heteroaryl, —$C_{1-3}$-aliphatic-aryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$; and $X_1$, $X_1'$, $X_2$, $X_2'$, $X_3$, $X_3'$ in each case independently of each other represent —H, —F, —Cl, —Br, —I, —NO$_2$, —CF$_3$, —O$R_5$, —S$R_5$, —SO$_2R_5$, —S(=O)$_2$O$R_5$, —CN, —COO$R_5$, —CON$R_5$, —N$R_6R_7$, or —$R_0$; or one of the radicals $X_1$ and $X_1'$ represents H and the other represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$; or $X_1$ and $X_1'$, or $X_2$ and $X_2'$, or $X_3$ and $X_3'$ together represent =O; or $X_1$ and $X_1'$ together represent $C_{3-6}$-cycloalkyl, which can be unsubstituted or substituted by one or more substituents independently of each other selected from the group consisting of —F, —Cl, —Br, —I, —O$R_5$, S$R_5$, $C_{1-3}$-alkyl or —CN.

5. A compound as claimed in claim 1, wherein $Y_1$, $Y_1'$, $Y_2$, $Y_2'$, $Y_3$, $Y_3'$, $Y_4$ and $Y_4'$ each represent —H.

6. A compound as claimed in claim 1, which has formula (3.1)

7. A compound as claimed in claim 1,
wherein $Y_1$, $Y_1'$, $Y_2$, $Y_2'$, $Y_3$, $Y_3'$, $Y_4$ and $Y_4'$ each represent —H;
$X_1$, $X_1'$, $X_2$, $X_2'$, $X_3$ and $X_3'$ represent H; or $X_2$ and $X_2'$, or $X_3$ and $X_3'$ together represent =O; or $X_i$ and $X_1'$ together represent a $C_{3-6}$-cycloalkyl;
$R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$;
$R_1$ represents CH$_3$;
$R_2$ represents —H or —CH$_3$; or
$R_1$ and $R_2$ together form a ring and represent —(CH$_2$)$_{3-4}$—; and
$R_3$ represents —$C_{1-8}$-aliphatic, -aryl, -heteroaryl, —$C_{1-3}$-aliphatic-aryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$;
$R_4$ represents H or —Z—$R_{11}$,
wherein
Z can be absent or —C(=O)—, and
$R_{11}$ represents —$C_{1-6}$-alkyl, —$C_{3-6}$-cycloalkyl or —$C_{1-3}$-alkyl-$C_{3-6}$-cycloalkyl, wherein in the $C_{3-6}$-cycloalkyl group a ring carbon atom can be replaced by an oxygen atom and —$C_{1-6}$-alkyl, —$C_{3-6}$-cycloalkyl or —$C_{1-3}$-alkyl-$C_{3-6}$-cycloalkyl can be unsubstituted, mono- or polysubstituted with substituents independently of each other selected from the group consisting of —F, —Cl, —Br, —I, —CN, —OH, —SH, —O—$C_{1-3}$-alkyl and —S—$C_{1-3}$-alkyl, wherein —$C_{1-3}$-alkyl can be substituted by one or more substituents from the group consisting of the substituents —F, —Cl, —Br, —I, —CN, —OH and —SH.

8. A compound as claimed in claim 1, wherein $R_1$ and $R_2$ each represent —CH$_3$.

9. A compound as claimed in claim 1, wherein $R_3$ is selected from the group consisting of phenyl, benzyl and 2-thienyl, in each case unsubstituted or mono- or polysubstituted by substituents independently of each other selected from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$.

10. A compound as claimed in claim 1, wherein $R_4$ is selected from the group consisting of H, CH$_3$, ethyl, n-propyl, i-propyl, n-butyl, s-butyl, iso-butyl, t-butyl, n-pentyl, s-pentyl, iso-pentyl,

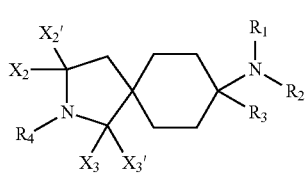

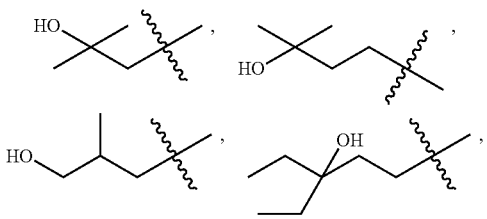

229
-continued
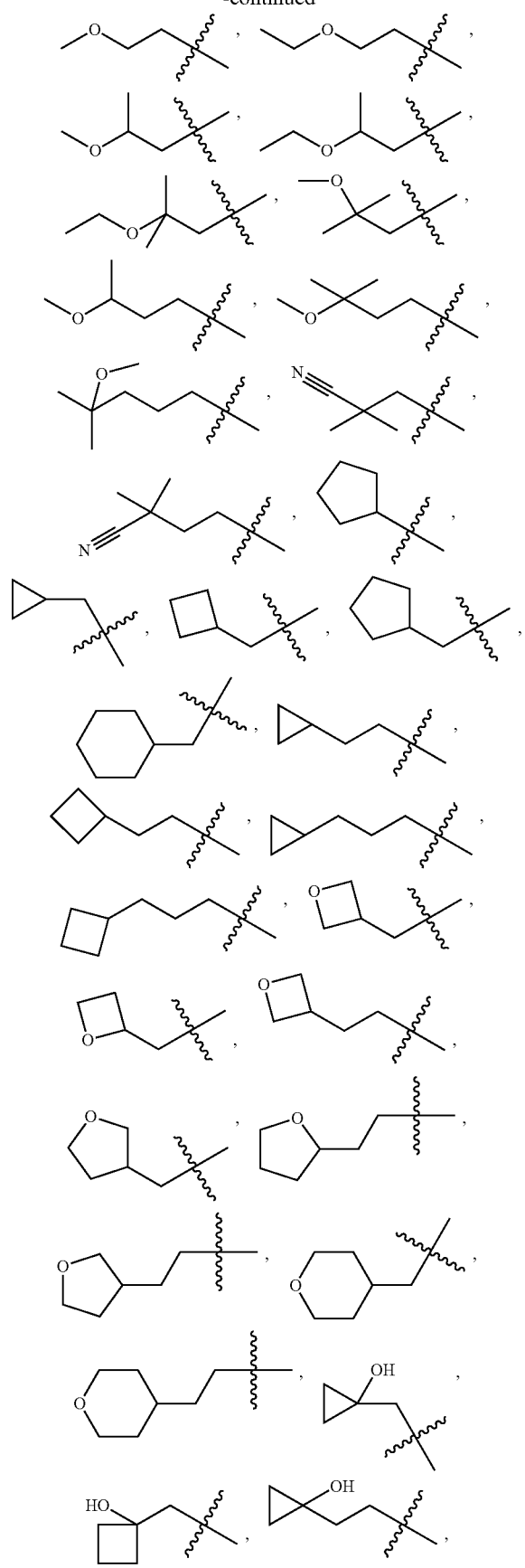
230
-continued
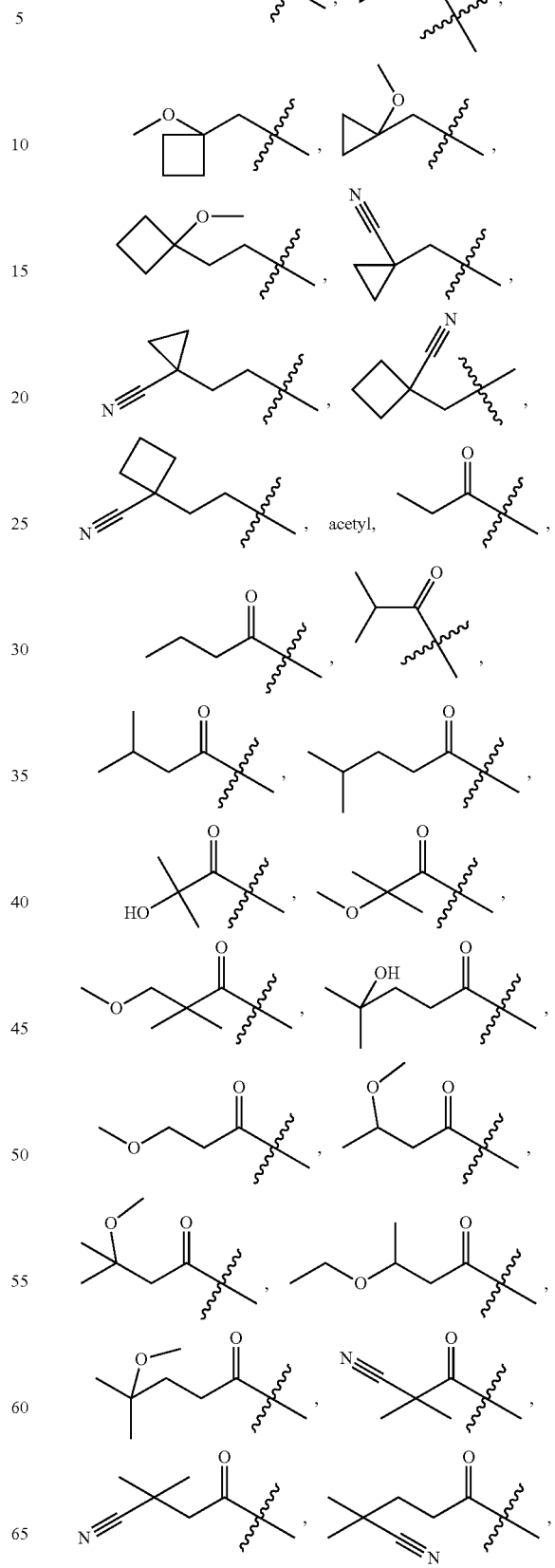

-continued

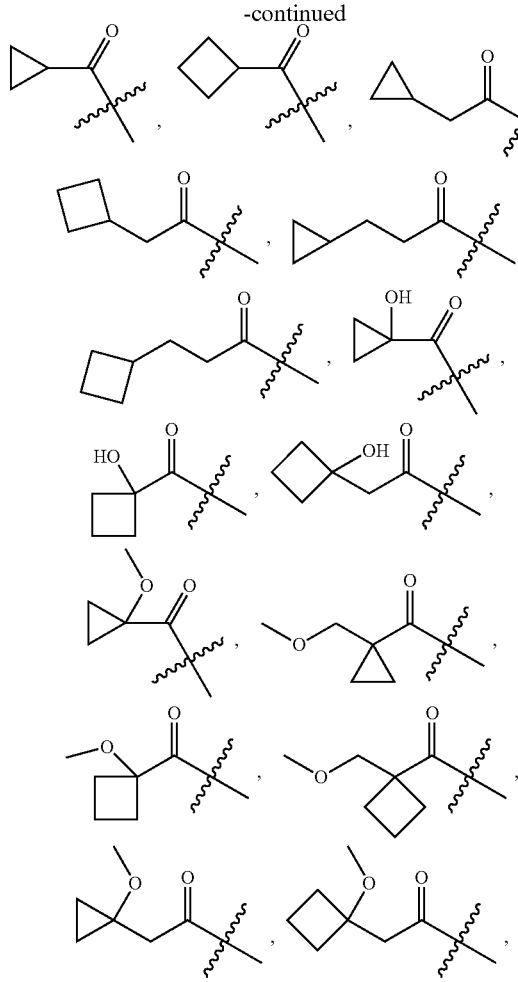

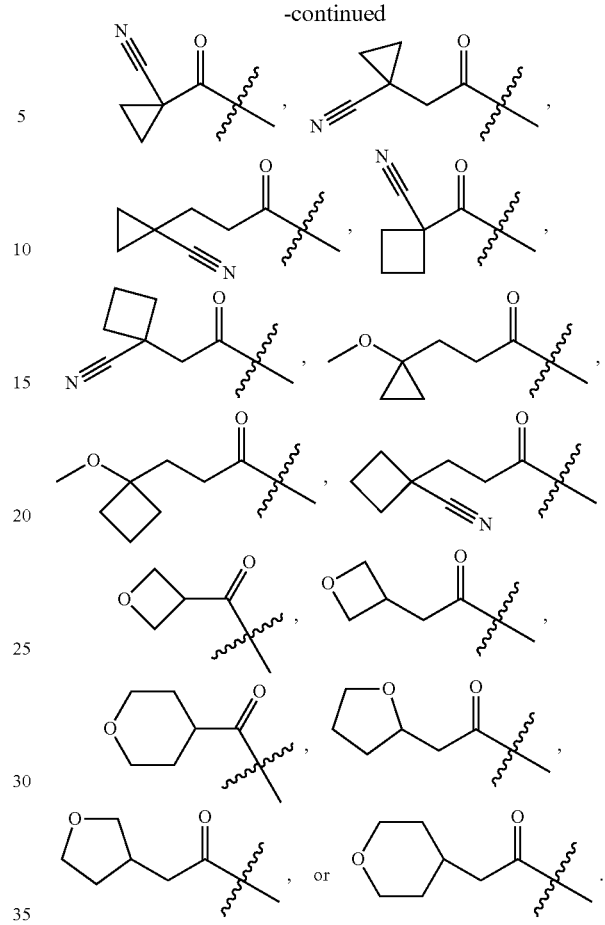

11. A compound as claimed in claim 1, selected from the group consisting of:

| | |
|---|---|
| 1; 2 | 8-Benzyl-8-(dimethylamino)-3-azaspiro[4.5]decan-4-one |
| 3; 4 | (8-Benzyl-3-azaspiro[4.5]decan-8-yl)-dimethylamine |
| 5; 6 | (8-Benzyl-3-methyl-3-azaspiro[4.5]decan-8-yl)-dimethylamine |
| 7; 8 | 1-[8-Benzyl-8-(dimethylamino)-3-azaspiro[4.5]decan-3-yl]-ethanone |
| 9 | (8-Benzyl-3-butyl-3-azaspiro[4.5]decan-8-yl)-dimethylamine |
| 10; 11 | 1-[8-Benzyl-8-(dimethylamino)-3-azaspiro[4.5]decan-3-yl]-butan-1-one |
| 12 | [8-Benzyl-3-(cyclopentylmethyl)-3-azaspiro[4.5]decan-8-yl]-dimethylamine |
| 13 | 8-Dimethylamino-8-phenyl-3-azaspiro[4.5]decan-4-one |
| 14; 15 | 8-(Dimethylamino)-8-phenyl-3-azaspiro[4.5]decan-2-one |
| 16 | 8-Butyl-8-dimethylamino-3-azaspiro[4.5]decan-4-one |
| 17 | 8-Dimethylamino-8-thiophen-2-yl-3-azaspiro[4.5]decan-4-one |
| 18; 25 | Dimethyl-(8-thiophen-2-yl-3-azaspiro[4.5]decan-8-yl)-amine |
| 19 | Dimethyl-(3-methyl-8-thiophen-2-yl-3-azaspiro[4.5]decan-8-yl)-amine |
| 20 | 1-(8-Dimethylamino-8-thiophen-2-yl-3-azaspiro[4.5]decan-3-yl)-butan-1-one |
| 21 | (3-Butyl-8-thiophen-2-yl-3-azaspiro[4.5]decan-8-yl)-dimethylamine |
| 22 | [3-(Cyclopentyl-methyl)-8-thiophen-2-yl-3-azaspiro[4.5]decan-8-yl]-dimethylamine |
| 23 | 8-(Dimethylamino)-8-thiophen-2-yl-2-azaspiro[4.5]decan-3-one |
| 24a/b | 8-(Dimethylamino)-8-thiophen-2-yl-2-azaspiro[4.5]decan-3-one |
| 26 | 1-[8-(Dimethylamino)-8-thiophen-2-yl-3-azaspiro[4.5]decan-3-yl]-butan-1-one |
| 27 | (8-Benzyl-3-butyl-3-azaspiro[4.5]decan-8-yl)-dimethylamine |
| 28; 29 | 1-[8-(Dimethylamino)-8-phenyl-3-azaspiro[4.5]decan-3-yl]-butan-1-one |
| 30 | 8-(Dimethylamino)-8-(5-methyl-thiophen-2-yl)-3-azaspiro[4.5]decan-4-one |
| 31 | Dimethyl-[8-(5-methylthiophen-2-yl)-3-azaspiro[4.5]decan-8-yl]-amine |
| 32 | 1-[8-(Dimethylamino)-8-(5-methylthiophen-2-yl)-3-azaspiro[4.5]decan-3-yl]-butan-1-one |
| 33 | 3-Butyl-8-(dimethylamino)-8-thiophen-2-yl-3-azaspiro[4.5]decan-2-one |
| 34 | 8-(Dimethylamino)-3-methyl-8-thiophen-2-yl-3-azaspiro[4.5]decan-2-one |
| 35 | [3-Butyl-8-(5-methylthiophen-2-yl)-3-azaspiro[4.5]decan-8-yl]-dimethylamine |
| 36 | Cyclobutyl-[8-dimethylamino-8-(5-methylthiophen-2-yl)-3-azaspiro[4.5]decan-3-yl]-methanon |

| | |
|---|---|
| 37 | Cyclopropyl-[8-dimethylamino-8-(5-methylthiophen-2-yl)-3-azaspiro[4.5]decan-3-yl]-methanone |
| 38 | 1-[8-Dimethylamino-8-(5-methylthiophen-2-yl)-3-azaspiro[4.5]decan-3-yl]-2-methylpropan-1-one |
| 39 | 1-[8-Dimethylamino-8-(5-methylthiophen-2-yl)-3-azaspiro[4.5]decan-3-yl]-3-methylbutan-1-one |
| 40 | 1-[8-Dimethylamino-8-(5-methylthiophen-2-yl)-3-azaspiro[4.5]decan-3-yl]-propan-1-one |
| 41 | [3-(2-Methoxyethyl)-8-(5-methylthiophen-2-yl)-3-azaspiro[4.5]decan-8-yl]-dimethylamine |
| 42 | 1-[8-(Dimethylamino)-8-thiophen-2-yl-3-azaspiro[4.5]decan-3-yl]-2-methoxyethanone |
| 43 | Cyclobutyl-[8-(dimethylamino)-8-thiophen-2-yl-3-azaspiro[4.5]decan-3-yl]-methanone |
| 44 | Cyclopropyl-[8-(dimethylamino)-8-thiophen-2-yl-3-azaspiro[4.5]decan-3-yl]-methanone |
| 45 | 1-[8-(Dimethylamino)-8-thiophen-2-yl-3-azaspiro[4.5]decan-3-yl]-2-methylpropan-1-one |
| 46 | 1-[8-(Dimethylamino)-8-thiophen-2-yl-3-azaspiro[4.5]decan-3-yl]-3-methylbutan-1-one |
| 47 | [3-(2-Methoxyethyl)-8-thiophen-2-yl-3-azaspiro[4.5]decan-8-yl]-dimethylamine |
| 48 | 2-Cyclopropyl-1-[8-(dimethylamino)-8-thiophen-2-yl-3-azaspiro[4.5]decan-3-yl]-ethanone |
| 49 | [3-(Cyclopropylmethyl)-8-thiophen-2-yl-3-azaspiro[4.5]decan-8-yl]-dimethylamine |
| 50 | 2-Cyclobutyl-1-[8-(dimethylamino)-8-thiophen-2-yl-3-azaspiro[4.5]decan-3-yl]-ethanone |
| 51 | [3-(2-Cyclopropylethyl)-8-thiophen-2-yl-3-azaspiro[4.5]decan-8-yl]-dimethylamine |
| 52 | [3-(2-Cyclobutylethyl)-8-thiophen-2-yl-3-azaspiro[4.5]decan-8-yl]-dimethylamine |
| 53 | [3-(Cyclobutylmethyl)-8-thiophen-2-yl-3-azaspiro[4.5]decan-8-yl]-dimethylamine |
| 54 | 1-[8-(Dimethylamino)-8-thiophen-2-yl-3-azaspiro[4.5]decan-3-yl]-4-methylpentan-1-one |
| 55 | 3-[8-(Dimethylamino)-8-thiophen-2-yl-3-azaspiro[4.5]decan-3-yl]-2,2-dimethyl-3-oxopropionitrile |
| 56 | 1-[8-(Dimethylamino)-8-thiophen-2-yl-3-azaspiro[4.5]decan-3-yl]-2-tetrahydrofuran-3-ylethanone |
| 57 | (8-Dimethylamino-8-thiophen-2-yl-3-azaspiro[4.5]decan-3-yl)-(oxetan-3-yl)-methanone |
| 58 | 1-(8-Dimethylamino-8-thiophen-2-yl-3-azaspiro[4.5]decane-3-carbonyl)-cyclopropane-1-carbonitrile |
| 59 | 1-(8-Dimethylamino-8-thiophen-2-yl-3-azaspiro[4.5]decan-3-yl)-4-methoxy-4-methylpentan-1-one |
| 60 | [8-(Dimethylamino)-8-thiophen-2-yl-3-azaspiro[4.5]decan-3-yl]-tetrahydropyran-4-ylmethanone |
| 61 | 1-[8-(Dimethylamino)-8-thiophen-2-yl-3-azaspiro[4.5]decane-3-carbonyl]-cyclobutane-1-carbonitrile |
| 62 | 3-Cyclopropyl-1-[8-(dimethylamino)-8-thiophen-2-yl-3-azaspiro[4.5]decan-3-yl]-propan-1-one |
| 63 | 1-[8-(Dimethylamino)-8-thiophen-2-yl-3-azaspiro[4.5]decan-3-yl]-2-methoxy-2-methylpropan-1-one |
| 64 | 1-[8-(Dimethylamino)-8-thiophen-2-yl-3-azaspiro[4.5]decan-3-yl]-2-tetrahydrofuran-2-ylethanone |
| 65 | 1-[8-(Dimethylamino)-8-thiophen-2-yl-3-azaspiro[4.5]decan-3-yl]-4-hydroxy-4-methylpentan-1-one |
| 66 | [8-(Dimethylamino)-8-thiophen-2-yl-3-azaspiro[4.5]decan-3-yl]-(1-hydroxycyclobutyp-methanone |
| 67 | 1-[2-[8-(Dimethylamino)-8-thiophen-2-yl-3-azaspiro[4.5]decan-3-yl]-2-oxoethyl]-cyclopropane-1-carbonitrile |
| 68 | 1-[2-[8-(Dimethylamino)-8-thiophen-2-yl-3-azaspiro[4.5]decan-3-yl]-2-oxoethyl]-cyclobutane-1-carbonitrile |
| 69 | 3-Cyclobutyl-1-[8-(dimethylamino)-8-thiophen-2-yl-3-azaspiro[4.5]decan-3-yl]-propan-1-one |
| 70 | Dimethyl-[3-(oxetan-3-yl-methyl)-8-thiophen-2-yl-3-azaspiro[4.5]decan-8-yl]-amine |
| 71 | Dimethyl-(8-phenyl-3-azaspiro[4.5]decan-8-yl)-amine |
| 72 | 1-[8-(Dimethylamino)-8-phenyl-3-azaspiro[4.5]decan-3-yl]-butan-1-one |
| 73 | 1-(8-Dimethylamino-8-phenyl-3-azaspiro[4.5]decan-3-yl)-ethanone |
| 74 | (3-Butyl-8-phenyl-3-azaspiro[4.5]decan-8-yl)-dimethylamine |
| 75 | 1-[8-(Dimethylamino)-8-phenyl-3-azaspiro[4.5]decan-3-yl]-2-tetrahydrofuran-2-ylethanone |
| 76 | 1-[2-[8-(Dimethylamino)-8-phenyl-3-azaspiro[4.5]decan-3-yl]-2-oxoethyl]-cyclobutane-1-carbonitrile |
| 77 | 1-[2-[8-(Dimethylamino)-8-phenyl-3-azaspiro[4.5]decan-3-yl]-2-oxoethyl]-cyclopropane-1-carbonitrile |
| 78 | 1-[8-(Dimethylamino)-8-phenyl-3-azaspiro[4.5]decan-3-yl]-2-(oxetan-3-yl)-ethanone |

| | |
|---|---|
| 79 | 1-[8-(Dimethylamino)-8-phenyl-3-azaspiro[4.5]decan-3-yl]-4-methylpentan-1-one |
| 80 | 3-[8-(Dimethylamino)-8-phenyl-3-azaspiro[4.5]decan-3-yl]-2,2-dimethyl-3-oxopropionitrile |
| 81 | [8-(Dimethylamino)-8-phenyl-3-azaspiro[4.5]decan-3-yl]-tetrahydropyran-4-yl-methanone |
| 82 | 1-[8-(Dimethylamino)-8-phenyl-3-azaspiro[4.5]decan-3-yl]-4-hydroxy-4-methylpentan-1-one |
| 83 | 1-[8-(Dimethylamino)-8-phenyl-3-azaspiro[4.5]decan-3-yl]-4-methoxy-4-methylpentan-1-one |
| 84 | [8-(Dimethylamino)-8-phenyl-3-azaspiro[4.5]decan-3-yl]-(1-hydroxycyclobutyl)-methanone |
| 85 | 2-Cyclopropyl-1-[8-(dimethylamino)-8-phenyl-3-azaspiro[4.5]decan-3-yl]-ethanone |
| 86 | 2-Cyclobutyl-1-[8-(dimethylamino)-8-phenyl-3-azaspiro[4.5]decan-3-yl]-ethanone |
| 87 | [3-(4-Methoxy-4-methylpentyl)-8-phenyl-3-azaspiro[4.5]decan-8-yl]-dimethylamine |
| 88 | 1-[8-(5-Chlorothiophen-2-yl)-8-dimethylamino-3-azaspiro[4.5]decan-3-yl]-butan-1-one |
| 89 | [3-Butyl-8-(5-chlorothiophen-2-yl)-3-azaspiro[4.5]decan-8-yl]-dimethylamine |
| 90 | 1-[8-Dimethylamino-8-(5-fluorothiophen-2-yl)-3-azaspiro[4.5]decan-3-yl]-butan-1-one |
| 91 | [3-Butyl-8-(5-fluorothiophen-2-yl)-3-azaspiro[4.5]decan-8-yl]-dimethylamine |
| 92 | 8-(Cyclohexylmethyl)-8-dimethylamino-3-azaspiro[4.5]decan-4-one |
| 93 | 1-[8-(Cyclohexylmethyl)-8-dimethylamino-3-azaspiro[4.5]decan-3-yl]-butan-1-one |
| 94 | [3-Butyl-8-(cyclohexylmethyl)-3-azaspiro[4.5]decan-8-yl]-dimethylamine |
| 95 | 1-[8-(Cyclopentylmethyl)-8-dimethylamino-3-azaspiro[4.5]decan-3-yl]-butan-1-one |
| 96 | [3-Butyl-8-(cyclopentylmethyl)-3-azaspiro[4.5]decan-8-yl]-dimethylamine |
| 97 | 1-(8-Cyclopentyl-8-dimethylamino-3-azaspiro[4.5]decan-3-yl)-butan-1-one |
| 98 | (3-Butyl-8-cyclopentyl-3-azaspiro[4.5]decan-8-yl)-dimethylamine |
| 99 | Cyclobutyl-(8-cyclopentyl-8-dimethylamino-3-azaspiro[4.5]decan-3-yl)-methanone |
| 100 | (8-Cyclopentyl-8-dimethylamino-3-azaspiro[4.5]decan-3-yl)-cyclopropylmethanone |
| 101 | [8-Cyclopentyl-3-(cyclopropylmethyl)-3-azaspiro[4.5]decan-8-yl]-dimethylamine |
| 102 | [3-(Cyclobutylmethyl)-8-cyclopentyl-3-azaspiro[4.5]decan-8-yl]-dimethylamine |
| 103 | 1-(8-Cyclopentyl-8-dimethylamino-3-azaspiro[4.5]decan-3-yl)-2-cyclopropylethanone |
| 104 | [8-Cyclopentyl-3-(2-cyclopropylethyl)-3-azaspiro[4.5]decan-8-yl]-dimethylamine |
| 105 | 2-Cyclobutyl-1-(8-cyclopentyl-8-dimethylamino-3-azaspiro[4.5]decan-3-yl)-ethanone |
| 106; 107 | [3-Butyl-8-(dimethylamino)-3-azaspiro[4.5]decan-8-yl]-phenylmethanone |
| 108; 109 | 1-[8-(Azetidin-1-yl)-8-thiophen-2-yl-3-azaspiro[4.5]decan-3-yl]-butan-1-one |
| 110; 111 | 1-[8-(Azetidin-1-yl)-8-phenyl-3-azaspiro[4.5]decan-3-yl]-butan-1-one |
| 112; 113 | 8-(Azetidin-1-yl)-3-butyl-8-phenyl-3-azaspiro[4.5]decan |
| 114 | 8-Dimethylamino-3-methyl-8-thiophen-2-yl-3-azaspiro[4.5]decan-4-one |
| 115 | 3-Butyl-8-dimethylamino-8-thiophen-2-yl-3-azaspiro[4.5]decan-4-one |
| 116 | 3-(Cyclopentylmethyl)-8-dimethylamino-8-thiophen-2-yl-3-azaspiro[4.5]decan-4-one |
| 117 | 8-(5-Chlorothiophen-2-yl)-8-dimethylamino-3-azaspiro[4.5]decan-4-one |
| 118; 119 | 8-Benzyl-8-(dimethylamino)-3-methyl-3-azaspiro[4.5]decan-4-one |
| 120; 121 | 8-Benzyl-3-butyl-8-(dimethylamino)-3-azaspiro[4.5]decan-4-one |
| 122; 123 | 8-Benzyl-3-(cyclopentylmethyl)-8-(dimethylamino)-3-azaspiro[4.5]decan-4-one |
| 124 | 8-(Dimethylamino)-3-methyl-8-thiophen-2-yl-3-azaspiro[4.5]decan-2-one |
| 125 | 3-Butyl-8-(dimethylamino)-8-thiophen-2-yl-3-azaspiro[4.5]decan-2-one |
| 126; 127 | 3-(Cyclopentylmethyl)-8-(dimethylamino)-8-thiophen-2-yl-3-azaspiro[4.5]decan-2-one |
| 128; 129 | 3-(2-Cyclobutylethyl)-8-(dimethylamino)-8-thiophen-2-yl-3-azaspiro[4.5]decan-2-one |
| 130; 131 | 3-(2-Cyclopropylethyl)-8-(dimethylamino)-8-thiophen-2-yl-3-azaspiro[4.5]decan-2-one |
| 132; 133 | 3-(Cyclobutylmethyl)-8-(dimethylamino)-8-thiophen-2-yl-3-azaspiro[4.5]decan-2-one |
| 134; 135 | 3-(Cyclopropylmethyl)-8-(dimethylamino)-8-thiophen-2-yl-3-azaspiro[4.5]decan-2-one |
| 136; 137 | 8-(Dimethylamino)-3-(2-tetrahydrofuran-2-ylethyl)-8-thiophen-2-yl-3-azaspiro[4.5]decan-2-one |
| 138; 139 | 8-(Dimethylamino)-3-(tetrahydropyran-4-ylmethyl)-8-thiophen-2-yl-3-azaspiro[4.5]decan-2-one |
| 140; 141 | 8-(Dimethylamino)-3-(2-tetrahydrofuran-3-ylethyl)-8-thiophen-2-yl-3-azaspiro[4.5]decan-2-one |
| 142; 143 | 8-(Dimethylamino)-3-[2-(oxetan-3-yl)-ethyl]-8-thiophen-2-yl-3-azaspiro[4.5]decan-2-one |

| | |
|---|---|
| 144; 145 | 1-[2-[8-(Dimethylamino)-2-oxo-8-thiophen-2-yl-3-azaspiro[4.5]decan-3-yl]-ethyl]-cyclopropane-1-carbonitrile |
| 146; 147 | 8-(Dimethylamino)-3-(oxetan-2-ylmethyl)-8-thiophen-2-yl-3-azaspiro[4.5]decan-2-one |
| 1-[8; 149 | 8-(Dimethylamino)-3-(oxetan-3-ylmethyl)-8-thiophen-2-yl-3-azaspiro[4.5]decan-2-one |
| 150; 151 | 1-[2-[8-(Dimethylamino)-2-oxo-8-thiophen-2-yl-3-azaspiro[4.5]decan-2-one ethyl]-cyclobutane-1-carbonitrile |
| 152; 153 | 8-(Dimethylamino)-8-(5-methylthiophen-2-yl)-3-azaspiro |
| 154; 155 | 8-(Dimethylamino)-3-methyl-8-(5-methylthiophen-2-yl)-3-azaspiro[4.5]decan-2-one |
| 156; 157 | 3-Butyl-8-(dimethylamino)-8-(5-methylthiophen-2-yl)-3-azaspiro[4.5]decan-2-one |
| 158; 159 | 3-(Cyclopentylmethyl)-8-(dimethylamino)-8-(5-methylthiophen-2-yl)-3-azaspiro[4.5]decan-2-one |
| 160 | 3-(Cyclopropylmethyl)-8-(dimethylamino)-8-(5-methylthiophen-2-yl)-3-azaspiro[4.5]decan-2-one |
| 161 | 3-(Cyclobutylmethyl)-8-(dimethylamino)-8-(5-methylthiophen-2-yl)-3-azaspiro[4.5]decan-2-one |
| 162 | 8-(Dimethylamino)-3-methyl-8-phenyl-3-azaspiro[4.5]decan-2-one |
| 163; 164 | 3-Butyl-8-(dimethylamino)-8-phenyl-3-azaspiro[4.5]decan-2-one |
| 165; 166 | 3-(Cyclopentylmethyl)-8-(dimethylamino)-8-phenyl-3-azaspiro[4.5]decan-2-one |
| 167; 168 | 3-(2-Cyclopropylethyl)-8-(dimethylamino)-8-phenyl-3-azaspiro[4.5]decan-2-one |
| 169; 170 | 3-(Cyclobutylmethyl)-8-(dimethylamino)-8-phenyl-3-azaspiro[4.5]decan-2-one |
| 171; 172 | 3-(Cyclopropylmethyl)-8-(dimethylamino)-8-phenyl-3-azaspiro[4.5]decan-2-one |
| 173; 174 | 3-(2-Cyclobutylethyl)-8-(dimethylamino)-8-phenyl-3-azaspiro[4.5]decan-2-one |
| 175; 176 | 1-[2-[8-(Dimethylamino)-2-oxo-8-phenyl-3-azaspiro[4.5]decan-3-yl]-ethyl]-cyclopropane-1-carbonitrile |
| 177; 178 | 1-[2-[8-(Dimethylamino)-2-oxo-8-phenyl-3-azaspiro[4.5]decan-3-yl]-ethyl]-cyclobutane-1-carbonitrile |
| 179; 180 | 8-(Dimethylamino)-3-[(1-hydroxycyclobutyl)-methyl]-8-phenyl-3-azaspiro[4.5]decan-2-one |
| 181 | 8-(Dimethylamino)-3-(2-hydroxy-2-methylpropyl)-8-phenyl-3-azaspiro[4.5]decan-2-one |
| 182; 183 | 8-(Dimethylamino)-3-(3-methoxy-3-methylbutyl)-8-phenyl-3-azaspiro[4.5]decan-2-one |
| 184; 185 | 8-(Dimethylamino)-3-[2-(1-methoxycyclobutyl)-ethyl]-8-phenyl-3-azaspiro[4.5]decan-2-one |
| 186; 187 | 8-(Dimethylamino)-3-(3-hydroxy-3-methylbutyl)-8-phenyl-3-azaspiro[4.5]decan-2-one |
| 188 | 1-[8-(Dimethylamino)-8-phenyl-3-azaspiro[4.5]decan-3-yl]-2-tetrahydrofuran-3-ylethanone |
| 189 | [8-(Dimethylamino)-8-phenyl-3-azaspiro[4.5]decan-3-yl]-(oxetan-3-yl)-methanone |
| 190 | 1-[8-(Dimethylamino)-8-phenyl-3-azaspiro[4.5]decan-3-yl]-2-methoxy-2-methylpropan-1-one |
| 191 | [3-(2-Cyclopropylethyl)-8-phenyl-3-azaspiro[4.5]decan-8-yl]-dimethylamine |
| 192 | [3-(2-Cyclobutylethyl)-8-phenyl-3-azaspiro[4.5]decan-8-yl]-dimethylamine |
| 193 | 1-[8-(Dimethylamino)-8-phenyl-3-azaspiro[4.5]decan-3-yl]-methyl]-cyclobutan-1-ol |
| 194 | 1-[2-[8-(Dimethylamino)-8-phenyl-3-azaspiro[4.5]decan-3-yl]-ethyl]-cyclobutane-1-carbonitrile |
| 195 | 3-Cyclobutyl-1-[8-(dimethylamino)-8-phenyl-3-azaspiro[4.5]decan-3-yl]-propan-1-one |
| 196 | Dimethyl-[3-(oxetan-3-ylmethyl)-8-phenyl-3-azaspiro[4.5]decan-8-yl]-amine |
| 197 | 3-Cyclopropyl-1-[8-(dimethylamino)-8-phenyl-3-azaspiro[4.5]decan-3-yl]-propan-1-one |
| 198 | 1-[8-(Dimethylamino)-8-phenyl-3-azaspiro[4.5]decane-3-carbonyl]-cyclopropane-1-carbonitrile |
| 199 | 1-[8-(Dimethylamino)-8-phenyl-3-azaspiro[4.5]decane-3-carbonyl]-cyclobutane-1-carbonitrile |
| 200 | 1-[2-[8-(Dimethylamino)-8-phenyl-3-azaspiro[4.5]decan-3-yl]-ethyl]-cyclopropane-1-carbonitrile |
| 201 | Dimethyl-[8-phenyl-3-(2-tetrahydrofuran-3-ylethyl)-3-azaspiro[4.5]decan-8-yl]-amine |
| 202 | [3-(2-Methoxy-2-methylpropyl)-8-phenyl-3-azaspiro[4.5]decan-8-yl]-dimethylamine |
| 203 | [3-(3-Cyclobutyl-propyl)-8-phenyl-3-azaspiro[4.5]decan-8-yl]-dimethylamine |
| 204 | [3-(3-Cyclopropyl-propyl)-8-phenyl-3-azaspiro[4.5]decan-8-yl]-dimethylamine |
| 205 | [8-(Dimethylamino)-8-phenyl-3-azaspiro[4.5]decan-3-yl]-(1-hydroxycyclopropyl)-methanone |
| 206 | 1-[8-(Dimethylamino)-8-phenyl-3-azaspiro[4.5]decan-3-yl]-methyl]-cyclopropan-1-ol |
| 207 | 1-[8-(Dimethylamino)-8-thiophen-2-yl-3-azaspiro[4.5]decan-3-yl]-methyl]-cyclobutan-1-ol |
| 208 | 1-[2-[8-(Dimethylamino)-8-thiophen-2-yl-3-azaspiro[4.5]decan-3-yl]-ethyl]-cyclobutane-1-carbonitrile |

| | |
|---|---|
| 209 | [8-(Dimethylamino)-8-thiophen-2-yl-3-azaspiro[4.5]decan-3-yl]-(1-hydroxycyclopropyl)-methanone |
| 210 | 1-[8-(Dimethylamino)-8-thiophen-2-yl-3-azaspiro[4.5]decan-3-yl]-methyl]-cyclopropan-1-ol |
| 211 | 1-[2-[8-(Dimethylamino)-8-thiophen-2-yl-3-azaspiro[4.5]decan-3-yl]-ethyl]-cyclopropane-1-carbonitrile |
| 212 | 1-(8-Dimethylamino-8-thiophen-2-yl-3-azaspiro[4.5]decan-3-yl)-2-(oxetan-3-yl)-ethanone |
| 213 | 1-[8-(Dimethylamino)-8-thiophen-2-yl-3-azaspiro[4.5]decan-3-yl]-3-ethylpentan-3-ol |
| 214 | 1-[8-(Dimethylamino)-8-(thiophen-2-ylmethyl)-3-azaspiro[4.5]decan-3-yl]-butan-1-one |
| 215; 216 | 8-(Dimethylamino)-3-[(1-hydroxycyclobutyl)-methyl]-8-thiophen-2-yl-3-azaspiro[4.5]decan-2-one |
| 217; 218 | 8-(Dimethylamino)-3-[2-(1-methoxycyclobutyl)-ethyl]-8-thiophen-2-yl-3-azaspiro[4.5]decan-2-one |
| 219; 220 | 8-(Dimethylamino)-3-(3-methoxy-3-methylbutyl)-8-thiophen-2-yl-3-azaspiro[4.5]decan-2-one |
| 221; 222 | 8-(Dimethylamino)-3-(3-hydroxy-3-methylbutyl)-8-thiophen-2-yl-3-azaspiro[4.5]decan-2-one |
| 223 | 1-[8-(Dimethylamino)-8-thiophen-2-yl-3-azaspiro[4.5]decan-3-yl]-2-hydroxy-2-methylpropan-1-one |
| 224; 225 | 8-(Dimethylamino)-3-(2-hydroxy-2-methylpropyl)-8-thiophen-2-yl-3-azaspiro[4.5]decan-2-one |
| 226 | 4-[8-(Dimethylamino)-8-thiophen-2-yl-3-azaspiro[4.5]decan-3-yl]-2-methylbutan-2-ol |
| 227 | 1-[8-(Dimethylamino)-8-thiophen-2-yl-3-azaspiro[4.5]decan-3-yl]-2-methylpropan-2-ol |
| 228 | 1-[8-(Dimethylamino)-8-phenyl-3-azaspiro[4.5]decan-3-yl]-2-hydroxy-2-methylpropan-1-one |
| 229 | 1-[8-(Dimethylamino)-8-phenyl-3-azaspiro[4.5]decan-3-yl]-2-methylpropan-2-ol |
| 230; 231 | 4-[8-(Dimethylamino)-2-oxo-8-phenyl-3-azaspiro[4.5]decan-3-yl]-2,2-dimethylbutyronitrile |
| 232 | 4-[8-(Dimethylamino)-8-phenyl-3-azaspiro[4.5]decan-3-yl]-2,2-dimethyl-4-oxobutyronitrile |
| 233 | 4-[8-(Dimethylamino)-8-thiophen-2-yl-3-azaspiro[4.5]decan-3-yl]-2,2-dimethyl-4-oxobutyronitrile |
| 234 | 8-Cyclopentyl-3-(2-cyclopropylethyl)-8-(dimethylamino)-3-azaspiro[4.5]decan-2-one |
| 235 | 1-[8-(Dimethylamino)-8-thiophen-2-yl-3-azaspiro[4.5]decan-3-yl]-2-(1-methoxycyclobutyl)-ethanone |
| 236 | 3-(2-Cyclobutylethyl)-8-cyclopentyl-8-(dimethylamino)-3-azaspiro[4.5]decan-2-one |
| 237 | 1-[8-(Dimethylamino)-8-phenyl-3-azaspiro[4.5]decan-3-yl]-2-(1-methoxycyclobutyl)-ethanone |
| 238 | [3-[2-(1-Methoxycyclobutyl)-ethyl]-8-thiophen-2-yl-3-azaspiro[4.5]decan-8-yl]-dimethylamine |
| 239 | [3-[2-(1-Methoxycyclobutyl)-ethyl]-8-phenyl-3-azaspiro[4.5]decan-8-yl]-dimethylamine |
| 240 | 4-[8-(Dimethylamino)-2-oxo-8-thiophen-2-yl-3-azaspiro[4.5]decan-3-yl]-2,2-dimethylbutyronitrile |
| 241; 242 | 8-(Dimethylamino)-3-[2-(oxetan-3-yl)-ethyl]-8-thiophen-2-yl-3-azaspiro[4.5]decan-2-one |
| 243 | 8-Cyclopentyl-3-(2-cyclopropylethyl)-8-(dimethylamino)-3-azaspiro[4.5]decan-2-one |
| 244 | 8-Cyclopentyl-8-(dimethylamino)-3-(oxetan-3-ylmethyl)-3-azaspiro[4.5]decan-2-one |
| 245 | 1-[2-[8-Cyclopentyl-8-(dimethylamino)-2-oxo-3-azaspiro[4.5]decan-3-yl]-ethyl]-cyclopropane-1-carbonitrile |
| 246 | 8-Cyclopentyl-8-(dimethylamino)-3-[2-(oxetan-3-yl)-ethyl]-3-azaspiro[4.5]decan-2-one |
| 247 | 1-(8-Cyclopentyl-8-dimethylamino-3-azaspiro[4.5]decan-3-yl)-2-(1-methoxycyclobutyl)-ethanone |
| 248 | 4-[8-(Dimethylamino)-8-thiophen-2-yl-3-azaspiro[4.5]decan-3-yl]-2,2-dimethylbutyronitrile |
| 249 | 4-[8-(Dimethylamino)-8-phenyl-3-azaspiro[4.5]decan-3-yl]-2,2-dimethylbutyronitrile |
| 250 | 4-[8-(Dimethylamino)-2-oxo-8-thiophen-2-yl-3-azaspiro[4.5]decan-3-yl]-2,2-dimethylbutyronitrile |
| 251; 252 | 8-(Dimethylamino)-3-(oxetan-3-ylmethyl)-8-phenyl-3-azaspiro[4.5]decan-2-one |
| 253 | 1-[2-[8-(Dimethylamino)-8-thiophen-2-yl-3-azaspiro[4.5]decan-3-yl]-ethyl]-cyclopropan-1-ol |
| 254; 255 | 8-(Dimethylamino)-342-(oxetan-3-yl)-ethyl]-8-phenyl-3-azaspiro[4.5]decan-2-one |
| 256 | 1-[2-[8-Cyclopentyl-8-(dimethylamino)-2-oxo-3-azaspiro[4.5]decan-3-yl]-ethyl]-cyclobutane-1-carbonitrile |
| 257 | [8-Cyclopentyl-3-[2-(1-methoxycyclobutyl)-ethyl]-3-azaspiro[4.5]decan-8-yl]-dimethylamine |

-continued

| | |
|---|---|
| 258 | 4-(8-Cyclopentyl-8-dimethylamino-3-azaspiro[4.5]decan-3-yl)-2,2-dimethylbutyronitrile |
| 259 | 4-(8-Cyclopentyl-8-dimethylamino-3-azaspiro[4.5]decan-3-yl)-2,2-dimethyl-4-oxobutyronitrile |
| 260; 261 | 8-(Dimethylamino)-8-phenyl-3-(tetrahydrofuran-3-ylmethyl)-3-azaspiro[4.5]decan-2-one |
| 262; 263 | 8-(Dimethylamino)-8-phenyl-3-(2-tetrahydrofuran-2-ylethyl)-3-azaspiro[4.5]decan-2-one |
| 264 | 8-(Dimethylamino)-8-phenyl-3-(2-tetrahydrofuran-3-ylethyl)-3-azaspiro[4.5]decan-2-one |
| 265 | [8-Cyclopentyl-3-(tetrahydropyran-4-ylmethyl)-3-azaspiro[4.5]decan-8-yl]-dimethylamine |
| 266 | [8-Cyclopentyl-3-(3-methylbutyl)-3-azaspiro[4.5]decan-8-yl]-dimethylamine |
| 267 | 1-[2-(8-Cyclopentyl-8-dimethylamino-3-azaspiro[4.5]decan-3-yl)-ethyl]-cyclopropane-1-carbonitrile |
| 268 | 1-[2-(8-Cyclopentyl-8-dimethylamino-3-azaspiro[4.5]decan-3-yl)-ethyl]-cyclobutane-1-carbonitrile |
| 269; 270 | 8-(Dimethylamino)-8-phenyl-3-(tetrahydropyran-4-ylmethyl)-3-azaspiro[4.5]decan-2-one |
| 271 | 8-(Dimethylamino)-8-phenyl-3-(2-tetrahydrofuran-3-ylethyl)-3-azaspiro[4.5]decan-2-one |
| 272 | 4-[8-(Dimethylamino)-8-phenyl-3-azaspiro[4.5]decan-3-yl]-2-methylbutan-2-ol |
| 273 | [8-Cyclopentyl-3-(2-methylpropyl)-3-azaspiro[4.5]decan-8-yl]-dimethylamine |
| 274 | 3-(Cyclobutylmethyl)-8-cyclopentyl-8-(dimethylamino)-3-azaspiro[4.5]decan-2-one |
| 275 | 3-(2-Cyclopropylethyl)-8-methylamino-8-phenyl-3-azaspiro[4.5]decan-2-one |
| 276 | 8-Cyclopentyl-3-(cyclopropylmethyl)-8-(dimethylamino)-3-azaspiro[4.5]decan-2-one |
| 277 | 3-(Cyclohexylmethyl)-8-cyclopentyl-8-(dimethylamino)-3-azaspiro[4.5]decan-2-one |
| 278 | 8-Cyclopentyl-3-(cyclopentylmethyl)-8-(dimethylamino)-3-azaspiro[4.5]decan-2-one |
| 279; 280 | 8-(Dimethylamino)-3-[[(3S)-tetrahydrofuran-3-yl]-methyl]-8-thiophen-2-yl-3-azaspiro[4.5]decan-2-one |
| 281 | 3-Butyl-8-cyclopentyl-8-(dimethylamino)-3-azaspiro[4.5]decan-2-one |
| 282 | 8-Cyclopentyl-8-(dimethylamino)-3-methyl-3-azaspiro[4.5]decan-2-one |
| 283 | Dimethyl-[3-[2-(oxetan-3-yl)-ethyl]-8-phenyl-3-azaspiro[4.5]decan-8-yl]-amine |
| 284 | Dimethyl-[8-phenyl-3-(tetrahydrofuran-3-ylmethyl)-3-azaspiro[4.5]decan-8-yl]-amine |
| 285 | 1-[2-[8-(Dimethylamino)-8-phenyl-3-azaspiro[4.5]decan-3-yl]-ethyl]-cyclopropan-1-ol |
| 286 | 3,8-Dicyclopentyl-8-(dimethylamino)-3-azaspiro |
| 287 | 8-Cyclopentyl-8-(dimethylamino)-3-[2-(1-methoxycyclobutyl)-ethyl]-3-azaspiro[4.5]decan-2-one |
| 288; 289 | 3-[8-(Dimethylamino)-2-oxo-8-thiophen-2-yl-3-azaspiro[4.5]decan-3-yl]-2,2-dimethylpropionitrile |
| 290 | 3-(2-Cyclopropylethyl)-8-methylamino-8-thiophen-2-yl-3-azaspiro[4.5]decan-2-one |
| 291 | (8-Cyclopentyl-8-dimethylamino-3-azaspiro[4.5]decan-3-yl)-(oxetan-3-yl)-methanone |
| 292 | [-Cyclopentyl-3-(3-methoxy-3-methylbutyl)-3-azaspiro[4.5]decan-8-yl]-dimethylamine |
| 293; 294 | 8-Cyclopentyl-8-(dimethylamino)-3-[(3S)-tetrahydrofuran-3-yl]-methyl]-3-azaspiro[4.5]decan-2-one |
| 295 | Dimethyl-[3-[2-(oxetan-3-yl)-ethyl]-8-thiophen-2-yl-3-azaspiro[4.5]decan-8-yl]-amine |
| 296 | Dimethyl-[3-(tetrahydrofuran-3-ylmethyl)-8-thiophen-2-yl-3-azaspiro[4.5]decan-8-yl]-amine |
| 297 | 1-(8-Cyclopentyl-8-dimethylamino-3-azaspiro[4.5]decan-3-yl)-2-methoxy-2-methylpropan-1-one |
| 298 | [8-Cyclopentyl-3-(2-methoxy-2-methylpropyl)-3-azaspiro[4.5]decan-8-yl]-dimethylamine |
| 299 | [3-(3-Methoxy-3-methylbutyl)-8-thiophen-2-yl-3-azaspiro[4.5]decan-8-yl]-dimethylamine |
| 300 | [3-(3-Methoxy-3-methylbutyl)-8-phenyl-3-azaspiro[4.5]decan-8-yl]-dimethylamine |
| 301 | 3-(8-Cyclopentyl-8-dimethylamino-3-azaspiro[4.5]decan-3-yl)-2-methylpropan-1-ol |
| 302 | [8-Cyclopentyl-3-(oxetan-3-ylmethyl)-3-azaspiro[4.5]decan-8-yl]-dimethylamine |
| 303 | Dimethyl-[-phenyl-3-(tetrahydropyran-4-ylmethyl)-3-azaspiro[4.5]decan-8-yl]-amine |
| 304 | Dimethyl-[3-(tetrahydropyran-4-ylmethyl)-8-thiophen-2-yl-3-azaspiro[4.5]decan-8-yl]-amine |
| 305 | Dimethyl-[-phenyl-3-(2-tetrahydrofuran-2-ylethyl)-3-azaspiro[4.5]decan-8-yl]-amine |
| 306 | Dimethyl-[3-(2-tetrahydrofuran-2-ylethyl)-8-thiophen-2-yl-3-azaspiro[4.5]decan-8-yl]-amine |

-continued

| | |
|---|---|
| 307; 308 | 3-(2-Cyclobutylethyl)-8-methylamino-8-thiophen-2-yl-3-azaspiro[4.5]decan-2-one |
| 309 | Dimethyl-[3-(2-tetrahydrofuran-3-ylethyl)-8-thiophen-2-yl-3-azaspiro[4.5]decan-8-yl]-amine |
| 310 | 3-(8-Dimethylamino-2-oxo-8-phenyl-3-azaspiro[4.5]decan-3-yl)-2,2-dimethylpropionitrile |
| 311 | 8-Dimethylamino-3-[(1-methoxycyclobutyl)-methyl]-8-thiophen-2-yl-3-azaspiro[4.5]decan-2-one |
| 312 | 8-Dimethylamino-3-[(1-methoxycyclobutyl)-methyl]-8-phenyl-3-azaspiro[4.5]decan-2-one |
| 313 | 8-Dimethylamino-3-(2-ethoxyethyl)-8-thiophen-2-yl-3-azaspiro[4.5]decan-2-one |
| 314 | 1-(8-Dimethylamino-8-thiophen-2-yl-3-azaspiro[4.5]decan-3-yl)-3-methoxy-3-methylbutan-1-one |
| 315 | 1-(8-Dimethylamino-8-thiophen-2-yl-3-azaspiro[4.5]decan-3-yl)-3-methoxy-propan-1-one |
| 316 | 3-(2-Cyclopropylethyl)-8-methylamino-8-thiophen-2-yl-3-azaspiro[4.5]decan-2-one |
| 317 | 8-(Dimethylamino)-3-(3-methoxybutyl)-8-thiophen-2-yl-3-azaspiro[4.5]decan-2-one |
| 318 | 8-(Dimethylamino)-3-(2-methoxypropyl)-8-thiophen-2-yl-3-azaspiro[4.5]decan-2-one |
| 319 | 3-[8-(Dimethylamino)-2-oxo-8-phenyl-3-azaspiro[4.5]decan-3-yl]-2,2-dimethylpropionitrile |
| 320 | 1-[8-(Dimethylamino)-8-phenyl-3-azaspiro[4.5]decan-3-yl]-3-methoxy-3-methylbutan-1-one |
| 321 | 8-(Dimethylamino)-3-[(1-methoxycyclobutyl)-methyl]-8-thiophen-2-yl-3-azaspiro[4.5]decan-2-one |
| 322 | 8-(Dimethylamino)-3-[(1-methoxycyclobutyl)-methyl]-8-phenyl-3-azaspiro[4.5]decan-2-one |
| 323 | 8-(Dimethylamino)-3-(2-methoxypropyl)-8-phenyl-3-azaspiro[4.5]decan-2-one |
| 324 | 8-(Dimethylamino)-3-(3-methoxybutyl)-8-phenyl-3-azaspiro[4.5]decan-2-one |
| 325 | 8-(Dimethylamino)-3-(2-methoxyethyl)-8-phenyl-3-azaspiro[4.5]decan-2-one |
| 326 | 8-(Dimethylamino)-3-(2-ethoxyethyl)-8-phenyl-3-azaspiro[4.5]decan-2-one |
| 327 | 1-[8-(Dimethylamino)-8-thiophen-2-yl-3-azaspiro[4.5]decan-3-yl]-3-methoxybutan-1-one |
| 328 | 1-[8-(Dimethylamino)-8-phenyl-3-azaspiro[4.5]decan-3-yl]-3-methoxybutan-1-one |
| 329 | 1-[8-(Dimethylamino)-8-phenyl-3-azaspiro[4.5]decan-3-yl]-3-methoxypropan-1-one |
| 330 | 3-(2-Cyclopropylethyl)-8-methylamino-8-phenyl-3-azaspiro[4.5]decan-2-one |
| 331 | 3-(2-Cyclobutylethyl)-8-methylamino-8-phenyl-3-azaspiro[4.5]decan-2-one |
| 332 | 8-(Dimethylamino)-3-(2-methoxy-2-methylpropyl)-8-thiophen-2-yl-3-azaspiro[4.5]decan-2-one |
| 333 | 2-Cyclobutyl-1-(8-methylamino-8-thiophen-2-yl-3-azaspiro[4.5]decan-3-yl)-ethanone |
| 334 | 8-(Dimethylamino)-3-(2-ethoxypropyl)-8-thiophen-2-yl-3-azaspiro[4.5]decan-2-one |
| 335 | 8-(Dimethylamino)-3-(2-ethoxypropyl)-8-phenyl-3-azaspiro[4.5]decan-2-one |
| 336 | 8-(Dimethylamino)-3-(3-methoxy-3-methylbutyl)-8-(5-methylthiophen-2-yl)-3-azaspiro[4.5]decan-2-one |
| 337 | 8-(5-Chlorothiophen-2-yl)-8-(dimethylamino)-3-(3-methoxy-3-methylbutyl)-3-azaspiro[4.5]decan-2-one |
| 338 | 1-[8-(Dimethylamino)-8-phenyl-3-azaspiro[4.5]decan-3-yl]-3-ethoxybutan-1-one |
| 339 | 1-[8-(Dimethylamino)-8-thiophen-2-yl-3-azaspiro[4.5]decan-3-yl]-3-ethoxybutan-1-one |
| 340 | 8-(Dimethylamino)-3-(2-methoxy-2-methylpropyl)-8-phenyl-3-azaspiro[4.5]decan-2-one |
| 341 | 3-[2-(1-Methoxycyclobutyl)-ethyl]-8-methylamino-8-thiophen-2-yl-3-azaspiro[4.5]decan-2-one |
| 342 | Cyclobutyl-[8-(dimethylamino)-8-phenyl-3-azaspiro[4.5]decan-3-yl]-methanone |
| 343 | 1-[8-(Dimethylamino)-8-phenyl-3-azaspiro[4.5]decan-3-yl]-2-methylpropan-1-one |
| 344 | 1-[[8-(Dimethylamino)-2-oxo-8-thiophen-2-yl-3-azaspiro[4.5]decan-3-yl]-methyl]-cyclopropane-1-carbonitrile |
| 345 | [8-(Dimethylamino)-8-phenyl-3-azaspiro[4.5]decan-3-yl]-(1-methoxycyclopropyl)-methanone |
| 346 | [3-(2-Cyclobutylethyl)-8-thiophen-2-yl-3-azaspiro[4.5]decan-8-yl]-methylamine |
| 347 | 8-(Dimethylamino)-3-(2-tetrahydropyran-4-ylethyl)-8-thiophen-2-yl-3-azaspiro[4.5]decan-2-one |
| 3-[8 | 8-(Dimethylamino)-8-phenyl-3-(2-tetrahydropyran-4-ylethyl)-3-azaspiro[4.5]decan-2-one |
| 349 | 1-[8-(Dimethylamino)-2-oxo-8-phenyl-3-azaspiro[4.5]decan-3-yl]-methyl]-cyclopropane-1-carbonitrile |
| 350 | 1-[8-(Dimethylamino)-8-phenyl-3-azaspiro[4.5]decan-3-yl]-2-tetrahydropyran-4-ylethanone |
| 351 | 1-[8-(Dimethylamino)-8-thiophen-2-yl-3-azaspiro[4.5]decan-3-yl]-2-tetrahydropyran-4-ylethanone |

| | |
|---|---|
| 352 | 1-[[8-(Dimethylamino)-8-phenyl-3-azaspiro[4.5]decan-3-yl]-methyl]-cyclopropane-1-carbonitrile |
| 353 | 1-[[8-(Dimethylamino)-2-oxo-8-thiophen-2-yl-3-azaspiro[4.5]decan-3-yl]-methyl]-cyclobutane-1-carbonitrile |
| 354 | 1-[8-(Dimethylamino)-8-phenyl-3-azaspiro[4.5]decan-3-yl]-3-(1-methoxycyclobutyl)-propan-1-one |
| 355 | 1-[8-(Dimethylamino)-8-thiophen-2-yl-3-azaspiro[4.5]decan-3-yl]-3-(1-methoxycyclobutyl)-propan-1-one |
| 356 | [8-(Dimethylamino)-8-thiophen-2-yl-3-azaspiro[4.5]decan-3-yl]-(1-methoxycyclopropyl)-methanone |
| 357 | 1-[[8-(Dimethylamino)-2-oxo-8-phenyl-3-azaspiro[4.5]decan-3-yl]-methyl]-cyclobutane-1-carbonitrile |
| 358 | [3-[(1-Methoxycyclopropyl)-methyl]-8-thiophen-2-yl-3-azaspiro[4.5]decan-8-yl]-dimethylamine |
| 359 | 1-[[8-(Dimethylamino)-8-phenyl-3-azaspiro[4.5]decan-3-yl]-methyl]-cyclobutane-1-carbonitrile |
| 360 | 1-[[8-(Dimethylamino)-8-thiophen-2-yl-3-azaspiro[4.5]decan-3-yl]-methyl]-cyclopropane-1-carbonitrile |
| 361 | 1-[[8-(Dimethylamino)-8-thiophen-2-yl-3-azaspiro[4.5]decan-3-yl]-methyl]-cyclobutane-1-carbonitrile |
| 362 | 1-[3-[8-(Dimethylamino)-8-phenyl-3-azaspiro[4.5]decan-3-yl]-3-oxopropyl]-cyclobutane-1-carbonitrile |
| 363 | 1-[3-[8-(Dimethylamino)-8-thiophen-2-yl-3-azaspiro[4.5]decan-3-yl]-3-oxopropyl]-cyclobutane-1-carbonitrile |
| 364 | 1-(8-Butyl-8-dimethylamino-3-azaspiro[4.5]decan-3-yl)-2-cyclopropylethanone |
| 365 | Cyclopropyl-(8-dimethylamino-8-phenyl-3-azaspiro[4.5]decan-3-yl)-methanone |
| 366 | 1-(8-Dimethylamino-8-phenyl-3-azaspiro[4.5]decan-3-yl)-3-methylbutan-1-one |
| 367 | 1-(8-Butyl-8-dimethylamino-3-azaspiro[4.5]decan-3-yl)-3-cyclopropylpropan-1-one |
| 368 | 1-(8-Butyl-8-dimethylamino-3-azaspiro[4.5]decan-3-yl)-4-methoxy-4-methylpentan-1-one |
| 369 | [3-[(1-Methoxycyclopropyl)-methyl]-8-phenyl-3-azaspiro[4.5]decan-8-yl]-dimethylamine |
| 370 | 8-(Dimethylamino)-3-(3-methylbutyl)-8-thiophen-2-yl-3-azaspiro[4.5]decan-2-one |
| 371 | 1-[3-[8-(Dimethylamino)-8-phenyl-3-azaspiro[4.5]decan-3-yl]-3-oxopropyl]-cyclopropane-1-carbonitrile |
| 372 | 1-[3-[8-(Dimethylamino)-8-thiophen-2-yl-3-azaspiro[4.5]decan-3-yl]-3-oxopropyl]-cyclopropane-1-carbonitrile |
| 373 | 1-(8-Dimethylamino-8-thiophen-2-yl-3-azaspiro[4.5]decan-3-yl)-2-(1-methoxycyclopropyl)-ethanone |
| 374 | 1-(8-Dimethylamino-8-phenyl-3-azaspiro[4.5]decan-3-yl)-2-(1-methoxycyclopropyl)-ethanone |
| 375 | 1-(8-Butyl-8-dimethylamino-2-azaspiro[4.5]decan-2-yl)-2-cyclobutylethanone |
| 376 | 8-Dimethylamino-3-(3-methylbutyl)-8-phenyl-3-azaspiro[4.5]decan-2-one |
| 377 | 8-Dimethylamino-3-(2-methylpropyl)-8-thiophen-2-yl-3-azaspiro[4.5]decan-2-one |
| 378 | 8-Dimethylamino-3-(2-methylpropyl)-8-phenyl-3-azaspiro[4.5]decan-2-one |
| 379 | (8-Dimethylamino-8-phenyl-2-azaspiro[4.5]decan-2-yl)-[1-(methoxymethyl)-cyclopropyl]-methanone |
| 380 | 1-(8-Dimethylamino-8-phenyl-2-azaspiro[4.5]decan-2-yl)-3-methoxy-2,2-dimethylpropan-1-one |
| 381 | (8-Dimethylamino-8-phenyl-2-azaspiro[4.5]decan-2-yl)-[1-(methoxymethyl)-cyclobutyl]-methanone |
| 382 | (8-Dimethylamino-8-thiophen-2-yl-3-azaspiro[4.5]decan-3-yl)-(1-methoxycyclobutyl)-methanone |
| 383 | (8-Dimethylamino-8-thiophen-2-yl-3-azaspiro[4.5]decan-3-yl)-[1-(methoxymethyl)-cyclopropyl]-methanone |
| 384 | 1-(8-Dimethylamino-8-thiophen-2-yl-3-azaspiro[4.5]decan-3-yl)-3-methoxy-2,2-dimethylpropan-1-one |
| 385 | (8-Dimethylamino-8-thiophen-2-yl-3-azaspiro[4.5]decan-3-yl)-[1-(methoxymethyl)-cyclobutyl]-methanone |
| 386 | 8-Dimethylamino-3-[2-(1-methoxycyclopropyl)-ethyl]-8-thiophen-2-yl-3-azaspiro[4.5]decan-2-one |
| 387 | 8-Dimethylamino-3-[2-(1-methoxycyclopropyl)-ethyl]-8-phenyl-3-azaspiro[4.5]decan-2-one |
| 388 | 1-(8-Butyl-8-dimethylamino-3-azaspiro[4.5]decan-3-yl)-2-(1-methoxycyclobutyl)-ethanone |
| 389 | 1-(8-Butyl-8-dimethylamino-3-azaspiro[4.5]decan-3-yl)-2-tetrahydrofuran-3-ylethanone |
| 390 | (8-Dimethylamino-8-phenyl-3-azaspiro[4.5]decan-3-yl)-(1-methoxycyclobutyl)-methanone |
| 391 | [8-Dimethylamino-8-(5-methylthiophen-2-yl)-3-azaspiro[4.5]decan-3-yl-[1-(methoxymethyl)-cyclopropyl]-methanone |
| 392 | [8-Dimethylamino-8-(5-methylthiophen-2-yl)-3-azaspiro[4.5]decan-3-yl-[1-(methoxymethyl)-cyclobutyl]-methanone |
| 393 | 1-[8-Dimethylamino-8-(5-methylthiophen-2-yl)-3-azaspiro[4.5]decan-3-yl]-3-methoxy-2,2-dimethylpropan-1-one |

| | |
|---|---|
| 394 | 5-(8-Dimethylamino-8-phenyl-3-azaspiro[4.5]decan-3-yl)-2,2-dimethyl-5-oxopentanenitrile |
| 395 | 5-(8-Dimethylamino-8-thiophen-2-yl-3-azaspiro[4.5]decan-3-yl)-2,2-dimethyl-5-oxopentanenitrile |
| 396 | [8-(5-Chlorothiophen-2-yl)-8-dimethylamino-3-azaspiro[4.5]decan-3-yl-[1-(methoxymethyl)-cyclopropyl]-methanone |
| 397 | [8-(5-Chlorothiophen-2-yl)-8-dimethylamino-3-azaspiro[4.5]decan-3-yl-[1-(methoxymethyl)-cyclobutyl]-methanone |
| 398 | 1-[8-(5-Chlorothiophen-2-yl)-8-dimethylamino-3-azaspiro[4.5]decan-3-yl]-3-methoxy-2,2-dimethylpropan-1-one |
| 399; 400 | 8-Butyl-8-(dimethylamino)-3-(2-tetrahydrofuran-3-ylethyl)-3-azaspiro[4.5]decan-2-one |
| 401; 402 | 1-[2-[8-Butyl-8-(dimethylamino)-2-oxo-3-azaspiro[4.5]decan-3-yl]-ethyl]-cyclopropane-1-carbonitrile |
| 403; 404 | 1-[2-[8-Butyl-8-(dimethylamino)-2-oxo-3-azaspiro[4.5]decan-3-yl]-ethyl]-cyclobutane-1-carbonitrile |
| 405 | 1-[8-(Dimethylamino)-8-phenyl-3-azaspiro[4.5]decan-3-yl]-3-(1-methoxycyclopropyl)-propan-1-one |
| 406 | 8-Butyl-8-(dimethylamino)-3-[2-(1-methoxycyclobutyl)-ethyl]-3-azaspiro[4.5]decan-2-one |
| 407 | [8-(Dimethylamino)-8-(5-fluorothiophen-2-yl)-3-azaspiro[4.5]decan-3-yl]-[1-(methoxymethyl)-cyclobutyl]-methanone |
| 408 | 2-Cyclopropyl-1-[8-(dimethylamino)-8-phenyl-3-azaspiro[4.5]decan-3-yl]-ethanone |
| 409; 410 | 8-Butyl-8-(dimethylamino)-342-(oxetan-3-yl)-ethyl]-3-azaspiro[4.5]decan-2-one |
| 411 | [8-(Dimethylamino)-8-(5-fluorothiophen-2-yl)-3-azaspiro[4.5]decan-3-yl]-[1-(methoxymethyl)-cyclopropyl]-methanone |
| 412 | 1-[8-(Dimethylamino)-8-thiophen-2-yl-3-azaspiro[4.5]decan-3-yl]-3-(1-methoxycyclopropyl)-propan-1-one |
| 413 | 8-Butyl-8-(dimethylamino)-3-[2-(1-methoxycyclobutyl)-ethyl]-3-azaspiro[4.5]decan-2-one |
| 414 | 2-Cyclobutyl-1-[8-(dimethylamino)-8-phenyl-3-azaspiro[4.5]decan-3-yl]-ethanone |
| 415 | 1-[8-(Dimethylamino)-8-thiophen-2-yl-3-azaspiro[4.5]decan-3-yl]-3-methoxy-propan-1-one |
| 416 | 1-[8-(Dimethylamino)-8-thiophen-2-yl-3-azaspiro[4.5]decan-3-yl]-3-methylbutan-1-one |
| 417 | 8-(Dimethylamino)-8-(5-fluorothiophen-2-yl)-3-(3-methoxy-3-methylbutyl)-3-azaspiro[4.5]decan-2-one |
| 418 | 1-[8-Dimethylamino-8-(5-fluorothiophen-2-yl)-3-azaspiro[4.5]decan-3-yl]-3-methoxy-3-methylbutan-1-one |
| 419 | 3-Methoxy-1-(8-methylamino-8-thiophen-2-yl-3-azaspiro[4.5]decan-3-yl)-propan-1-one |
| 420 | 2-Cyclobutyl-1-(8-methylamino-8-phenyl-3-azaspiro[4.5]decan-3-yl)-ethanone |
| 421 | 8-(Dimethylamino)-8-(5-fluorothiophen-2-yl)-3-[2-(1-methoxycyclopropyl)-ethyl]-3-azaspiro[4.5]decan-2-one |
| 422 | 2-Cyclopropyl-1-(8-methylamino-8-phenyl-3-azaspiro[4.5]decan-3-yl)-ethanone |
| 423 | 3-Methyl-1-(8-methylamino-8-thiophen-2-yl-3-azaspiro[4.5]decan-3-yl)-butan-1-one |
| 424 | 8-Cyclopentyl-8-dimethylamino-2-azaspiro[4.5]decane |
| 425 | 8-(5-Chloro-2-thiophen-2-yl)-2-azaspiro[4.5]dec-8-yl]-dimethylamine |
| 426 | [8-(5-Fluorothiophen-2-yl)-2-azaspiro[4.5]dec-8-yl]-dimethylamine |
| 427; 428 | 8-(Azetidin-1-yl)-8-(2-thienyl)-3-azaspiro[4.5]decane |
| 429, 430 | 8-Azetidin-1-yl-8-phenyl-2-azaspiro[4.5]decane |
| 431 | 8-Dimethylamino-8-phenyl-2-azaspiro[4.5]decan-3-one |
| 432; 433 | 8-Butyl-8-dimethylamino-2-azaspiro[4.5]decan-3-one | in the form of an individual stereoisomer or mixture thereof, the free compound and/or its physiologically acceptable salt and/or solvate.

12. A medicament containing at least one compound as claimed in claim 1 in the form of an individual stereoisomer or mixture thereof, the free compound and/or its physiologically acceptable salt and/or solvate, and optionally suitable additives and/or auxiliary substances.

13. A compound as claimed in claim 1 in the form of an individual stereoisomer or mixture thereof, the free compound and/or its physiologically acceptable salt and/or solvate for use in the treatment of pain.

14. A method of treating anxiety states, of stress and syndromes associated with stress, depressions, epilepsy, Alzheimer's disease, senile dementia, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, urinary incontinence or as a muscle relaxant, anticonvulsive or anaesthetic or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids comprising administering a therapeutically active dose of the compound of claim 1.

15. The medicament of claim 12, further comprising at least one additional active compound selected from the group consisting of an opioid and an anaesthetic.

* * * * *